US007504411B2

(12) United States Patent
Watanabe et al.

(10) Patent No.: US 7,504,411 B2
(45) Date of Patent: Mar. 17, 2009

(54) 2,3,6-TRISUBSTITUTED-4-PYRIMIDONE DERIVATIVES

(75) Inventors: Kazutoshi Watanabe, Kanagawa (JP);
Fumiaki Uehara, Kanagawa (JP);
Shinsuke Hiki, Chiba (JP); Satoshi Yokoshima, Tokyo (JP); Yoshihiro Usui, Ibaraki (JP); Masahiro Okuyama, Kanagawa (JP); Aya Shoda, Chiba (JP); Keiichi Aritomo, Tokyo (JP); Toshiyuki Kohara, Kanagawa (JP); Kenji Fukunaga, Kanagawa (JP)

(73) Assignees: Mitsubishi Tanabe Pharma Corporation, Osaka (JP);
Sanofi-Aventis, Paris (FR)

( * ) Notice: Subject to any disclaimer, the term of this patent is extended or adjusted under 35 U.S.C. 154(b) by 0 days.

(21) Appl. No.: 10/550,299

(22) PCT Filed: Mar. 26, 2004

(86) PCT No.: PCT/JP2004/004320

§ 371 (c)(1),
(2), (4) Date: May 31, 2006

(87) PCT Pub. No.: WO2004/085408

PCT Pub. Date: Oct. 7, 2004

(65) Prior Publication Data

US 2006/0252768 A1 Nov. 9, 2006

(30) Foreign Application Priority Data

Mar. 26, 2003 (JP) ............................. 2003-126021
Mar. 26, 2003 (JP) ............................. 2003-126022

(51) Int. Cl.
*C07D 401/14* (2006.01)
*C07D 403/14* (2006.01)
*A61K 31/496* (2006.01)
*A61K 31/506* (2006.01)
*A61P 3/10* (2006.01)
*A61P 25/28* (2006.01)

(52) U.S. Cl. .................. 514/273; 544/320; 514/252.14
(58) Field of Classification Search ................. 544/320; 514/273
See application file for complete search history.

(56) References Cited

U.S. PATENT DOCUMENTS

| 4,166,180 A | 8/1979 | Kato et al. |
| 4,507,302 A | 3/1985 | Fast et al. |
| 4,619,933 A | 10/1986 | Stringfellow et al. |
| 4,725,600 A | 2/1988 | Takaya et al. |
| 5,612,286 A | 3/1997 | Mayer et al. |
| 6,096,753 A | 8/2000 | Spohr et al. |
| 6,107,301 A | 8/2000 | Aldrich et al. |
| 6,410,729 B1 | 6/2002 | Spohr et al. |
| 6,420,385 B1 | 7/2002 | Spohr et al. |
| 6,586,441 B2 | 7/2003 | Borroni et al. |
| 6,844,335 B2 * | 1/2005 | Almario Garcia et al. ............ 514/211.15 |
| 2003/0187004 A1 | 10/2003 | Almario Garcio et al. |
| 2005/0090490 A1 | 4/2005 | Uehara et al. |
| 2005/0130967 A1 | 6/2005 | Uehara et al. |
| 2005/0130998 A1 | 6/2005 | Almario Garcia et al. |

FOREIGN PATENT DOCUMENTS

EP 0168262 1/1986

(Continued)

OTHER PUBLICATIONS

West, Anthony R., Solid State Chemistry and its Applications, Wiley, New York, 1988, pp. 358 & 365.*

(Continued)

*Primary Examiner*—Venkataraman Balasubramanian
(74) *Attorney, Agent, or Firm*—Greenblum & Bernstein, P.L.C.

(57) ABSTRACT

A pyrimidone derivative having tau protein kinase 1 inhibitory activity which is represented by formula (I) or a salt thereof, or a solvate thereof or a hydrate thereof; useful for prventive and/or therapeutic treatment of diseass such as neurodegenerative diseases (e.g. Alzheimer disease); wherein Q represents CH or nitrogen atom; R represents a $C_1$-$C_{12}$ alkyl group; the ring of Formula (I): represents piperazine ring or piperidine ring; each X independently represents a $C_1$-$C_8$ alkyl group, an optionally partially hydrogenated $C_6$-$C_{10}$ aryl ring, an indan ring or the like; m represents an integer of 1 to 3; each independently represents a halogen atom, a hydroxy group, a cyano group, a $C_1$-$C_6$ alkyl group or the like; n represents an integer of 0 to 8; when X and Y or two Y groups are attached on the same carbon atom, they may combine to each other to form a $C_2$-$C_6$ alkylene group.

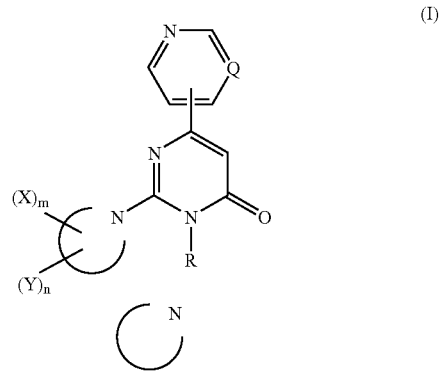

12 Claims, No Drawings

FOREIGN PATENT DOCUMENTS

| | | |
|---|---|---|
| EP | 0354179 | 7/1989 |
| EP | 1 136 482 A1 * | 9/2001 |
| EP | 1136482 | 9/2001 |
| HU | 218974 | 8/1995 |
| HU | P0001698 | 4/2001 |
| JP | 49-035631 | 4/1974 |
| JP | 49-035632 | 4/1974 |
| JP | 49-035633 | 4/1974 |
| JP | 49-35634 | 4/1974 |
| JP | 52-071481 | 6/1977 |
| JP | 52-139085 | 11/1977 |
| JP | 6-239893 | 8/1994 |
| JP | 6-329551 | 11/1994 |
| WO | 93/11231 | 6/1998 |
| WO | 98/24780 | 6/1998 |
| WO | 98/24782 | 6/1998 |
| WO | 00/18758 | 4/2000 |
| WO | 01/70728 | 9/2001 |
| WO | 01/70729 | 9/2001 |
| WO | 03/027080 | 4/2003 |
| WO | 03/037888 | 5/2003 |
| WO | 2004/055007 | 7/2004 |

OTHER PUBLICATIONS

Vippagunta et al., Advanced Drug Delivery Reviews 48: 3-26, 2001.*
Cecil Textbook of Medicine, edited by Bennet, J.C., and Plum F., 20th edition, vol. 2, 2050-2057, 1996.*
Cecil Textbook of Medicine, edited by Bennet, J.C., and Plum F., 20th edition, vol. 2, 1992-1996, 1996.*
Julien et al., Prog Nucleic Acid Res Mol Biol. 61: 1-23, 1998 (PubMed Abstract).*
Simone, Oncology: Introduction, Cecil Textbook of Medicine, 20th Edition, vol. 1, pp. 1004-1010, 1996.*
Hutton et al., Analysis of taupathies with transgenic mice, Trends in Molecular Medicine, vol. 7, No. 10, pp. 467-470, 2001.*
G. Glenner et al., Biochemical and Biophysical Research Communications, vol. 120, No. 3, 1984, pp. 885-890.
C.L. Masters et al., The EMBO Journal, vol. 4, No. 11, 1985, pp. 2757-2763.
C.L. Masters et al., Proc. Natl. Acad. Sci. USA, vol. 82, Jun. 1985, pp. 4245-4249.
C.M. Wischik et al., Proc. Natl. Acad. Sci. USA, vol. 85, Jun. 1988, pp. 4506-4510.
J. Kondo et al., Neuron, vol. 1, Nov. 1988, pp. 827-834.
R. Sherrington et al., Nature, vol. 375, Jun. 29, 1995, pp. 754-760.
E. Levy-Lahad et al., Science, vol. 269, Aug. 18, 1995, pp. 973-977.
E.I. Rogaev et al., Nature, vol. 376, Aug. 31, 1995, pp. 775-778.
D.R. Borchelt et al., Neuron, vol. 17, Nov. 1996, pp. 1005-1013.
T. Tomita et al., Proc. Natl. Acad. Sci. USA, vol. 94, Mar. 1997, pp. 2025-2030.
Sai-Shin Igaku, vol. 49, No. 9, 1994, pp. 1506-1512.
D.W. Dickson et al., Society of Neuroscience Abstracts, vol. 17, 1991, p. 1445.
R. Siman et al., The Journal of Neuroscience, vol. 10, No. 7, Jul. 1990, pp. 2400-2411.
Shin-kei Shinpo, vol. 34, 1990, pp. 343-349.
Tanpaku-shitu Kaku-san Koso, vol. 41, 1996, pp. 1476-1483.
Tanpaku-shitu Kaku-san Koso, vol. 36, 1991, pp. 2-11.
Igaku no Ayumi, vol. 158, No. 9, Aug. 31, 1991, pp. 511-514.
Y. Ihara et al., J. Biochem., vol. 99, 1986, pp. 1807-1810.
I. Grundke-Iqbal et al., Proc. Natl. Acad. Sci. USA, vol. 83, Jul. 1986, pp. 4913-4917.
Seikagaku, vol. 64, No. 5, pp. 308-312.
K. Ishiguro et al. J. Biol. Chem., vol. 267, No. 15, May 25, 1992, pp. 10897-10901.
K. Ishiguro et al., FEBS Lett., vol. 325, Jul. 1993, pp. 167-172.
English Language Abstract of JP 6-239893, Date Publication Aug. 30, 1994.
B.A. Yankner et al., Science, vol. 250, 1990, pp. 279-283.
A. Takashima et al., Proc. Natl. Acad. Sci. USA, vol. 90, Aug. 1993, pp. 7789-7793.
H. Yinglin, Tetrahedron Letters, vol. 30, No. 39, 1989, pp. 5285-5286.
English language Abstract of JP 6-329551 Date Publication Nov. 29, 1994.
H. Yinglin, Synthesis, pp. 122-124, Feb. 1990.
R.L. Duncan Jr. et al., J. Med. Chem., vol. 13, No. 1, Jan. 1970, pp. 1-6.
D.L. Thai et al., J. Med. Chem., vol. 41, 1998, pp. 591-601.
Chemical Abstracts, vol. 100, No. 28, 1984, Columbus, Ohio, US, Abstract No. 174768e, M.F. Brana et al., "Reaction of N-1(1-Oxido-4-Pyridylmethyl)-3,5-Dimethylbenzamide with Malononitrile in Acetic Anhydride", p. 627; XP002127059.
Chemical Abstracts, vol. 84, No. 7, 1976, Columbus, Ohio, US, Abstract No. 44112b, Tani et al., "4-Hydroxy-Pyridylpyrimidine Derivatives", p. 502, XP002127060.
Chemical Abstracts, vol. 82, No. 28, 1975, Columbus, Ohio, US, Abstract No. 171028n, Tani et al., "2,4,5-Trisubstituted-6-Pyridylpyrimidine Derivatives", p. 555, XP002127061.
Chemical Abstracts, vol. 83, No. 28, 1975, Columbus, Ohio, US, Abstract No. 10127z, Tani et al., "5-Nitro-6-Pyridylpyrimidine Derivatives", p. 853, XP002127062.
Chemical Abstract 1992, vol. 116, Abstract # 59167.
Chemical Abtract 1966, vol. 65, Abstact # 90645.
Von Hans-Joachim KABBE, "Substituierte 4-Hydroxy- und 4-Amino-Pyrimidine", Liebigs. Ann. Chem., vol. 701, pp. 144-149 (1967).
Harvey I. Skulnick et al., "Pyrimidinones. 1. 2-Amino-5-Halo-6-Arly-4(3H)-Pyrimidinones. Interferon-Inducing Antiviral Agents", J. Med. Chem., vol. 28, pp. 1864-1869 (1985).
U.S. Appl. No. 09/787,426, filed Jul. 2, 2001 to Watanabe et al.
English language Abstract of JP 52-071481, published Jun. 14, 1977.
U.S. Appl. No. 10/538,766, filed Dec. 12, 2003 to Usui et al.
Tani et al, Caplus Abstract 84:44112 (1976).
Joachim Ulrich, Chapter 4: Crystallization, Krik-Othmer Encyclopedia of Chemical Technology (Aug. 2002).

* cited by examiner

2,3,6-TRISUBSTITUTED-4-PYRIMIDONE DERIVATIVES

TECHNICAL FIELD

The present invention relates to compounds that are useful as an active ingredient of a medicament for preventive and/or therapeutic treatment of diseases mainly caused by abnormal activity of tau protein kinase 1, such as neurodegenerative diseases (e.g. Alzheimer disease).

BACKGROUND ART

Alzheimer disease is progressive senile dementia, in which marked cerebral cortical atrophy is observed due to degeneration of nerve cells and decrease of nerve cell number. Pathologically, numerous senile plaques and neurofibrillary tangles are observed in brain. The number of patients has been increased with the increment of aged population, and the disease arises a serious social problem. Although various theories have been proposed, a cause of the disease has not yet been elucidated. Early resolution of the cause has been desired.

It has been known that the degree of appearance of two characteristic pathological changes of Alzheimer disease well correlates to the degree of intellectual dysfunction. Therefore, researches have been conducted from early 1980's to reveal the cause of the disease through molecular level investigations of components of the two pathological changes. Senile plaques accumulate extracellularly, and β amyloid protein has been elucidated as their main component (abbreviated as "A β" hereinafter in the specification: Biochem. Biophys. Res. Commun., 120, 855 (1984); EMBO J., 4, 2757 (1985); Proc. Natl. Acad. Sci. USA, 82, 4245 (1985)). In the other pathological change, i.e., the neurofibrillary tangles, a double-helical filamentous substance called paired helical filament (abbreviated as "PHF" hereinafter in the specification) accumulate intracellularly, and tau protein, which is a kind of microtubule-associated protein specific for brain, has been revealed as its main component (Proc. Natl. Acad. Sci. USA, 85, 4506 (1988); Neuron, 1, 827 (1988)).

Furthermore, on the basis of genetic investigations, presenilins 1 and 2 were found as causative genes of familial Alzheimer disease (Nature, 375, 754 (1995); Science, 269, 973 (1995); Nature. 376, 775 (1995)), and it has been revealed that presence of mutants of presenilins 1 and 2 promotes the secretion of A β (Neuron, 17, 1005 (1996); Proc. Natl. Acad. Sci. USA, 94, 2025 (1997)). From these results, it is considered that, in Alzheimer disease, A β abnormally accumulates and agglomerates due to a certain reason, which engages with the formation of PHF to cause death of nerve cells. It is also expected that extracellular outflow of glutamic acid and activation of glutamate receptor responding to the outflow may possibly be important factors in an early process of the nerve cell death caused by ischemic cerebrovascular accidents (Saishin Igaku [Latest Medicine], 49, 1506 (1994)).

It has been reported that kainic acid treatment that stimulates the AMPA receptor, one of glutamate receptor, increases mRNA of the amyloid precursor protein (abbreviated as "APP" hereinafter in the specification) as a precursor of A β (Society for Neuroscience Abstracts, 17, 1445 (1991)), and also promotes metabolism of APP (The Journal of Neuroscience, 10, 2400 (1990)). Therefore, it has been strongly suggested that the accumulation of A β is involved in cellular death due to ischemic cerebrovascular disorders. Other diseases in which abnormal accumulation and agglomeration of A β are observed include, for example, Down syndrome, cerebral bleeding due to solitary cerebral amyloid angiopathy, Lewy body disease (Shin-kei Shinpo [Nerve Advance], 34, 343 (1990); Tanpaku-shitu Kaku-san Koso [Protein, Nucleic Acid, Enzyme], 41, 1476 (1996)) and the like. Furthermore, as diseases showing neurofibrillary tangles due to the PHF accumulation, examples include progressive supranuclear palsy, subacute sclerosing panencephalitic parkinsonism, postencephalitic parkinsonism, pugilistic encephalitis, Guam parkinsonism-dementia complex, Lewy body disease and the like (Tanpakushitu Kakusan Koso [Protein, Nucleic Acid, Enzyme], 36, 2 (1991); Igaku no Ayumi [Progress of Medicine], 158, 511 (1991); Tanpakushitu Kakusan Koso [Protein, Nucleic Acid, Enzyme], 41, 1476 (1996)).

The tau protein is generally composed of a group of related proteins that forms several bands at molecular weights of 48-65 kDa in SDS-polyacrylamide gel electrophoresis, and it promotes the formation of microtubules. It has been verified that tau protein incorporated in the PHF in the brain suffering from Alzheimer disease is abnormally phosphorylated compared with usual tau protein (J. Biochem., 99, 1807 (1986); Proc. Natl. Acad. Sci. USA, 83, 4913 (1986)). An enzyme catalyzing the abnormal phosphorylation has been isolated. The protein was named as tau protein kinase 1 (abbreviated as "TPK1" hereinafter in the specification), and its physicochemical properties have been elucidated (Seikagaku [Biochemistry], 64, 308 (1992); J. Biol. Chem., 267, 10897 (1992)). Moreover, cDNA of rat TPK1 was cloned from a rat cerebral cortex cDNA library based on a partial amino acid sequence of TPK1, and its nucleotide sequence was determined and an amino acid sequence was deduced (Japanese Patent Un-examined Publication [Kokai] No. 6-239893/1994). As a result, it has been revealed that the primary structure of the rat TPK1 corresponds to that of the enzyme known as rat GSK-3 β (glycogen synthase kinase 3 β, FEBS Lett., 325, 167 (1993)).

It has been reported that A β, the main component of senile plaques, is neurotoxic (Science, 250, 279 (1990)). However, various theories have been proposed as for the reason why A β causes the cell death, and any authentic theory has not yet been established. Takashima et al. observed that the cell death was caused by A β treatment of fetal rat hippocampus primary culture system, and then found that the TPK1 activity was increased by A β treatment and the cell death by A β was inhibited by antisense of TPK1 (Proc. Natl. Acad. Sci. USA, 90, 7789 (1993); Japanese Patent Un-examined Publication [Kokai] No. 6-329551/1994).

In view of the foregoing, compounds which inhibit the TPK1 activity may possibly suppress the neurotoxicity of A β and the formation of PHF and inhibit the nerve cell death in the Alzheimer disease, thereby cease or defer the progress of the disease. The compounds may also be possibly used as a medicament for therapeutic treatment of ischemic cerebrovascular disorder, Down syndrome, cerebral amyloid angiopathy, cerebral bleeding due to Lewy body disease and the like by suppressing the cytotoxicity of A β. Furthermore, the compounds may possibly be used as a medicament for therapeutic treatment of neurodegenerative diseases such as progressive supranuclear palsy, subacute sclerosing panencephalitic parkinsonism, postencephalitic parkinsonism, pugilistic encephalitis, Guam parkinsonism-dementia complex, Lewy body disease, Pick's disease, corticobasal degeneration, frontotemporal dementia, vascular dementia, acute stroke and traumatic injuries, brain and spinal cord trauma, peripheral neuropathies, retinopathies and glaucoma; non-insulin dependent diabetes (such as diabetes type II), and obesity, manic depressive illness, schizophrenia, alopecia, cancers such as breast cancer, non-small cell lung carcinoma, thyroid cancer, T or B-cell leukemia and several virus-induced tumors.

As structurally similar compounds to the compounds of the present invention represented by formula (I) described later, compounds represented by the following formula (A) are known:

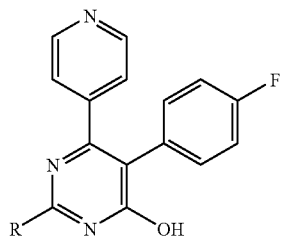

(A)

wherein R represents 2,6-dichlorobenzyl group, 2-(2-chlorophenyl)ethylamino group, 3-phenylpropylamino group, or 1-methyl-3-phenylpropylamino group (WO98/24782). The compounds represented by formula (A) are characterized to have 4-fluorophenyl group at the 5-position of the pyrimidine ring and a hydroxy group at the 4-position, and not falling within the scope of the present invention. Moreover, main pharmacological activity of the compounds represented by formula (A) is anti-inflammatory effect, whereas the compounds of the present invention represented by formula (I) are useful as a TPK1 inhibitor or a medicament for therapeutic treatment of neurodegenerative diseases, and therefore, their pharmacological activities are totally different to each other.

Patent Document 1: WO 00/18758

Patent Document 2: WO 01/70728

Patent Document 3: WO 01/70729

DISCLOSURE OF THE INVENTION

An object of the present invention is to provide compounds useful as an active ingredient of a medicament for preventive and/or therapeutic treatment of diseases such as Alzheimer disease. More specifically, the object is to provide novel compounds useful as an active ingredient of a medicament that enables radical prevention and/or treatment of the neurodegenerative diseases such as Alzheimer disease by inhibiting the TPK1 activity to suppress the neurotoxicity of A β and the formation of the PHF and by inhibiting the death of nerve cells.

In order to achieve the foregoing object, the inventors of the present invention conducted screenings of various compounds having inhibitory activity against the phosphorylation of TPK1. As a result, they found that compounds represented by the following formula (I) had the desired activity and were useful as an active ingredient of a medicament for preventive and/or therapeutic treatment of the aforementioned diseases. The present invention was achieved on the basis of these findings.

The present invention thus provides 3-substituted-4-pyrimidone derivatives represented by formula (I) or salts thereof, or solvates thereof or hydrates thereof:

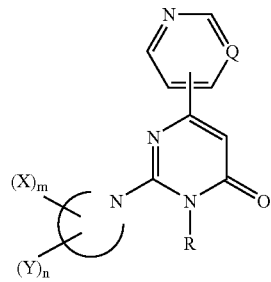

(I)

wherein Q represents CH or nitrogen atom;
R represents a $C_1$-$C_{12}$ alkyl group which may be substituted;
the ring of:

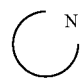

represents piperazine ring or piperidine ring;
each X independently represents $$X^1-X^2-$$

wherein $X^1$ represents an oxo group; a $C_1$-$C_8$ alkyl group which may be substituted;
a $C_3$-$C_8$ cycloalkyl-group which may be substituted; an optionally partially hydrogenated $C_6$-$C_{10}$ aryl ring which may be substituted; an indan ring which may be substituted; an optionally substituted heterocyclic ring having 1 to 4 hetero atoms selected from the group consisting of oxygen atom, sulfur atom, and nitrogen atom, and having 5 to 10 ring-constituting atoms in total; an aralkyloxy group; a group represented by —N(Ra)(Rb) wherein Ra and Rb are the same or different and each is hydrogen, a $C_1$-$C_4$ alkyl group which may be substituted, an aralkyl group which may be substituted, a $C_3$-$C_8$ cycloalkyl group which may be substituted, an aryl group which may be substituted, $C_1$-$C_8$ alkylcarbonyl group which may be substituted, $C_3$-$C_8$ cycloalkylcarbonyl group which may be substituted,
aralkycarbonyl group which may be substituted,
$C_6$-$C_{10}$ arylcarbonyl group which may be substituted,
$C_1$-$C_8$ alkysulfonyl group which may be substituted,
$C_3$-$C_8$ cycloalkylsulfonyl group which may be substituted,
aralkysulfonyl group which may be substituted,
$C_6$-$C_{10}$ arylsulfonyl group which may be substituted,
$C_1$-$C_8$ alkyloxycarbonyl group which may be substituted,
$C_3$-$C_8$ cycloalkyloxycarbonyl group which may be substituted,
aralkyoxycarbonyl group which may be substituted,
$C_6$-$C_{10}$ aryloxycarbonyl group which may be substituted,
aminocarbonyl,
N—$C_1$-$C_8$ alkylaminocarbonyl group which may be substituted,
N,N'—$C_1$-$C_8$ dialkylaminocarbonyl group which may be substituted,
N—$C_1$-$C_8$ alkyl-N'—$C_3$-$C_8$ cycloalkylaminocarbonyl group which may be substituted,
N—$C_1$-$C_8$ alkyl-N'-aralkylaminocarbonyl group which may be substituted, N—$C_1$-$C_8$ alkyl-N'—$C_6$-$C_{10}$ arylaminocarbonyl group which may be substituted,
$C_3$-$C_8$ cycloalkylaminocarbonyl group which may be substituted,
N,N'—$C_3$-$C_8$ dicycloalkylaminoycarbonyl group which may be substituted,
N—$C_3$-$C_8$ cycloalkyl-N'-aralkylaminocarbonyl group which may be substituted,
N—$C_3$-$C_8$ cycloalkyl-N'—$C_6$-$C_{10}$ arylaminocarbonyl group which may be substituted,
aralkylaminocarbonyl group which may be substituted,
N,N'-diaralkylaminocarbonyl group which may be substituted,
N-aralkyl-N'—$C_6$-$C_{10}$ arylaminocarbonyl group which may be substituted,
$C_6$-$C_{10}$ arylaminocarbonyl group which may be substituted,
N,N'—$C_6$-$C_{10}$ diarylaminocarbonyl group which may be substituted,
or an optionally substituted heterocyclic ring having 1 to 4 hetero atoms selected from the group consisting of oxygen atom, sulfur atom, and nitrogen atom, and having 5 to 10 ring-constituting atoms in total; or Ra and Rb together with the adjacent nitrogen atom form a 4 to 7 membered heterocyclic ring which may further contain 1 to 4 groups selected from an oxygen atom, a sulfur atom, N-Rc (wherein Rc represents a hydrogen atom, a $C_1$-$C_4$ alkyl group which may be substituted, an aralkyl group which may be substituted, $C_3$-$C_8$ cycloalkyl group which may be substituted or an aryl group which may be substituted,
$C_1$-$C_8$ alkylcarbonyl group which may be substituted,
$C_3$-$C_8$ cycloalkylcarbonyl group which may be substituted,
aralkycarbonyl group which may be substituted,
$C_6$-$C_{10}$ arylcarbonyl group which may be substituted,
$C_1$-$C_8$ alkysulfonyl group which may be substituted,
$C_3$-$C_8$ cycloalkylsulfonyl group which may be substituted,
aralkysulfonyl group which may be substituted,
$C_6$-$C_{10}$ arylsulfonyl group which may be substituted,
$C_1$-$C_8$ alkyloxycarbonyl group which may be substituted,
$C_3$-$C_8$ cycloalkyloxycarbonyl group which may be substituted,
aralkyoxycarbonyl group which may be substituted,
$C_6$-$C_{10}$ aryloxycarbonyl group which may be substituted,
aminocarbonyl,
N—$C_1$-$C_8$ alkylaminocarbonyl group which may be substituted,
N,N'—$C_1$-$C_8$ dialkylaminocarbonyl group which may be substituted,
N—$C_1$-$C_8$ alkyl-N'—$C_3$-$C_8$ cycloalkylaminocarbonyl group which may be substituted,
N—$C_1$-$C_8$ alkyl-N'-aralkylaminocarbonyl group which may be substituted,
N—$C_1$-$C_8$ alkyl-N'—$C_6$-$C_{10}$ arylaminocarbonyl group which may be substituted,
$C_3$-$C_8$ cycloalkylaminocarbonyl group which may be substituted,
N,N'—$C_3$-$C_8$ dicycloalkylaminoycarbonyl group which may be substituted,
N—$C_3$-$C_8$ cycloalkyl-N'-aralkylaminocarbonyl group which may be substituted,
N—$C_3$-$C_8$ cycloalkyl-N'—$C_6$-$C_{10}$ arylaminocarbonyl group which may be substituted,
aralkylaminocarbonyl group which may be substituted,
N,N'-diaralkylaminocarbonyl group which may be substituted,
N-aralkyl-N'—$C_6$-$C_{10}$ arylaminocarbonyl group which may be substituted,
$C_6$-$C_{10}$ arylaminocarbonyl group which may be substituted,
N,N'—$C_6$-$C_{10}$ diarylaminocarbonyl group which may be substituted,
or an optionally substituted heterocyclic ring having 1 to 4 hetero atoms selected from the group consisting of oxygen atom, sulfur atom, and nitrogen atom, and having 5 to 10 ring-constituting atoms in total),
a carbonyl group, a sulfinyl group or a sulfonyl group in the ring, and said 4 to 7 membered heterocyclic ring may optionally be fused with an aryl group which may be substituted;
$X^2$ represents a bond, a carbonyl group, a sulfinyl group, a sulfonyl group, an oxygen atom, a sulfur atom, a $C_1$-$C_4$ alkylene group which may be substituted or
N-Rd (Rd represents a hydrogen atom, a $C_1$-$C_4$ alkyl group which may be substituted, an aralkyl group which may be substituted, $C_3$-$C_8$ cycloalkyl group which may be substituted or an aryl group which may be substituted,
$C_1$-$C_8$ alkylcarbonyl group which may be substituted,
$C_3$-$C_8$ cycloalkylcarbonyl group which may be substituted,
aralkycarbonyl group which may be substituted,
$C_6$-$C_{10}$ arylcarbonyl group which may be substituted,
$C_1$-$C_8$ alkysulfonyl group which may be substituted,
$C_3$-$C_8$ cycloalkylsulfonyl group which may be substituted,
aralkysulfonyl group which may be substituted,
$C_6$-$C_{10}$ arylsulfonyl group which may be substituted,
$C_1$-$C_8$ alkyloxycarbonyl group which may be substituted,
$C_3$-$C_8$ cycloalkyloxycarbonyl group which may be substituted,
aralkyoxycarbonyl group which may be substituted,
$C_6$-$C_{10}$ aryloxycarbonyl group which may be substituted,
aminocarbonyl,
N—$C_1$-$C_8$ alkylaminocarbonyl group which may be substituted,
N,N'—$C_1$-$C_8$ dialkylaminocarbonyl group which may be substituted,
N—$C_1$-$C_8$ alkyl-N'—$C_3$-$C_8$ cycloalkylaminocarbonyl group which may be substituted,
N—$C_1$-$C_8$ alkyl-N'-aralkylaminocarbonyl group which may be substituted,
N—$C_1$-$C_8$ alkyl-N'—$C_6$-$C_{10}$ arylaminocarbonyl group which may be substituted,
$C_3$-$C_8$ cycloalkylaminocarbonyl group which may be substituted,
N,N'—$C_3$-$C_8$ dicycloalkylaminoycarbonyl group which may be substituted,
N—$C_3$-$C_8$ cycloalkyl-N'-aralkylaminocarbonyl group which may be substituted,
N—$C_3$-$C_8$ cycloalkyl-N'—$C_6$-$C_{10}$ arylaminocarbonyl group which may be substituted,
aralkylaminocarbonyl group which may be substituted,
N,N'-diaralkylaminocarbonyl group which may be substituted,
N-aralkyl-N'—$C_6$-$C_{10}$ arylaminocarbonyl group which may be substituted,
$C_6$-$C_{10}$ arylaminocarbonyl group which may be substituted,
N,N'—$C_6$-$C_{10}$ diarylaminocarbonyl group which may be substituted,
or an optionally substituted heterocyclic ring having 1 to 4 hetero atoms selected from the group consisting of oxygen atom, sulfur atom, and nitrogen atom, and having 5 to 10 ring-constituting atoms in total);
m represents an integer of 1 to 3;
each Y independently represents a halogen atom, a hydroxy group, a cyano group,
$Y^1$-$Y^3$—wherein $Y^1$ represents a $C_1$-$C_8$ alkyl group which may be substituted; a $C_3$-$C_8$ cycloalkyl group which may be substituted or a $C_6$-$C_{10}$ aryl ring which may be substituted; $Y^3$ represents a carbonyl group, a sulfinyl group, a sulfonyl group, an oxygen atom, a sulfur atom, a $C_1$-$C_4$ alkylene group which may be substituted or N-Re (Re represents a hydrogen atom, a $C_1$-$C_4$ alkyl group which may be substituted, an aralkyl group which may be substituted, $C_3$-$C_8$ cycloalkyl group which may be substituted or an aryl group which may be substituted,
$C_1$-$C_8$ alkylcarbonyl group which may be substituted,
$C_3$-$C_8$ cycloalkylcarbonyl group which may be substituted,
aralkycarbonyl group which may be substituted,
$C_6$-$C_{10}$ arylcarbonyl group which may be substituted,
$C_1$-$C_8$ alkysulfonyl group which may be substituted,
$C_3$-$C_8$ cycloalkylsulfonyl group which may be substituted,
aralkysulfonyl group which may be substituted,
$C_6$-$C_{10}$ arylsulfonyl group which may be substituted,
$C_1$-$C_8$ alkyloxycarbonyl group which may be substituted,
$C_3$-$C_8$ cycloalkyloxycarbonyl group which may be substituted,
aralkyoxycarbonyl group which may be substituted,
$C_6$-$C_{10}$ aryloxycarbonyl group which may be substituted,
aminocarbonyl,
N—$C_1$-$C_8$ alkylaminocarbonyl group which may be substituted,
N,N'—$C_1$-$C_8$ dialkylaminocarbonyl group which may be substituted,
N—$C_1$-$C_8$ alkyl-N'—$C_3$-$C_8$ cycloalkylaminocarbonyl group which may be substituted,
N—$C_1$-$C_8$ alkyl-N'-aralkylaminocarbonyl group which may be substituted,
N—$C_1$-$C_8$ alkyl-N'—$C_6$-$C_{10}$ arylaminocarbonyl group which may be substituted,
$C_3$-$C_8$ cycloalkylaminocarbonyl group which may be substituted,
N,N'—$C_3$-$C_8$ dicycloalkylaminoycarbonyl group which may be substituted,
N—$C_3$-$C_8$ cycloalkyl-N'-aralkylaminocarbonyl group which may be substituted,
N—$C_3$-$C_8$ cycloalkyl-N'—$C_6$-$C_{10}$ arylaminocarbonyl group which may be substituted,
aralkylaminocarbonyl group which may be substituted,
N,N'-diaralkylaminocarbonyl group which may be substituted,
N-aralkyl-N'—$C_6$-$C_{10}$ arylaminocarbonyl group which may be substituted,
$C_6$-$C_{10}$ arylaminocarbonyl group which may be substituted,
N,N'—$C_6$-$C_{10}$ diarylaminocarbonyl group which may be substituted,
or an optionally substituted heterocyclic ring having 1 to 4 hetero atoms selected from the group consisting of oxygen atom, sulfur atom, and nitrogen atom, and having 5 to 10 ring-constituting atoms in total),
n represents an integer of 0 to 8;
when X and Y or two Y groups are attached on the same carbon atom, they may combine to each other to form a $C_2$-$C_6$ alkylene group;
and when m is 1, n is 0, and X is $X^1$—CO—,
(1) X does not bind to 3-position of unsubstituted 1-piperazinyl group or does not bind to 3-position of a 4-alkyl-1-piperazinyl group; or
(2) X does not bind to 3-position or 4-position of non-substituted 1-piperidinyl group.

According to another aspect of the present invention, there is provided a medicament comprising as an active ingredient a substance selected from the group consisting of the 3-substituted-4-pyrimidone derivatives represented by formula (I) and the physiologically acceptable salts thereof, and the solvates thereof and the hydrates thereof. As preferred embodiments of the medicament, there are provided the aforementioned medicament which is used for preventive and/or therapeutic treatment of diseases caused by tau protein kinase 1 hyperactivity, and the aforementioned medicament which is used for preventive and/or therapeutic treatment of neurodegenerative diseases.

As further preferred embodiments of the present invention, there are provided the aforementioned medicament wherein the diseases are selected from the group consisting of Alzheimer disease, ischemic cerebrovascular accidents, Down syndrome, cerebral bleeding due to cerebral amyloid angiopathy, progressive supranuclear palsy, subacute sclerosing panencephalitic parkinsonism, postencephalitic parkinsonism, pugilistic encephalitis, Guam parkinsonism-dementia complex, Lewy body disease, Pick's disease, corticobasal degeneration and frontotemporal dementia, vascular dementia, acute stroke and traumatic injuries, brain and spinal cord trauma, peripheral neuropathies, retinopathies and glaucoma, non-insulin dependent diabetes (such as diabetes type II), and obesity, manic depressive illness, schizophrenia, alopecia, cancers such as breast cancer, non-small cell lung carcinoma, thyroid cancer, T or B-cell leukemia and several virus-induced tumors; and the aforementioned medicament in the form of pharmaceutical composition containing the above substance as an active ingredient together with one or more pharmaceutical additives.

The present invention further provides an inhibitor of tau protein kinase 1 comprising as an active ingredient a substance selected from the group consisting of the 3-substituted-4-pyrimidone derivatives of formula (I) and the salts thereof, and the solvates thereof and the hydrates thereof.

According to further aspects of the present invention, there are provided a method for preventive and/or therapeutic treatment of diseases caused by tau protein kinase 1 hyperactivity, which comprises the step of administering to a patient a preventively and/or therapeutically effective amount of a substance selected from the group consisting of the 3-substituted-4-pyrimidone derivatives of formula (I) and the physiologically acceptable salts thereof, and the solvates thereof and the hydrates thereof, and a use of a substance selected from the group consisting of the 3-substituted-4-pyrimidone derivatives of formula (I) and the physiologically acceptable salts thereof, and the solvates thereof and the hydrates thereof for the manufacture of the aforementioned medicament.

BEST MODE FOR CARRYING OUT THE INVENTION

In the present specification, each group has the following meanings.

The alkyl group used herein may be either linear or branched.

The $C_1$-$C_{12}$ alkyl group represented by R may be, for example, methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, or a linear or branched heptyl group, octyl group, nonyl group, decyl group, undecyl group or dodecyl group. Particularly preferred R is methyl group.

In the specification, when a functional group is defined as "which may be substituted" or "optionally substituted", the number of substituents as well as their types and substituting positions are not particularly limited, and when two or more substituents are present, they may be the same or different.

When the $C_1$-$C_{12}$ alkyl group represented by R has one or more substituents, the alkyl group may have one or more substituents selected from, for example, the groups consisting of a $C_3$-$C_8$ cycloalkyl group such as cyclopropyl group, cyclobutyl group, cyclopentyl group, cyclohexyl group, cycloheptyl group, cyclooctyl group; a $C_1$-$C_5$ alkoxy group such as methoxy group, ethoxy group, propoxy group, isopropoxy group, butoxy group, isobutoxy group, tert-butoxy group; $C_1$-$C_8$ alkylamino group or $C_2$-$C_6$ dialkylamino group; a $C_6$-$C_{10}$ aryl group such as phenyl group, 1-naphthyl group, and 2-naphthyl group.

The $C_1$-$C_8$ alkyl group may be, for example, methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, or a linear or branched heptyl group or octyl group.

The $C_1$-$C_4$ alkyl group may be, for example, methyl group, ethyl group, n-propyl group, isopropyl group, n-butyl group, isobutyl group, sec-butyl group or tert-butyl group.

The $C_3$-$C_8$ cycloalkyl group may be, for example, cyclopropyl group, cyclobutyl group, cyclopentyl group, cyclohexyl group, cycloheptyl group or cyclooctyl group.

The optionally partially hydrogenated $C_6$-$C_{10}$ aryl ring may be, for example a benzene ring, a naphthalene ring, an indan ring or a 1,2,3,4-tetrahydronaphthalene ring.

The heterocyclic ring having 1 to 4 hetero atoms selected from the group consisting of oxygen atom, sulfur atom, and nitrogen atom, and having 5 to 10 ring-constituting atoms in total may be, for example, furan ring, dihydrofuran ring, tetrahydrofuran ring, pyran ring, dihydropyran ring, tetrahydropyran ring, benzofuran ring, dihydrobenzofuran, isobenzofuran ring, benzodioxol ring, chromene ring, chroman ring, isochroman ring, thiophene ring, benzothiophene ring, pyrrole ring, pyrroline ring, pyrrolidine ring, 2-oxopyrrolidine ring, imidazole ring, imidazoline ring, imidazolidine ring, pyrazole ring, pyrazoline ring, pyrazolidine ring, triazole ring, tetrazole ring, pyridine ring, pyridine oxide ring, piperidine ring, 4-oxopiperidine ring, pyrazine ring, piperazine ring, homopiperazine ring, pyrimidine ring, pyridazine ring, indole ring, indoline ring, isoindole ring, isoindoline ring, indazole ring, benzimidazole ring, benzotriazole ring, tetrahydroisoquinoline ring, benzothiazolinone ring, benzoxazolinone ring, purine ring, quinolizine ring, quinoline ring, phthalazine ring, naphthyridine ring, quinoxaline ring, quinazoline ring, cinnoline ring, pteridine ring, oxazole ring, oxazolidine ring, isoxazole ring, isoxazolidine ring, oxadiazole ring, thiazole ring, benzothiazole ring, thiazylidine ring, isothiazole ring, isothiazolidine ring, benzodioxole ring, dioxane ring, benzodioxane ring, dithian ring, morpholine ring, thiomorpholine ring, or phthalimide ring.

The aralkyl group may be, for example, benzyl group, 2-phenylethyl group, 3-phenylpropyl group or 4-phenylbutyl group.

The $C_1$-$C_4$ alkylene group may be, for example, methylene, ethylene, trimethylene or tetramethylene.

The 4 to 7 membered heterocyclic ring which may further contain 1 to 4 groups may be, for example, pyrrolidine, piperidine, morpholine, thiomorpholine, piperazine, homopiperazine, 2-oxopyrrolidine, pyrrole, imidazoline, imidazole, pyrazole, pyrroline, pyrrolidine, imidazolidine, imidazolone, succinimide or glutarimide.

The $C_6$-$C_{10}$ aryl ring may be, for example, a benzene ring or a naphthalene ring, and the aryl group or the $C_6$-$C_{10}$ aryl group may be, for example, a phenyl group or naphthyl group.

When the ring represented by X or $X^1$ has one or more substituents, the ring may have one or more substituents selected from the group consisting of a $C_1$-$C_5$ alkyl group such as methyl group, ethyl group, propyl group, isopropyl group, butyl group, isobutyl group, sec-butyl group, tert-butyl group, pentyl group, isopentyl group, neopentyl group, 1,1-dimethylpropyl group; $C_3$-$C_6$ cycloalkyl group such as cyclopropyl group, cyclobutyl group, cyclopentyl group, cyclohexyl group; a $C_3$-$C_6$ cycloalkyl-$C_1$-$C_4$ alkyl group such as cyclopropylmethyl, cyclopentylmethyl, cyclohexylmethyl; a $C_1$-$C_4$ hydroxyalkyl group such as hydroxymethyl, hydroxyethyl, hydroxypropyl; a halogen atom such as fluorine atom, chlorine atom, bromine atom, and iodine atom; a $C_1$-$C_5$ halogenated alkyl group such as trifluoromethyl group; hydroxyl group; cyano group; nitro group; formyl group; a benzene ring which may be substituted; a naphthalene ring which may be substituted; an optionally substituted heterocyclic ring having 1 to 4 hetero atoms selected from the group consisting of oxygen atom, sulfur atom and nitrogen atom, and having 5 to 10 ring-constituting atoms in total (same as the above); an amino group; an N—$C_3$-$C_6$ cycloalkyl-N—$C_1$-$C_4$ alkylaminoalkyl group wherein said $C_1$-$C_4$ alkyl may be substituted by hydroxy group or $C_1$-$C_4$ alkoxy group such as N-cyclopropyl-N-methylaminomethyl group, N-cyclohexyl-N-methylaminomethyl group; a $C_1$-$C_6$ monoalkylaminomethyl group such as methylaminomethyl group, ethylaminomethyl group, propylaminomethyl group, isoproylaminomethyl group, butylaminomethyl group, isobutylaminomethyl group, tert-butylaminomethyl group, pentylaminomethyl group, isopentylaminomethyl group; a $C_2$-$C_{10}$ dialkylaminomethyl group such as dimethylaminomethyl group, diethylaminomethyl group, ethylmethylaminomethyl group, methylpropylaminomethyl group; pyrrolidinylmethyl group; piperidinylmethyl group; morpholinomethyl group; piperazinylmethyl group; pyrrolylmethyl group; imidazolylmethyl group; pyrazolylmethyl group; triazolylmethyl group; and a group of the formula -E-Rf wherein E represents O, S, SO, $SO_2$, CO or $N(R^4)$ and Rf represents a $C_1$-$C_5$ alkyl group (same as the above), a $C_4$-$C_7$ cycloalkyl group (same as the above), a $C_4$-$C_7$ cycloalkylalkl group (same as the above), a $C_1$-$C_5$ hydroxyalkyl group (same as the above), a benzene ring which may be substituted, a naphthalene ring which may be substituted, an optionally substituted heterocyclic ring having 1 to 4 hetero atoms selected from the group consisting of oxygen atom, sulfur atom and nitrogen atom, and having 5 to 10 ring-constituting atoms in total (same as the above), an N—$C_3$-$C_6$ cycloalkyl-N—$C_1$-$C_4$ alkylaminoalkyl group (same as the above), a $C_1$-$C_5$ monoalkylaminoalkyl group (same as the above), $C_2$-$C_{10}$ dialkylaminoalkyl group (same as the above), pyrrolidinylmethyl group, piperidinylmethyl group, morpholinomethyl group, piperazinylmethyl group, pyrrolylmethyl group, imidazolylmethyl group, pyrazolylmethyl group or triazolylmethyl group, $C_1$-$C_8$ alkylcarbonyl group which may be substituted,
$C_3$-$C_8$ cycloalkylcarbonyl group which may be substituted,
aralkycarbonyl group which may be substituted,
$C_6$-$C_{10}$ arylcarbonyl group which may be substituted,
$C_1$-$C_8$ alkysulfonyl group which may be substituted,
$C_3$-$C_8$ cycloalkylsulfonyl group which may be substituted,
aralkysulfonyl group which may be substituted,
$C_6$-$C_{10}$ arylsulfonyl group which may be substituted,
$C_1$-$C_8$ alkyloxycarbonyl group which may be substituted,
$C_3$-$C_8$ cycloalkyloxycarbonyl group which may be substituted,
aralkyoxycarbonyl group which may be substituted,
$C_6$-$C_{10}$ aryloxycarbonyl group which may be substituted,
aminocarbonyl,
N—$C_1$-$C_8$ alkylaminocarbonyl group which may be substituted, N,N'—$C_1$-$C_8$ dialkylaminocarbonyl group which may be substituted,
N—$C_1$-$C_8$ alkyl-N'—$C_3$-$C_8$ cycloalkylaminocarbonyl group which may be substituted,
N—$C_1$-$C_8$ alkyl-N'-aralkylaminocarbonyl group which may be substituted,
N—$C_1$-$C_8$ alkyl-N'—$C_6$-$C_{10}$ arylaminocarbonyl group which may be substituted,
$C_3$-$C_8$ cycloalkylaminocarbonyl group which may be substituted,
N,N'—$C_3$-$C_8$ dicycloalkylaminoycarbonyl group which may be substituted,
N—$C_3$-$C_8$ cycloalkyl-N'-aralkylaminocarbonyl group which may be substituted,
N—$C_3$-$C_8$ cycloalkyl-N'—$C_6$-$C_{10}$ arylaminocarbonyl group which may be substituted,
aralkylaminocarbonyl group which may be substituted,
N,N'-diaralkylaminocarbonyl group which may be substituted,
N-aralkyl-N'—$C_6$-$C_{10}$ arylaminocarbonyl group which may be substituted,
$C_6$-$C_{10}$ arylaminocarbonyl group which may be substituted,
N,N'—$C_6$-$C_{10}$ diarylaminocarbonyl group which may be substituted,
and $R^4$ represents a hydrogen atom, a $C_1$-$C_4$ alkyl group which may be substituted,
an aralkyl group which may be substituted, $C_3$-$C_8$ cycloalkyl group which may be substituted or an aryl group which may be substituted,
$C_1$-$C_8$ alkylcarbonyl group which may be substituted,
$C_3$-$C_8$ cycloalkylcarbonyl group which may be substituted,
aralkycarbonyl group which may be substituted,
$C_6$-$C_{10}$ arylcarbonyl group which may be substituted,
$C_1$-$C_8$ alkysulfonyl group which may be substituted,
$C_3$-$C_8$ cycloalkylsulfonyl group which may be substituted,
aralkysulfonyl group which may be substituted,
$C_6$-$C_{10}$ arylsulfonyl group which may be substituted,
$C_1$-$C_8$ alkyloxycarbonyl group which may be substituted,
$C_3$-$C_8$ cycloalkyloxycarbonyl group which may be substituted,
aralkyoxycarbonyl group which may be substituted,
$C_6$-$C_{10}$ aryloxycarbonyl group which may be substituted,
aminocarbonyl,
N—$C_1$-$C_8$ alkylaminocarbonyl group which may be substituted,
N,N'—$C_1$-$C_8$ dialkylaminocarbonyl group which may be substituted,
N—$C_1$-$C_8$ alkyl-N'—$C_3$-$C_8$ cycloalkylaminocarbonyl group which may be substituted,
N—$C_1$-$C_8$ alkyl-N'-aralkylaminocarbonyl group which may be substituted,
N—$C_1$-$C_8$ alkyl-N'—$C_6$-$C_{10}$ arylaminocarbonyl group which may be substituted,
$C_3$-$C_8$ cycloalkylaminocarbonyl group which may be substituted,
N,N'—$C_3$-$C_8$ dicycloalkylaminoycarbonyl group which may be substituted,
N—$C_3$-$C_8$ cycloalkyl-N'-aralkylaminocarbonyl group which may be substituted,
N—$C_3$-$C_8$ cycloalkyl-N'—$C_6$-$C_{10}$ arylaminocarbonyl group which may be substituted,
aralkylaminocarbonyl group which may be substituted,
N,N'-diaralkylaminocarbonyl group which may be substituted,
N-aralkyl-N'—$C_6$-$C_{10}$ arylaminocarbonyl group which may be substituted,
$C_6$-$C_{10}$ arylaminocarbonyl group which may be substituted,
N,N'—$C_6$-$C_{10}$ diarylaminocarbonyl group which may be substituted,
or an optionally substituted heterocyclic ring having 1 to 4 hetero atoms selected from the group consisting of oxygen atom, sulfur atom, and nitrogen atom, and having 5 to 10 ring-constituting atoms in total.

When the $C_6$-$C_{10}$ aryl ring represented by $Y^1$ has one or more substituents, the ring may be substituted by one or more substituents selected from the groups consisting of halogen atoms, a $C_1$-$C_5$ alkyl group, a $C_3$-$C_6$ cycloalkyl group, a $C_3$-$C_6$ cycloalkyloxy group, a $C_1$-$C_5$ alkoxy group, a $C_4$-$C_7$ cycloalkylalkoxy, a $C_1$-$C_5$ alkylthio group, a $C_1$-$C_5$ alkylsulfonyl group, a $C_1$-$C_5$ halogenated alkyl, and a benzene ring.

When the ring represented by X, $X^1$ or $Y^1$ has one or more substituents, the substituent may further have one or more substituents selected from the group consisting of a $C_1$-$C_5$ alkyl group such as methyl group, ethyl group, propyl group, isopropyl group, butyl group, isobutyl group, sec-butyl group, tert-butyl group, pentyl group, isopentyl group, neopentyl group, 1,1-dimethylpropyl group; $C_3$-$C_6$ cycloalkyl group such as cyclopropyl group, cyclobutyl group, cyclopentyl group, cyclohexyl group; a $C_3$-$C_6$ cycloalkyloxy group such as cyclopropyloxy group, cyclobutyloxy group, cyclopentyloxy group, cyclohexyloxy group; $C_1$-$C_4$ hydroxyalkyl group such as hydroxymethyl group, hydroxyethyl group, hydroxypropyl group, hydroxybutyl group; a $C_1$-$C_5$ alkoxy group such as methoxy group, ethoxy group, propoxy group, isopropoxy group, butoxy group, isobutoxy group, tert-butoxy group, pentyloxy group, and isopentyloxy group; a $C_4$-$C_7$ cycloalkylalkoxy group such as cyclopropylmethoxy group, cyclopentylmethoxy group; a $C_1$-$C_5$ alkylthio group such as methylthio group, ethylthio group, propylthio group, butylthio group, and pentylthio group; a $C_1$-$C_5$ alkylsulfonyl group such as methanesulfonyl group, ethanesulfonyl group, propanesulfonyl group, butanesulfonyl group, and pentanesulfonyl group; a halogen atom such as fluorine atom, chlorine atom, bromine atom, and iodine atom; a $C_1$-$C_5$ halogenated alkyl group such as trifluoromethyl group; a $C_1$-$C_5$ halogenated alkoxy group such as trifluoromethoxy group, 2,2,2-trifluoroethoxy group; hydroxyl group; cyano group; nitro group; formyl group; a $C_2$-$C_6$ alkylcarbonyl group such as acetyl group, propionyl group, butyryl group, and valeryl group; amino group; a $C_1$-$C_5$ monoalkylamino group such as methylamino group, ethylamino group, propylamino group, isopropylamino group, butylamino group, isobutylamino group, tert-butylamino group, pentylamino group, and isopentylamino group; a $C_2$-$C_{10}$ dialkylamino group such as dimethylamino group, ethylmethylamino group, diethylamino group, methylpropylamino group, and diisopropylamino group; a cyclic amino group such as pyrrolidinyl group, piperidino group, morpholino group; a $C_2$-$C_{10}$ monoalkylaminomethyl group such as methylaminomethyl group, ethylaminomethyl group, propylaminomethyl group, isoproylaminomethyl group, butylaminomethyl group, isobutylaminomethyl group, tert-butylaminomethyl group, pentylaminomethyl group, isopentylaminomethyl; a $C_3$-$C_{11}$ dialkylaminomethyl group such as dimethylaminomethyl group, diethylaminomethyl group, ethylmethylaminomethyl group, methylpropylaminomethyl group; a phenyl group; an aralkyloxy group such as benzyloxy, 2-phenylethyloxy, 3-phenylpropyloxy; an aralkyloxycarbonyl group such as benzyloxycarbonyl, 2-phenylehoxycarbonyl; an $C_2$-$C_4$ alkanoyloxy-$C_1$-$C_4$ alkyl group such as acetyloxymethyl, 2-acetyloxyethyl, 2-propionyloxyethyl; an alkanoylamino group such as acetylamino, propionylamino, butyrylamino; N—$C_1$-$C_4$ alkyl-N-alkanoylamino group such as N-methyl-N-acetylamino, N-ethyl-N-acetylamino, N-methyl-N-propionylamino, N-methyl-N-butyrylamino; a heterocyclic ring amino group such as pyridylamino, pyrimidinylamino, thienylamino, furylamino; N—$C_1$-$C_4$ alkyl-N-heterocyclic ring amino group such as N-methyl-N-pyridylamino, N-methyl-N-pyrimidinylamino, N-methyl-N-thienylamino, N-methyl-N-furylamino; a diheterocyclic ring amino group such as dipyridylamino, dipyrimidinylamino, dithienylamino, difurylamino, and the like.

R may preferably be a $C_1$-$C_3$ alkyl group, more preferably a methyl group or an ethyl group. The substituent of the alkyl group may preferably be a $C_3$-$C_8$ alkyl group.

X may preferably be a benzene ring which may be substituted, a benzyl group which may be substituted, a naphthyl group which may be substituted, a benzofuran ring which may be substituted, a dihydrobenzofuran ring which may be substituted, a benzoxazole ring which may be substituted, a benzisoxazole ring which may be substituted, a benzothiophene ring which may be substituted, a benzothiazole ring which may be substituted, a benzisothiazole ring which may be substituted, and a benzopyrazole ring which may be substituted; more preferably a benzene ring which may be substituted, a benzyl group which may be substituted. Substituent of X may preferably be selected from the group consisting of a halogen atom, a $C_1$-$C_4$ alkyl group, a $C_1$-$C_4$ alkoxy group, a hydroxy group, a nitro group, a cyano group, a perhalogenated $C_1$-$C_4$ alkyl group, a carboxyl group, a $C_1$-$C_4$ alkoxycarbonyl group, a $C_1$-$C_4$ alkylthio group, a $C_1$-$C_4$ alkoxysulfonyl group, amino group which may be substituted by a $C_1$-$C_4$ alkyl group, a benzene ring which may be substituted, and a cyclic amino group which may be substituted.

The compounds represented by the aforementioned formula (I) may form a salt. Examples of the salt include, when an acidic group exists, salts of alkali metals and alkaline earth metals such as lithium, sodium, potassium, magnesium, and calcium; salts of ammonia and amines such as methylamine, dimethylamine, trimethylamine, dicyclohexylamine, tris(hydroxymethyl)aminomethane, N,N-bis(hydroxyethyl)piperazine, 2-amino-2-methyl-1-propanol, ethanolamine, N-methylglucamine, and L-glucamine; or salts with basic amino acids such as lysine, δ-hydroxylysine, and arginine. When a basic group exists, examples include salts with mineral acids such as hydrochloric acid, hydrobromic acid, sulfuric acid, nitric acid, phosphoric acid; salts with organic acids such as methanesulfonic acid, benzenesulfonic acid, p-toluenesulfonic acid, acetic acid, propionic acid, tartaric acid, fumaric acid, maleic acid, malic acid, oxalic acid, succinic acid, citric acid, benzoic acid, mandelic acid, cinnamic acid, lactic acid, glycolic acid, glucuronic acid, ascorbic acid, nicotinic acid, and salicylic acid; or salts with acidic amino acids such as aspartic acid, and glutamic acid.

In addition to the 3-substituted-4-pyrimidone derivatives represented by the aforementioned formula (I) and salts thereof, their solvates and hydrates also fall within the scope of the present invention. The 3-substituted-4-pyrimidone derivatives represented by the aforementioned formula (I) may have one or more asymmetric carbon atoms. As for the stereochemistry of such asymmetric carbon atoms, they may independently be in either (R) and (S) configuration, and the pyrimidone derivative may exist as stereoisomers such as optical isomers, or diastereoisomers. Any stereoisomers in a pure form, any mixtures of stereoisomers, racemates and the like fall within the scope of the present invention.

Preferred compounds of the present invention are represented by formula (II):

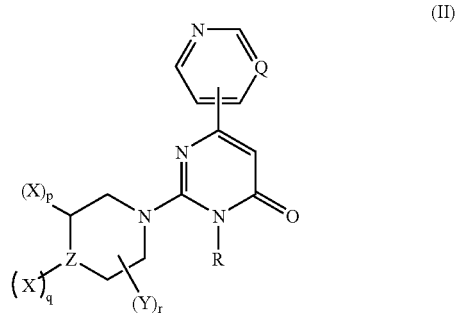

wherein Q, R, X, Y are the same as those defined above; p is 0 or 1; q is 0 or 1; r is an integer of 0 to 6; p+q is 1 or 2; and Z represents N or $CZ^1$ wherein $Z^1$ represents hydrogen atom or Y.

Examples of more preferred classes of compounds represented by formula (II) include:

(1) those wherein R represents a $C_1$-$C_3$ alkyl group which may be substituted by a $C_3$-$C_8$ cycloalkyl group;

(2) the compounds of the above (1) wherein R is methyl group or ethyl group; Y is in 3-, 4- or 5-position of the piperazine ring or the piperidine ring; p+q is 1; and r is an integer of 0 to 3;

(3) the compounds of the above (2) wherein X is a $C_1$-$C_8$ alkyl group which may be substituted or a $C_6$-$C_{10}$ aryl ring which may be substituted; Y is a $C_1$-$C_6$ alkyl group which may be substituted; p is 1; q is 0; r is an integer of 0 to 3; and Z is N or CH;

(4) the compounds of the above (3) wherein X is a benzene ring which may be substituted, a benzyl group which may be substituted; Y is a methyl group which may be substituted; Z is N and r is 0 or 1;

(5) the compounds of the above (2) wherein X is a benzene ring which may be substituted, a benzyl group which may be substituted, a benzoyl group which may be substituted, or a benzisothiazol ring which may be substituted; Y is a methyl group which may be substituted; Z is N and p is 0;

(6) the compounds of the above (2) wherein X is a $C_1$-$C_8$ alkyl group substituted by a benzene ring which may be substituted or a benzene ring which may be substituted;

Y is a hydroxy group, a cyano group, or $Y^1$—CO— wherein $Y^1$ is a $C_1$-$C_8$ alkyl group; Z is CH or C—Y and r is 0 or 1; and (7) the compounds of the above (6) wherein X is a benzyl group which may be substituted or a benzene ring which may be substituted; Y is a hydroxy group, a cyano group, or an acetyl group; Z is CH or C—Y and r is 0 or 1.

Examples of particularly preferred classes of compounds represented by formula (II) include:

(1) those wherein R is methyl group, Y is $CH_3O$—CO— group or $CH_3CH_2O$—CO— group, Z is N, p is, 0, q is 1, r is 0 or 1 and Y is in 3-position of the piperazine ring;

(2) those wherein R is methyl group, Y is methyl group, benzyl group or acetyl group, Z is N, p is 1, q is 0, r is 0 or 1 and Y is in 4-position of the piperazine ring;

(3) those wherein R is methyl group, Y is methyl group, Z is N, p is 1, q is 0, r is 1 to 3 and Y is in 3-, 4-, or 5-position of the piperazine ring;

(4) those wherein R is methyl group, Y is hydroxyl group or cyano group, Z is CH, p is 1, q is 0, r is 0 or 1 and X and Y are attached on the same carbon atom;

(5) those wherein R is methyl group, Y is hydroxyl group, cyano group or acetyl group, Z is C—Y, p is 0, q is 1 and r is 1.

Examples of preferred compounds of the present invention are shown in the tables below. However, the scope of the present invention is not limited to the following compounds.

TABLE 1

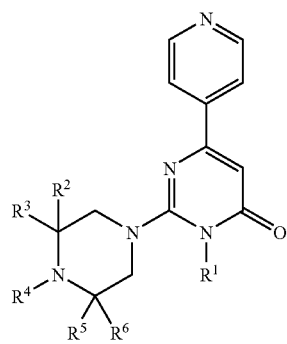

| No. | R1 | R2 | R3 | R4 | R5 | R6 |
|---|---|---|---|---|---|---|
| XA1 | CH3— | H | H | CH3— | H | H |
| XA2 | CH3— | H | H | CH3CH2— | H | H |
| XA3 | CH3— | H | H | n-propyl | H | H |
| XA4 | CH3— | H | H | isopropyl | H | H |
| XA5 | CH3— | H | H | n-butyl | H | H |
| XA6 | CH3— | H | H | isobutyl | H | H |
| XA7 | CH3— | H | H | sec-butyl | H | H |
| XA8 | CH3— | H | H | tert-butyl | H | H |
| XA9 | CH3— | H | H | n-pentyl | H | H |
| XA10 | CH3— | H | H | isopentyl | H | H |
| XA11 | CH3— | H | H | neopentyl | H | H |

-continued
| | | | | | | | |
|---|---|---|---|---|---|---|---|
| XA12 | CH3— | H | H | 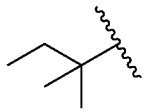 | | H | H |
| XA13 | CH3— | H | H | 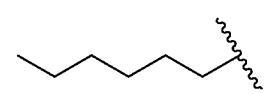 | | H | H |
| XA14 | CH3— | H | H | 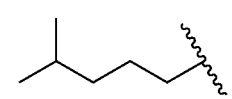 | | H | H |
| XA15 | CH3— | H | H | 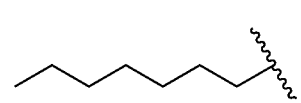 | | H | H |
| XA16 | CH3— | H | H | 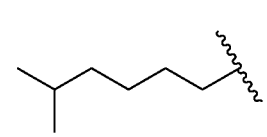 | | H | H |
| XA17 | CH3— | H | H | n-C8H17— | | H | H |
| XA18 | CH3— | H | H | 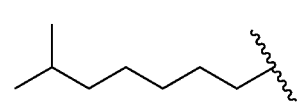 | | H | H |
| XA19 | CH3— | H | H | 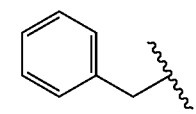 | | H | H |
| XA20 | CH3— | H | H | 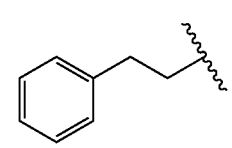 | | H | H |
| XA21 | CH3— | H | H | 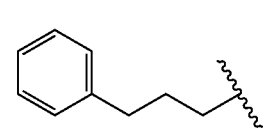 | | H | H |
| XA22 | CH3— | H | H | 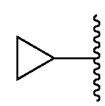 | | H | H |
| XA23 | CH3— | H | H | 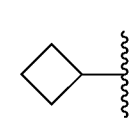 | | H | H |
| XA24 | CH3— | H | H | 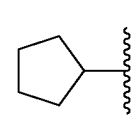 | | H | H |
| XA25 | CH3— | H | H | 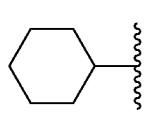 | | H | H |

-continued
| | | | | | | | |
|---|---|---|---|---|---|---|---|
| XA26 | CH3— | H | H | 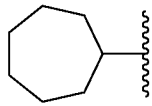 | H | H | |
| XA27 | CH3— | H | H | 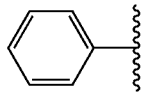 | H | H | |
| XA28 | CH3— | H | H | 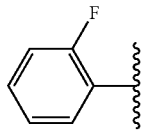 | H | H | |
| XA29 | CH3— | H | H | 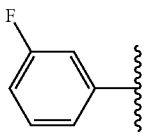 | H | H | |
| XA30 | CH3— | H | H | 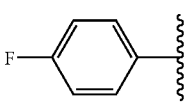 | H | H | |
| XA31 | CH3— | H | H | 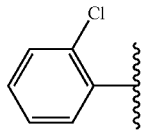 | H | H | |
| XA32 | CH3— | H | H | 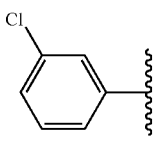 | H | H | |
| XA33 | CH3— | H | H | 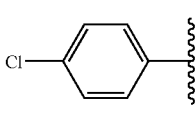 | H | H | |
| XA34 | CH3— | H | H | 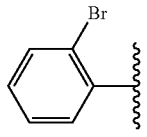 | H | H | |
| XA35 | CH3— | H | H | 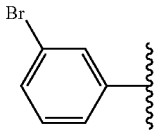 | H | H | |
| XA36 | CH3— | H | H | 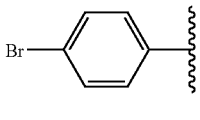 | H | H | |
| XA37 | CH3— | H | H | 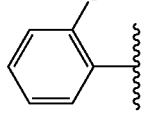 | H | H | |

-continued
| | | | | | | |
|---|---|---|---|---|---|---|
| XA38 | CH3— | H | H | 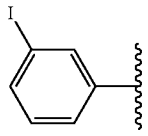 3-iodophenyl | H | H |
| XA39 | CH3— | H | H | 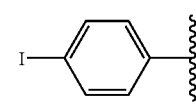 4-iodophenyl | H | H |
| XA40 | CH3— | H | H | 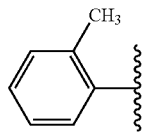 2-methylphenyl | H | H |
| XA41 | CH3— | H | H | 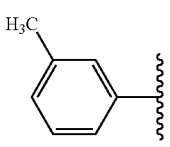 3-methylphenyl | H | H |
| XA42 | CH3— | H | H | 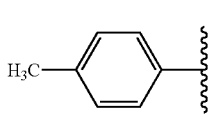 4-methylphenyl | H | H |
| XA43 | CH3— | H | H | 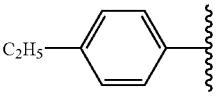 4-ethylphenyl | H | H |
| XA44 | CH3— | H | H | 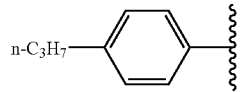 4-n-propylphenyl | H | H |
| XA45 | CH3— | H | H | 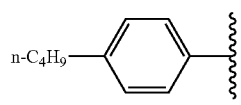 4-n-butylphenyl | H | H |
| XA46 | CH3— | H | H | 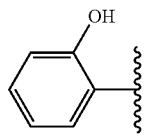 2-hydroxyphenyl | H | H |
| XA47 | CH3— | H | H | 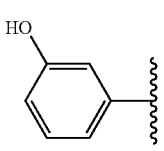 3-hydroxyphenyl | H | H |
| XA48 | CH3— | H | H | 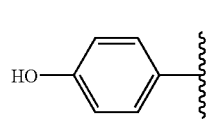 4-hydroxyphenyl | H | H |
| XA49 | CH3— | H | H | 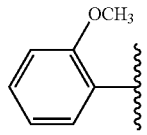 2-methoxyphenyl | H | H |

-continued
| | | | | | | | |
|---|---|---|---|---|---|---|---|
| XA50 | CH3— | H | H | 3-H3CO-C6H4- 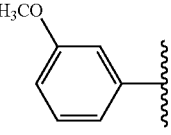 | H | H | |
| XA51 | CH3— | H | H | 4-H3CO-C6H4-  | H | H | |
| XA52 | CH3— | H | H | 4-C2H5O-C6H4- 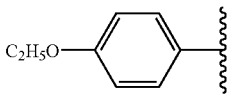 | H | H | |
| XA53 | CH3— | H | H | 4-n-C3H7O-C6H4- 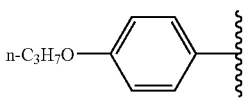 | H | H | |
| XA54 | CH3— | H | H | 4-n-C4H9O-C6H4-  | H | H | |
| XA55 | CH3— | H | H | 2-NO2-C6H4- 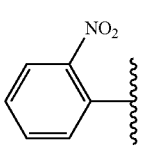 | H | H | |
| XA56 | CH3— | H | H | 3-O2N-C6H4- 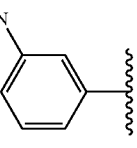 | H | H | |
| XA57 | CH3— | H | H | 4-O2N-C6H4- 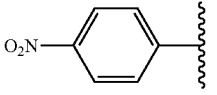 | H | H | |
| XA58 | CH3— | H | H | 2-CN-C6H4- 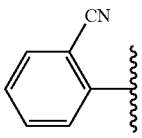 | H | H | |
| XA59 | CH3— | H | H | 3-NC-C6H4- 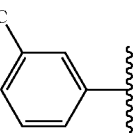 | H | H | |
| XA60 | CH3— | H | H | 4-NC-C6H4- 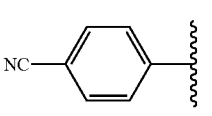 | H | H | |
| XA61 | CH3— | H | H | 2-CF3-C6H4- 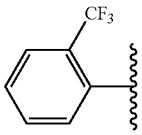 | H | H | |

-continued
| | | | | | | | |
|---|---|---|---|---|---|---|---|
| XA62 | CH3— | H | H | 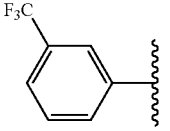 3-CF3-phenyl | H | H | |
| XA63 | CH3— | H | H | 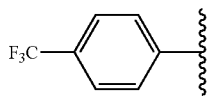 4-CF3-phenyl | H | H | |
| XA64 | CH3— | H | H | 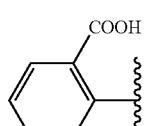 2-COOH-phenyl | H | H | |
| XA65 | CH3— | H | H | 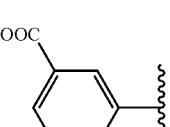 3-COOH-phenyl | H | H | |
| XA66 | CH3— | H | H | 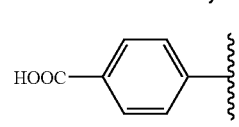 4-COOH-phenyl | H | H | |
| XA67 | CH3— | H | H | 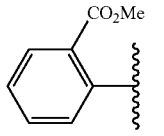 2-CO2Me-phenyl | H | H | |
| XA68 | CH3— | H | H |  3-CO2Me-phenyl | H | H | |
| XA69 | CH3— | H | H | 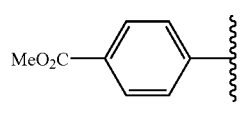 4-CO2Me-phenyl | H | H | |
| XA70 | CH3— | H | H | 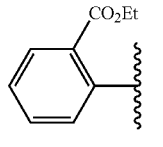 2-CO2Et-phenyl | H | H | |
| XA71 | CH3— | H | H | 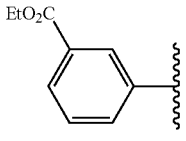 3-CO2Et-phenyl | H | H | |
| XA72 | CH3— | H | H | 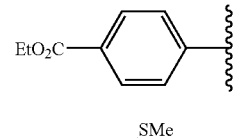 4-CO2Et-phenyl | H | H | |
| XA73 | CH3— | H | H | 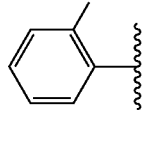 2-SMe-phenyl | H | H | |

-continued
| | | | | | | |
|---|---|---|---|---|---|---|
| XA74 | CH3— | H | H | 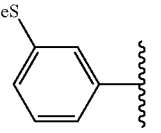 3-MeS-C6H4- | H | H |
| XA75 | CH3— | H | H | 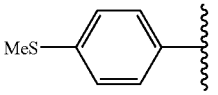 4-MeS-C6H4- | H | H |
| XA76 | CH3— | H | H | 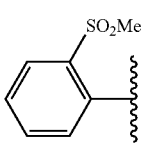 2-SO2Me-C6H4- | H | H |
| XA77 | CH3— | H | H | 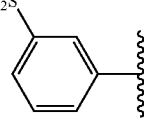 3-MeO2S-C6H4- | H | H |
| XA78 | CH3— | H | H | 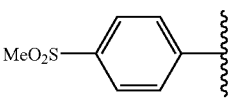 4-MeO2S-C6H4- | H | H |
| XA79 | CH3— | H | H | 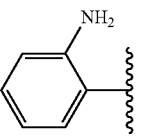 2-NH2-C6H4- | H | H |
| XA80 | CH3— | H | H | 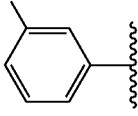 3-NH2-C6H4- | H | H |
| XA81 | CH3— | H | H | 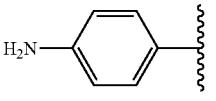 4-NH2-C6H4- | H | H |
| XA82 | CH3— | H | H | 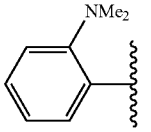 2-NMe2-C6H4- | H | H |
| XA83 | CH3— | H | H | 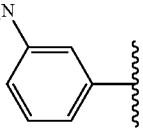 3-NMe2-C6H4- | H | H |
| XA84 | CH3— | H | H | 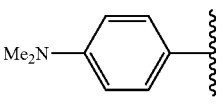 4-NMe2-C6H4- | H | H |

-continued

| | | | | | | |
|---|---|---|---|---|---|---|
| XA85 | CH3— | H | H | 1-naphthyl | H | H |
| XA86 | CH3— | H | H | 2-naphthyl | H | H |
| XA87 | CH3— | H | H | 1H-pyrrol-2-yl | H | H |
| XA88 | CH3— | H | H | 1H-pyrrol-3-yl | H | H |
| XA89 | CH3— | H | H | furan-2-yl | H | H |
| XA90 | CH3— | H | H | furan-3-yl | H | H |
| XA91 | CH3— | H | H | thiophen-2-yl | H | H |
| XA92 | CH3— | H | H | thiophen-3-yl | H | H |
| XA93 | CH3— | H | H | 1H-pyrazol-3-yl | H | H |
| XA94 | CH3— | H | H | 1H-pyrazol-4-yl | H | H |
| XA95 | CH3— | H | H | 1H-imidazol-4-yl | H | H |
| XA96 | CH3— | H | H | 1H-imidazol-2-yl | H | H |

-continued
| | | | | | | | |
|---|---|---|---|---|---|---|---|
| XA97 | CH3— | H | H | 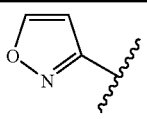 | | H | H |
| XA98 | CH3— | H | H | 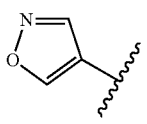 | | H | H |
| XA99 | CH3— | H | H | 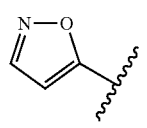 | | H | H |
| XA100 | CH3— | H | H | 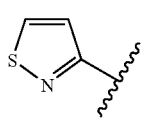 | | H | H |
| XA101 | CH3— | H | H | 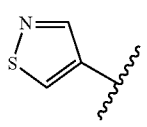 | | H | H |
| XA102 | CH3— | H | H | 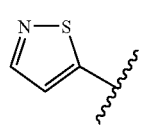 | | H | H |
| XA103 | CH3— | H | H | 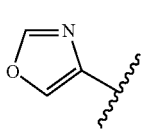 | | H | H |
| XA104 | CH3— | H | H | 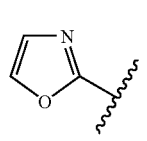 | | H | H |
| XA105 | CH3— | H | H | 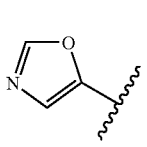 | | H | H |
| XA106 | CH3— | H | H | 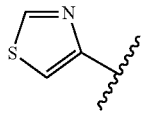 | | H | H |
| XA107 | CH3— | H | H |  | | H | H |
| XA108 | CH3— | H | H | 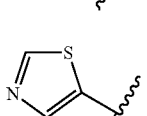 | | H | H |

-continued
| | | | | | | | |
|---|---|---|---|---|---|---|---|
| XA109 | CH3— | H | H | 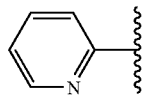 | H | H | |
| XA110 | CH3— | H | H | 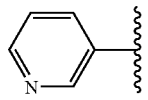 | H | H | |
| XA111 | CH3— | H | H | 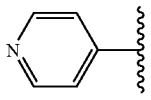 | H | H | |
| XA112 | CH3— | H | H | 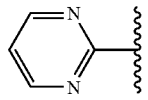 | H | H | |
| XA113 | CH3— | H | H | 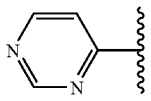 | H | H | |
| XA114 | CH3— | H | H | 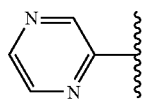 | H | H | |
| XA115 | CH3— | H | H | 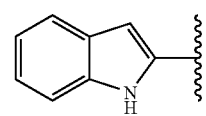 | H | H | |
| XA116 | CH3— | H | H | 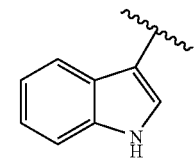 | H | H | |
| XA117 | CH3— | H | H | 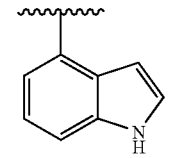 | H | H | |
| XA118 | CH3— | H | H | 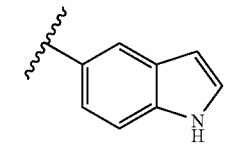 | H | H | |
| XA119 | CH3— | H | H | 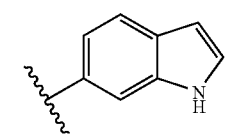 | H | H | |
| XA120 | CH3— | H | H | 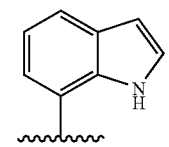 | H | H | |

-continued
| | | | | | | | |
|---|---|---|---|---|---|---|---|
| XA121 | CH3— | H | H | 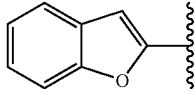 | H | H | |
| XA122 | CH3— | H | H | 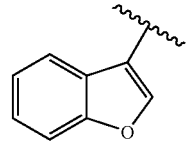 | H | H | |
| XA123 | CH3— | H | H | 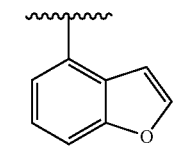 | H | H | |
| XA124 | CH3— | H | H | 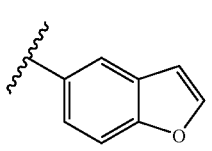 | H | H | |
| XA125 | CH3— | H | H | 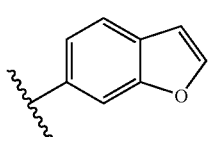 | H | H | |
| XA126 | CH3— | H | H | 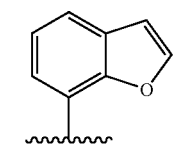 | H | H | |
| XA127 | CH3— | H | H | 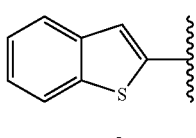 | H | H | |
| XA128 | CH3— | H | H | 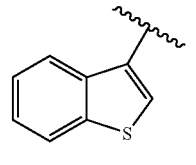 | H | H | |
| XA129 | CH3— | H | H | 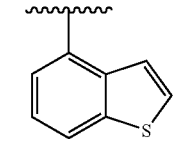 | H | H | |
| XA130 | CH3— | H | H | 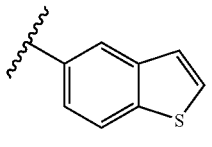 | H | H | |
| XA131 | CH3— | H | H | 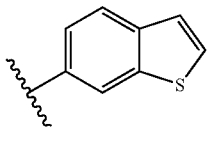 | H | H | |

-continued
| | | | | | | |
|---|---|---|---|---|---|---|
| XA132 | CH3— | H | H | 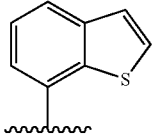 | H | H |
| XA133 | CH3— | H | H | 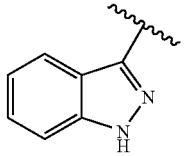 | H | H |
| XA134 | CH3— | H | H | 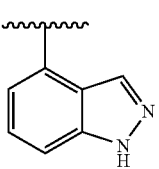 | H | H |
| XA135 | CH3— | H | H | 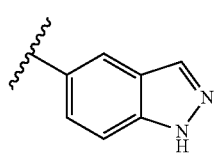 | H | H |
| XA136 | CH3— | H | H | 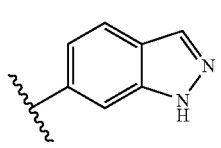 | H | H |
| XA137 | CH3— | H | H | 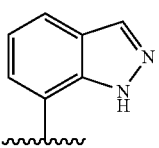 | H | H |
| XA138 | CH3— | H | H | 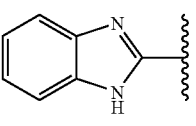 | H | H |
| XA139 | CH3— | H | H | 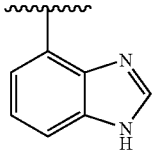 | H | H |
| XA140 | CH3— | H | H | 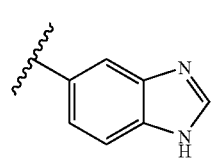 | H | H |
| XA141 | CH3— | H | H | 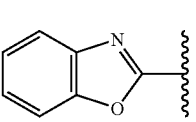 | H | H |

-continued
| | | | | | | | |
|---|---|---|---|---|---|---|---|
| XA142 | CH3— | H | H | 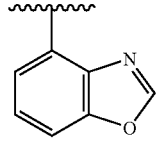 | H | H | |
| XA143 | CH3— | H | H | 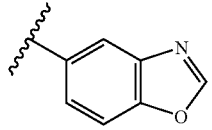 | H | H | |
| XA144 | CH3— | H | H | 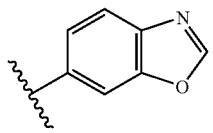 | H | H | |
| XA145 | CH3— | H | H | 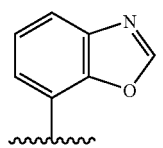 | H | H | |
| XA146 | CH3— | H | H | 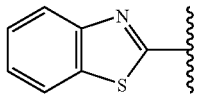 | H | H | |
| XA147 | CH3— | H | H | 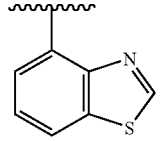 | H | H | |
| XA148 | CH3— | H | H | 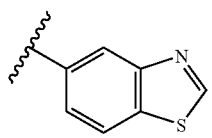 | H | H | |
| XA149 | CH3— | H | H | 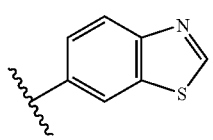 | H | H | |
| XA150 | CH3— | H | H | 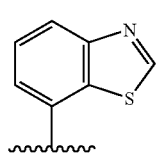 | H | H | |
| XA151 | CH3— | H | H | 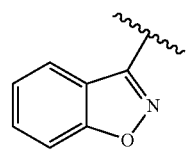 | H | H | |
| XA152 | CH3— | H | H | 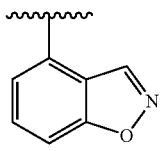 | H | H | |

-continued

| | | | | | | |
|---|---|---|---|---|---|---|
| XA153 | CH3— | H | H | 5-benzo[d]isoxazolyl (O-N, attached at 5) | H | H |
| XA154 | CH3— | H | H | 6-benzo[d]isoxazolyl | H | H |
| XA155 | CH3— | H | H | 7-benzo[c]isoxazolyl (N-O) | H | H |
| XA156 | CH3— | H | H | 3-benzo[d]isothiazolyl | H | H |
| XA157 | CH3— | H | H | 4-benzo[d]isothiazolyl | H | H |
| XA158 | CH3— | H | H | 5-benzo[d]isothiazolyl | H | H |
| XA159 | CH3— | H | H | 6-benzo[d]isothiazolyl | H | H |
| XA160 | CH3— | H | H | 7-benzo[c]isothiazolyl | H | H |
| XA161 | CH3— | H | H | benzoyl (C(=O)Ph) | H | H |
| XA162 | CH3— | H | H | 2-fluorobenzoyl | H | H |

-continued
| | | | | | | |
|---|---|---|---|---|---|---|
| XA163 | CH3— | H | H | 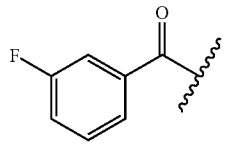 | H | H |
| XA164 | CH3— | H | H | 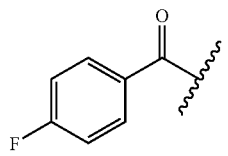 | H | H |
| XA165 | CH3— | H | H | 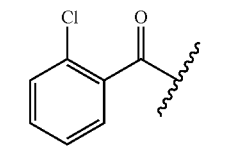 | H | H |
| XA166 | CH3— | H | H |  | H | H |
| XA167 | CH3— | H | H | 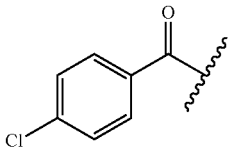 | H | H |
| XA168 | CH3— | H | H |  | H | H |
| XA169 | CH3— | H | H | 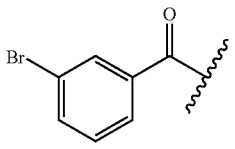 | H | H |
| XA170 | CH3— | H | H |  | H | H |
| XA171 | CH3— | H | H |  | H | H |
| XA172 | CH3— | H | H |  | H | H |

-continued
| | | | | | | |
|---|---|---|---|---|---|---|
| XA173 | CH3— | H | H | 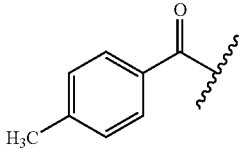 | H | H |
| XA174 | CH3— | H | H | 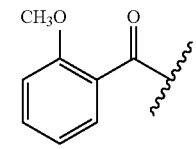 | H | H |
| XA175 | CH3— | H | H | 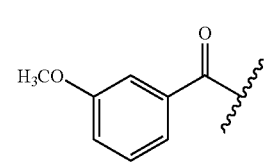 | H | H |
| XA176 | CH3— | H | H | 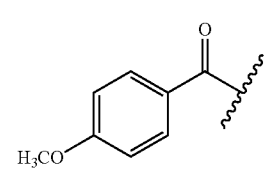 | H | H |
| XA177 | CH3— | H | H | 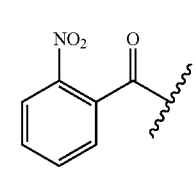 | H | H |
| XA178 | CH3— | H | H | 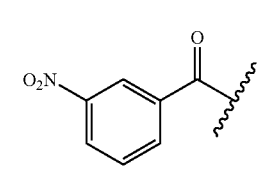 | H | H |
| XA179 | CH3— | H | H | 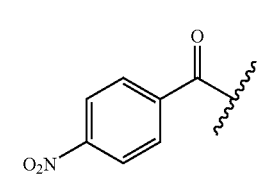 | H | H |
| XA180 | CH3— | H | H | 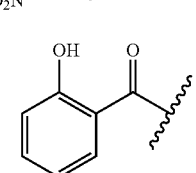 | H | H |
| XA181 | CH3— | H | H | 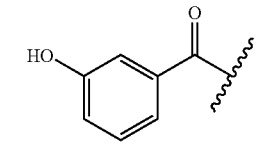 | H | H |
| XA182 | CH3— | H | H | 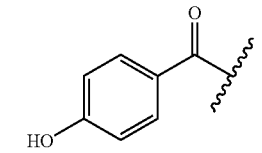 | H | H |

-continued
| | | | | | | |
|---|---|---|---|---|---|---|
| XA183 | CH3— | H | H | 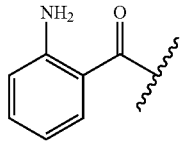 | H | H |
| XA184 | CH3— | H | H | 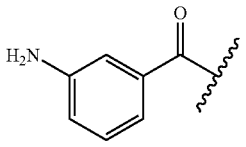 | H | H |
| XA185 | CH3— | H | H | 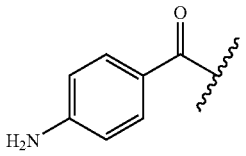 | H | H |
| XA186 | CH3— | H | H | 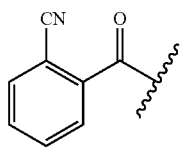 | H | H |
| XA187 | CH3— | H | H | 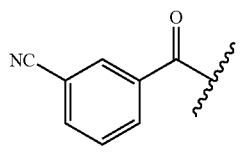 | H | H |
| XA188 | CH3— | H | H | 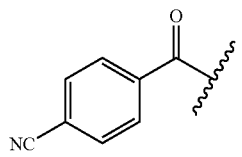 | H | H |
| XA189 | CH3— | H | H | 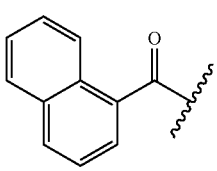 | H | H |
| XA190 | CH3— | H | H | 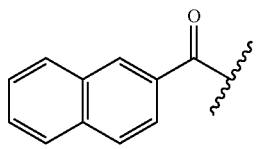 | H | H |
| XA191 | CH3— | H | H | 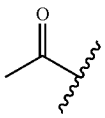 | H | H |
| XA192 | CH3— | H | H | 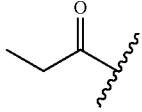 | H | H |

-continued
| | | | | | | |
|---|---|---|---|---|---|---|
| XA193 | CH3— | H | H | 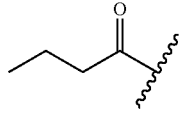 | H | H |
| XA194 | CH3— | H | H | 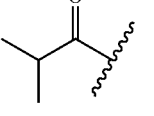 | H | H |
| XA195 | CH3— | H | H | 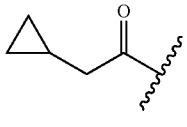 | H | H |
| XA196 | CH3— | H | H | 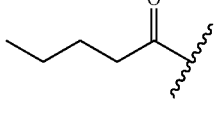 | H | H |
| XA197 | CH3— | H | H | 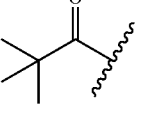 | H | H |
| XA198 | CH3— | H | H | 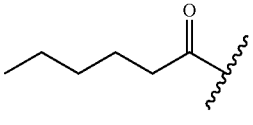 | H | H |
| XA199 | CH3— | H | H | 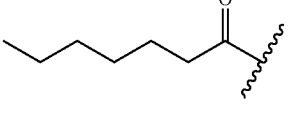 | H | H |
| XA200 | CH3— | H | H | 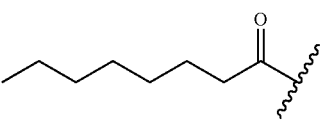 | H | H |
| XA201 | CH3— | H | H | 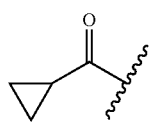 | H | H |
| XA202 | CH3— | H | H | 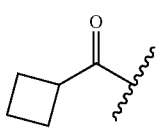 | H | H |
| XA203 | CH3— | H | H | 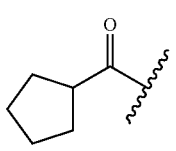 | H | H |
| XA204 | CH3— | H | H | 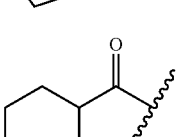 | H | H |

-continued
| | | | | | | |
|---|---|---|---|---|---|---|
| XA205 | CH3— | 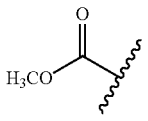 | H | H | H | H |
| XA206 | CH3— | 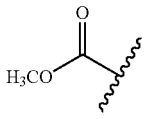 | H | CH3— | H | H |
| XA207 | CH3— | 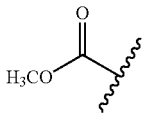 | H | CH3CH2— | H | H |
| XA208 | CH3— | 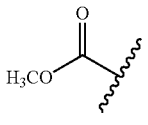 | H | 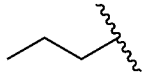 | H | H |
| XA209 | CH3— | 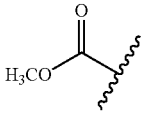 | H | 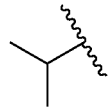 | H | H |
| XA210 | CH3— | 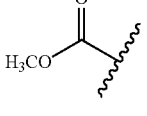 | H | 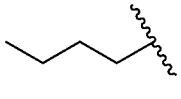 | H | H |
| XA211 | CH3— | 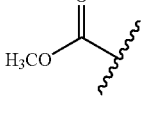 | H | 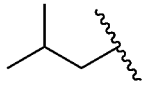 | H | H |
| XA212 | CH3— | 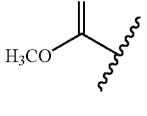 | H | 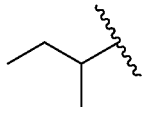 | H | H |
| XA213 | CH3— | 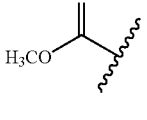 | H | 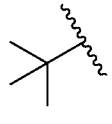 | H | H |
| XA214 | CH3— | 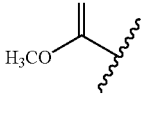 | H | 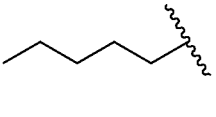 | H | H |
| XA215 | CH3— | 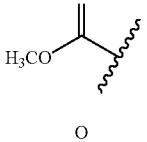 | H | 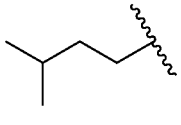 | H | H |
| XA216 | CH3— | 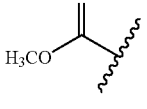 | H | 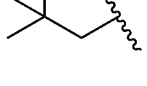 | H | H |

-continued
| | | | | | | |
|---|---|---|---|---|---|---|
| XA217 | CH3— | 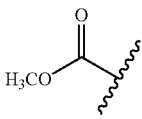 | H | 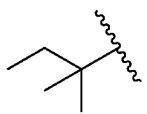 | H | H |
| XA218 | CH3— | 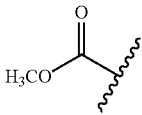 | H | 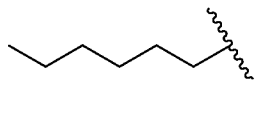 | H | H |
| XA219 | CH3— | 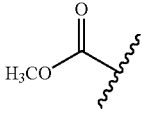 | H | 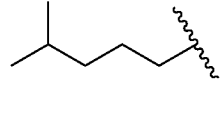 | H | H |
| XA220 | CH3— | 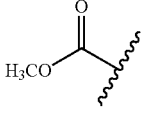 | H | 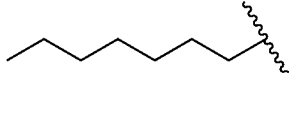 | H | H |
| XA221 | CH3— | 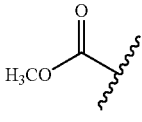 | H | 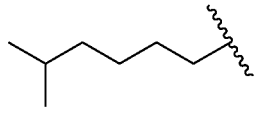 | H | H |
| XA222 | CH3— | 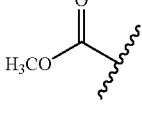 | H | n-C8H17— | H | H |
| XA223 | CH3— | 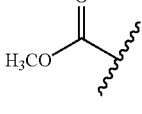 | H | 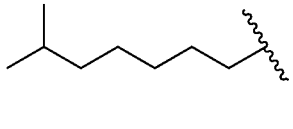 | H | H |
| XA224 | CH3— | 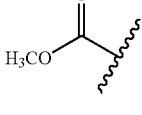 | H | 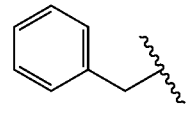 | H | H |
| XA225 | CH3— | 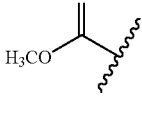 | H | 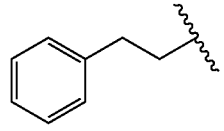 | H | H |
| XA226 | CH3— | 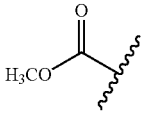 | H | 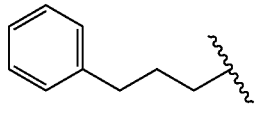 | H | H |
| XA227 | CH3— | 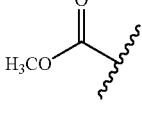 | H | 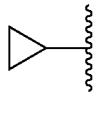 | H | H |
| XA228 | CH3— | 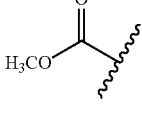 | H | 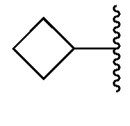 | H | H |

-continued
| | | | | | | |
|---|---|---|---|---|---|---|
| XA229 | CH3— | 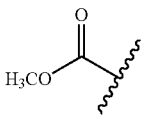 | H | 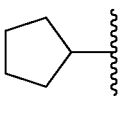 | H | H |
| XA230 | CH3— | 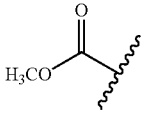 | H | 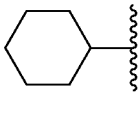 | H | H |
| XA231 | CH3— | 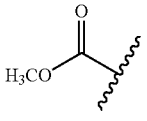 | H | 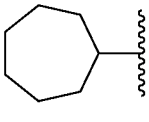 | H | H |
| XA232 | CH3— | 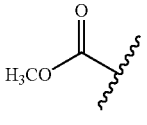 | H | 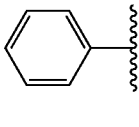 | H | H |
| XA233 | CH3— | 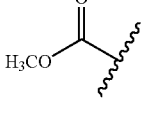 | H | 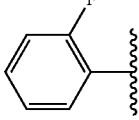 | H | H |
| XA234 | CH3— | 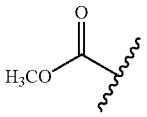 | H | 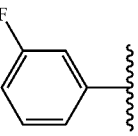 | H | H |
| XA235 | CH3— | 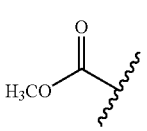 | H | 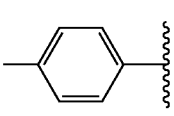 | H | H |
| XA236 | CH3— | 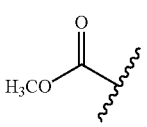 | H | 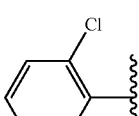 | H | H |
| XA237 | CH3— | 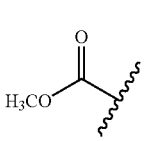 | H | 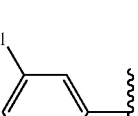 | H | H |
| XA238 | CH3— | 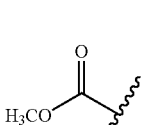 | H | 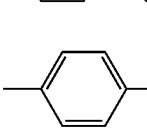 | H | H |
| XA239 | CH3— | 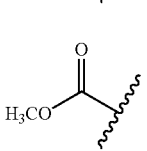 | H | 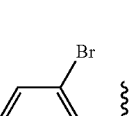 | H | H |

-continued
| | | | | | | |
|---|---|---|---|---|---|---|
| XA240 | CH3— | 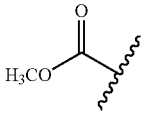 | H | 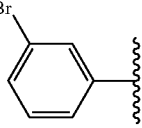 | H | H |
| XA241 | CH3— | 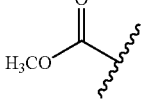 | H | 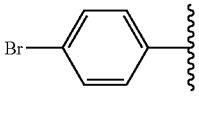 | H | H |
| XA242 | CH3— | 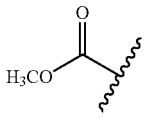 | H | 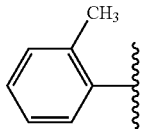 | H | H |
| XA243 | CH3— | 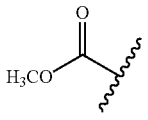 | H | 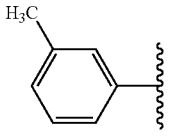 | H | H |
| XA244 | CH3— | 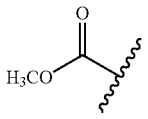 | H | 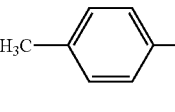 | H | H |
| XA245 | CH3— | 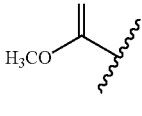 | H | 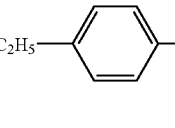 | H | H |
| XA246 | CH3— | 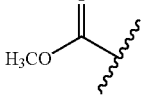 | H | 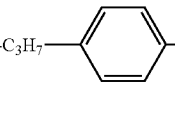 | H | H |
| XA247 | CH3— | 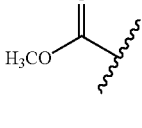 | H | 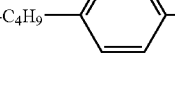 | H | H |
| XA248 | CH3— | 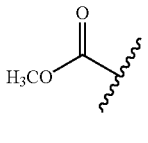 | H | 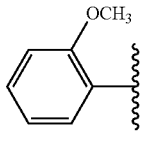 | H | H |
| XA249 | CH3— | 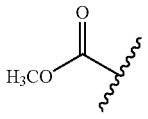 | H | 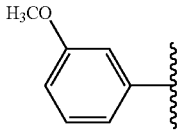 | H | H |
| XA250 | CH3— | 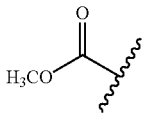 | H | 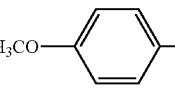 | H | H |

-continued
| | | | | | | |
|---|---|---|---|---|---|---|
| XA251 | CH3— | 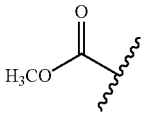 | H | 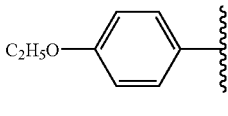 4-C2H5O-C6H4— | H | H |
| XA252 | CH3— | 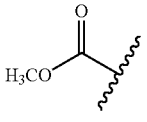 | H | 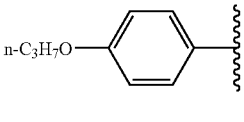 4-(n-C3H7O)-C6H4— | H | H |
| XA253 | CH3— | 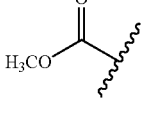 | H | 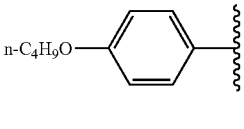 4-(n-C4H9O)-C6H4— | H | H |
| XA254 | CH3— | 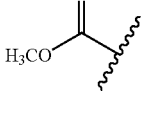 | H | 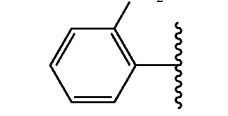 2-NO2-C6H4— | H | H |
| XA255 | CH3— | 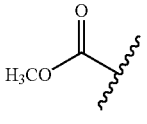 | H | 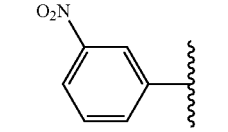 3-NO2-C6H4— | H | H |
| XA256 | CH3— | 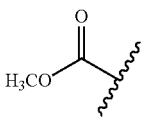 | H | 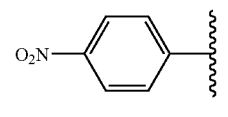 4-NO2-C6H4— | H | H |
| XA257 | CH3— | 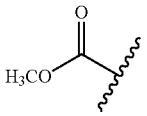 | H | 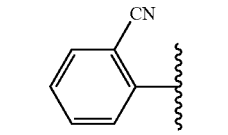 2-CN-C6H4— | H | H |
| XA258 | CH3— | 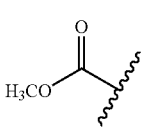 | H | 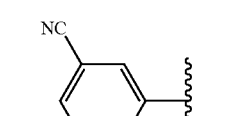 3-CN-C6H4— | H | H |
| XA259 | CH3— | 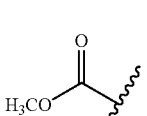 | H | 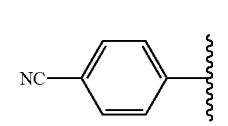 4-CN-C6H4— | H | H |
| XA260 | CH3— | 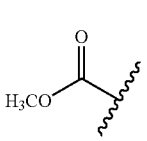 | H | 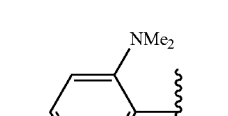 2-NMe2-C6H4— | H | H |
| XA261 | CH3— | 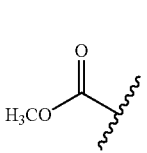 | H | 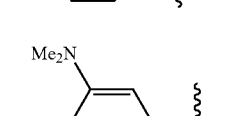 3-NMe2-C6H4— | H | H |

-continued
| | | | | | | |
|---|---|---|---|---|---|---|
| XA262 | CH3— | 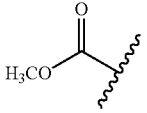 | H | 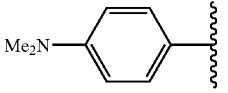 | H | H |
| XA263 | CH3— | 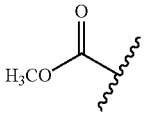 | H | 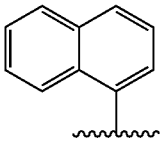 | H | H |
| XA264 | CH3— | 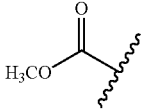 | H | 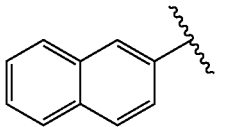 | H | H |
| XA265 | CH3— | 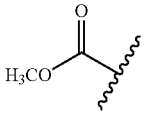 | H | 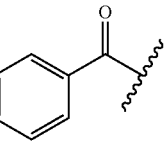 | H | H |
| XA266 | CH3— | 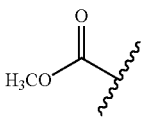 | H | 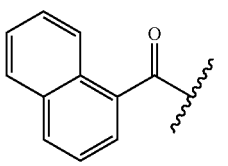 | H | H |
| XA267 | CH3— | 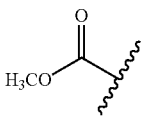 | H | 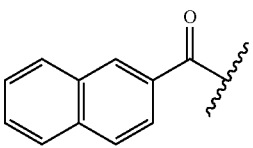 | H | H |
| XA268 | CH3— | 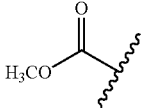 | H | 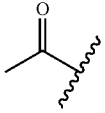 | H | H |
| XA269 | CH3— | 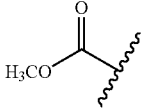 | H | 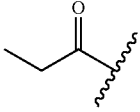 | H | H |
| XA270 | CH3— | 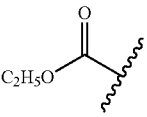 | H | H | H | H |
| XA271 | CH3— | 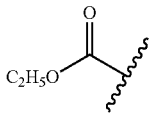 | H | CH3— | H | H |
| XA272 | CH3— | 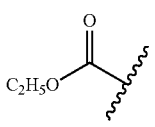 | H | CH3CH2— | H | H |

-continued
| | | | | | | |
|---|---|---|---|---|---|---|
| XA273 | CH3— | 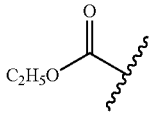 | H | 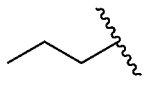 | H | H |
| XA274 | CH3— | 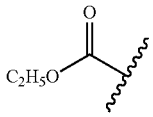 | H | 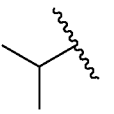 | H | H |
| XA275 | CH3— | 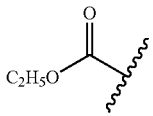 | H | 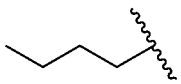 | H | H |
| XA276 | CH3— | 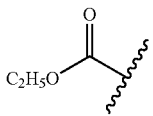 | H | 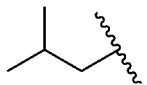 | H | H |
| XA277 | CH3— | 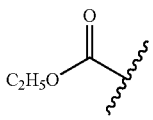 | H | 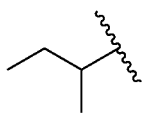 | H | H |
| XA278 | CH3— | 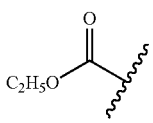 | H | 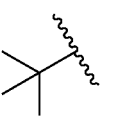 | H | H |
| XA279 | CH3— | 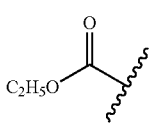 | H | 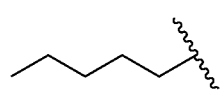 | H | H |
| XA280 | CH3— | 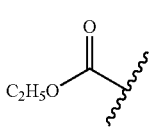 | H | 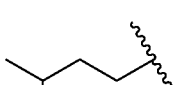 | H | H |
| XA281 | CH3— | 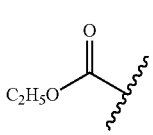 | H | 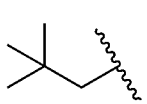 | H | H |
| XA282 | CH3— | 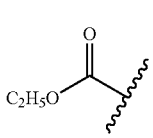 | H | 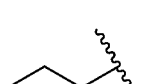 | H | H |
| XA283 | CH3— | 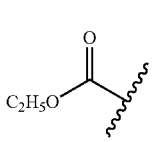 | H | 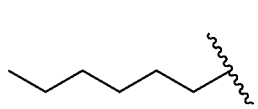 | H | H |
| XA284 | CH3— | 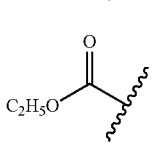 | H | 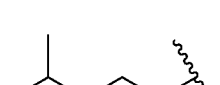 | H | H |

-continued
| | | | | | | |
|---|---|---|---|---|---|---|
| XA285 | CH3— | 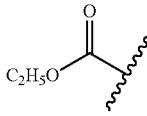 | H | 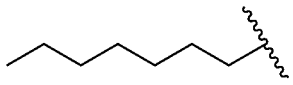 | H | H |
| XA286 | CH3— | 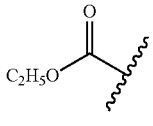 | H | 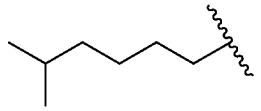 | H | H |
| XA287 | CH3— | 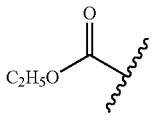 | H | n-C8H17— | H | H |
| XA288 | CH3— | 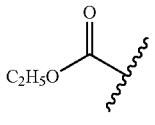 | H | 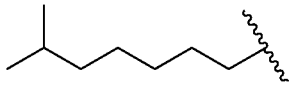 | H | H |
| XA289 | CH3— | 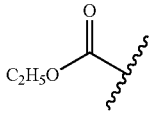 | H | 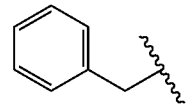 | H | H |
| XA290 | CH3— | 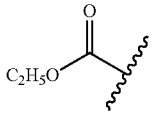 | H | 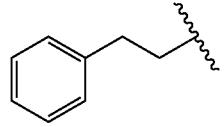 | H | H |
| XA291 | CH3— | 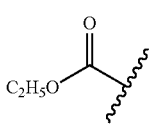 | H | 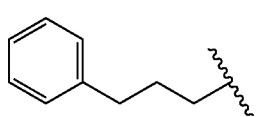 | H | H |
| XA292 | CH3— | 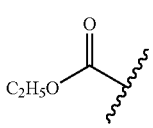 | H | 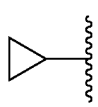 | H | H |
| XA293 | CH3— | 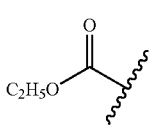 | H | 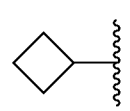 | H | H |
| XA294 | CH3— | 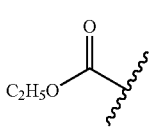 | H | 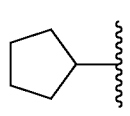 | H | H |
| XA295 | CH3— | 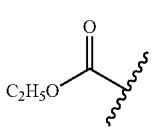 | H | 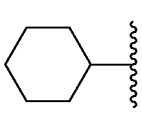 | H | H |
| XA296 | CH3— | 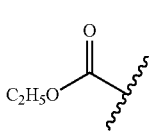 | H | 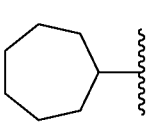 | H | H |

-continued
| | | | | | | |
|---|---|---|---|---|---|---|
| XA297 | CH3— | 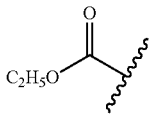 | H | 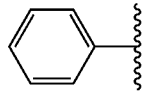 | H | H |
| XA298 | CH3— | 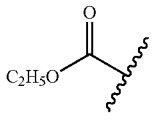 | H | 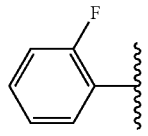 | H | H |
| XA299 | CH3— | 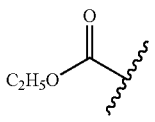 | H | 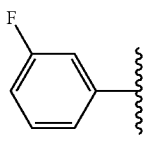 | H | H |
| XA300 | CH3— | 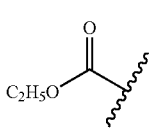 | H | 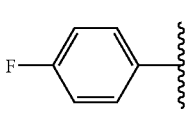 | H | H |
| XA301 | CH3— | 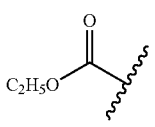 | H | 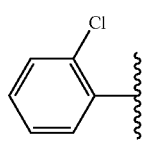 | H | H |
| XA302 | CH3— | 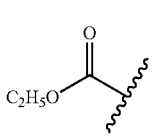 | H | 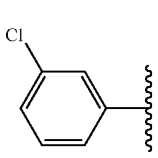 | H | H |
| XA303 | CH3— | 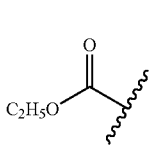 | H | 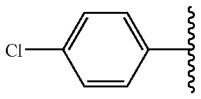 | H | H |
| XA304 | CH3— | 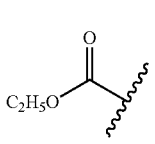 | H |  | H | H |
| XA305 | CH3— | 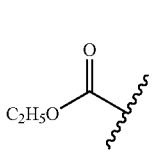 | H |  | H | H |
| XA306 | CH3— | 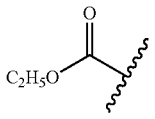 | H |  | H | H |
| XA307 | CH3— | 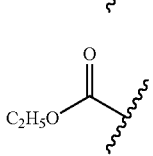 | H | 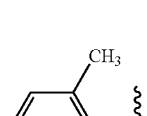 | H | H |

| | | | | | | |
|---|---|---|---|---|---|---|
| XA308 | CH3— | -CH(COOC2H5)- | H | 3-CH3-C6H4- | H | H |
| XA309 | CH3— | -CH(COOC2H5)- | H | 4-CH3-C6H4- | H | H |
| XA310 | CH3— | -CH(COOC2H5)- | H | 4-C2H5-C6H4- | H | H |
| XA311 | CH3— | -CH(COOC2H5)- | H | 4-n-C3H7-C6H4- | H | H |
| XA312 | CH3— | -CH(COOC2H5)- | H | 4-n-C4H9-C6H4- | H | H |
| XA313 | CH3— | -CH(COOC2H5)- | H | 2-OCH3-C6H4- | H | H |
| XA314 | CH3— | -CH(COOC2H5)- | H | 3-OCH3-C6H4- | H | H |
| XA315 | CH3— | -CH(COOC2H5)- | H | 4-OCH3-C6H4- | H | H |
| XA316 | CH3— | -CH(COOC2H5)- | H | 4-OC2H5-C6H4- | H | H |
| XA317 | CH3— | -CH(COOC2H5)- | H | 4-O-n-C3H7-C6H4- | H | H |
| XA318 | CH3— | -CH(COOC2H5)- | H | 4-O-n-C4H9-C6H4- | H | H |
| XA319 | CH3— | -CH(COOC2H5)- | H | 2-NO2-C6H4- | H | H |

-continued
| | | | | | | | |
|---|---|---|---|---|---|---|---|
| XA320 | CH3— | 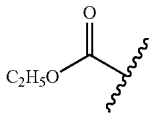 | H | 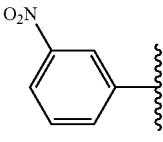 | H | H | |
| XA321 | CH3— | 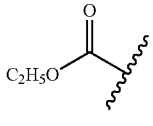 | H | 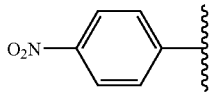 | H | H | |
| XA322 | CH3— | 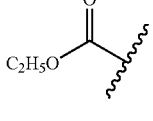 | H | 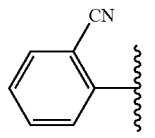 | H | H | |
| XA323 | CH3— | 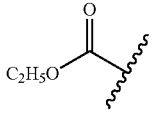 | H | 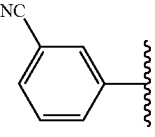 | H | H | |
| XA324 | CH3— | 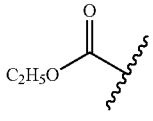 | H | 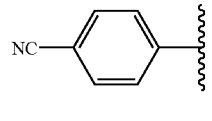 | H | H | |
| XA325 | CH3— | 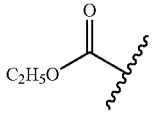 | H | 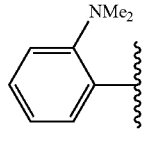 | H | H | |
| XA326 | CH3— | 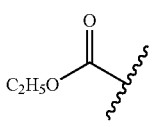 | H | 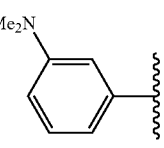 | H | H | |
| XA327 | CH3— | 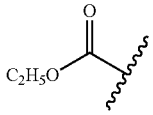 | H | 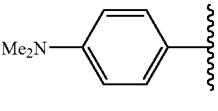 | H | H | |
| XA328 | CH3— | 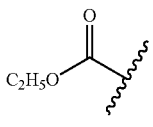 | H | 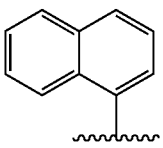 | H | H | |
| XA329 | CH3— | 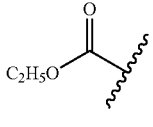 | H | 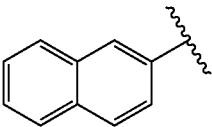 | H | H | |
| XA330 | CH3— | 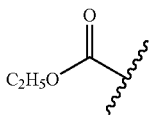 | H | 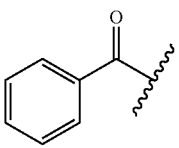 | H | H | |

-continued
| | | | | | | |
|---|---|---|---|---|---|---|
| XA331 | CH3— | 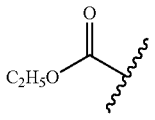 | H | 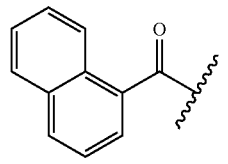 | H | H |
| XA332 | CH3— | 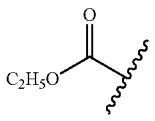 | H | 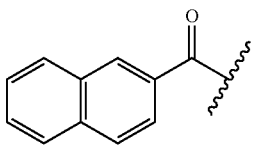 | H | H |
| XA333 | CH3— | 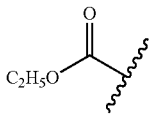 | H | 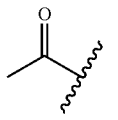 | H | H |
| XA334 | CH3— | 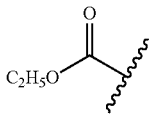 | H | 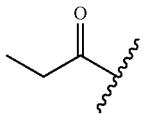 | H | H |
| XA335 | CH3— | CH3— | H | H | H | H |
| XA336 | CH3— | CH3CH2— | H | H | H | H |
| XA337 | CH3— | 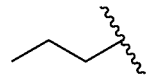 | H | H | H | H |
| XA338 | CH3— | 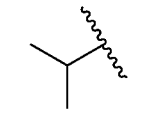 | H | H | H | H |
| XA339 | CH3— | 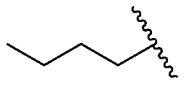 | H | H | H | H |
| XA340 | CH3— | 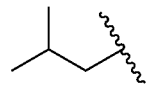 | H | H | H | H |
| XA341 | CH3— | 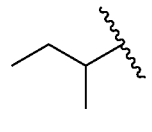 | H | H | H | H |
| XA342 | CH3— | 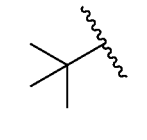 | H | H | H | H |
| XA343 | CH3— | 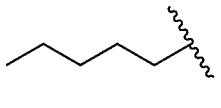 | H | H | H | H |
| XA344 | CH3— | 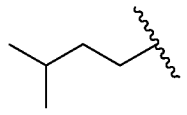 | H | H | H | H |

-continued
| | | | | | | |
|---|---|---|---|---|---|---|
| XA345 | CH3— | 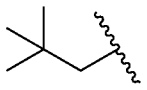 | H | H | H | H |
| XA346 | CH3— | 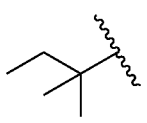 | H | H | H | H |
| XA347 | CH3— | 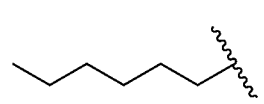 | H | H | H | H |
| XA348 | CH3— | 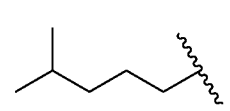 | H | H | H | H |
| XA349 | CH3— | 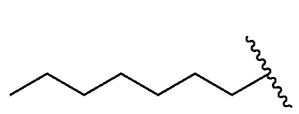 | H | H | H | H |
| XA350 | CH3— | 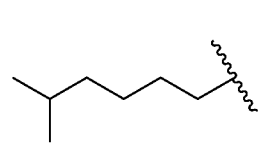 | H | H | H | H |
| XA351 | CH3— | n-C8H17— | H | H | H | H |
| XA352 | CH3— | 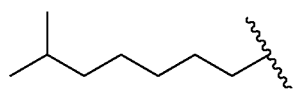 | H | H | H | H |
| XA353 | CH3— | 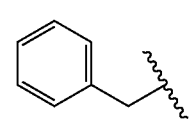 | H | H | H | H |
| XA354 | CH3— | 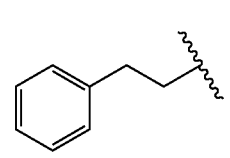 | H | H | H | H |
| XA355 | CH3— | 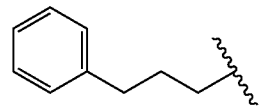 | H | H | H | H |
| XA356 | CH3— | 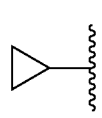 | H | H | H | H |
| XA357 | CH3— | 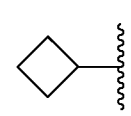 | H | H | H | H |
| XA358 | CH3— | 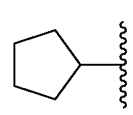 | H | H | H | H |

-continued
| | | | | | | |
|---|---|---|---|---|---|---|
| XA359 | CH3— | 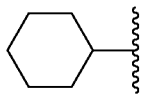 | H | H | H | H |
| XA360 | CH3— | 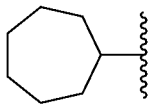 | H | H | H | H |
| XA361 | CH3— | 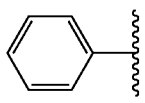 | H | H | H | H |
| XA362 | CH3— | 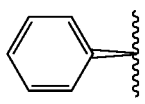 | H | H | H | H |
| XA363 | CH3— | 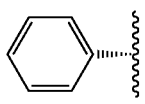 | H | H | H | H |
| XA364 | CH3— | 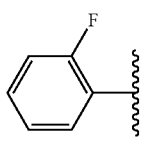 | H | H | H | H |
| XA365 | CH3— | 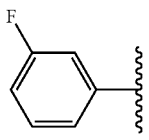 | H | H | H | H |
| XA366 | CH3— | 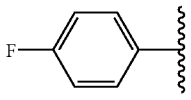 | H | H | H | H |
| XA367 | CH3— | 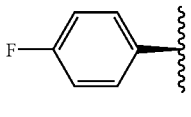 | H | H | H | H |
| XA368 | CH3— | 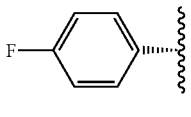 | H | H | H | H |
| XA369 | CH3— | 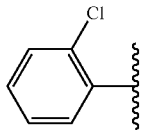 | H | H | H | H |
| XA370 | CH3— | 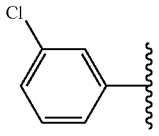 | H | H | H | H |
| XA371 | CH3— | 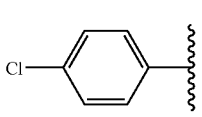 | H | H | H | H |

-continued
| | | | | | | |
|---|---|---|---|---|---|---|
| XA372 | CH3— | 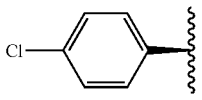 | H | H | H | H |
| XA373 | CH3— | 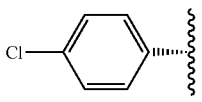 | H | H | H | H |
| XA374 | CH3— | 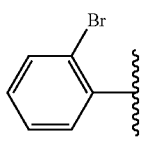 | H | H | H | H |
| XA375 | CH3— | 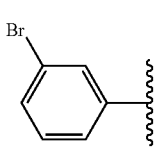 | H | H | H | H |
| XA376 | CH3— | 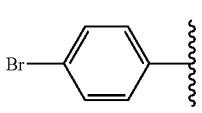 | H | H | H | H |
| XA377 | CH3— | 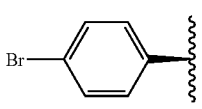 | H | H | H | H |
| XA378 | CH3— | 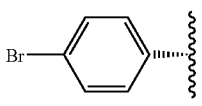 | H | H | H | H |
| XA379 | CH3— | 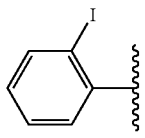 | H | H | H | H |
| XA380 | CH3— | 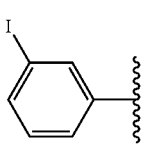 | H | H | H | H |
| XA381 | CH3— | 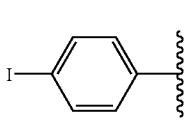 | H | H | H | H |
| XA382 | CH3— | 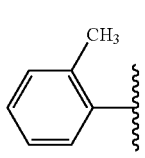 | H | H | H | H |
| XA383 | CH3— | 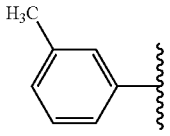 | H | H | H | H |

-continued
| | | | | | | |
|---|---|---|---|---|---|---|
| XA384 | CH3— | 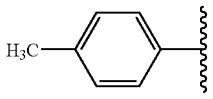 | H | H | H | H |
| XA385 | CH3— | 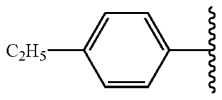 | H | H | H | H |
| XA386 | CH3— | 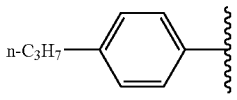 | H | H | H | H |
| XA387 | CH3— | 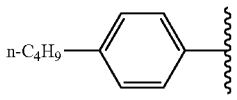 | H | H | H | H |
| XA388 | CH3— | 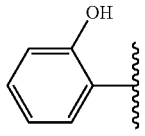 | H | H | H | H |
| XA389 | CH3— | 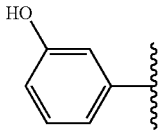 | H | H | H | H |
| XA390 | CH3— | 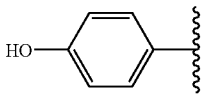 | H | H | H | H |
| XA391 | CH3— | 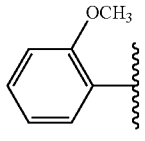 | H | H | H | H |
| XA392 | CH3— | 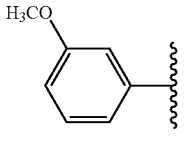 | H | H | H | H |
| XA393 | CH3— | 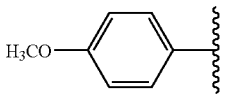 | H | H | H | H |
| XA394 | CH3— | 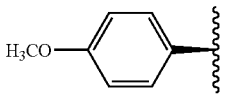 | H | H | H | H |
| XA395 | CH3— | 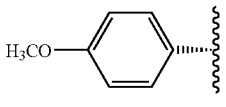 | H | H | H | H |

-continued

| | | | | | | |
|---|---|---|---|---|---|---|
| XA396 | CH3— | 2-(OC₂H₅)C₆H₄— | H | H | H | H |
| XA397 | CH3— | 3-(C₂H₅O)C₆H₄— | H | H | H | H |
| XA398 | CH3— | 4-(C₂H₅O)C₆H₄— | H | H | H | H |
| XA399 | CH3— | 4-(n-C₃H₇O)C₆H₄— | H | H | H | H |
| XA400 | CH3— | 4-(n-C₄H₉O)C₆H₄— | H | H | H | H |
| XA401 | CH3— | 2-(NO₂)C₆H₄— | H | H | H | H |
| XA402 | CH3— | 3-(O₂N)C₆H₄— | H | H | H | H |
| XA403 | CH3— | 4-(O₂N)C₆H₄— | H | H | H | H |
| XA404 | CH3— | 2-(CN)C₆H₄— | H | H | H | H |
| XA405 | CH3— | 3-(NC)C₆H₄— | H | H | H | H |
| XA406 | CH3— | 4-(NC)C₆H₄— | H | H | H | H |
| XA407 | CH3— | 2-(CF₃)C₆H₄— | H | H | H | H |

-continued

| | | | | | | |
|---|---|---|---|---|---|---|
| XA408 | CH3— | 3-(F₃C)-C₆H₄— | H | H | H | H |
| XA409 | CH3— | 4-(F₃C)-C₆H₄— | H | H | H | H |
| XA410 | CH3— | 2-(HOOC)-C₆H₄— | H | H | H | H |
| XA411 | CH3— | 3-(HOOC)-C₆H₄— | H | H | H | H |
| XA412 | CH3— | 4-(HOOC)-C₆H₄— | H | H | H | H |
| XA413 | CH3— | 2-(MeO₂C)-C₆H₄— | H | H | H | H |
| XA414 | CH3— | 3-(MeO₂C)-C₆H₄— | H | H | H | H |
| XA415 | CH3— | 4-(MeO₂C)-C₆H₄— | H | H | H | H |
| XA416 | CH3— | 2-(EtO₂C)-C₆H₄— | H | H | H | H |
| XA417 | CH3— | 3-(EtO₂C)-C₆H₄— | H | H | H | H |
| XA418 | CH3— | 4-(EtO₂C)-C₆H₄— | H | H | H | H |
| XA419 | CH3— | 2-(MeS)-C₆H₄— | H | H | H | H |

-continued
| | | | | | | |
|---|---|---|---|---|---|---|
| XA420 | CH3— | 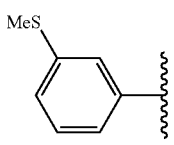 | H | H | H | H |
| XA421 | CH3— | 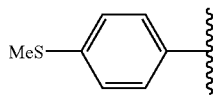 | H | H | H | H |
| XA422 | CH3— | 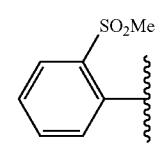 | H | H | H | H |
| XA423 | CH3— | 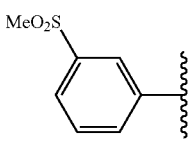 | H | H | H | H |
| XA424 | CH3— | 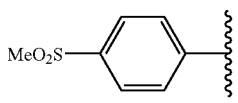 | H | H | H | H |
| XA425 | CH3— | 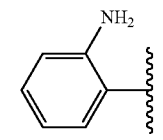 | H | H | H | H |
| XA426 | CH3— | 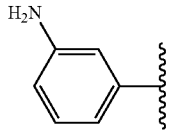 | H | H | H | H |
| XA427 | CH3— | 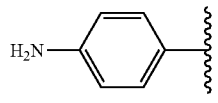 | H | H | H | H |
| XA428 | CH3— | 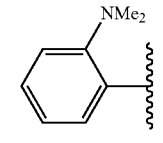 | H | H | H | H |
| XA429 | CH3— | 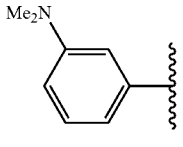 | H | H | H | H |
| XA430 | CH3— | 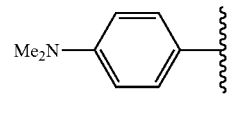 | H | H | H | H |

-continued
| | | | | | | |
|---|---|---|---|---|---|---|
| XA431 | CH3— | 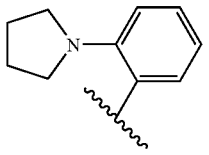 | H | H | H | H |
| XA432 | CH3— | 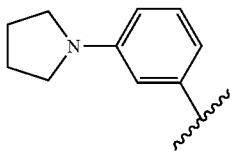 | H | H | H | H |
| XA433 | CH3— | 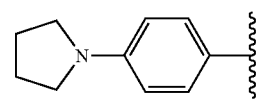 | H | H | H | H |
| XA434 | CH3— | 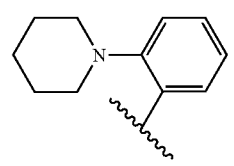 | H | H | H | H |
| XA435 | CH3— | 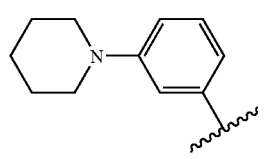 | H | H | H | H |
| XA436 | CH3— | 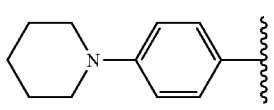 | H | H | H | H |
| XA437 | CH3— | 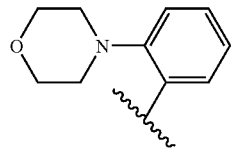 | H | H | H | H |
| XA438 | CH3— | 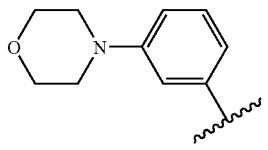 | H | H | H | H |
| XA439 | CH3— | 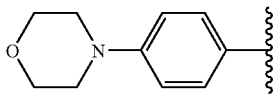 | H | H | H | H |
| XA440 | CH3— | 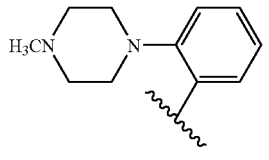 | H | H | H | H |
| XA441 | CH3— | 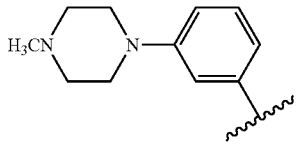 | H | H | H | H |

-continued
| | | | | | | |
|---|---|---|---|---|---|---|
| XA442 | CH3— | 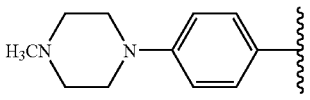 | H | H | H | H |
| XA443 | CH3— | 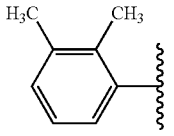 | H | H | H | H |
| XA444 | CH3— | 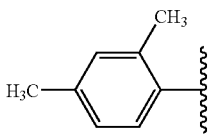 | H | H | H | H |
| XA445 | CH3— | 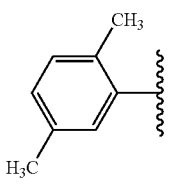 | H | H | H | H |
| XA446 | CH3— | 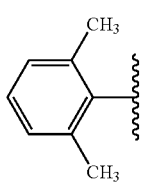 | H | H | H | H |
| XA447 | CH3— | 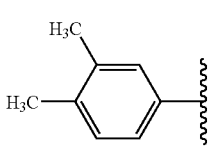 | H | H | H | H |
| XA448 | CH3— | 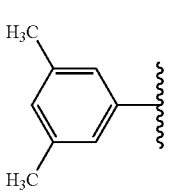 | H | H | H | H |
| XA449 | CH3— | 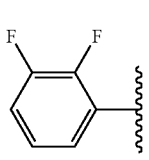 | H | H | H | H |
| XA450 | CH3— | 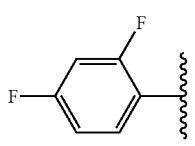 | H | H | H | H |
| XA451 | CH3— | 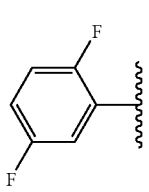 | H | H | H | H |

-continued
| | | | | | | |
|---|---|---|---|---|---|---|
| XA452 | CH3— | 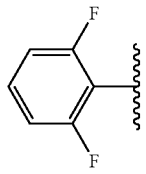 2,6-difluorophenyl | H | H | H | H |
| XA453 | CH3— | 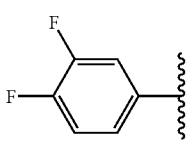 3,4-difluorophenyl | H | H | H | H |
| XA454 | CH3— | 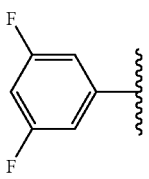 3,5-difluorophenyl | H | H | H | H |
| XA455 | CH3— | 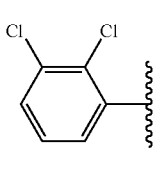 2,3-dichlorophenyl | H | H | H | H |
| XA456 | CH3— | 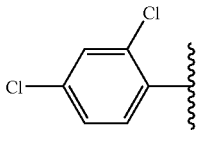 2,4-dichlorophenyl | H | H | H | H |
| XA457 | CH3— | 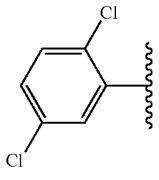 2,5-dichlorophenyl | H | H | H | H |
| XA458 | CH3— | 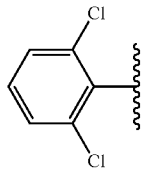 2,6-dichlorophenyl | H | H | H | H |
| XA459 | CH3— | 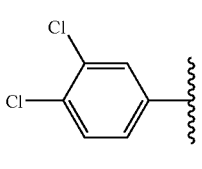 3,4-dichlorophenyl | H | H | H | H |
| XA460 | CH3— | 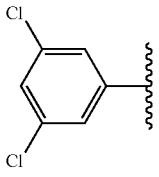 3,5-dichlorophenyl | H | H | H | H |

-continued
| | | | | | | |
|---|---|---|---|---|---|---|
| XA461 | CH3— | 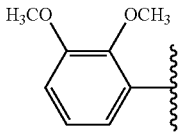 | H | H | H | H |
| XA462 | CH3— | 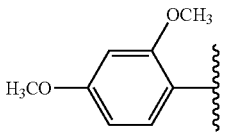 | H | H | H | H |
| XA463 | CH3— | 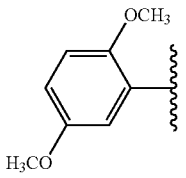 | H | H | H | H |
| XA464 | CH3— | 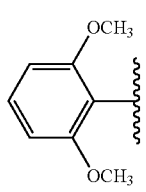 | H | H | H | H |
| XA465 | CH3— | 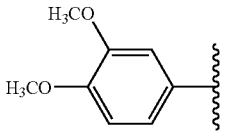 | H | H | H | H |
| XA466 | CH3— | 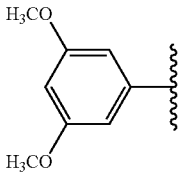 | H | H | H | H |
| XA467 | CH3— | 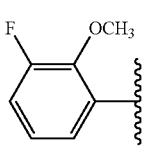 | H | H | H | H |
| XA468 | CH3— | 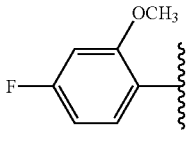 | H | H | H | H |
| XA469 | CH3— | 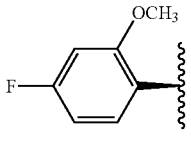 | H | H | H | H |
| XA470 | CH3— | 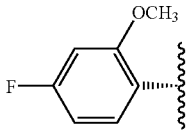 | H | H | H | H |

-continued
| | | | | | | |
|---|---|---|---|---|---|---|
| XA471 | CH3— | 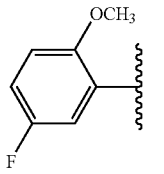 | H | H | H | H |
| XA472 | CH3— | 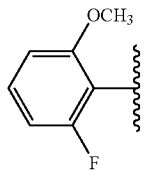 | H | H | H | H |
| XA473 | CH3— | 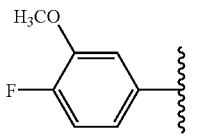 | H | H | H | H |
| XA474 | CH3— | 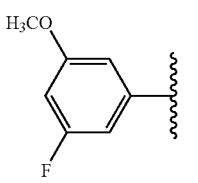 | H | H | H | H |
| XA475 | CH3— | 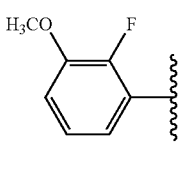 | H | H | H | H |
| XA476 | CH3— | 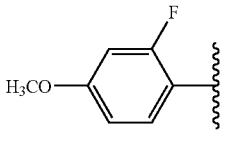 | H | H | H | H |
| XA477 | CH3— | 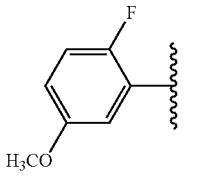 | H | H | H | H |
| XA478 | CH3— | 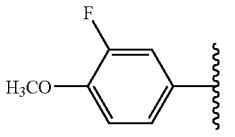 | H | H | H | H |
| XA479 | CH3— | 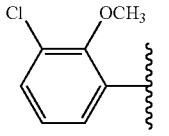 | H | H | H | H |
| XA480 | CH3— | 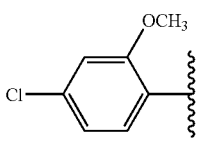 | H | H | H | H |

-continued
| | | | | | | |
|---|---|---|---|---|---|---|
| XA481 | CH3— | 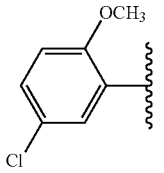 | H | H | H | H |
| XA482 | CH3— | 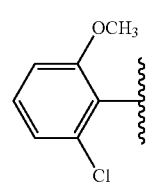 | H | H | H | H |
| XA483 | CH3— | 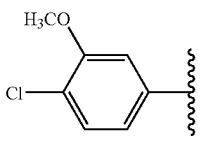 | H | H | H | H |
| XA484 | CH3— | 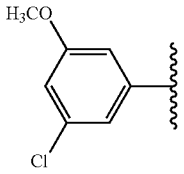 | H | H | H | H |
| XA485 | CH3— | 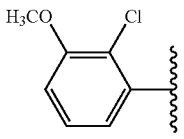 | H | H | H | H |
| XA486 | CH3— | 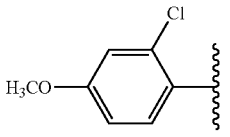 | H | H | H | H |
| XA487 | CH3— | 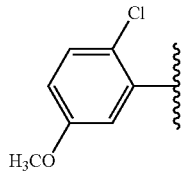 | H | H | H | H |
| XA488 | CH3— | 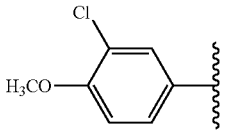 | H | H | H | H |
| XA489 | CH3— | 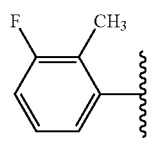 | H | H | H | H |

-continued
| | | | | | | |
|---|---|---|---|---|---|---|
| XA490 | CH3— | 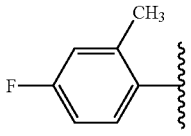 | H | H | H | H |
| XA491 | CH3— |  | H | H | H | H |
| XA492 | CH3— | 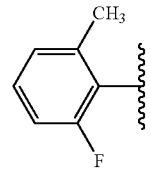 | H | H | H | H |
| XA493 | CH3— | 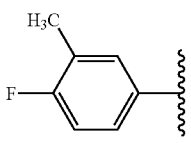 | H | H | H | H |
| XA494 | CH3— | 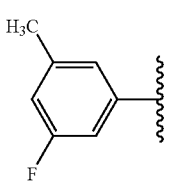 | H | H | H | H |
| XA495 | CH3— |  | H | H | H | H |
| XA496 | CH3— |  | H | H | H | H |
| XA497 | CH3— |  | H | H | H | H |
| XA498 | CH3— |  | H | H | H | H |
| XA499 | CH3— | 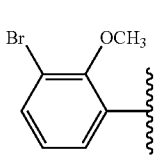 | H | H | H | H |

-continued
| | | | | | | |
|---|---|---|---|---|---|---|
| XA500 | CH3— | 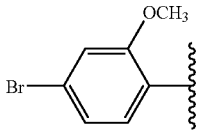 | H | H | H | H |
| XA501 | CH3— | 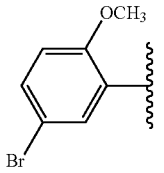 | H | H | H | H |
| XA502 | CH3— | 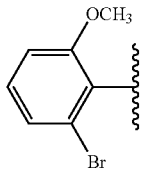 | H | H | H | H |
| XA503 | CH3— | 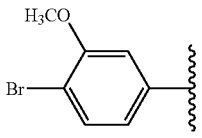 | H | H | H | H |
| XA504 | CH3— | 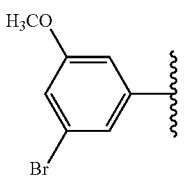 | H | H | H | H |
| XA505 | CH3— | 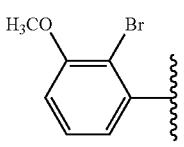 | H | H | H | H |
| XA506 | CH3— | 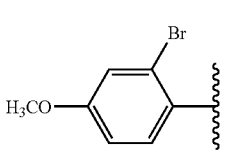 | H | H | H | H |
| XA507 | CH3— | 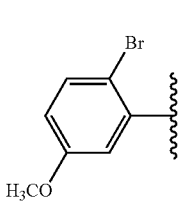 | H | H | H | H |
| XA508 | CH3— | 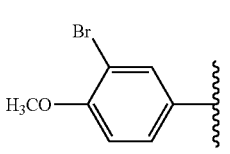 | H | H | H | H |

-continued
| | | | | | | |
|---|---|---|---|---|---|---|
| XA509 | CH3— |  | H | H | H | H |
| XA510 | CH3— | 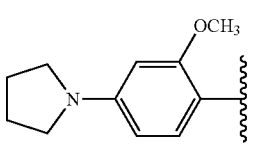 | H | H | H | H |
| XA511 | CH3— | 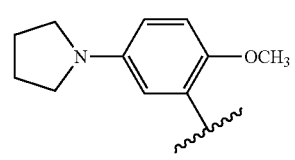 | H | H | H | H |
| XA512 | CH3— | 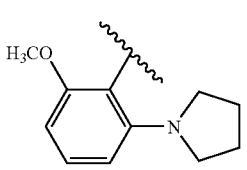 | H | H | H | H |
| XA513 | CH3— | 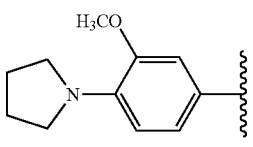 | H | H | H | H |
| XA514 | CH3— | 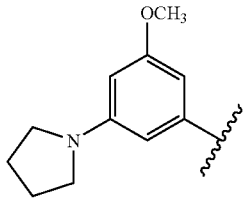 | H | H | H | H |
| XA515 | CH3— | 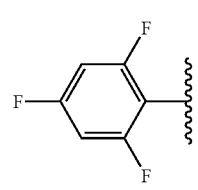 | H | H | H | H |
| XA516 | CH3— | 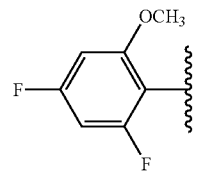 | H | H | H | H |
| XA517 | CH3— | 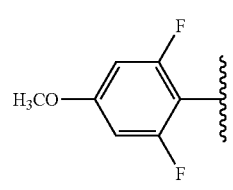 | H | H | H | H |

-continued

| | | | | | | |
|---|---|---|---|---|---|---|
| XA518 | CH3— | 5-fluoro-2,6-dimethoxyphenyl | H | H | H | H |
| XA519 | CH3— | 2,4,6-trimethoxyphenyl (3,5-dimethoxy-...) | H | H | H | H |
| XA520 | CH3— | 2,3,5-trichlorophenyl | H | H | H | H |
| XA521 | CH3— | 3,5-dichloro-2-methoxyphenyl | H | H | H | H |
| XA522 | CH3— | 2,6-dichloro-4-methoxyphenyl | H | H | H | H |
| XA523 | CH3— | 5-chloro-2,6-dimethoxyphenyl | H | H | H | H |
| XA524 | CH3— | 2,4,6-trimethoxyphenyl | H | H | H | H |
| XA525 | CH3— | 2'-methoxybiphenyl-4-yl | H | H | H | H |
| XA526 | CH3— | 3'-methoxybiphenyl-4-yl | H | H | H | H |

-continued
| | | | | | | |
|---|---|---|---|---|---|---|
| XA527 | CH3— | 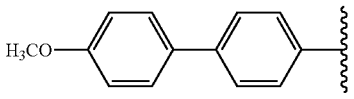 | H | H | H | H |
| XA528 | CH3— | 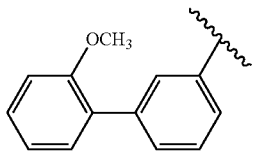 | H | H | H | H |
| XA529 | CH3— | 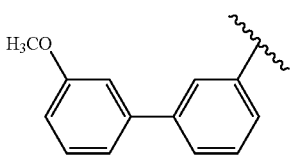 | H | H | H | H |
| XA530 | CH3— | 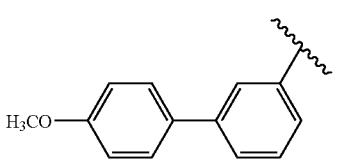 | H | H | H | H |
| XA531 | CH3— | 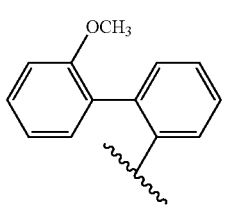 | H | H | H | H |
| XA532 | CH3— | 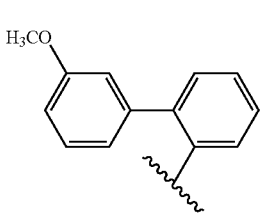 | H | H | H | H |
| XA533 | CH3— | 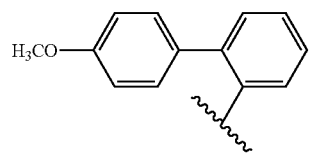 | H | H | H | H |
| XA534 | CH3— | 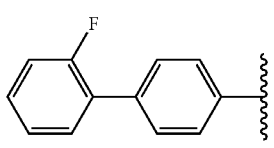 | H | H | H | H |
| XA535 | CH3— | 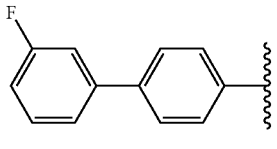 | H | H | H | H |
| XA536 | CH3— | 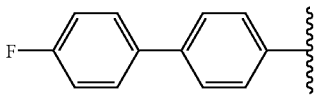 | H | H | H | H |

-continued
| | | | | | | |
|---|---|---|---|---|---|---|
| XA537 | CH3— | 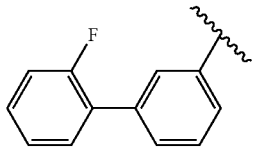 | H | H | H | H |
| XA538 | CH3— | 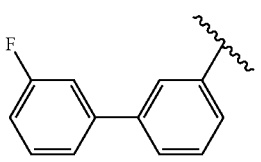 | H | H | H | H |
| XA539 | CH3— | 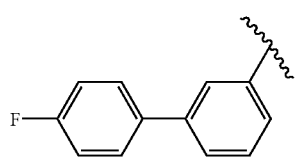 | H | H | H | H |
| XA540 | CH3— | 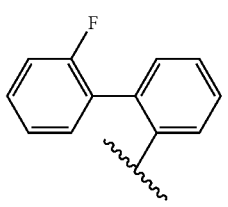 | H | H | H | H |
| XA541 | CH3— | 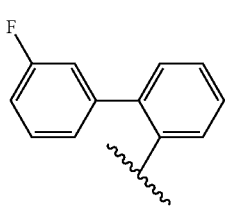 | H | H | H | H |
| XA542 | CH3— | 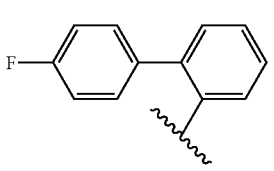 | H | H | H | H |
| XA543 | CH3— | 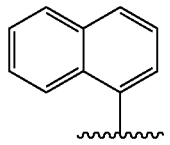 | H | H | H | H |
| XA544 | CH3— | 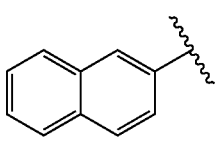 | H | H | H | H |
| XA545 | CH3— | 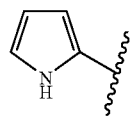 | H | H | H | H |
| XA546 | CH3— | 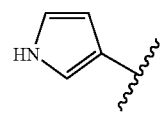 | H | H | H | H |

-continued

| | | | | | | |
|---|---|---|---|---|---|---|
| XA547 | CH3— | furan-2-yl | H | H | H | H |
| XA548 | CH3— | furan-3-yl | H | H | H | H |
| XA549 | CH3— | thiophen-2-yl | H | H | H | H |
| XA550 | CH3— | thiophen-3-yl | H | H | H | H |
| XA551 | CH3— | 1H-pyrazol-3-yl | H | H | H | H |
| XA552 | CH3— | 1H-pyrazol-4-yl | H | H | H | H |
| XA553 | CH3— | 1H-imidazol-4-yl | H | H | H | H |
| XA554 | CH3— | 1H-imidazol-2-yl | H | H | H | H |
| XA555 | CH3— | isoxazol-3-yl | H | H | H | H |
| XA556 | CH3— | isoxazol-4-yl | H | H | H | H |
| XA557 | CH3— | isoxazol-5-yl | H | H | H | H |
| XA558 | CH3— | isothiazol-3-yl | H | H | H | H |

-continued
| | | | | | | |
|---|---|---|---|---|---|---|
| XA559 | CH3— | 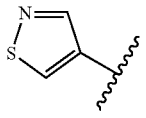 | H | H | H | H |
| XA560 | CH3— | 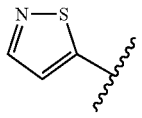 | H | H | H | H |
| XA561 | CH3— | 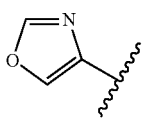 | H | H | H | H |
| XA562 | CH3— | 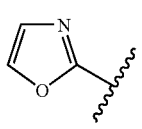 | H | H | H | H |
| XA563 | CH3— |  | H | H | H | H |
| XA564 | CH3— | 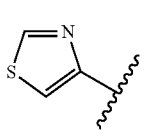 | H | H | H | H |
| XA565 | CH3— | 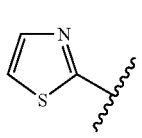 | H | H | H | H |
| XA566 | CH3— | 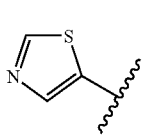 | H | H | H | H |
| XA567 | CH3— | 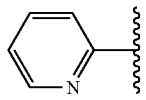 | H | H | H | H |
| XA568 | CH3— | 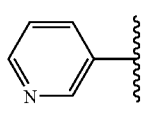 | H | H | H | H |
| XA569 | CH3— | 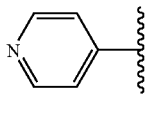 | H | H | H | H |
| XA570 | CH3— | 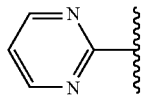 | H | H | H | H |
| XA571 | CH3— | 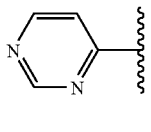 | H | H | H | H |

-continued
| | | | | | | |
|---|---|---|---|---|---|---|
| XA572 | CH3— | 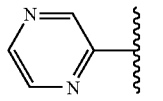 | H | H | H | H |
| XA573 | CH3— | 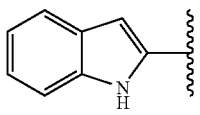 | H | H | H | H |
| XA574 | CH3— | 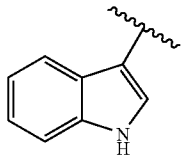 | H | H | H | H |
| XA575 | CH3— | 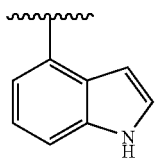 | H | H | H | H |
| XA576 | CH3— |  | H | H | H | H |
| XA577 | CH3— | 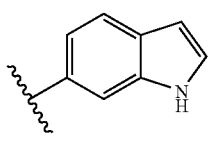 | H | H | H | H |
| XA578 | CH3— | 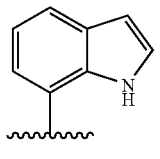 | H | H | H | H |
| XA579 | CH3— | 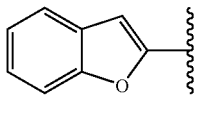 | H | H | H | H |
| XA580 | CH3— | 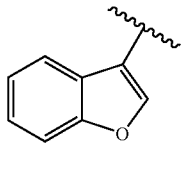 | H | H | H | H |
| XA581 | CH3— | 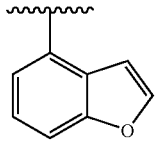 | H | H | H | H |
| XA582 | CH3— | 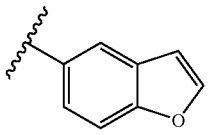 | H | H | H | H |

-continued
| | | | | | | |
|---|---|---|---|---|---|---|
| XA583 | CH3— | 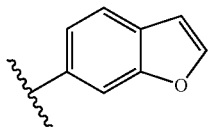 | H | H | H | H |
| XA584 | CH3— | 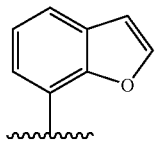 | H | H | H | H |
| XA585 | CH3— | 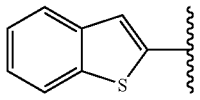 | H | H | H | H |
| XA586 | CH3— | 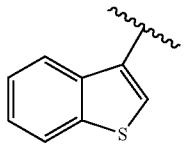 | H | H | H | H |
| XA587 | CH3— | 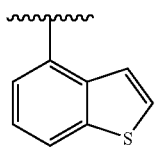 | H | H | H | H |
| XA588 | CH3— | 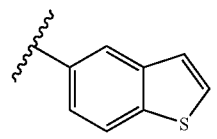 | H | H | H | H |
| XA589 | CH3— | 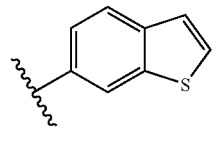 | H | H | H | H |
| XA590 | CH3— | 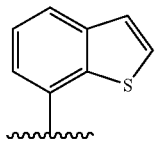 | H | H | H | H |
| XA591 | CH3— | 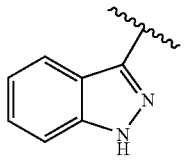 | H | H | H | H |
| XA592 | CH3— | 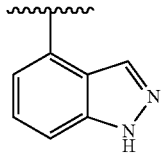 | H | H | H | H |

-continued
| | | | | | | |
|---|---|---|---|---|---|---|
| XA593 | CH3— |  | H | H | H | H |
| XA594 | CH3— |  | H | H | H | H |
| XA595 | CH3— |  | H | H | H | H |
| XA596 | CH3— |  | H | H | H | H |
| XA597 | CH3— |  | H | H | H | H |
| XA598 | CH3— |  | H | H | H | H |
| XA599 | CH3— |  | H | H | H | H |
| XA600 | CH3— |  | H | H | H | H |
| XA601 | CH3— |  | H | H | H | H |
| XA602 | CH3— |  | H | H | H | H |
| XA603 | CH3— |  | H | H | H | H |

-continued
| | | | | | | |
|---|---|---|---|---|---|---|
| XA604 | CH3— | 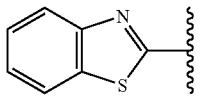 | H | H | H | H |
| XA605 | CH3— | 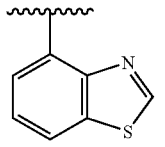 | H | H | H | H |
| XA606 | CH3— | 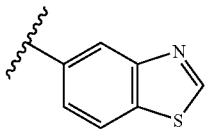 | H | H | H | H |
| XA607 | CH3— | 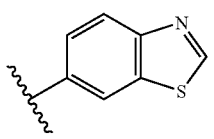 | H | H | H | H |
| XA608 | CH3— | 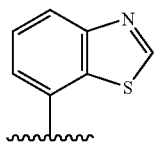 | H | H | H | H |
| XA609 | CH3— | 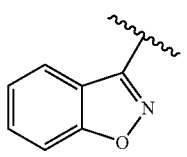 | H | H | H | H |
| XA610 | CH3— | 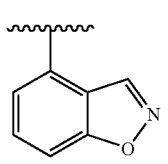 | H | H | H | H |
| XA611 | CH3— | 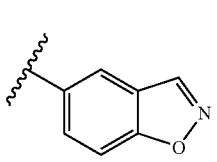 | H | H | H | H |
| XA612 | CH3— | 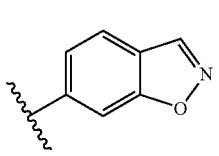 | H | H | H | H |
| XA613 | CH3— | 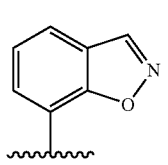 | H | H | H | H |

-continued
| | | | | | | |
|---|---|---|---|---|---|---|
| XA614 | CH3— | 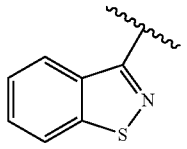 | H | H | H | H |
| XA615 | CH3— | 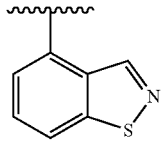 | H | H | H | H |
| XA616 | CH3— | 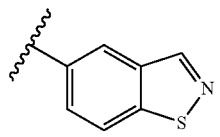 | H | H | H | H |
| XA617 | CH3— | 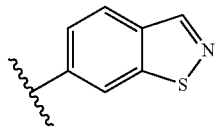 | H | H | H | H |
| XA618 | CH3— | 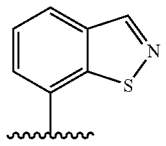 | H | H | H | H |
| XA619 | CH3— | 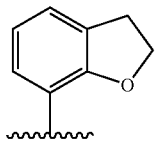 | H | H | H | H |
| XA620 | CH3— | 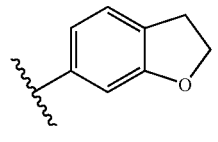 | H | H | H | H |
| XA621 | CH3— | 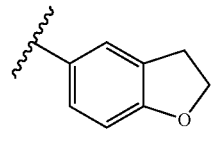 | H | H | H | H |
| XA622 | CH3— | 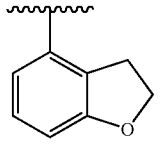 | H | H | H | H |
| XA623 | CH3— | CH3— | H | CH3 | H | H |
| XA624 | CH3— | CH3CH2— | H | CH3 | H | H |
| XA625 | CH3— | 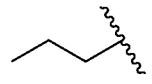 | H | CH3 | H | H |

-continued
| | | | | | | |
|---|---|---|---|---|---|---|
| XA626 | CH3— | 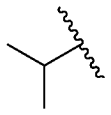 | H | CH3 | H | H |
| XA627 | CH3— | 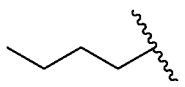 | H | CH3 | H | H |
| XA628 | CH3— | 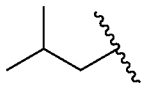 | H | CH3 | H | H |
| XA629 | CH3— | 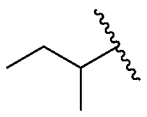 | H | CH3 | H | H |
| XA630 | CH3— | 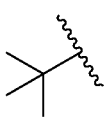 | H | CH3 | H | H |
| XA631 | CH3— | 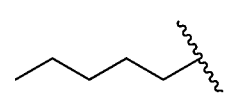 | H | CH3 | H | H |
| XA632 | CH3— | 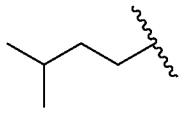 | H | CH3 | H | H |
| XA633 | CH3— | 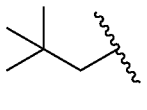 | H | CH3 | H | H |
| XA634 | CH3— | 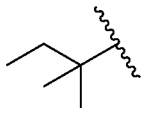 | H | CH3 | H | H |
| XA635 | CH3— | 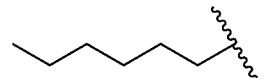 | H | CH3 | H | H |
| XA636 | CH3— | 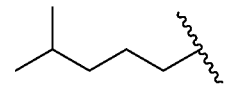 | H | CH3 | H | H |
| XA637 | CH3— | 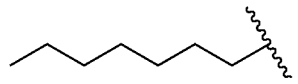 | H | CH3 | H | H |
| XA638 | CH3— |  | H | CH3 | H | H |
| XA639 | CH3— | n-C8H17— | H | CH3 | H | H |
| XA640 | CH3— | 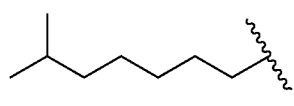 | H | CH3 | H | H |

-continued
| | | | | | | |
|---|---|---|---|---|---|---|
| XA641 | CH3— | 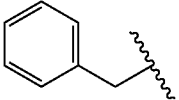 | H | CH3 | H | H |
| XA642 | CH3— | 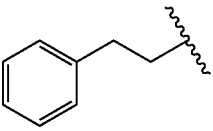 | H | CH3 | H | H |
| XA643 | CH3— | 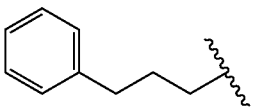 | H | CH3 | H | H |
| XA644 | CH3— | 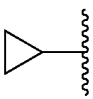 | H | CH3 | H | H |
| XA645 | CH3— | 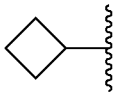 | H | CH3 | H | H |
| XA646 | CH3— | 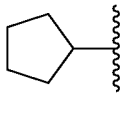 | H | CH3 | H | H |
| XA647 | CH3— | 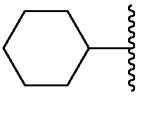 | H | CH3 | H | H |
| XA648 | CH3— | 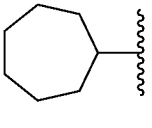 | H | CH3 | H | H |
| XA649 | CH3— | 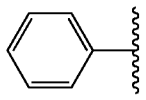 | H | CH3 | H | H |
| XA650 | CH3— | 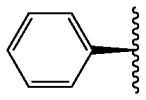 | H | CH3 | H | H |
| XA651 | CH3— | 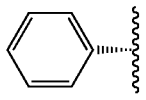 | H | CH3 | H | H |
| XA652 | CH3— | 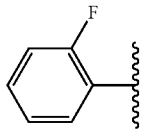 | H | CH3 | H | H |
| XA653 | CH3— | 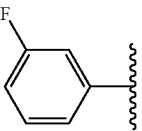 | H | CH3 | H | H |

-continued
| | | | | | | |
|---|---|---|---|---|---|---|
| XA654 | CH3— | 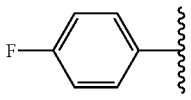 | H | CH3 | H | H |
| XA655 | CH3— | 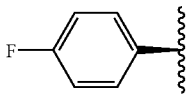 | H | CH3 | H | H |
| XA656 | CH3— | 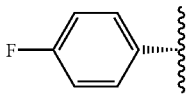 | H | CH3 | H | H |
| XA657 | CH3— | 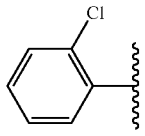 | H | CH3 | H | H |
| XA658 | CH3— | 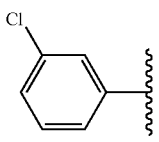 | H | CH3 | H | H |
| XA659 | CH3— | 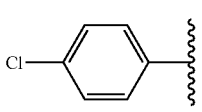 | H | CH3 | H | H |
| XA660 | CH3— | 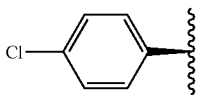 | H | CH3 | H | H |
| XA661 | CH3— | 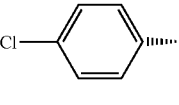 | H | CH3 | H | H |
| XA662 | CH3— | 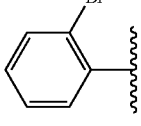 | H | CH3 | H | H |
| XA663 | CH3— | 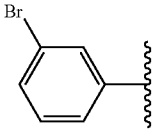 | H | CH3 | H | H |
| XA664 | CH3— | 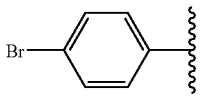 | H | CH3 | H | H |
| XA665 | CH3— | 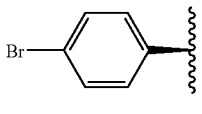 | H | CH3 | H | H |
| XA666 | CH3— | 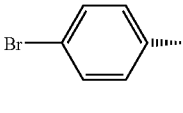 | H | CH3 | H | H |

-continued
| | | | | | | | |
|---|---|---|---|---|---|---|---|
| XA667 | CH3— | 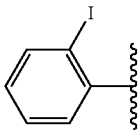 (2-iodophenyl) | H | CH3 | | H | H |
| XA668 | CH3— | 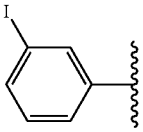 (3-iodophenyl) | H | CH3 | | H | H |
| XA669 | CH3— | 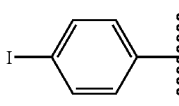 (4-iodophenyl) | H | CH3 | | H | H |
| XA670 | CH3— | 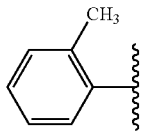 (2-methylphenyl) | H | CH3 | | H | H |
| XA671 | CH3— | 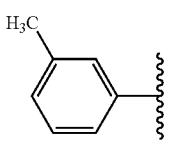 (3-methylphenyl) | H | CH3 | | H | H |
| XA672 | CH3— | 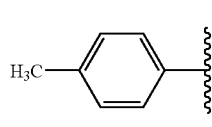 (4-methylphenyl) | H | CH3 | | H | H |
| XA673 | CH3— | 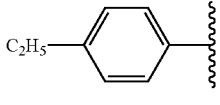 (4-ethylphenyl) | H | CH3 | | H | H |
| XA674 | CH3— | 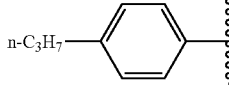 (4-n-propylphenyl) | H | CH3 | | H | H |
| XA675 | CH3— | 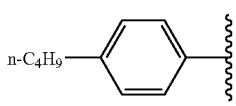 (4-n-butylphenyl) | H | CH3 | | H | H |
| XA676 | CH3— | 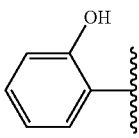 (2-hydroxyphenyl) | H | CH3 | | H | H |
| XA677 | CH3— | 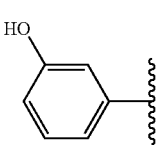 (3-hydroxyphenyl) | H | CH3 | | H | H |
| XA678 | CH3— | 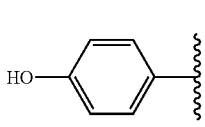 (4-hydroxyphenyl) | H | CH3 | | H | H |

-continued
| | | | | | | |
|---|---|---|---|---|---|---|
| XA679 | CH3— | 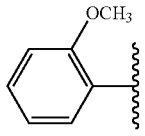 (2-OCH3-phenyl) | H | CH3 | H | H |
| XA680 | CH3— | 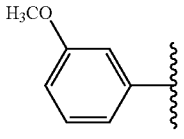 (3-OCH3-phenyl) | H | CH3 | H | H |
| XA681 | CH3— | 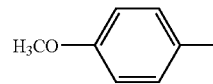 (4-OCH3-phenyl) | H | CH3 | H | H |
| XA682 | CH3— | 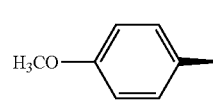 (4-OCH3-phenyl) | H | CH3 | H | H |
| XA683 | CH3— | 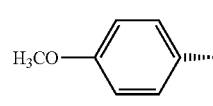 (4-OCH3-phenyl) | H | CH3 | H | H |
| XA684 | CH3— | 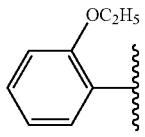 (2-OC2H5-phenyl) | H | CH3 | H | H |
| XA685 | CH3— | 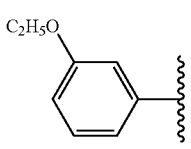 (3-OC2H5-phenyl) | H | CH3 | H | H |
| XA686 | CH3— | 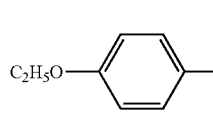 (4-OC2H5-phenyl) | H | CH3 | H | H |
| XA687 | CH3— | 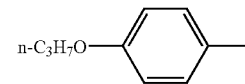 (4-O-n-C3H7-phenyl) | H | CH3 | H | H |
| XA688 | CH3— | 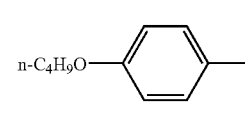 (4-O-n-C4H9-phenyl) | H | CH3 | H | H |
| XA689 | CH3— | 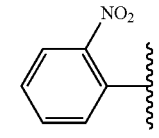 (2-NO2-phenyl) | H | CH3 | H | H |
| XA690 | CH3— | 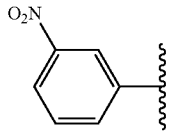 (3-NO2-phenyl) | H | CH3 | H | H |

-continued
| | | | | | | | |
|---|---|---|---|---|---|---|---|
| XA691 | CH3— | 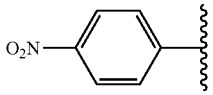 | | H | CH3 | H | H |
| XA692 | CH3— | 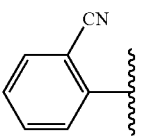 | | H | CH3 | H | H |
| XA693 | CH3— | 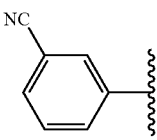 | | H | CH3 | H | H |
| XA694 | CH3— | 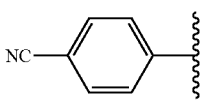 | | H | CH3 | H | H |
| XA695 | CH3— | 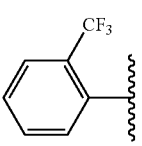 | | H | CH3 | H | H |
| XA696 | CH3— | 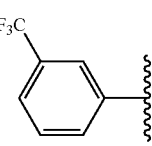 | | H | CH3 | H | H |
| XA697 | CH3— | 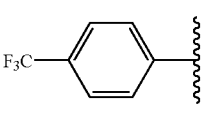 | | H | CH3 | H | H |
| XA698 | CH3— | 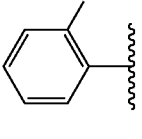 | | H | CH3 | H | H |
| XA699 | CH3— | 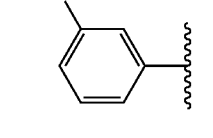 | | H | CH3 | H | H |
| XA700 | CH3— | 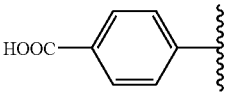 | | H | CH3 | H | H |
| XA701 | CH3— | 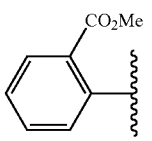 | | H | CH3 | H | H |
| XA702 | CH3— | 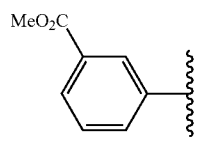 | | H | CH3 | H | H |

-continued
| | | | | | | |
|---|---|---|---|---|---|---|
| XA703 | CH3— | 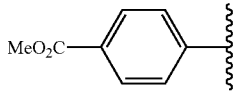 | H | CH3 | H | H |
| XA704 | CH3— | 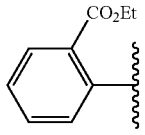 | H | CH3 | H | H |
| XA705 | CH3— | 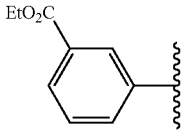 | H | CH3 | H | H |
| XA706 | CH3— | 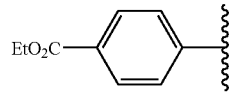 | H | CH3 | H | H |
| XA707 | CH3— | 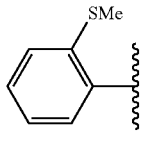 | H | CH3 | H | H |
| XA708 | CH3— | 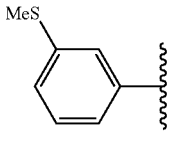 | H | CH3 | H | H |
| XA709 | CH3— | 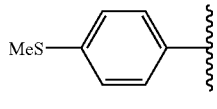 | H | CH3 | H | H |
| XA710 | CH3— | 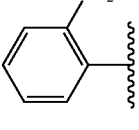 | H | CH3 | H | H |
| XA711 | CH3— | 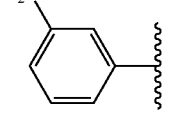 | H | CH3 | H | H |
| XA712 | CH3— | 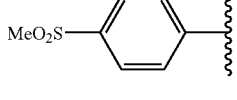 | H | CH3 | H | H |
| XA713 | CH3— | 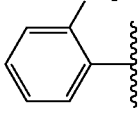 | H | CH3 | H | H |

-continued
| | | | | | | |
|---|---|---|---|---|---|---|
| XA714 | CH3— | 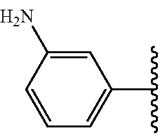 | H | CH3 | H | H |
| XA715 | CH3— | 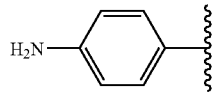 | H | CH3 | H | H |
| XA716 | CH3— | 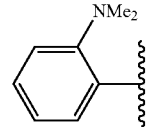 | H | CH3 | H | H |
| XA717 | CH3— | 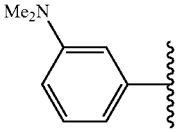 | H | CH3 | H | H |
| XA718 | CH3— | 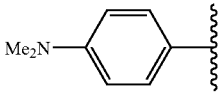 | H | CH3 | H | H |
| XA719 | CH3— | 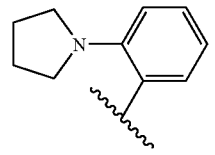 | H | CH3 | H | H |
| XA720 | CH3— | 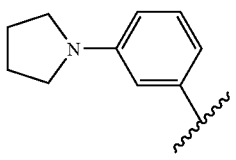 | H | CH3 | H | H |
| XA721 | CH3— | 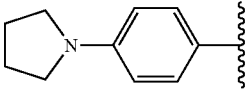 | H | CH3 | H | H |
| XA722 | CH3— | 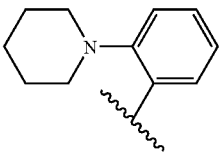 | H | CH3 | H | H |
| XA723 | CH3— | 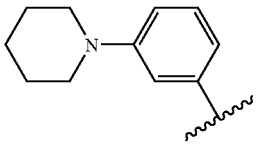 | H | CH3 | H | H |
| XA724 | CH3— | 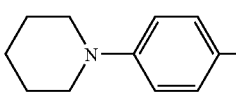 | H | CH3 | H | H |

-continued
| | | | | | | |
|---|---|---|---|---|---|---|
| XA725 | CH3— | 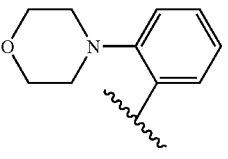 | H | CH3 | H | H |
| XA726 | CH3— | 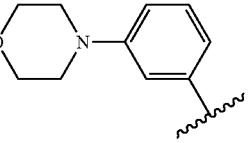 | H | CH3 | H | H |
| XA727 | CH3— | 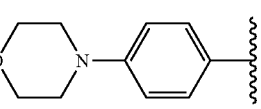 | H | CH3 | H | H |
| XA728 | CH3— | 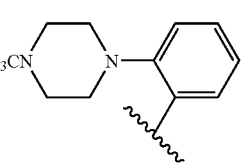 | H | CH3 | H | H |
| XA729 | CH3— | 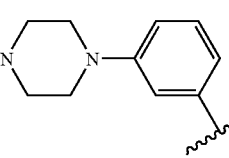 | H | CH3 | H | H |
| XA730 | CH3— | 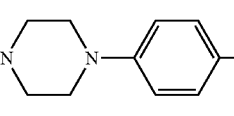 | H | CH3 | H | H |
| XA731 | CH3— | 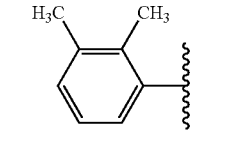 | H | CH3 | H | H |
| XA732 | CH3— | 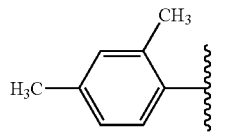 | H | CH3 | H | H |
| XA733 | CH3— | 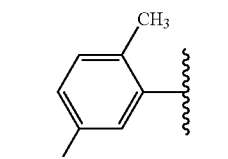 | H | CH3 | H | H |
| XA734 | CH3— | 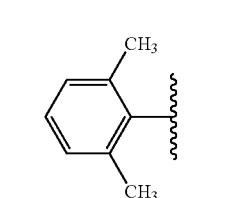 | H | CH3 | H | H |

-continued
| | | | | | | |
|---|---|---|---|---|---|---|
| XA735 | CH3— | 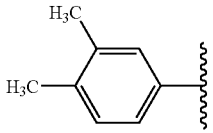 | H | CH3 | H | H |
| XA736 | CH3— | 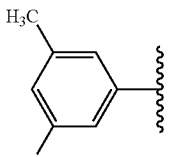 | H | CH3 | H | H |
| XA737 | CH3— | 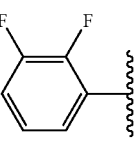 | H | CH3 | H | H |
| XA738 | CH3— | 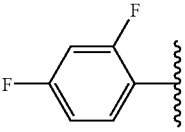 | H | CH3 | H | H |
| XA739 | CH3— | 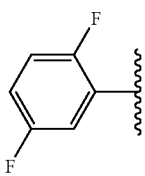 | H | CH3 | H | H |
| XA740 | CH3— | 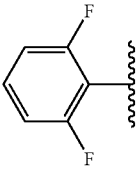 | H | CH3 | H | H |
| XA741 | CH3— | 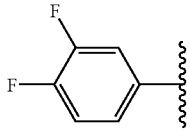 | H | CH3 | H | H |
| XA742 | CH3— | 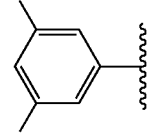 | H | CH3 | H | H |
| XA743 | CH3— | 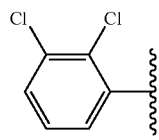 | H | CH3 | H | H |
| XA744 | CH3— | 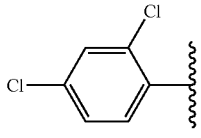 | H | CH3 | H | H |

-continued
| | | | | | | |
|---|---|---|---|---|---|---|
| XA745 | CH3— | 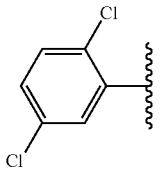 | H | CH3 | H | H |
| XA746 | CH3— | 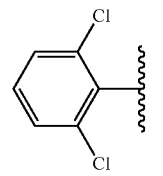 | H | CH3 | H | H |
| XA747 | CH3— | 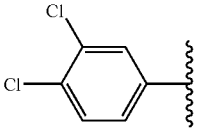 | H | CH3 | H | H |
| XA748 | CH3— | 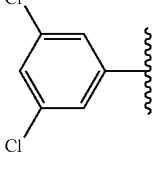 | H | CH3 | H | H |
| XA749 | CH3— | 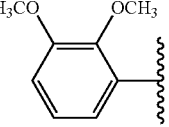 | H | CH3 | H | H |
| XA750 | CH3— | 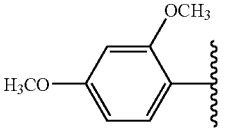 | H | CH3 | H | H |
| XA751 | CH3— | 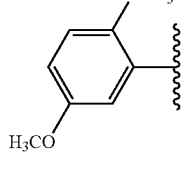 | H | CH3 | H | H |
| XA752 | CH3— | 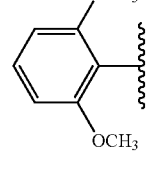 | H | CH3 | H | H |
| XA753 | CH3— | 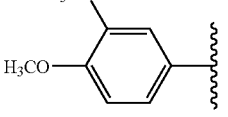 | H | CH3 | H | H |

-continued
| | | | | | | |
|---|---|---|---|---|---|---|
| XA754 | CH3— | 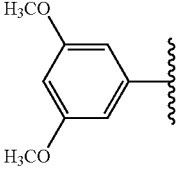 3,5-dimethoxyphenyl | H | CH3 | H | H |
| XA755 | CH3— | 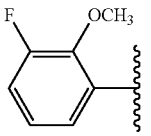 3-fluoro-2-methoxyphenyl | H | CH3 | H | H |
| XA756 | CH3— | 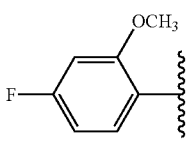 4-fluoro-2-methoxyphenyl | H | CH3 | H | H |
| XA757 | CH3— | 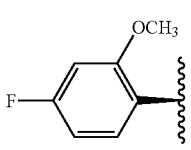 4-fluoro-2-methoxyphenyl | H | CH3 | H | H |
| XA758 | CH3— | 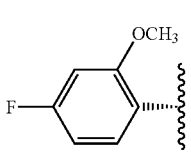 4-fluoro-2-methoxyphenyl | H | CH3 | H | H |
| XA759 | CH3— | 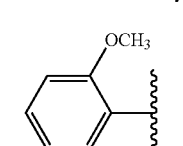 5-fluoro-2-methoxyphenyl | H | CH3 | H | H |
| XA760 | CH3— | 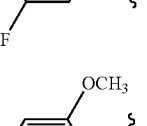 3-fluoro-2-methoxyphenyl | H | CH3 | H | H |
| XA761 | CH3— |  4-fluoro-3-methoxyphenyl | H | CH3 | H | H |
| XA762 | CH3— |  3-fluoro-5-methoxyphenyl | H | CH3 | H | H |
| XA763 | CH3— | 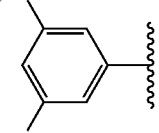 2-fluoro-3-methoxyphenyl | H | CH3 | H | H |

-continued
| | | | | | | |
|---|---|---|---|---|---|---|
| XA764 | CH3— | 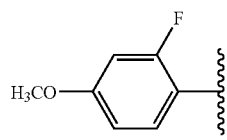 | H | CH3 | H | H |
| XA765 | CH3— | 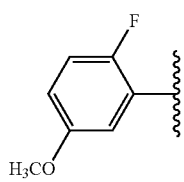 | H | CH3 | H | H |
| XA766 | CH3— | 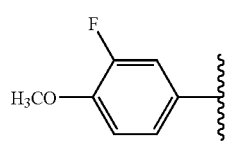 | H | CH3 | H | H |
| XA767 | CH3— | 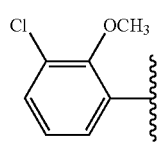 | H | CH3 | H | H |
| XA768 | CH3— | 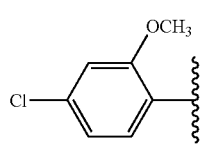 | H | CH3 | H | H |
| XA769 | CH3— | 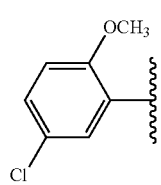 | H | CH3 | H | H |
| XA770 | CH3— | 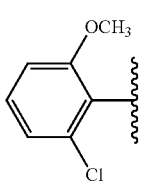 | H | CH3 | H | H |
| XA771 | CH3— | 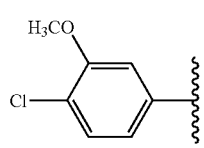 | H | CH3 | H | H |
| XA772 | CH3— | 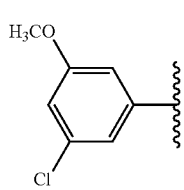 | H | CH3 | H | H |

-continued
| | | | | | | |
|---|---|---|---|---|---|---|
| XA773 | CH3— | 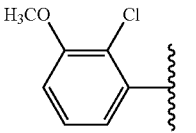 | H | CH3 | H | H |
| XA774 | CH3— | 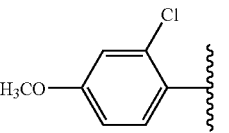 | H | CH3 | H | H |
| XA775 | CH3— | 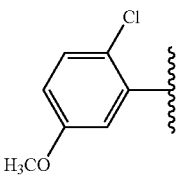 | H | CH3 | H | H |
| XA776 | CH3— | 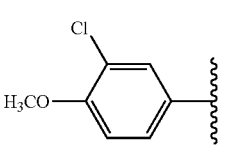 | H | CH3 | H | H |
| XA777 | CH3— | 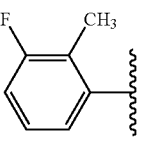 | H | CH3 | H | H |
| XA778 | CH3— | 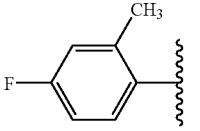 | H | CH3 | H | H |
| XA779 | CH3— | 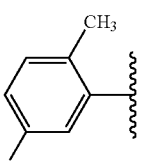 | H | CH3 | H | H |
| XA780 | CH3— | 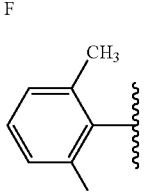 | H | CH3 | H | H |
| XA781 | CH3— | 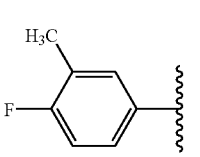 | H | CH3 | H | H |
| XA782 | CH3— | 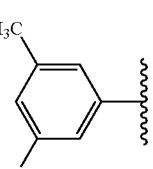 | H | CH3 | H | H |

-continued
| | | | | | | |
|---|---|---|---|---|---|---|
| XA783 | CH3— | 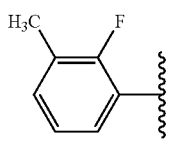 | H | CH3 | H | H |
| XA784 | CH3— | 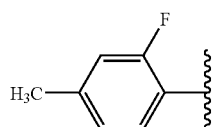 | H | CH3 | H | H |
| XA785 | CH3— | 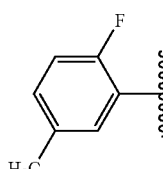 | H | CH3 | H | H |
| XA786 | CH3— | 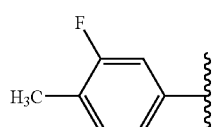 | H | CH3 | H | H |
| XA787 | CH3— | 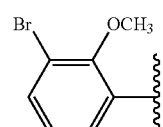 | H | CH3 | H | H |
| XA788 | CH3— | 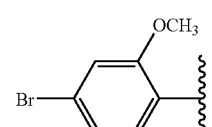 | H | CH3 | H | H |
| XA789 | CH3— | 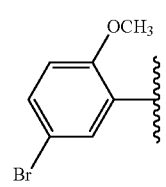 | H | CH3 | H | H |
| XA790 | CH3— | 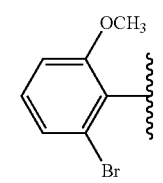 | H | CH3 | H | H |
| XA791 | CH3— | 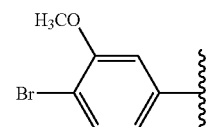 | H | CH3 | H | H |

-continued
| | | | | | | |
|---|---|---|---|---|---|---|
| XA792 | CH3— | 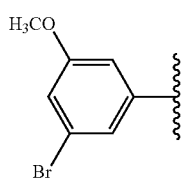 | H | CH3 | H | H |
| XA793 | CH3— | 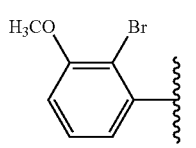 | H | CH3 | H | H |
| XA794 | CH3— |  | H | CH3 | H | H |
| XA795 | CH3— | 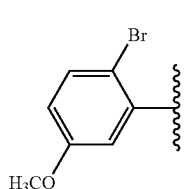 | H | CH3 | H | H |
| | | | | | | |
|---|---|---|---|---|---|---|
| XA796 | CH3— | 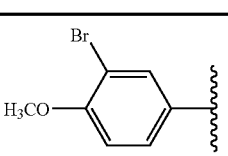 | H | CH3 | H | H |
| XA797 | CH3— | 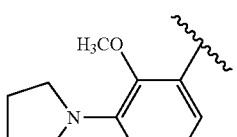 | H | CH3 | H | H |
| XA798 | CH3— | 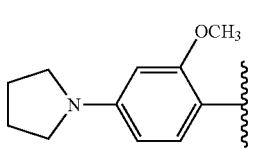 | H | CH3 | H | H |
| XA799 | CH3— | 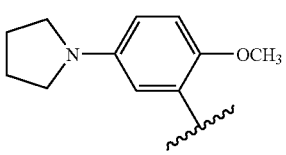 | H | CH3 | H | H |
| XA800 | CH3— | 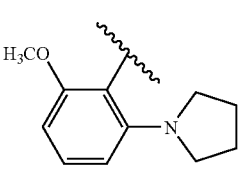 | H | CH3 | H | H |

-continued
| | | | | | | |
|---|---|---|---|---|---|---|
| XA801 | CH3— | 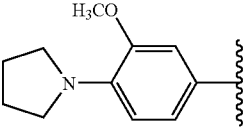 | H | CH3 | H | H |
| XA802 | CH3— | 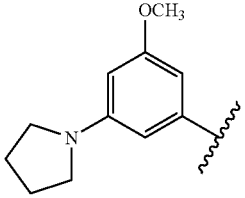 | H | CH3 | H | H |
| XA803 | CH3— | 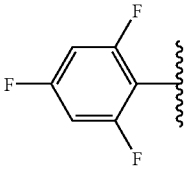 | H | CH3 | H | H |
| XA804 | CH3— | 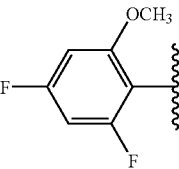 | H | CH3 | H | H |
| XA805 | CH3— | 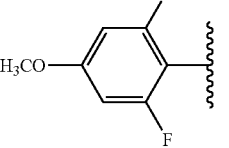 | H | CH3 | H | H |
| XA806 | CH3— | 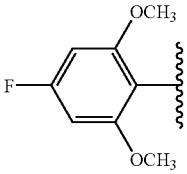 | H | CH3 | H | H |
| XA807 | CH3— | 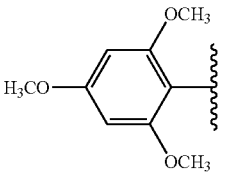 | H | CH3 | H | H |
| XA808 | CH3— | 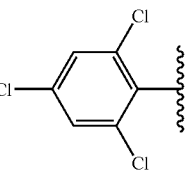 | H | CH3 | H | H |

-continued
| | | | | | | |
|---|---|---|---|---|---|---|
| XA809 | CH3— | 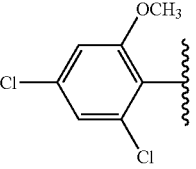 | H | CH3 | H | H |
| XA810 | CH3— | 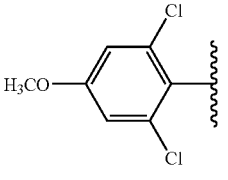 | H | CH3 | H | H |
| XA811 | CH3— | 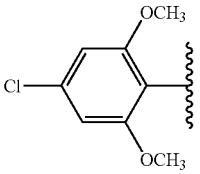 | H | CH3 | H | H |
| XA812 | CH3— | 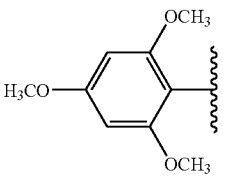 | H | CH3 | H | H |
| XA813 | CH3— | 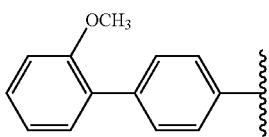 | H | CH3 | H | H |
| XA814 | CH3— | 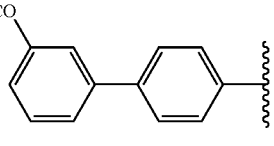 | H | CH3 | H | H |
| XA815 | CH3— | 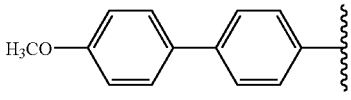 | H | CH3 | H | H |
| XA816 | CH3— | 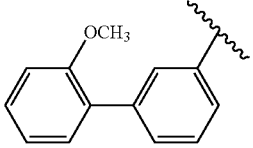 | H | CH3 | H | H |
| XA817 | CH3— | 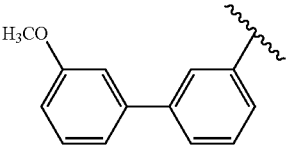 | H | CH3 | H | H |
| XA818 | CH3— | 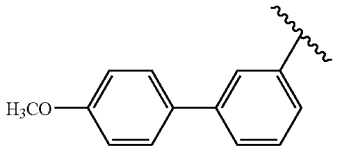 | H | CH3 | H | H |

-continued
| | | | | | | | |
|---|---|---|---|---|---|---|---|
| XA819 | CH3— | 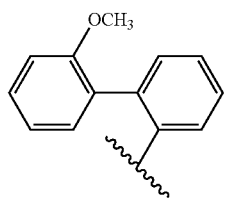 | H | CH3 | H | H | |
| XA820 | CH3— | 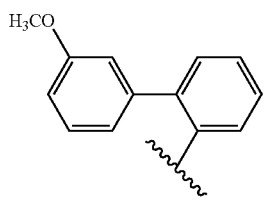 | H | CH3 | H | H | |
| XA821 | CH3— | 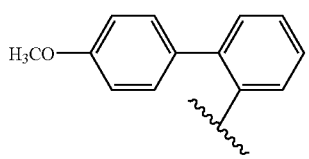 | H | CH3 | H | H | |
| XA822 | CH3— | 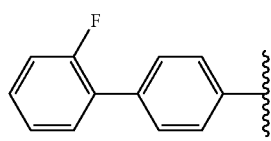 | H | CH3 | H | H | |
| XA823 | CH3— | 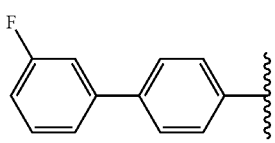 | H | CH3 | H | H | |
| XA824 | CH3— | 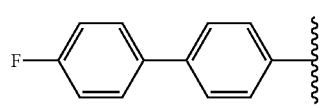 | H | CH3 | H | H | |
| XA825 | CH3— | 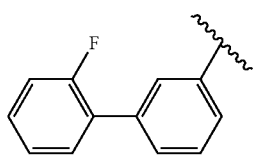 | H | CH3 | H | H | |
| XA826 | CH3— | 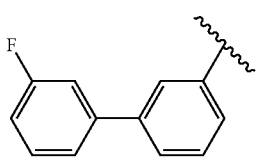 | H | CH3 | H | H | |
| XA827 | CH3— | 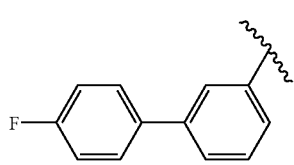 | H | CH3 | H | H | |

-continued
| | | | | | | |
|---|---|---|---|---|---|---|
| XA828 | CH3— | 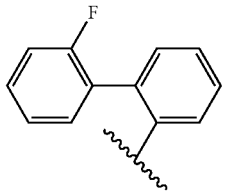 | H | CH3 | H | H |
| XA829 | CH3— | 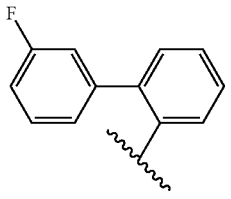 | H | CH3 | H | H |
| XA830 | CH3— | 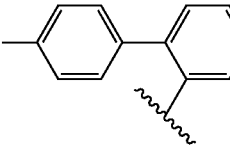 | H | CH3 | H | H |
| XA831 | CH3— | 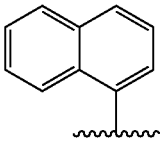 | H | CH3 | H | H |
| XA832 | CH3— | 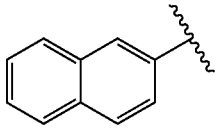 | H | CH3 | H | H |
| XA833 | CH3— | 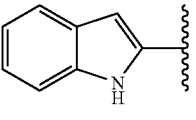 | H | CH3 | H | H |
| XA834 | CH3— | 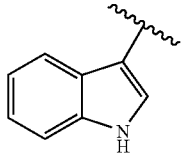 | H | CH3 | H | H |
| XA835 | CH3— | 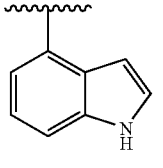 | H | CH3 | H | H |
| XA836 | CH3— | 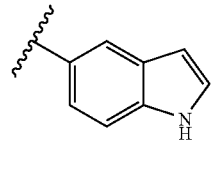 | H | CH3 | H | H |

-continued
| | | | | | | |
|---|---|---|---|---|---|---|
| XA837 | CH3— | 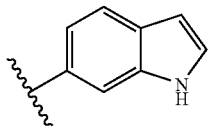 | H | CH3 | H | H |
| XA838 | CH3— | 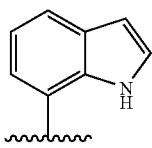 | H | CH3 | H | H |
| XA839 | CH3— | 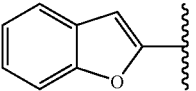 | H | CH3 | H | H |
| XA840 | CH3— | 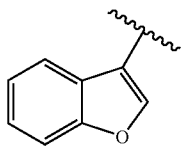 | H | CH3 | H | H |
| XA841 | CH3— | 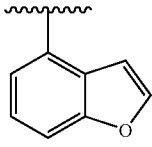 | H | CH3 | H | H |
| XA842 | CH3— | 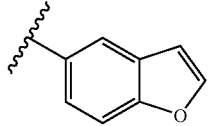 | H | CH3 | H | H |
| XA843 | CH3— | 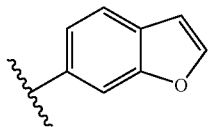 | H | CH3 | H | H |
| XA844 | CH3— | 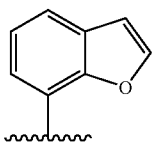 | H | CH3 | H | H |
| XA845 | CH3— | 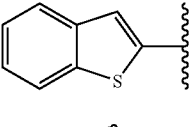 | H | CH3 | H | H |
| XA846 | CH3— | 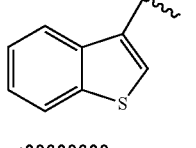 | H | CH3 | H | H |
| XA847 | CH3— | 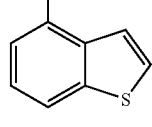 | H | CH3 | H | H |

-continued
| | | | | | | | |
|---|---|---|---|---|---|---|---|
| XA848 | CH3— | 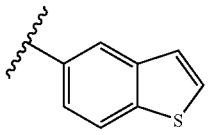 | H | CH3 | H | H | |
| XA849 | CH3— | 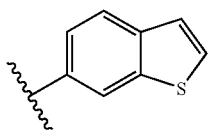 | H | CH3 | H | H | |
| XA850 | CH3— | 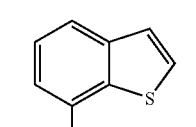 | H | CH3 | H | H | |
| XA851 | CH3— | 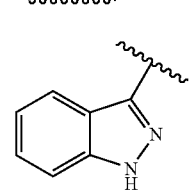 | H | CH3 | H | H | |
| XA852 | CH3— | 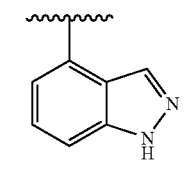 | H | CH3 | H | H | |
| XA853 | CH3— | 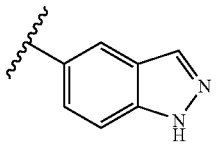 | H | CH3 | H | H | |
| XA854 | CH3— | 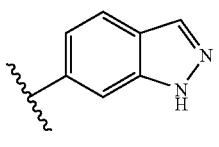 | H | CH3 | H | H | |
| XA855 | CH3— | 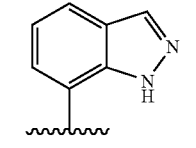 | H | CH3 | H | H | |
| XA856 | CH3— | 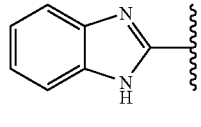 | H | CH3 | H | H | |
| XA857 | CH3— | 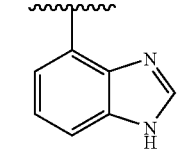 | H | CH3 | H | H | |

-continued
| | | | | | | | |
|---|---|---|---|---|---|---|---|
| XA858 | CH3— | 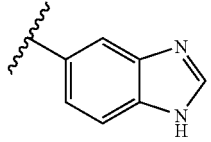 | H | CH3 | H | H | |
| XA859 | CH3— | 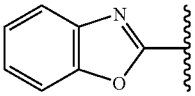 | H | CH3 | H | H | |
| XA860 | CH3— | 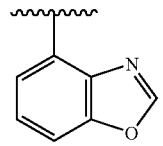 | H | CH3 | H | H | |
| XA861 | CH3— | 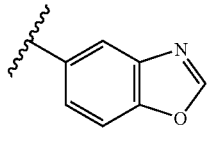 | H | CH3 | H | H | |
| XA862 | CH3— | 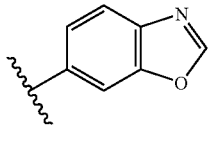 | H | CH3 | H | H | |
| XA863 | CH3— | 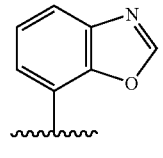 | H | CH3 | H | H | |
| XA864 | CH3— | 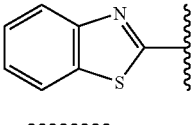 | H | CH3 | H | H | |
| XA865 | CH3— | 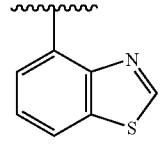 | H | CH3 | H | H | |
| XA866 | CH3— | 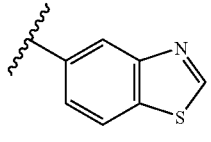 | H | CH3 | H | H | |
| XA867 | CH3— | 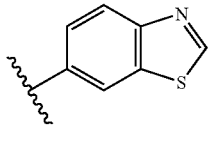 | H | CH3 | H | H | |
| XA868 | CH3— | 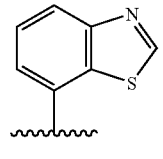 | H | CH3 | H | H | |

-continued
| | | | | | | |
|---|---|---|---|---|---|---|
| XA869 | CH3— | 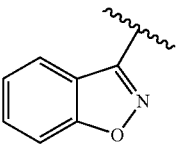 | H | CH3 | H | H |
| XA870 | CH3— | 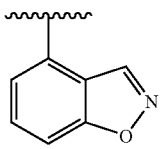 | H | CH3 | H | H |
| XA871 | CH3— | 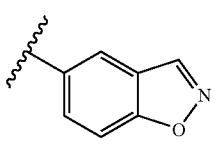 | H | CH3 | H | H |
| XA872 | CH3— | 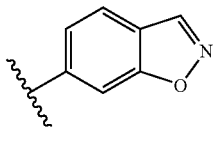 | H | CH3 | H | H |
| XA873 | CH3— | 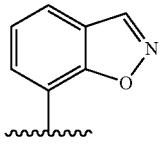 | H | CH3 | H | H |
| XA874 | CH3— | 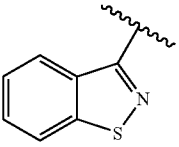 | H | CH3 | H | H |
| XA875 | CH3— | 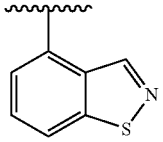 | H | CH3 | H | H |
| XA876 | CH3— | 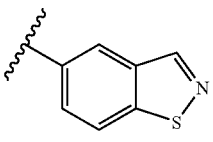 | H | CH3 | H | H |
| XA877 | CH3— | 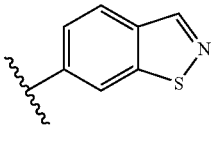 | H | CH3 | H | H |
| XA878 | CH3— | 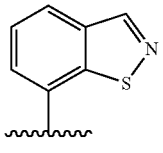 | H | CH3 | H | H |

-continued
| | | | | | | |
|---|---|---|---|---|---|---|
| XA879 | CH3— | 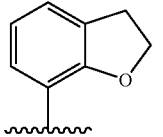 | H | CH3 | H | H |
| XA880 | CH3— | 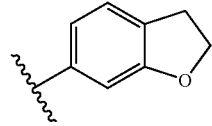 | H | CH3 | H | H |
| XA881 | CH3— | 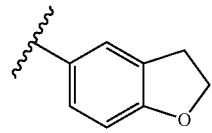 | H | CH3 | H | H |
| XA882 | CH3— | 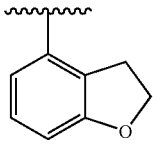 | H | CH3 | H | H |
| XA883 | CH3— | CH3— | H | 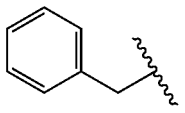 | H | H |
| XA884 | CH3— | CH3CH2— | H | 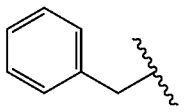 | H | H |
| XA885 | CH3— | 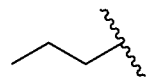 | H | 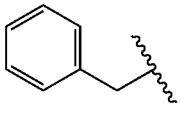 | H | H |
| XA886 | CH3— | 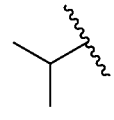 | H | 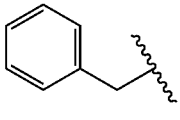 | H | H |
| XA887 | CH3— | 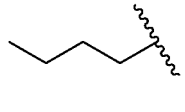 | H | 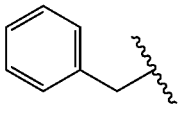 | H | H |
| XA888 | CH3— | 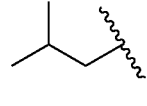 | H | 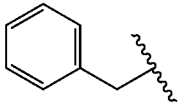 | H | H |
| XA889 | CH3— | 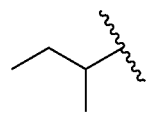 | H | 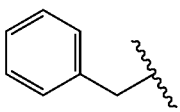 | H | H |
| XA890 | CH3— | 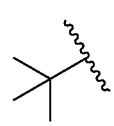 | H | 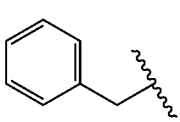 | H | H |

-continued
| | | | | | | |
|---|---|---|---|---|---|---|
| XA891 | CH3— | 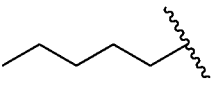 | H | 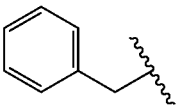 | H | H |
| XA892 | CH3— | 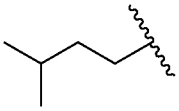 | H | 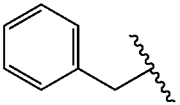 | H | H |
| XA893 | CH3— | 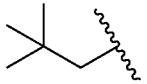 | H | 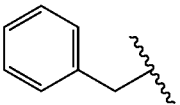 | H | H |
| XA894 | CH3— | 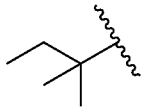 | H | 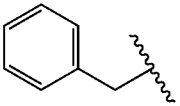 | H | H |
| XA895 | CH3— | 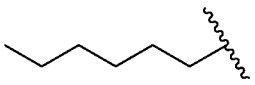 | H | 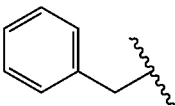 | H | H |
| XA896 | CH3— | 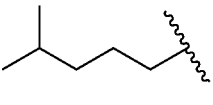 | H | 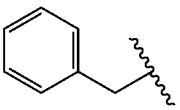 | H | H |
| XA897 | CH3— | 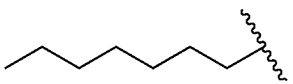 | H | 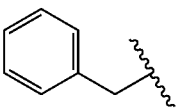 | H | H |
| XA898 | CH3— | 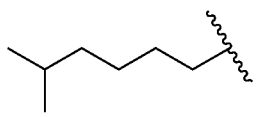 | H | 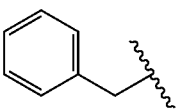 | H | H |
| XA899 | CH3— | n-C8H17— | H | 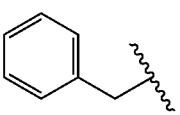 | H | H |
| XA900 | CH3— | 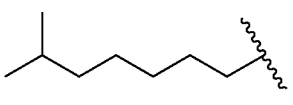 | H | 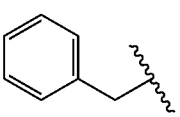 | H | H |
| XA901 | CH3— | 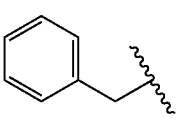 | H | 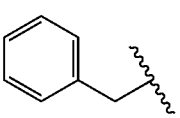 | H | H |
| XA902 | CH3— | 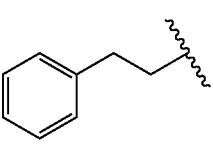 | H | 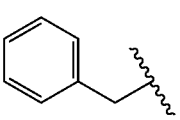 | H | H |

-continued
| | | | | | | |
|---|---|---|---|---|---|---|
| XA903 | CH3— | 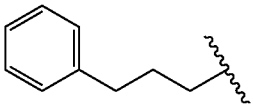 | H | 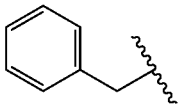 | H | H |
| XA904 | CH3— | 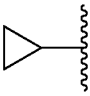 | H | 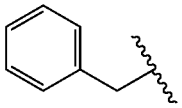 | H | H |
| XA905 | CH3— | 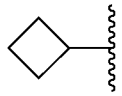 | H | 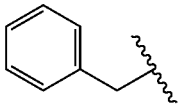 | H | H |
| XA906 | CH3— | 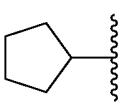 | H | 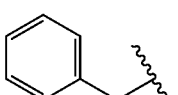 | H | H |
| XA907 | CH3— | 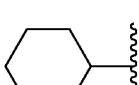 | H | 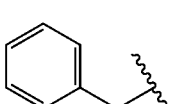 | H | H |
| XA908 | CH3— | 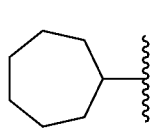 | H | 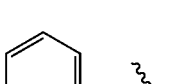 | H | H |
| XA909 | CH3— | 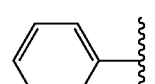 | H | 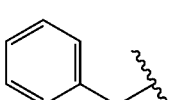 | H | H |
| XA910 | CH3— | 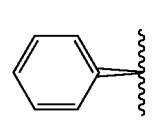 | H | 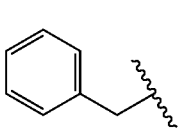 | H | H |
| XA911 | CH3— | 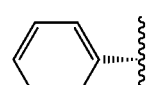 | H | 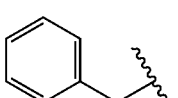 | H | H |
| XA912 | CH3— | 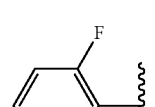 | H | 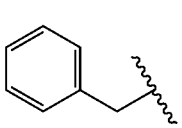 | H | H |
| XA913 | CH3— | 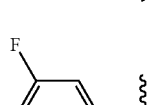 | H | 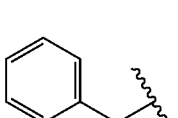 | H | H |
| XA914 | CH3— | 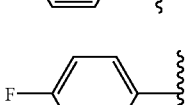 | H | 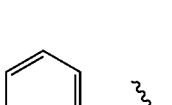 | H | H |

-continued
| | | | | | | |
|---|---|---|---|---|---|---|
| XA915 | CH3— | 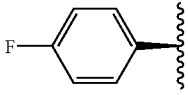 | H | 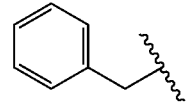 | H | H |
| XA916 | CH3— | 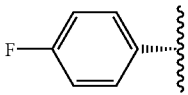 | H | 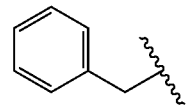 | H | H |
| XA917 | CH3— | 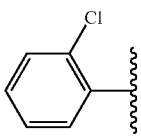 | H | 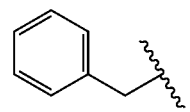 | H | H |
| XA918 | CH3— | 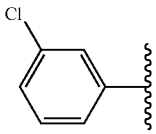 | H | 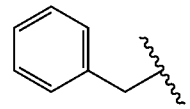 | H | H |
| XA919 | CH3— | 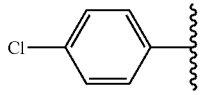 | H | 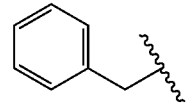 | H | H |
| XA920 | CH3— | 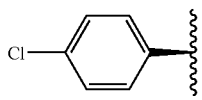 | H | 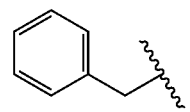 | H | H |
| XA921 | CH3— | 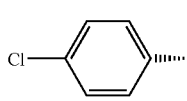 | H | 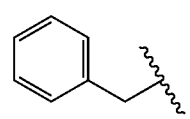 | H | H |
| XA922 | CH3— | 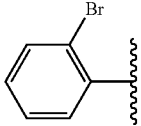 | H | 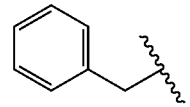 | H | H |
| XA923 | CH3— | 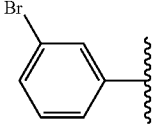 | H | 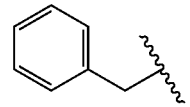 | H | H |
| XA924 | CH3— | 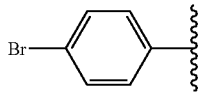 | H | 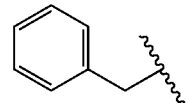 | H | H |
| XA925 | CH3— | 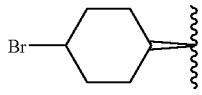 | H | 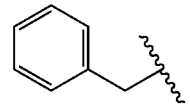 | H | H |
| XA926 | CH3— | 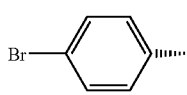 | H | 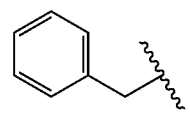 | H | H |

-continued
| | | | | | | |
|---|---|---|---|---|---|---|
| XA927 | CH3— | 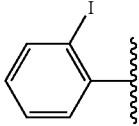 | H | 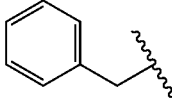 | H | H |
| XA928 | CH3— | 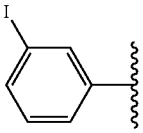 | H | 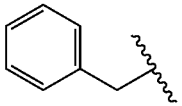 | H | H |
| XA929 | CH3— | 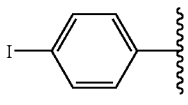 | H | 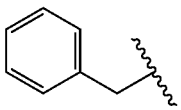 | H | H |
| XA930 | CH3— | 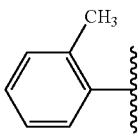 | H | 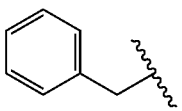 | H | H |
| XA931 | CH3— | 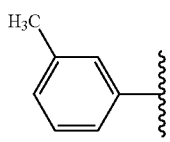 | H | 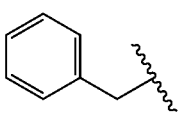 | H | H |
| XA932 | CH3— | 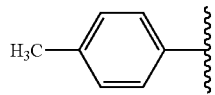 | H | 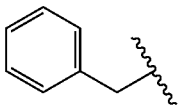 | H | H |
| XA933 | CH3— | 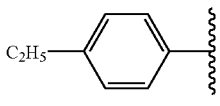 | H | 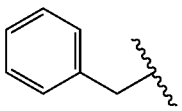 | H | H |
| XA934 | CH3— | 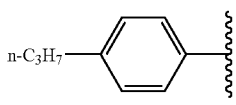 | H | 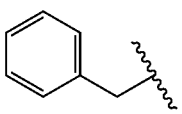 | H | H |
| XA935 | CH3— | 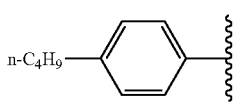 | H | 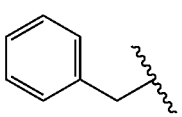 | H | H |
| XA936 | CH3— | 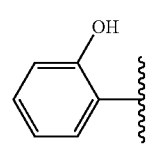 | H | 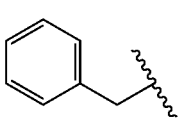 | H | H |
| XA937 | CH3— | 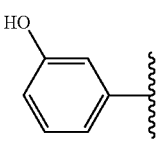 | H | 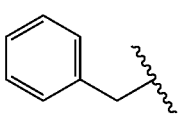 | H | H |

-continued
| | | | | | | |
|---|---|---|---|---|---|---|
| XA938 | CH3— | 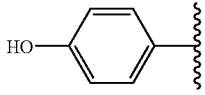 | H | 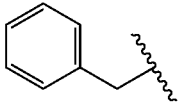 | H | H |
| XA939 | CH3— | 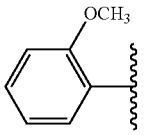 | H | 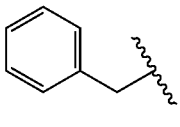 | H | H |
| XA940 | CH3— | 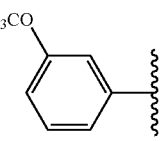 | H | 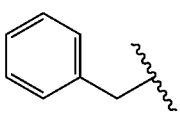 | H | H |
| XA941 | CH3— | 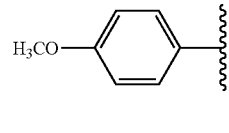 | H | 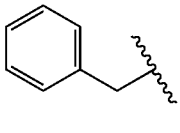 | H | H |
| XA942 | CH3— | 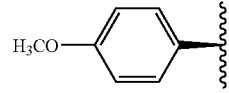 | H | 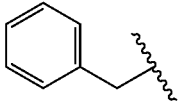 | H | H |
| XA943 | CH3— | 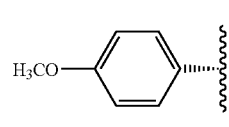 | H | 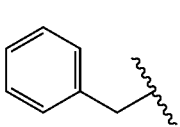 | H | H |
| XA944 | CH3— | 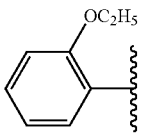 | H | 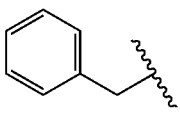 | H | H |
| XA945 | CH3— | 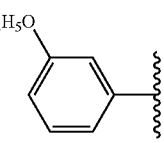 | H | 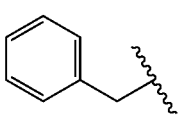 | H | H |
| XA946 | CH3— | 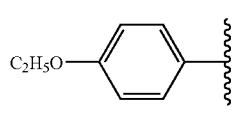 | H | 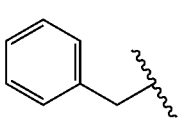 | H | H |
| XA947 | CH3— | 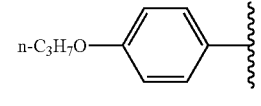 | H | 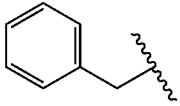 | H | H |
| XA948 | CH3— | 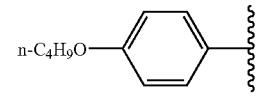 | H | 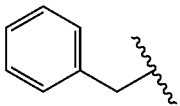 | H | H |
| XA949 | CH3— | 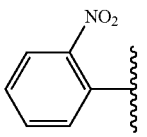 | H | 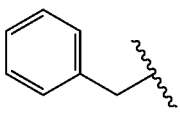 | H | H |

-continued
| | | | | | | |
|---|---|---|---|---|---|---|
| XA950 | CH3— | 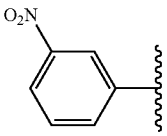 3-O2N-C6H4— | H | 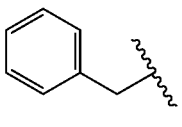 benzyl | H | H |
| XA951 | CH3— | 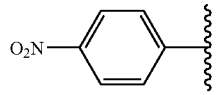 4-O2N-C6H4— | H | 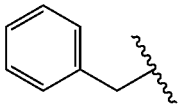 benzyl | H | H |
| XA952 | CH3— | 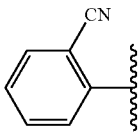 2-NC-C6H4— | H | 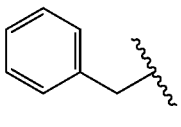 benzyl | H | H |
| XA953 | CH3— | 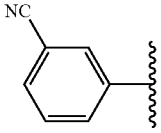 3-NC-C6H4— | H | 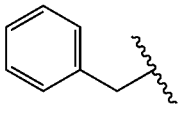 benzyl | H | H |
| XA954 | CH3— | 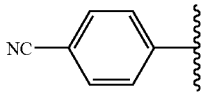 4-NC-C6H4— | H | 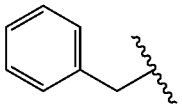 benzyl | H | H |
| XA955 | CH3— | 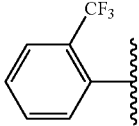 2-F3C-C6H4— | H | 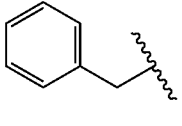 benzyl | H | H |
| XA956 | CH3— | 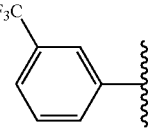 3-F3C-C6H4— | H | 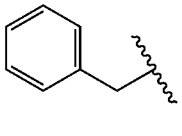 benzyl | H | H |
| XA957 | CH3— | 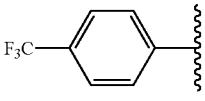 4-F3C-C6H4— | H | 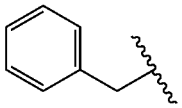 benzyl | H | H |
| XA958 | CH3— | 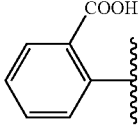 2-HOOC-C6H4— | H | 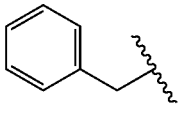 benzyl | H | H |
| XA959 | CH3— | 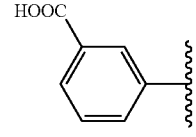 3-HOOC-C6H4— | H | 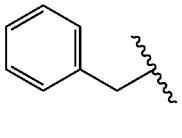 benzyl | H | H |
| XA960 | CH3— | 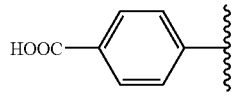 4-HOOC-C6H4— | H | 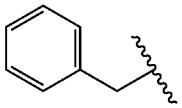 benzyl | H | H |

-continued
| | | | | | | |
|---|---|---|---|---|---|---|
| XA961 | CH3— | 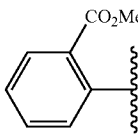 (2-CO2Me-C6H4-) | H | 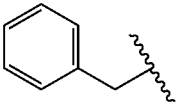 (benzyl) | H | H |
| XA962 | CH3— | 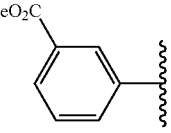 (3-MeO2C-C6H4-) | H | 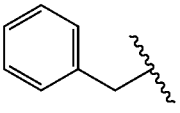 | H | H |
| XA963 | CH3— | 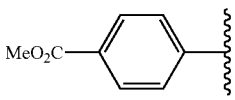 (4-MeO2C-C6H4-) | H | 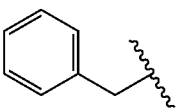 | H | H |
| XA964 | CH3— | 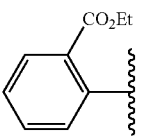 (2-CO2Et-C6H4-) | H | 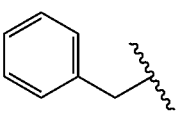 | H | H |
| XA965 | CH3— | 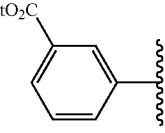 (3-EtO2C-C6H4-) | H | 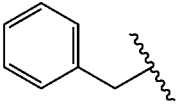 | H | H |
| XA966 | CH3— | 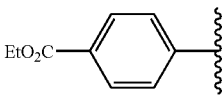 (4-EtO2C-C6H4-) | H | 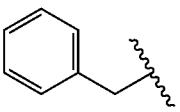 | H | H |
| XA967 | CH3— | 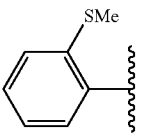 (2-SMe-C6H4-) | H | 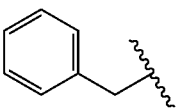 | H | H |
| XA968 | CH3— | 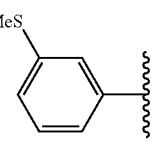 (3-MeS-C6H4-) | H | 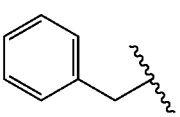 | H | H |
| XA969 | CH3— | 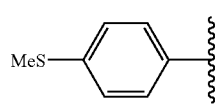 (4-MeS-C6H4-) | H | 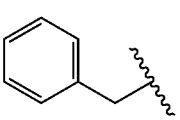 | H | H |
| XA970 | CH3— | 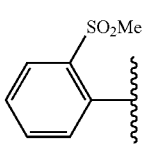 (2-SO2Me-C6H4-) | H | 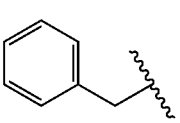 | H | H |
| XA971 | CH3— | 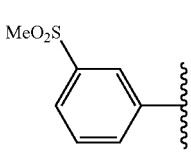 (3-MeO2S-C6H4-) | H | 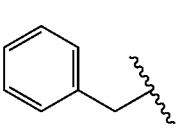 | H | H |

-continued
| | | | | | | |
|---|---|---|---|---|---|---|
| XA972 | CH3— | 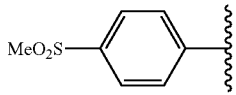 | H | 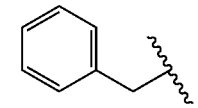 | H | H |
| XA973 | CH3— | 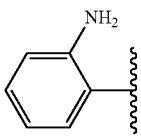 | H | 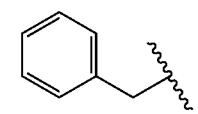 | H | H |
| XA974 | CH3— | 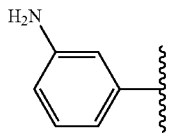 | H | 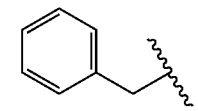 | H | H |
| XA975 | CH3— | 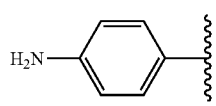 | H | 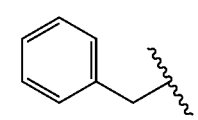 | H | H |
| XA976 | CH3— | 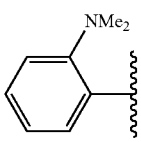 | H | 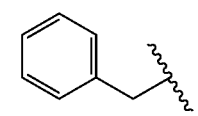 | H | H |
| XA977 | CH3— | 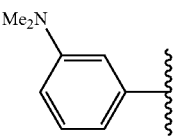 | H | 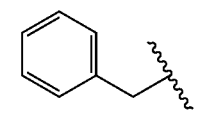 | H | H |
| XA978 | CH3— | 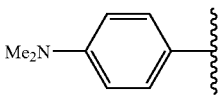 | H | 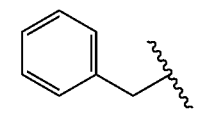 | H | H |
| XA979 | CH3— | 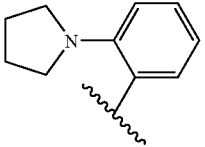 | H | 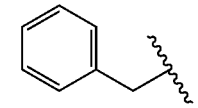 | H | H |
| XA980 | CH3— | 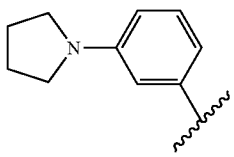 | H | 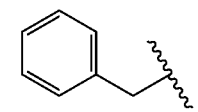 | H | H |
| XA981 | CH3— | 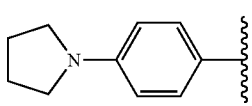 | H | 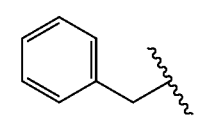 | H | H |
| XA982 | CH3— | 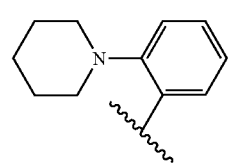 | H | 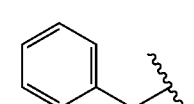 | H | H |

-continued
| | | | | | | |
|---|---|---|---|---|---|---|
| XA983 | CH3— | 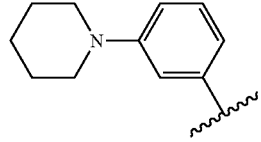 | H | 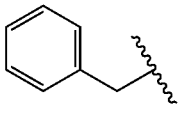 | H | H |
| XA984 | CH3— | 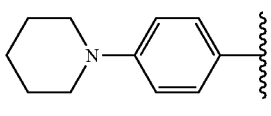 | H | 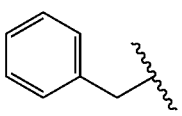 | H | H |
| XA985 | CH3— | 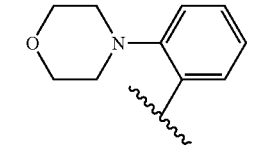 | H | 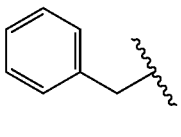 | H | H |
| XA986 | CH3— | 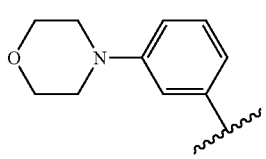 | H | 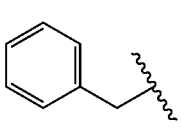 | H | H |
| XA987 | CH3— | 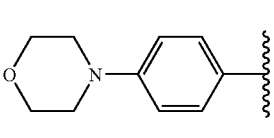 | H | 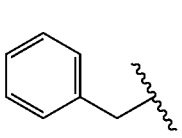 | H | H |
| XA988 | CH3— | 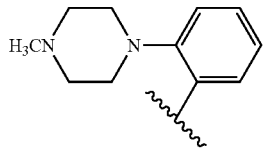 | H | 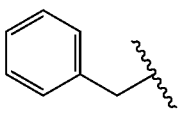 | H | H |
| XA989 | CH3— | 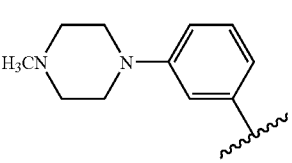 | H | 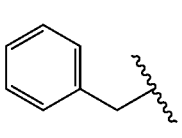 | H | H |
| XA990 | CH3— | 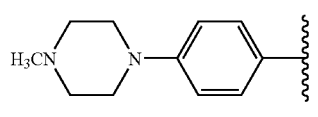 | H | 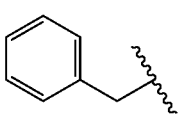 | H | H |
| XA991 | CH3— | 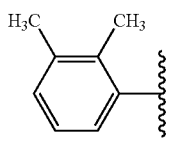 | H | 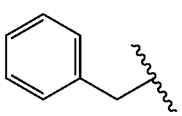 | H | H |
| XA992 | CH3— | 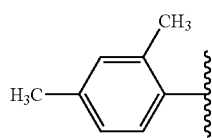 | H | 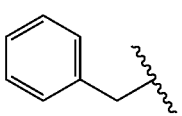 | H | H |

-continued
| | | | | | | |
|---|---|---|---|---|---|---|
| XA993 | CH3— | 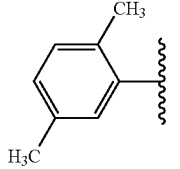 | H | 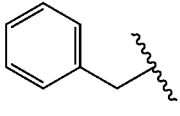 | H | H |
| XA994 | CH3— | 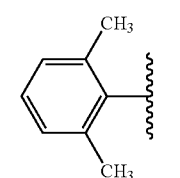 | H | 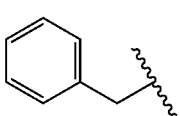 | H | H |
| XA995 | CH3— | 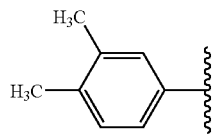 | H | 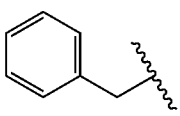 | H | H |
| XA996 | CH3— | 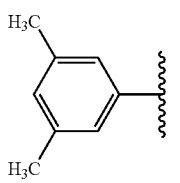 | H | 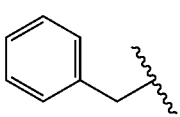 | H | H |
| XA997 | CH3— | 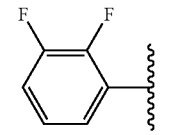 | H | 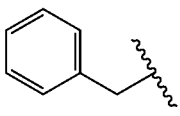 | H | H |
| XA998 | CH3— | 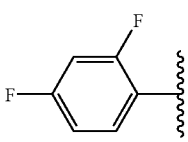 | H | 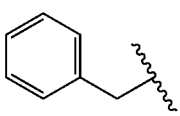 | H | H |
| XA999 | CH3— | 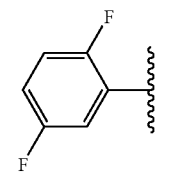 | H | 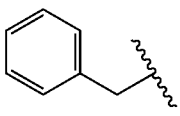 | H | H |
| XA1000 | CH3— | 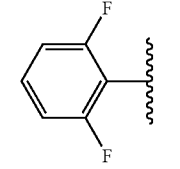 | H | 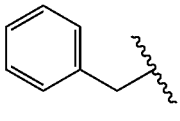 | H | H |
| XA1001 | CH3— | 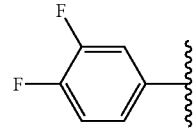 | H | 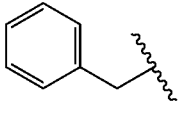 | H | H |

-continued
| | | | | | | |
|---|---|---|---|---|---|---|
| XA1002 | CH3— | 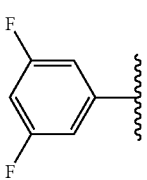 | H | 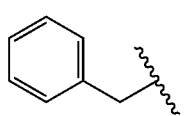 | H | H |
| XA1003 | CH3— | 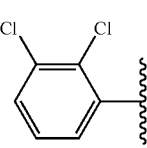 | H | 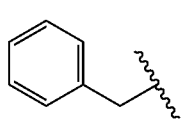 | H | H |
| XA1004 | CH3— | 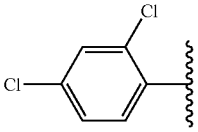 | H | 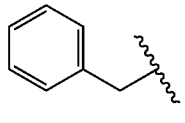 | H | H |
| XA1005 | CH3— | 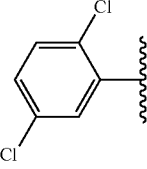 | H | 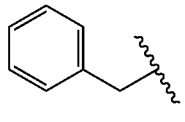 | H | H |
| XA1006 | CH3— | 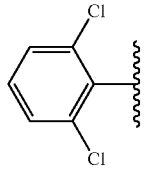 | H | 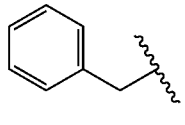 | H | H |
| XA1007 | CH3— | 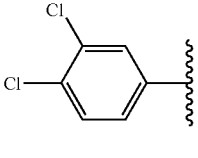 | H | 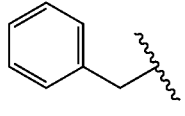 | H | H |
| XA1008 | CH3— | 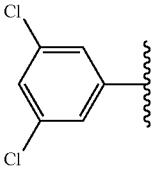 | H | 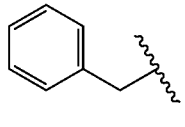 | H | H |
| XA1009 | CH3— | 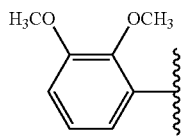 | H | 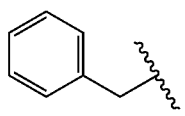 | H | H |
| XA1010 | CH3— | 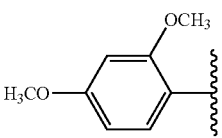 | H | 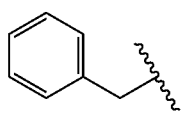 | H | H |

-continued
| | | | | | | |
|---|---|---|---|---|---|---|
| XA1011 | CH3— | 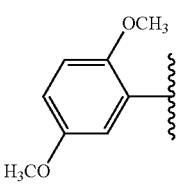 | H | 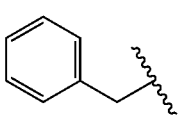 | H | H |
| XA1012 | CH3— | 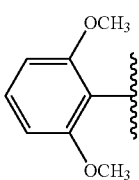 | H | 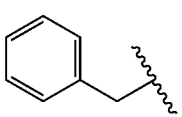 | H | H |
| XA1013 | CH3— | 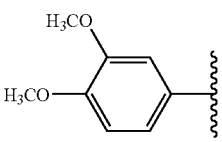 | H | 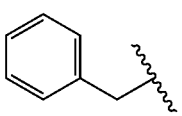 | H | H |
| XA1014 | CH3— | 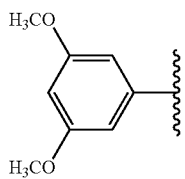 | H | 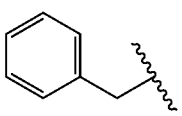 | H | H |
| XA1015 | CH3— | 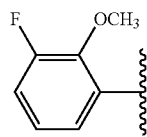 | H | 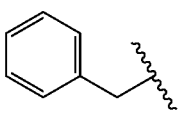 | H | H |
| XA1016 | CH3— | 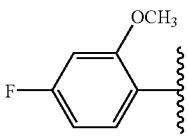 | H | 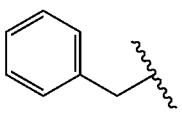 | H | H |
| XA1017 | CH3— | 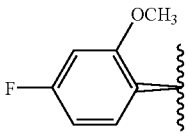 | H | 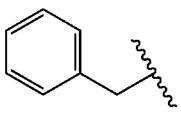 | H | H |
| XA1018 | CH3— | 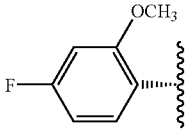 | H | 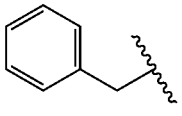 | H | H |
| XA1019 | CH3— | 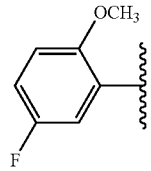 | H | 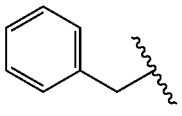 | H | H |

-continued
| | | | | | | |
|---|---|---|---|---|---|---|
| XA1020 | CH3— | 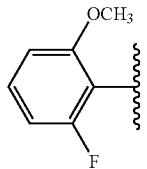 | H | 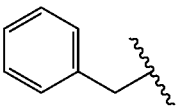 | H | H |
| XA1021 | CH3— | 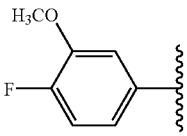 | H | 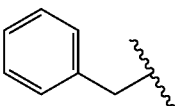 | H | H |
| XA1022 | CH3— | 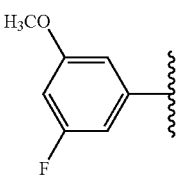 | H | 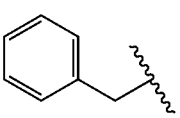 | H | H |
| XA1023 | CH3— | 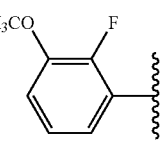 | H | 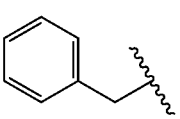 | H | H |
| XA1024 | CH3— | 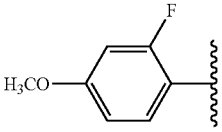 | H | 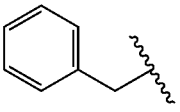 | H | H |
| XA1025 | CH3— | 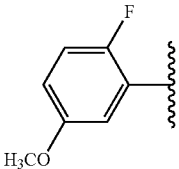 | H | 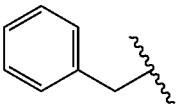 | H | H |
| XA1026 | CH3— | 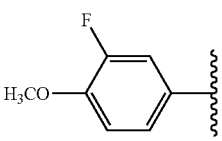 | H | 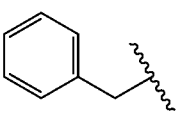 | H | H |
| XA1027 | CH3— | 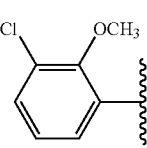 | H | 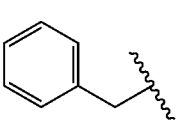 | H | H |
| XA1028 | CH3— | 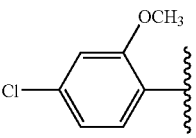 | H | 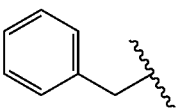 | H | H |
| XA1029 | CH3— | 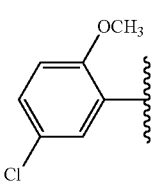 | H | 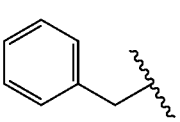 | H | H |

-continued
| | | | | | | |
|---|---|---|---|---|---|---|
| XA1030 | CH3— | 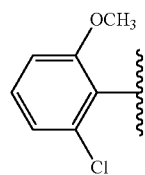 | H | 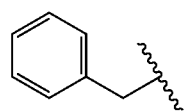 | H | H |
| XA1031 | CH3— | 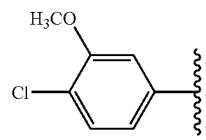 | H | 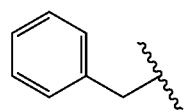 | H | H |
| XA1032 | CH3— | 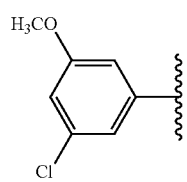 | H | 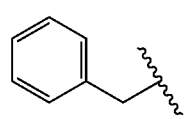 | H | H |
| XA1033 | CH3— | 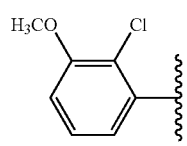 | H | 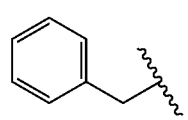 | H | H |
| XA1034 | CH3— | 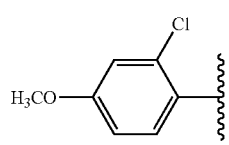 | H | 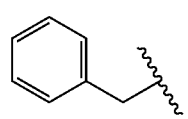 | H | H |
| XA1035 | CH3— | 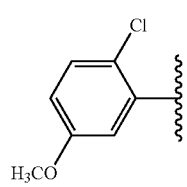 | H | 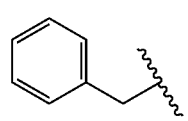 | H | H |
| XA1036 | CH3— | 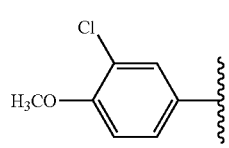 | H | 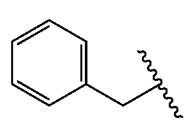 | H | H |
| XA1037 | CH3— | 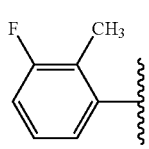 | H | 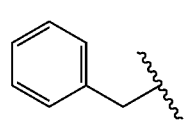 | H | H |
| XA1038 | CH3— | 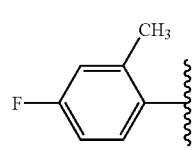 | H | 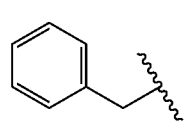 | H | H |

-continued
| | | | | | | |
|---|---|---|---|---|---|---|
| XA1039 | CH3— | 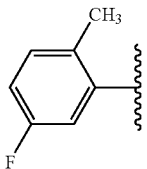 | H | 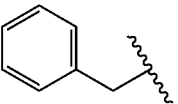 | H | H |
| XA1040 | CH3— | 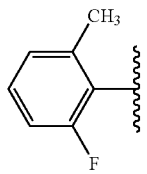 | H | 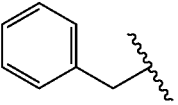 | H | H |
| XA1041 | CH3— | 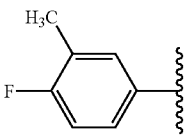 | H | 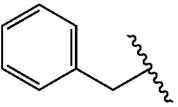 | H | H |
| XA1042 | CH3— | 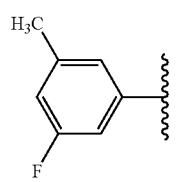 | H | 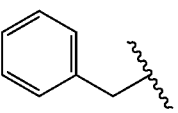 | H | H |
| XA1043 | CH3— | 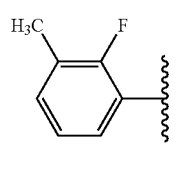 | H | 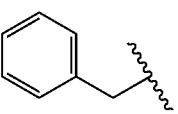 | H | H |
| XA1044 | CH3— | 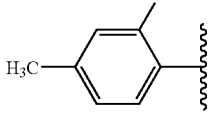 | H | 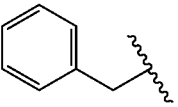 | H | H |
| XA1045 | CH3— | 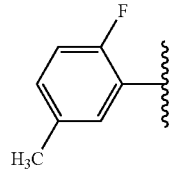 | H | 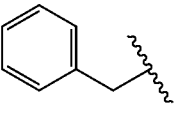 | H | H |
| XA1046 | CH3— | 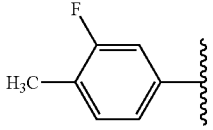 | H | 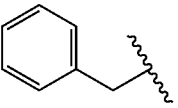 | H | H |
| XA1047 | CH3— | 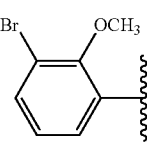 | H | 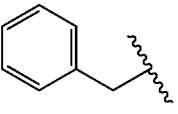 | H | H |
| XA1048 | CH3— | 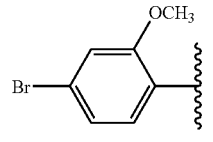 | H | 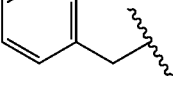 | H | H |

-continued
| | | | | | | |
|---|---|---|---|---|---|---|
| XA1049 | CH3— | 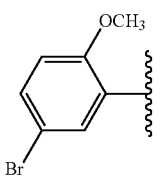 | H | 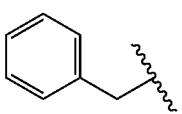 | H | H |
| XA1050 | CH3— | 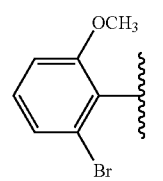 | H | 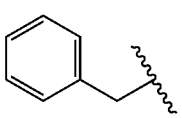 | H | H |
| XA1051 | CH3— | 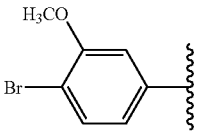 | H | 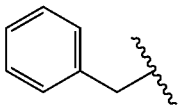 | H | H |
| XA1052 | CH3— | 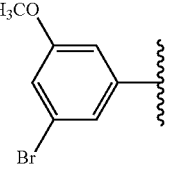 | H | 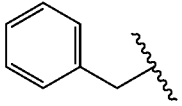 | H | H |
| XA1053 | CH3— | 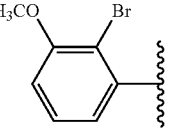 | H | 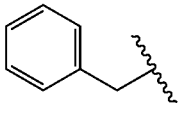 | H | H |
| XA1054 | CH3— | 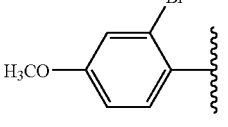 | H | 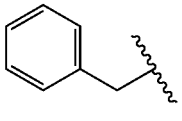 | H | H |
| XA1055 | CH3— | 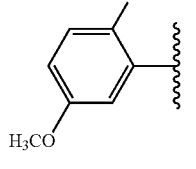 | H | 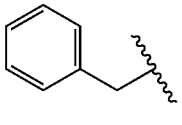 | H | H |
| XA1056 | CH3— | 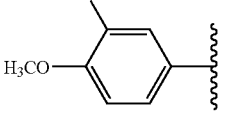 | H | 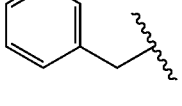 | H | H |
| XA1057 | CH3— | 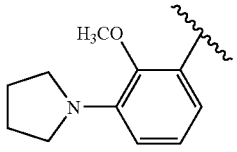 | H | 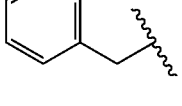 | H | H |

-continued
| | | | | | | |
|---|---|---|---|---|---|---|
| XA1058 | CH3— | 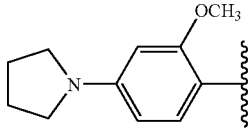 | H | 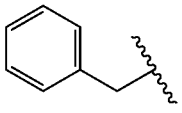 | H | H |
| XA1059 | CH3— | 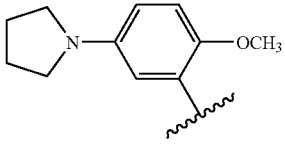 | H | 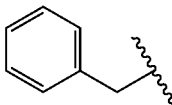 | H | H |
| XA1060 | CH3— | 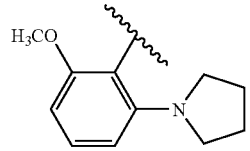 | H | 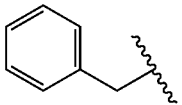 | H | H |
| XA1061 | CH3— | 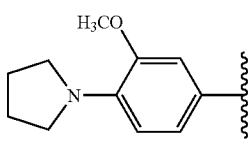 | H | 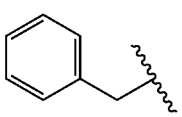 | H | H |
| XA1062 | CH3— | 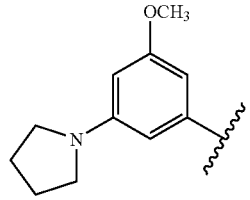 | H | 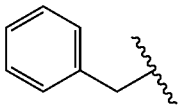 | H | H |
| XA1063 | CH3— | 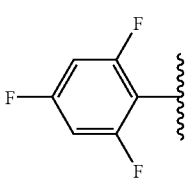 | H | 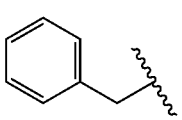 | H | H |
| XA1064 | CH3— | 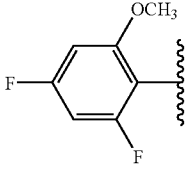 | H | 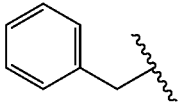 | H | H |
| XA1065 | CH3— | 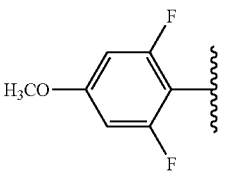 | H | 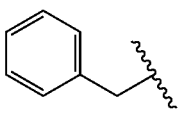 | H | H |
| XA1066 | CH3— | 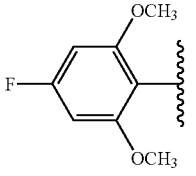 | H | 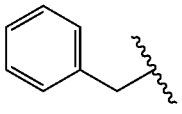 | H | H |

-continued
| | | | | | | |
|---|---|---|---|---|---|---|
| XA1067 | CH3— | 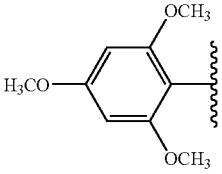 | H | 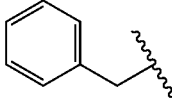 | H | H |
| XA1068 | CH3— | 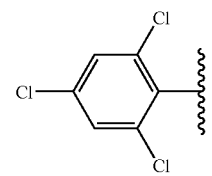 | H | 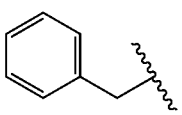 | H | H |
| XA1069 | CH3— | 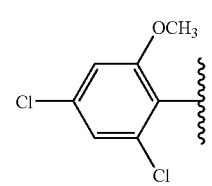 | H | 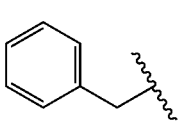 | H | H |
| XA1070 | CH3— | 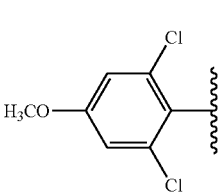 | H | 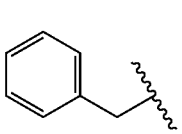 | H | H |
| XA1071 | CH3— | 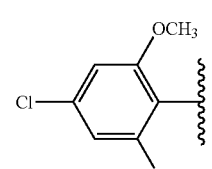 | H | 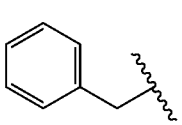 | H | H |
| XA1072 | CH3— | 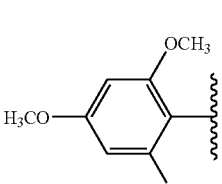 | H | 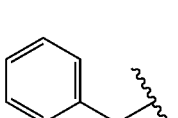 | H | H |
| XA1073 | CH3— | 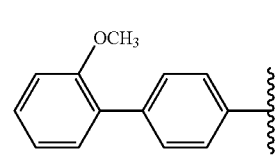 | H | 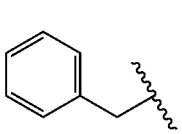 | H | H |
| XA1074 | CH3— | 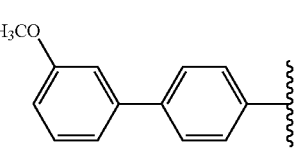 | H | 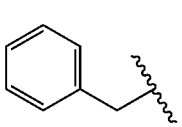 | H | H |
| XA1075 | CH3— | 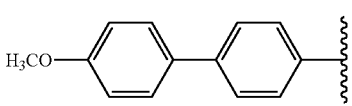 | H | 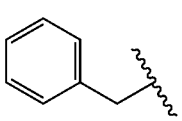 | H | H |

-continued

| | | | | | | |
|---|---|---|---|---|---|---|
| XA1076 | CH3— | 2'-methoxy-biphenyl-3-yl | H | benzyl | H | H |
| XA1077 | CH3— | 3'-methoxy-biphenyl-3-yl | H | benzyl | H | H |
| XA1078 | CH3— | 4'-methoxy-biphenyl-3-yl | H | benzyl | H | H |
| XA1079 | CH3— | 2'-methoxy-biphenyl-2-yl | H | benzyl | H | H |
| XA1080 | CH3— | 3'-methoxy-biphenyl-2-yl | H | benzyl | H | H |
| XA1081 | CH3— | 4'-methoxy-biphenyl-2-yl | H | benzyl | H | H |
| XA1082 | CH3— | 2'-fluoro-biphenyl-4-yl | H | benzyl | H | H |
| XA1083 | CH3— | 3'-fluoro-biphenyl-4-yl | H | benzyl | H | H |
| XA1084 | CH3— | 4'-fluoro-biphenyl-4-yl | H | benzyl | H | H |

-continued
| | | | | | | |
|---|---|---|---|---|---|---|
| XA1085 | CH3— | 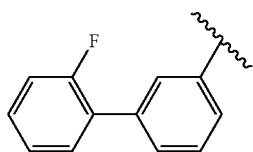 | H | 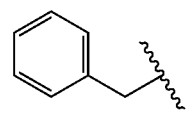 | H | H |
| XA1086 | CH3— | 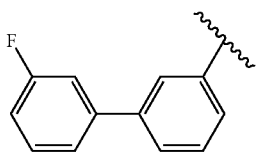 | H | 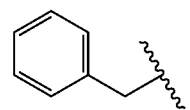 | H | H |
| XA1087 | CH3— | 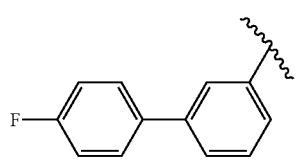 | H | 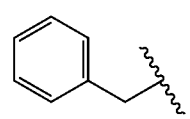 | H | H |
| XA1088 | CH3— | 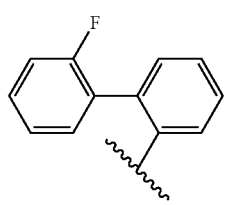 | H | 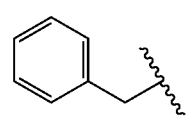 | H | H |
| XA1089 | CH3— | 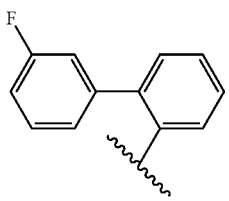 | H | 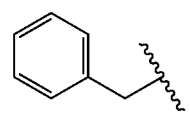 | H | H |
| XA1090 | CH3— | 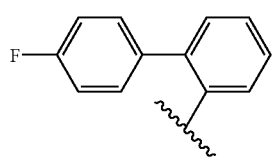 | H | 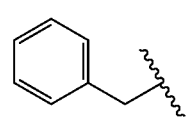 | H | H |
| XA1091 | CH3— | 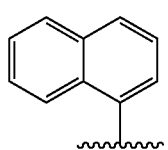 | H | 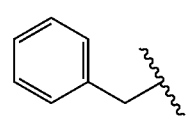 | H | H |
| XA1092 | CH3— | 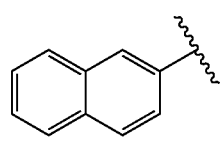 | H | 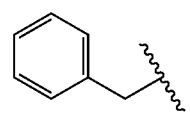 | H | H |
| XA1093 | CH3— | 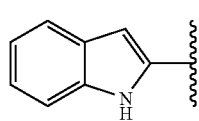 | H | 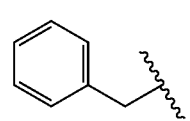 | H | H |

-continued
| | | | | | | |
|---|---|---|---|---|---|---|
| XA1094 | CH3— | 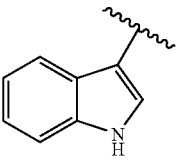 | H | 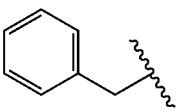 | H | H |
| XA1095 | CH3— | 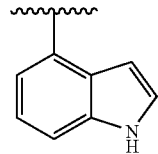 | H | 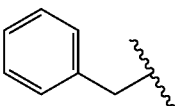 | H | H |
| XA1096 | CH3— | 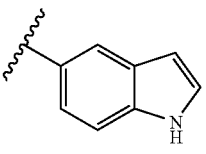 | H | 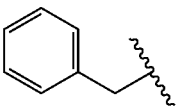 | H | H |
| XA1097 | CH3— | 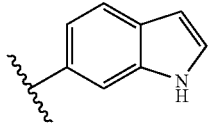 | H | 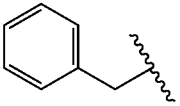 | H | H |
| XA1098 | CH3— | 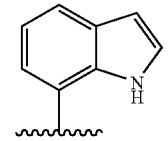 | H | 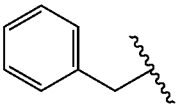 | H | H |
| XA1099 | CH3— | 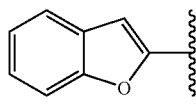 | H | 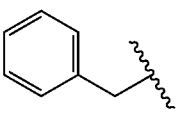 | H | H |
| XA1100 | CH3— | 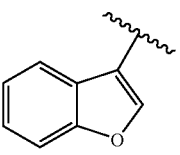 | H | 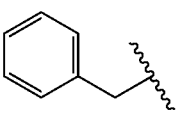 | H | H |
| XA1101 | CH3— | 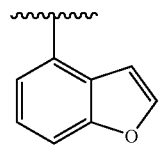 | H | 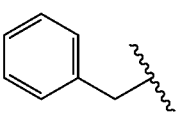 | H | H |
| XA1102 | CH3— | 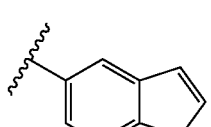 | H | 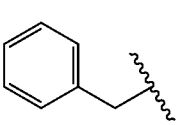 | H | H |
| XA1103 | CH3— | 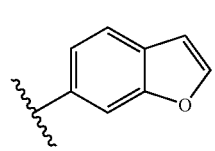 | H | 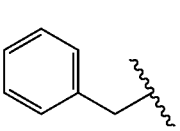 | H | H |

-continued
| | | | | | | |
|---|---|---|---|---|---|---|
| XA1104 | CH3— | 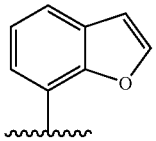 | H | 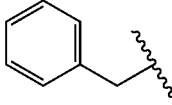 | H | H |
| XA1105 | CH3— | 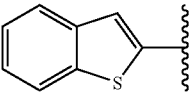 | H | 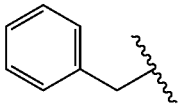 | H | H |
| XA1106 | CH3— | 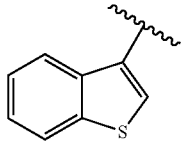 | H | 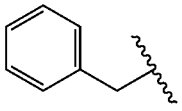 | H | H |
| XA1107 | CH3— | 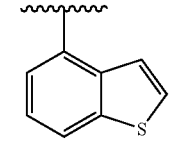 | H | 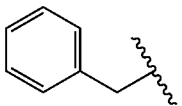 | H | H |
| XA1108 | CH3— | 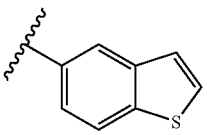 | H | 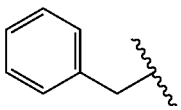 | H | H |
| XA1109 | CH3— | 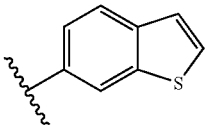 | H | 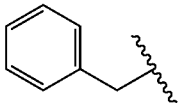 | H | H |
| XA1110 | CH3— | 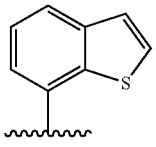 | H | 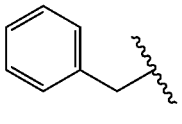 | H | H |
| XA1111 | CH3— | 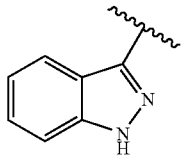 | H | 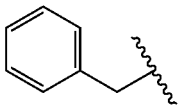 | H | H |
| XA1112 | CH3— | 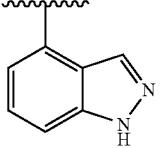 | H | 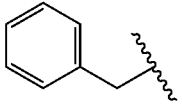 | H | H |
| XA1113 | CH3— | 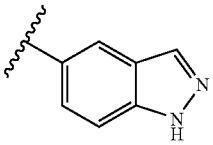 | H | 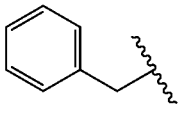 | H | H |

-continued
| | | | | | | | |
|---|---|---|---|---|---|---|---|
| XA1114 | CH3— | 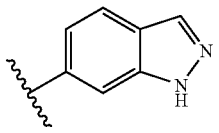 | H | 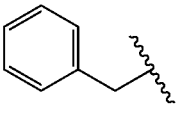 | H | H | |
| XA1115 | CH3— | 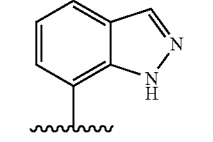 | H | 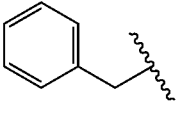 | H | H | |
| XA1116 | CH3— | 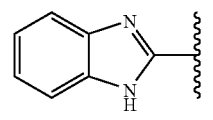 | H | 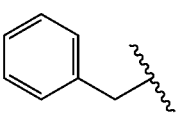 | H | H | |
| XA1117 | CH3— | 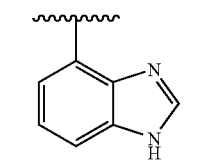 | H | 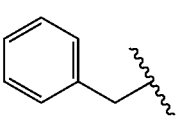 | H | H | |
| XA1118 | CH3— | 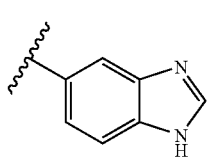 | H | 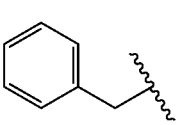 | H | H | |
| XA1119 | CH3— | 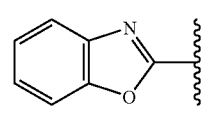 | H | 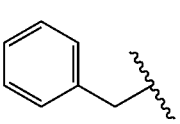 | H | H | |
| XA1120 | CH3— | 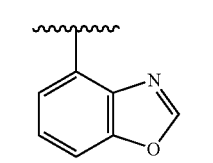 | H | 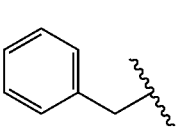 | H | H | |
| XA1121 | CH3— | 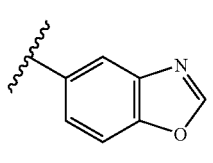 | H | 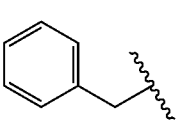 | H | H | |
| XA1122 | CH3— | 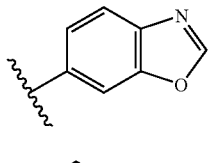 | H | 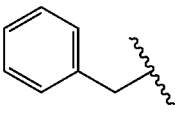 | H | H | |
| XA1123 | CH3— | 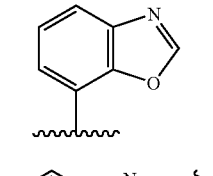 | H | 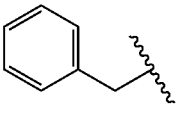 | H | H | |
| XA1124 | CH3— | 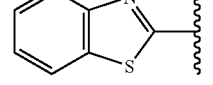 | H | 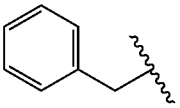 | H | H | |

-continued
| | | | | | | |
|---|---|---|---|---|---|---|
| XA1125 | CH3— | 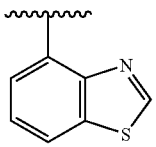 | H |  | H | H |
| XA1126 | CH3— | 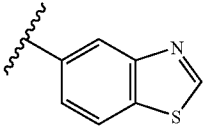 | H | 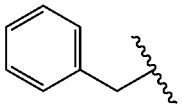 | H | H |
| XA1127 | CH3— |  | H | 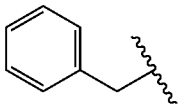 | H | H |
| XA1128 | CH3— | 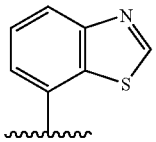 | H | 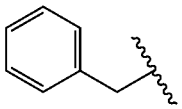 | H | H |
| XA1129 | CH3— | 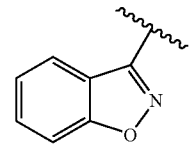 | H | 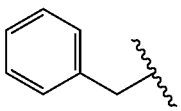 | H | H |
| XA1130 | CH3— | 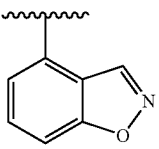 | H | 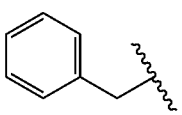 | H | H |
| XA1131 | CH3— | 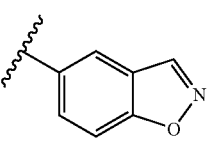 | H | 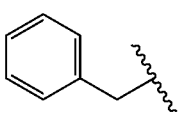 | H | H |
| XA1132 | CH3— | 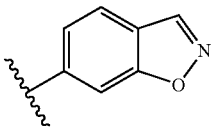 | H | 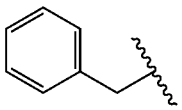 | H | H |
| XA1133 | CH3— | 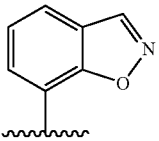 | H | 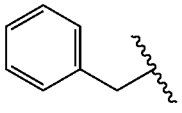 | H | H |
| XA1134 | CH3— | 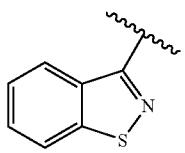 | H | 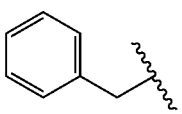 | H | H |

-continued
| | | | | | | |
|---|---|---|---|---|---|---|
| XA1135 | CH3— | 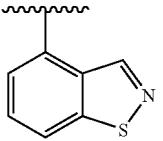 | H | 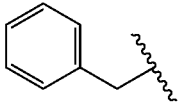 | H | H |
| XA1136 | CH3— | 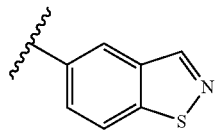 | H | 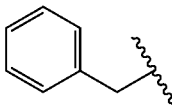 | H | H |
| XA1137 | CH3— | 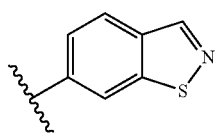 | H | 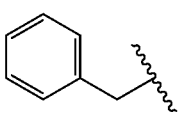 | H | H |
| XA1138 | CH3— |  | H | 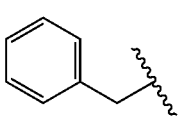 | H | H |
| XA1139 | CH3— | 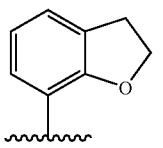 | H | 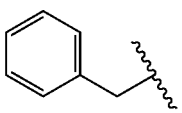 | H | H |
| XA1140 | CH3— | 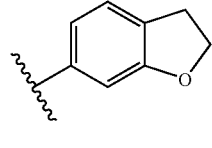 | H | 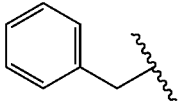 | H | H |
| XA1141 | CH3— | 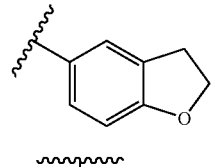 | H | 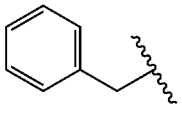 | H | H |
| XA1142 | CH3— | 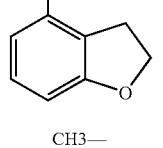 | H | 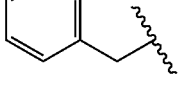 | H | H |
| XA1143 | CH3— | CH3— | H | 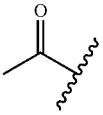 | H | H |
| XA1144 | CH3— | CH3CH2— | H | 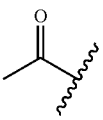 | H | H |
| XA1145 | CH3— | 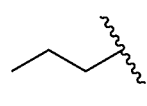 | H | 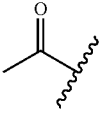 | H | H |

-continued
| | | | | | | |
|---|---|---|---|---|---|---|
| XA1146 | CH3— | 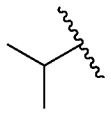 | H | 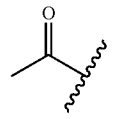 | H | H |
| XA1147 | CH3— | 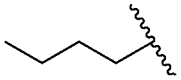 | H | 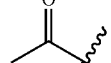 | H | H |
| XA1148 | CH3— | 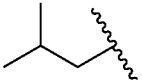 | H | 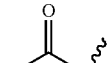 | H | H |
| XA1149 | CH3— | 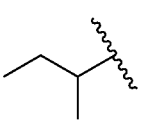 | H | 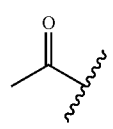 | H | H |
| XA1150 | CH3— | 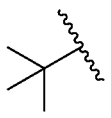 | H | 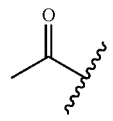 | H | H |
| XA1151 | CH3— | 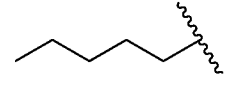 | H | 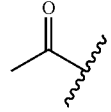 | H | H |
| XA1152 | CH3— | 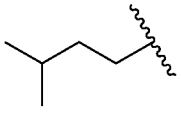 | H | 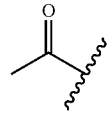 | H | H |
| XA1153 | CH3— | 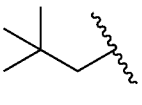 | H | 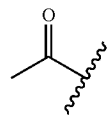 | H | H |
| XA1154 | CH3— | 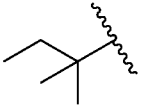 | H | 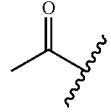 | H | H |
| XA1155 | CH3— | 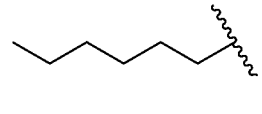 | H | 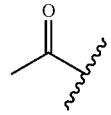 | H | H |
| XA1156 | CH3— | 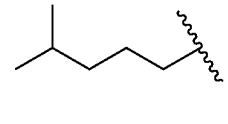 | H | 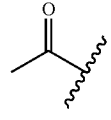 | H | H |
| XA1157 | CH3— | 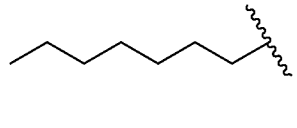 | H | 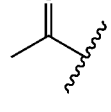 | H | H |

-continued
| | | | | | | |
|---|---|---|---|---|---|---|
| XA1158 | CH3— | 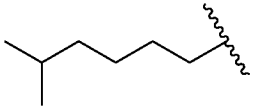 | H | 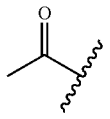 | H | H |
| XA1159 | CH3— | n-C8H17— | H | 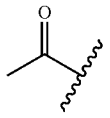 | H | H |
| XA1160 | CH3— | 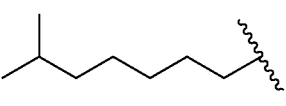 | H | 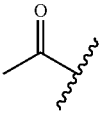 | H | H |
| XA1161 | CH3— | 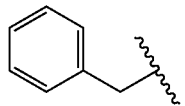 | H | 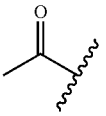 | H | H |
| XA1162 | CH3— | 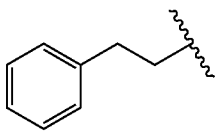 | H | 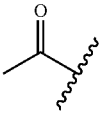 | H | H |
| XA1163 | CH3— | 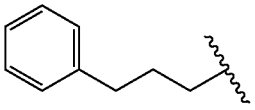 | H | 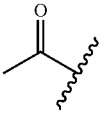 | H | H |
| XA1164 | CH3— | 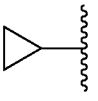 | H | 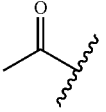 | H | H |
| XA1165 | CH3— | 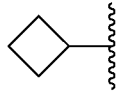 | H | 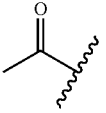 | H | H |
| XA1166 | CH3— | 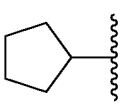 | H | 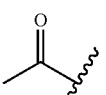 | H | H |
| XA1167 | CH3— | 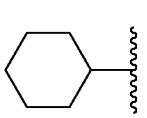 | H | 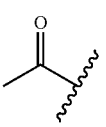 | H | H |
| XA1168 | CH3— | 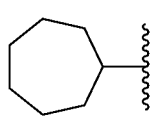 | H | 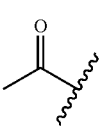 | H | H |
| XA1169 | CH3— | 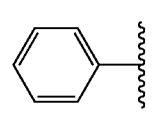 | H | 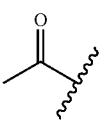 | H | H |

-continued
| | | | | | | |
|---|---|---|---|---|---|---|
| XA1170 | CH3— | 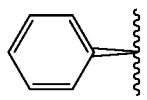 | H | 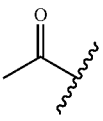 | H | H |
| XA1171 | CH3— | 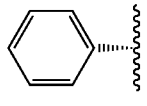 | H | 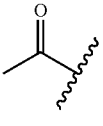 | H | H |
| XA1172 | CH3— | 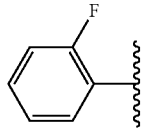 | H | 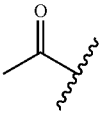 | H | H |
| XA1173 | CH3— | 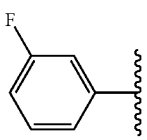 | H | 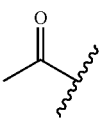 | H | H |
| XA1174 | CH3— | 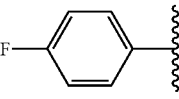 | H | 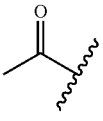 | H | H |
| XA1175 | CH3— |  | H | 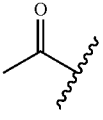 | H | H |
| XA1176 | CH3— | 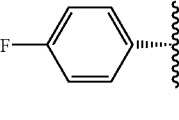 | H | 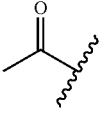 | H | H |
| XA1177 | CH3— | 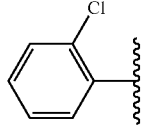 | H | 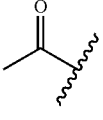 | H | H |
| XA1178 | CH3— | 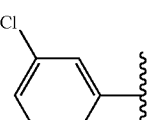 | H | 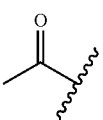 | H | H |
| XA1179 | CH3— | 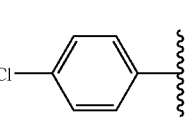 | H | 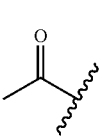 | H | H |
| XA1180 | CH3— | 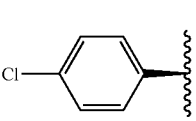 | H | 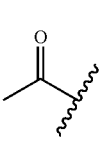 | H | H |

-continued
| | | | | | | |
|---|---|---|---|---|---|---|
| XA1181 | CH3— | 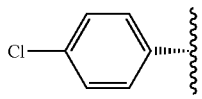 | H | 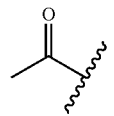 | H | H |
| XA1182 | CH3— | 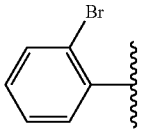 | H | 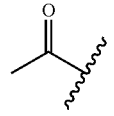 | H | H |
| XA1183 | CH3— | 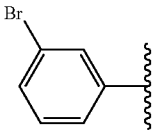 | H | 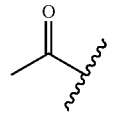 | H | H |
| XA1184 | CH3— | 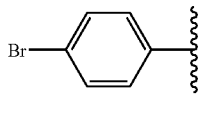 | H | 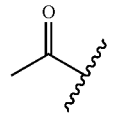 | H | H |
| XA1185 | CH3— | 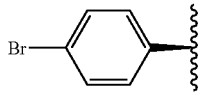 | H | 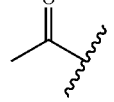 | H | H |
| XA1186 | CH3— | 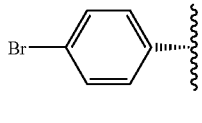 | H | 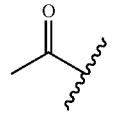 | H | H |
| XA1187 | CH3— | 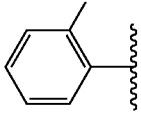 | H | 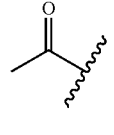 | H | H |
| XA1188 | CH3— | 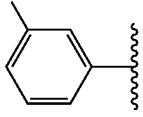 | H | 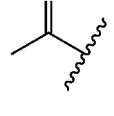 | H | H |
| XA1189 | CH3— | 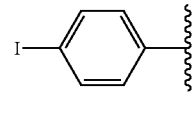 | H | 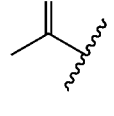 | H | H |
| XA1190 | CH3— | 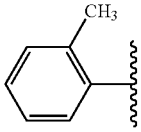 | H | 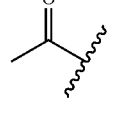 | H | H |
| XA1191 | CH3— | 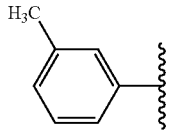 | H | 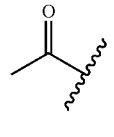 | H | H |

-continued
| | | | | | | |
|---|---|---|---|---|---|---|
| XA1192 | CH3— | 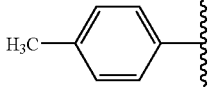 | H | 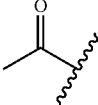 | H | H |
| XA1193 | CH3— | 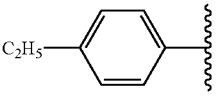 | H | 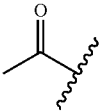 | H | H |
| XA1194 | CH3— | 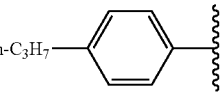 | H | 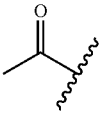 | H | H |
| XA1195 | CH3— | 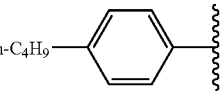 | H | 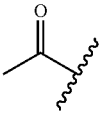 | H | H |
| XA1196 | CH3— | 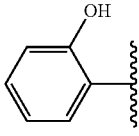 | H | 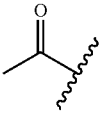 | H | H |
| XA1197 | CH3— | 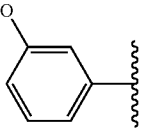 | H | 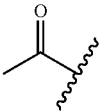 | H | H |
| XA1198 | CH3— | 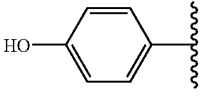 | H | 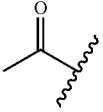 | H | H |
| XA1199 | CH3— | 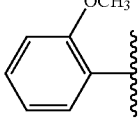 | H | 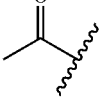 | H | H |
| XA1200 | CH3— | 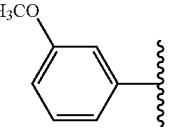 | H | 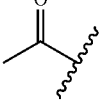 | H | H |
| XA1201 | CH3— | 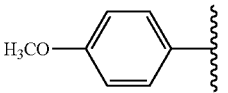 | H | 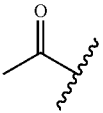 | H | H |
| XA1202 | CH3— | 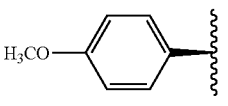 | H | 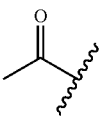 | H | H |

| | | | | -continued | | | |
|---|---|---|---|---|---|---|---|
| XA1203 | CH3— | 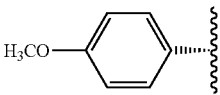 | | H | 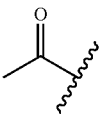 | H | H |
| XA1204 | CH3— | 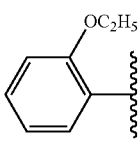 | | H | 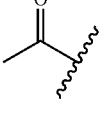 | H | H |
| XA1205 | CH3— | 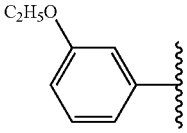 | | H | 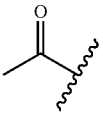 | H | H |
| XA1206 | CH3— | 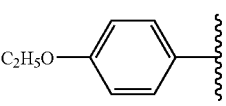 | | H | 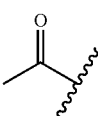 | H | H |
| XA1207 | CH3— | 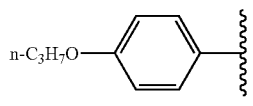 | | H | 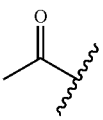 | H | H |
| XA1208 | CH3— | 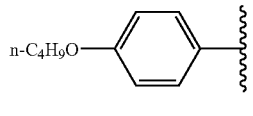 | | H | 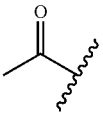 | H | H |
| XA1209 | CH3— | 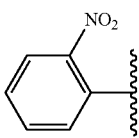 | | H | 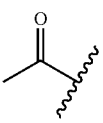 | H | H |
| XA1210 | CH3— | 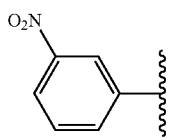 | | H | 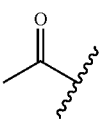 | H | H |
| XA1211 | CH3— | 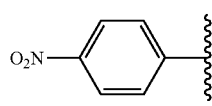 | | H | 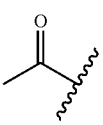 | H | H |
| XA1212 | CH3— | 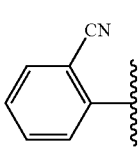 | | H | 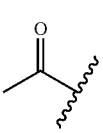 | H | H |
| XA1213 | CH3— | 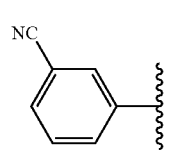 | | H | 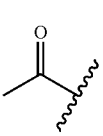 | H | H |

-continued
| | | | | | | |
|---|---|---|---|---|---|---|
| XA1214 | CH3— | 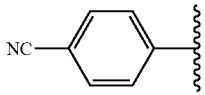 4-NC-C6H4- | H | 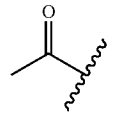 C(=O)CH3 | H | H |
| XA1215 | CH3— | 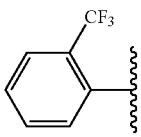 2-CF3-C6H4- | H | 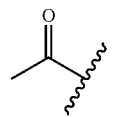 C(=O)CH3 | H | H |
| XA1216 | CH3— | 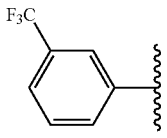 3-CF3-C6H4- | H | 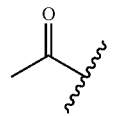 C(=O)CH3 | H | H |
| XA1217 | CH3— | 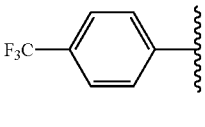 4-CF3-C6H4- | H | 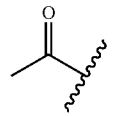 C(=O)CH3 | H | H |
| XA1218 | CH3— | 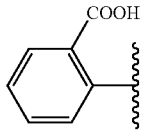 2-HOOC-C6H4- | H | 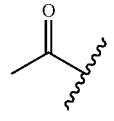 C(=O)CH3 | H | H |
| XA1219 | CH3— | 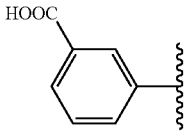 3-HOOC-C6H4- | H | 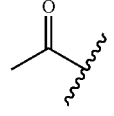 C(=O)CH3 | H | H |
| XA1220 | CH3— | 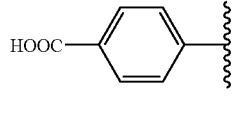 4-HOOC-C6H4- | H | 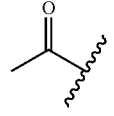 C(=O)CH3 | H | H |
| XA1221 | CH3— | 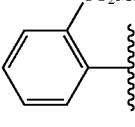 2-MeO2C-C6H4- | H | 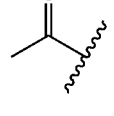 C(=O)CH3 | H | H |
| XA1222 | CH3— | 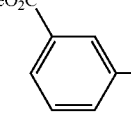 3-MeO2C-C6H4- | H | 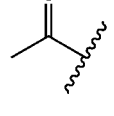 C(=O)CH3 | H | H |
| XA1223 | CH3— | 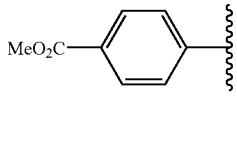 4-MeO2C-C6H4- | H | 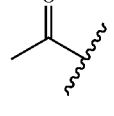 C(=O)CH3 | H | H |
| XA1224 | CH3— | 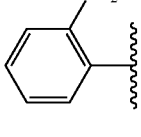 2-EtO2C-C6H4- | H | 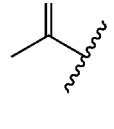 C(=O)CH3 | H | H |

-continued
| | | | | | | |
|---|---|---|---|---|---|---|
| XA1225 | CH3— | 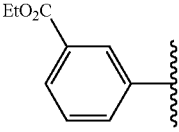 | H | 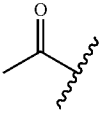 | H | H |
| XA1226 | CH3— | 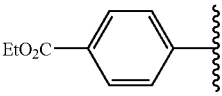 | H | 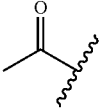 | H | H |
| XA1227 | CH3— | 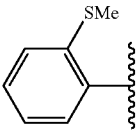 | H | 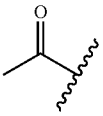 | H | H |
| XA1228 | CH3— | 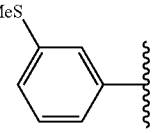 | H | 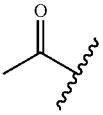 | H | H |
| XA1229 | CH3— | 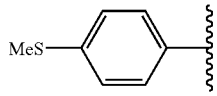 | H | 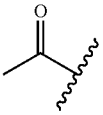 | H | H |
| XA1230 | CH3— | 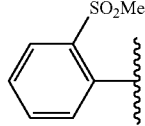 | H |  | H | H |
| XA1231 | CH3— | 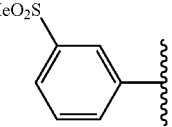 | H | 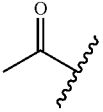 | H | H |
| XA1232 | CH3— | 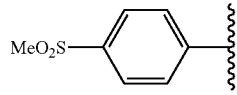 | H | 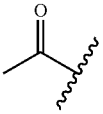 | H | H |
| XA1233 | CH3— | 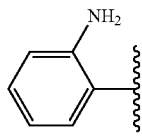 | H | 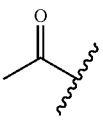 | H | H |
| XA1234 | CH3— | 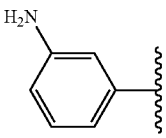 | H | 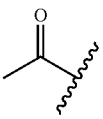 | H | H |
| XA1235 | CH3— | 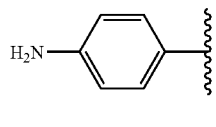 | H | 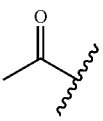 | H | H |

-continued
| | | | | | | |
|---|---|---|---|---|---|---|
| XA1236 | CH3— | 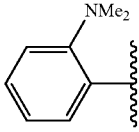 | H | 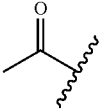 | H | H |
| XA1237 | CH3— | 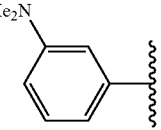 | H |  | H | H |
| XA1238 | CH3— | 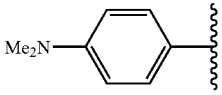 | H |  | H | H |
| XA1239 | CH3— | 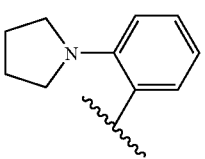 | H |  | H | H |
| XA1240 | CH3— |  | H |  | H | H |
| XA1241 | CH3— | 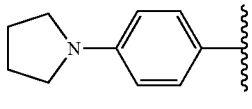 | H |  | H | H |
| XA1242 | CH3— | 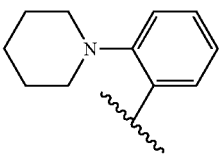 | H |  | H | H |
| XA1243 | CH3— | 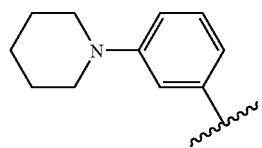 | H |  | H | H |
| XA1244 | CH3— | 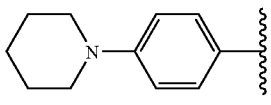 | H |  | H | H |
| XA1245 | CH3— | 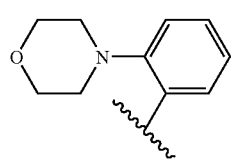 | H |  | H | H |

-continued
| | | | | | | |
|---|---|---|---|---|---|---|
| XA1246 | CH3— | 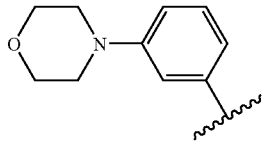 | H | 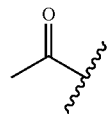 | H | H |
| XA1247 | CH3— | 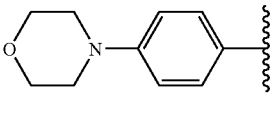 | H | 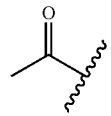 | H | H |
| XA1248 | CH3— | 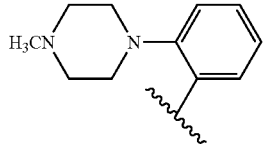 | H | 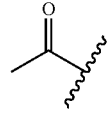 | H | H |
| XA1249 | CH3— | 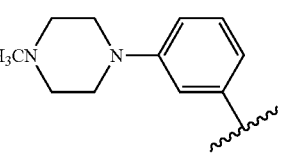 | H | 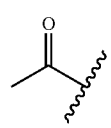 | H | H |
| XA1250 | CH3— | 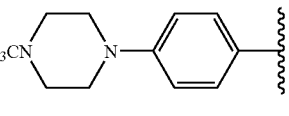 | H | 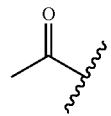 | H | H |
| XA1251 | CH3— | 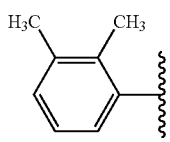 | H | 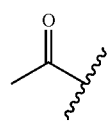 | H | H |
| XA1252 | CH3— | 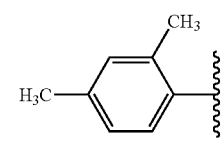 | H | 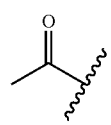 | H | H |
| XA1253 | CH3— | 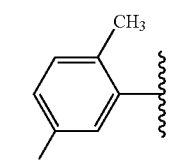 | H | 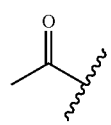 | H | H |
| XA1254 | CH3— | 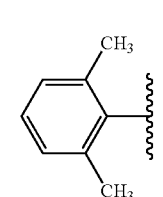 | H | 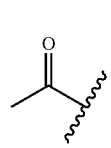 | H | H |
| XA1255 | CH3— | 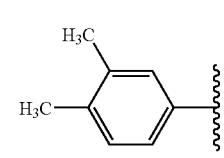 | H | 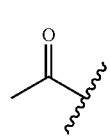 | H | H |

-continued
| | | | | | | |
|---|---|---|---|---|---|---|
| XA1256 | CH3— | 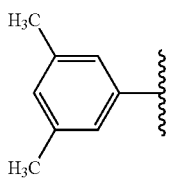 | H | 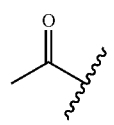 | H | H |
| XA1257 | CH3— | 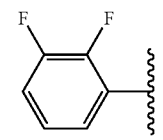 | H | 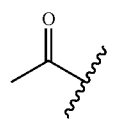 | H | H |
| XA1258 | CH3— | 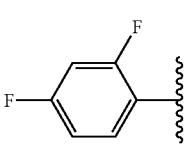 | H | 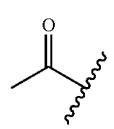 | H | H |
| XA1259 | CH3— | 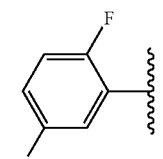 | H | 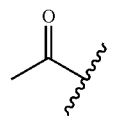 | H | H |
| XA1260 | CH3— | 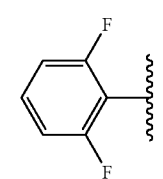 | H | 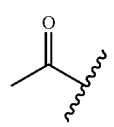 | H | H |
| XA1261 | CH3— | 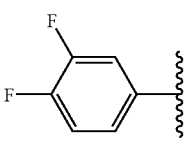 | H | 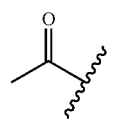 | H | H |
| XA1262 | CH3— | 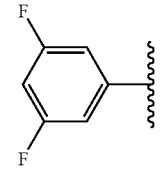 | H | 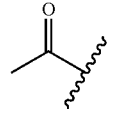 | H | H |
| XA1263 | CH3— | 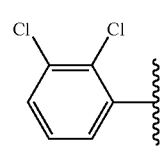 | H | 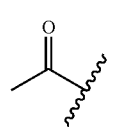 | H | H |
| XA1264 | CH3— | 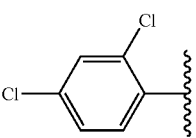 | H | 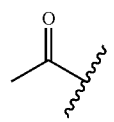 | H | H |

-continued
| | | | | | | |
|---|---|---|---|---|---|---|
| XA1265 | CH3— | 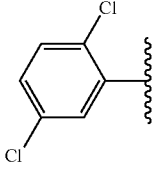 | H | 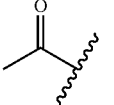 | H | H |
| XA1266 | CH3— | 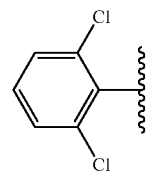 | H | 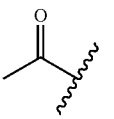 | H | H |
| XA1267 | CH3— | 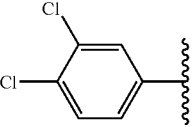 | H | 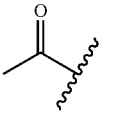 | H | H |
| XA1268 | CH3— | 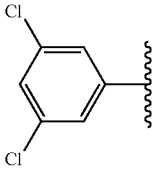 | H | 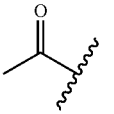 | H | H |
| XA1269 | CH3— | 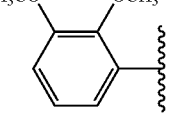 | H | 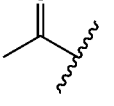 | H | H |
| XA1270 | CH3— | 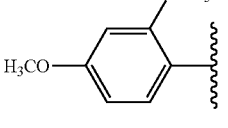 | H | 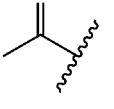 | H | H |
| XA1271 | CH3— | 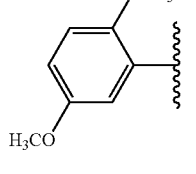 | H | 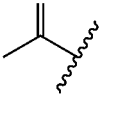 | H | H |
| XA1272 | CH3— | 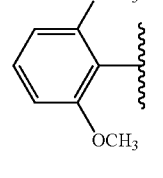 | H | 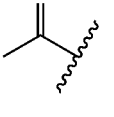 | H | H |
| XA1273 | CH3— | 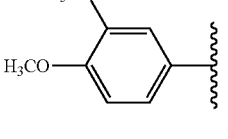 | H | 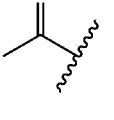 | H | H |

-continued
| | | | | | | |
|---|---|---|---|---|---|---|
| XA1274 | CH3— | 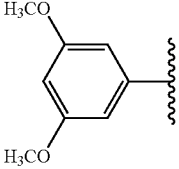 | H | 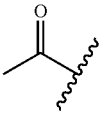 | H | H |
| XA1275 | CH3— | 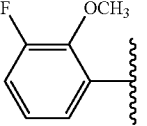 | H | 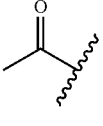 | H | H |
| XA1276 | CH3— | 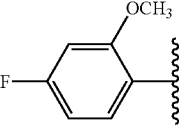 | H | 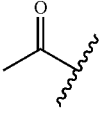 | H | H |
| XA1277 | CH3— | 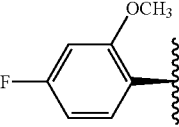 | H | 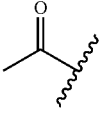 | H | H |
| XA1278 | CH3— | 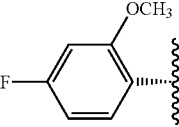 | H | 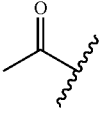 | H | H |
| XA1279 | CH3— | 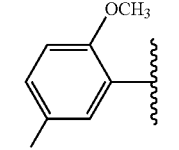 | H | 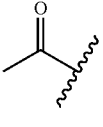 | H | H |
| XA1280 | CH3— | 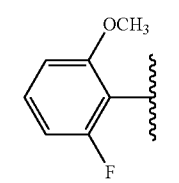 | H | 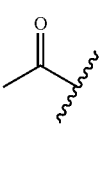 | H | H |
| XA1281 | CH3— | 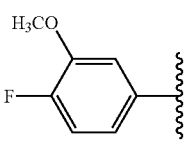 | H | 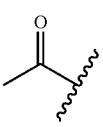 | H | H |
| XA1282 | CH3— | 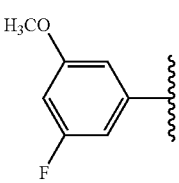 | H | 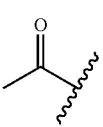 | H | H |
| XA1283 | CH3— | 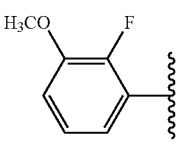 | H | 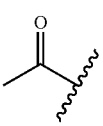 | H | H |

-continued
| | | | | | | |
|---|---|---|---|---|---|---|
| XA1284 | CH3— | 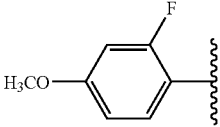 | H | 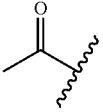 | H | H |
| XA1285 | CH3— | 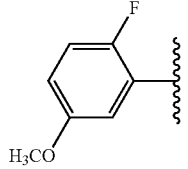 | H | 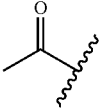 | H | H |
| XA1286 | CH3— | 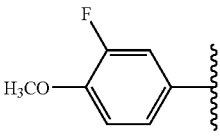 | H | 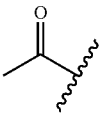 | H | H |
| XA1287 | CH3— | 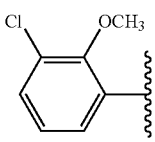 | H | 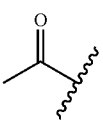 | H | H |
| XA1288 | CH3— | 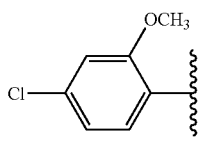 | H | 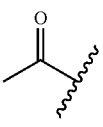 | H | H |
| XA1289 | CH3— | 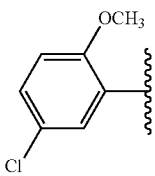 | H | 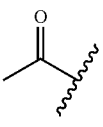 | H | H |
| XA1290 | CH3— | 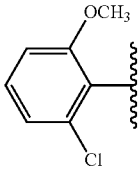 | H | 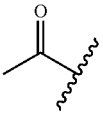 | H | H |
| XA1291 | CH3— | 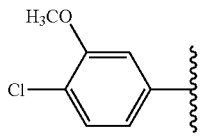 | H | 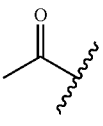 | H | H |
| XA1292 | CH3— | 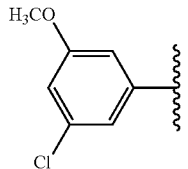 | H | 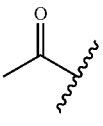 | H | H |

-continued
| | | | | | | |
|---|---|---|---|---|---|---|
| XA1293 | CH3— | 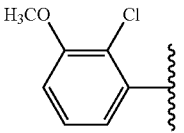 | H | 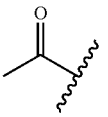 | H | H |
| XA1294 | CH3— | 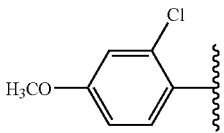 | H | 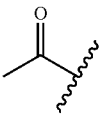 | H | H |
| XA1295 | CH3— | 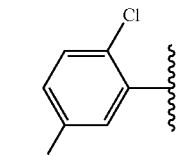 | H | 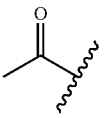 | H | H |
| XA1296 | CH3— | 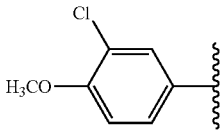 | H | 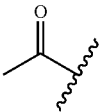 | H | H |
| XA1297 | CH3— | 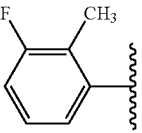 | H | 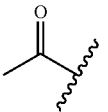 | H | H |
| XA1298 | CH3— | 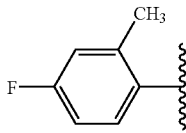 | H | 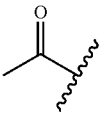 | H | H |
| XA1299 | CH3— | 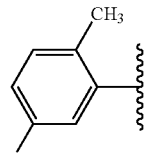 | H | 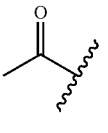 | H | H |
| XA1300 | CH3— | 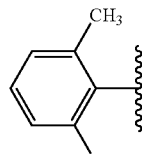 | H | 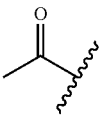 | H | H |
| XA1301 | CH3— | 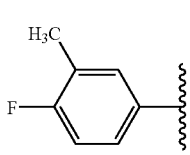 | H | 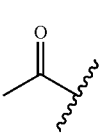 | H | H |
| XA1302 | CH3— | 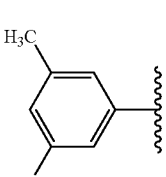 | H | 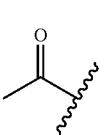 | H | H |

-continued
| | | | | | | |
|---|---|---|---|---|---|---|
| XA1303 | CH3— | 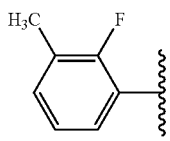 | H | 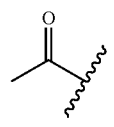 | H | H |
| XA1304 | CH3— | 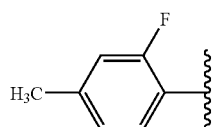 | H | 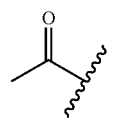 | H | H |
| XA1305 | CH3— | 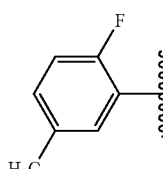 | H | 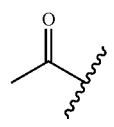 | H | H |
| XA1306 | CH3— | 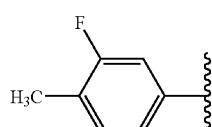 | H | 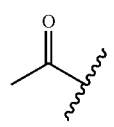 | H | H |
| XA1307 | CH3— | 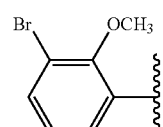 | H | 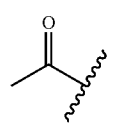 | H | H |
| XA1308 | CH3— | 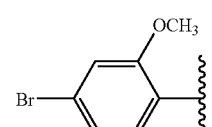 | H | 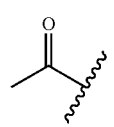 | H | H |
| XA1309 | CH3— | 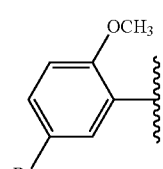 | H | 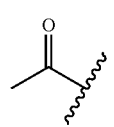 | H | H |
| XA1310 | CH3— | 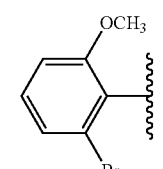 | H | 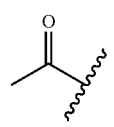 | H | H |
| XA1311 | CH3— | 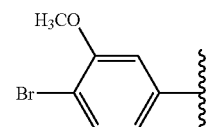 | H | 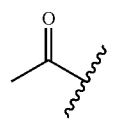 | H | H |

-continued
| | | | | | | |
|---|---|---|---|---|---|---|
| XA1312 | CH3— | 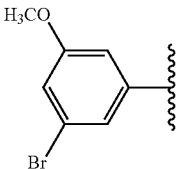 | H | 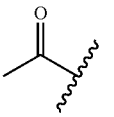 | H | H |
| XA1313 | CH3— | 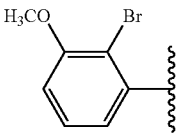 | H | 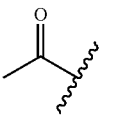 | H | H |
| XA1314 | CH3— | 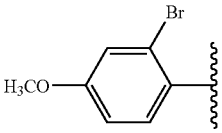 | H | 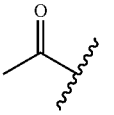 | H | H |
| XA1315 | CH3— | 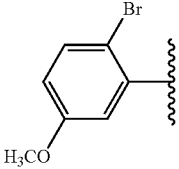 | H | 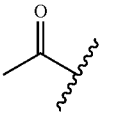 | H | H |
| XA1316 | CH3— | 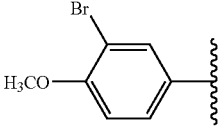 | H | 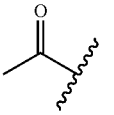 | H | H |
| XA1317 | CH3— | 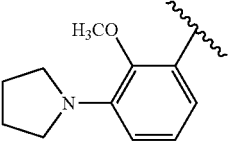 | H | 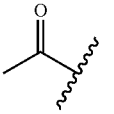 | H | H |
| XA1318 | CH3— | 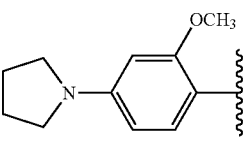 | H | 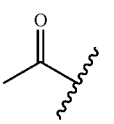 | H | H |
| XA1319 | CH3— | 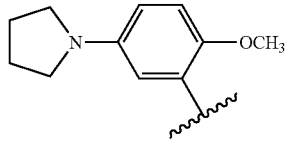 | H | 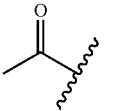 | H | H |
| XA1320 | CH3— | 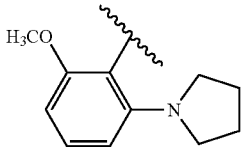 | H | 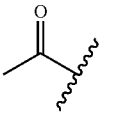 | H | H |
| XA1321 | CH3— | 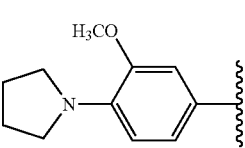 | H | 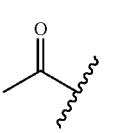 | H | H |

-continued
| | | | | | | |
|---|---|---|---|---|---|---|
| XA1322 | CH3— | 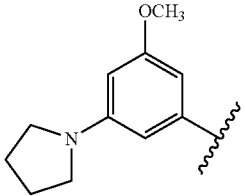 | H | 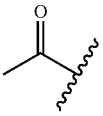 | H | H |
| XA1323 | CH3— | 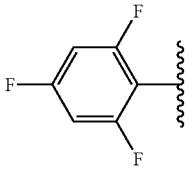 | H | 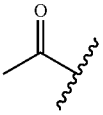 | H | H |
| XA1324 | CH3— | 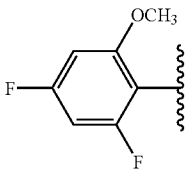 | H | 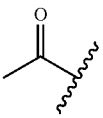 | H | H |
| XA1325 | CH3— | 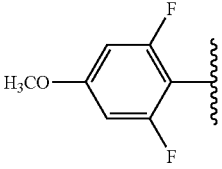 | H | 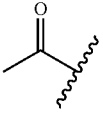 | H | H |
| XA1326 | CH3— | 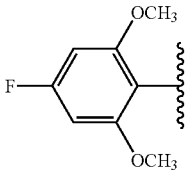 | H | 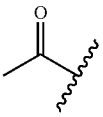 | H | H |
| XA1327 | CH3— | 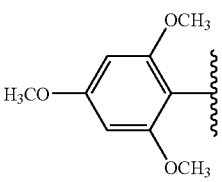 | H | 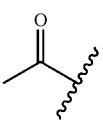 | H | H |
| XA1328 | CH3— | 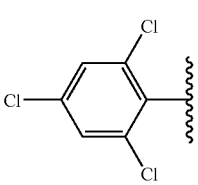 | H | 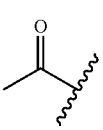 | H | H |
| XA1329 | CH3— | 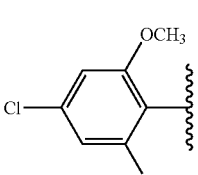 | H | 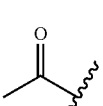 | H | H |

-continued

| | | | | | | |
|---|---|---|---|---|---|---|
| XA1330 | CH3— | 2,6-dichloro-4-methoxyphenyl | H | acetyl | H | H |
| XA1331 | CH3— | 4-chloro-2,6-dimethoxyphenyl | H | acetyl | H | H |
| XA1332 | CH3— | 2,4,6-trimethoxyphenyl | H | acetyl | H | H |
| XA1333 | CH3— | 2'-methoxybiphenyl-4-yl | H | acetyl | H | H |
| XA1334 | CH3— | 3'-methoxybiphenyl-4-yl | H | acetyl | H | H |
| XA1335 | CH3— | 4'-methoxybiphenyl-4-yl | H | acetyl | H | H |
| XA1336 | CH3— | 2'-methoxybiphenyl-3-yl | H | acetyl | H | H |
| XA1337 | CH3— | 3'-methoxybiphenyl-3-yl | H | acetyl | H | H |
| XA1338 | CH3— | 4'-methoxybiphenyl-3-yl | H | acetyl | H | H |

-continued
| | | | | | | |
|---|---|---|---|---|---|---|
| XA1339 | CH3— | 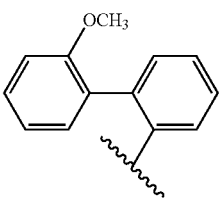 | H | 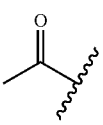 | H | H |
| XA1340 | CH3— | 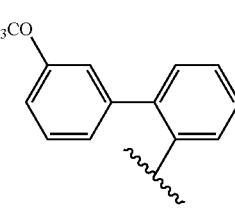 | H | 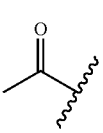 | H | H |
| XA1341 | CH3— | 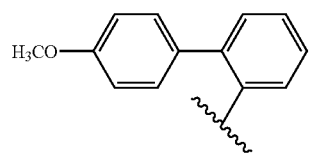 | H | 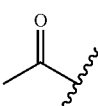 | H | H |
| XA1342 | CH3— | 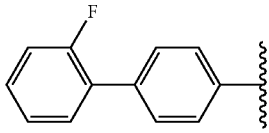 | H | 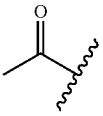 | H | H |
| XA1343 | CH3— | 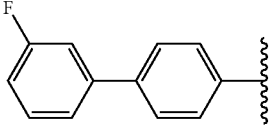 | H | 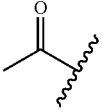 | H | H |
| XA1344 | CH3— | 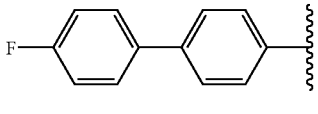 | H | 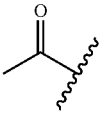 | H | H |
| XA1345 | CH3— | 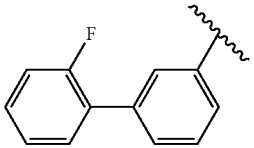 | H | 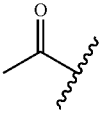 | H | H |
| XA1346 | CH3— | 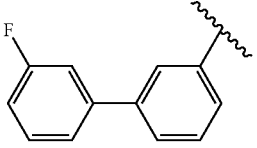 | H | 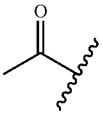 | H | H |
| XA1347 | CH3— | 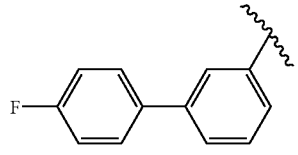 | H | 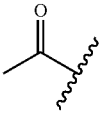 | H | H |

-continued
| | | | | | | |
|---|---|---|---|---|---|---|
| XA1348 | CH3— | 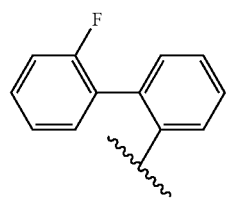 | H | 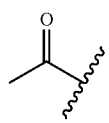 | H | H |
| XA1349 | CH3— | 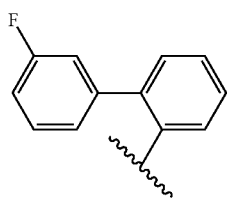 | H | 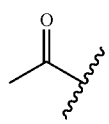 | H | H |
| XA1350 | CH3— | 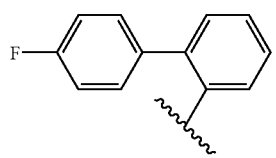 | H | 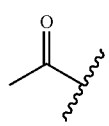 | H | H |
| XA1351 | CH3— | 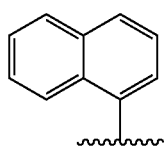 | H | 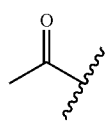 | H | H |
| XA1352 | CH3— | 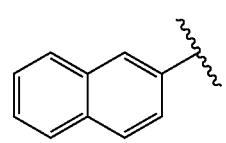 | H | 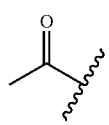 | H | H |
| XA1353 | CH3— | 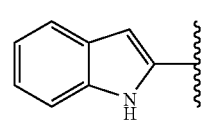 | H | 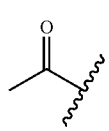 | H | H |
| XA1354 | CH3— | 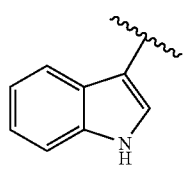 | H | 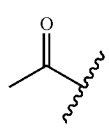 | H | H |
| XA1355 | CH3— | 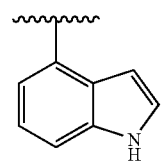 | H | 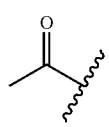 | H | H |
| XA1356 | CH3— | 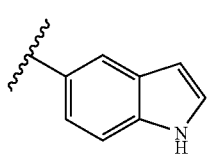 | H | 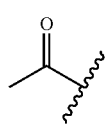 | H | H |

-continued
| | | | | | | |
|---|---|---|---|---|---|---|
| XA1357 | CH3— | 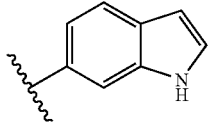 | H | 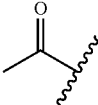 | H | H |
| XA1358 | CH3— | 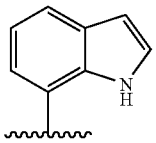 | H | 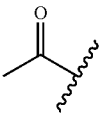 | H | H |
| XA1359 | CH3— | 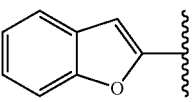 | H |  | H | H |
| XA1360 | CH3— | 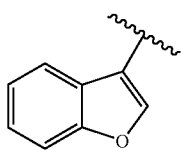 | H | 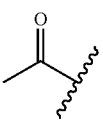 | H | H |
| XA1361 | CH3— | 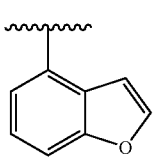 | H |  | H | H |
| XA1362 | CH3— | 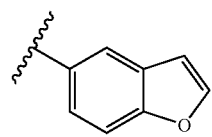 | H | 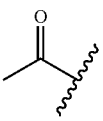 | H | H |
| XA1363 | CH3— | 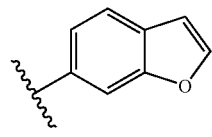 | H | 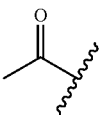 | H | H |
| XA1364 | CH3— | 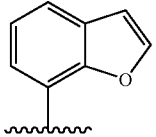 | H | 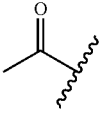 | H | H |
| XA1365 | CH3— | 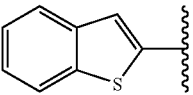 | H | 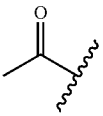 | H | H |
| XA1366 | CH3— | 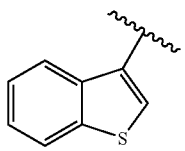 | H | 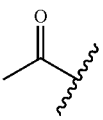 | H | H |

-continued
| | | | | | | |
|---|---|---|---|---|---|---|
| XA1367 | CH3— | 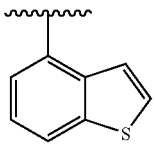 | H | 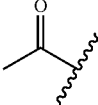 | H | H |
| XA1368 | CH3— | 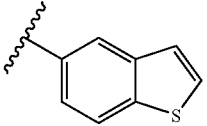 | H | 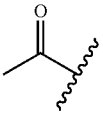 | H | H |
| XA1369 | CH3— | 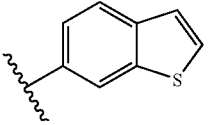 | H | 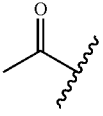 | H | H |
| XA1370 | CH3— | 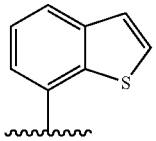 | H | 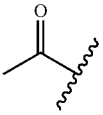 | H | H |
| XA1371 | CH3— | 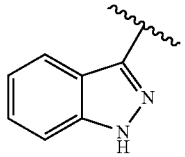 | H | 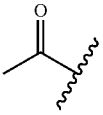 | H | H |
| XA1372 | CH3— | 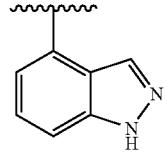 | H | 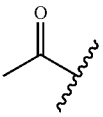 | H | H |
| XA1373 | CH3— | 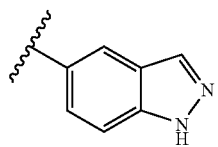 | H | 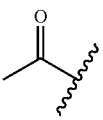 | H | H |
| XA1374 | CH3— | 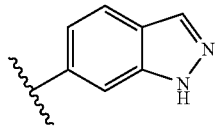 | H | 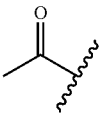 | H | H |
| XA1375 | CH3— | 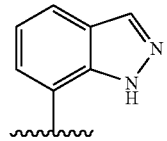 | H | 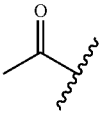 | H | H |
| XA1376 | CH3— | 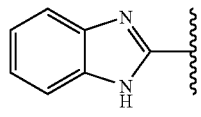 | H | 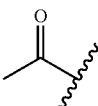 | H | H |

-continued
| | | | | | | |
|---|---|---|---|---|---|---|
| XA1377 | CH3— | 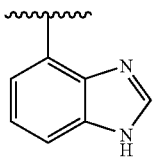 | H | 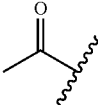 | H | H |
| XA1378 | CH3— | 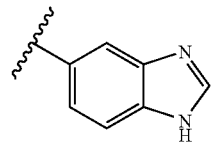 | H | 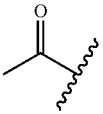 | H | H |
| XA1379 | CH3— | 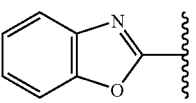 | H | 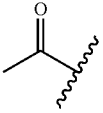 | H | H |
| XA1380 | CH3— | 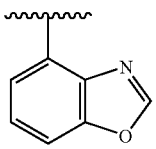 | H | 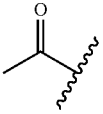 | H | H |
| XA1381 | CH3— | 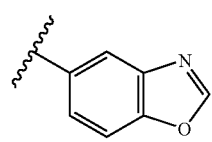 | H | 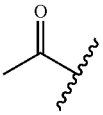 | H | H |
| XA1382 | CH3— | 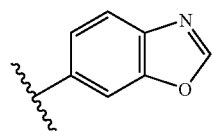 | H | 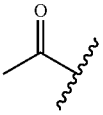 | H | H |
| XA1383 | CH3— | 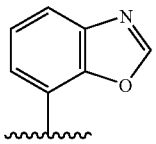 | H | 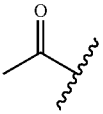 | H | H |
| XA1384 | CH3— | 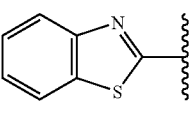 | H | 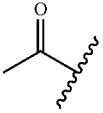 | H | H |
| XA1385 | CH3— | 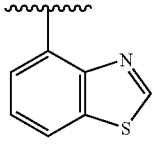 | H | 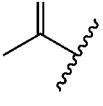 | H | H |
| XA1386 | CH3— | 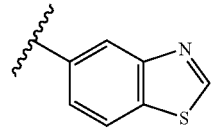 | H | 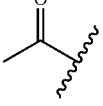 | H | H |

-continued
| | | | | | | |
|---|---|---|---|---|---|---|
| XA1387 | CH3— | 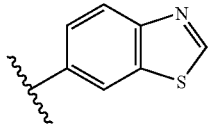 | H | 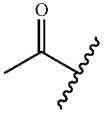 | H | H |
| XA1388 | CH3— | 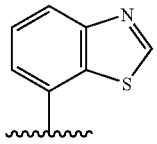 | H | 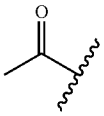 | H | H |
| XA1389 | CH3— | 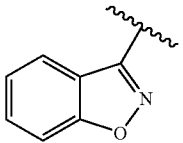 | H | 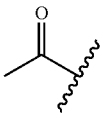 | H | H |
| XA1390 | CH3— | 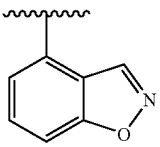 | H | 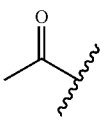 | H | H |
| XA1391 | CH3— | 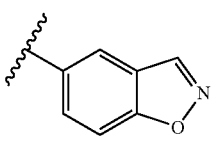 | H | 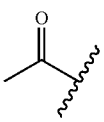 | H | H |
| XA1392 | CH3— | 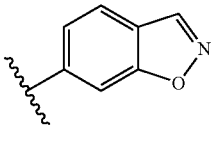 | H | 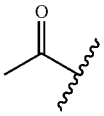 | H | H |
| XA1393 | CH3— | 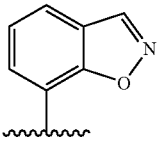 | H | 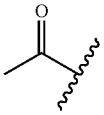 | H | H |
| XA1394 | CH3— | 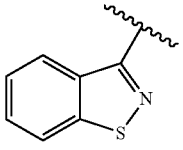 | H | 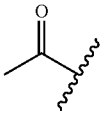 | H | H |
| XA1395 | CH3— | 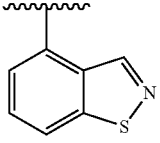 | H | 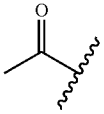 | H | H |
| XA1396 | CH3— | 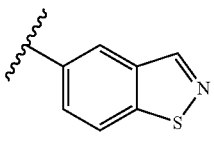 | H | 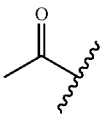 | H | H |

-continued
| | | | | | | |
|---|---|---|---|---|---|---|
| XA1397 | CH3— | 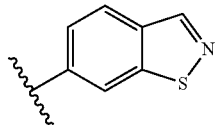 | H | 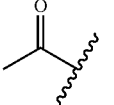 | H | H |
| XA1398 | CH3— | 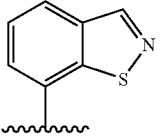 | H | 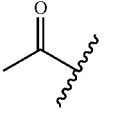 | H | H |
| XA1399 | CH3— | 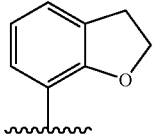 | H | 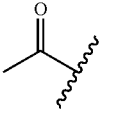 | H | H |
| XA1400 | CH3— | 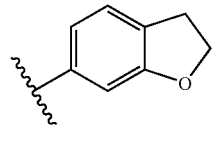 | H | 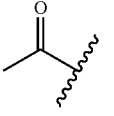 | H | H |
| XA1401 | CH3— | 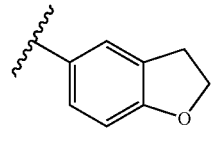 | H | 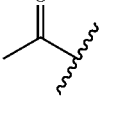 | H | H |
| XA1402 | CH3— | 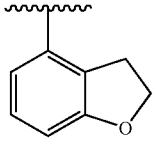 | H | 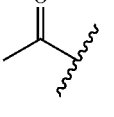 | H | H |
| XA1403 | CH3— | CH3— | CH3— | H | H | H |
| XA1404 | CH3— | CH3CH2— | CH3— | H | H | H |
| XA1405 | CH3— | 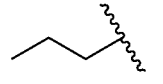 | CH3— | H | H | H |
| XA1406 | CH3— | 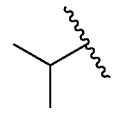 | CH3— | H | H | H |
| XA1407 | CH3— | 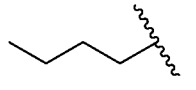 | CH3— | H | H | H |
| XA1408 | CH3— | 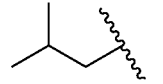 | CH3— | H | H | H |
| XA1409 | CH3— | 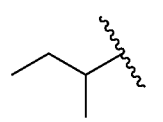 | CH3— | H | H | H |

-continued
| | | | | | | |
|---|---|---|---|---|---|---|
| XA1410 | CH3— | 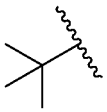 | CH3— | H | H | H |
| XA1411 | CH3— | 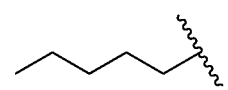 | CH3— | H | H | H |
| XA1412 | CH3— | 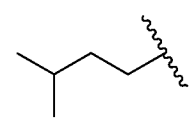 | CH3— | H | H | H |
| XA1413 | CH3— | 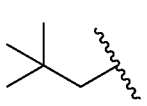 | CH3— | H | H | H |
| XA1414 | CH3— | 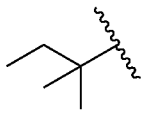 | CH3— | H | H | H |
| XA1415 | CH3— | 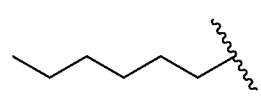 | CH3— | H | H | H |
| XA1416 | CH3— | 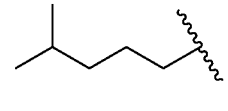 | CH3— | H | H | H |
| XA1417 | CH3— | 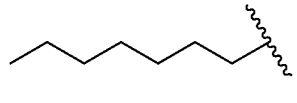 | CH3— | H | H | H |
| XA1418 | CH3— | 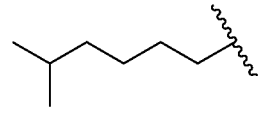 | CH3— | H | H | H |
| XA1419 | CH3— | n-C8H17— | CH3— | H | H | H |
| XA1420 | CH3— | 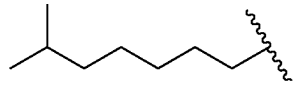 | CH3— | H | H | H |
| XA1421 | CH3— | 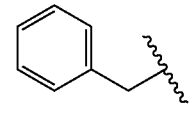 | CH3— | H | H | H |
| XA1422 | CH3— | 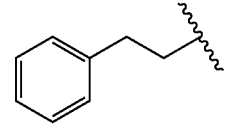 | CH3— | H | H | H |
| XA1423 | CH3— | 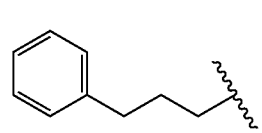 | CH3— | H | H | H |

-continued
| | | | | | | |
|---|---|---|---|---|---|---|
| XA1424 | CH3— | 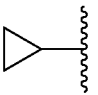 | CH3— | H | H | H |
| XA1425 | CH3— | 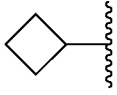 | CH3— | H | H | H |
| XA1426 | CH3— | 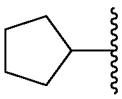 | CH3— | H | H | H |
| XA1427 | CH3— | 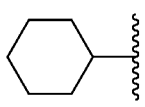 | CH3— | H | H | H |
| XA1428 | CH3— | 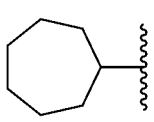 | CH3— | H | H | H |
| XA1429 | CH3— | 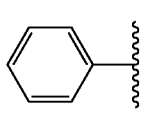 | CH3— | H | H | H |
| XA1430 | CH3— | 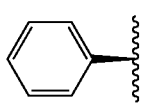 | CH3— | H | H | H |
| XA1431 | CH3— | 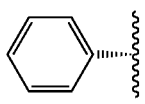 | CH3— | H | H | H |
| XA1432 | CH3— | 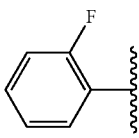 | CH3— | H | H | H |
| XA1433 | CH3— | 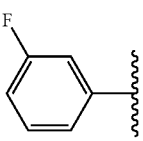 | CH3— | H | H | H |
| XA1434 | CH3— | 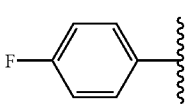 | CH3— | H | H | H |
| XA1435 | CH3— | 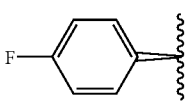 | CH3— | H | H | H |
| XA1436 | CH3— | 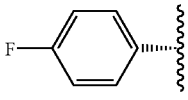 | CH3— | H | H | H |

-continued
| | | | | | | |
|---|---|---|---|---|---|---|
| XA1437 | CH3— | 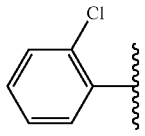 2-Cl-phenyl | CH3— | H | H | H |
| XA1438 | CH3— | 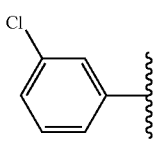 3-Cl-phenyl | CH3— | H | H | H |
| XA1439 | CH3— | 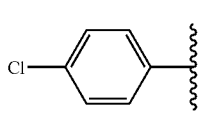 4-Cl-phenyl | CH3— | H | H | H |
| XA1440 | CH3— | 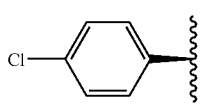 4-Cl-phenyl | CH3— | H | H | H |
| XA1441 | CH3— | 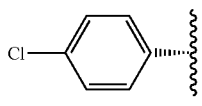 4-Cl-phenyl | CH3— | H | H | H |
| XA1442 | CH3— | 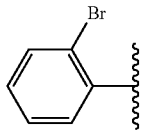 2-Br-phenyl | CH3— | H | H | H |
| XA1443 | CH3— | 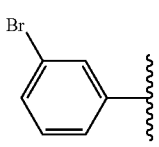 3-Br-phenyl | CH3— | H | H | H |
| XA1444 | CH3— | 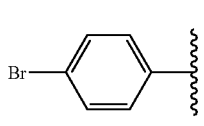 4-Br-phenyl | CH3— | H | H | H |
| XA1445 | CH3— | 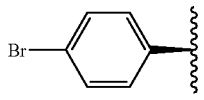 4-Br-phenyl | CH3— | H | H | H |
| XA1446 | CH3— | 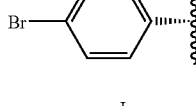 4-Br-phenyl | CH3— | H | H | H |
| XA1447 | CH3— | 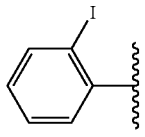 2-I-phenyl | CH3— | H | H | H |
| XA1448 | CH3— | 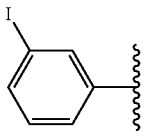 3-I-phenyl | CH3— | H | H | H |

-continued
| | | | | | | |
|---|---|---|---|---|---|---|
| XA1449 | CH3— | 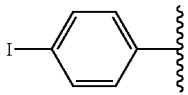 | CH3— | H | H | H |
| XA1450 | CH3— | 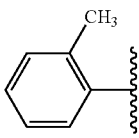 | CH3— | H | H | H |
| XA1451 | CH3— | 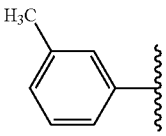 | CH3— | H | H | H |
| XA1452 | CH3— | 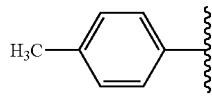 | CH3— | H | H | H |
| XA1453 | CH3— | 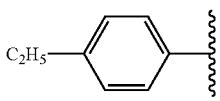 | CH3— | H | H | H |
| XA1454 | CH3— | 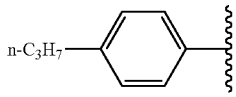 | CH3— | H | H | H |
| XA1455 | CH3— | 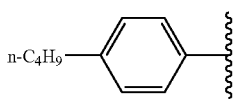 | CH3— | H | H | H |
| XA1456 | CH3— | 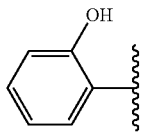 | CH3— | H | H | H |
| XA1457 | CH3— | 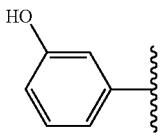 | CH3— | H | H | H |
| XA1458 | CH3— | 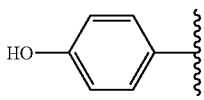 | CH3— | H | H | H |
| XA1459 | CH3— | 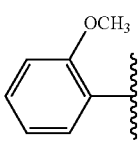 | CH3— | H | H | H |
| XA1460 | CH3— | 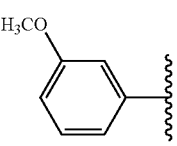 | CH3— | H | H | H |

-continued
| | | | | | | |
|---|---|---|---|---|---|---|
| XA1461 | CH3— | 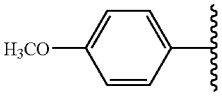 | CH3— | H | H | H |
| XA1462 | CH3— | 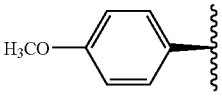 | CH3— | H | H | H |
| XA1463 | CH3— | 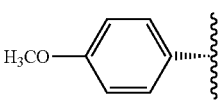 | CH3— | H | H | H |
| XA1464 | CH3— | 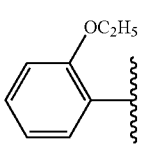 | CH3— | H | H | H |
| XA1465 | CH3— | 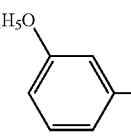 | CH3— | H | H | H |
| XA1466 | CH3— | 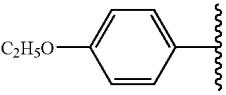 | CH3— | H | H | H |
| XA1467 | CH3— | 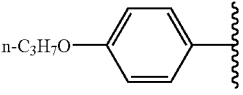 | CH3— | H | H | H |
| XA1468 | CH3— | 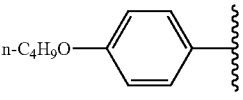 | CH3— | H | H | H |
| XA1469 | CH3— | 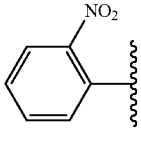 | CH3— | H | H | H |
| XA1470 | CH3— | 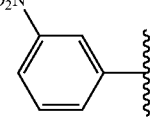 | CH3— | H | H | H |
| XA1471 | CH3— | 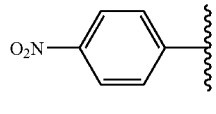 | CH3— | H | H | H |
| XA1472 | CH3— | 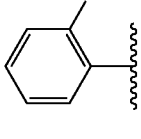 | CH3— | H | H | H |

-continued
| | | | | | | |
|---|---|---|---|---|---|---|
| XA1473 | CH3— | 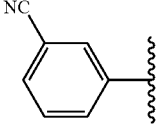 | CH3— | H | H | H |
| XA1474 | CH3— | 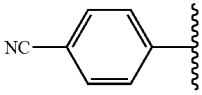 | CH3— | H | H | H |
| XA1475 | CH3— | 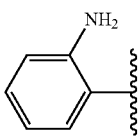 | CH3— | H | H | H |
| XA1476 | CH3— | 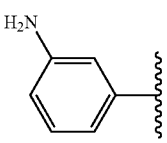 | CH3— | H | H | H |
| XA1477 | CH3— | 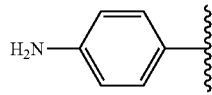 | CH3— | H | H | H |
| XA1478 | CH3— | 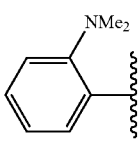 | CH3— | H | H | H |
| XA1479 | CH3— | 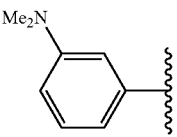 | CH3— | H | H | H |
| XA1480 | CH3— | 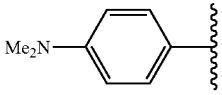 | CH3— | H | H | H |
| XA1481 | CH3— | 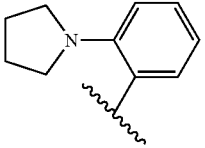 | CH3— | H | H | H |
| XA1482 | CH3— | 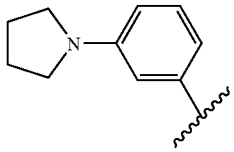 | CH3— | H | H | H |
| XA1483 | CH3— | 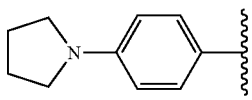 | CH3— | H | H | H |

-continued
| | | | | | | |
|---|---|---|---|---|---|---|
| XA1484 | CH3— | 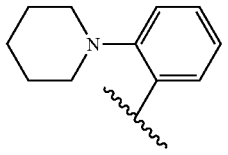 | CH3— | H | H | H |
| XA1485 | CH3— | 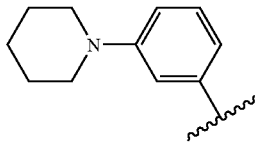 | CH3— | H | H | H |
| XA1486 | CH3— | 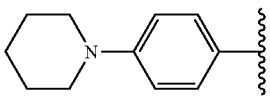 | CH3— | H | H | H |
| XA1487 | CH3— | 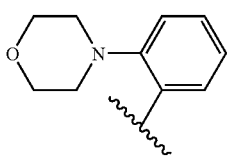 | CH3— | H | H | H |
| XA1488 | CH3— | 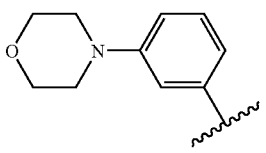 | CH3— | H | H | H |
| XA1489 | CH3— | 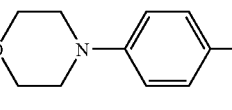 | CH3— | H | H | H |
| XA1490 | CH3— | 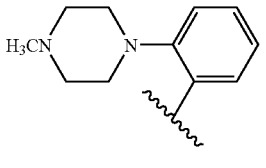 | CH3— | H | H | H |
| XA1491 | CH3— | 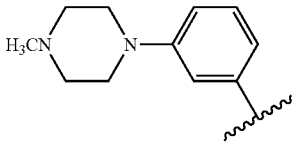 | CH3— | H | H | H |
| XA1492 | CH3— | 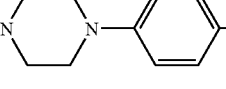 | CH3— | H | H | H |
| XA1493 | CH3— | 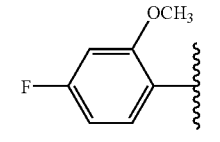 | CH3— | H | H | H |
| XA1494 | CH3— | 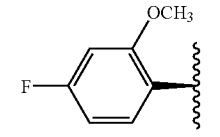 | CH3— | H | H | H |

-continued
| | | | | | | |
|---|---|---|---|---|---|---|
| XA1495 | CH3— | 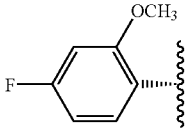 | CH3— | H | H | H |
| XA1496 | CH3— | 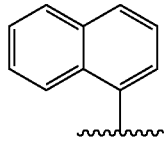 | CH3— | H | H | H |
| XA1497 | CH3— | 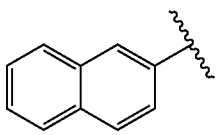 | CH3— | H | H | H |
| XA1498 | CH3— | CH3— | H | H | CH3— | H |
| XA1499 | CH3— | CH3CH2— | H | H | CH3— | H |
| XA1500 | CH3— |  | H | H | CH3— | H |
| XA1501 | CH3— |  | H | H | CH3— | H |
| XA1502 | CH3— | 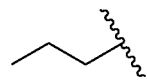 | H | H | CH3— | H |
| XA1503 | CH3— | 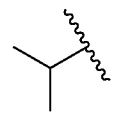 | H | H | CH3— | H |
| XA1504 | CH3— | 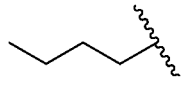 | H | H | CH3— | H |
| XA1505 | CH3— | 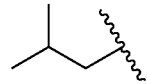 | H | H | CH3— | H |
| XA1506 | CH3— | 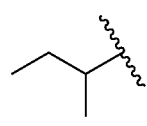 | H | H | CH3— | H |
| XA1507 | CH3— | 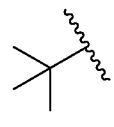 | H | H | CH3— | H |
| XA1508 | CH3— | 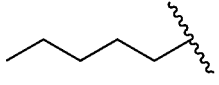 | H | H | CH3— | H |

-continued
| | | | | | | |
|---|---|---|---|---|---|---|
| XA1509 | CH3— | 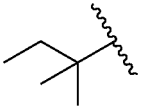 | H | H | CH3— | H |
| XA1510 | CH3— | 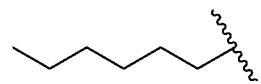 | H | H | CH3— | H |
| XA1511 | CH3— | 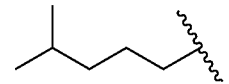 | H | H | CH3— | H |
| XA1512 | CH3— | 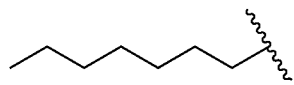 | H | H | CH3— | H |
| XA1513 | CH3— | 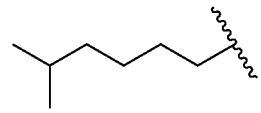 | H | H | CH3— | H |
| XA1514 | CH3— | n-C8H17— | H | H | CH3— | H |
| XA1515 | CH3— | 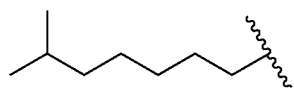 | H | H | CH3— | H |
| XA1516 | CH3— | 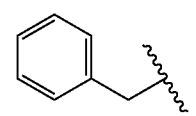 | H | H | CH3— | H |
| XA1517 | CH3— | 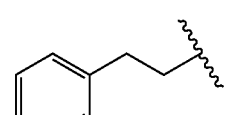 | H | H | CH3— | H |
| XA1518 | CH3— | 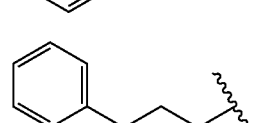 | H | H | CH3— | H |
| XA1519 | CH3— | 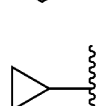 | H | H | CH3— | H |
| XA1520 | CH3— | 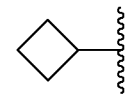 | H | H | CH3— | H |
| XA1521 | CH3— | 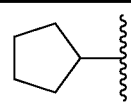 | H | H | CH3— | H |
| XA1522 | CH3— | 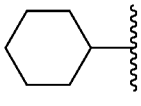 | H | H | CH3— | H |

-continued
| | | | | | | |
|---|---|---|---|---|---|---|
| XA1523 | CH3— | 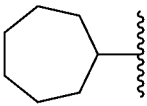 | H | H | CH3— | H |
| XA1524 | CH3— | 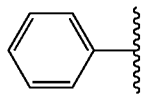 | H | H | CH3— | H |
| XA1525 | CH3— | 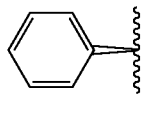 | H | H | CH3— | H |
| XA1526 | CH3— | 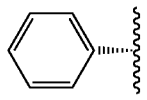 | H | H | CH3— | H |
| XA1527 | CH3— | 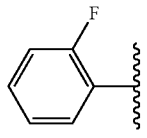 | H | H | CH3— | H |
| XA1528 | CH3— | 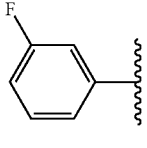 | H | H | CH3— | H |
| XA1529 | CH3— | 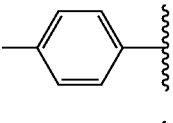 | H | H | CH3— | H |
| XA1530 | CH3— | 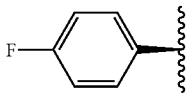 | H | H | CH3— | H |
| XA1531 | CH3— |  | H | H | CH3— | H |
| XA1532 | CH3— | 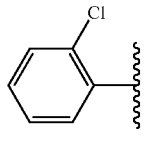 | H | H | CH3— | H |
| XA1533 | CH3— | 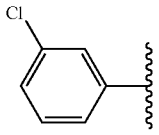 | H | H | CH3— | H |
| XA1534 | CH3— | 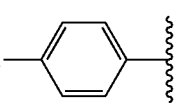 | H | H | CH3— | H |
| XA1535 | CH3— | 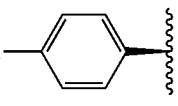 | H | H | CH3— | H |

-continued
| | | | | | | |
|---|---|---|---|---|---|---|
| XA1536 | CH3— | 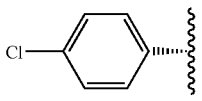 4-Cl-C6H4- (dashed) | H | H | CH3— | H |
| XA1537 | CH3— | 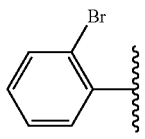 2-Br-C6H4- | H | H | CH3— | H |
| XA1538 | CH3— | 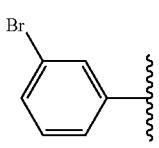 3-Br-C6H4- | H | H | CH3— | H |
| XA1539 | CH3— | 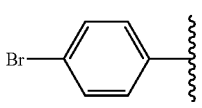 4-Br-C6H4- | H | H | CH3— | H |
| XA1540 | CH3— | 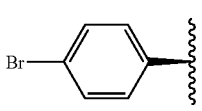 4-Br-C6H4- (wedge) | H | H | CH3— | H |
| XA1541 | CH3— | 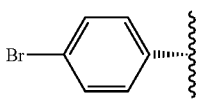 4-Br-C6H4- (dashed) | H | H | CH3— | H |
| XA1542 | CH3— | 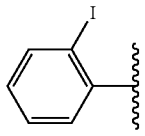 2-I-C6H4- | H | H | CH3— | H |
| XA1543 | CH3— | 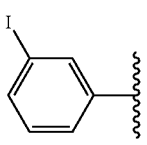 3-I-C6H4- | H | H | CH3— | H |
| XA1544 | CH3— | 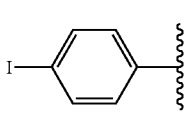 4-I-C6H4- | H | H | CH3— | H |
| XA1545 | CH3— | 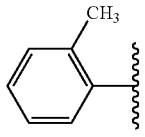 2-CH3-C6H4- | H | H | CH3— | H |
| XA1546 | CH3— | 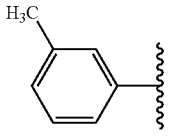 3-CH3-C6H4- | H | H | CH3— | H |
| XA1547 | CH3— | 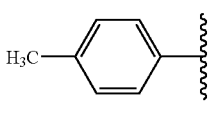 4-CH3-C6H4- | H | H | CH3— | H |

-continued
| | | | | | | |
|---|---|---|---|---|---|---|
| XA1548 | CH3— | 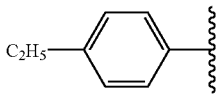 | H | H | CH3— | H |
| XA1549 | CH3— |  | H | H | CH3— | H |
| XA1550 | CH3— | 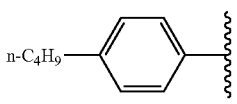 | H | H | CH3— | H |
| XA1551 | CH3— | 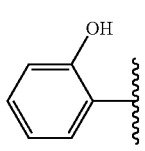 | H | H | CH3— | H |
| XA1552 | CH3— | 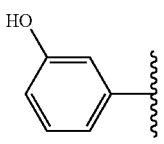 | H | H | CH3— | H |
| XA1553 | CH3— | 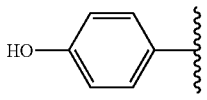 | H | H | CH3— | H |
| XA1554 | CH3— |  | H | H | CH3— | H |
| XA1555 | CH3— |  | H | H | CH3— | H |
| XA1556 | CH3— | 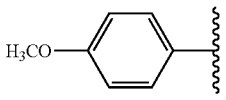 | H | H | CH3— | H |
| XA1557 | CH3— | 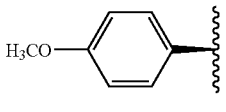 | H | H | CH3— | H |
| XA1558 | CH3— | 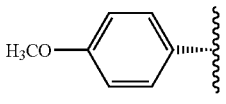 | H | H | CH3— | H |
| XA1559 | CH3— |  | H | H | CH3— | H |

-continued
| | | | | | | |
|---|---|---|---|---|---|---|
| XA1560 | CH3— | 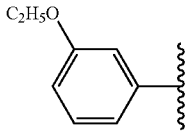 3-C2H5O-C6H4– | H | H | CH3— | H |
| XA1561 | CH3— | 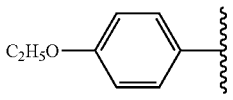 4-C2H5O-C6H4– | H | H | CH3— | H |
| XA1562 | CH3— | 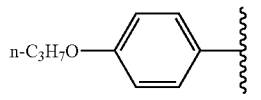 4-n-C3H7O-C6H4– | H | H | CH3— | H |
| XA1563 | CH3— | 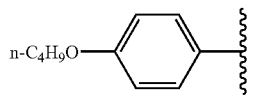 4-n-C4H9O-C6H4– | H | H | CH3— | H |
| XA1564 | CH3— | 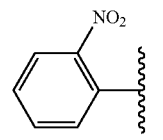 2-NO2-C6H4– | H | H | CH3— | H |
| XA1565 | CH3— | 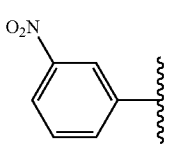 3-NO2-C6H4– | H | H | CH3— | H |
| XA1566 | CH3— | 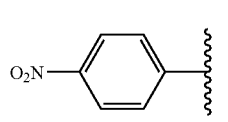 4-NO2-C6H4– | H | H | CH3— | H |
| XA1567 | CH3— | 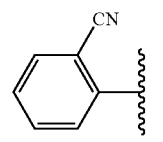 2-CN-C6H4– | H | H | CH3— | H |
| XA1568 | CH3— | 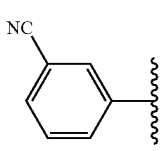 3-CN-C6H4– | H | H | CH3— | H |
| XA1569 | CH3— | 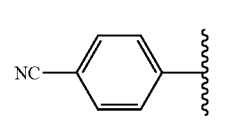 4-CN-C6H4– | H | H | CH3— | H |
| XA1570 | CH3— | 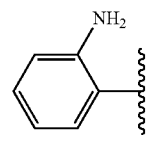 2-NH2-C6H4– | H | H | CH3— | H |
| XA1571 | CH3— | 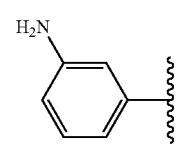 3-NH2-C6H4– | H | H | CH3— | H |

-continued
| | | | | | | |
|---|---|---|---|---|---|---|
| XA1572 | CH3— | 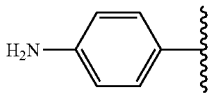 | H | H | CH3— | H |
| XA1573 | CH3— | 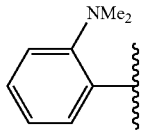 | H | H | CH3— | H |
| XA1574 | CH3— | 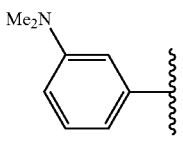 | H | H | CH3— | H |
| XA1575 | CH3— | 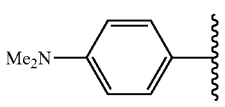 | H | H | CH3— | H |
| XA1576 | CH3— | 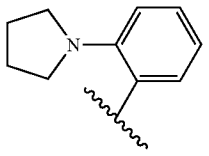 | H | H | CH3— | H |
| XA1577 | CH3— | 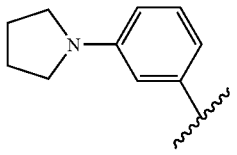 | H | H | CH3— | H |
| XA1578 | CH3— | 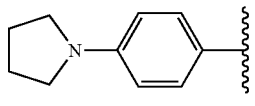 | H | H | CH3— | H |
| XA1579 | CH3— | 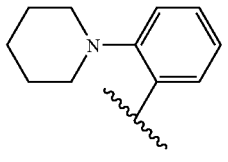 | H | H | CH3— | H |
| XA1580 | CH3— | 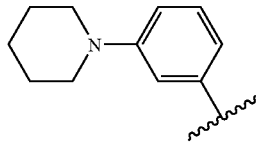 | H | H | CH3— | H |
| XA1581 | CH3— | 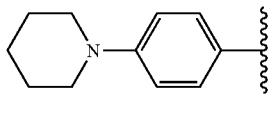 | H | H | CH3— | H |
| XA1582 | CH3— | 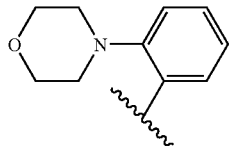 | H | H | CH3— | H |

-continued
| | | | | | | |
|---|---|---|---|---|---|---|
| XA1583 | CH3— | 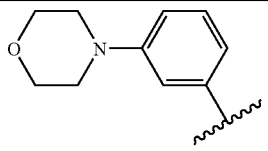 | H | H | CH3— | H |
| XA1584 | CH3— | 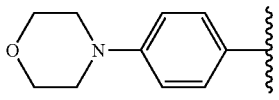 | H | H | CH3— | H |
| XA1585 | CH3— | 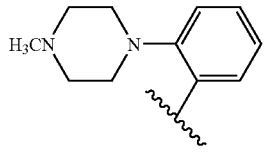 | H | H | CH3— | H |
| XA1586 | CH3— | 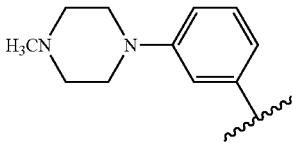 | H | H | CH3— | H |
| XA1587 | CH3— | 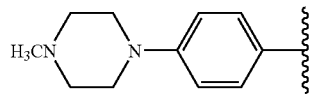 | H | H | CH3— | H |
| XA1588 | CH3— | 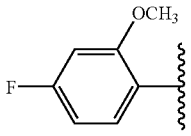 | H | H | CH3— | H |
| XA1589 | CH3— | 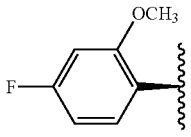 | H | H | CH3— | H |
| XA1590 | CH3— | 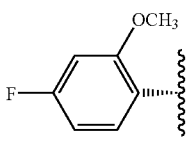 | H | H | CH3— | H |
| XA1591 | CH3— | 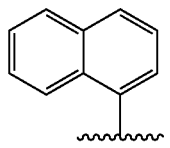 | H | H | CH3— | H |
| XA1592 | CH3— | 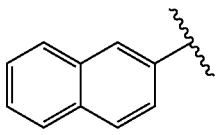 | H | H | CH3— | H |
| XA1593 | CH3— | CH3— | H | H | CH3— | CH3— |
| XA1594 | CH3— | CH3CH2— | H | H | CH3— | CH3— |
| XA1595 | CH3— | 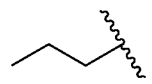 | H | H | CH3— | CH3— |

-continued
| | | | | | | |
|---|---|---|---|---|---|---|
| XA1596 | CH3— | 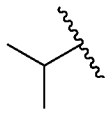 | H | H | CH3— | CH3— |
| XA1597 | CH3— | 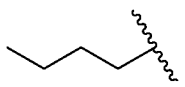 | H | H | CH3— | CH3— |
| XA1598 | CH3— | 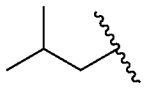 | H | H | CH3— | CH3— |
| XA1599 | CH3— | 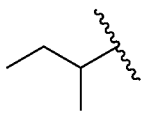 | H | H | CH3— | CH3— |
| XA1600 | CH3— |  | H | H | CH3— | CH3— |
| XA1601 | CH3— | 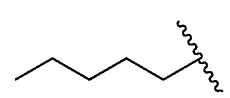 | H | H | CH3— | CH3— |
| XA1602 | CH3— | 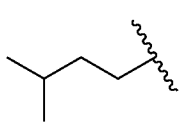 | H | H | CH3— | CH3— |
| XA1603 | CH3— | 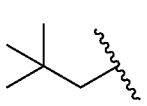 | H | H | CH3— | CH3— |
| XA1604 | CH3— | 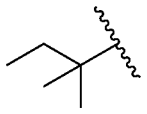 | H | H | CH3— | CH3— |
| XA1605 | CH3— | 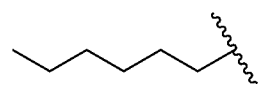 | H | H | CH3— | CH3— |
| XA1606 | CH3— | 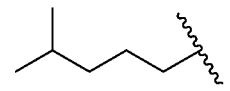 | H | H | CH3— | CH3— |
| XA1607 | CH3— | 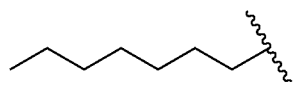 | H | H | CH3— | CH3— |
| XA1608 | CH3— | 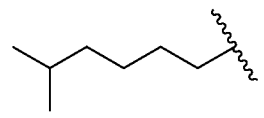 | H | H | CH3— | CH3— |
| XA1609 | CH3— | n-C8H17— | H | H | CH3— | CH3— |
| XA1610 | CH3— |  | H | H | CH3— | CH3— |

| | | | | | | |
|---|---|---|---|---|---|---|
| XA1611 | CH3— | benzyl (CH2-Ph) | H | H | CH3— | CH3— |
| XA1612 | CH3— | phenethyl (CH2CH2-Ph) | H | H | CH3— | CH3— |
| XA1613 | CH3— | 3-phenylpropyl (CH2CH2CH2-Ph) | H | H | CH3— | CH3— |
| XA1614 | CH3— | cyclopropyl | H | H | CH3— | CH3— |
| XA1615 | CH3— | cyclobutyl | H | H | CH3— | CH3— |
| XA1616 | CH3— | cyclopentyl | H | H | CH3— | CH3— |
| XA1617 | CH3— | cyclohexyl | H | H | CH3— | CH3— |
| XA1618 | CH3— | cycloheptyl | H | H | CH3— | CH3— |
| XA1619 | CH3— | phenyl | H | H | CH3— | CH3— |
| XA1620 | CH3— | phenyl (wedge) | H | H | CH3— | CH3— |
| XA1621 | CH3— | phenyl (dashed) | H | H | CH3— | CH3— |
| XA1622 | CH3— | 2-fluorophenyl | H | H | CH3— | CH3— |
| XA1623 | CH3— | 3-fluorophenyl | H | H | CH3— | CH3— |

-continued
| | | | | | | |
|---|---|---|---|---|---|---|
| XA1624 | CH3— | 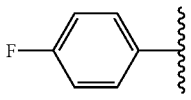 | H | H | CH3— | CH3— |
| XA1625 | CH3— | 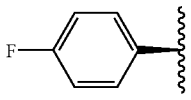 | H | H | CH3— | CH3— |
| XA1626 | CH3— | 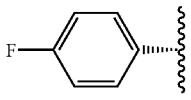 | H | H | CH3— | CH3— |
| XA1627 | CH3— | 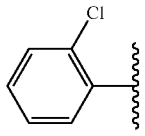 | H | H | CH3— | CH3— |
| XA1628 | CH3— | 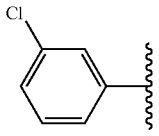 | H | H | CH3— | CH3— |
| XA1629 | CH3— | 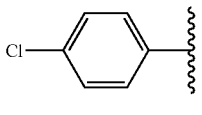 | H | H | CH3— | CH3— |
| XA1630 | CH3— | 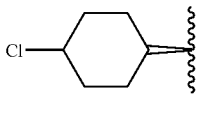 | H | H | CH3— | CH3— |
| XA1631 | CH3— | 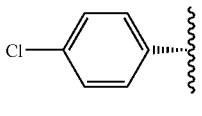 | H | H | CH3— | CH3— |
| XA1632 | CH3— | 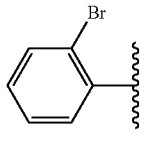 | H | H | CH3— | CH3— |
| XA1633 | CH3— | 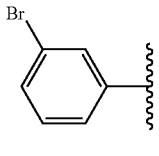 | H | H | CH3— | CH3— |
| XA1634 | CH3— | 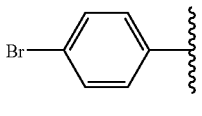 | H | H | CH3— | CH3— |
| XA1635 | CH3— | 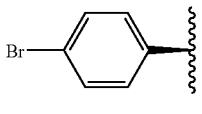 | H | H | CH3— | CH3— |
| XA1636 | CH3— | 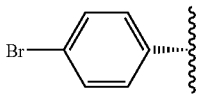 | H | H | CH3— | CH3— |

-continued
| | | | | | | |
|---|---|---|---|---|---|---|
| XA1637 | CH3— | 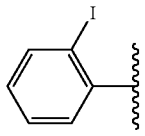 | H | H | CH3— | CH3— |
| XA1638 | CH3— | 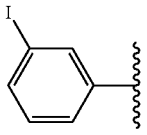 | H | H | CH3— | CH3— |
| XA1639 | CH3— | 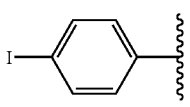 | H | H | CH3— | CH3— |
| XA1640 | CH3— | 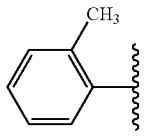 | H | H | CH3— | CH3— |
| XA1641 | CH3— |  | H | H | CH3— | CH3— |
| XA1642 | CH3— | 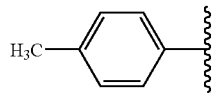 | H | H | CH3— | CH3— |
| XA1643 | CH3— | 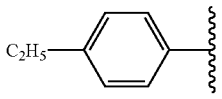 | H | H | CH3— | CH3— |
| XA1644 | CH3— | 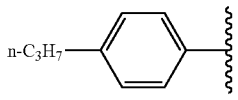 | H | H | CH3— | CH3— |
| XA1645 | CH3— | 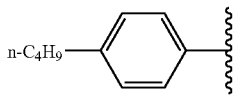 | H | H | CH3— | CH3— |
| XA1646 | CH3— | 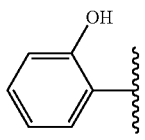 | H | H | CH3— | CH3— |
| XA1647 | CH3— | 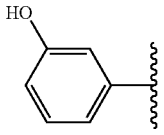 | H | H | CH3— | CH3— |
| XA1648 | CH3— | 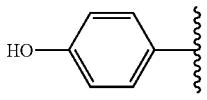 | H | H | CH3— | CH3— |

-continued
| | | | | | | |
|---|---|---|---|---|---|---|
| XA1649 | CH3— | 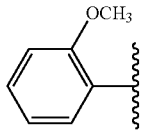 (2-OCH3-C6H4—) | H | H | CH3— | CH3— |
| XA1650 | CH3— | 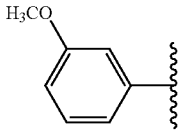 (3-OCH3-C6H4—) | H | H | CH3— | CH3— |
| XA1651 | CH3— | 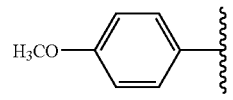 (4-OCH3-C6H4—) | H | H | CH3— | CH3— |
| XA1652 | CH3— | 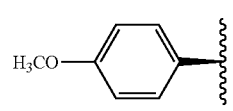 (4-OCH3-C6H4—, wedge) | H | H | CH3— | CH3— |
| XA1653 | CH3— |  (4-OCH3-C6H4—, dashed) | H | H | CH3— | CH3— |
| XA1654 | CH3— | 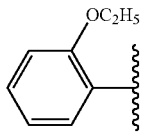 (2-OC2H5-C6H4—) | H | H | CH3— | CH3— |
| XA1655 | CH3— | 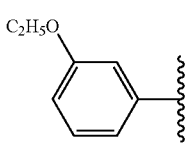 (3-OC2H5-C6H4—) | H | H | CH3— | CH3— |
| XA1656 | CH3— | 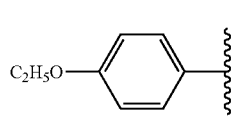 (4-OC2H5-C6H4—) | H | H | CH3— | CH3— |
| XA1657 | CH3— | 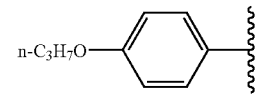 (4-O-n-C3H7-C6H4—) | H | H | CH3— | CH3— |
| XA1658 | CH3— | 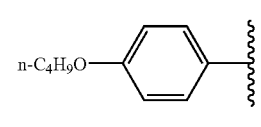 (4-O-n-C4H9-C6H4—) | H | H | CH3— | CH3— |
| XA1659 | CH3— | 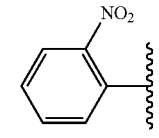 (2-NO2-C6H4—) | H | H | CH3— | CH3— |
| XA1660 | CH3— | 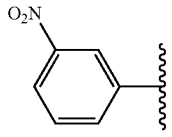 (3-NO2-C6H4—) | H | H | CH3— | CH3— |

-continued
| | | | | | | |
|---|---|---|---|---|---|---|
| XA1661 | CH3— | 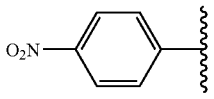 | H | H | CH3— | CH3— |
| XA1662 | CH3— | 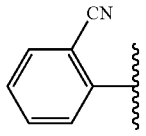 | H | H | CH3— | CH3— |
| XA1663 | CH3— | 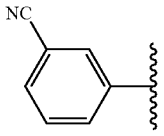 | H | H | CH3— | CH3— |
| XA1664 | CH3— | 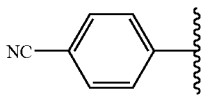 | H | H | CH3— | CH3— |
| XA1665 | CH3— | 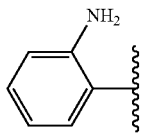 | H | H | CH3— | CH3— |
| XA1666 | CH3— | 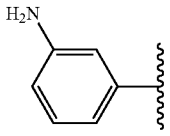 | H | H | CH3— | CH3— |
| XA1667 | CH3— | 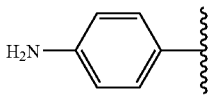 | H | H | CH3— | CH3— |
| XA1668 | CH3— | 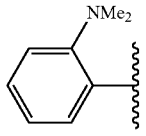 | H | H | CH3— | CH3— |
| XA1669 | CH3— | 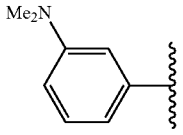 | H | H | CH3— | CH3— |
| XA1670 | CH3— | 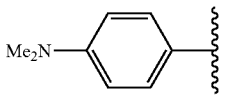 | H | H | CH3— | CH3— |
| XA1671 | CH3— | 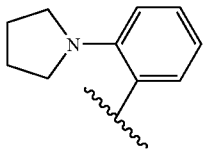 | H | H | CH3— | CH3— |

-continued
| | | | | | | |
|---|---|---|---|---|---|---|
| XA1672 | CH3— | 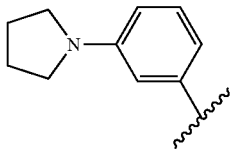 | H | H | CH3— | CH3— |
| XA1673 | CH3— | 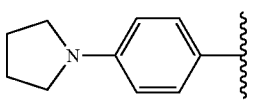 | H | H | CH3— | CH3— |
| XA1674 | CH3— | 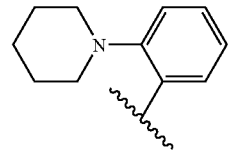 | H | H | CH3— | CH3— |
| XA1675 | CH3— | 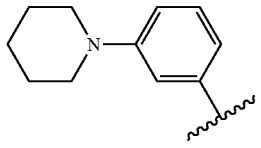 | H | H | CH3— | CH3— |
| XA1676 | CH3— | 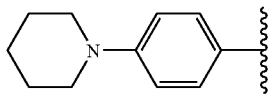 | H | H | CH3— | CH3— |
| XA1677 | CH3— |  | H | H | CH3— | CH3— |
| XA1678 | CH3— |  | H | H | CH3— | CH3— |
| XA1679 | CH3— |  | H | H | CH3— | CH3— |
| XA1680 | CH3— |  | H | H | CH3— | CH3— |
| XA1681 | CH3— |  | H | H | CH3— | CH3— |
| XA1682 | CH3— |  | H | H | CH3— | CH3— |

-continued
| | | | | | | |
|---|---|---|---|---|---|---|
| XA1683 | CH3— | 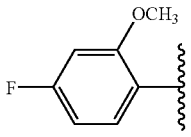 | H | H | CH3— | CH3— |
| XA1684 | CH3— | 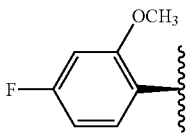 | H | H | CH3— | CH3— |
| XA1685 | CH3— | 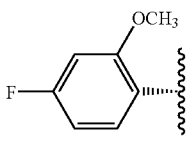 | H | H | CH3— | CH3— |
| XA1686 | CH3— | 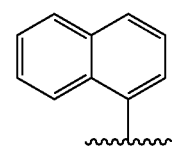 | H | H | CH3— | CH3— |
| XA1687 | CH3— | 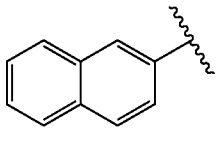 | H | H | CH3— | CH3— |
| XA1688 | CH3— | CH3— | H | CH3— | CH3— | CH3— |
| XA1689 | CH3— | CH3CH2— | H | CH3— | CH3— | CH3— |
| XA1690 | CH3— |  | H | CH3— | CH3— | CH3— |
| XA1691 | CH3— | 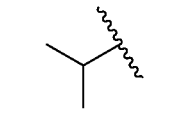 | H | CH3— | CH3— | CH3— |
| XA1692 | CH3— |  | H | CH3— | CH3— | CH3— |
| XA1693 | CH3— |  | H | CH3— | CH3— | CH3— |
| XA1694 | CH3— |  | H | CH3— | CH3— | CH3— |
| XA1695 | CH3— |  | H | CH3— | CH3— | CH3— |
| XA1696 | CH3— |  | H | CH3— | CH3— | CH3— |

-continued

| | | | | | | |
|---|---|---|---|---|---|---|
| XA1697 | CH3— | isohexyl | H | CH3— | CH3— | CH3— |
| XA1698 | CH3— | neopentyl (3,3-dimethylbutyl) | H | CH3— | CH3— | CH3— |
| XA1699 | CH3— | 2,2-dimethylbutyl | H | CH3— | CH3— | CH3— |
| XA1700 | CH3— | n-heptyl | H | CH3— | CH3— | CH3— |
| XA1701 | CH3— | 5-methylhexyl | H | CH3— | CH3— | CH3— |
| XA1702 | CH3— | n-octyl chain | H | CH3— | CH3— | CH3— |
| XA1703 | CH3— | 6-methylheptyl | H | CH3— | CH3— | CH3— |
| XA1704 | CH3— | n-C8H17— | H | CH3— | CH3— | CH3— |
| XA1705 | CH3— | 7-methyloctyl | H | CH3— | CH3— | CH3— |
| XA1706 | CH3— | benzyl | H | CH3— | CH3— | CH3— |
| XA1707 | CH3— | 2-phenylethyl | H | CH3— | CH3— | CH3— |
| XA1708 | CH3— | 3-phenylpropyl | H | CH3— | CH3— | CH3— |
| XA1709 | CH3— | cyclopropyl | H | CH3— | CH3— | CH3— |
| XA1710 | CH3— | cyclobutyl | H | CH3— | CH3— | CH3— |

-continued
| | | | | | | |
|---|---|---|---|---|---|---|
| XA1711 | CH3— | 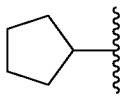 | H | CH3— | CH3— | CH3— |
| XA1712 | CH3— | 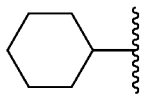 | H | CH3— | CH3— | CH3— |
| XA1713 | CH3— | 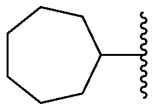 | H | CH3— | CH3— | CH3— |
| XA1714 | CH3— | 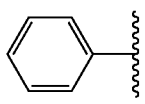 | H | CH3— | CH3— | CH3— |
| XA1715 | CH3— | 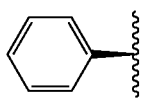 | H | CH3— | CH3— | CH3— |
| XA1716 | CH3— | 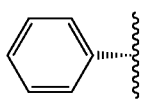 | H | CH3— | CH3— | CH3— |
| XA1717 | CH3— | 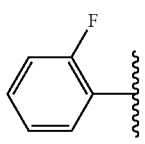 | H | CH3— | CH3— | CH3— |
| XA1718 | CH3— | 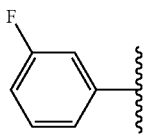 | H | CH3— | CH3— | CH3— |
| XA1719 | CH3— | 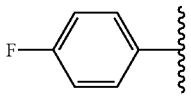 | H | CH3— | CH3— | CH3— |
| XA1720 | CH3— | 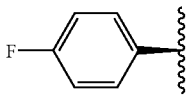 | H | CH3— | CH3— | CH3— |
| XA1721 | CH3— | 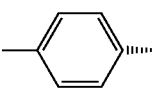 | H | CH3— | CH3— | CH3— |
| XA1722 | CH3— | 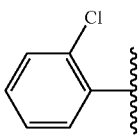 | H | CH3— | CH3— | CH3— |
| XA1723 | CH3— | 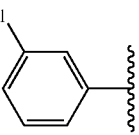 | H | CH3— | CH3— | CH3— |

-continued
| | | | | | | |
|---|---|---|---|---|---|---|
| XA1724 | CH3— | 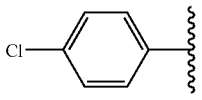 | H | CH3— | CH3— | CH3— |
| XA1725 | CH3— | 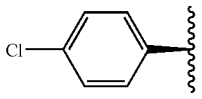 | H | CH3— | CH3— | CH3— |
| XA1726 | CH3— | 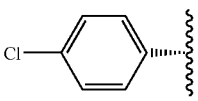 | H | CH3— | CH3— | CH3— |
| XA1727 | CH3— | 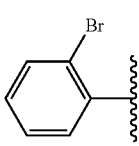 | H | CH3— | CH3— | CH3— |
| XA1728 | CH3— | 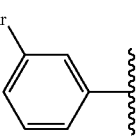 | H | CH3— | CH3— | CH3— |
| XA1729 | CH3— | 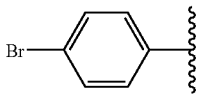 | H | CH3— | CH3— | CH3— |
| XA1730 | CH3— | 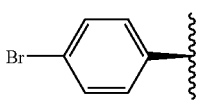 | H | CH3— | CH3— | CH3— |
| XA1731 | CH3— | 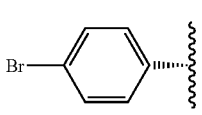 | H | CH3— | CH3— | CH3— |
| XA1732 | CH3— | 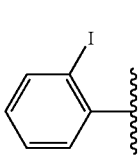 | H | CH3— | CH3— | CH3— |
| XA1733 | CH3— | 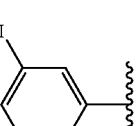 | H | CH3— | CH3— | CH3— |
| XA1734 | CH3— | 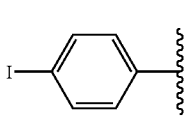 | H | CH3— | CH3— | CH3— |
| XA1735 | CH3— | 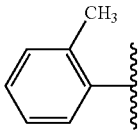 | H | CH3— | CH3— | CH3— |

-continued
| | | | | | | |
|---|---|---|---|---|---|---|
| XA1736 | CH3— | 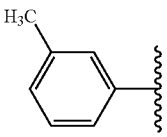 | H | CH3— | CH3— | CH3— |
| XA1737 | CH3— | 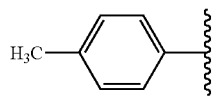 | H | CH3— | CH3— | CH3— |
| XA1738 | CH3— | 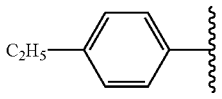 | H | CH3— | CH3— | CH3— |
| XA1739 | CH3— | 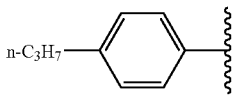 | H | CH3— | CH3— | CH3— |
| XA1740 | CH3— | 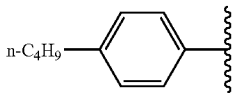 | H | CH3— | CH3— | CH3— |
| XA1741 | CH3— | 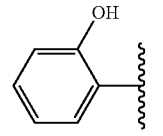 | H | CH3— | CH3— | CH3— |
| XA1742 | CH3— | 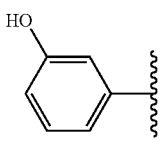 | H | CH3— | CH3— | CH3— |
| XA1743 | CH3— | 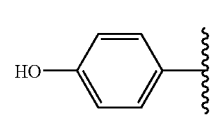 | H | CH3— | CH3— | CH3— |
| XA1744 | CH3— | 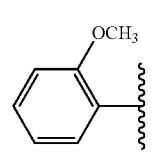 | H | CH3— | CH3— | CH3— |
| XA1745 | CH3— | 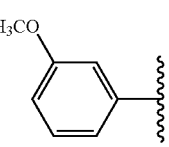 | H | CH3— | CH3— | CH3— |
| XA1746 | CH3— | 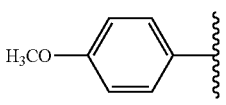 | H | CH3— | CH3— | CH3— |
| XA1747 | CH3— | 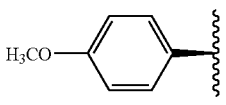 | H | CH3— | CH3— | CH3— |

-continued
| | | | | | | |
|---|---|---|---|---|---|---|
| XA1748 | CH3— | 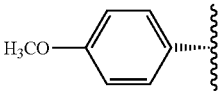 | H | CH3— | CH3— | CH3— |
| XA1749 | CH3— | 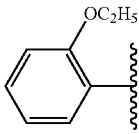 | H | CH3— | CH3— | CH3— |
| XA1750 | CH3— | 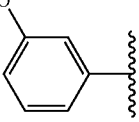 | H | CH3— | CH3— | CH3— |
| XA1751 | CH3— | 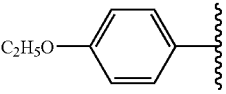 | H | CH3— | CH3— | CH3— |
| XA1752 | CH3— | 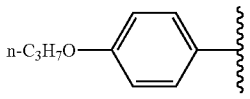 | H | CH3— | CH3— | CH3— |
| XA1753 | CH3— | 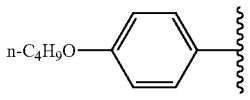 | H | CH3— | CH3— | CH3— |
| XA1754 | CH3— | 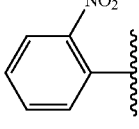 | H | CH3— | CH3— | CH3— |
| XA1755 | CH3— | 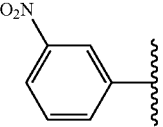 | H | CH3— | CH3— | CH3— |
| XA1756 | CH3— | 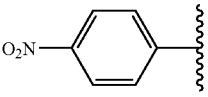 | H | CH3— | CH3— | CH3— |
| XA1757 | CH3— | 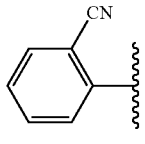 | H | CH3— | CH3— | CH3— |
| XA1758 | CH3— | 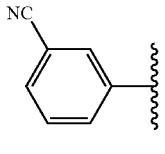 | H | CH3— | CH3— | CH3— |
| XA1759 | CH3— | 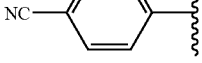 | H | CH3— | CH3— | CH3— |

-continued
| | | | | | | |
|---|---|---|---|---|---|---|
| XA1760 | CH3— | 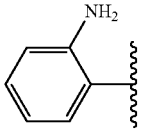 (2-NH2-phenyl) | H | CH3— | CH3— | CH3— |
| XA1761 | CH3— | 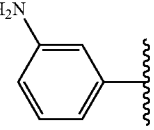 (3-NH2-phenyl) | H | CH3— | CH3— | CH3— |
| XA1762 | CH3— | 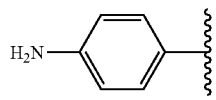 (4-NH2-phenyl) | H | CH3— | CH3— | CH3— |
| XA1763 | CH3— | 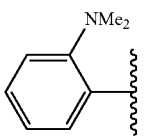 (2-NMe2-phenyl) | H | CH3— | CH3— | CH3— |
| XA1764 | CH3— | 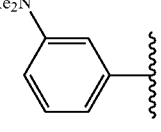 (3-NMe2-phenyl) | H | CH3— | CH3— | CH3— |
| XA1765 | CH3— | 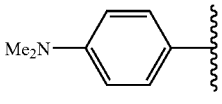 (4-NMe2-phenyl) | H | CH3— | CH3— | CH3— |
| XA1766 | CH3— | 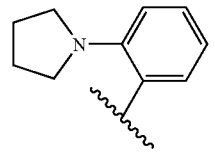 (2-pyrrolidinyl-phenyl) | H | CH3— | CH3— | CH3— |
| XA1767 | CH3— | 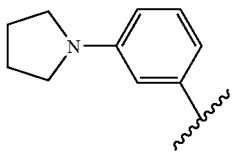 (3-pyrrolidinyl-phenyl) | H | CH3— | CH3— | CH3— |
| XA1768 | CH3— | 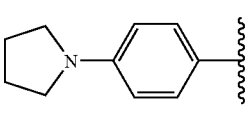 (4-pyrrolidinyl-phenyl) | H | CH3— | CH3— | CH3— |
| XA1769 | CH3— | 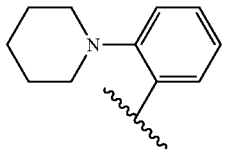 (2-piperidinyl-phenyl) | H | CH3— | CH3— | CH3— |
| XA1770 | CH3— | 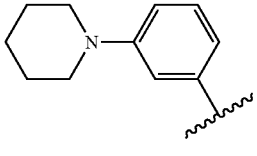 (3-piperidinyl-phenyl) | H | CH3— | CH3— | CH3— |

-continued
| | | | | | | |
|---|---|---|---|---|---|---|
| XA1771 | CH3— | 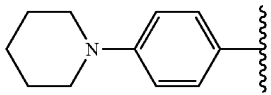 | H | CH3— | CH3— | CH3— |
| XA1772 | CH3— | 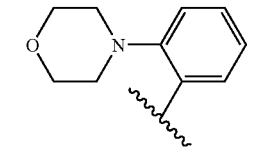 | H | CH3— | CH3— | CH3— |
| XA1773 | CH3— | 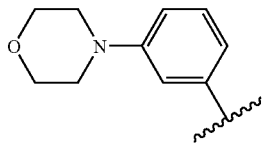 | H | CH3— | CH3— | CH3— |
| XA1774 | CH3— | 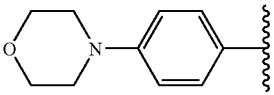 | H | CH3— | CH3— | CH3— |
| XA1775 | CH3— | 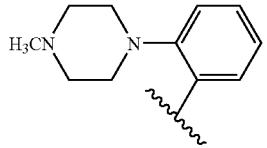 | H | CH3— | CH3— | CH3— |
| XA1776 | CH3— | 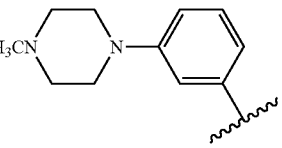 | H | CH3— | CH3— | CH3— |
| XA1777 | CH3— | 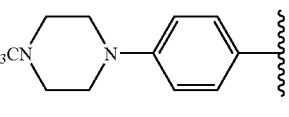 | H | CH3— | CH3— | CH3— |
| XA1778 | CH3— | 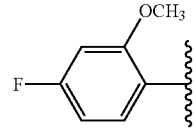 | H | CH3— | CH3— | CH3— |
| XA1779 | CH3— | 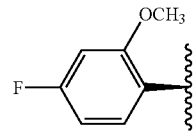 | H | CH3— | CH3— | CH3— |
| XA1780 | CH3— | 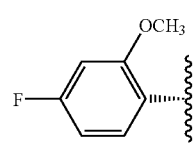 | H | CH3— | CH3— | CH3— |
| XA1781 | CH3— | 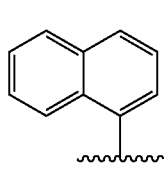 | H | CH3— | CH3— | CH3— |

-continued

| | | | | | | |
|---|---|---|---|---|---|---|
| XA1782 | CH3— | 2-naphthyl | H | CH3— | CH3— | CH3— |
| XA1783 | CH3CH2— | CH3— | H | H | H | H |
| XA1784 | CH3CH2— | CH3CH2— | H | H | H | H |
| XA1785 | CH3CH2— | n-propyl | H | H | H | H |
| XA1786 | CH3CH2— | isopropyl | H | H | H | H |
| XA1787 | CH3CH2— | n-butyl | H | H | H | H |
| XA1788 | CH3CH2— | isobutyl | H | H | H | H |
| XA1789 | CH3CH2— | sec-butyl | H | H | H | H |
| XA1790 | CH3CH2— | tert-butyl | H | H | H | H |
| XA1791 | CH3CH2— | n-pentyl | H | H | H | H |
| XA1792 | CH3CH2— | isopentyl | H | H | H | H |
| XA1793 | CH3CH2— | neopentyl | H | H | H | H |
| XA1794 | CH3CH2— | tert-pentyl | H | H | H | H |
| XA1795 | CH3CH2— | n-heptyl | H | H | H | H |
| XA1796 | CH3CH2— | isohexyl | H | H | H | H |

-continued
| | | | | | | |
|---|---|---|---|---|---|---|
| XA1797 | CH3CH2— | 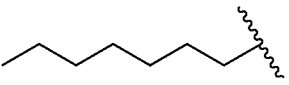 | H | H | H | H |
| XA1798 | CH3CH2— | 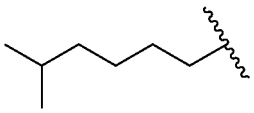 | H | H | H | H |
| XA1799 | CH3CH2— | n-C8H17— | H | H | H | H |
| XA1800 | CH3CH2— | 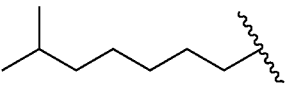 | H | H | H | H |
| XA1801 | CH3CH2— | 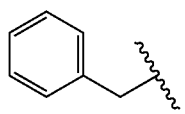 | H | H | H | H |
| XA1802 | CH3CH2— | 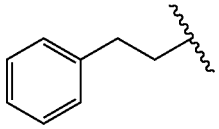 | H | H | H | H |
| XA1803 | CH3CH2— | 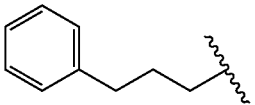 | H | H | H | H |
| XA1804 | CH3CH2— | 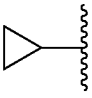 | H | H | H | H |
| XA1805 | CH3CH2— | 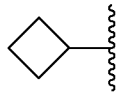 | H | H | H | H |
| XA1806 | CH3CH2— | 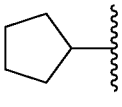 | H | H | H | H |
| XA1807 | CH3CH2— | 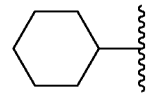 | H | H | H | H |
| XA1808 | CH3CH2— | 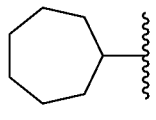 | H | H | H | H |
| XA1809 | CH3CH2— | 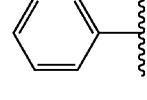 | H | H | H | H |
| XA1810 | CH3CH2— | 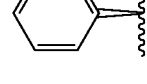 | H | H | H | H |

-continued
| | | | | | | |
|---|---|---|---|---|---|---|
| XA1811 | CH3CH2— | 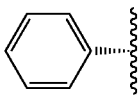 | H | H | H | H |
| XA1812 | CH3CH2— | 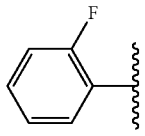 | H | H | H | H |
| XA1813 | CH3CH2— | 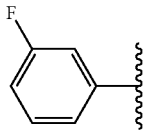 | H | H | H | H |
| XA1814 | CH3CH2— | 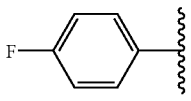 | H | H | H | H |
| XA1815 | CH3CH2— | 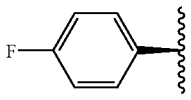 | H | H | H | H |
| XA1816 | CH3CH2— | 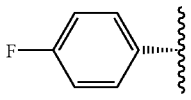 | H | H | H | H |
| XA1817 | CH3CH2— | 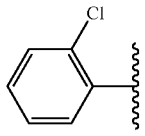 | H | H | H | H |
| XA1818 | CH3CH2— | 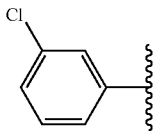 | H | H | H | H |
| XA1819 | CH3CH2— | 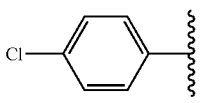 | H | H | H | H |
| XA1820 | CH3CH2— | 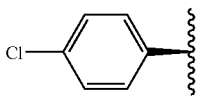 | H | H | H | H |
| XA1821 | CH3CH2— | 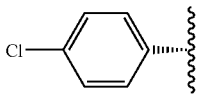 | H | H | H | H |
| XA1822 | CH3CH2— | 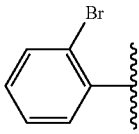 | H | H | H | H |

-continued
| | | | | | | |
|---|---|---|---|---|---|---|
| XA1823 | CH3CH2— | 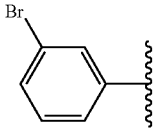 3-Br-C6H4 | H | H | H | H |
| XA1824 | CH3CH2— | 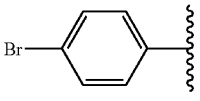 4-Br-C6H4 | H | H | H | H |
| XA1825 | CH3CH2— | 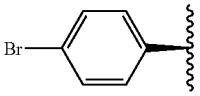 4-Br-C6H4 | H | H | H | H |
| XA1826 | CH3CH2— | 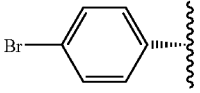 4-Br-C6H4 | H | H | H | H |
| XA1827 | CH3CH2— | 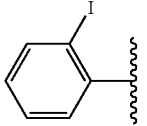 2-I-C6H4 | H | H | H | H |
| XA1828 | CH3CH2— | 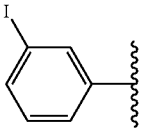 3-I-C6H4 | H | H | H | H |
| XA1829 | CH3CH2— | 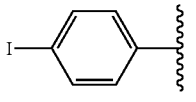 4-I-C6H4 | H | H | H | H |
| XA1830 | CH3CH2— | 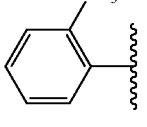 2-CH3-C6H4 | H | H | H | H |
| XA1831 | CH3CH2— | 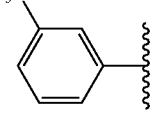 3-CH3-C6H4 | H | H | H | H |
| XA1832 | CH3CH2— | 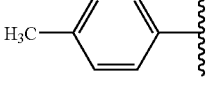 4-CH3-C6H4 | H | H | H | H |
| XA1833 | CH3CH2— | 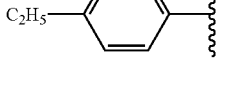 4-C2H5-C6H4 | H | H | H | H |
| XA1834 | CH3CH2— | 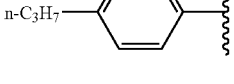 4-n-C3H7-C6H4 | H | H | H | H |

-continued
| | | | | | | |
|---|---|---|---|---|---|---|
| XA1835 | CH3CH2— | 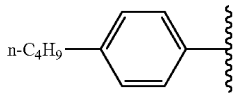 | H | H | H | H |
| XA1836 | CH3CH2— | 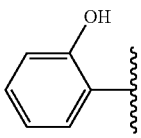 | H | H | H | H |
| XA1837 | CH3CH2— | 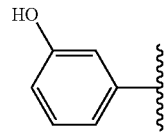 | H | H | H | H |
| XA1838 | CH3CH2— | 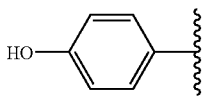 | H | H | H | H |
| XA1839 | CH3CH2— | 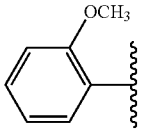 | H | H | H | H |
| XA1840 | CH3CH2— | 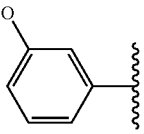 | H | H | H | H |
| XA1841 | CH3CH2— | 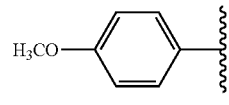 | H | H | H | H |
| XA1842 | CH3CH2— | 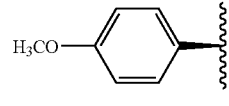 | H | H | H | H |
| XA1843 | CH3CH2— | 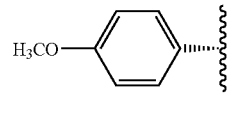 | H | H | H | H |
| XA1844 | CH3CH2— | 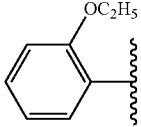 | H | H | H | H |
| XA1845 | CH3CH2— | 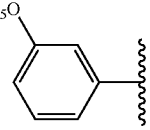 | H | H | H | H |
| XA1846 | CH3CH2— | 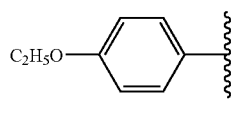 | H | H | H | H |

-continued
| | | | | | | |
|---|---|---|---|---|---|---|
| XA1847 | CH3CH2— | 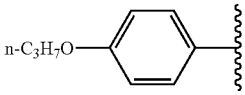 n-C$_3$H$_7$O— | H | H | H | H |
| XA1848 | CH3CH2— | 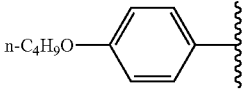 n-C$_4$H$_9$O— | H | H | H | H |
| XA1849 | CH3CH2— | 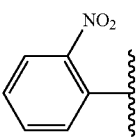 NO$_2$ | H | H | H | H |
| XA1850 | CH3CH2— | 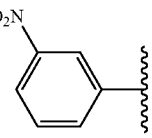 O$_2$N— | H | H | H | H |
| XA1851 | CH3CH2— | 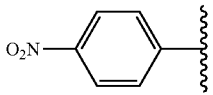 O$_2$N— | H | H | H | H |
| XA1852 | CH3CH2— | 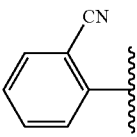 CN | H | H | H | H |
| XA1853 | CH3CH2— | 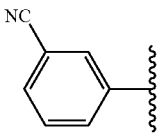 NC— | H | H | H | H |
| XA1854 | CH3CH2— | 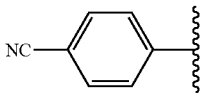 NC— | H | H | H | H |
| XA1855 | CH3CH2— | 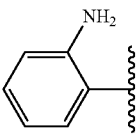 NH$_2$ | H | H | H | H |
| XA1856 | CH3CH2— | 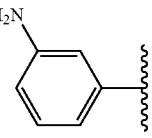 H$_2$N— | H | H | H | H |
| XA1857 | CH3CH2— | 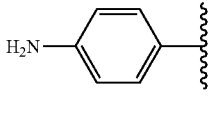 H$_2$N— | H | H | H | H |
| XA1858 | CH3CH2— | 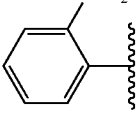 NMe$_2$ | H | H | H | H |

-continued
| | | | | | | | |
|---|---|---|---|---|---|---|---|
| XA1859 | CH3CH2— | 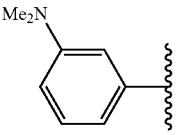 | H | H | H | H |
| XA1860 | CH3CH2— | 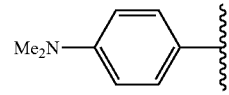 | H | H | H | H |
| XA1861 | CH3CH2— | 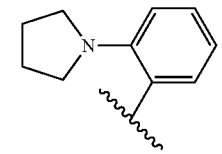 | H | H | H | H |
| XA1862 | CH3CH2— | 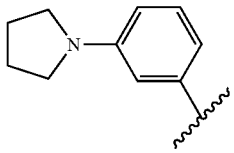 | H | H | H | H |
| XA1863 | CH3CH2— | 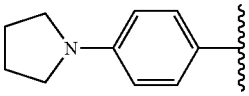 | H | H | H | H |
| XA1864 | CH3CH2— | 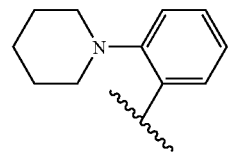 | H | H | H | H |
| XA1865 | CH3CH2— | 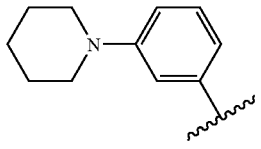 | H | H | H | H |
| XA1866 | CH3CH2— | 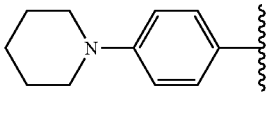 | H | H | H | H |
| XA1867 | CH3CH2— | 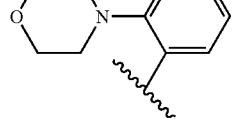 | H | H | H | H |
| XA1868 | CH3CH2— | 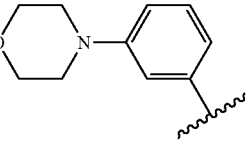 | H | H | H | H |
| XA1869 | CH3CH2— | 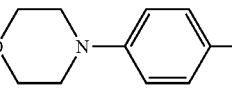 | H | H | H | H |

-continued
| | | | | | | |
|---|---|---|---|---|---|---|
| XA1870 | CH3CH2— | 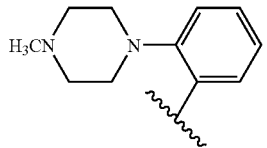 | H | H | H | H |
| XA1871 | CH3CH2— | 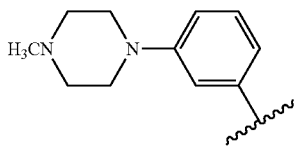 | H | H | H | H |
| XA1872 | CH3CH2— | 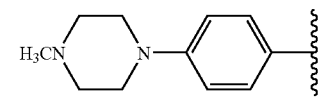 | H | H | H | H |
| XA1873 | CH3CH2— | 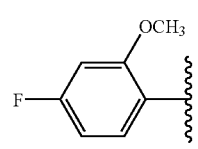 | H | H | H | H |
| XA1874 | CH3CH2— | 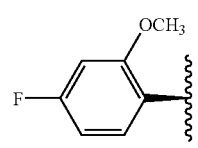 | H | H | H | H |
| XA1875 | CH3CH2— | 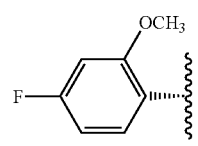 | H | H | H | H |
| XA1876 | CH3CH2— | 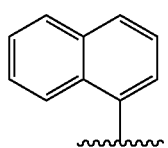 | H | H | H | H |
| XA1877 | CH3CH2— | 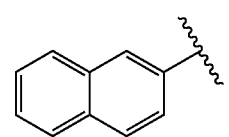 | H | H | H | H |
| XA1878 | CH3CH2— | CH3— | H | CH3— | H | H |
| XA1879 | CH3CH2— | CH3CH2— | H | CH3— | H | H |
| XA1880 | CH3CH2— | 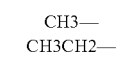 | H | CH3— | H | H |
| XA1881 | CH3CH2— | 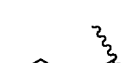 | H | CH3— | H | H |
| XA1882 | CH3CH2— | 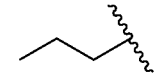 | H | CH3— | H | H |

-continued
| | | | | | | |
|---|---|---|---|---|---|---|
| XA1883 | CH3CH2— | 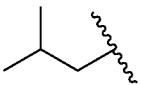 | H | CH3— | H | H |
| XA1884 | CH3CH2— | 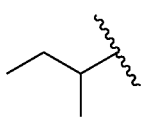 | H | CH3— | H | H |
| XA1885 | CH3CH2— | 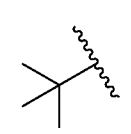 | H | CH3— | H | H |
| XA1886 | CH3CH2— | 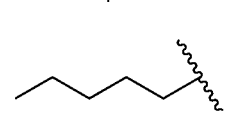 | H | CH3— | H | H |
| XA1887 | CH3CH2— | 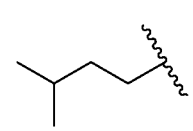 | H | CH3— | H | H |
| XA1888 | CH3CH2— | 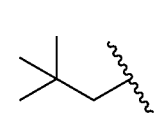 | H | CH3— | H | H |
| XA1889 | CH3CH2— | 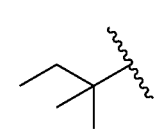 | H | CH3— | H | H |
| XA1890 | CH3CH2— | 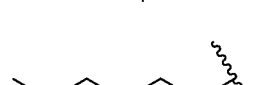 | H | CH3— | H | H |
| XA1891 | CH3CH2— | 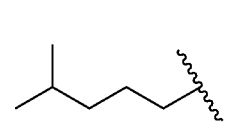 | H | CH3— | H | H |
| XA1892 | CH3CH2— | 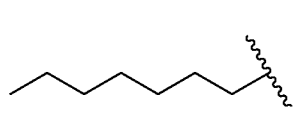 | H | CH3— | H | H |
| XA1893 | CH3CH2— | 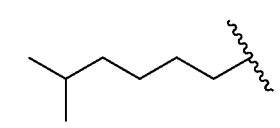 | H | CH3— | H | H |
| XA1894 | CH3CH2— | n-C8H17— | H | CH3— | H | H |
| XA1895 | CH3CH2— | 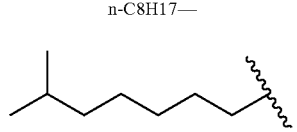 | H | CH3— | H | H |
| XA1896 | CH3CH2— | 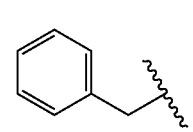 | H | CH3— | H | H |

-continued
| | | | | | | |
|---|---|---|---|---|---|---|
| XA1897 | CH3CH2— | 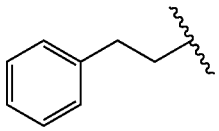 | H | CH3— | H | H |
| XA1898 | CH3CH2— | 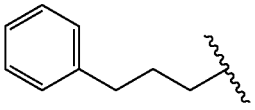 | H | CH3— | H | H |
| XA1899 | CH3CH2— |  | H | CH3— | H | H |
| XA1900 | CH3CH2— | 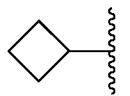 | H | CH3— | H | H |
| XA1901 | CH3CH2— | 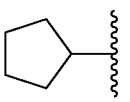 | H | CH3— | H | H |
| XA1902 | CH3CH2— | 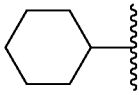 | H | CH3— | H | H |
| XA1903 | CH3CH2— | 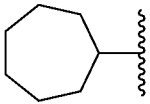 | H | CH3— | H | H |
| XA1904 | CH3CH2— | 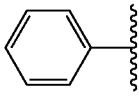 | H | CH3— | H | H |
| XA1905 | CH3CH2— | 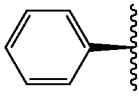 | H | CH3— | H | H |
| XA1906 | CH3CH2— | 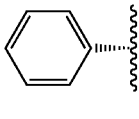 | H | CH3— | H | H |
| XA1907 | CH3CH2— | 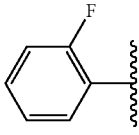 | H | CH3— | H | H |
| XA1908 | CH3CH2— | 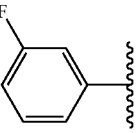 | H | CH3— | H | H |
| XA1909 | CH3CH2— | 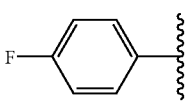 | H | CH3— | H | H |

-continued
| | | | | | | |
|---|---|---|---|---|---|---|
| XA1910 | CH3CH2— | 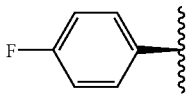 | H | CH3— | H | H |
| XA1911 | CH3CH2— | 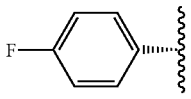 | H | CH3— | H | H |
| XA1912 | CH3CH2— | 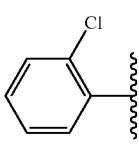 | H | CH3— | H | H |
| XA1913 | CH3CH2— | 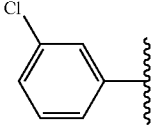 | H | CH3— | H | H |
| XA1914 | CH3CH2— | 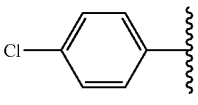 | H | CH3— | H | H |
| XA1915 | CH3CH2— | 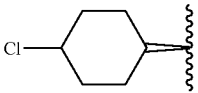 | H | CH3— | H | H |
| XA1916 | CH3CH2— | 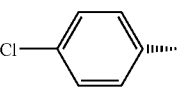 | H | CH3— | H | H |
| XA1917 | CH3CH2— | 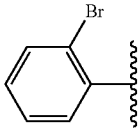 | H | CH3— | H | H |
| XA1918 | CH3CH2— | 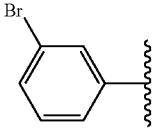 | H | CH3— | H | H |
| XA1919 | CH3CH2— | 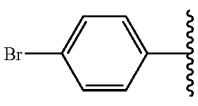 | H | CH3— | H | H |
| XA1920 | CH3CH2— | 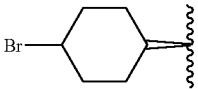 | H | CH3— | H | H |
| XA1921 | CH3CH2— | 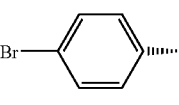 | H | CH3— | H | H |
| XA1922 | CH3CH2— | 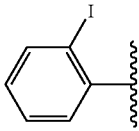 | H | CH3— | H | H |

-continued
| | | | | | | |
|---|---|---|---|---|---|---|
| XA1923 | CH3CH2— | 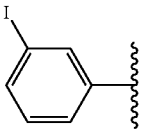 | H | CH3— | H | H |
| XA1924 | CH3CH2— | 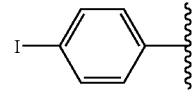 | H | CH3— | H | H |
| XA1925 | CH3CH2— | 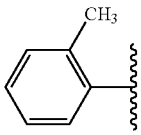 | H | CH3— | H | H |
| XA1926 | CH3CH2— | 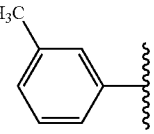 | H | CH3— | H | H |
| XA1927 | CH3CH2— | 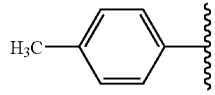 | H | CH3— | H | H |
| XA1928 | CH3CH2— | 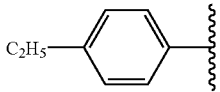 | H | CH3— | H | H |
| XA1929 | CH3CH2— | 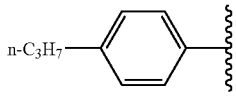 | H | CH3— | H | H |
| XA1930 | CH3CH2— | 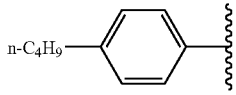 | H | CH3— | H | H |
| XA1931 | CH3CH2— | 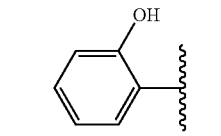 | H | CH3— | H | H |
| XA1932 | CH3CH2— | 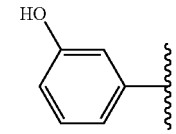 | H | CH3— | H | H |
| XA1933 | CH3CH2— | 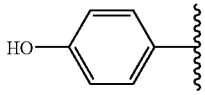 | H | CH3— | H | H |
| XA1934 | CH3CH2— | 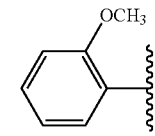 | H | CH3— | H | H |

-continued
| | | | | | | |
|---|---|---|---|---|---|---|
| XA1935 | CH3CH2— | 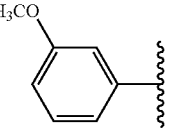 | H | CH3— | H | H |
| XA1936 | CH3CH2— | 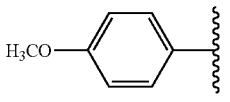 | H | CH3— | H | H |
| XA1937 | CH3CH2— | 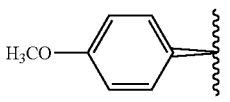 | H | CH3— | H | H |
| XA1938 | CH3CH2— | 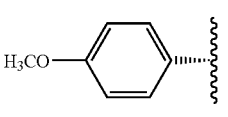 | H | CH3— | H | H |
| XA1939 | CH3CH2— | 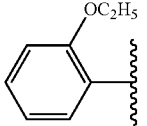 | H | CH3— | H | H |
| XA1940 | CH3CH2— | 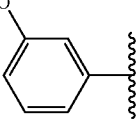 | H | CH3— | H | H |
| XA1941 | CH3CH2— | 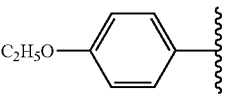 | H | CH3— | H | H |
| XA1942 | CH3CH2— | 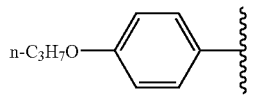 | H | CH3— | H | H |
| XA1943 | CH3CH2— | 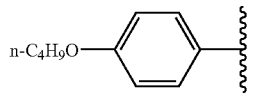 | H | CH3— | H | H |
| XA1944 | CH3CH2— | 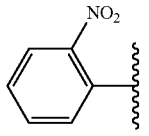 | H | CH3— | H | H |
| XA1945 | CH3CH2— | 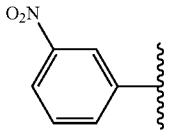 | H | CH3— | H | H |
| XA1946 | CH3CH2— | 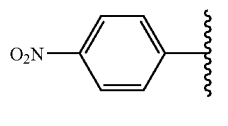 | H | CH3— | H | H |

-continued
| | | | | | | |
|---|---|---|---|---|---|---|
| XA1947 | CH3CH2— | 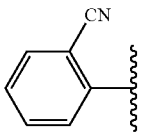 (2-CN-phenyl) | H | CH3— | H | H |
| XA1948 | CH3CH2— | 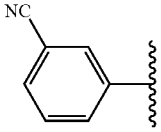 (2-CN-pyridin-3-yl) | H | CH3— | H | H |
| XA1949 | CH3CH2— | 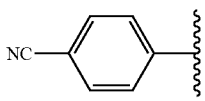 (4-CN-phenyl) | H | CH3— | H | H |
| XA1950 | CH3CH2— | 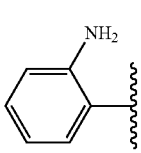 (2-NH2-phenyl) | H | CH3— | H | H |
| XA1951 | CH3CH2— | 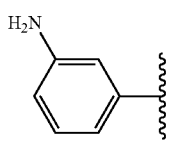 (3-NH2-phenyl) | H | CH3— | H | H |
| XA1952 | CH3CH2— | 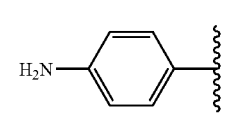 (4-NH2-phenyl) | H | CH3— | H | H |
| XA1953 | CH3CH2— | 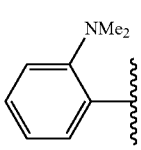 (2-NMe2-phenyl) | H | CH3— | H | H |
| XA1954 | CH3CH2— | 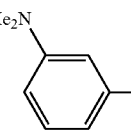 (3-NMe2-phenyl) | H | CH3— | H | H |
| XA1955 | CH3CH2— | 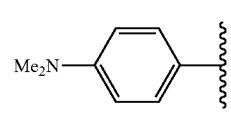 (4-NMe2-phenyl) | H | CH3— | H | H |
| XA1956 | CH3CH2— | 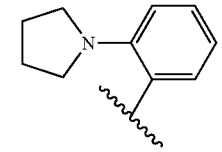 (2-pyrrolidinyl-phenyl) | H | CH3— | H | H |
| XA1957 | CH3CH2— | 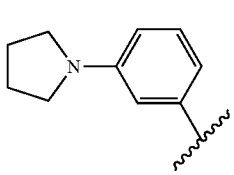 (3-pyrrolidinyl-phenyl) | H | CH3— | H | H |

-continued

| | | | | | | |
|---|---|---|---|---|---|---|
| XA1958 | CH3CH2— | 4-(pyrrolidin-1-yl)phenyl | H | CH3— | H | H |
| XA1959 | CH3CH2— | 2-(piperidin-1-yl)phenyl | H | CH3— | H | H |
| XA1960 | CH3CH2— | 3-(piperidin-1-yl)phenyl | H | CH3— | H | H |
| XA1961 | CH3CH2— | 4-(piperidin-1-yl)phenyl | H | CH3— | H | H |
| XA1962 | CH3CH2— | 2-(morpholin-4-yl)phenyl | H | CH3— | H | H |
| XA1963 | CH3CH2— | 3-(morpholin-4-yl)phenyl | H | CH3— | H | H |
| XA1964 | CH3CH2— | 4-(morpholin-4-yl)phenyl | H | CH3— | H | H |
| XA1965 | CH3CH2— | 2-(4-methylpiperazin-1-yl)phenyl | H | CH3— | H | H |
| XA1966 | CH3CH2— | 3-(4-methylpiperazin-1-yl)phenyl | H | CH3— | H | H |
| XA1967 | CH3CH2— | 4-(4-methylpiperazin-1-yl)phenyl | H | CH3— | H | H |
| XA1968 | CH3CH2— | 4-fluoro-2-methoxyphenyl | H | CH3— | H | H |

-continued
| No. | | | | | | |
|---|---|---|---|---|---|---|
| XA1969 | CH3CH2— | 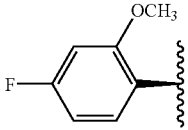 | H | CH3— | H | H |
| XA1970 | CH3CH2— | 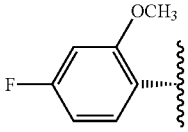 | H | CH3— | H | H |
| XA1971 | CH3CH2— | 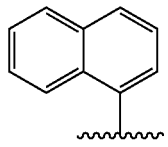 | H | CH3— | H | H |
| XA1972 | CH3CH2— | 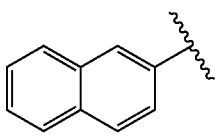 | H | CH3— | H | H |
| No. | STRUCTURE |
|---|---|
| XA1973 | 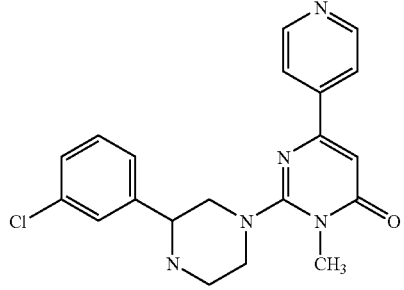 |
| XA1974 | 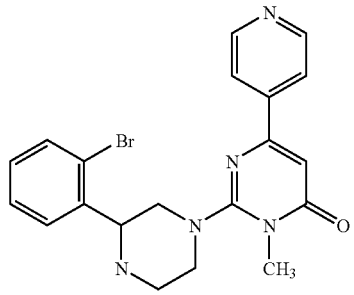 |
| XA1975 | 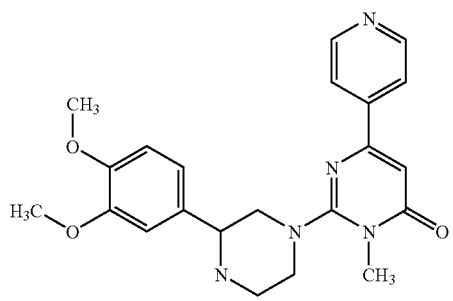 |

-continued
XA1976
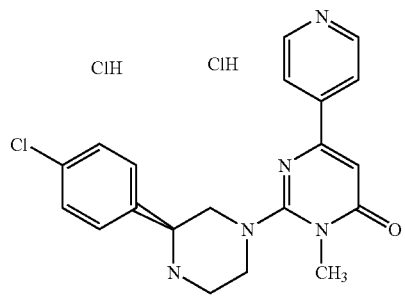
XA1977
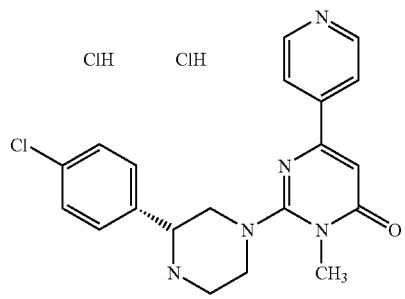
XA1978
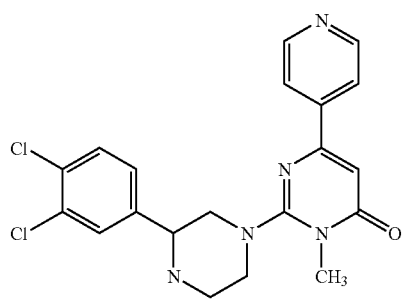
XA1979
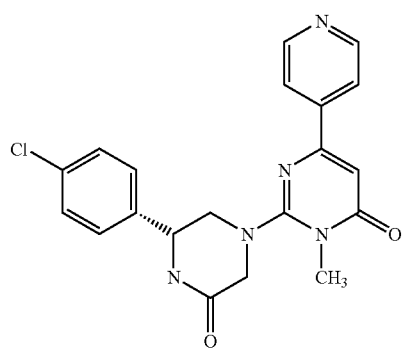
XA1980
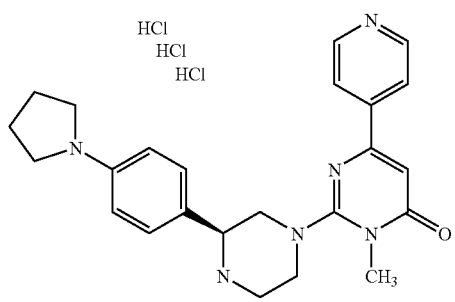

-continued
XA1981 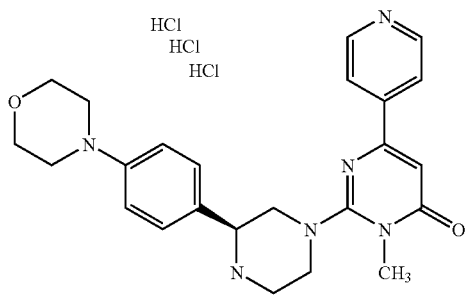
XA1982 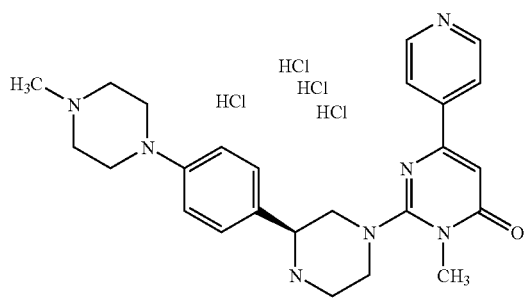
XA1983 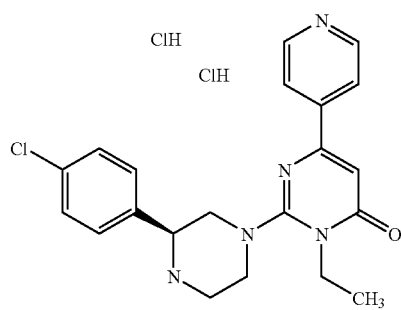
XA1984 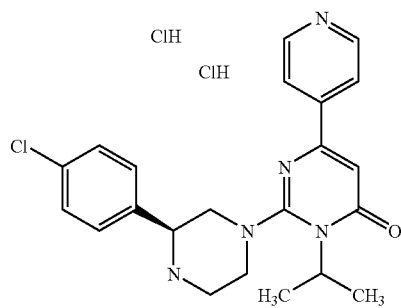
XA1985 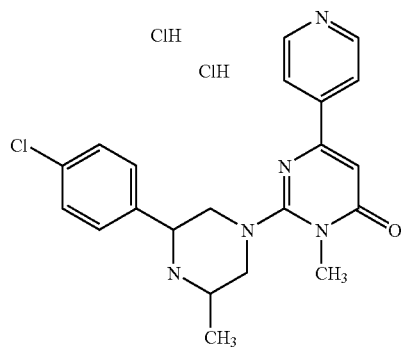

| | |
|---|---|
| XA1986 | 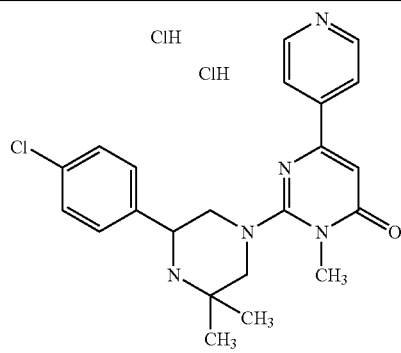 |
| XA1987 | 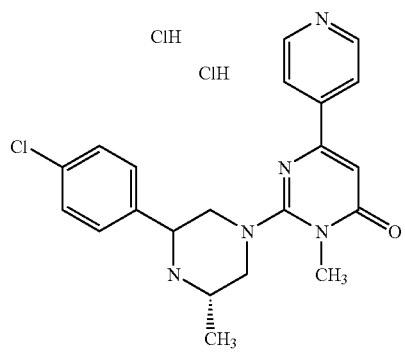 |
| XA1988 | 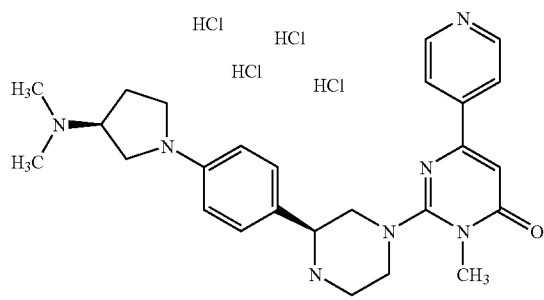 |
| XA1989 | 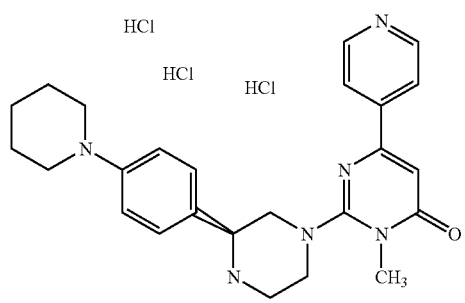 |
| XA1990 | 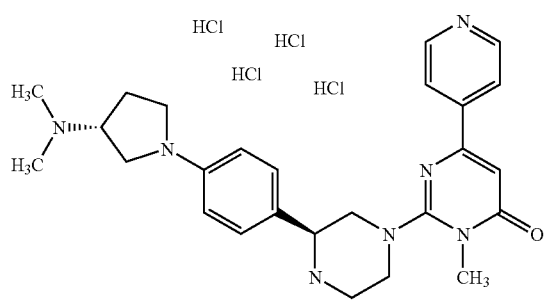 |

XA1991 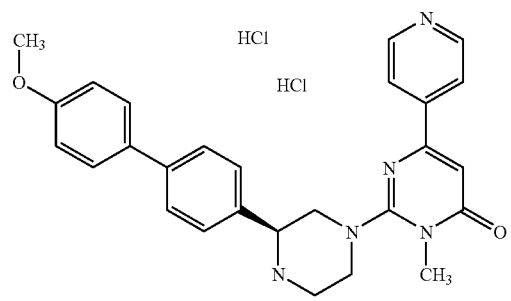
XA1992 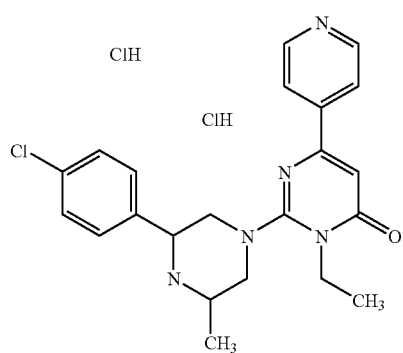
XA1993 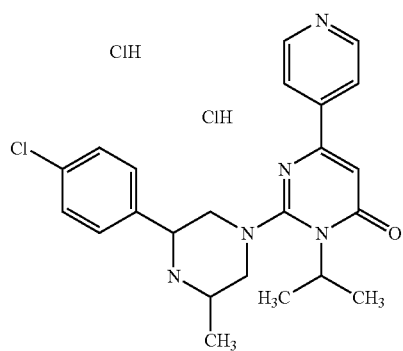
XA1994 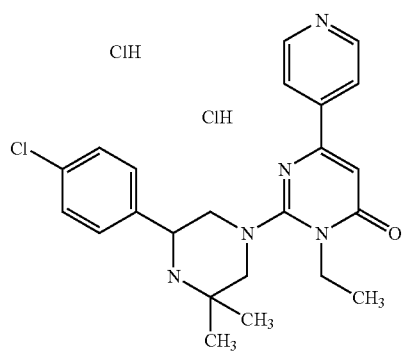

-continued
XA1995 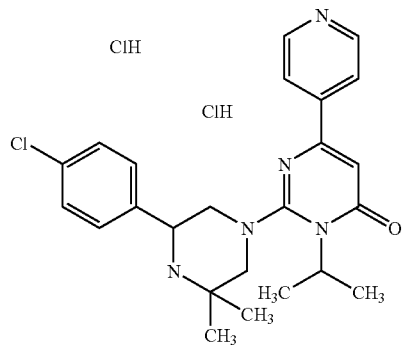
XA1996 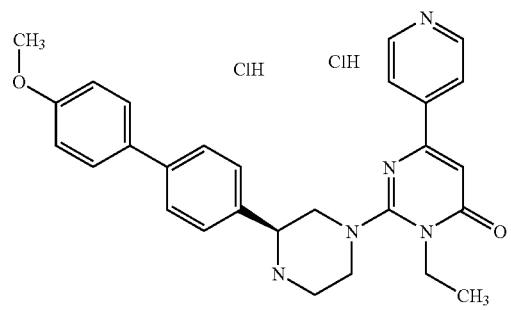
XA1997 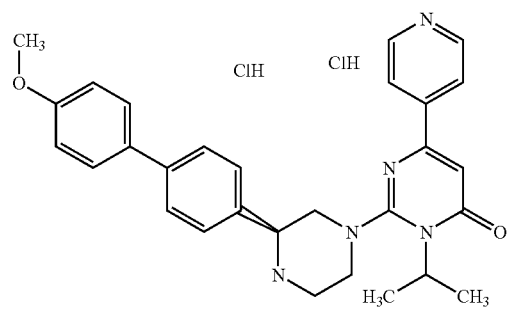
XA1998 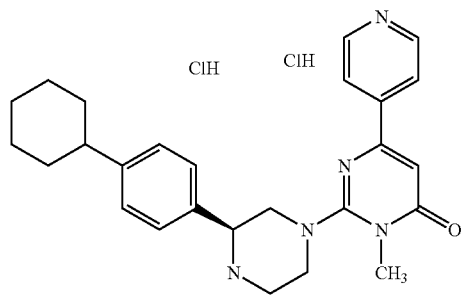
XA1999 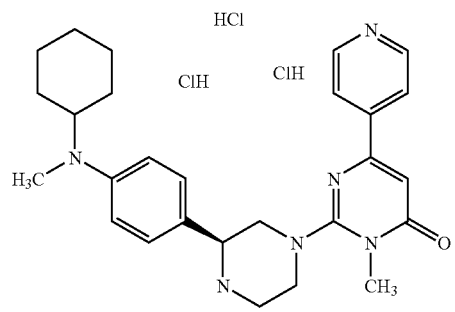

-continued
XA2000
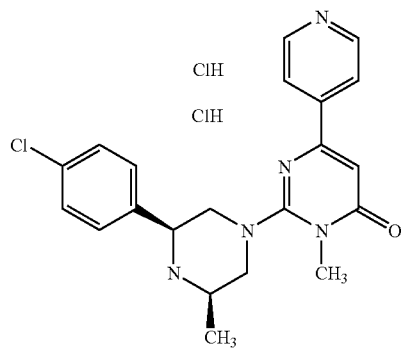
XA2001
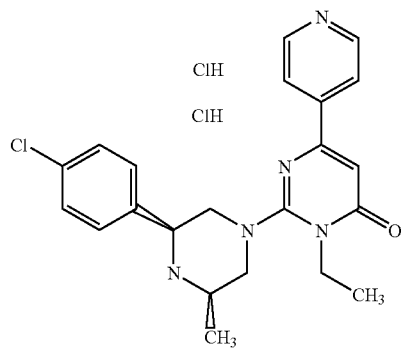
XA2002
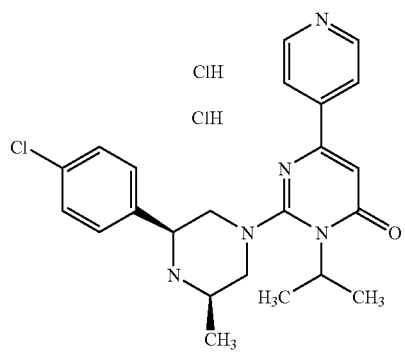
XA2003
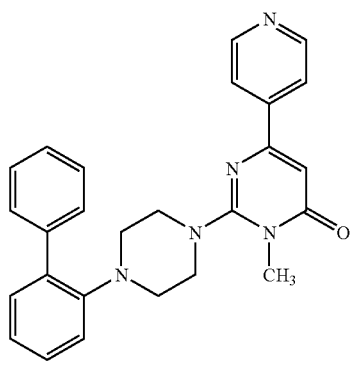

-continued
XA2004 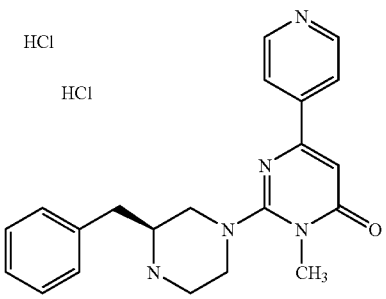
XA2005 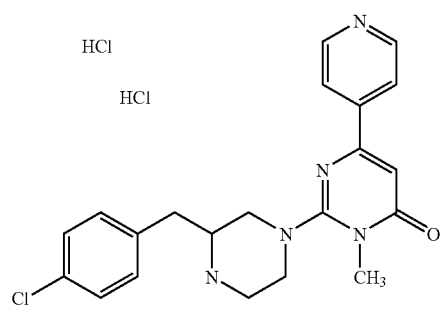
XA2006 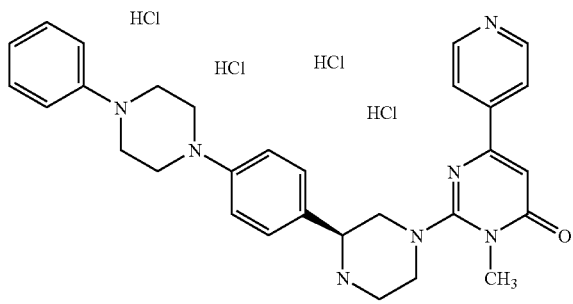
XA2007 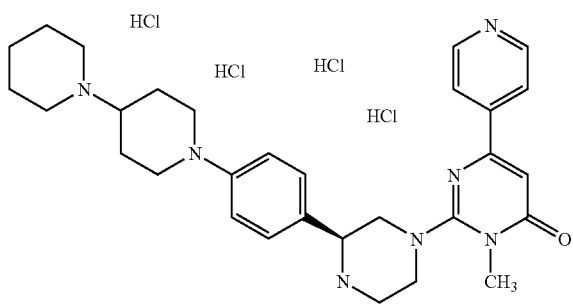
XA2008 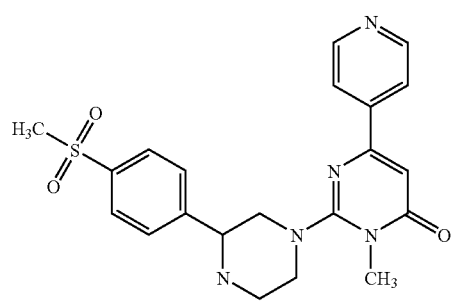

-continued
XA2009 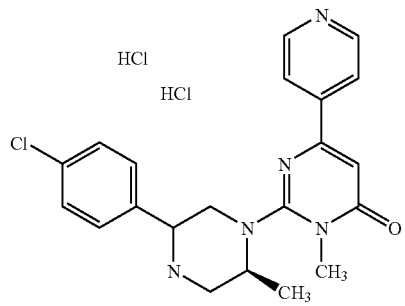
XA2010 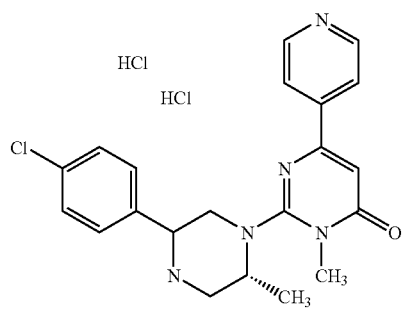
XA2011 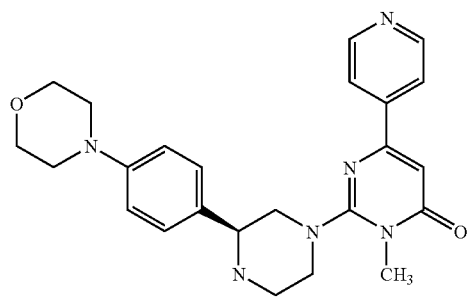
XA2012 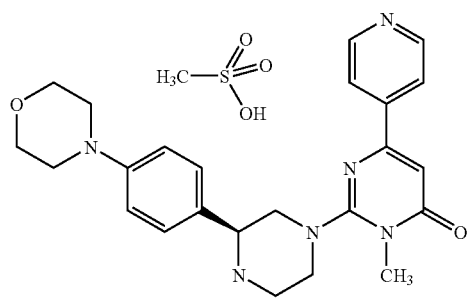
XA2013 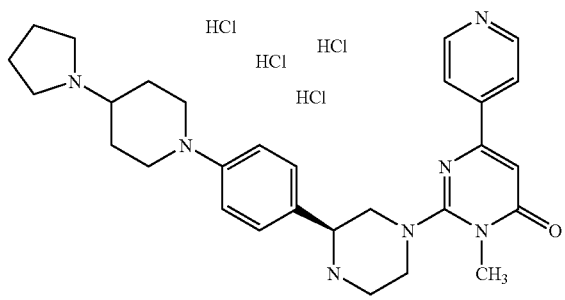

-continued
XA2014
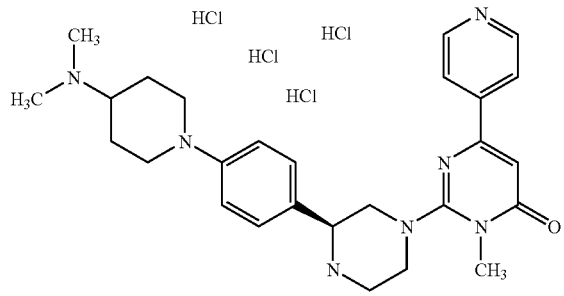
XA2015
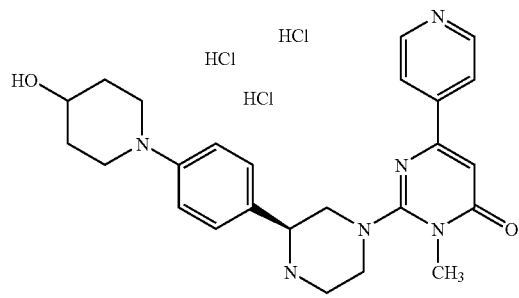
XA2016
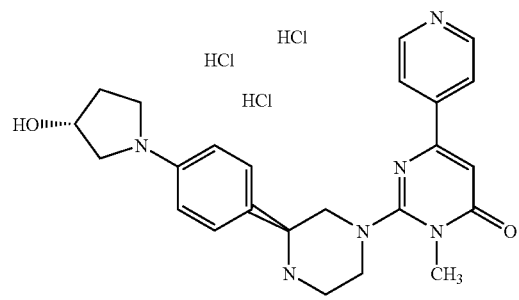
XA2017
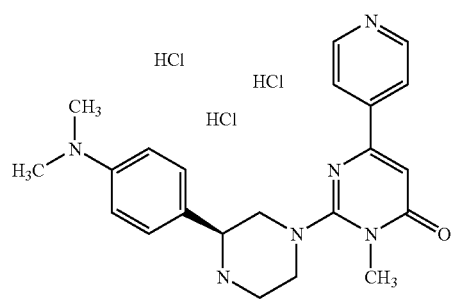
XA2018
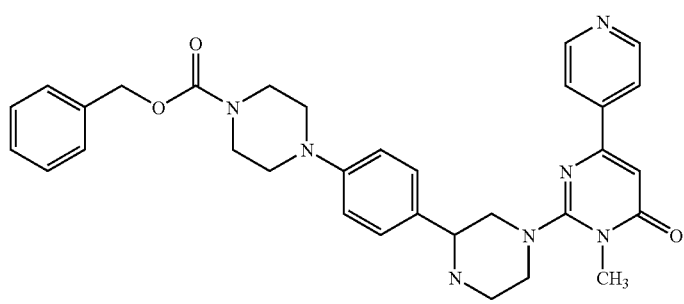

-continued
XA2019
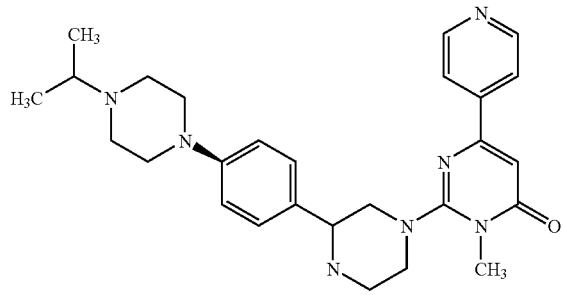
XA2020
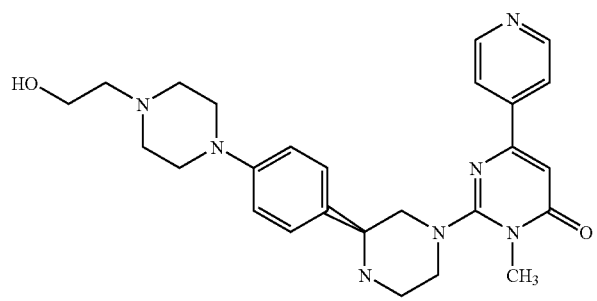
XA2021
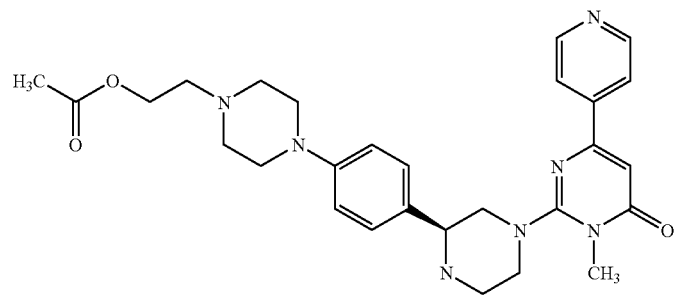
XA2022
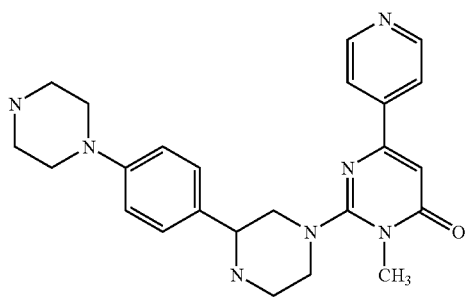
XA2023
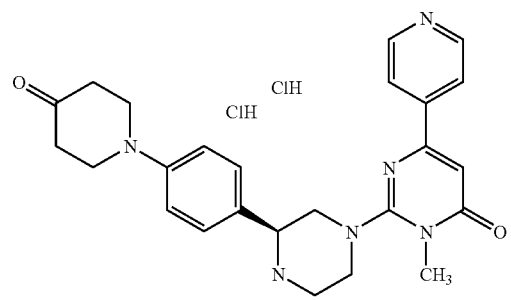

-continued
XA2024
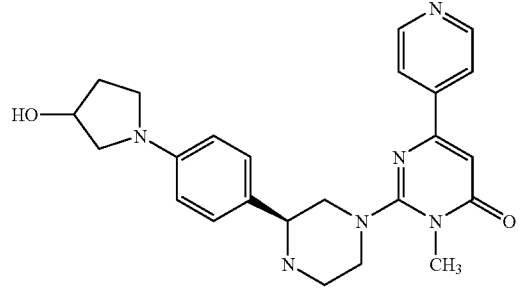
XA2025
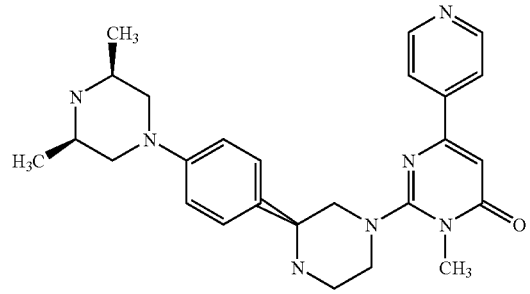
XA2026
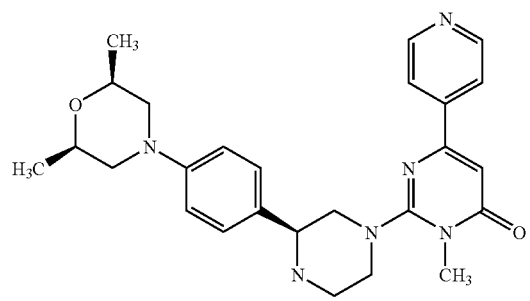
XA2027
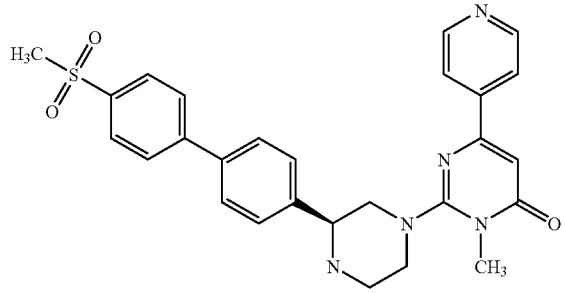
XA2028
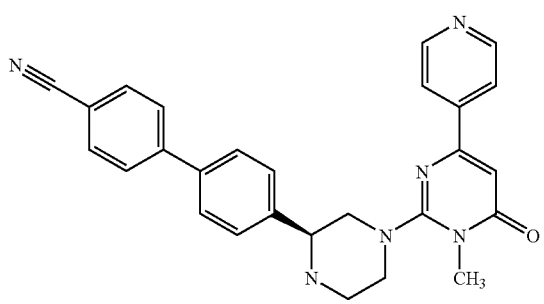

-continued
XA2029
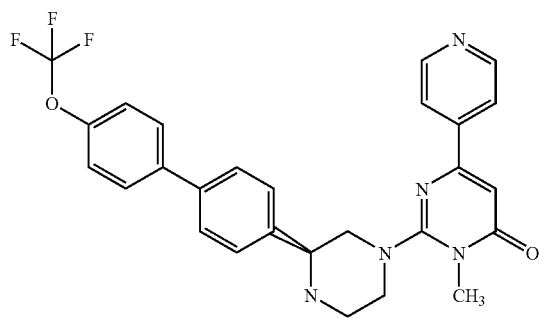
XA2030
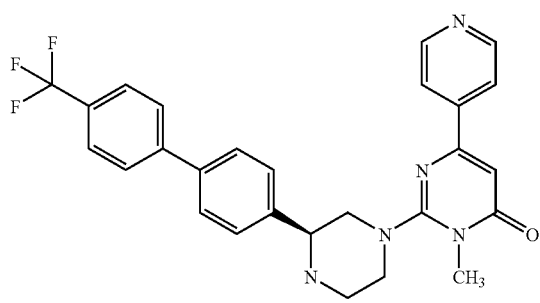
XA2031
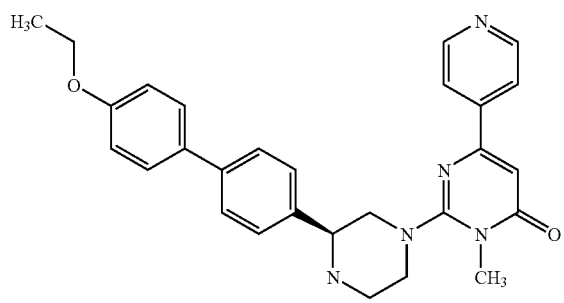
XA2032
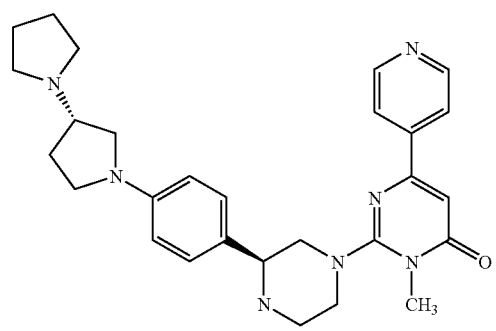

-continued
XA2033
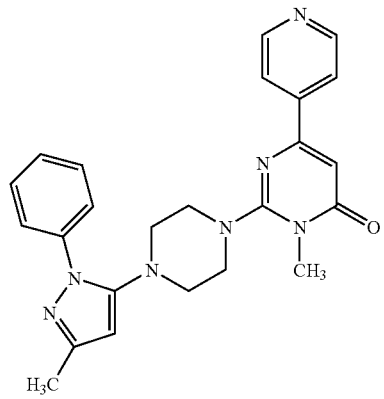
XA2034
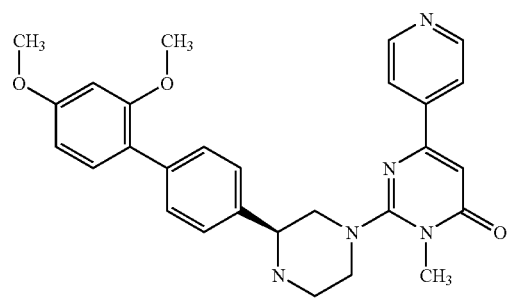
XA2035
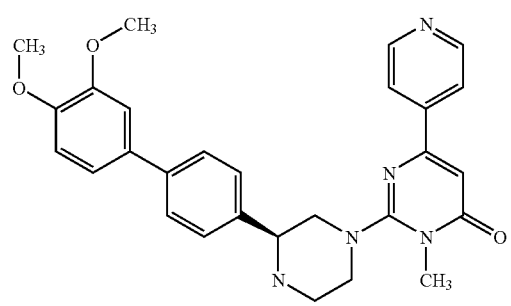
XA2036
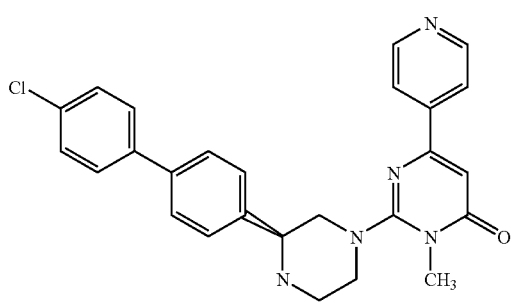
XA2037
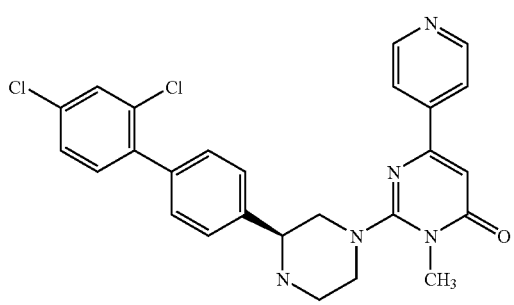

-continued
XA2038
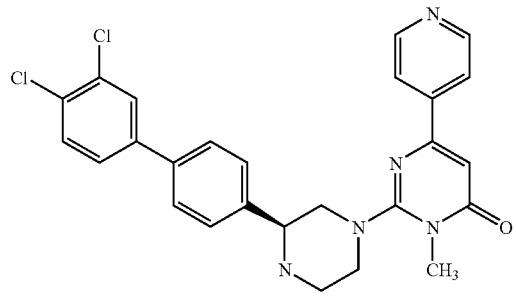
XA2039
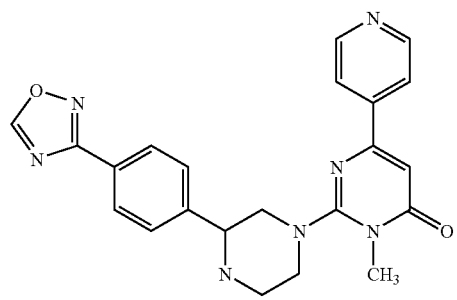
XA2040
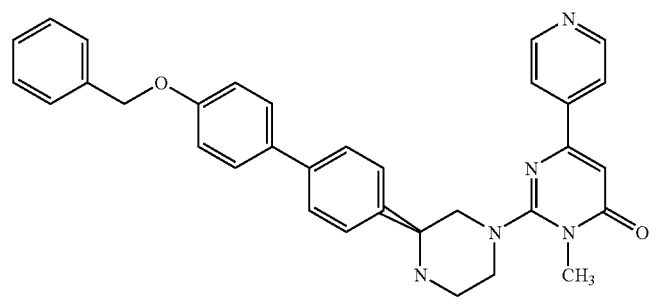
XA2041
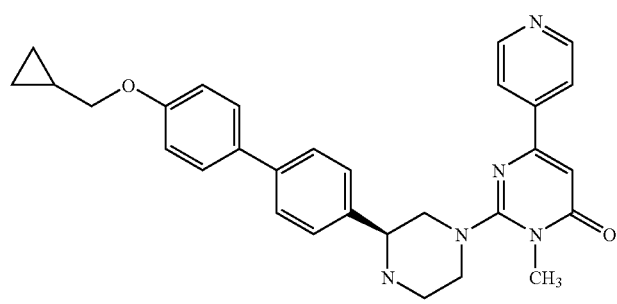
XA2042
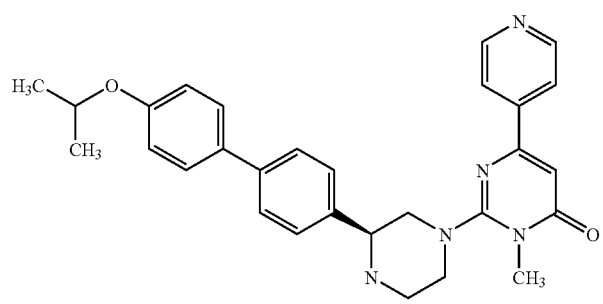

-continued
XA2043
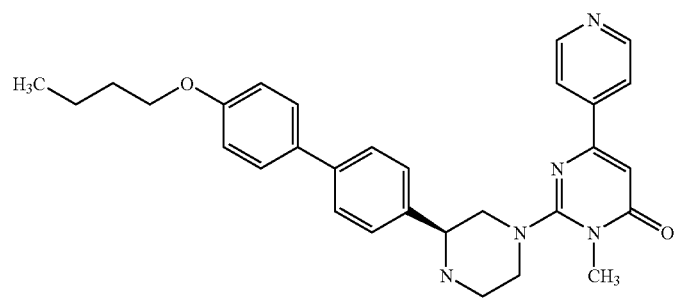
XA2044
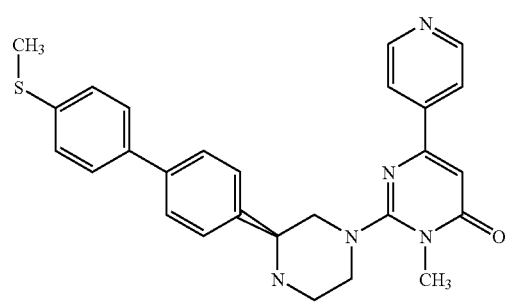
XA2045
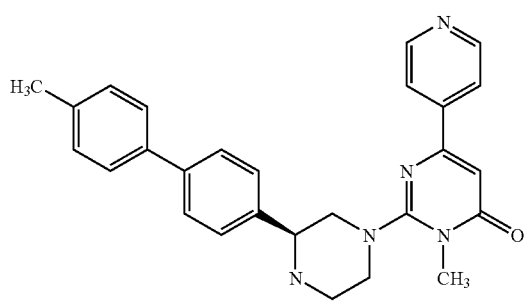
XA2046
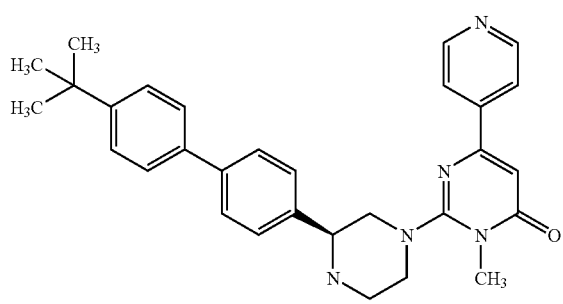
XA2047
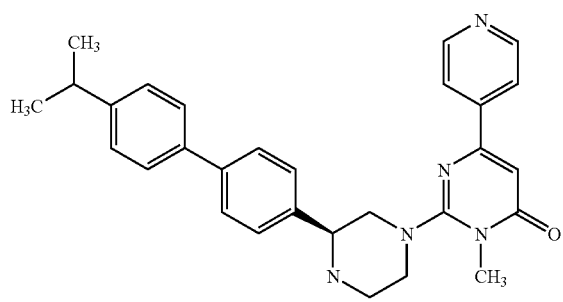

-continued
XA2048
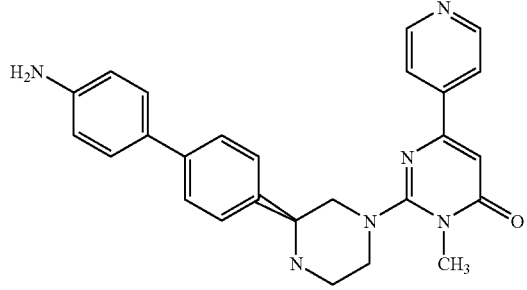
XA2049
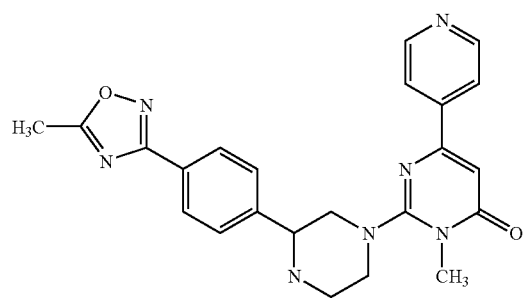
XA2050
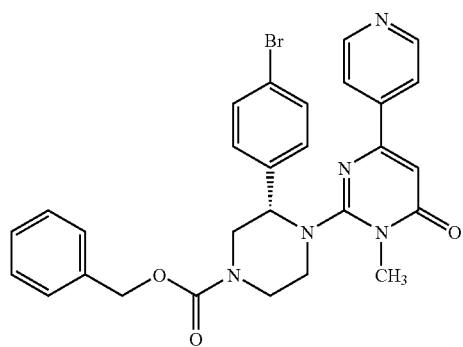
XA2051
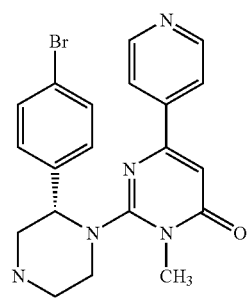

-continued
XA2052
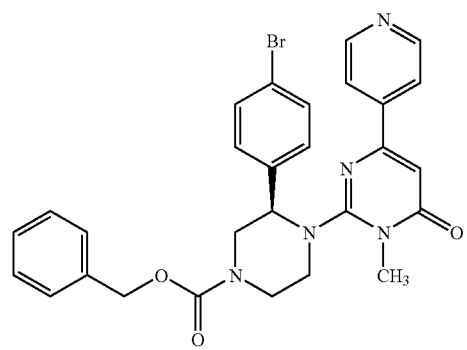
XA2053
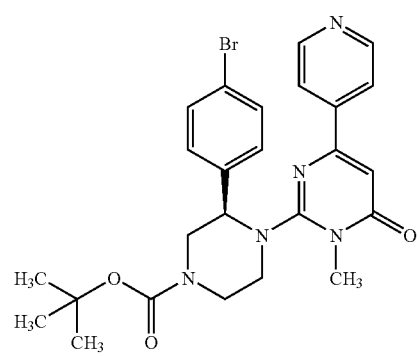
XA2054
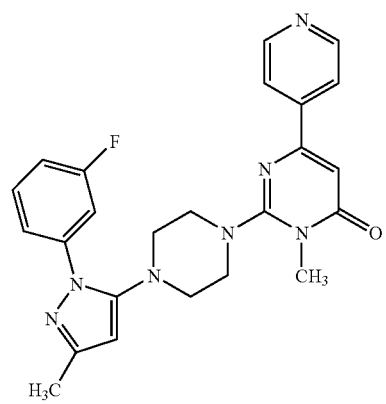
XA2055
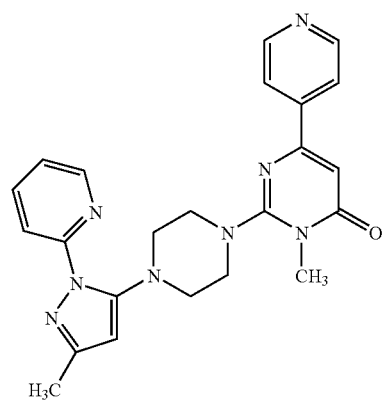

TABLE 2
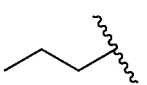
| No | R1 | R2 | R3 | R4 | R5 |
|---|---|---|---|---|---|
| XB1 | CH3— | CH3— | H | H | H |
| XB2 | CH3— | CH3CH2— | H | H | H |
| XB3 | CH3— | 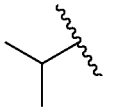 | H | H | H |
| XB4 | CH3— | 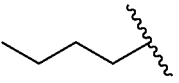 | H | H | H |
| XB5 | CH3— | 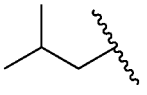 | H | H | H |
| XB6 | CH3— | 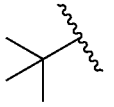 | H | H | H |
| XB7 | CH3— | 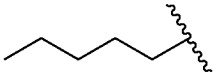 | H | H | H |
| XB8 | CH3— | 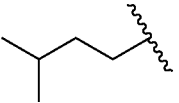 | H | H | H |
| XB9 | CH3— |  | H | H | H |
| XB10 | CH3— |  | H | H | H |
| XB11 | CH3— |  | H | H | H |
| XB12 | CH3— | 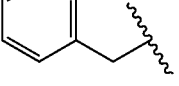 | H | H | H |
| XB13 | CH3— |  | H | H | H |

TABLE 2-continued
| | | | | | |
|---|---|---|---|---|---|
| XB14 | CH3— | 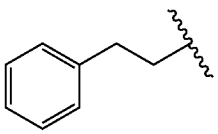 | H | H | H |
| XB15 | CH3— | 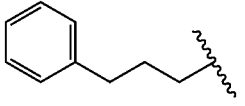 | H | H | H |
| XB16 | CH3— | 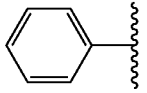 | H | H | H |
| XB17 | CH3— | 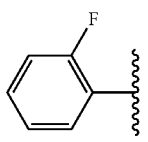 | H | H | H |
| XB18 | CH3— | 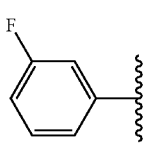 | H | H | H |
| XB19 | CH3— | 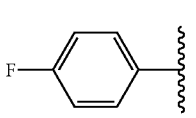 | H | H | H |
| XB20 | CH3— | 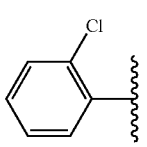 | H | H | H |
| XB21 | CH3— | 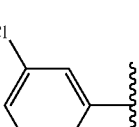 | H | H | H |
| XB22 | CH3— | 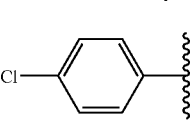 | H | H | H |
| XB23 | CH3— | 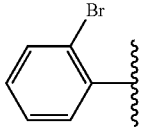 | H | H | H |
| XB24 | CH3— | 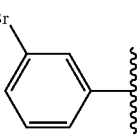 | H | H | H |
| XB25 | CH3— | 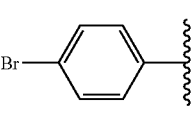 | H | H | H |

TABLE 2-continued

| XB26 | CH3— | 2-methylphenyl | H | H | H |
| XB27 | CH3— | 3-methylphenyl | H | H | H |
| XB28 | CH3— | 4-methylphenyl | H | H | H |
| XB29 | CH3— | 4-ethylphenyl | H | H | H |
| XB30 | CH3— | 2-hydroxyphenyl | H | H | H |
| XB31 | CH3— | 3-hydroxyphenyl | H | H | H |
| XB32 | CH3— | 4-hydroxyphenyl | H | H | H |
| XB33 | CH3— | 2-methoxyphenyl | H | H | H |
| XB34 | CH3— | 3-methoxyphenyl | H | H | H |
| XB35 | CH3— | 4-methoxyphenyl | H | H | H |
| XB36 | CH3— | 4-ethoxyphenyl | H | H | H |
| XB37 | CH3— | 2-nitrophenyl | H | H | H |

TABLE 2-continued
| | | | | | |
|---|---|---|---|---|---|
| XB38 | CH3— | 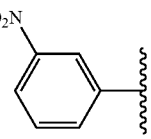 | H | H | H |
| XB39 | CH3— | 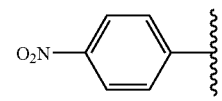 | H | H | H |
| XB40 | CH3— | 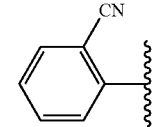 | H | H | H |
| XB41 | CH3— | 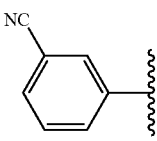 | H | H | H |
| XB42 | CH3— | 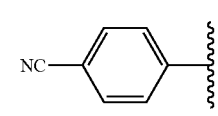 | H | H | H |
| XB43 | CH3— | 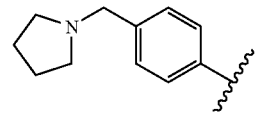 | H | H | H |
| XB44 | CH3— | 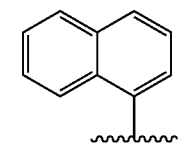 | H | H | H |
| XB45 | CH3— | 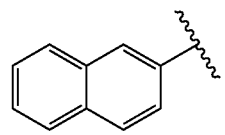 | H | H | H |
| XB46 | CH3— | 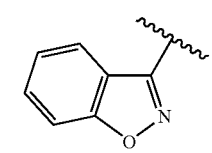 | H | H | H |
| XB47 | CH3— | 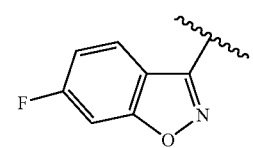 | H | H | H |
| XB48 | CH3— | 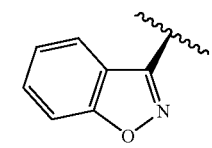 | H | H | H |

TABLE 2-continued
| | | | | | |
|---|---|---|---|---|---|
| XB49 | CH3— | 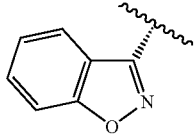 | H | H | H |
| XB50 | CH3— | 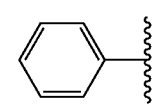 | OH | H | H |
| XB51 | CH3— | 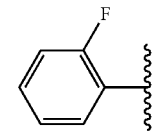 | OH | H | H |
| XB52 | CH3— | 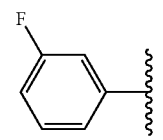 | OH | H | H |
| XB53 | CH3— | 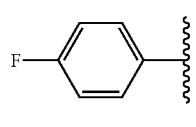 | OH | H | H |
| XB54 | CH3— | 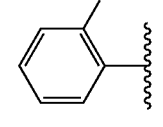 | OH | H | H |
| XB55 | CH3— | 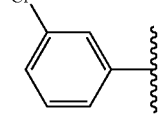 | OH | H | H |
| XB56 | CH3— | 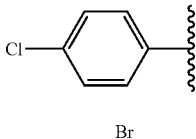 | OH | H | H |
| XB57 | CH3— | 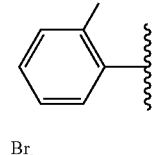 | OH | H | H |
| XB58 | CH3— | 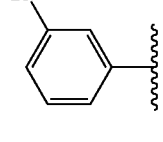 | OH | H | H |
| XB59 | CH3— | 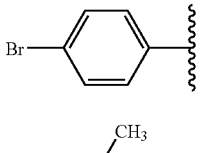 | OH | H | H |
| XB60 | CH3— | 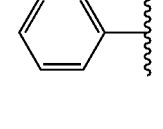 | OH | H | H |

TABLE 2-continued
| | | | | | |
|---|---|---|---|---|---|
| XB61 | CH3— | 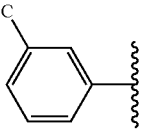 | OH | H | H |
| XB62 | CH3— | 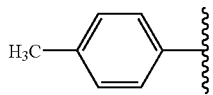 | OH | H | H |
| XB63 | CH3— | 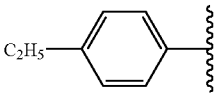 | OH | H | H |
| XB64 | CH3— | 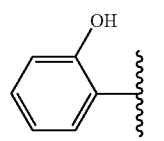 | OH | H | H |
| XB65 | CH3— | 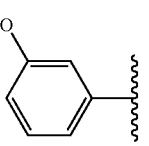 | OH | H | H |
| XB66 | CH3— | 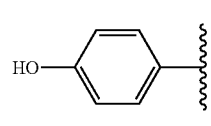 | OH | H | H |
| XB67 | CH3— | 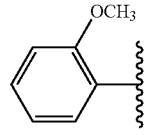 | OH | H | H |
| XB68 | CH3— | 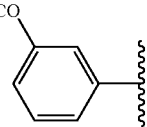 | OH | H | H |
| XB69 | CH3— | 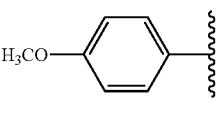 | OH | H | H |
| XB70 | CH3— | 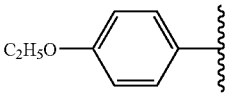 | OH | H | H |
| XB71 | CH3— | 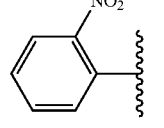 | OH | H | H |
| XB72 | CH3— | 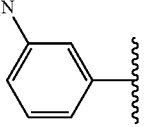 | OH | H | H |

TABLE 2-continued
| XB73 | CH3— | 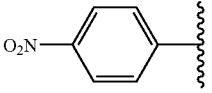 | OH | H | H |
| XB74 | CH3— | 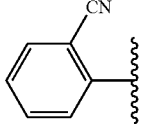 | OH | H | H |
| XB75 | CH3— | 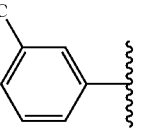 | OH | H | H |
| XB76 | CH3— | 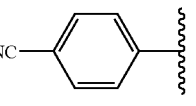 | OH | H | H |
| XB77 | CH3— | 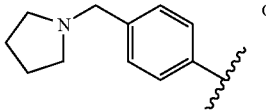 | OH | H | H |
| XB78 | CH3— | 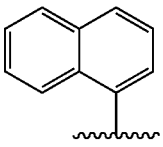 | OH | H | H |
| XB79 | CH3— | 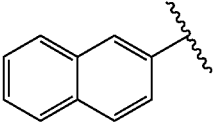 | OH | H | H |
| XB80 | CH3— | 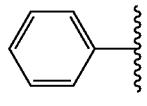 | CN | H | H |
| XB81 | CH3— | 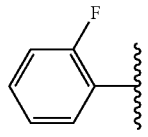 | CN | H | H |
| XB82 | CH3— | 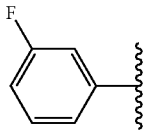 | CN | H | H |
| XB83 | CH3— | 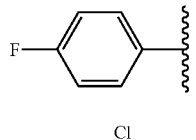 | CN | H | H |
| XB84 | CH3— | 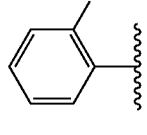 | CN | H | H |

TABLE 2-continued
| XB85 | CH3— | 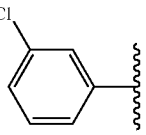 | CN | H | H |
| XB86 | CH3— | 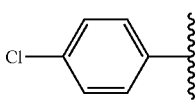 | CN | H | H |
| XB87 | CH3— | 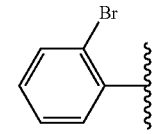 | CN | H | H |
| XB88 | CH3— | 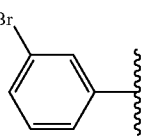 | CN | H | H |
| XB89 | CH3— | 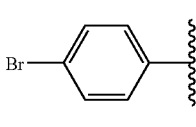 | CN | H | H |
| XB90 | CH3— | 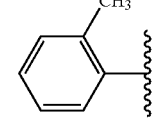 | CN | H | H |
| XB91 | CH3— | 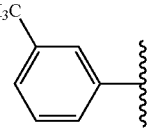 | CN | H | H |
| XB92 | CH3— | 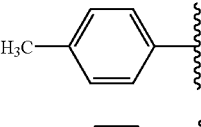 | CN | H | H |
| XB93 | CH3— | 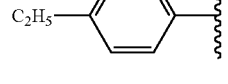 | CN | H | H |
| XB94 | CH3— | 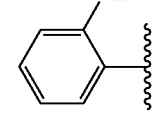 | CN | H | H |
| XB95 | CH3— | 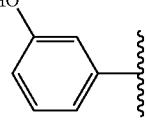 | CN | H | H |
| XB96 | CH3— | 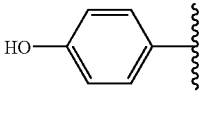 | CN | H | H |

TABLE 2-continued
| | | | | | |
|---|---|---|---|---|---|
| XB97 | CH3— | 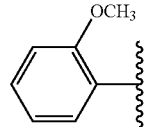 | CN | H | H |
| XB98 | CH3— | 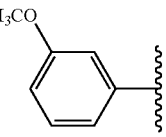 | CN | H | H |
| XB99 | CH3— | 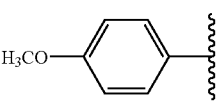 | CN | H | H |
| XB100 | CH3— | 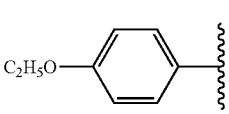 | CN | H | H |
| XB101 | CH3— | 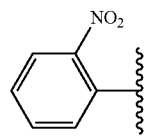 | CN | H | H |
| XB102 | CH3— | 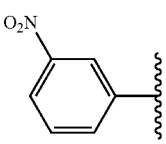 | CN | H | H |
| XB103 | CH3— | 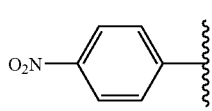 | CN | H | H |
| XB104 | CH3— | 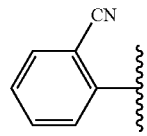 | CN | H | H |
| XB105 | CH3— | 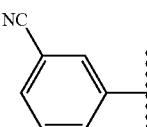 | CN | H | H |
| XB106 | CH3— | 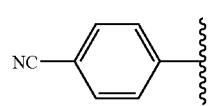 | CN | H | H |
| XB107 | CH3— | 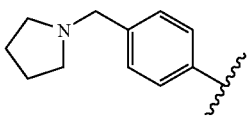 | CN | H | H |
| XB108 | CH3— | 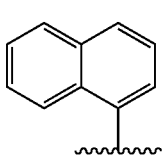 | CN | H | H |

TABLE 2-continued
| | | | | | | |
|---|---|---|---|---|---|---|
| XB109 | CH3— | 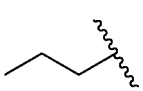 | CN | H | | H |
| XB110 | CH3— | H | H | CH3— | | H |
| XB111 | CH3— | H | H | CH3CH2— | | H |
| XB112 | CH3— | H | H |  | | H |
| XB113 | CH3— | H | H | 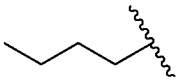 | | H |
| XB114 | CH3— | H | H | 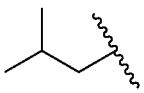 | | H |
| XB115 | CH3— | H | H |  | | H |
| XB116 | CH3— | H | H | 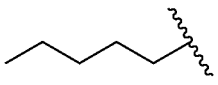 | | H |
| XB117 | CH3— | H | H | 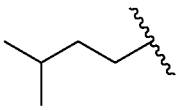 | | H |
| XB118 | CH3— | H | H | 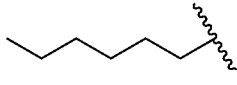 | | H |
| XB119 | CH3— | H | H | 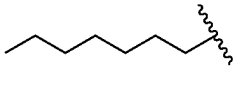 | | H |
| XB120 | CH3— | H | H | 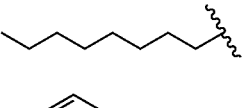 | | H |
| XB121 | CH3— | H | H | 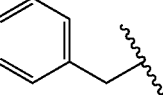 | | H |
| XB122 | CH3— | H | H | 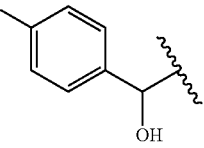 | | H |
| XB123 | CH3— | H | H |  | | H |

TABLE 2-continued
| XB124 | CH3— | H | H | 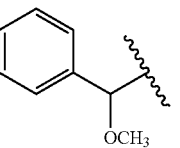 | H |
| XB125 | CH3— | H | H | 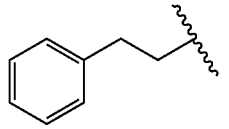 | H |
| XB126 | CH3— | H | H | 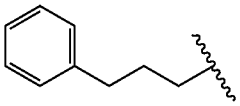 | H |
| XB127 | CH3— | H | H | 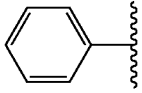 | H |
| XB128 | CH3— | H | H | 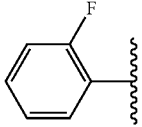 | H |
| XB129 | CH3— | H | H | 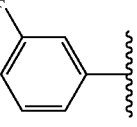 | H |
| XB130 | CH3— | H | H |  | H |
| XB131 | CH3— | H | H | 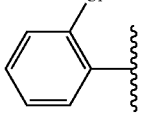 | H |
| XB132 | CH3— | H | H | 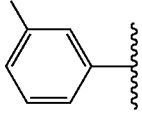 | H |
| XB133 | CH3— | H | H | 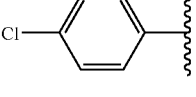 | H |
| XB134 | CH3— | H | H | 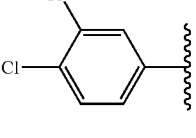 | H |

TABLE 2-continued
| XB135 | CH3— | H | H | 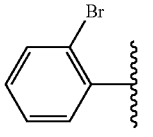 | H |
| XB136 | CH3— | H | H | 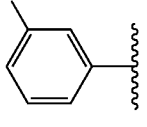 | H |
| XB137 | CH3— | H | H | 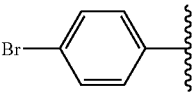 | H |
| XB138 | CH3— | H | H | 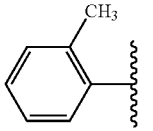 | H |
| XB139 | CH3— | H | H | 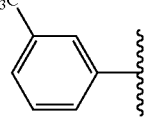 | H |
| XB140 | CH3— | H | H | 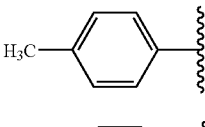 | H |
| XB141 | CH3— | H | H | 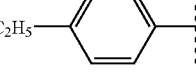 | H |
| XB142 | CH3— | H | H | 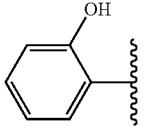 | H |
| XB143 | CH3— | H | H | 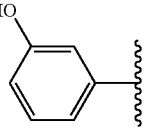 | H |
| XB144 | CH3— | H | H | 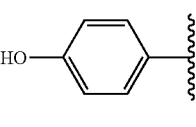 | H |
| XB145 | CH3— | H | H | 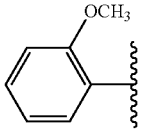 | H |
| XB146 | CH3— | H | H | 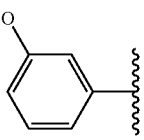 | H |

TABLE 2-continued
| XB147 | CH3— | H | H | 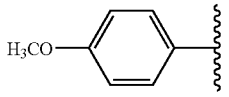 | H |
| XB148 | CH3— | H | H | 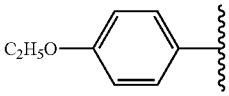 | H |
| XB149 | CH3— | H | H | 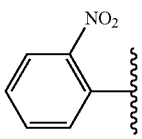 | H |
| XB150 | CH3— | H | H | 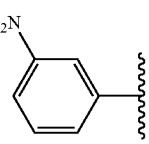 | H |
| XB151 | CH3— | H | H | 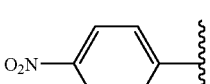 | H |
| XB152 | CH3— | H | H | 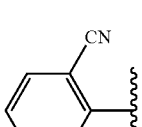 | H |
| XB153 | CH3— | H | H | 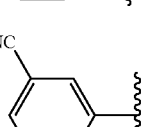 | H |
| XB154 | CH3— | H | H | 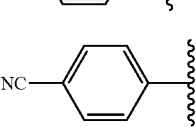 | H |
| XB155 | CH3— | H | H | 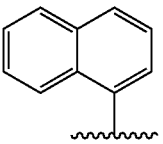 | H |
| XB156 | CH3— | H | H | 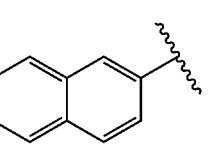 | H |
| XB157 | CH3— | H | H | 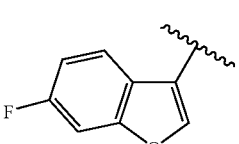 | H |
| XB158 | CH3— | H | H | 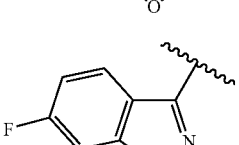 | H |

TABLE 2-continued
| | | | | | | |
|---|---|---|---|---|---|---|
| XB159 | CH3— | H | H | 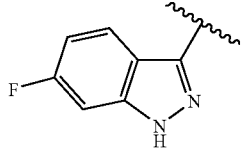 | H | |
| XB160 | CH3— | H | H | 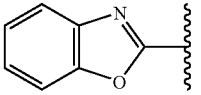 | H | |
| XB161 | CH3— | H | H | 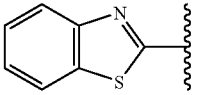 | H | |
| XB162 | CH3— | H | H | 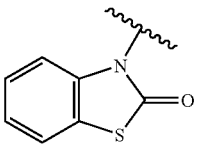 | H | |
| XB163 | CH3— | H | H | 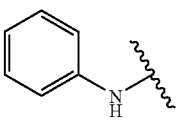 | H | |
| XB164 | CH3— | H | H | 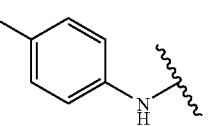 | H | |
| XB165 | CH3— | H | H | 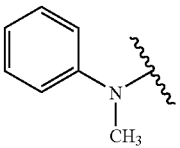 | H | |
| XB166 | CH3— | H | H | 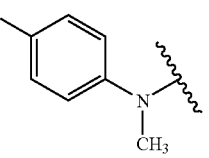 | H | |
| XB167 | CH3— | H | H | 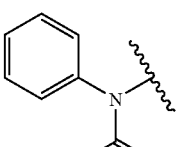 | H | |
| XB168 | CH3— | H | H | 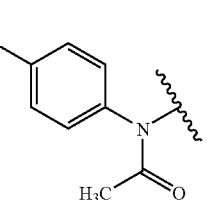 | H | |

TABLE 2-continued
| | | | | | | |
|---|---|---|---|---|---|---|
| XB169 | CH3— | H | H | 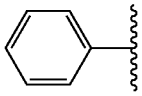 | OH | |
| XB170 | CH3— | H | H | 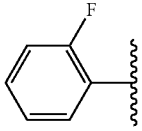 | OH | |
| XB171 | CH3— | H | H | 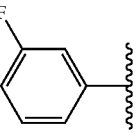 | OH | |
| XB172 | CH3— | H | H | 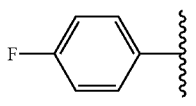 | OH | |
| XB173 | CH3— | H | H | 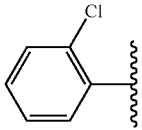 | OH | |
| XB174 | CH3— | H | H | 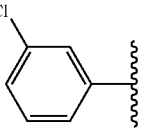 | OH | |
| XB175 | CH3— | H | H | 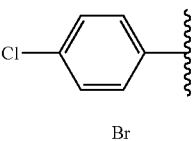 | OH | |
| XB176 | CH3— | H | H | 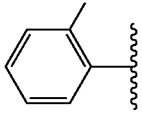 | OH | |
| XB177 | CH3— | H | H | 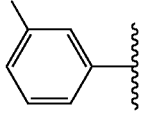 | OH | |
| XB178 | CH3— | H | H | 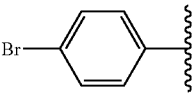 | OH | |
| XB179 | CH3— | H | H | 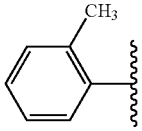 | OH | |
| XB180 | CH3— | H | H | 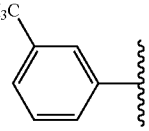 | OH | |

TABLE 2-continued
| XB181 | CH3— | H | H | 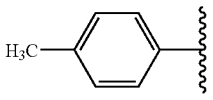 | OH |
| XB182 | CH3— | H | H | 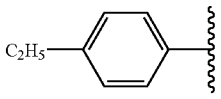 | OH |
| XB183 | CH3— | H | H | 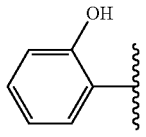 | OH |
| XB184 | CH3— | H | H | 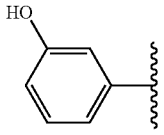 | OH |
| XB185 | CH3— | H | H | 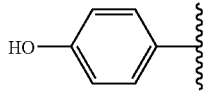 | OH |
| XB186 | CH3— | H | H | 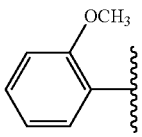 | OH |
| XB187 | CH3— | H | H | 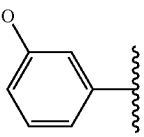 | OH |
| XB188 | CH3— | H | H | 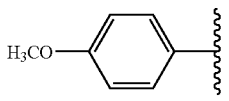 | OH |
| XB189 | CH3— | H | H | 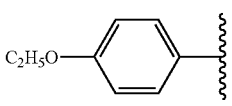 | OH |
| XB190 | CH3— | H | H | 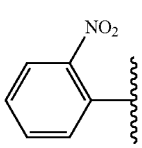 | OH |
| XB191 | CH3— | H | H | 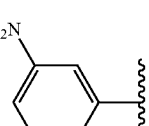 | OH |
| XB192 | CH3— | H | H | 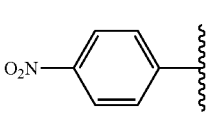 | OH |

TABLE 2-continued
| XB193 | CH3— | H | H | 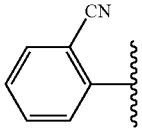 | OH |
| XB194 | CH3— | H | H | 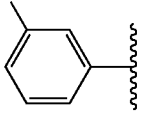 | OH |
| XB195 | CH3— | H | H | 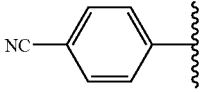 | OH |
| XB196 | CH3— | H | H | 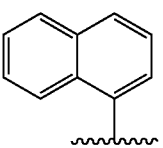 | OH |
| XB197 | CH3— | H | H | 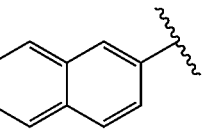 | OH |
| XB198 | CH3— | H | H | 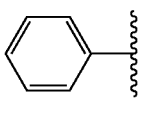 | CN |
| XB199 | CH3— | H | H | 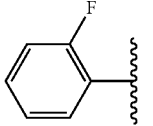 | CN |
| XB200 | CH3— | H | H | 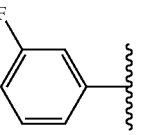 | CN |
| XB201 | CH3— | H | H | 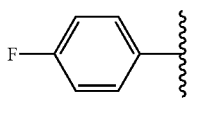 | CN |
| XB202 | CH3— | H | H | 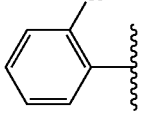 | CN |
| XB203 | CH3— | H | H | 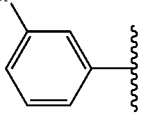 | CN |
| XB204 | CH3— | H | H | 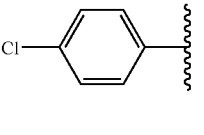 | CN |

TABLE 2-continued
| XB205 | CH3— | H | H | 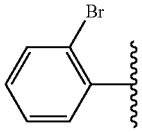 | CN |
| XB206 | CH3— | H | H | 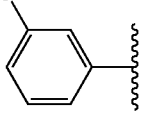 | CN |
| XB207 | CH3— | H | H | 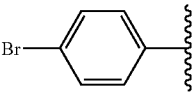 | CN |
| XB208 | CH3— | H | H | 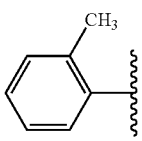 | CN |
| XB209 | CH3— | H | H | 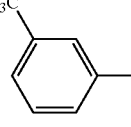 | CN |
| XB210 | CH3— | H | H | 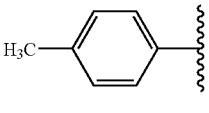 | CN |
| XB211 | CH3— | H | H | 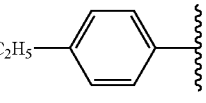 | CN |
| XB212 | CH3— | H | H | 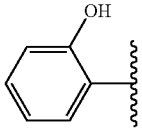 | CN |
| XB213 | CH3— | H | H | 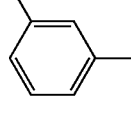 | CN |
| XB214 | CH3— | H | H | 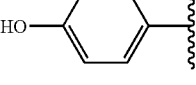 | CN |
| XB215 | CH3— | H | H | 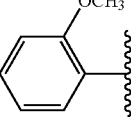 | CN |
| XB216 | CH3— | H | H | 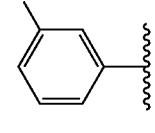 | CN |

TABLE 2-continued
| | | | | | |
|---|---|---|---|---|---|
| XB217 | CH3— | H | H | 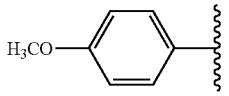 | CN |
| XB218 | CH3— | H | H | 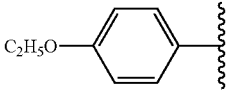 | CN |
| XB219 | CH3— | H | H | 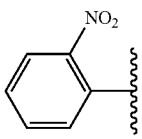 | CN |
| XB220 | CH3— | H | H | 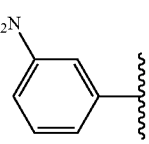 | CN |
| XB221 | CH3— | H | H | 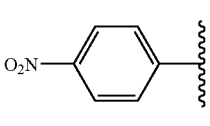 | CN |
| XB222 | CH3— | H | H | 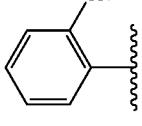 | CN |
| XB223 | CH3— | H | H | 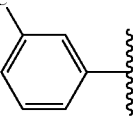 | CN |
| XB224 | CH3— | H | H | 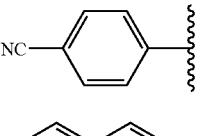 | CN |
| XB225 | CH3— | H | H | 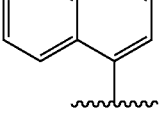 | CN |
| XB226 | CH3— | H | H | 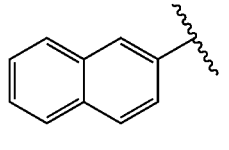 | CN |
| XB227 | CH3— | H | H | 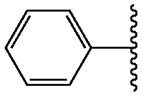 |  |
| XB228 | CH3— | H | H | 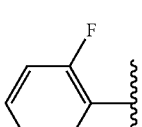 | 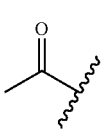 |

TABLE 2-continued
| | | | | | |
|---|---|---|---|---|---|
| XB229 | CH3— | H | H | 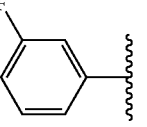 | 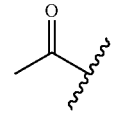 |
| XB230 | CH3— | H | H | 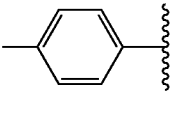 |  |
| XB231 | CH3— | H | H | 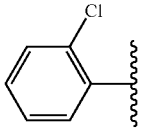 |  |
| XB232 | CH3— | H | H | 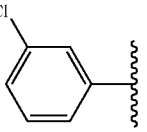 |  |
| XB233 | CH3— | H | H |  |  |
| XB234 | CH3— | H | H | 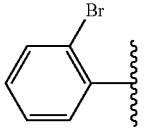 |  |
| XB235 | CH3— | H | H | 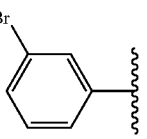 |  |
| XB236 | CH3— | H | H | 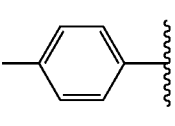 |  |
| XB237 | CH3— | H | H | 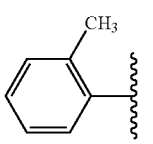 |  |
| XB238 | CH3— | H | H | 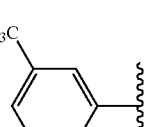 |  |
| XB239 | CH3— | H | H | 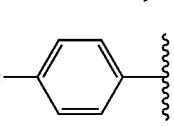 |  |

TABLE 2-continued
| | | | | | |
|---|---|---|---|---|---|
| XB240 | CH3— | H | H | 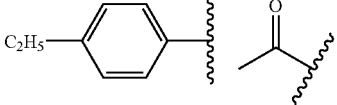 | 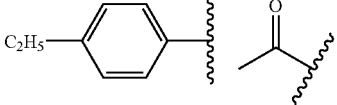 |
| XB241 | CH3— | H | H | 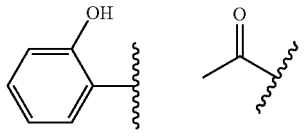 | |
| XB242 | CH3— | H | H | 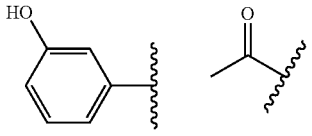 | |
| XB243 | CH3— | H | H | 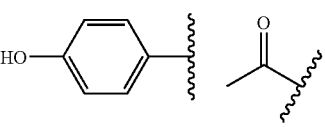 | |
| XB244 | CH3— | H | H | 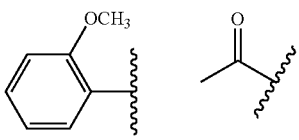 | |
| XB245 | CH3— | H | H | 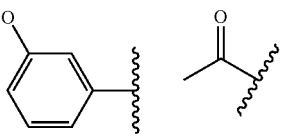 | |
| XB246 | CH3— | H | H | 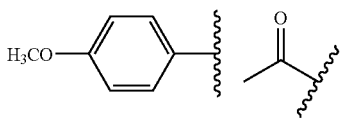 | |
| XB247 | CH3— | H | H | 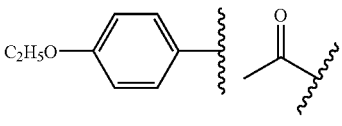 | |
| XB248 | CH3— | H | H | 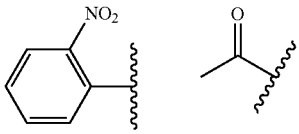 | |
| XB249 | CH3— | H | H | 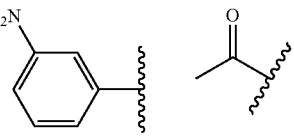 | |
| XB250 | CH3— | H | H | 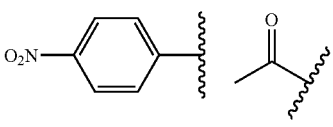 | |

TABLE 2-continued
| | | | | | |
|---|---|---|---|---|---|
| XB251 | CH3— | H | H | 2-CN-phenyl | C(=O)CH3 |
| XB252 | CH3— | H | H | 3-CN-phenyl | C(=O)CH3 |
| XB253 | CH3— | H | H | 4-CN-phenyl | C(=O)CH3 |
| XB254 | CH3— | H | H | naphthalen-1-yl | C(=O)CH3 |
| XB255 | CH3— | H | H | naphthalen-2-yl | C(=O)CH3 |
| No. | STRUCTURE |
|---|---|
| XB256 | 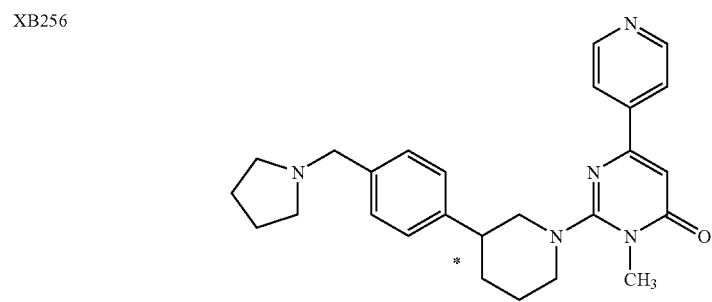 |
| XB257 | 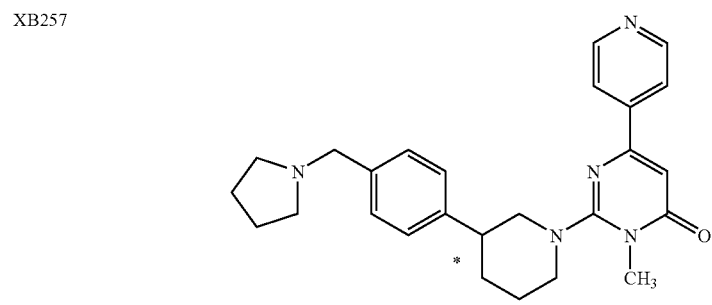 |

TABLE 2-continued
XB258
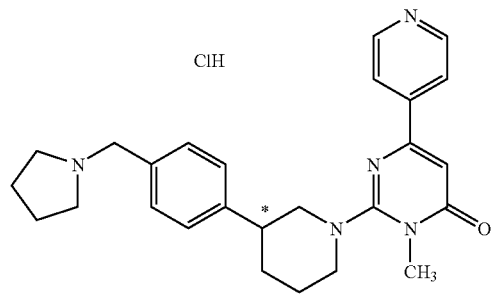
XB259
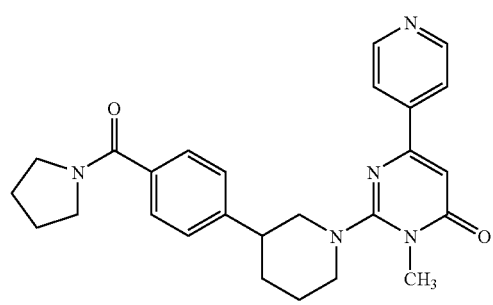
XB260
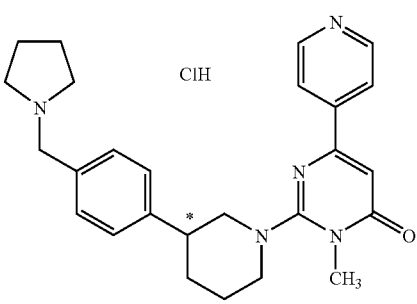
XB261
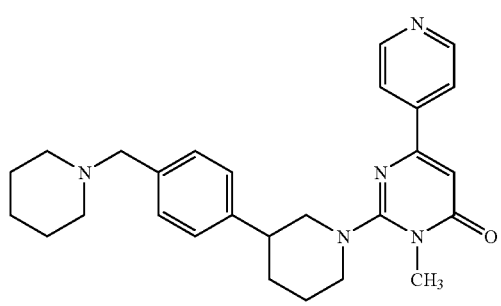
XB262
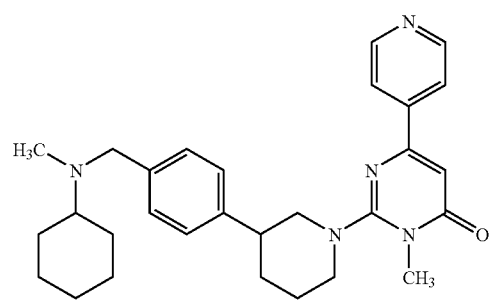

TABLE 2-continued
| XB263 | 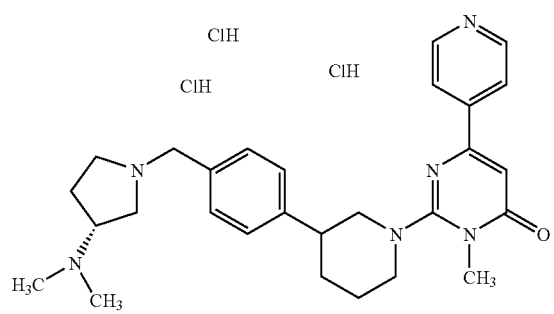 |
| --- | --- |
| XB264 | 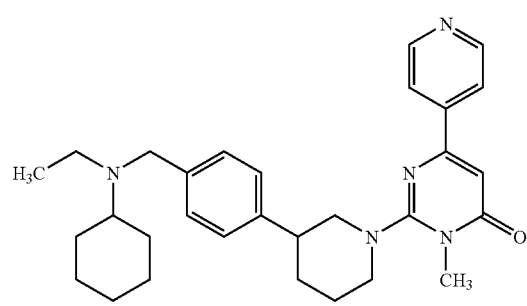 |
| XB265 | 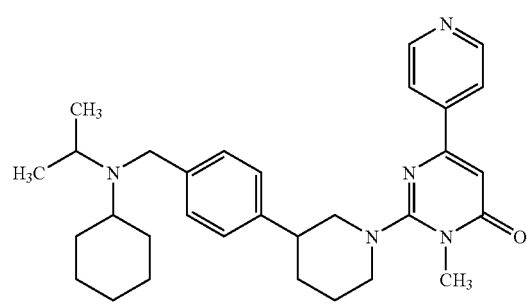 |
| XB266 | 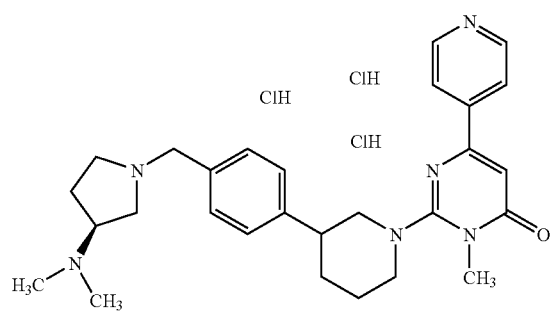 |
| XB267 | 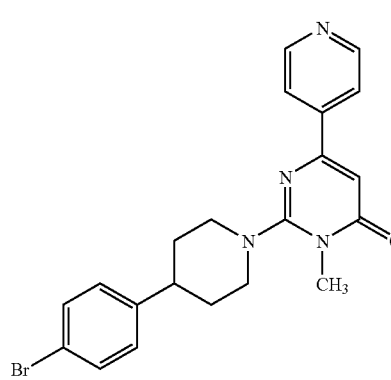 |

TABLE 2-continued
XB268 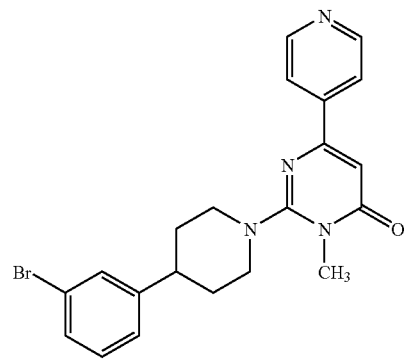
XB269 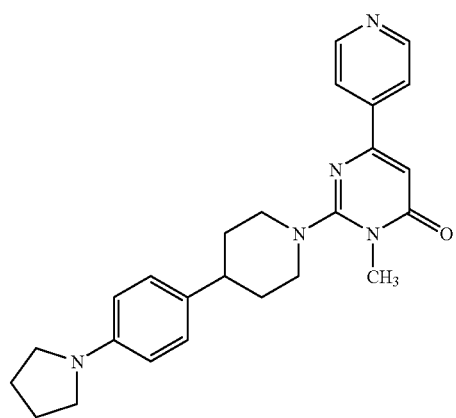
XB270 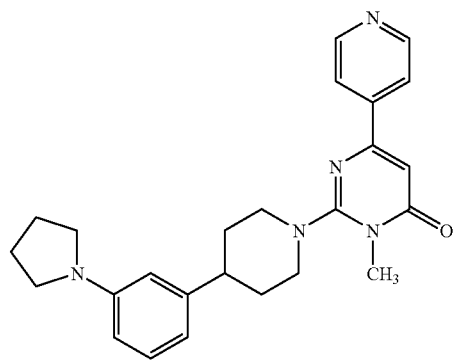
XB271 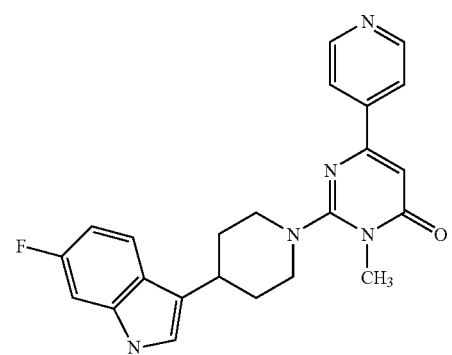

TABLE 2-continued
XB272
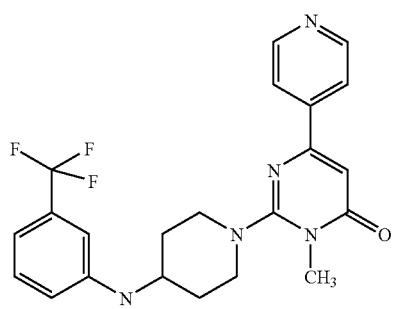
XB273
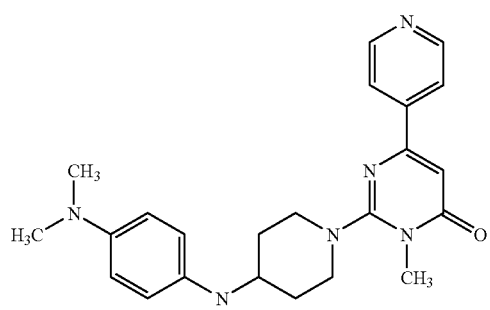
XB274
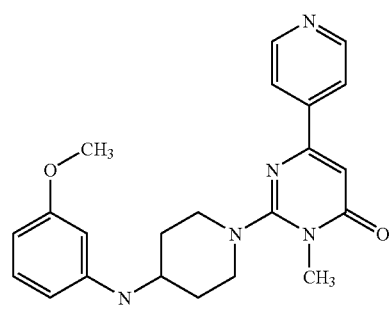
XB275
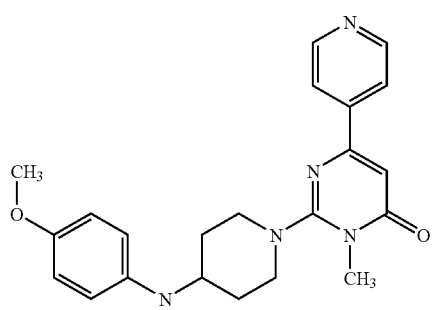
XB276
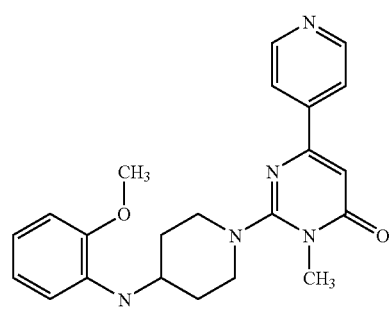

TABLE 2-continued
XB277
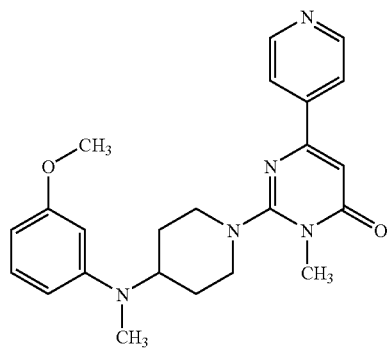
XB278
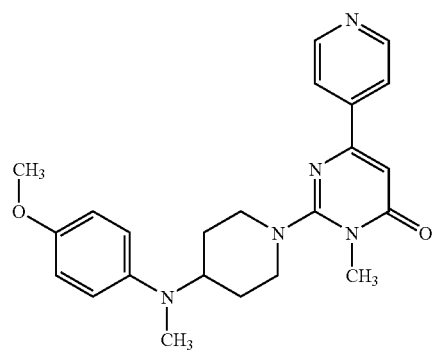
XB279
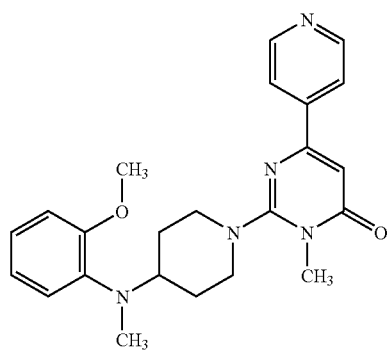
XB280
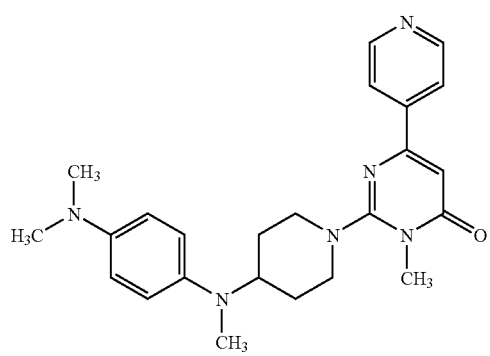

TABLE 2-continued
XB281
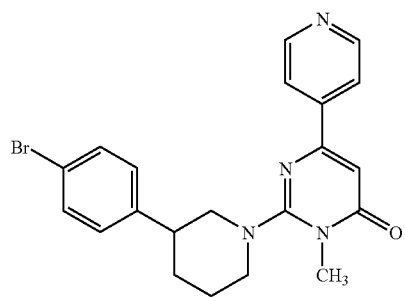
XB282
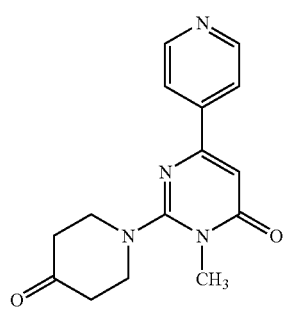
XB283
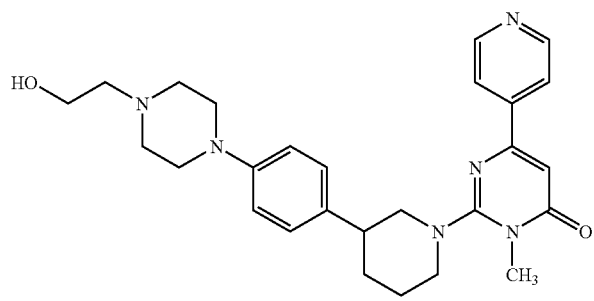
XB284
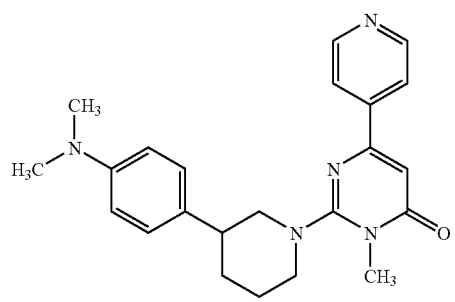
XB285
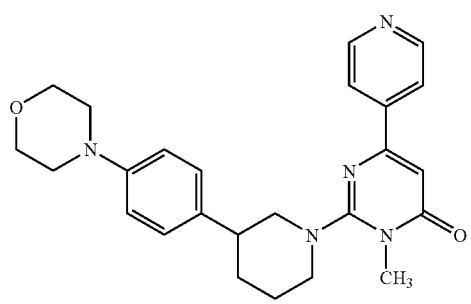

TABLE 2-continued
XB286
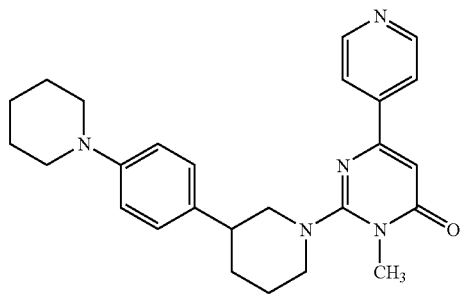
XB287
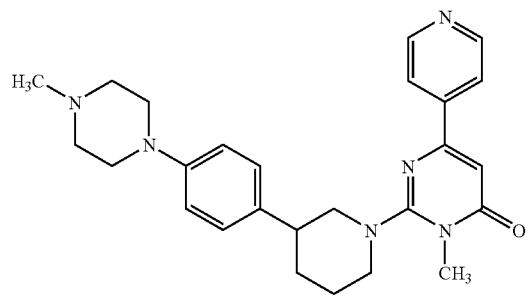
XB288
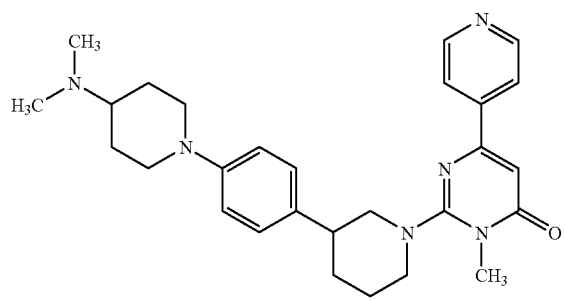
XB289
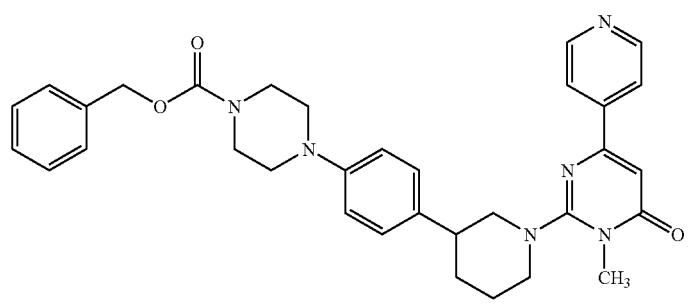
XB290
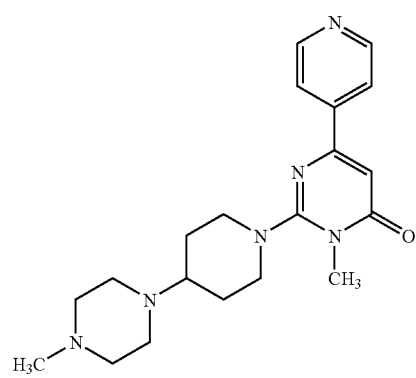

TABLE 2-continued
XB291
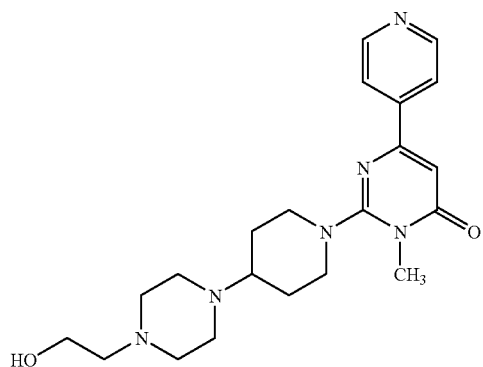
XB292
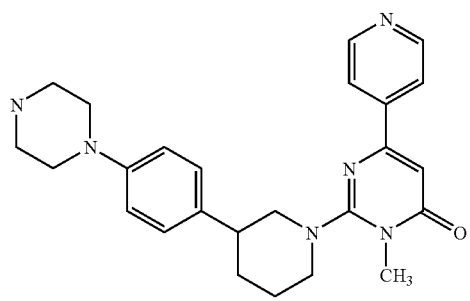
XB293
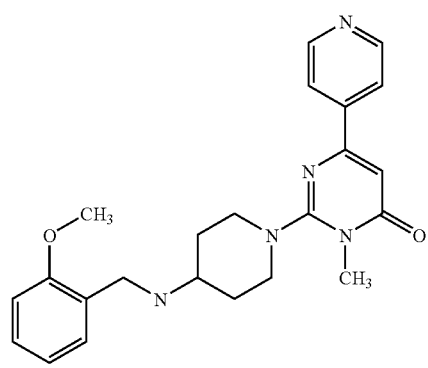
XB294
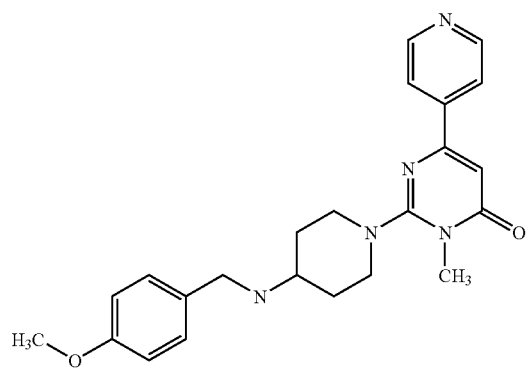

TABLE 2-continued
XB295
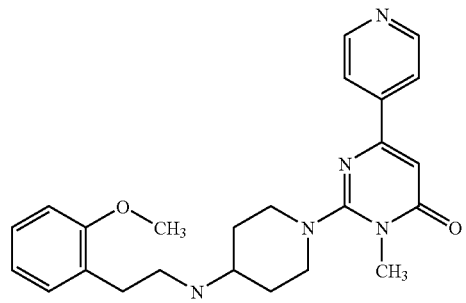
XB296
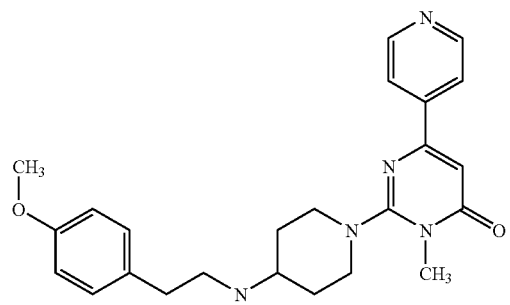
XB297
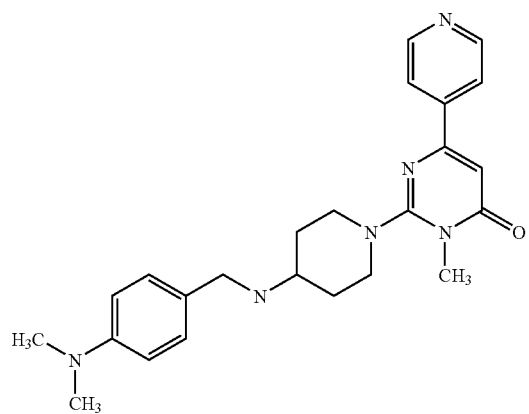
XB298
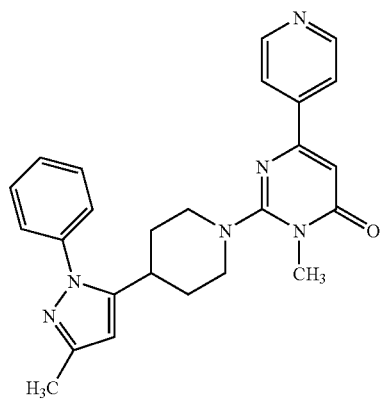

TABLE 2-continued
XB299
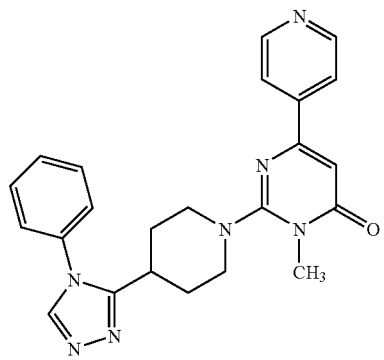
XB300
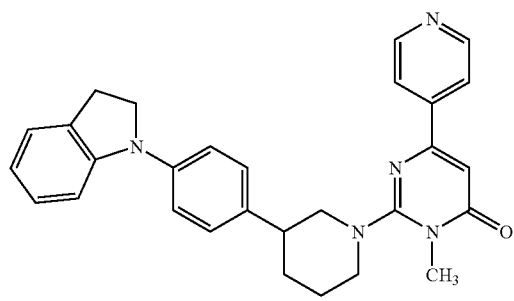
XB301
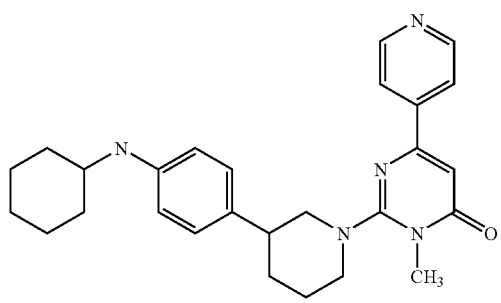
XB302
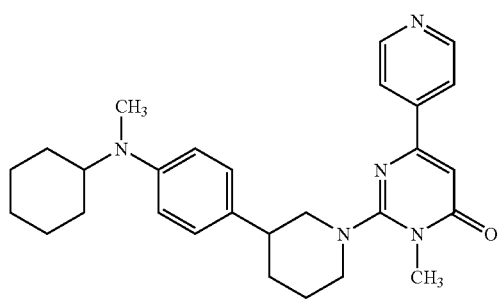

TABLE 3
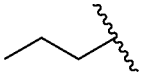
| No. | R1 | R2 | R3 | R4 |
|---|---|---|---|---|
| YA0001 | CH3— | H | H | CH3— |
| YA0002 | CH3— | H | H | CH3CH2— |
| YA0003 | CH3— | H | H | 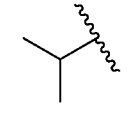 |
| YA0004 | CH3— | H | H | 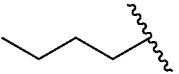 |
| YA0005 | CH3— | H | H | 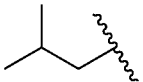 |
| YA0006 | CH3— | H | H | 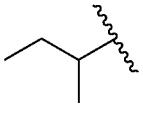 |
| YA0007 | CH3— | H | H |  |
| YA0008 | CH3— | H | H | 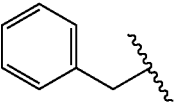 |
| YA0009 | CH3— | H | H | 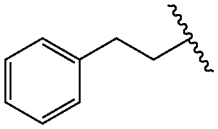 |
| YA0010 | CH3— | H | H | 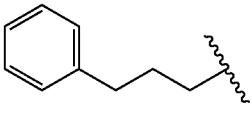 |
| YA0011 | CH3— | H | H |  |
| YA0012 | CH3— | H | H |  |

-continued
| | | | | |
|---|---|---|---|---|
| YA0013 | CH3— | H | H | 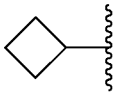 |
| YA0014 | CH3— | H | H | 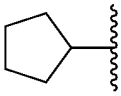 |
| YA0015 | CH3— | H | H | 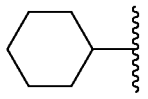 |
| YA0016 | CH3— | H | H | 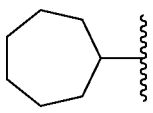 |
| YA0017 | CH3— | H | H | 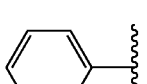 |
| YA0018 | CH3— | H | H | 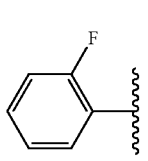 |
| YA0019 | CH3— | H | H | 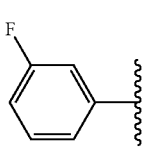 |
| YA0020 | CH3— | H | H | 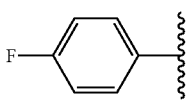 |
| YA0021 | CH3— | H | H | 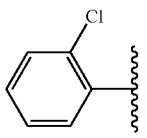 |
| YA0022 | CH3— | H | H | 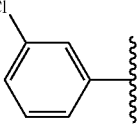 |
| YA0023 | CH3— | H | H | 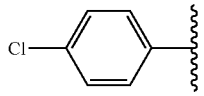 |
| YA0024 | CH3— | H | H | 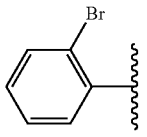 |

-continued
| | | | | |
|---|---|---|---|---|
| YA0025 | CH3— | H | H | 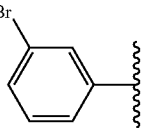 |
| YA0026 | CH3— | H | H | 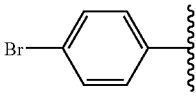 |
| YA0027 | CH3— | H | H | 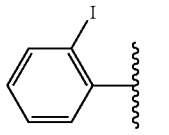 |
| YA0028 | CH3— | H | H | 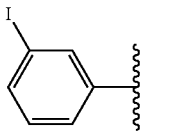 |
| YA0029 | CH3— | H | H | 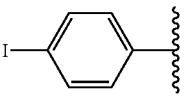 |
| YA0030 | CH3— | H | H | 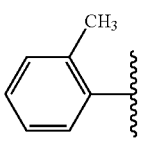 |
| YA0031 | CH3— | H | H | 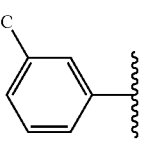 |
| YA0032 | CH3— | H | H | 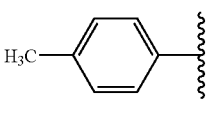 |
| YA0033 | CH3— | H | H | 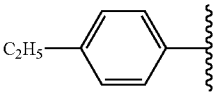 |
| YA0034 | CH3— | H | H | 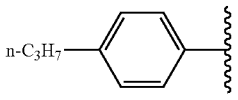 |
| YA0035 | CH3— | H | H | 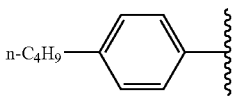 |
| YA0036 | CH3— | H | H | 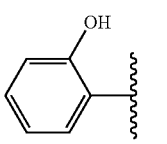 |

-continued
| | | | | |
|---|---|---|---|---|
| YA0037 | CH3— | H | H | 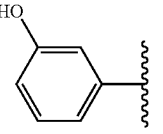 |
| YA0038 | CH3— | H | H | 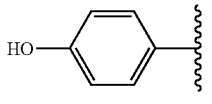 |
| YA0039 | CH3— | H | H | 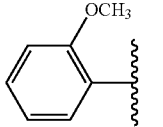 |
| YA0040 | CH3— | H | H | 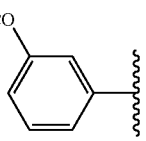 |
| YA0041 | CH3— | H | H | 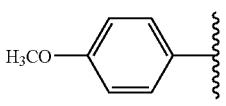 |
| YA0042 | CH3— | H | H | 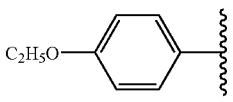 |
| YA0043 | CH3— | H | H | 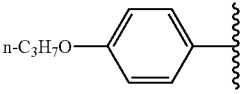 |
| YA0044 | CH3— | H | H | 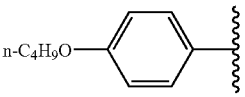 |
| YA0045 | CH3— | H | H | 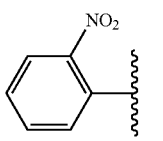 |
| YA0046 | CH3— | H | H | 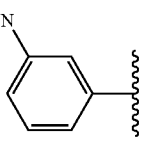 |
| YA0047 | CH3— | H | H | 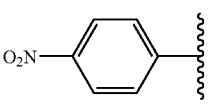 |
| YA0048 | CH3— | H | H | 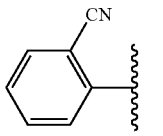 |

-continued
| | | | | |
|---|---|---|---|---|
| YA0049 | CH3— | H | H | 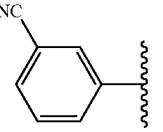 |
| YA0050 | CH3— | H | H | 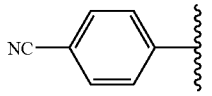 |
| YA0051 | CH3— | H | H | 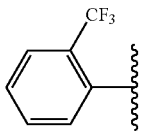 |
| YA0052 | CH3— | H | H | 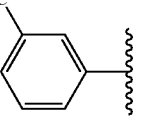 |
| YA0053 | CH3— | H | H | 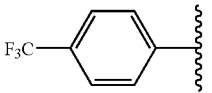 |
| YA0054 | CH3— | H | H | 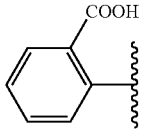 |
| YA0055 | CH3— | H | H | 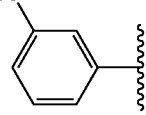 |
| YA0056 | CH3— | H | H | 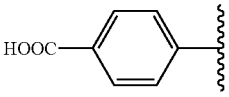 |
| YA0057 | CH3— | H | H | 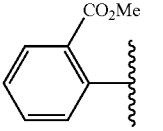 |
| YA0058 | CH3— | H | H | 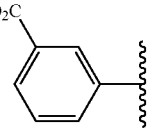 |
| YA0059 | CH3— | H | H | 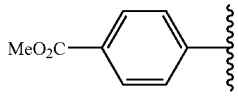 |
| YA0060 | CH3— | H | H | 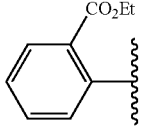 |

-continued
| | | | | |
|---|---|---|---|---|
| YA0061 | CH3— | H | H | 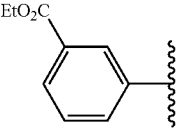 |
| YA0062 | CH3— | H | H | 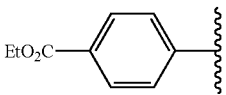 |
| YA0063 | CH3— | H | H | 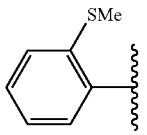 |
| YA0064 | CH3— | H | H | 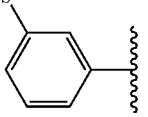 |
| YA0065 | CH3— | H | H | 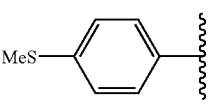 |
| YA0066 | CH3— | H | H | 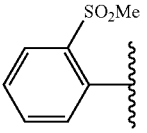 |
| YA0067 | CH3— | H | H | 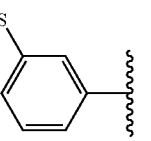 |
| YA0068 | CH3— | H | H | 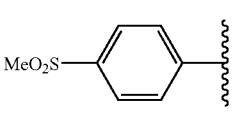 |
| YA0069 | CH3— | H | H | 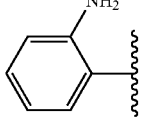 |
| YA0070 | CH3— | H | H | 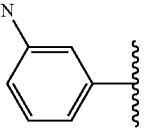 |
| YA0071 | CH3— | H | H | 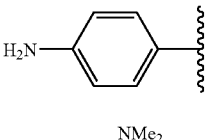 |
| YA0072 | CH3— | H | H | 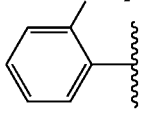 |

-continued
| | | | | |
|---|---|---|---|---|
| YA0073 | CH3— | H | H | 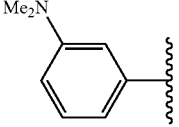 |
| YA0074 | CH3— | H | H | 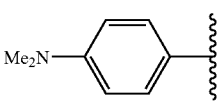 |
| YA0075 | CH3— | H | H | 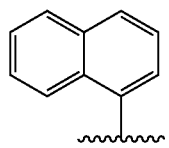 |
| YA0076 | CH3— | H | H | 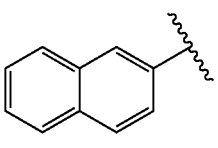 |
| YA0077 | CH3— | H | H | 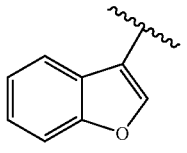 |
| YA0078 | CH3— | H | H | 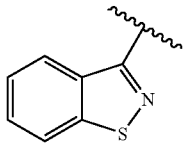 |
| YA0079 | CH3— | H | H | 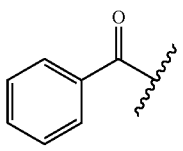 |
| YA0080 | CH3— | H | H | 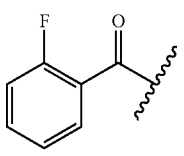 |
| YA0081 | CH3— | H | H | 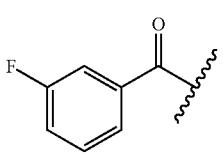 |
| YA0082 | CH3— | H | H | 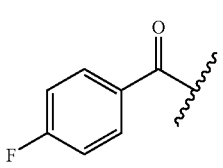 |

-continued
| | | | | |
|---|---|---|---|---|
| YA0083 | CH3— | H | H | 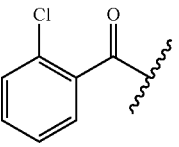 |
| YA0084 | CH3— | H | H | 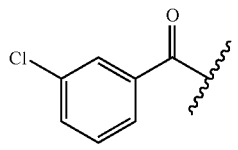 |
| YA0085 | CH3— | H | H | 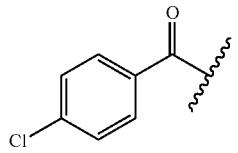 |
| YA0086 | CH3— | H | H | 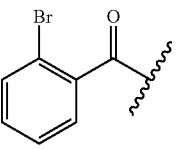 |
| YA0087 | CH3— | H | H | 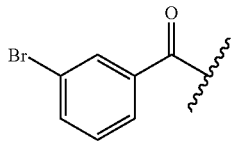 |
| YA0088 | CH3— | H | H | 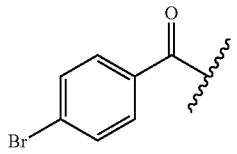 |
| YA0089 | CH3— | H | H | 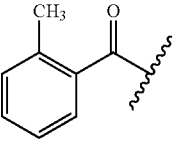 |
| YA0090 | CH3— | H | H | 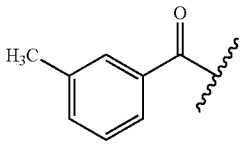 |
| YA0091 | CH3— | H | H | 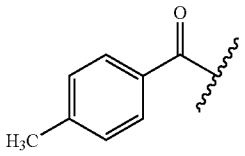 |
| YA0092 | CH3— | H | H | 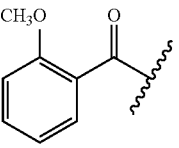 |

-continued
| | | | | |
|---|---|---|---|---|
| YA0093 | CH3— | H | H | 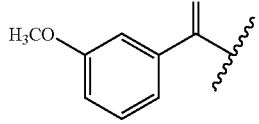 |
| YA0094 | CH3— | H | H | 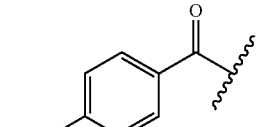 |
| YA0095 | CH3— | H | H | 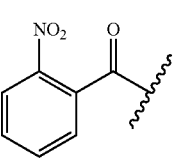 |
| YA0096 | CH3— | H | H | 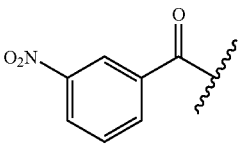 |
| YA0097 | CH3— | H | H | 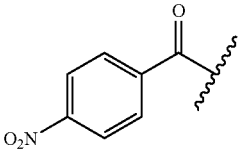 |
| YA0098 | CH3— | H | H | 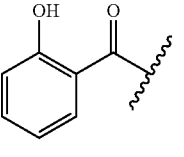 |
| YA0099 | CH3— | H | H | 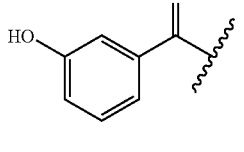 |
| YA0100 | CH3— | H | H | 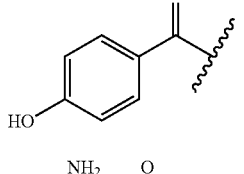 |
| YA0101 | CH3— | H | H | 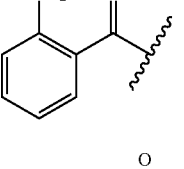 |
| YA0102 | CH3— | H | H | 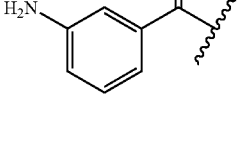 |

-continued
| | | | | |
|---|---|---|---|---|
| YA0103 | CH3— | H | H | 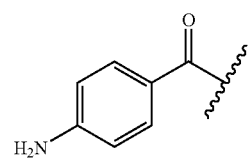 |
| YA0104 | CH3— | H | H | 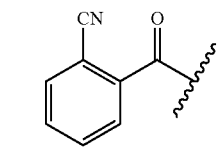 |
| YA0105 | CH3— | H | H | 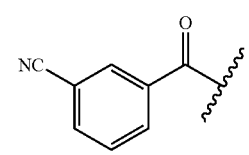 |
| YA0106 | CH3— | H | H | 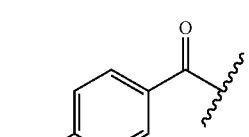 |
| YA0107 | CH3— | H | H | 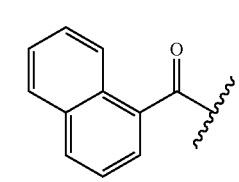 |
| YA0108 | CH3— | H | H | 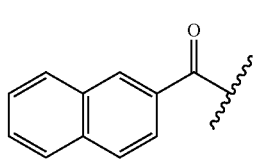 |
| YA0109 | CH3— | H | H | 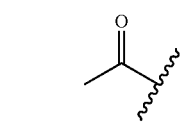 |
| YA0110 | CH3— | H | H | 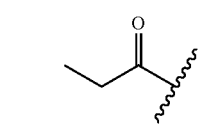 |
| YA0111 | CH3— | H | H | 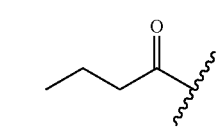 |
| YA0112 | CH3— | H | H | 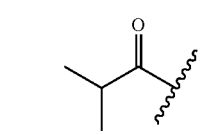 |

-continued
| | | | | |
|---|---|---|---|---|
| YA0113 | CH3— | H | H | 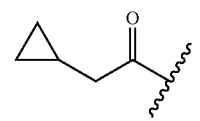 |
| YA0114 | CH3— | H | H | 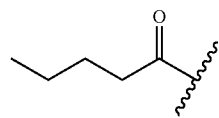 |
| YA0115 | CH3— | H | H | 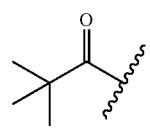 |
| YA0116 | CH3— | H | H | 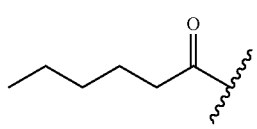 |
| YA0117 | CH3— | H | H | 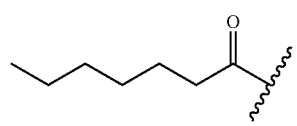 |
| YA0118 | CH3— | H | H | 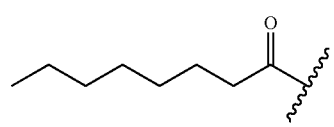 |
| YA0119 | CH3— | H | H | 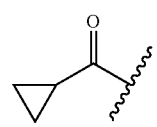 |
| YA0120 | CH3— | H | H | 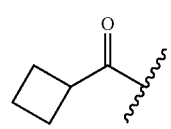 |
| YA0121 | CH3— | H | H | 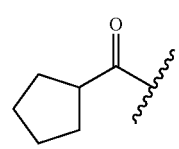 |
| YA0122 | CH3— | H | H | 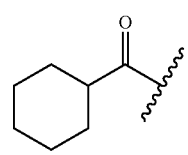 |
| YA0123 | CH3— | 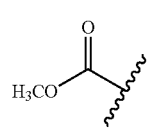 | H | H |

-continued
| | | | | |
|---|---|---|---|---|
| YA0124 | CH3— | 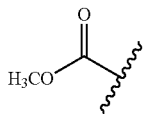 | H | CH3— |
| YA0125 | CH3— | 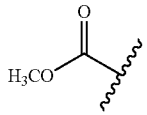 | H | CH3CH2— |
| YA0126 | CH3— | 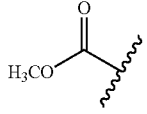 | H | 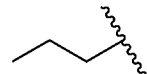 |
| YA0127 | CH3— | 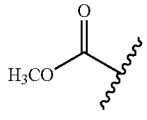 | H | 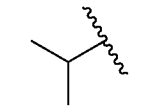 |
| YA0128 | CH3— | 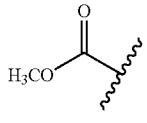 | H | 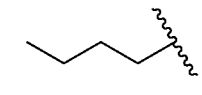 |
| YA0129 | CH3— | 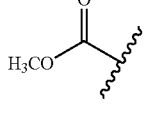 | H | 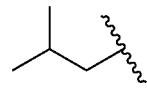 |
| YA0130 | CH3— | 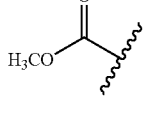 | H | 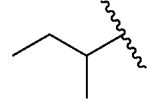 |
| YA0131 | CH3— | 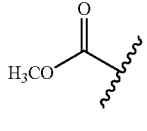 | H | 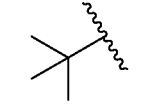 |
| YA0132 | CH3— | 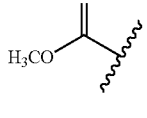 | H | 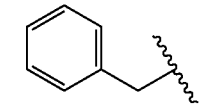 |
| YA0133 | CH3— | 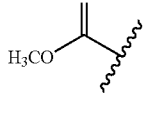 | H | 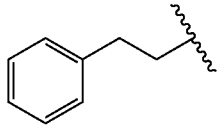 |
| YA0134 | CH3— | 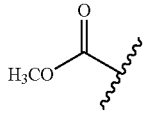 | H | 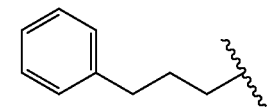 |
| YA0135 | CH3— | 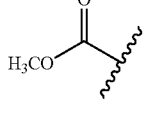 | H | 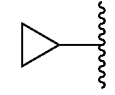 |

-continued
| | | | | |
|---|---|---|---|---|
| YA0136 | CH3— | 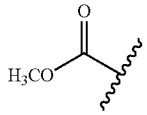 | H | 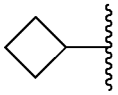 |
| YA0137 | CH3— | 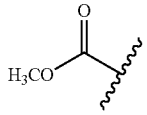 | H | 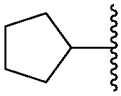 |
| YA0138 | CH3— | 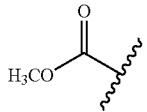 | H | 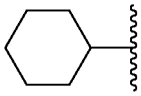 |
| YA0139 | CH3— | 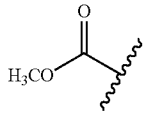 | H | 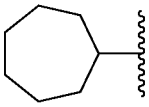 |
| YA0140 | CH3— | 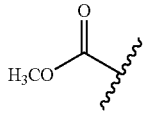 | H | 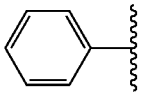 |
| YA0141 | CH3— | 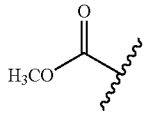 | H | 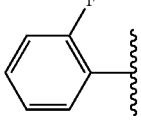 |
| YA0142 | CH3— | 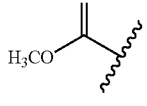 | H | 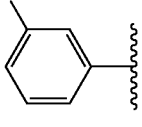 |
| YA0143 | CH3— | 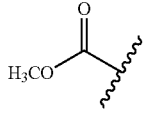 | H | 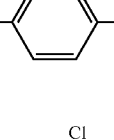 |
| YA0144 | CH3— | 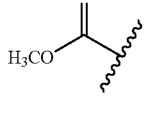 | H | 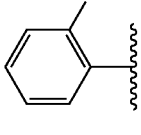 |
| YA0145 | CH3— | 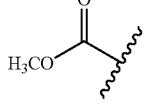 | H | 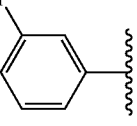 |
| YA0146 | CH3— | 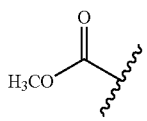 | H | 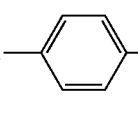 |

-continued
| | | | | |
|---|---|---|---|---|
| YA0147 | CH3— | 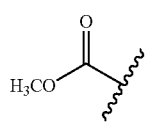 | H | 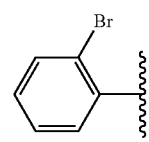 |
| YA0148 | CH3— | 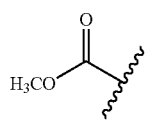 | H | 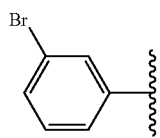 |
| YA0149 | CH3— | 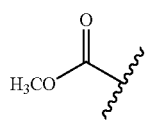 | H | 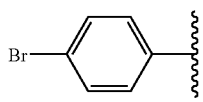 |
| YA0150 | CH3— | 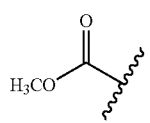 | H | 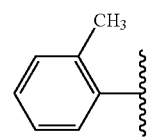 |
| YA0151 | CH3— | 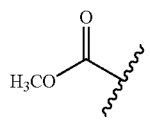 | H | 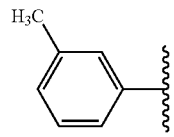 |
| YA0152 | CH3— | 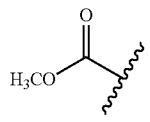 | H | 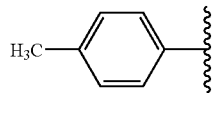 |
| YA0153 | CH3— | 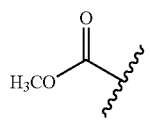 | H | 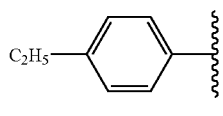 |
| YA0154 | CH3— | 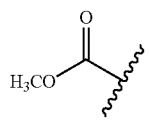 | H | 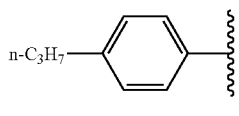 |
| YA0155 | CH3— | 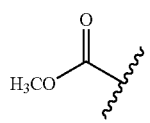 | H | 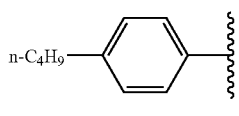 |
| YA0156 | CH3— | 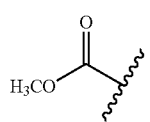 | H | 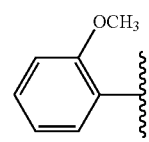 |
| YA0157 | CH3— | 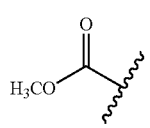 | H | 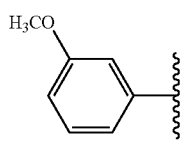 |

-continued

| | | | | |
|---|---|---|---|---|
| YA0158 | CH3— | H3CO(C=O)~ | H | H3CO–C6H4–~ (para) |
| YA0159 | CH3— | H3CO(C=O)~ | H | C2H5O–C6H4–~ (para) |
| YA0160 | CH3— | H3CO(C=O)~ | H | n-C3H7O–C6H4–~ (para) |
| YA0161 | CH3— | H3CO(C=O)~ | H | n-C4H9O–C6H4–~ (para) |
| YA0162 | CH3— | H3CO(C=O)~ | H | 2-NO2–C6H4–~ |
| YA0163 | CH3— | H3CO(C=O)~ | H | 3-O2N–C6H4–~ |
| YA0164 | CH3— | H3CO(C=O)~ | H | 4-O2N–C6H4–~ |
| YA0165 | CH3— | H3CO(C=O)~ | H | 2-CN–C6H4–~ |
| YA0166 | CH3— | H3CO(C=O)~ | H | 3-NC–C6H4–~ |
| YA0167 | CH3— | H3CO(C=O)~ | H | 4-NC–C6H4–~ |
| YA0168 | CH3— | H3CO(C=O)~ | H | 2-NMe2–C6H4–~ |

-continued
| | | | | |
|---|---|---|---|---|
| YA0169 | CH3— | 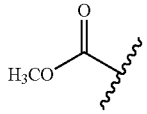 | H | 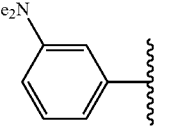 |
| YA0170 | CH3— | 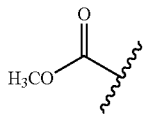 | H | 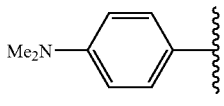 |
| YA0171 | CH3— | 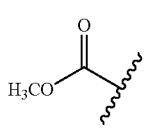 | H | 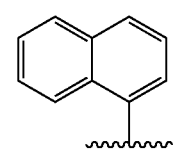 |
| YA0172 | CH3— | 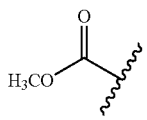 | H | 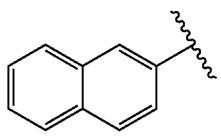 |
| YA0173 | CH3— | 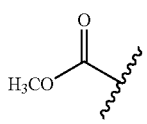 | H | 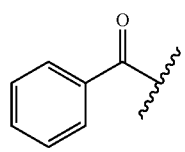 |
| YA0174 | CH3— | 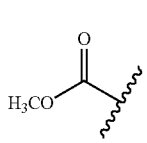 | H | 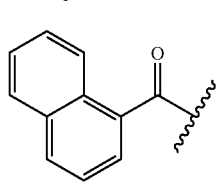 |
| YA0175 | CH3— | 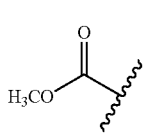 | H | 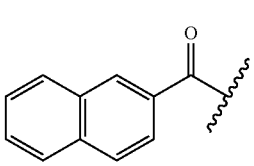 |
| YA0176 | CH3— | 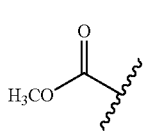 | H | 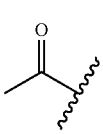 |
| YA0177 | CH3— | 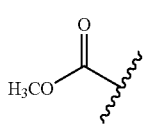 | H | 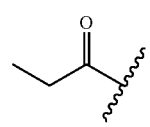 |
| YA0178 | CH3— | 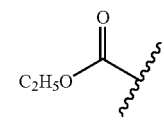 | H | H |
| YA0179 | CH3— | 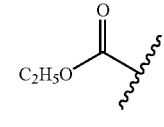 | H | CH3— |

-continued
| | | | | |
|---|---|---|---|---|
| YA0180 | CH3— | 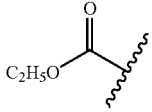 | H | CH3CH2— |
| YA0181 | CH3— |  | H | 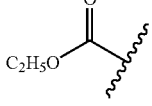 |
| YA0182 | CH3— | 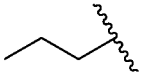 | H | 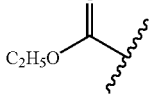 |
| YA0183 | CH3— | 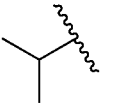 | H |  |
| YA0184 | CH3— |  | H | 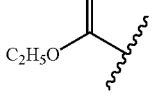 |
| YA0185 | CH3— | 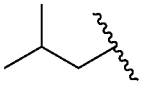 | H | 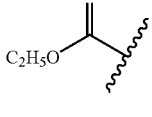 |
| YA0186 | CH3— |  | H | 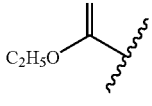 |
| YA0187 | CH3— | 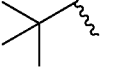 | H | 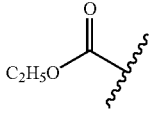 |
| YA0188 | CH3— | 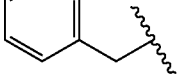 | H | 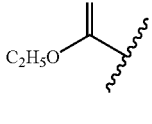 |
| YA0189 | CH3— | 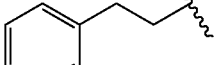 | H | 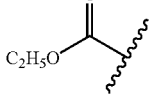 |
| YA0190 | CH3— | 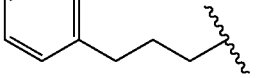 | H | 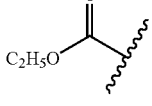 |
| YA0191 | CH3— |  | H | 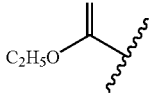 |

-continued
| | | | | |
|---|---|---|---|---|
| YA0192 | CH3— | 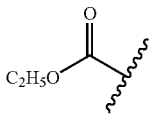 | H | 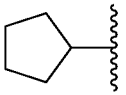 |
| YA0193 | CH3— | 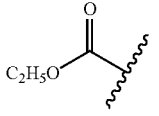 | H | 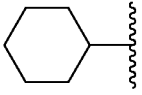 |
| YA0194 | CH3— | 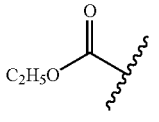 | H | 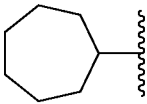 |
| YA0195 | CH3— | 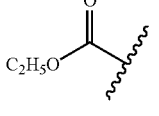 | H | 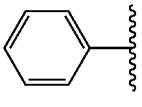 |
| YA0196 | CH3— | 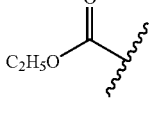 | H | 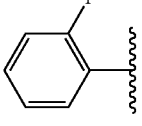 |
| YA0197 | CH3— | 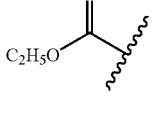 | H | 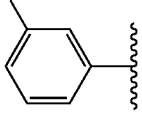 |
| YA0198 | CH3— | 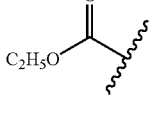 | H | 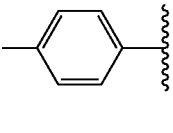 |
| YA0199 | CH3— | 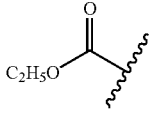 | H | 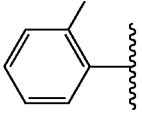 |
| YA0200 | CH3— | 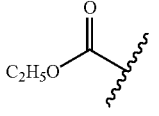 | H | 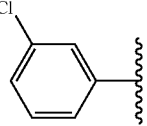 |
| YA0201 | CH3— | 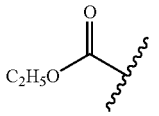 | H | 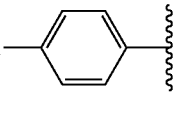 |
| YA0202 | CH3— | 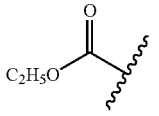 | H | 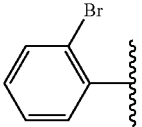 |

-continued
| | | | | |
|---|---|---|---|---|
| YA0203 | CH3— | 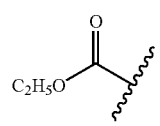 | H | 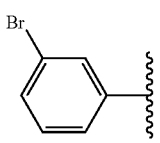 |
| YA0204 | CH3— | 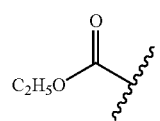 | H | 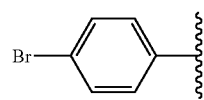 |
| YA0205 | CH3— | 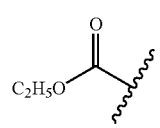 | H | 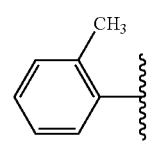 |
| YA0206 | CH3— | 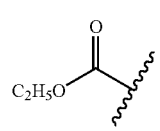 | H | 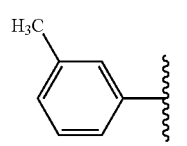 |
| YA0207 | CH3— | 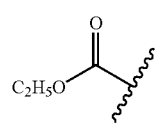 | H | 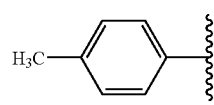 |
| YA0208 | CH3— | 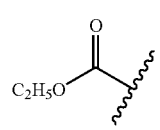 | H | 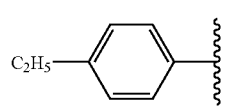 |
| YA0209 | CH3— | 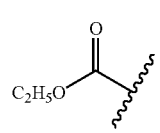 | H | 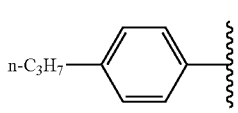 |
| YA0210 | CH3— | 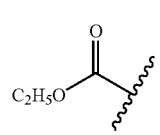 | H | 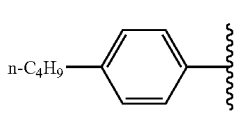 |
| YA0211 | CH3— | 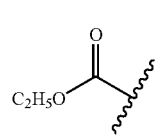 | H | 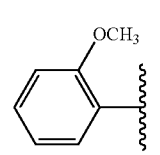 |
| YA0212 | CH3— | 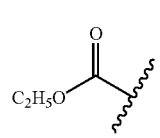 | H | 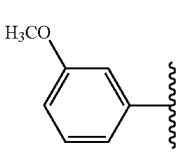 |
| YA0213 | CH3— | 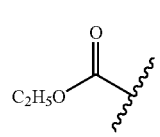 | H | 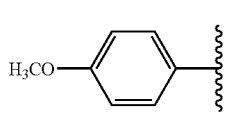 |

-continued
| | | | | |
|---|---|---|---|---|
| YA0214 | CH3— | 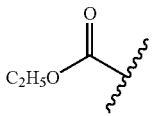 | H | 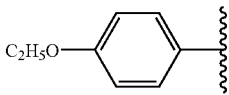 |
| YA0215 | CH3— | 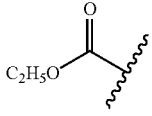 | H | 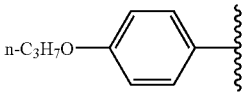 |
| YA0216 | CH3— | 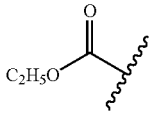 | H | 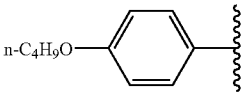 |
| YA0217 | CH3— | 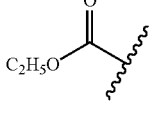 | H | 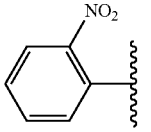 |
| YA0218 | CH3— | 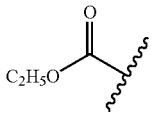 | H | 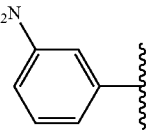 |
| YA0219 | CH3— | 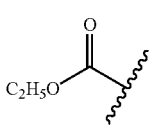 | H | 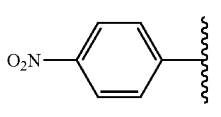 |
| YA0220 | CH3— | 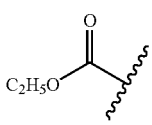 | H | 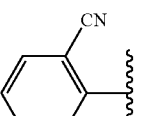 |
| YA0221 | CH3— | 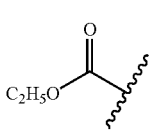 | H | 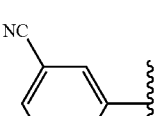 |
| YA0222 | CH3— | 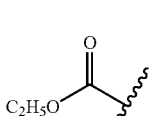 | H | 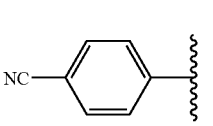 |
| YA0223 | CH3— | 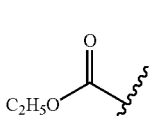 | H | 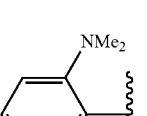 |
| YA0224 | CH3— | 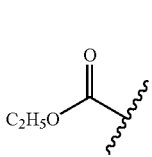 | H | 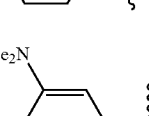 |

-continued
| | | | | |
|---|---|---|---|---|
| YA0225 | CH3— | 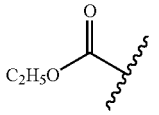 | H | 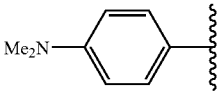 |
| YA0226 | CH3— | 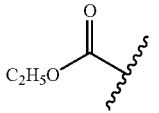 | H | 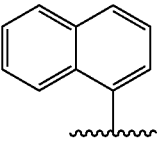 |
| YA0227 | CH3— | 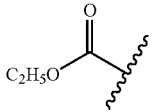 | H | 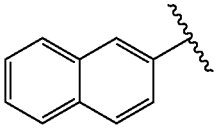 |
| YA0228 | CH3— | 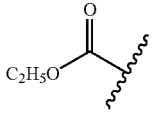 | H | 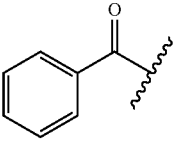 |
| YA0229 | CH3— | 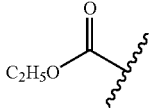 | H | 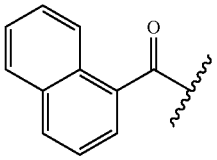 |
| YA0230 | CH3— | 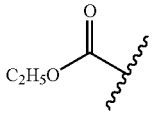 | H | 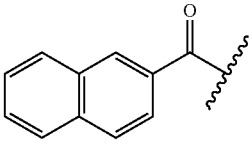 |
| YA0231 | CH3— | 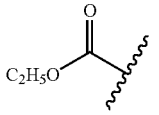 | H | 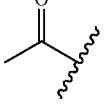 |
| YA0232 | CH3— | 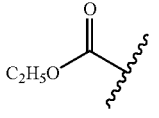 | H | 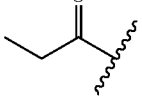 |
| YA0233 | CH3— | CH3— | H | H |
| YA0234 | CH3— | CH3CH2— | H | H |
| YA0235 | CH3— | 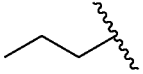 | H | H |
| YA0236 | CH3— | 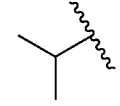 | H | H |
| YA0237 | CH3— | 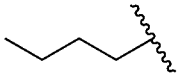 | H | H |

-continued
| | | | | |
|---|---|---|---|---|
| YA0238 | CH3— | 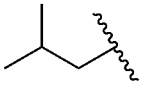 | H | H |
| YA0239 | CH3— | 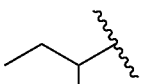 | H | H |
| YA0240 | CH3— | 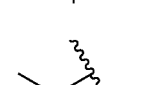 | H | H |
| YA0241 | CH3— | 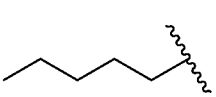 | H | H |
| YA0242 | CH3— | 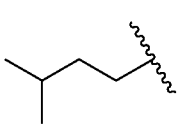 | H | H |
| YA0243 | CH3— | 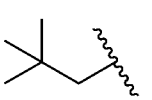 | H | H |
| YA0244 | CH3— | 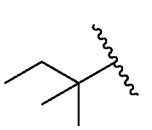 | H | H |
| YA0245 | CH3— | 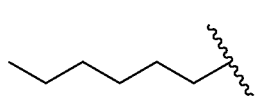 | H | H |
| YA0246 | CH3— | 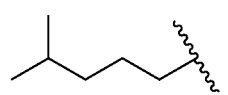 | H | H |
| YA0247 | CH3— | 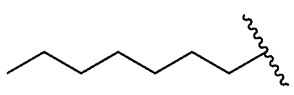 | H | H |
| YA0248 | CH3— | 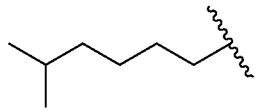 | H | H |
| YA0249 | CH3— | 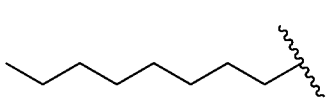 | H | H |
| YA0250 | CH3— | 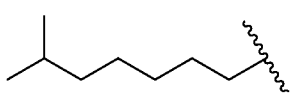 | H | H |
| YA0251 | CH3— | 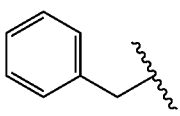 | H | H |

-continued
| | | | | |
|---|---|---|---|---|
| YA0252 | CH3— | 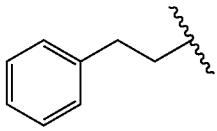 | H | H |
| YA0253 | CH3— | 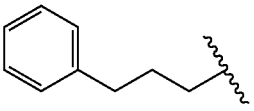 | H | H |
| YA0254 | CH3— | 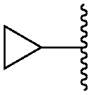 | H | H |
| YA0255 | CH3— | 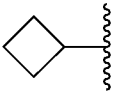 | H | H |
| YA0256 | CH3— | 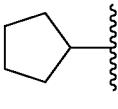 | H | H |
| YA0257 | CH3— | 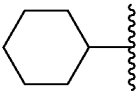 | H | H |
| YA0258 | CH3— | 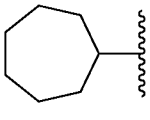 | H | H |
| YA0259 | CH3— | 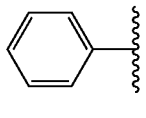 | H | H |
| YA0260 | CH3— | 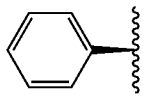 | H | H |
| YA0261 | CH3— | 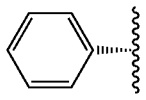 | H | H |
| YA0262 | CH3— | 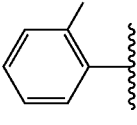 | H | H |
| YA0263 | CH3— | 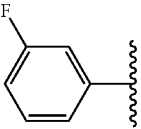 | H | H |
| YA0264 | CH3— | 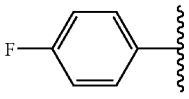 | H | H |

-continued
| | | | | |
|---|---|---|---|---|
| YA0265 | CH3— | 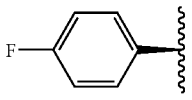 | H | H |
| YA0266 | CH3— | 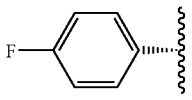 | H | H |
| YA0267 | CH3— | 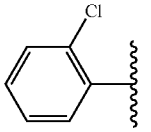 | H | H |
| YA0268 | CH3— | 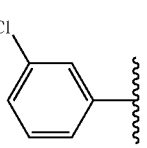 | H | H |
| YA0269 | CH3— |  | H | H |
| YA0270 | CH3— | 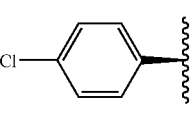 | H | H |
| YA0271 | CH3— | 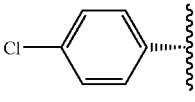 | H | H |
| YA0272 | CH3— | 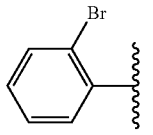 | H | H |
| YA0273 | CH3— | 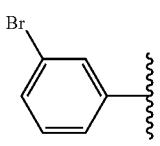 | H | H |
| YA0274 | CH3— | 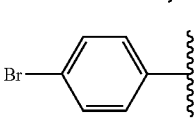 | H | H |
| YA0275 | CH3— | 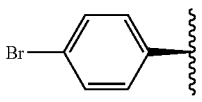 | H | H |
| YA0276 | CH3— | 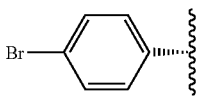 | H | H |
| YA0277 | CH3— | 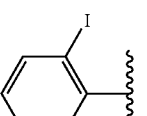 | H | H |

-continued
| | | | | |
|---|---|---|---|---|
| YA0278 | CH3— | 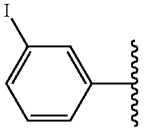 | H | H |
| YA0279 | CH3— | 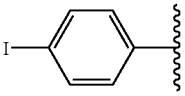 | H | H |
| YA0280 | CH3— | 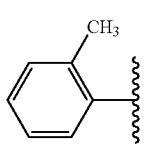 | H | H |
| YA0281 | CH3— | 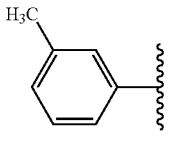 | H | H |
| YA0282 | CH3— |  | H | H |
| YA0283 | CH3— | 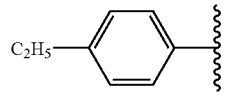 | H | H |
| YA0284 | CH3— | 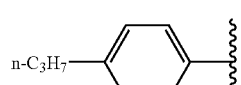 | H | H |
| YA0285 | CH3— | 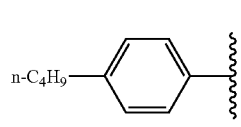 | H | H |
| YA0286 | CH3— | 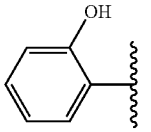 | H | H |
| YA0287 | CH3— | 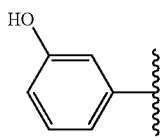 | H | H |
| YA0288 | CH3— | 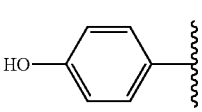 | H | H |
| YA0289 | CH3— | 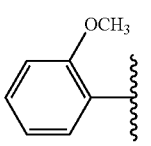 | H | H |

-continued
| | | | | |
|---|---|---|---|---|
| YA0290 | CH3— | 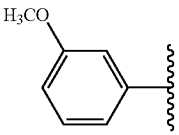 | H | H |
| YA0291 | CH3— | 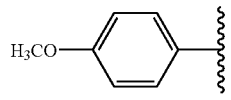 | H | H |
| YA0292 | CH3— | 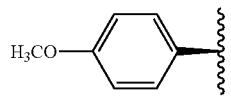 | H | H |
| YA0293 | CH3— | 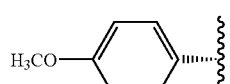 | H | H |
| YA0294 | CH3— | 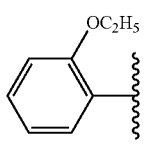 | H | H |
| YA0295 | CH3— | 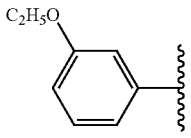 | H | H |
| YA0296 | CH3— | 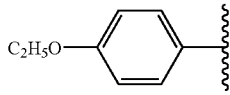 | H | H |
| YA0297 | CH3— | 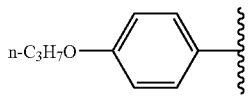 | H | H |
| YA0298 | CH3— | 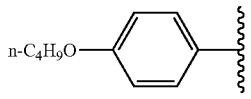 | H | H |
| YA0299 | CH3— | 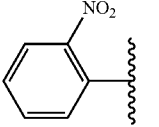 | H | H |
| YA0300 | CH3— | 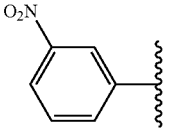 | H | H |
| YA0301 | CH3— | 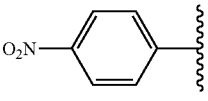 | H | H |

-continued
| | | | | |
|---|---|---|---|---|
| YA0302 | CH3— | 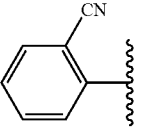 2-CN-C6H4 | H | H |
| YA0303 | CH3— | 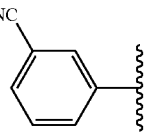 3-CN-C6H4 | H | H |
| YA0304 | CH3— | 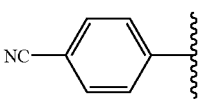 4-CN-C6H4 | H | H |
| YA0305 | CH3— | 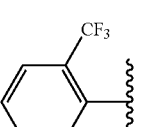 2-CF3-C6H4 | H | H |
| YA0306 | CH3— | 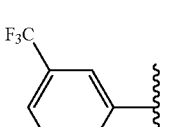 3-CF3-C6H4 | H | H |
| YA0307 | CH3— | 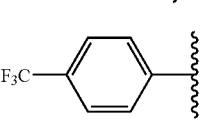 4-CF3-C6H4 | H | H |
| YA0308 | CH3— | 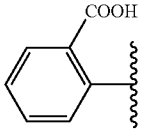 2-COOH-C6H4 | H | H |
| YA0309 | CH3— | 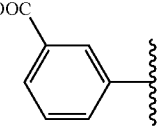 3-COOH-C6H4 | H | H |
| YA0310 | CH3— | 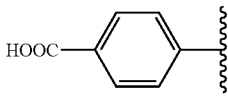 4-COOH-C6H4 | H | H |
| YA0311 | CH3— | 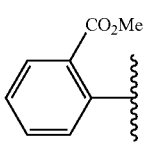 2-CO2Me-C6H4 | H | H |
| YA0312 | CH3— | 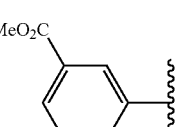 3-CO2Me-C6H4 | H | H |
| YA0313 | CH3— | 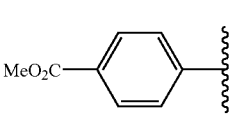 4-CO2Me-C6H4 | H | H |

-continued

| | | | | |
|---|---|---|---|---|
| YA0314 | CH3— | 2-(CO2Et)-phenyl | H | H |
| YA0315 | CH3— | 3-(EtO2C)-phenyl | H | H |
| YA0316 | CH3— | 4-(EtO2C)-phenyl | H | H |
| YA0317 | CH3— | 2-(SMe)-phenyl | H | H |
| YA0318 | CH3— | 3-(MeS)-phenyl | H | H |
| YA0319 | CH3— | 4-(MeS)-phenyl | H | H |
| YA0320 | CH3— | 2-(SO2Me)-phenyl | H | H |
| YA0321 | CH3— | 3-(MeO2S)-phenyl | H | H |
| YA0322 | CH3— | 4-(MeO2S)-phenyl | H | H |
| YA0323 | CH3— | 2-(NH2)-phenyl | H | H |
| YA0324 | CH3— | 3-(H2N)-phenyl | H | H |
| YA0325 | CH3— | 4-(H2N)-phenyl | H | H |

-continued
| | | | | |
|---|---|---|---|---|
| YA0326 | CH3— | 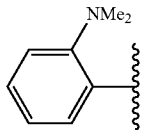 | H | H |
| YA0327 | CH3— | 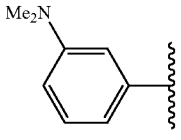 | H | H |
| YA0328 | CH3— | 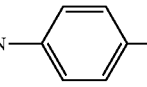 | H | H |
| YA0329 | CH3— | 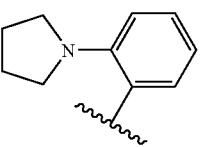 | H | H |
| YA0330 | CH3— | 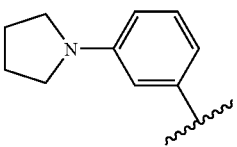 | H | H |
| YA0331 | CH3— | 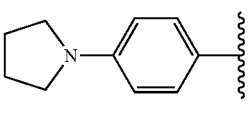 | H | H |
| YA0332 | CH3— | 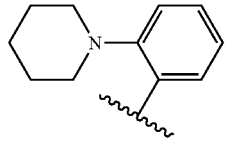 | H | H |
| YA0333 | CH3— | 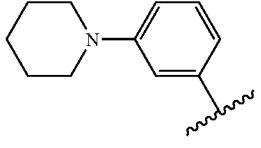 | H | H |
| YA0334 | CH3— | 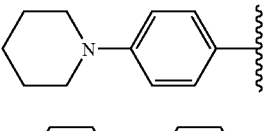 | H | H |
| YA0335 | CH3— | 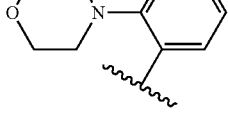 | H | H |
| YA0336 | CH3— | 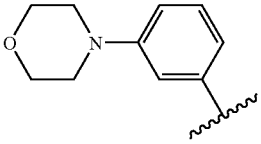 | H | H |

-continued
| | | | | |
|---|---|---|---|---|
| YA0337 | CH3— | 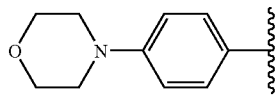 | H | H |
| YA0338 | CH3— | 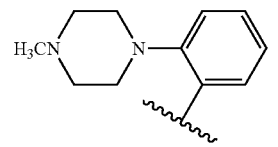 | H | H |
| YA0339 | CH3— | 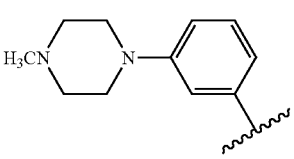 | H | H |
| YA0340 | CH3— | 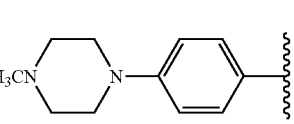 | H | H |
| YA0341 | CH3— | 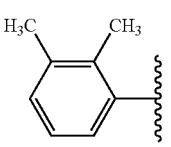 | H | H |
| YA0342 | CH3— | 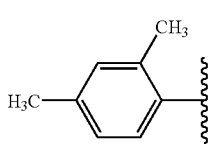 | H | H |
| YA0343 | CH3— | 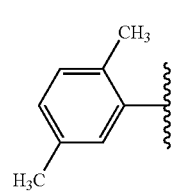 | H | H |
| YA0344 | CH3— | 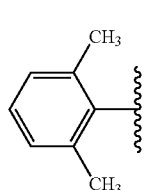 | H | H |
| YA0345 | CH3— | 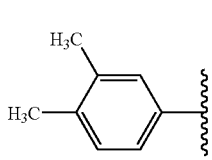 | H | H |
| YA0346 | CH3— | 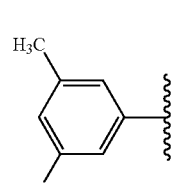 | H | H |

-continued
| | | | | |
|---|---|---|---|---|
| YA0347 | CH3— | 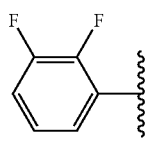 | H | H |
| YA0348 | CH3— | 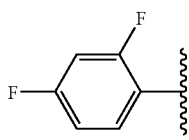 | H | H |
| YA0349 | CH3— | 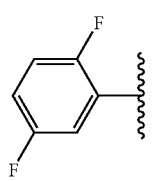 | H | H |
| YA0350 | CH3— | 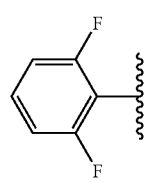 | H | H |
| YA0351 | CH3— | 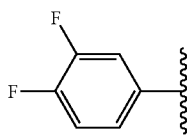 | H | H |
| YA0352 | CH3— | 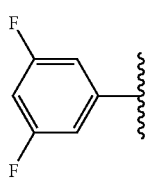 | H | H |
| YA0353 | CH3— | 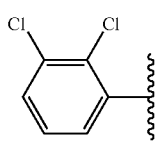 | H | H |
| YA0354 | CH3— | 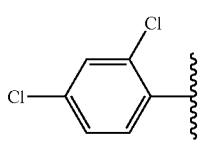 | H | H |
| YA0355 | CH3— | 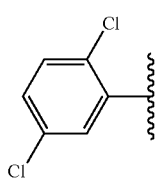 | H | H |

-continued
| | | | | |
|---|---|---|---|---|
| YA0356 | CH3— | 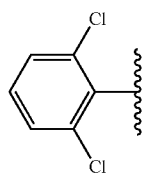 | H | H |
| YA0357 | CH3— | 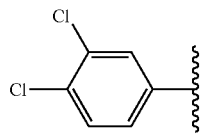 | H | H |
| YA0358 | CH3— | 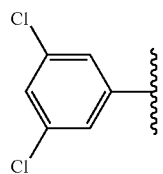 | H | H |
| YA0359 | CH3— | 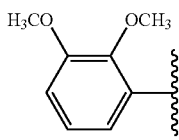 | H | H |
| YA0360 | CH3— | 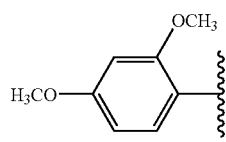 | H | H |
| YA0361 | CH3— | 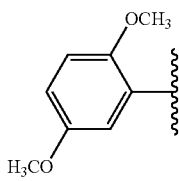 | H | H |
| YA0362 | CH3— | 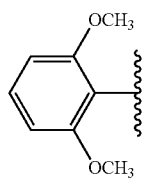 | H | H |
| YA0363 | CH3— | 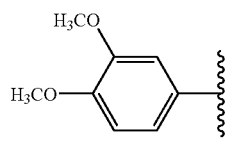 | H | H |
| YA0364 | CH3— | 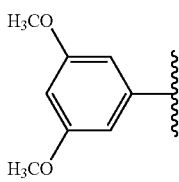 | H | H |

-continued
| | | | | |
|---|---|---|---|---|
| YA0365 | CH3— | 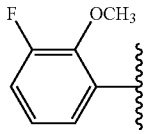 | H | H |
| YA0366 | CH3— | 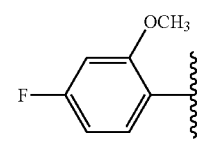 | H | H |
| YA0367 | CH3— | 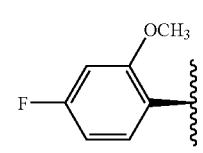 | H | H |
| YA0368 | CH3— | 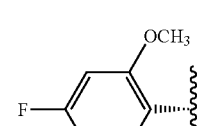 | H | H |
| YA0369 | CH3— | 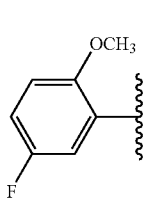 | H | H |
| YA0370 | CH3— | 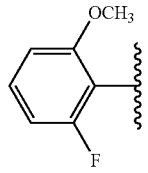 | H | H |
| YA0371 | CH3— | 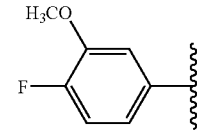 | H | H |
| YA0372 | CH3— | 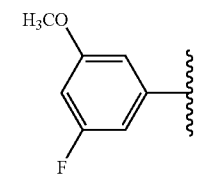 | H | H |
| YA0373 | CH3— | 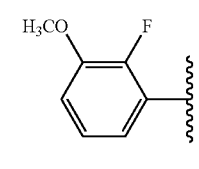 | H | H |
| YA0374 | CH3— | 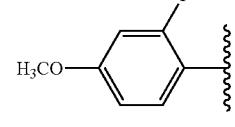 | H | H |

-continued
| | | | | |
|---|---|---|---|---|
| YA0375 | CH3— | 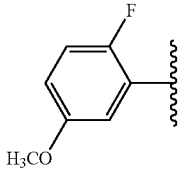 | H | H |
| YA0376 | CH3— | 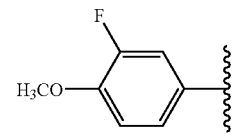 | H | H |
| YA0377 | CH3— | 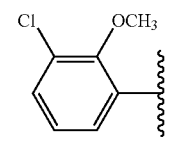 | H | H |
| YA0378 | CH3— | 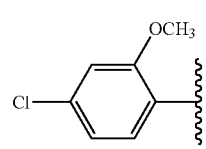 | H | H |
| YA0379 | CH3— | 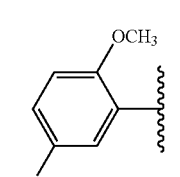 | H | H |
| YA0380 | CH3— | 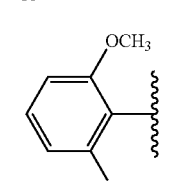 | H | H |
| YA0381 | CH3— | 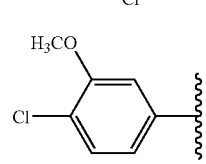 | H | H |
| YA0382 | CH3— | 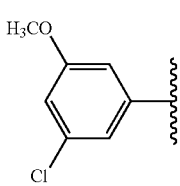 | H | H |
| YA0383 | CH3— | 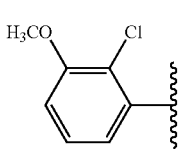 | H | H |
| YA0384 | CH3— | 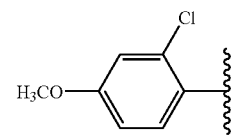 | H | H |

-continued
| | | | | |
|---|---|---|---|---|
| YA0385 | CH3— | 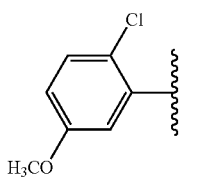 | H | H |
| YA0386 | CH3— | 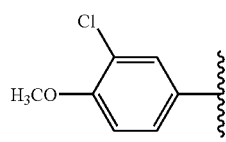 | H | H |
| YA0387 | CH3— | 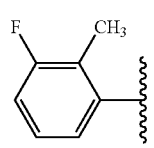 | H | H |
| YA0388 | CH3— | 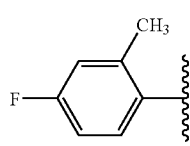 | H | H |
| YA0389 | CH3— | 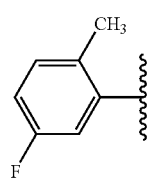 | H | H |
| YA0390 | CH3— | 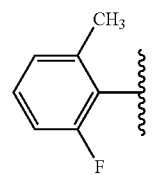 | H | H |
| YA0391 | CH3— | 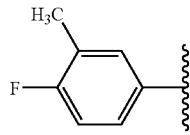 | H | H |
| YA0392 | CH3— | 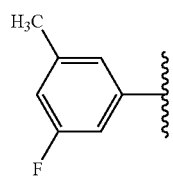 | H | H |
| YA0393 | CH3— | 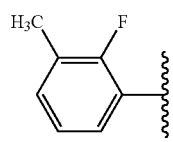 | H | H |

-continued
| | | | | |
|---|---|---|---|---|
| YA0394 | CH3— | 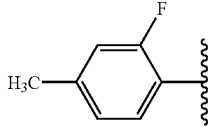 | H | H |
| YA0395 | CH3— | 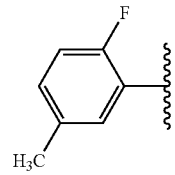 | H | H |
| YA0396 | CH3— | 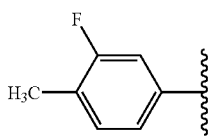 | H | H |
| YA0397 | CH3— | 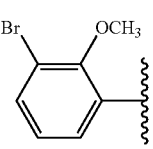 | H | H |
| YA0398 | CH3— | 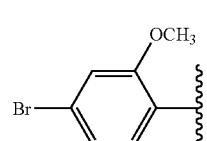 | H | H |
| YA0399 | CH3— | 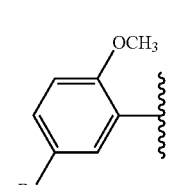 | H | H |
| YA0400 | CH3— | 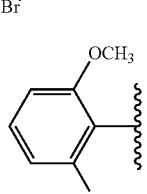 | H | H |
| YA0401 | CH3— | 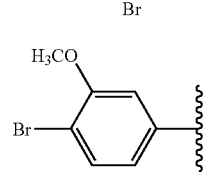 | H | H |
| YA0402 | CH3— | 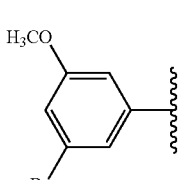 | H | H |
| YA0403 | CH3— | 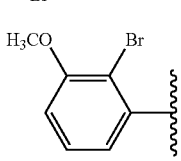 | H | H |

-continued
| | | | | |
|---|---|---|---|---|
| YA0404 | CH3— | 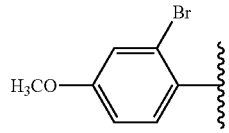 | H | H |
| YA0405 | CH3— | 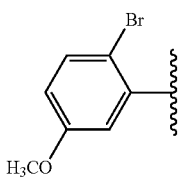 | H | H |
| YA0406 | CH3— | 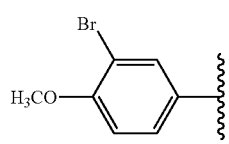 | H | H |
| YA0407 | CH3— | 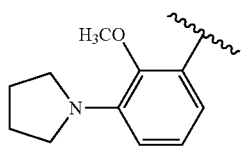 | H | H |
| YA0408 | CH3— | 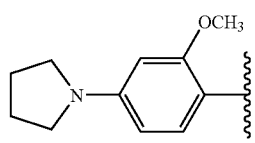 | H | H |
| YA0409 | CH3— | 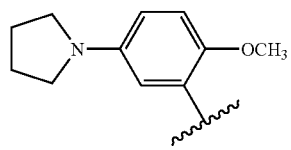 | H | H |
| YA0410 | CH3— | 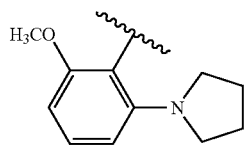 | H | H |
| YA0411 | CH3— | 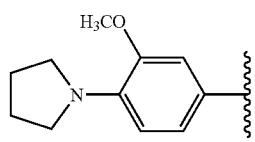 | H | H |
| YA0412 | CH3— | 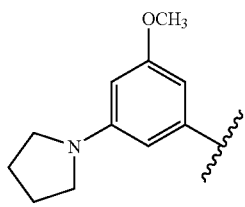 | H | H |

-continued
| | | | | |
|---|---|---|---|---|
| YA0413 | CH3— | 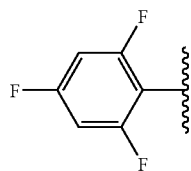 | H | H |
| YA0414 | CH3— | 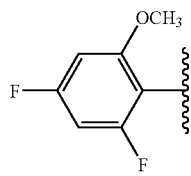 | H | H |
| YA0415 | CH3— | 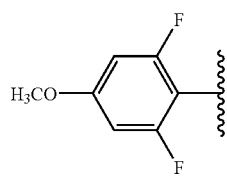 | H | H |
| YA0416 | CH3— | 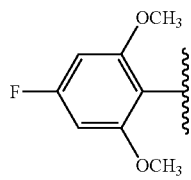 | H | H |
| YA0417 | CH3— | 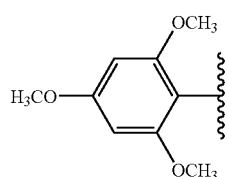 | H | H |
| YA0418 | CH3— | 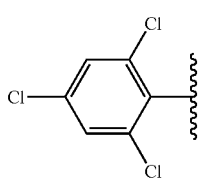 | H | H |
| YA0419 | CH3— | 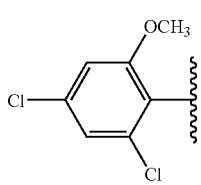 | H | H |
| YA0420 | CH3— | 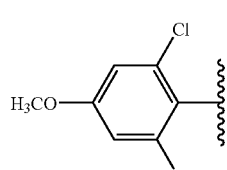 | H | H |

| | | | | |
|---|---|---|---|---|
| YA0421 | CH3— | 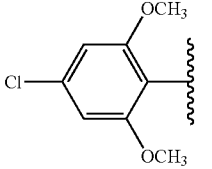 | H | H |
| YA0422 | CH3— | 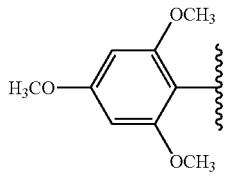 | H | H |
| YA0423 | CH3— | 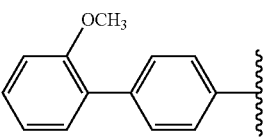 | H | H |
| YA0424 | CH3— | 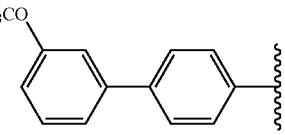 | H | H |
| YA0425 | CH3— | 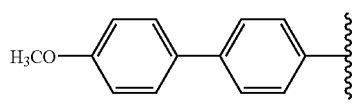 | H | H |
| YA0426 | CH3— | 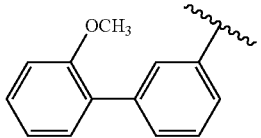 | H | H |
| YA0427 | CH3— | 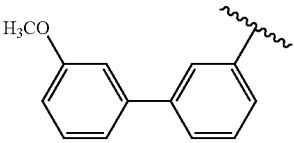 | H | H |
| YA0428 | CH3— | 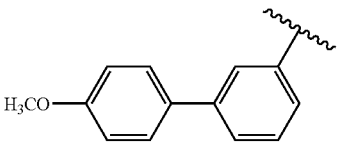 | H | H |
| YA0429 | CH3— | 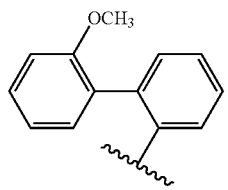 | H | H |
| YA0430 | CH3— | 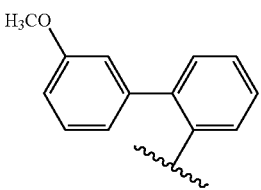 | H | H |

-continued
| | | | | |
|---|---|---|---|---|
| YA0431 | CH3— | 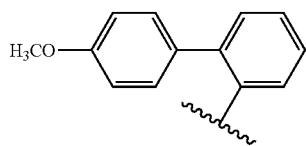 | H | H |
| YA0432 | CH3— | 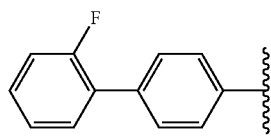 | H | H |
| YA0433 | CH3— | 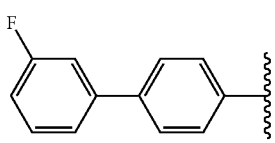 | H | H |
| YA0434 | CH3— | 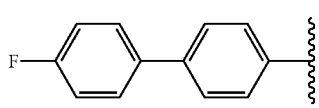 | H | H |
| YA0435 | CH3— | 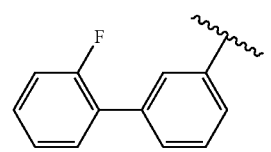 | H | H |
| YA0436 | CH3— | 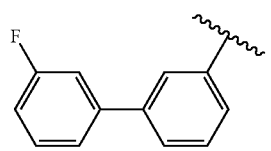 | H | H |
| YA0437 | CH3— | 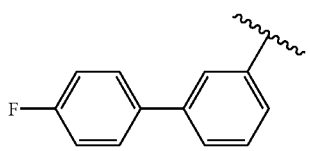 | H | H |
| YA0438 | CH3— | 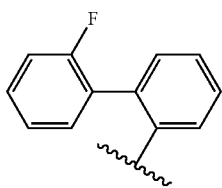 | H | H |
| YA0439 | CH3— | 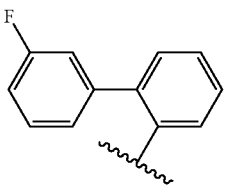 | H | H |
| YA0440 | CH3— | 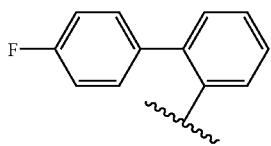 | H | H |

-continued

| | | | | |
|---|---|---|---|---|
| YA0441 | CH3— | naphthalen-1-yl | H | H |
| YA0442 | CH3— | naphthalen-2-yl | H | H |
| YA0443 | CH3— | 1H-pyrrol-2-yl | H | H |
| YA0444 | CH3— | 1H-pyrazol-3-yl | H | H |
| YA0445 | CH3— | furan-2-yl | H | H |
| YA0446 | CH3— | furan-3-yl | H | H |
| YA0447 | CH3— | thiophen-2-yl | H | H |
| YA0448 | CH3— | thiophen-3-yl | H | H |
| YA0449 | CH3— | 1H-pyrazol-3-yl | H | H |
| YA0450 | CH3— | 1H-pyrazol-4-yl | H | H |
| YA0451 | CH3— | 1H-imidazol-4-yl | H | H |
| YA0452 | CH3— | 1H-imidazol-2-yl | H | H |

-continued
| | | | | |
|---|---|---|---|---|
| YA0453 | CH3— | 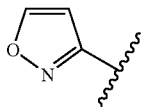 | H | H |
| YA0454 | CH3— | 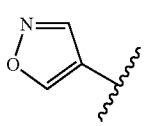 | H | H |
| YA0455 | CH3— | 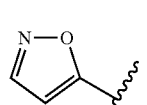 | H | H |
| YA0456 | CH3— | 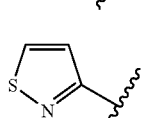 | H | H |
| YA0457 | CH3— | 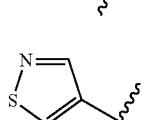 | H | H |
| YA0458 | CH3— | 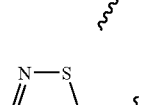 | H | H |
| YA0459 | CH3— | 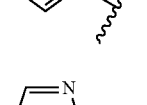 | H | H |
| YA0460 | CH3— | 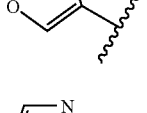 | H | H |
| YA0461 | CH3— | 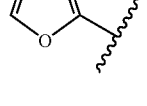 | H | H |
| YA0462 | CH3— | 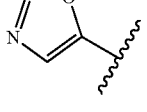 | H | H |
| YA0463 | CH3— | 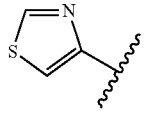 | H | H |
| YA0464 | CH3— | 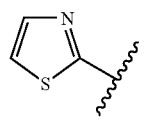 | H | H |

-continued
| | | | | |
|---|---|---|---|---|
| YA0465 | CH3— | 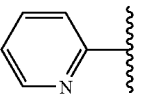 | H | H |
| YA0466 | CH3— | 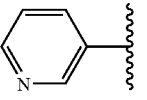 | H | H |
| YA0467 | CH3— | 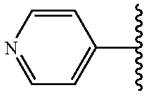 | H | H |
| YA0468 | CH3— | 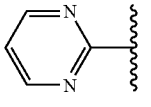 | H | H |
| YA0469 | CH3— | 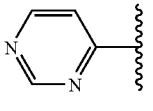 | H | H |
| YA0470 | CH3— | 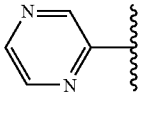 | H | H |
| YA0471 | CH3— | 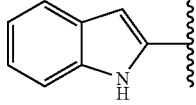 | H | H |
| YA0472 | CH3— | 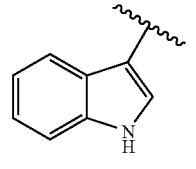 | H | H |
| YA0473 | CH3— | 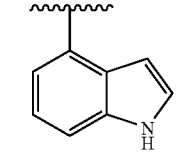 | H | H |
| YA0474 | CH3— | 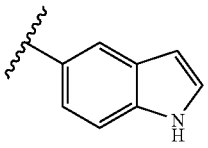 | H | H |
| YA0475 | CH3— | 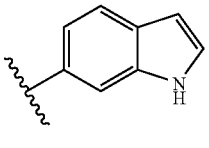 | H | H |
| YA0476 | CH3— | 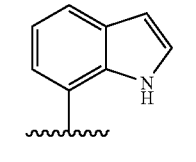 | H | H |

-continued
| | | | | |
|---|---|---|---|---|
| YA0477 | CH3— | 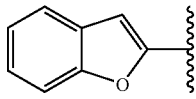 | H | H |
| YA0478 | CH3— | 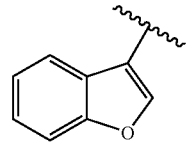 | H | H |
| YA0479 | CH3— | 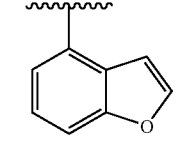 | H | H |
| YA0480 | CH3— | 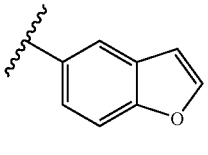 | H | H |
| YA0481 | CH3— | 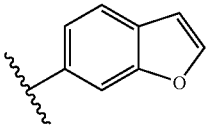 | H | H |
| YA0482 | CH3— | 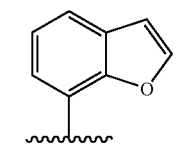 | H | H |
| YA0483 | CH3— | 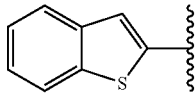 | H | H |
| YA0484 | CH3— | 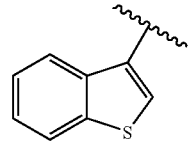 | H | H |
| YA0485 | CH3— | 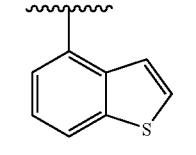 | H | H |
| YA0486 | CH3— | 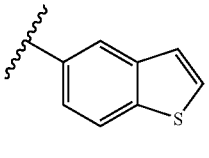 | H | H |
| YA0487 | CH3— | 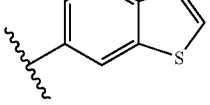 | H | H |

-continued
| | | | | |
|---|---|---|---|---|
| YA0488 | CH3— | 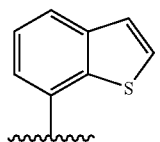 | H | H |
| YA0489 | CH3— | 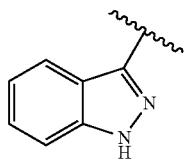 | H | H |
| YA0490 | CH3— | 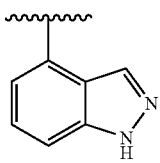 | H | H |
| YA0491 | CH3— | 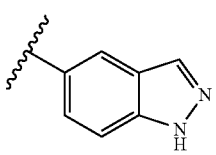 | H | H |
| YA0492 | CH3— | 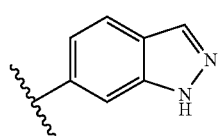 | H | H |
| YA0493 | CH3— | 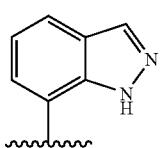 | H | H |
| YA0494 | CH3— | 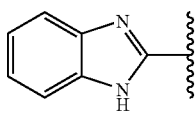 | H | H |
| YA0495 | CH3— | 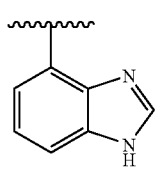 | H | H |
| YA0496 | CH3— | 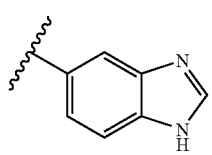 | H | H |
| YA0497 | CH3— | 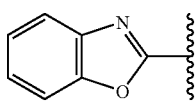 | H | H |

-continued
| | | | | |
|---|---|---|---|---|
| YA0498 | CH3— | 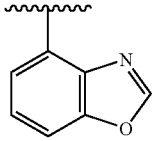 | H | H |
| YA0499 | CH3— | 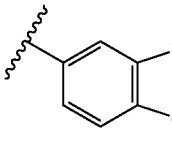 | H | H |
| YA0500 | CH3— | 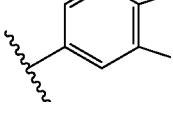 | H | H |
| YA0501 | CH3— | 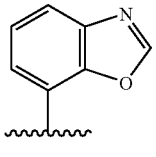 | H | H |
| YA0502 | CH3— | 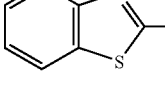 | H | H |
| YA0503 | CH3— | 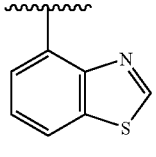 | H | H |
| YA0504 | CH3— | 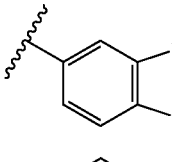 | H | H |
| YA0505 | CH3— | 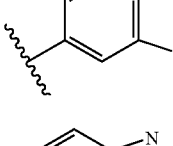 | H | H |
| YA0506 | CH3— | 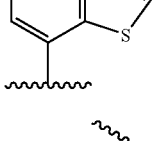 | H | H |
| YA0507 | CH3— | 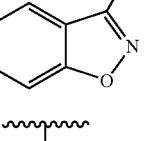 | H | H |
| YA0508 | CH3— | 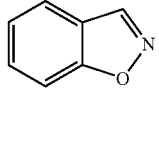 | H | H |

-continued
| | | | | |
|---|---|---|---|---|
| YA0509 | CH3— | 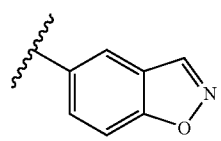 | H | H |
| YA0510 | CH3— | 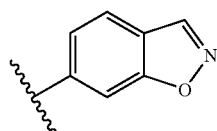 | H | H |
| YA0511 | CH3— | 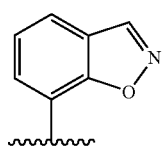 | H | H |
| YA0512 | CH3— | 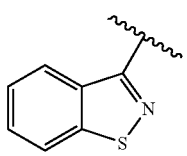 | H | H |
| YA0513 | CH3— | 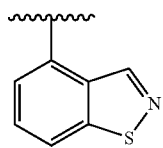 | H | H |
| YA0514 | CH3— | 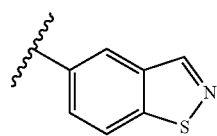 | H | H |
| YA0515 | CH3— | 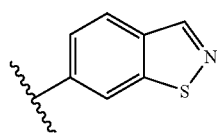 | H | H |
| YA0516 | CH3— | 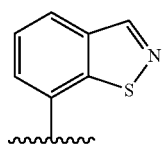 | H | H |
| YA0517 | CH3— | 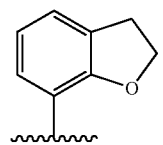 | H | H |
| YA0518 | CH3— | 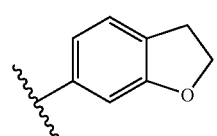 | H | H |

-continued
| | | | | |
|---|---|---|---|---|
| YA0519 | CH3— | 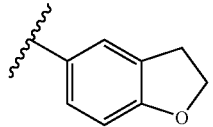 | H | H |
| YA0520 | CH3— | 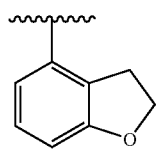 | H | H |
| YA0521 | CH3— | CH3— | H | CH3 |
| YA0522 | CH3— | CH3CH2— | H | CH3 |
| YA0523 | CH3— | 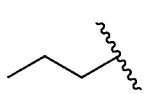 | H | CH3 |
| YA0524 | CH3— | 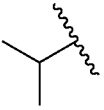 | H | CH3 |
| YA0525 | CH3— | 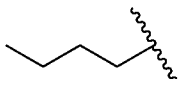 | H | CH3 |
| YA0526 | CH3— | 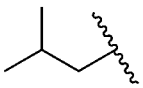 | H | CH3 |
| YA0527 | CH3— | 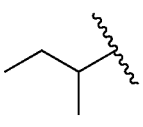 | H | CH3 |
| YA0528 | CH3— | 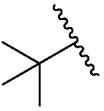 | H | CH3 |
| YA0529 | CH3— | 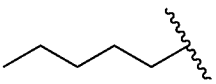 | H | CH3 |
| YA0530 | CH3— | 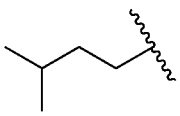 | H | CH3 |
| YA0531 | CH3— | 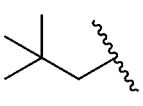 | H | CH3 |
| YA0532 | CH3— | 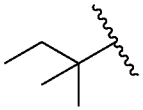 | H | CH3 |
| YA0533 | CH3— | 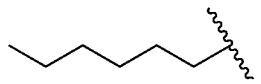 | H | CH3 |

|  |  |  |  |  |
|---|---|---|---|---|
| YA0534 | CH3— | (isohexyl chain) | H | CH3 |
| YA0535 | CH3— | (n-heptyl chain) | H | CH3 |
| YA0536 | CH3— | (isoheptyl chain) | H | CH3 |
| YA0537 | CH3— | (n-nonyl chain) | H | CH3 |
| YA0538 | CH3— | (isooctyl chain) | H | CH3 |
| YA0539 | CH3— | benzyl | H | CH3 |
| YA0540 | CH3— | phenethyl | H | CH3 |
| YA0541 | CH3— | phenylpropyl | H | CH3 |
| YA0542 | CH3— | cyclopropyl | H | CH3 |
| YA0543 | CH3— | cyclobutyl | H | CH3 |
| YA0544 | CH3— | cyclopentyl | H | CH3 |
| YA0545 | CH3— | cyclohexyl | H | CH3 |
| YA0546 | CH3— | cycloheptyl | H | CH3 |
| YA0547 | CH3— | phenyl | H | CH3 |

-continued
| | | | | |
|---|---|---|---|---|
| YA0548 | CH3— | 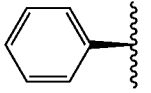 | H | CH3 |
| YA0549 | CH3— | 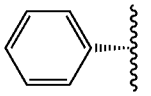 | H | CH3 |
| YA0550 | CH3— | 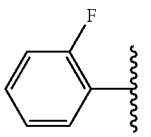 | H | CH3 |
| YA0551 | CH3— | 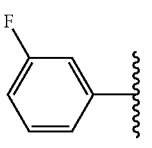 | H | CH3 |
| YA0552 | CH3— | 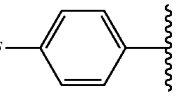 | H | CH3 |
| YA0553 | CH3— | 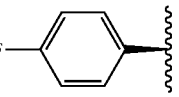 | H | CH3 |
| YA0554 | CH3— | 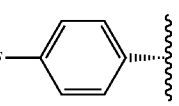 | H | CH3 |
| YA0555 | CH3— | 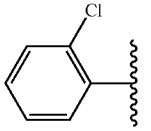 | H | CH3 |
| YA0556 | CH3— | 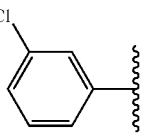 | H | CH3 |
| YA0557 | CH3— | 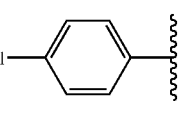 | H | CH3 |
| YA0558 | CH3— | 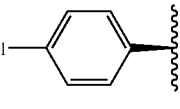 | H | CH3 |
| YA0559 | CH3— |  | H | CH3 |
| YA0560 | CH3— | 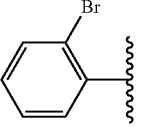 | H | CH3 |

-continued
| | | | | |
|---|---|---|---|---|
| YA0561 | CH3— | 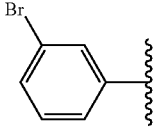 | H | CH3 |
| YA0562 | CH3— | 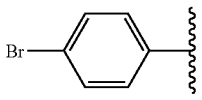 | H | CH3 |
| YA0563 | CH3— | 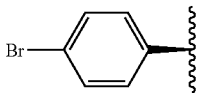 | H | CH3 |
| YA0564 | CH3— | 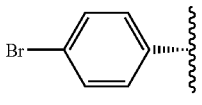 | H | CH3 |
| YA0565 | CH3— | 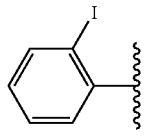 | H | CH3 |
| YA0566 | CH3— | 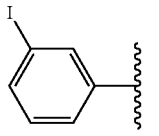 | H | CH3 |
| YA0567 | CH3— | 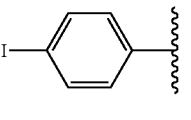 | H | CH3 |
| YA0568 | CH3— | 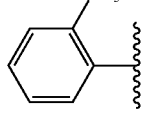 | H | CH3 |
| YA0569 | CH3— | 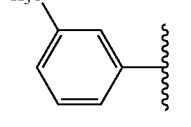 | H | CH3 |
| YA0570 | CH3— | 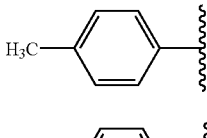 | H | CH3 |
| YA0571 | CH3— | 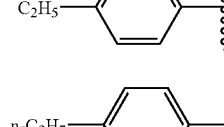 | H | CH3 |
| YA0572 | CH3— | 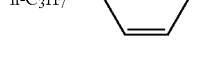 | H | CH3 |
| YA0573 | CH3— | 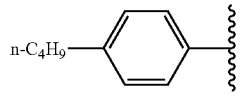 | H | CH3 |

-continued
| | | | | |
|---|---|---|---|---|
| YA0574 | CH3— | 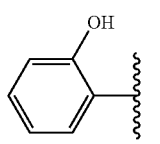 | H | CH3 |
| YA0575 | CH3— | 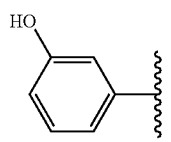 | H | CH3 |
| YA0576 | CH3— | 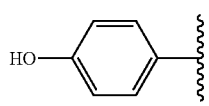 | H | CH3 |
| YA0577 | CH3— | 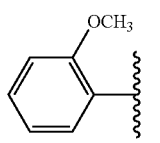 | H | CH3 |
| YA0578 | CH3— | 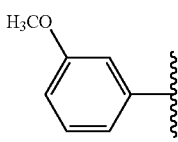 | H | CH3 |
| YA0579 | CH3— | 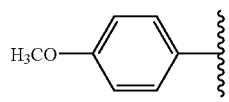 | H | CH3 |
| YA0580 | CH3— | 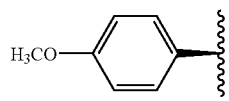 | H | CH3 |
| YA0581 | CH3— | 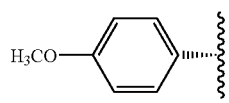 | H | CH3 |
| YA0582 | CH3— | 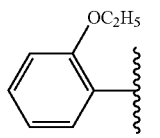 | H | CH3 |
| YA0583 | CH3— | 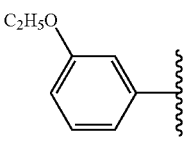 | H | CH3 |
| YA0584 | CH3— | 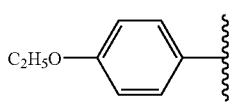 | H | CH3 |
| YA0585 | CH3— | 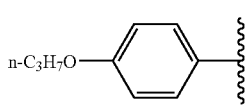 | H | CH3 |

-continued
| | | | | |
|---|---|---|---|---|
| YA0586 | CH3— | 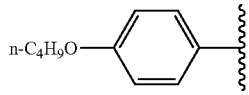 | H | CH3 |
| YA0587 | CH3— | 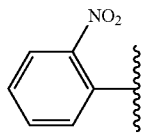 | H | CH3 |
| YA0588 | CH3— | 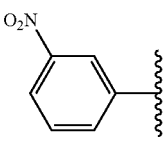 | H | CH3 |
| YA0589 | CH3— | 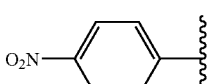 | H | CH3 |
| YA0590 | CH3— | 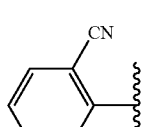 | H | CH3 |
| YA0591 | CH3— | 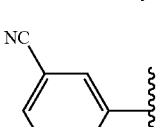 | H | CH3 |
| YA0592 | CH3— | 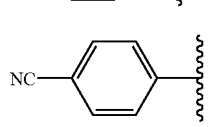 | H | CH3 |
| YA0593 | CH3— | 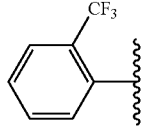 | H | CH3 |
| YA0594 | CH3— | 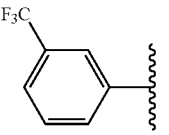 | H | CH3 |
| YA0595 | CH3— | 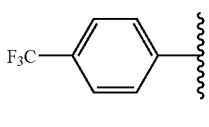 | H | CH3 |
| YA0596 | CH3— | 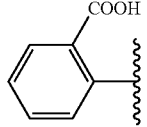 | H | CH3 |
| YA0597 | CH3— | 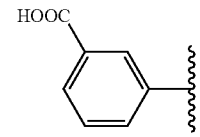 | H | CH3 |

-continued
| | | | | |
|---|---|---|---|---|
| YA0598 | CH3— | 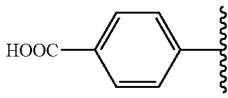 | H | CH3 |
| YA0599 | CH3— | 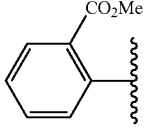 | H | CH3 |
| YA0600 | CH3— | 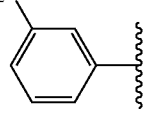 | H | CH3 |
| YA0601 | CH3— | 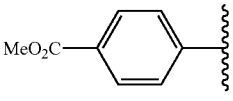 | H | CH3 |
| YA0602 | CH3— | 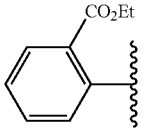 | H | CH3 |
| YA0603 | CH3— | 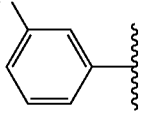 | H | CH3 |
| YA0604 | CH3— | 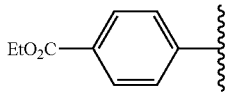 | H | CH3 |
| YA0605 | CH3— | 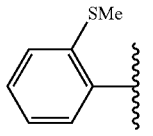 | H | CH3 |
| YA0606 | CH3— | 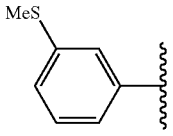 | H | CH3 |
| YA0607 | CH3— | 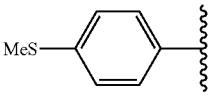 | H | CH3 |
| YA0608 | CH3— | 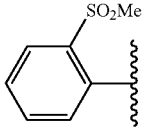 | H | CH3 |
| YA0609 | CH3— | 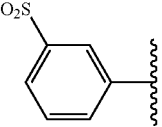 | H | CH3 |

-continued
| | | | | |
|---|---|---|---|---|
| YA0610 | CH3— | 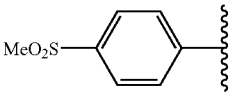 | H | CH3 |
| YA0611 | CH3— | 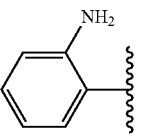 | H | CH3 |
| YA0612 | CH3— | 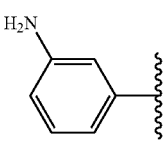 | H | CH3 |
| YA0613 | CH3— | 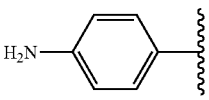 | H | CH3 |
| YA0614 | CH3— | 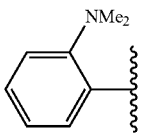 | H | CH3 |
| YA0615 | CH3— | 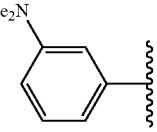 | H | CH3 |
| YA0616 | CH3— | 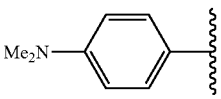 | H | CH3 |
| YA0617 | CH3— | 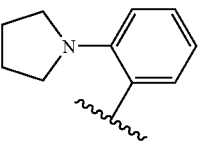 | H | CH3 |
| YA0618 | CH3— | 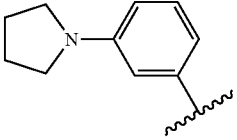 | H | CH3 |
| YA0619 | CH3— | 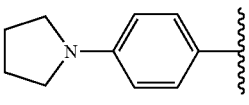 | H | CH3 |
| YA0620 | CH3— | 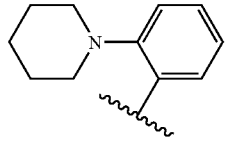 | H | CH3 |

-continued
| | | | | |
|---|---|---|---|---|
| YA0621 | CH3— | 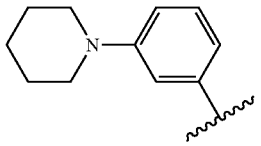 | H | CH3 |
| YA0622 | CH3— | 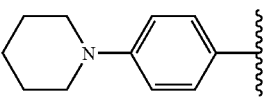 | H | CH3 |
| YA0623 | CH3— | 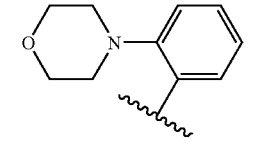 | H | CH3 |
| YA0624 | CH3— | 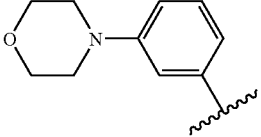 | H | CH3 |
| YA0625 | CH3— | 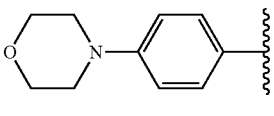 | H | CH3 |
| YA0626 | CH3— | 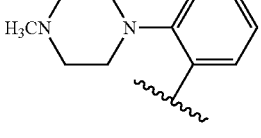 | H | CH3 |
| YA0627 | CH3— | 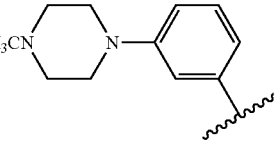 | H | CH3 |
| YA0628 | CH3— | 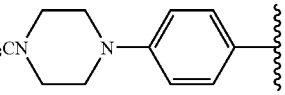 | H | CH3 |
| YA0629 | CH3— | 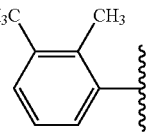 | H | CH3 |
| YA0630 | CH3— | 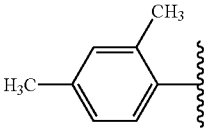 | H | CH3 |
| YA0631 | CH3— | 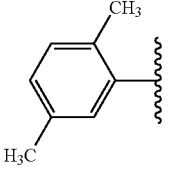 | H | CH3 |

-continued
| | | | | |
|---|---|---|---|---|
| YA0632 | CH3— | 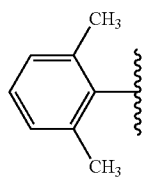 | H | CH3 |
| YA0633 | CH3— | 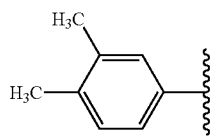 | H | CH3 |
| YA0634 | CH3— | 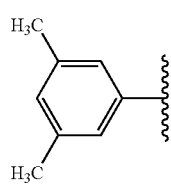 | H | CH3 |
| YA0635 | CH3— | 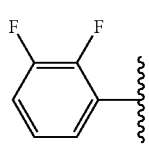 | H | CH3 |
| YA0636 | CH3— | 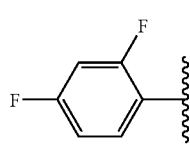 | H | CH3 |
| YA0637 | CH3— | 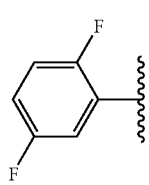 | H | CH3 |
| YA0638 | CH3— | 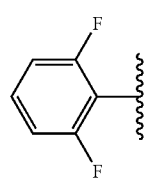 | H | CH3 |
| YA0639 | CH3— | 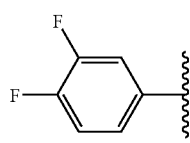 | H | CH3 |
| YA0640 | CH3— | 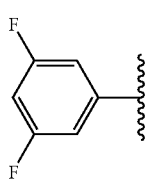 | H | CH3 |

-continued
| | | | | |
|---|---|---|---|---|
| YA0641 | CH3— | 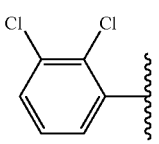 | H | CH3 |
| YA0642 | CH3— | 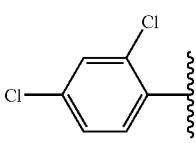 | H | CH3 |
| YA0643 | CH3— | 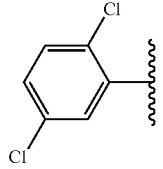 | H | CH3 |
| YA0644 | CH3— | 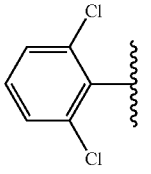 | H | CH3 |
| YA0645 | CH3— | 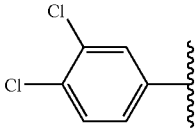 | H | CH3 |
| YA0646 | CH3— | 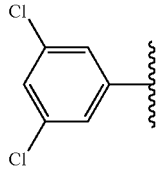 | H | CH3 |
| YA0647 | CH3— | 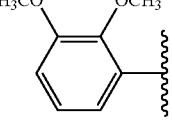 | H | CH3 |
| YA0648 | CH3— | 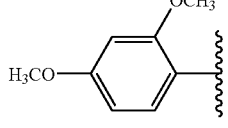 | H | CH3 |
| YA0649 | CH3— | 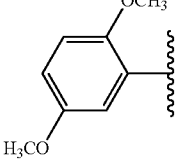 | H | CH3 |

-continued
| | | | | |
|---|---|---|---|---|
| YA0650 | CH3— | 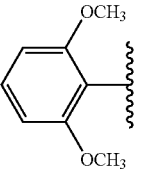 | H | CH3 |
| YA0651 | CH3— | 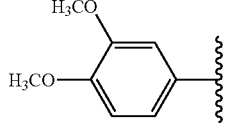 | H | CH3 |
| YA0652 | CH3— | 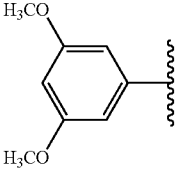 | H | CH3 |
| YA0653 | CH3— | 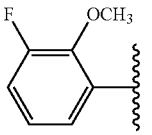 | H | CH3 |
| YA0654 | CH3— | 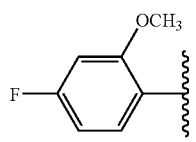 | H | CH3 |
| YA0655 | CH3— | 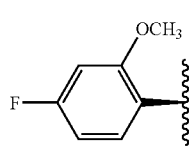 | H | CH3 |
| YA0656 | CH3— | 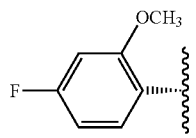 | H | CH3 |
| YA0657 | CH3— | 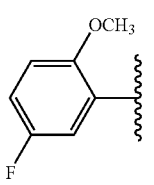 | H | CH3 |
| YA0658 | CH3— | 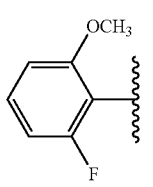 | H | CH3 |
| YA0659 | CH3— | 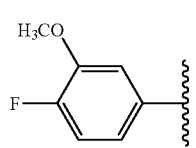 | H | CH3 |

-continued
| | | | | |
|---|---|---|---|---|
| YA0660 | CH3— | 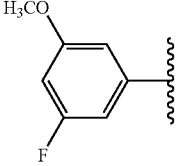 | H | CH3 |
| YA0661 | CH3— | 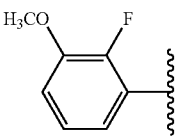 | H | CH3 |
| YA0662 | CH3— | 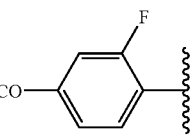 | H | CH3 |
| YA0663 | CH3— | 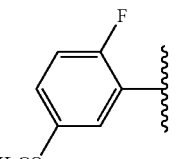 | H | CH3 |
| YA0664 | CH3— | 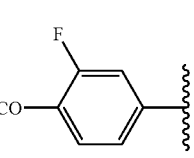 | H | CH3 |
| YA0665 | CH3— | 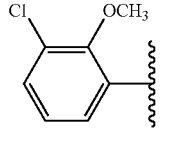 | H | CH3 |
| YA0666 | CH3— | 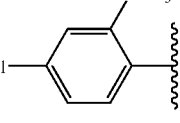 | H | CH3 |
| YA0667 | CH3— | 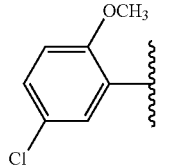 | H | CH3 |
| YA0668 | CH3— | 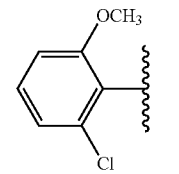 | H | CH3 |

-continued
| | | | | |
|---|---|---|---|---|
| YA0669 | CH3— | 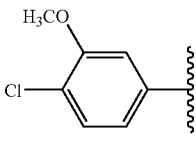 | H | CH3 |
| YA0670 | CH3— | 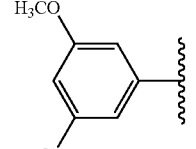 | H | CH3 |
| YA0671 | CH3— | 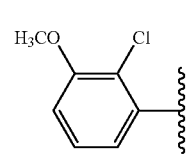 | H | CH3 |
| YA0672 | CH3— | 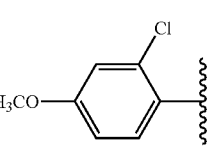 | H | CH3 |
| YA0673 | CH3— | 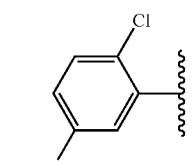 | H | CH3 |
| YA0674 | CH3— | 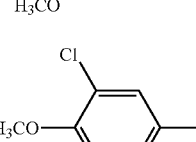 | H | CH3 |
| YA0675 | CH3— | 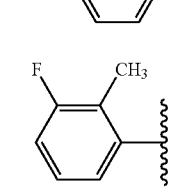 | H | CH3 |
| YA0676 | CH3— | 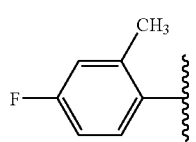 | H | CH3 |
| YA0677 | CH3— | 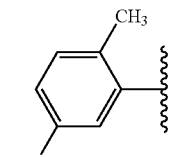 | H | CH3 |
| YA0678 | CH3— | 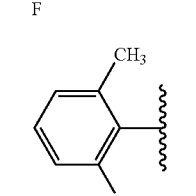 | H | CH3 |

| | | | | |
|---|---|---|---|---|
| YA0679 | CH3— | 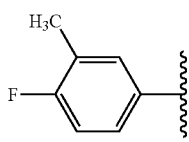 | H | CH3 |
| YA0680 | CH3— | 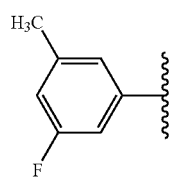 | H | CH3 |
| YA0681 | CH3— | 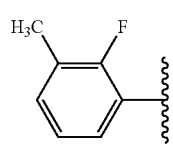 | H | CH3 |
| YA0682 | CH3— | 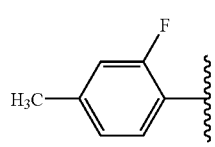 | H | CH3 |
| YA0683 | CH3— | 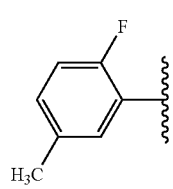 | H | CH3 |
| YA0684 | CH3— | 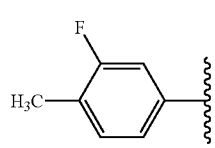 | H | CH3 |
| YA0685 | CH3— | 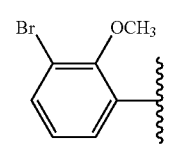 | H | CH3 |
| YA0686 | CH3— | 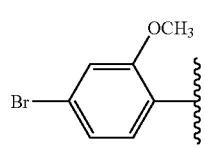 | H | CH3 |
| YA0687 | CH3— | 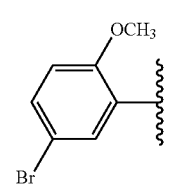 | H | CH3 |

-continued
| | | | | |
|---|---|---|---|---|
| YA0688 | CH3— | 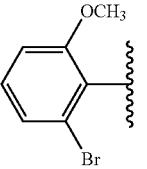 | H | CH3 |
| YA0689 | CH3— | 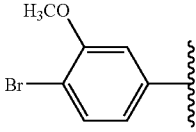 | H | CH3 |
| YA0690 | CH3— | 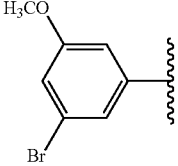 | H | CH3 |
| YA0691 | CH3— | 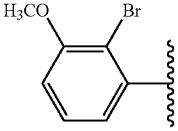 | H | CH3 |
| YA0692 | CH3— | 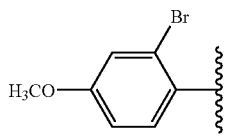 | H | CH3 |
| YA0693 | CH3— | 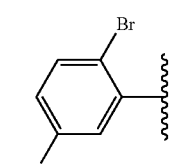 | H | CH3 |
| YA0694 | CH3— | 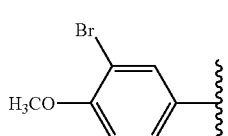 | H | CH3 |
| YA0695 | CH3— | 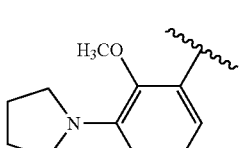 | H | CH3 |
| YA0696 | CH3— | 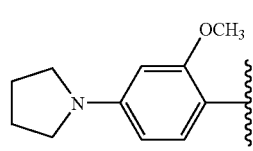 | H | CH3 |
| YA0697 | CH3— | 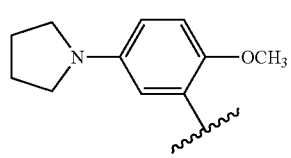 | H | CH3 |

-continued
| | | | | |
|---|---|---|---|---|
| YA0698 | CH3— | 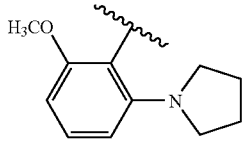 | H | CH3 |
| YA0699 | CH3— | 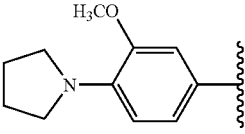 | H | CH3 |
| YA0700 | CH3— | 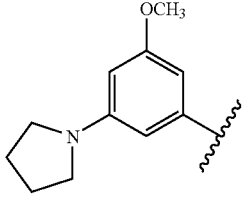 | H | CH3 |
| YA0701 | CH3— | 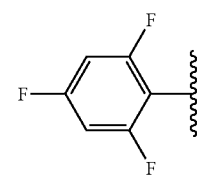 | H | CH3 |
| YA0702 | CH3— | 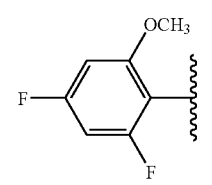 | H | CH3 |
| YA0703 | CH3— | 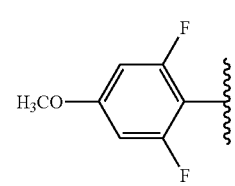 | H | CH3 |
| YA0704 | CH3— | 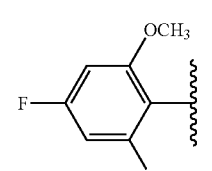 | H | CH3 |
| YA0705 | CH3— | 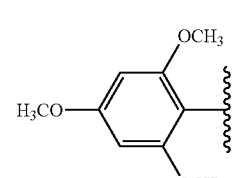 | H | CH3 |
| YA0706 | CH3— | 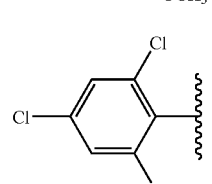 | H | CH3 |

-continued

| | | | | |
|---|---|---|---|---|
| YA0707 | CH3— | 2,5-dichloro-6-methoxyphenyl | H | CH3 |
| YA0708 | CH3— | 2,6-dichloro-4-methoxyphenyl | H | CH3 |
| YA0709 | CH3— | 4-chloro-2,6-dimethoxyphenyl | H | CH3 |
| YA0710 | CH3— | 2,4,6-trimethoxyphenyl | H | CH3 |
| YA0711 | CH3— | 2'-methoxy-[1,1'-biphenyl]-4-yl | H | CH3 |
| YA0712 | CH3— | 3'-methoxy-[1,1'-biphenyl]-4-yl | H | CH3 |
| YA0713 | CH3— | 4'-methoxy-[1,1'-biphenyl]-4-yl | H | CH3 |
| YA0714 | CH3— | 2'-methoxy-[1,1'-biphenyl]-3-yl | H | CH3 |
| YA0715 | CH3— | 3'-methoxy-[1,1'-biphenyl]-3-yl | H | CH3 |

-continued
| | | | | |
|---|---|---|---|---|
| YA0716 | CH3— | 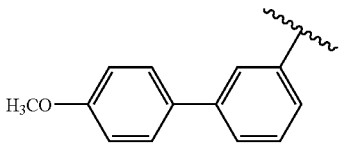 | H | CH3 |
| YA0717 | CH3— | 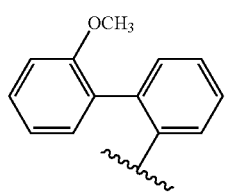 | H | CH3 |
| YA0718 | CH3— | 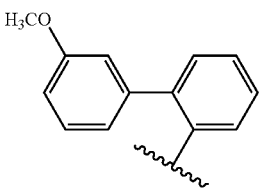 | H | CH3 |
| YA0719 | CH3— | 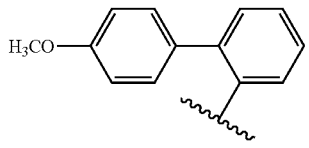 | H | CH3 |
| YA0720 | CH3— | 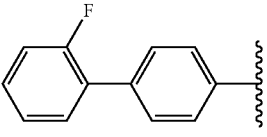 | H | CH3 |
| YA0721 | CH3— | 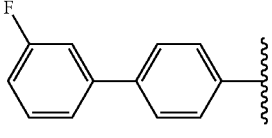 | H | CH3 |
| YA0722 | CH3— | 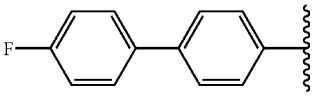 | H | CH3 |
| YA0723 | CH3— | 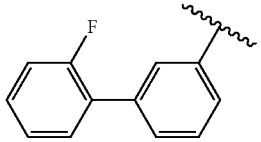 | H | CH3 |
| YA0724 | CH3— | 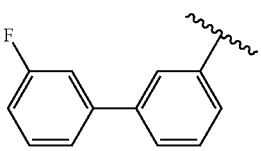 | H | CH3 |
| YA0725 | CH3— | 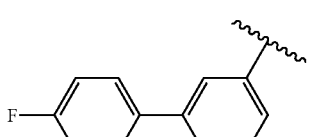 | H | CH3 |

-continued
| | | | | |
|---|---|---|---|---|
| YA0726 | CH3— | 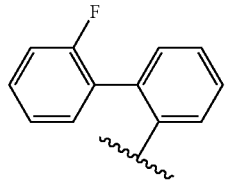 | H | CH3 |
| YA0727 | CH3— | 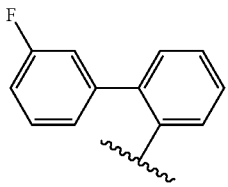 | H | CH3 |
| YA0728 | CH3— | 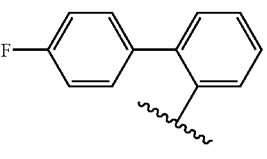 | H | CH3 |
| YA0729 | CH3— | 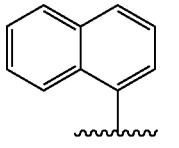 | H | CH3 |
| YA0730 | CH3— | 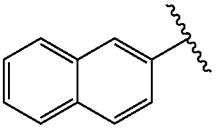 | H | CH3 |
| YA0731 | CH3— | CH3— | H | 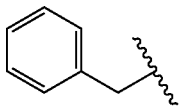 |
| YA0732 | CH3— | CH3CH2— | H | 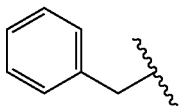 |
| YA0733 | CH3— | 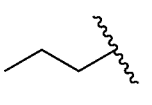 | H | 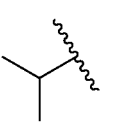 |
| YA0734 | CH3— | 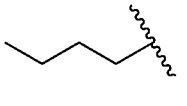 | H | 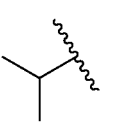 |
| YA0735 | CH3— | 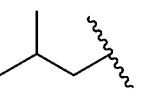 | H | 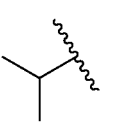 |
| YA0736 | CH3— | 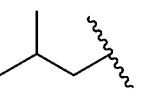 | H | 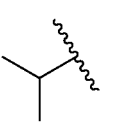 |

-continued

| | | | | |
|---|---|---|---|---|
| YA0737 | CH3— | sec-butyl | H | benzyl |
| YA0738 | CH3— | tert-butyl | H | benzyl |
| YA0739 | CH3— | n-hexyl | H | benzyl |
| YA0740 | CH3— | isopentyl | H | benzyl |
| YA0741 | CH3— | neopentyl | H | benzyl |
| YA0742 | CH3— | 2,2-dimethylbutyl | H | benzyl |
| YA0743 | CH3— | n-heptyl | H | benzyl |
| YA0744 | CH3— | 5-methylhexyl | H | benzyl |
| YA0745 | CH3— | n-octyl | H | benzyl |
| YA0746 | CH3— | 6-methylheptyl | H | benzyl |
| YA0747 | CH3— | n-nonyl | H | benzyl |
| YA0748 | CH3— | 7-methyloctyl | H | benzyl |
| YA0749 | CH3— | benzyl | H | benzyl |

-continued
| | | | | |
|---|---|---|---|---|
| YA0750 | CH3— | 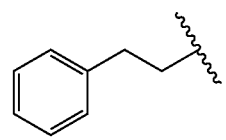 | H | 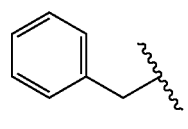 |
| YA0751 | CH3— | 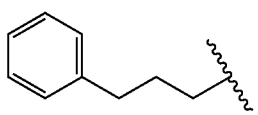 | H | 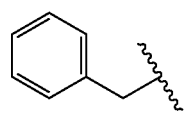 |
| YA0752 | CH3— |  | H | 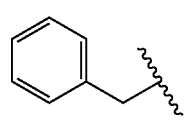 |
| YA0753 | CH3— | 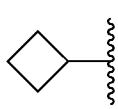 | H | 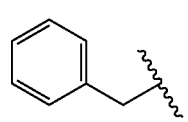 |
| YA0754 | CH3— | 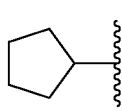 | H | 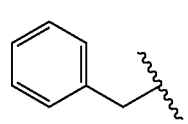 |
| YA0755 | CH3— | 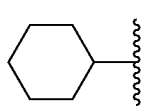 | H | 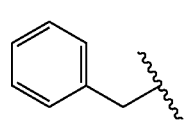 |
| YA0756 | CH3— | 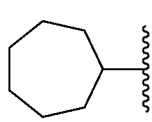 | H | 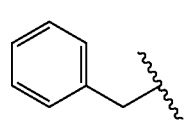 |
| YA0757 | CH3— | 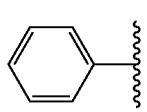 | H | 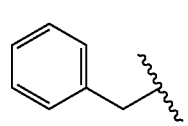 |
| YA0758 | CH3— | 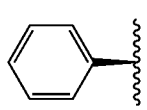 | H | 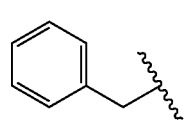 |
| YA0759 | CH3— | 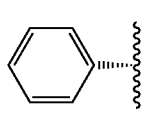 | H | 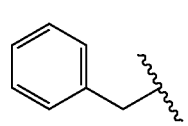 |
| YA0760 | CH3— | 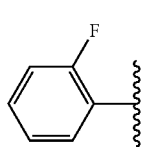 | H | 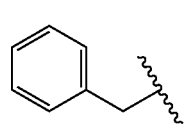 |
| YA0761 | CH3— | 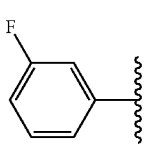 | H | 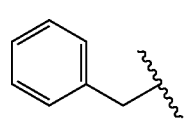 |

-continued
| | | | | |
|---|---|---|---|---|
| YA0762 | CH3— | 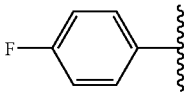 | H | 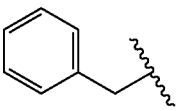 |
| YA0763 | CH3— | 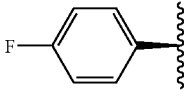 | H | 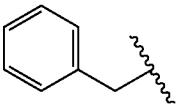 |
| YA0764 | CH3— | 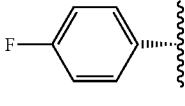 | H | 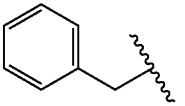 |
| YA0765 | CH3— | 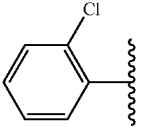 | H | 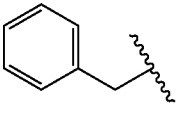 |
| YA0766 | CH3— | 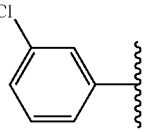 | H | 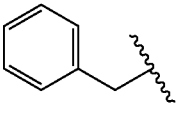 |
| YA0767 | CH3— | 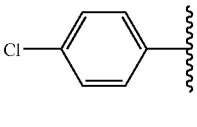 | H | 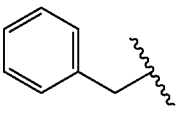 |
| YA0768 | CH3— | 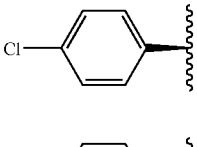 | H | 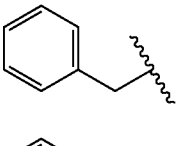 |
| YA0769 | CH3— | 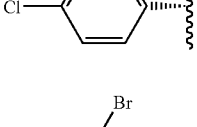 | H | 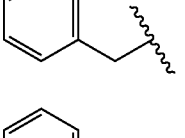 |
| YA0770 | CH3— | 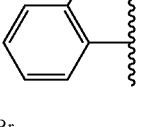 | H | 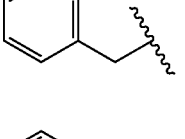 |
| YA0771 | CH3— | 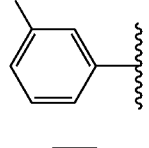 | H | 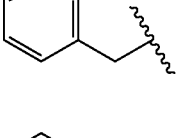 |
| YA0772 | CH3— | 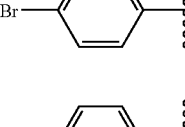 | H | 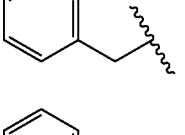 |
| YA0773 | CH3— | 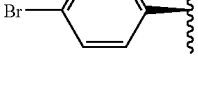 | H | 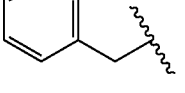 |

-continued
| | | | | |
|---|---|---|---|---|
| YA0774 | CH3— | 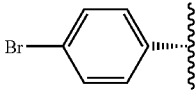 | H | 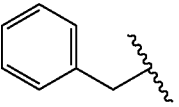 |
| YA0775 | CH3— | 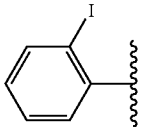 | H | 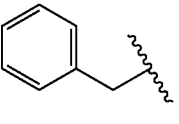 |
| YA0776 | CH3— | 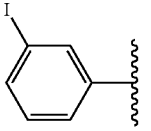 | H | 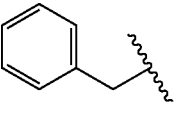 |
| YA0777 | CH3— | 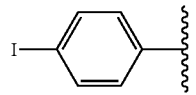 | H | 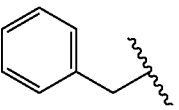 |
| YA0778 | CH3— | 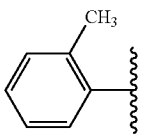 | H | 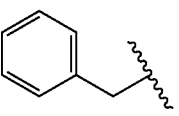 |
| YA0779 | CH3— | 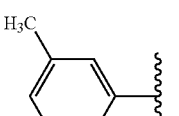 | H | 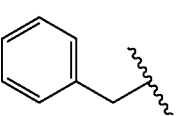 |
| YA0780 | CH3— | 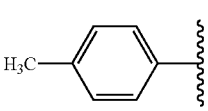 | H | 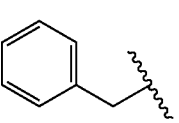 |
| YA0781 | CH3— | 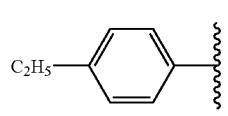 | H | 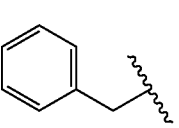 |
| YA0782 | CH3— | 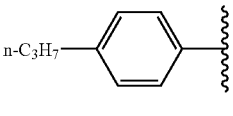 | H | 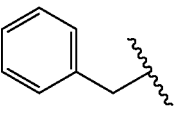 |
| YA0783 | CH3— | 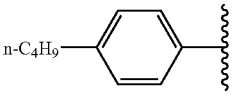 | H | 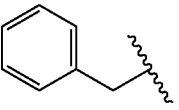 |
| YA0784 | CH3— | 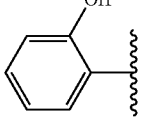 | H | 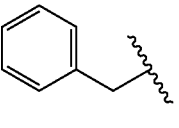 |
| YA0785 | CH3— | 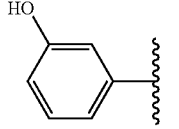 | H | 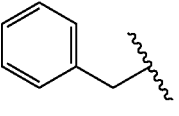 |

-continued
| | | | | |
|---|---|---|---|---|
| YA0786 | CH3— | 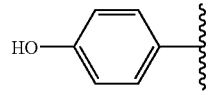 | H | 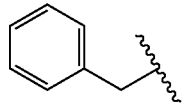 |
| YA0787 | CH3— | 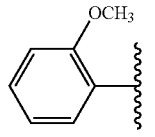 | H | 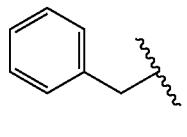 |
| YA0788 | CH3— | 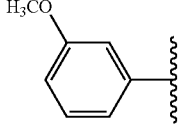 | H | 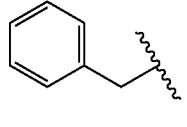 |
| YA0789 | CH3— | 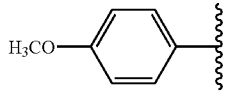 | H | 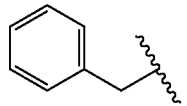 |
| YA0790 | CH3— | 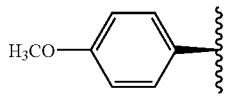 | H | 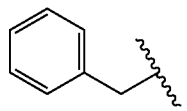 |
| YA0791 | CH3— | 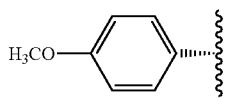 | H | 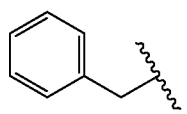 |
| YA0792 | CH3— | 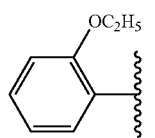 | H | 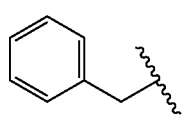 |
| YA0793 | CH3— | 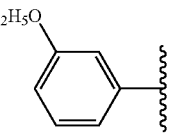 | H | 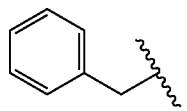 |
| YA0794 | CH3— | 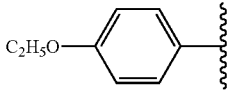 | H | 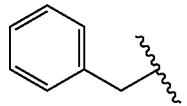 |
| YA0795 | CH3— | 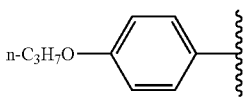 | H | 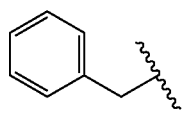 |
| YA0796 | CH3— | 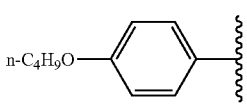 | H | 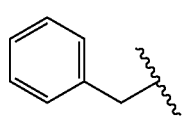 |
| YA0797 | CH3— | 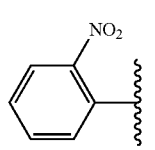 | H | 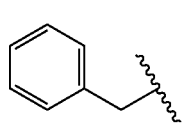 |

| | | | | |
|---|---|---|---|---|
| | | -continued | | |
| YA0798 | CH3— | 3-O₂N-C₆H₄— | H | benzyl |
| YA0799 | CH3— | 4-O₂N-C₆H₄— | H | benzyl |
| YA0800 | CH3— | 2-NC-C₆H₄— | H | benzyl |
| YA0801 | CH3— | 3-NC-C₆H₄— | H | benzyl |
| YA0802 | CH3— | 4-NC-C₆H₄— | H | benzyl |
| YA0803 | CH3— | 2-CF₃-C₆H₄— | H | benzyl |
| YA0804 | CH3— | 3-CF₃-C₆H₄— | H | benzyl |
| YA0805 | CH3— | 4-CF₃-C₆H₄— | H | benzyl |
| YA0806 | CH3— | 2-HOOC-C₆H₄— | H | benzyl |
| YA0807 | CH3— | 3-HOOC-C₆H₄— | H | benzyl |
| YA0808 | CH3— | 4-HOOC-C₆H₄— | H | benzyl |

-continued
| | | | | |
|---|---|---|---|---|
| YA0809 | CH3— | 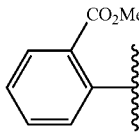 | H | 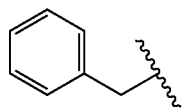 |
| YA0810 | CH3— | 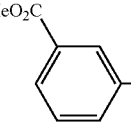 | H | 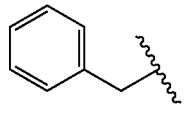 |
| YA0811 | CH3— | 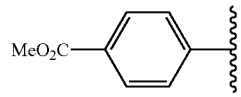 | H | 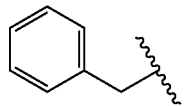 |
| YA0812 | CH3— | 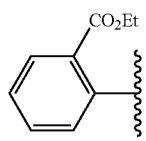 | H | 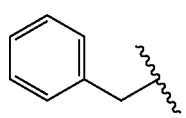 |
| YA0813 | CH3— | 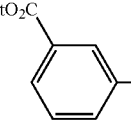 | H | 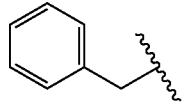 |
| YA0814 | CH3— | 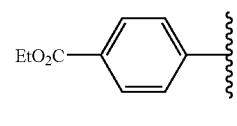 | H | 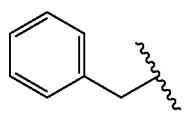 |
| YA0815 | CH3— | 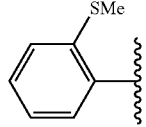 | H | 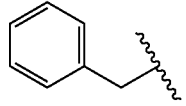 |
| YA0816 | CH3— | 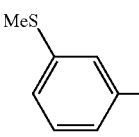 | H | 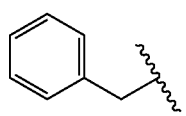 |
| YA0817 | CH3— | 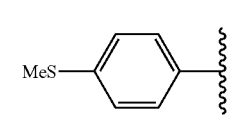 | H | 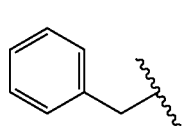 |
| YA0818 | CH3— | 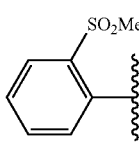 | H | 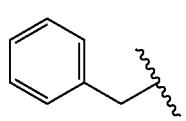 |
| YA0819 | CH3— | 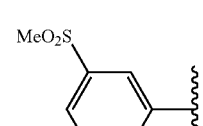 | H | 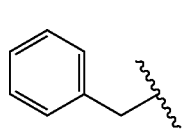 |

-continued
| | | | | |
|---|---|---|---|---|
| YA0820 | CH3— | 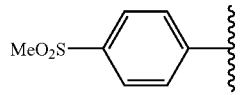 | H | 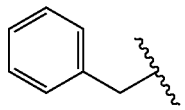 |
| YA0821 | CH3— | 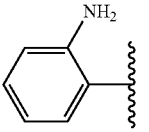 | H | 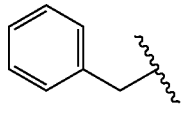 |
| YA0822 | CH3— | 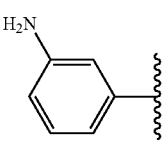 | H | 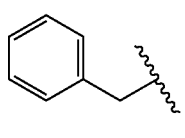 |
| YA0823 | CH3— | 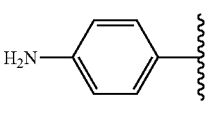 | H | 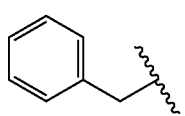 |
| YA0824 | CH3— | 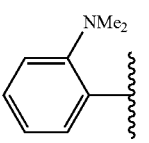 | H | 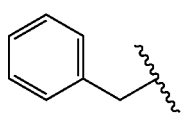 |
| YA0825 | CH3— | 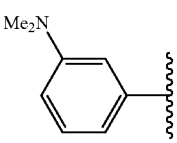 | H | 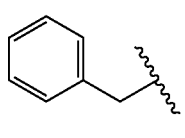 |
| YA0826 | CH3— | 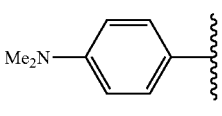 | H | 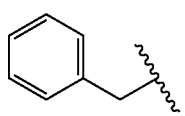 |
| YA0827 | CH3— | 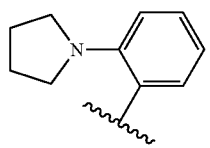 | H | 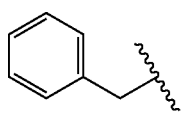 |
| YA0828 | CH3— | 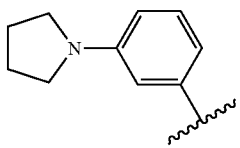 | H | 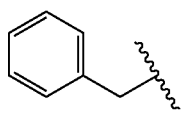 |
| YA0829 | CH3— | 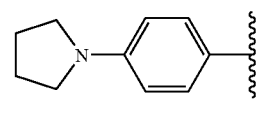 | H | 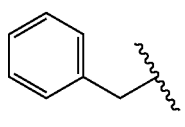 |
| YA0830 | CH3— | 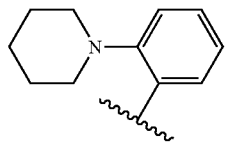 | H | 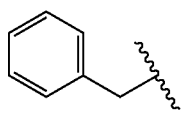 |

-continued
| | | | | |
|---|---|---|---|---|
| YA0831 | CH3— | 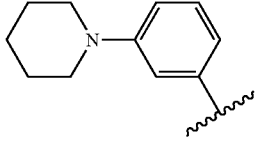 | H | 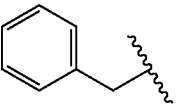 |
| YA0832 | CH3— | 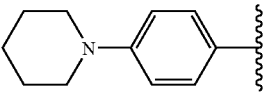 | H | 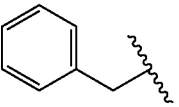 |
| YA0833 | CH3— | 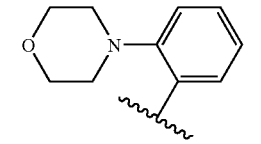 | H | 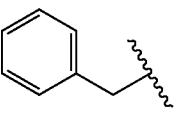 |
| YA0834 | CH3— | 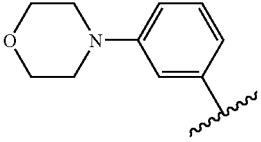 | H | 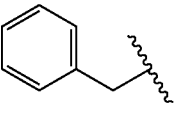 |
| YA0835 | CH3— | 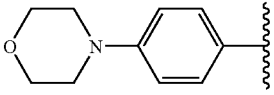 | H | 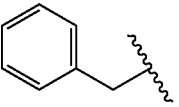 |
| YA0836 | CH3— | 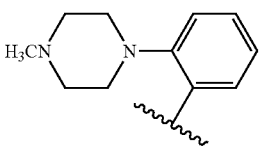 | H | 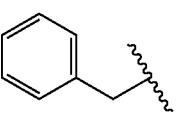 |
| YA0837 | CH3— | 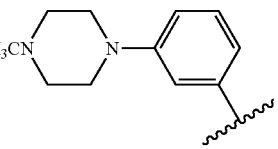 | H | 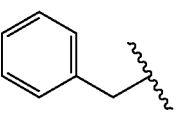 |
| YA0838 | CH3— | 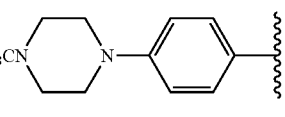 | H | 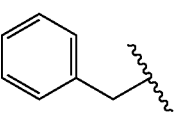 |
| YA0839 | CH3— | 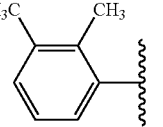 | H | 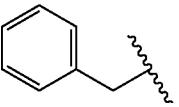 |
| YA0840 | CH3— | 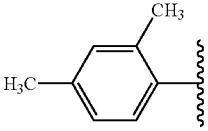 | H | 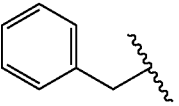 |

-continued
| | | | | |
|---|---|---|---|---|
| YA0841 | CH3— | 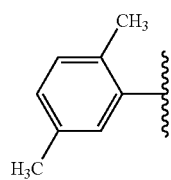 | H | 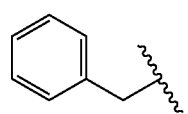 |
| YA0842 | CH3— | 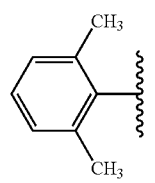 | H | 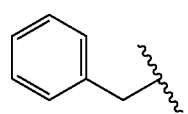 |
| YA0843 | CH3— | 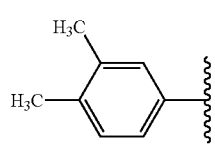 | H | 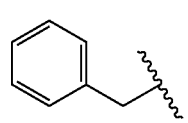 |
| YA0844 | CH3— | 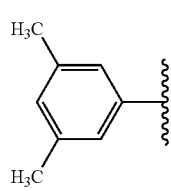 | H | 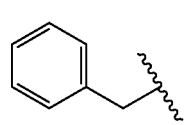 |
| YA0845 | CH3— | 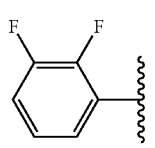 | H | 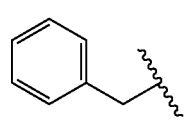 |
| YA0846 | CH3— | 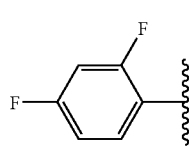 | H | 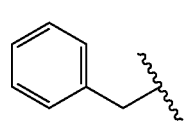 |
| YA0847 | CH3— | 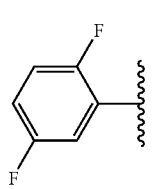 | H | 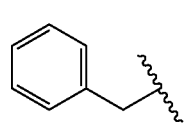 |
| YA0848 | CH3— | 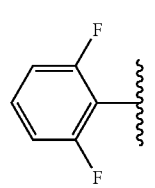 | H | 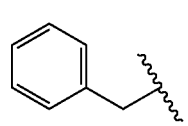 |
| YA0849 | CH3— | 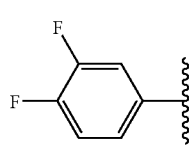 | H | 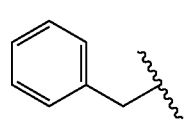 |

-continued
| | | | | |
|---|---|---|---|---|
| YA0850 | CH3— | 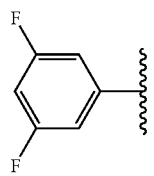 | H | 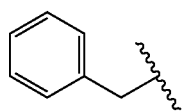 |
| YA0851 | CH3— | 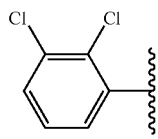 | H | 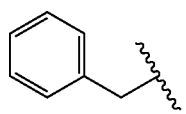 |
| YA0852 | CH3— | 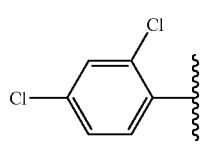 | H | 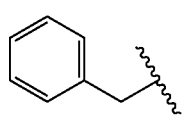 |
| YA0853 | CH3— | 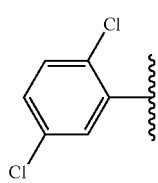 | H | 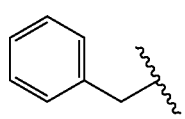 |
| YA0854 | CH3— | 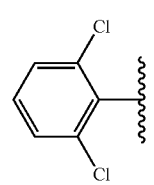 | H | 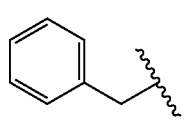 |
| YA0855 | CH3— | 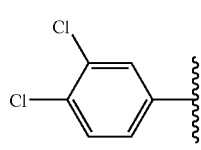 | H | 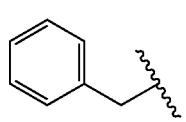 |
| | | | | |
|---|---|---|---|---|
| YA0856 | CH3— | 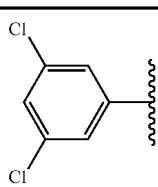 | H | 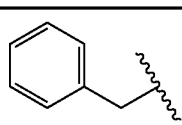 |
| YA0857 | CH3— | 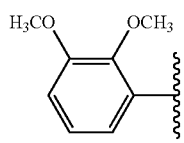 | H | 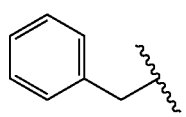 |
| YA0858 | CH3— | 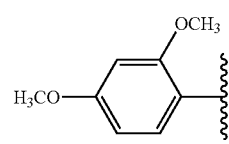 | H | 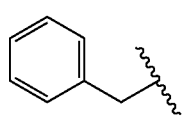 |

-continued
| | | | | |
|---|---|---|---|---|
| YA0859 | CH3— | 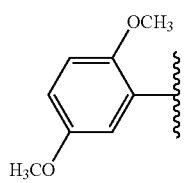 | H | 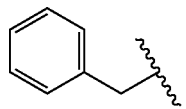 |
| YA0860 | CH3— | 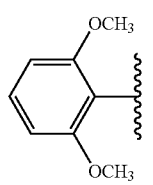 | H | 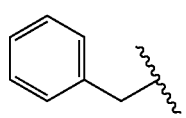 |
| YA0861 | CH3— | 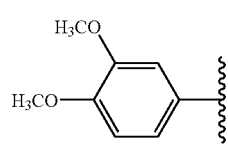 | H | 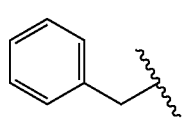 |
| YA0862 | CH3— | 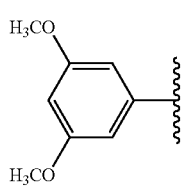 | H | 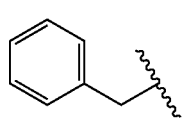 |
| YA0863 | CH3— | 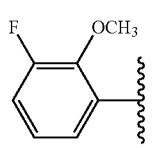 | H | 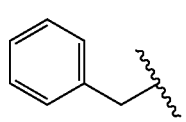 |
| YA0864 | CH3— | 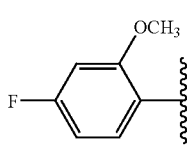 | H | 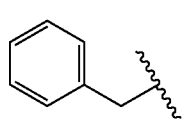 |
| YA0865 | CH3— | 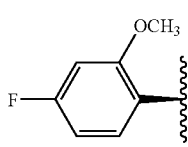 | H | 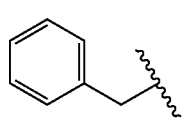 |
| YA0866 | CH3— | 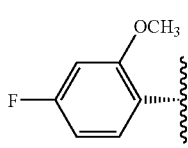 | H | 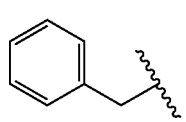 |
| YA0867 | CH3— | 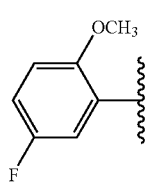 | H | 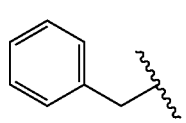 |

-continued
| | | | | |
|---|---|---|---|---|
| YA0868 | CH3— | 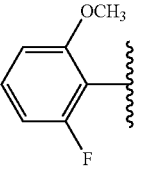 | H | 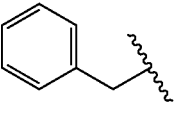 |
| YA0869 | CH3— | 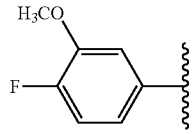 | H | 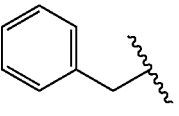 |
| YA0870 | CH3— | 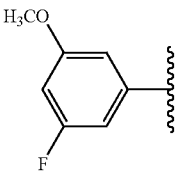 | H | 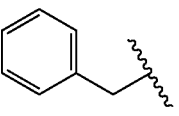 |
| YA0871 | CH3— | 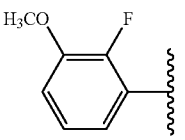 | H | 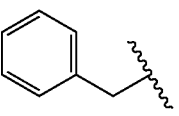 |
| YA0872 | CH3— | 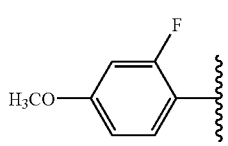 | H | 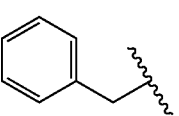 |
| YA0873 | CH3— | 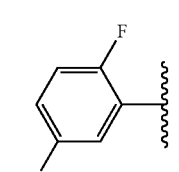 | H | 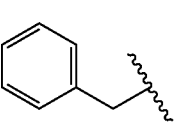 |
| YA0874 | CH3— | 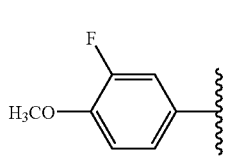 | H | 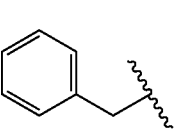 |
| YA0875 | CH3— | 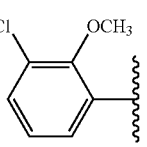 | H | 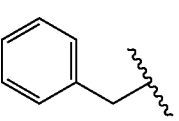 |
| YA0876 | CH3— | 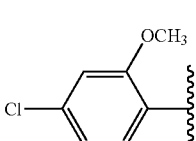 | H | 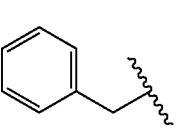 |
| YA0877 | CH3— | 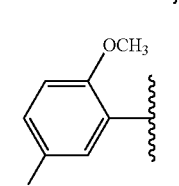 | H | 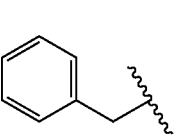 |

| | | | | |
|---|---|---|---|---|
| YA0878 | CH3— | 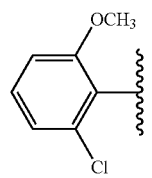 | H | 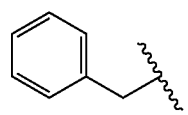 |
| YA0879 | CH3— | 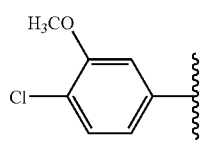 | H | 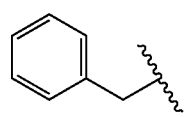 |
| YA0880 | CH3— | 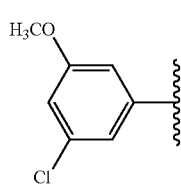 | H | 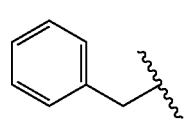 |
| YA0881 | CH3— | 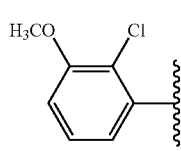 | H | 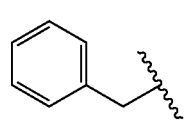 |
| YA0882 | CH3— | 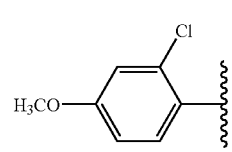 | H | 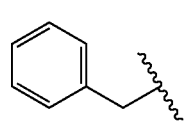 |
| YA0883 | CH3— | 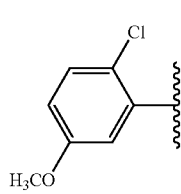 | H | 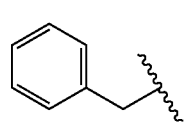 |
| YA0884 | CH3— | 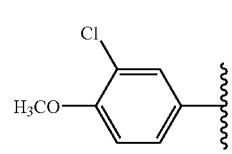 | H | 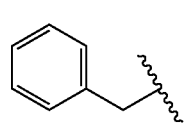 |
| YA0885 | CH3— | 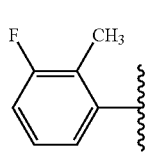 | H | 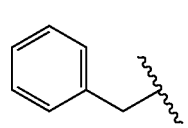 |
| YA0886 | CH3— | 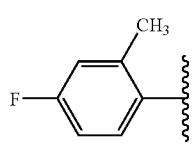 | H | 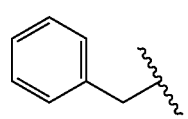 |

-continued
| | | | | |
|---|---|---|---|---|
| YA0887 | CH3— | 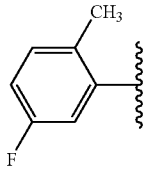 | H | 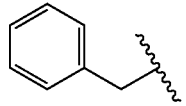 |
| YA0888 | CH3— | 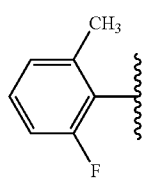 | H | 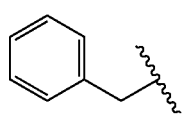 |
| YA0889 | CH3— | 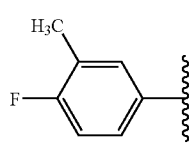 | H | 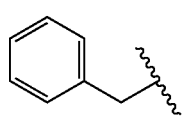 |
| YA0890 | CH3— | 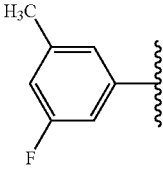 | H | 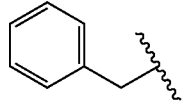 |
| YA0891 | CH3— | 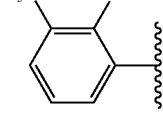 | H | 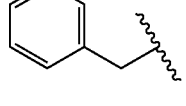 |
| YA0892 | CH3— |  | H | 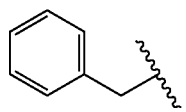 |
| YA0893 | CH3— | 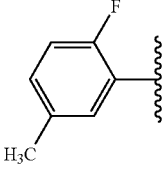 | H | 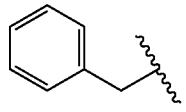 |
| YA0894 | CH3— | 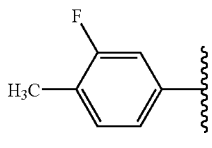 | H | 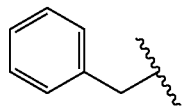 |
| YA0895 | CH3— | 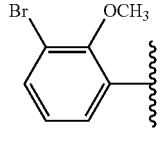 | H | 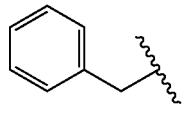 |
| YA0896 | CH3— | 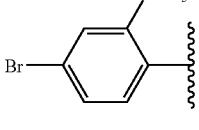 | H | 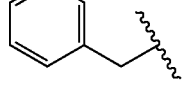 |

-continued
| | | | | |
|---|---|---|---|---|
| YA0897 | CH3— | 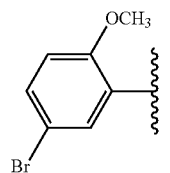 | H | 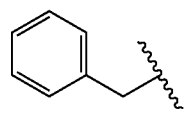 |
| YA0898 | CH3— | 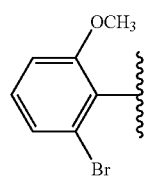 | H | 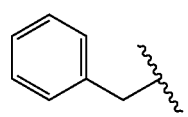 |
| YA0899 | CH3— | 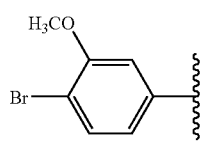 | H | 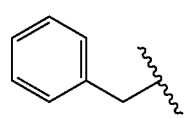 |
| YA0900 | CH3— | 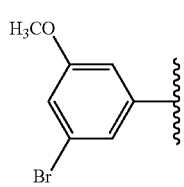 | H | 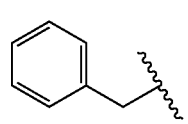 |
| YA0901 | CH3— | 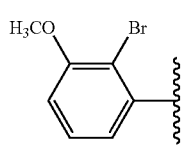 | H | 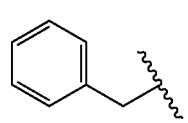 |
| YA0902 | CH3— | 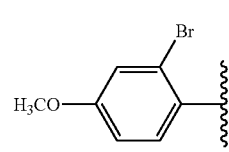 | H | 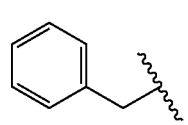 |
| YA0903 | CH3— | 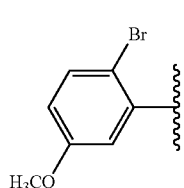 | H | 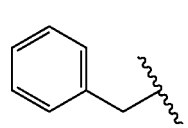 |
| YA0904 | CH3— | 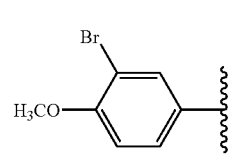 | H | 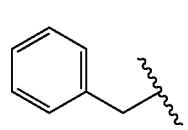 |
| YA0905 | CH3— | 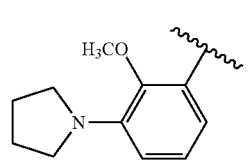 | H | 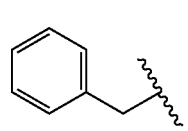 |

-continued
| | | | | |
|---|---|---|---|---|
| YA0906 | CH3— | 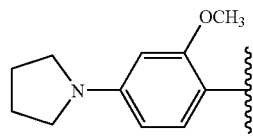 | H | 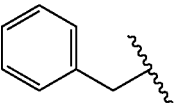 |
| YA0907 | CH3— | 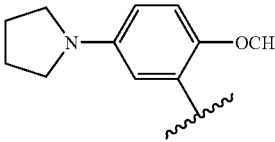 | H | 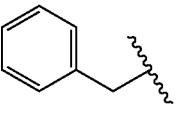 |
| YA0908 | CH3— | 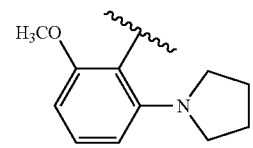 | H | 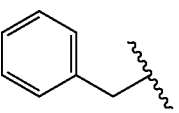 |
| YA0909 | CH3— | 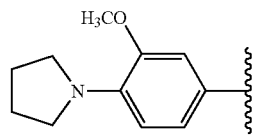 | H | 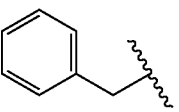 |
| YA0910 | CH3— | 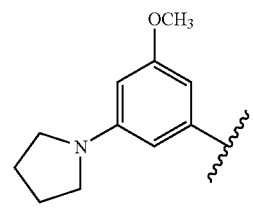 | H | 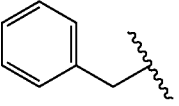 |
| YA0911 | CH3— | 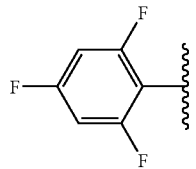 | H | 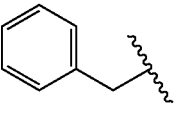 |
| YA0912 | CH3— | 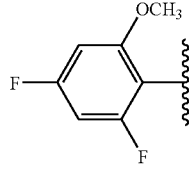 | H | 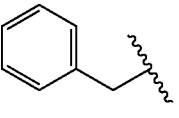 |
| YA0913 | CH3— | 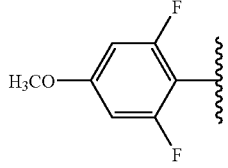 | H | 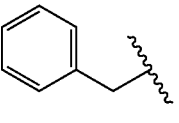 |
| YA0914 | CH3— | 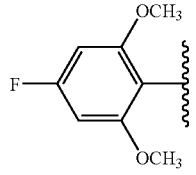 | H | 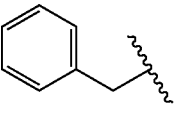 |

-continued
| | | | | |
|---|---|---|---|---|
| YA0915 | CH3— | 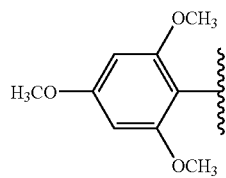 | H | 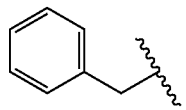 |
| YA0916 | CH3— | 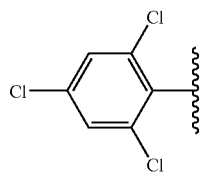 | H | 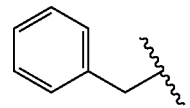 |
| YA0917 | CH3— | 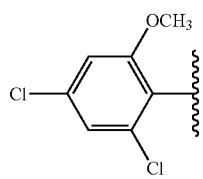 | H | 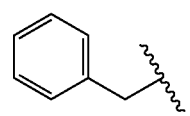 |
| YA0918 | CH3— | 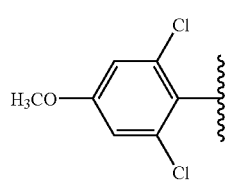 | H | 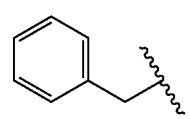 |
| YA0919 | CH3— | 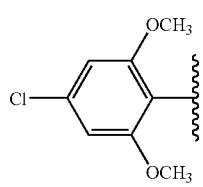 | H | 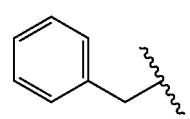 |
| YA0920 | CH3— | 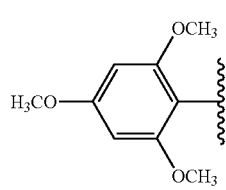 | H | 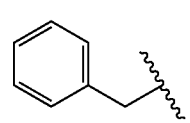 |
| YA0921 | CH3— | 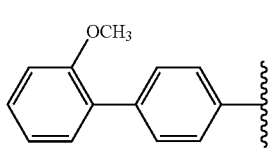 | H | 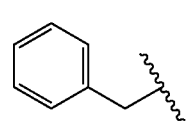 |
| YA0922 | CH3— | 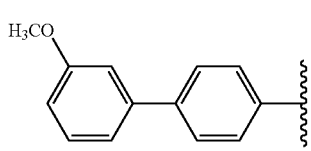 | H | 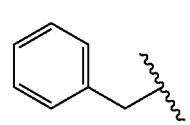 |
| YA0923 | CH3— | 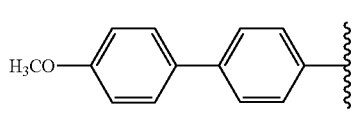 | H | 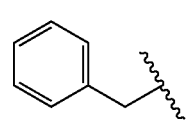 |

-continued

| | | | | |
|---|---|---|---|---|
| YA0924 | CH3— | 2'-methoxy-biphenyl-3-yl | H | benzyl |
| YA0925 | CH3— | 3'-methoxy-biphenyl-3-yl | H | benzyl |
| YA0926 | CH3— | 4'-methoxy-biphenyl-3-yl | H | benzyl |
| YA0927 | CH3— | 2'-methoxy-biphenyl-2-yl | H | benzyl |
| YA0928 | CH3— | 3'-methoxy-biphenyl-2-yl | H | benzyl |
| YA0929 | CH3— | 4'-methoxy-biphenyl-2-yl | H | benzyl |
| YA0930 | CH3— | 2'-fluoro-biphenyl-4-yl | H | benzyl |
| YA0931 | CH3— | 3'-fluoro-biphenyl-4-yl | H | benzyl |
| YA0932 | CH3— | 4'-fluoro-biphenyl-4-yl | H | benzyl |
| YA0933 | CH3— | 2'-fluoro-biphenyl-3-yl | H | benzyl |

-continued
| | | | | |
|---|---|---|---|---|
| YA0934 | CH3— | 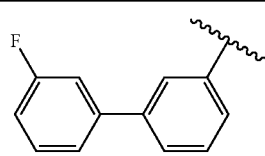 | H | 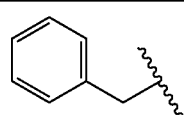 |
| YA0935 | CH3— | 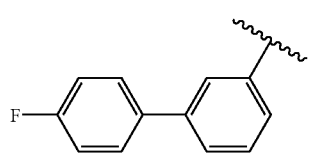 | H | 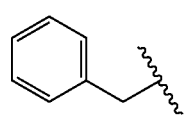 |
| YA0936 | CH3— | 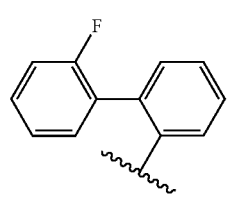 | H | 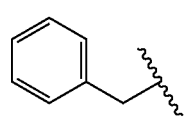 |
| YA0937 | CH3— | 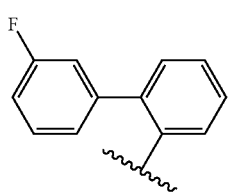 | H | 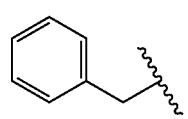 |
| YA0938 | CH3— | 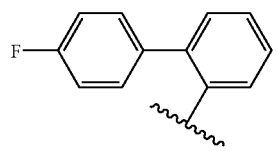 | H | 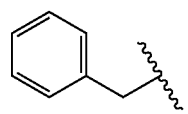 |
| YA0939 | CH3— | 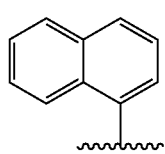 | H | 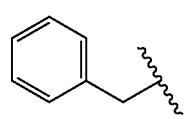 |
| YA0940 | CH3— | 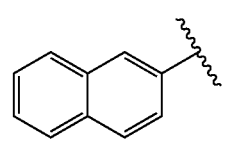 | H | 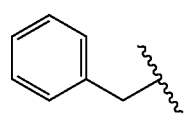 |
| YA0941 | CH3— | CH3— | H | 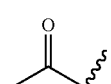 |
| YA0942 | CH3— | CH3CH2— | H | 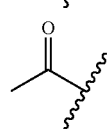 |
| YA0943 | CH3— | 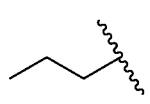 | H | 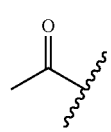 |

-continued
| | | | | |
|---|---|---|---|---|
| YA0944 | CH3— | 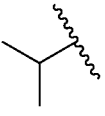 | H | 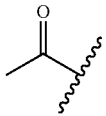 |
| YA0945 | CH3— | 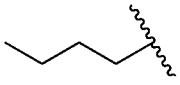 | H |  |
| YA0946 | CH3— | 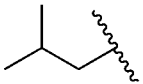 | H |  |
| YA0947 | CH3— | 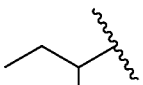 | H |  |
| YA0948 | CH3— |  | H |  |
| YA0949 | CH3— | 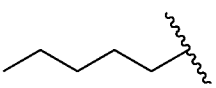 | H |  |
| YA0950 | CH3— | 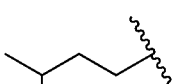 | H |  |
| YA0951 | CH3— | 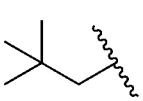 | H |  |
| YA0952 | CH3— | 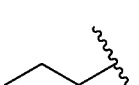 | H |  |
| YA0953 | CH3— | 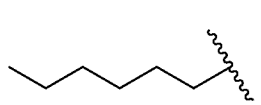 | H |  |
| YA0954 | CH3— | 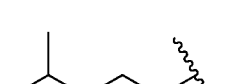 | H |  |
| YA0955 | CH3— | 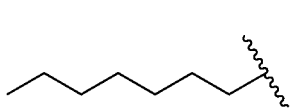 | H |  |

-continued
| | | | | |
|---|---|---|---|---|
| YA0956 | CH3— | 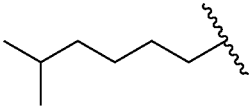 | H | 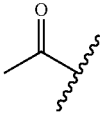 |
| YA0957 | CH3— | 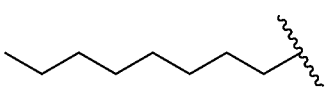 | H | 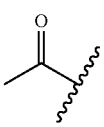 |
| YA0958 | CH3— | 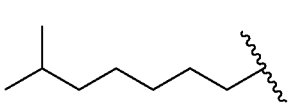 | H | 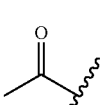 |
| YA0959 | CH3— | 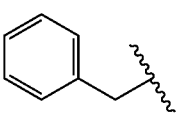 | H | 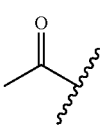 |
| YA0960 | CH3— | 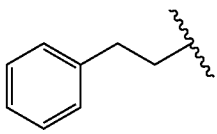 | H | 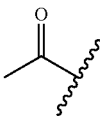 |
| YA0961 | CH3— | 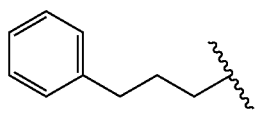 | H | 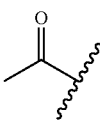 |
| YA0962 | CH3— | 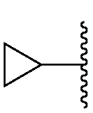 | H | 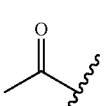 |
| YA0963 | CH3— | 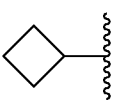 | H | 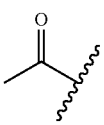 |
| YA0964 | CH3— | 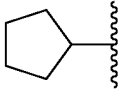 | H | 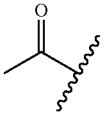 |
| YA0965 | CH3— | 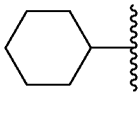 | H | 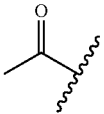 |
| YA0966 | CH3— | 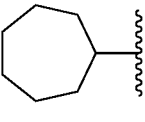 | H | 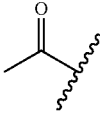 |
| YA0967 | CH3— | 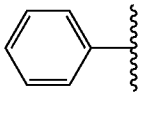 | H | 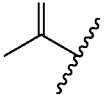 |

-continued
| | | | | |
|---|---|---|---|---|
| YA0968 | CH3— | 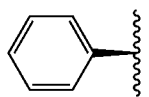 | H | 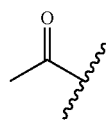 |
| YA0969 | CH3— | 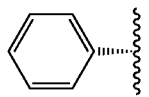 | H | 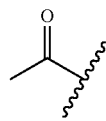 |
| YA0970 | CH3— | 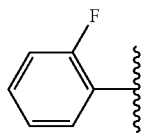 | H | 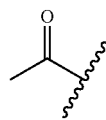 |
| YA0971 | CH3— | 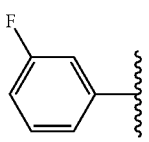 | H | 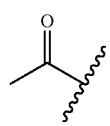 |
| YA0972 | CH3— | 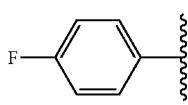 | H | 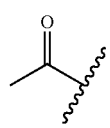 |
| YA0973 | CH3— | 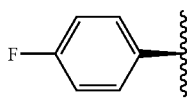 | H | 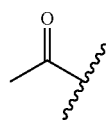 |
| YA0974 | CH3— | 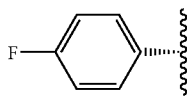 | H | 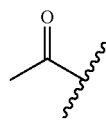 |
| YA0975 | CH3— | 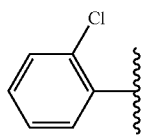 | H | 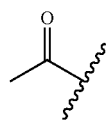 |
| YA0976 | CH3— | 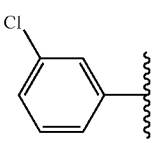 | H | 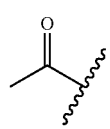 |
| YA0977 | CH3— | 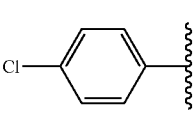 | H | 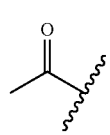 |
| YA0978 | CH3— | 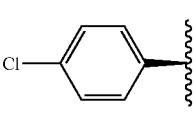 | H | 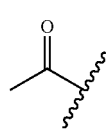 |

-continued
| | | | | |
|---|---|---|---|---|
| YA0979 | CH3— | 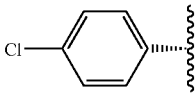 | H | 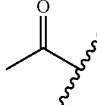 |
| YA0980 | CH3— | 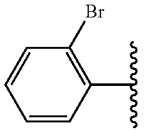 | H | 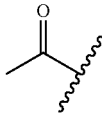 |
| YA0981 | CH3— | 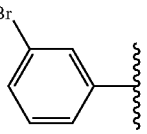 | H | 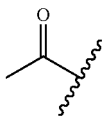 |
| YA0982 | CH3— | 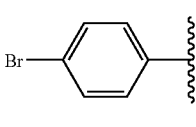 | H | 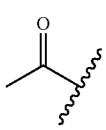 |
| YA0983 | CH3— | 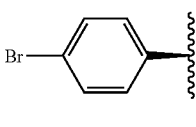 | H | 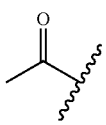 |
| YA0984 | CH3— | 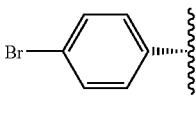 | H | 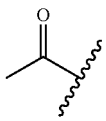 |
| YA0985 | CH3— | 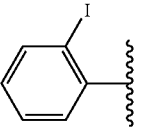 | H | 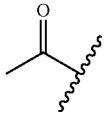 |
| YA0986 | CH3— | 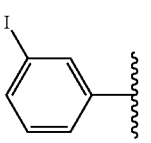 | H | 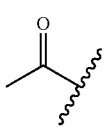 |
| YA0987 | CH3— | 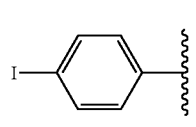 | H | 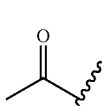 |
| YA0988 | CH3— | 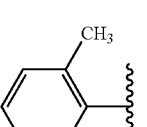 | H | 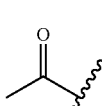 |
| YA0989 | CH3— | 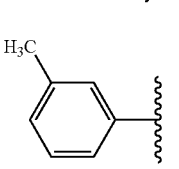 | H | 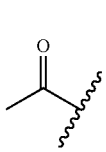 |

-continued

| | | | | |
|---|---|---|---|---|
| YA0990 | CH3— | 4-CH3-C6H4- | H | -C(O)CH3 |
| YA0991 | CH3— | 4-C2H5-C6H4- | H | -C(O)CH3 |
| YA0992 | CH3— | 4-n-C3H7-C6H4- | H | -C(O)CH3 |
| YA0993 | CH3— | 4-n-C4H9-C6H4- | H | -C(O)CH3 |
| YA0994 | CH3— | 2-OH-C6H4- | H | -C(O)CH3 |
| YA0995 | CH3— | 3-OH-C6H4- | H | -C(O)CH3 |
| YA0996 | CH3— | 4-OH-C6H4- | H | -C(O)CH3 |
| YA0997 | CH3— | 2-OCH3-C6H4- | H | -C(O)CH3 |
| YA0998 | CH3— | 3-OCH3-C6H4- | H | -C(O)CH3 |
| YA0999 | CH3— | 4-OCH3-C6H4- | H | -C(O)CH3 |
| YA1000 | CH3— | 4-OCH3-C6H4- (stereo) | H | -C(O)CH3 |

-continued
| | | | | |
|---|---|---|---|---|
| YA1001 | CH3— | 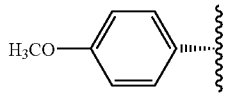 | H | 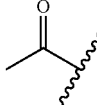 |
| YA1002 | CH3— | 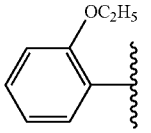 | H | 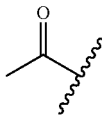 |
| YA1003 | CH3— | 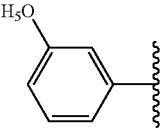 | H | 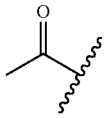 |
| YA1004 | CH3— | 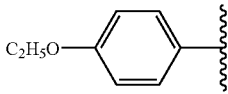 | H | 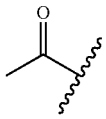 |
| YA1005 | CH3— | 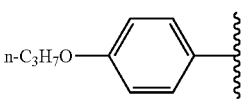 | H | 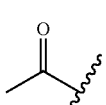 |
| YA1006 | CH3— | 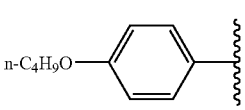 | H | 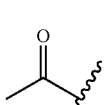 |
| YA1007 | CH3— | 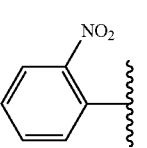 | H | 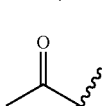 |
| YA1008 | CH3— | 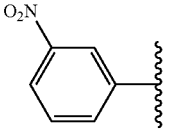 | H | 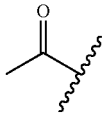 |
| YA1009 | CH3— | 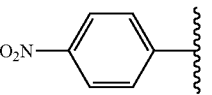 | H | 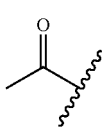 |
| YA1010 | CH3— | 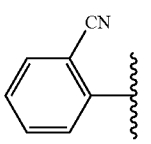 | H | 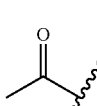 |
| YA1011 | CH3— | 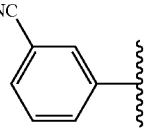 | H | 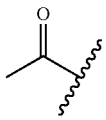 |

-continued
| | | | | |
|---|---|---|---|---|
| YA1012 | CH3— | 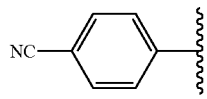 | H | 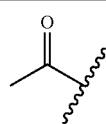 |
| YA1013 | CH3— | 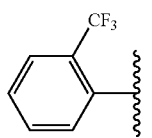 | H | 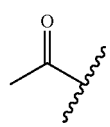 |
| YA1014 | CH3— | 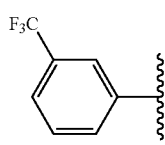 | H | 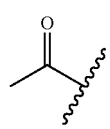 |
| YA1015 | CH3— | 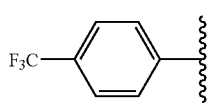 | H | 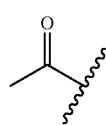 |
| YA1016 | CH3— | 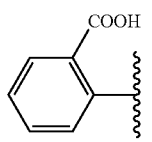 | H | 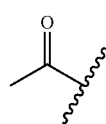 |
| YA1017 | CH3— | 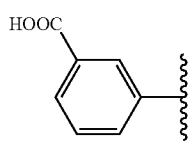 | H | 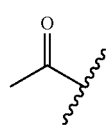 |
| YA1018 | CH3— | 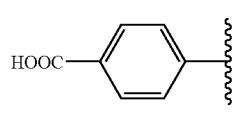 | H | 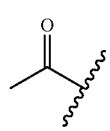 |
| YA1019 | CH3— | 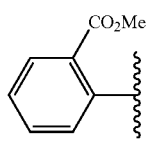 | H | 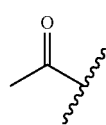 |
| YA1020 | CH3— | 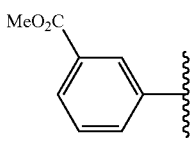 | H | 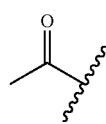 |
| YA1021 | CH3— | 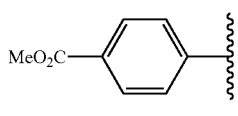 | H | 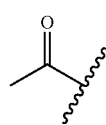 |
| YA1022 | CH3— | 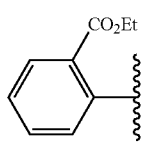 | H | 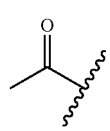 |

-continued
| | | | | |
|---|---|---|---|---|
| YA1023 | CH3— | 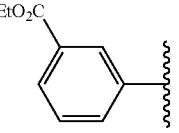 (3-EtO2C-C6H4-) | H | 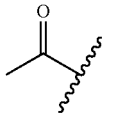 |
| YA1024 | CH3— | 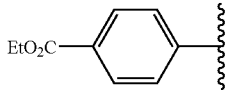 (4-EtO2C-C6H4-) | H | 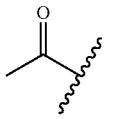 |
| YA1025 | CH3— | 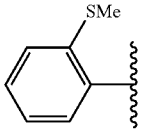 (2-SMe-C6H4-) | H | 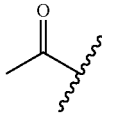 |
| YA1026 | CH3— | 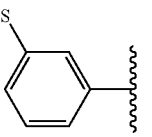 (3-MeS-C6H4-) | H | 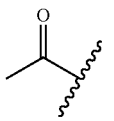 |
| YA1027 | CH3— | 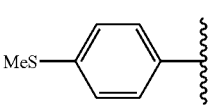 (4-MeS-C6H4-) | H | 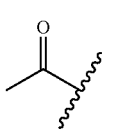 |
| YA1028 | CH3— | 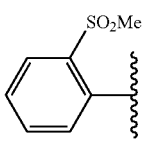 (2-SO2Me-C6H4-) | H | 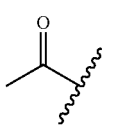 |
| YA1029 | CH3— | 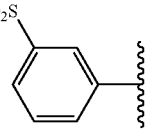 (3-MeO2S-C6H4-) | H | 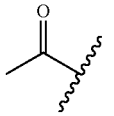 |
| YA1030 | CH3— | 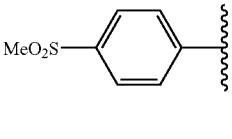 (4-MeO2S-C6H4-) | H | 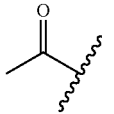 |
| YA1031 | CH3— | 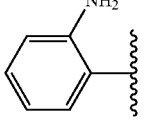 (2-NH2-C6H4-) | H | 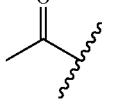 |
| YA1032 | CH3— | 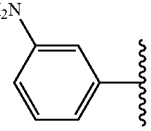 (3-H2N-C6H4-) | H | 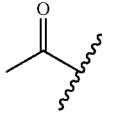 |
| YA1033 | CH3— | 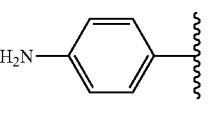 (4-H2N-C6H4-) | H | 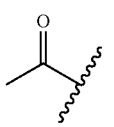 |

-continued
| | | | | |
|---|---|---|---|---|
| YA1034 | CH3— | 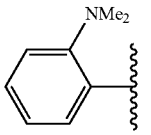 | H | 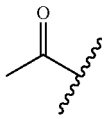 |
| YA1035 | CH3— | 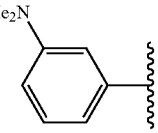 | H | 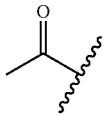 |
| YA1036 | CH3— | 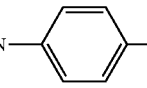 | H | 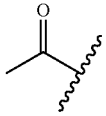 |
| YA1037 | CH3— | 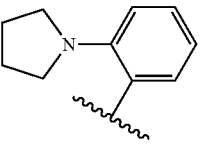 | H | 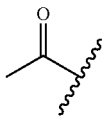 |
| YA1038 | CH3— | 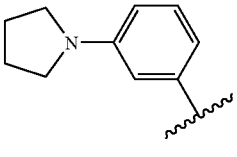 | H | 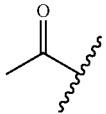 |
| YA1039 | CH3— | 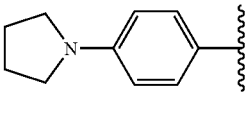 | H | 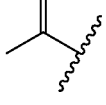 |
| YA1040 | CH3— | 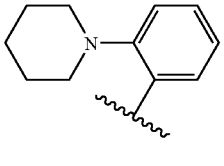 | H | 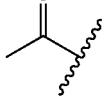 |
| YA1041 | CH3— | 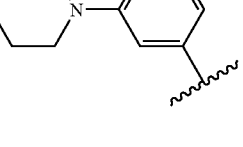 | H | 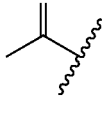 |
| YA1042 | CH3— | 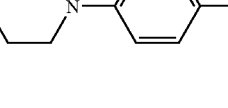 | H | 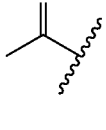 |
| YA1043 | CH3— | 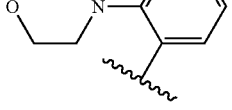 | H | 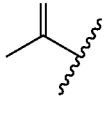 |

-continued
| | | | | |
|---|---|---|---|---|
| YA1044 | CH3— | 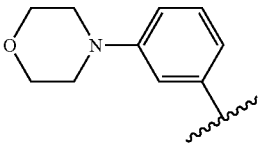 | H | 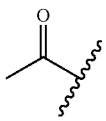 |
| YA1045 | CH3— | 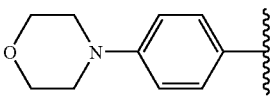 | H | 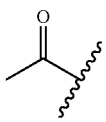 |
| YA1046 | CH3— | 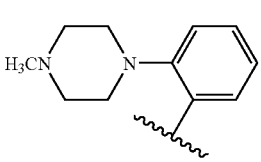 | H | 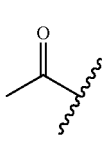 |
| YA1047 | CH3— | 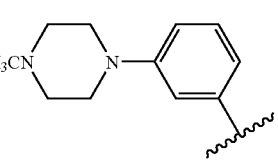 | H | 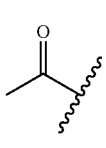 |
| YA1048 | CH3— | 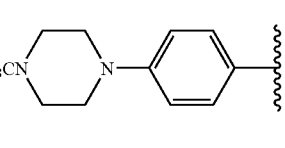 | H | 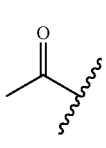 |
| YA1049 | CH3— | 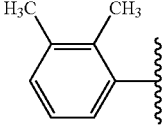 | H | 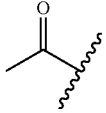 |
| YA1050 | CH3— | 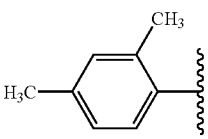 | H | 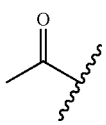 |
| YA1051 | CH3— | 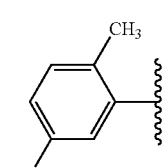 | H | 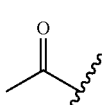 |
| YA1052 | CH3— | 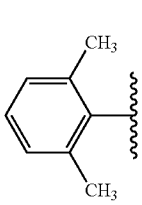 | H | 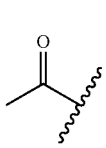 |
| YA1053 | CH3— | 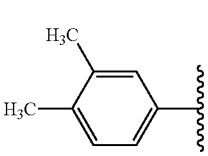 | H | 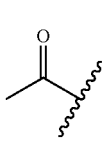 |

-continued

| | | | | |
|---|---|---|---|---|
| YA1054 | CH3— | 3,5-dimethylphenyl | H | C(=O)CH3 |
| YA1055 | CH3— | 2,3-difluorophenyl | H | C(=O)CH3 |
| YA1056 | CH3— | 2,4-difluorophenyl | H | C(=O)CH3 |
| YA1057 | CH3— | 2,5-difluorophenyl | H | C(=O)CH3 |
| YA1058 | CH3— | 2,6-difluorophenyl | H | C(=O)CH3 |
| YA1059 | CH3— | 3,4-difluorophenyl | H | C(=O)CH3 |
| YA1060 | CH3— | 3,5-difluorophenyl | H | C(=O)CH3 |
| YA1061 | CH3— | 2,3-dichlorophenyl | H | C(=O)CH3 |
| YA1062 | CH3— | 2,4-dichlorophenyl | H | C(=O)CH3 |

-continued
| YA1063 | CH3— | 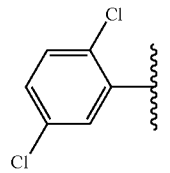 | H | 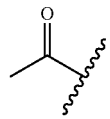 |
| YA1064 | CH3— | 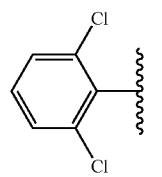 | H | 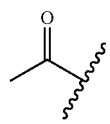 |
| YA1065 | CH3— | 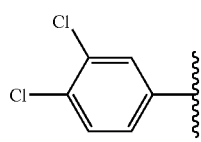 | H | 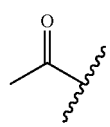 |
| YA1066 | CH3— | 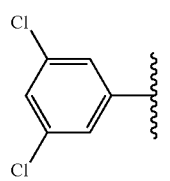 | H | 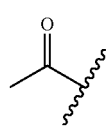 |
| YA1067 | CH3— | 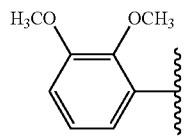 | H | 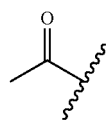 |
| YA1068 | CH3— | 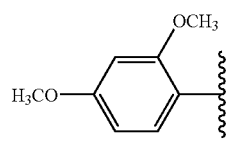 | H | 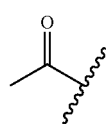 |
| YA1069 | CH3— | 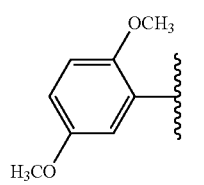 | H | 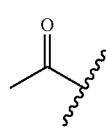 |
| YA1070 | CH3— | 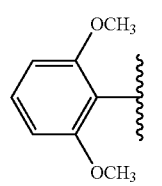 | H | 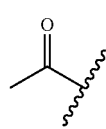 |
| YA1071 | CH3— | 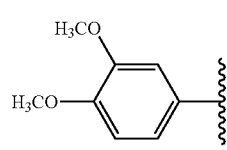 | H | 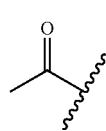 |

-continued
| | | | | |
|---|---|---|---|---|
| YA1072 | CH3— | 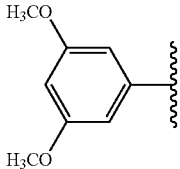 | H | 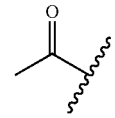 |
| YA1073 | CH3— | 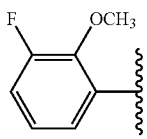 | H | 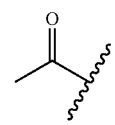 |
| YA1074 | CH3— | 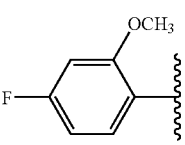 | H | 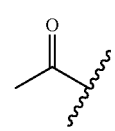 |
| YA1075 | CH3— | 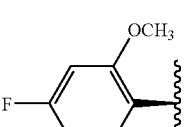 | H | 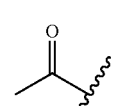 |
| YA1076 | CH3— | 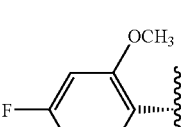 | H | 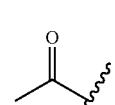 |
| YA1077 | CH3— | 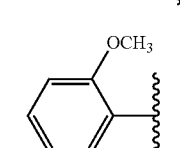 | H | 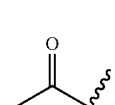 |
| YA1078 | CH3— | 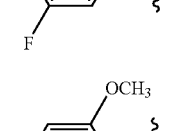 | H | 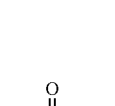 |
| YA1079 | CH3— | 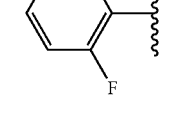 | H |  |
| YA1080 | CH3— | 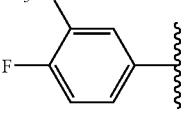 | H | 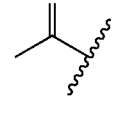 |
| YA1081 | CH3— | 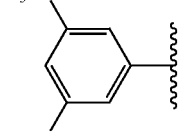 | H | 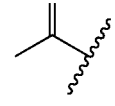 |

-continued
| | | | | |
|---|---|---|---|---|
| YA1082 | CH3— | 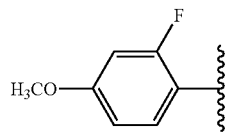 | H | 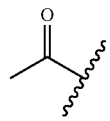 |
| YA1083 | CH3— | 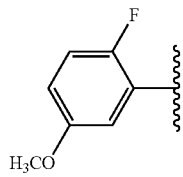 | H | 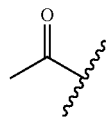 |
| YA1084 | CH3— | 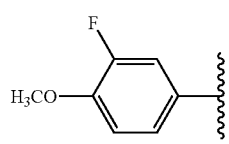 | H | 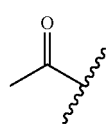 |
| YA1085 | CH3— | 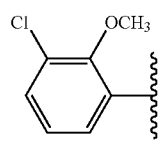 | H | 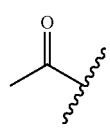 |
| YA1086 | CH3— | 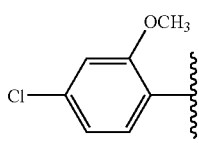 | H | 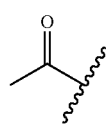 |
| YA1087 | CH3— | 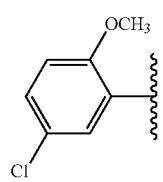 | H | 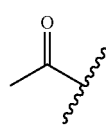 |
| YA1088 | CH3— | 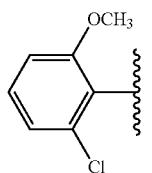 | H | 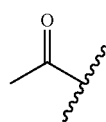 |
| YA1089 | CH3— | 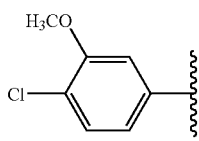 | H | 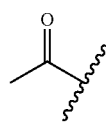 |
| YA1090 | CH3— | 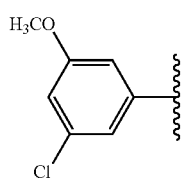 | H | 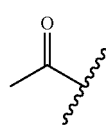 |

-continued
| | | | | |
|---|---|---|---|---|
| YA1091 | CH3— | 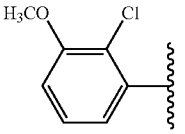 | H | 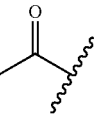 |
| YA1092 | CH3— | 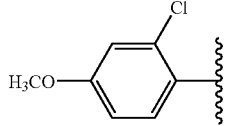 | H | 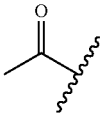 |
| YA1093 | CH3— | 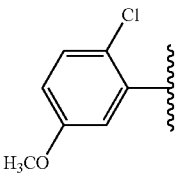 | H | 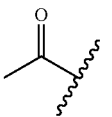 |
| YA1094 | CH3— | 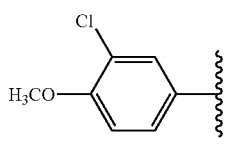 | H | 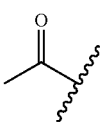 |
| YA1095 | CH3— | 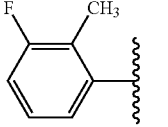 | H | 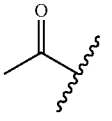 |
| YA1096 | CH3— | 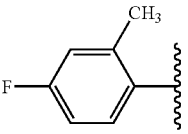 | H | 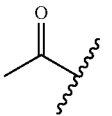 |
| YA1097 | CH3— | 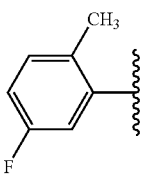 | H | 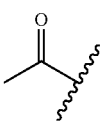 |
| YA1098 | CH3— | 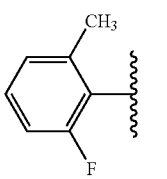 | H | 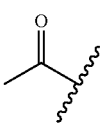 |
| YA1099 | CH3— | 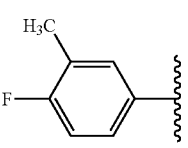 | H | 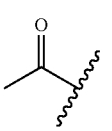 |
| YA1100 | CH3— | 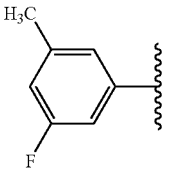 | H | 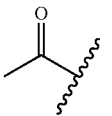 |

-continued
| | | | | |
|---|---|---|---|---|
| YA1101 | CH3— | 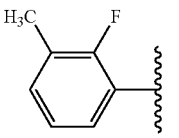 | H | 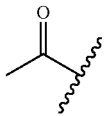 |
| YA1102 | CH3— | 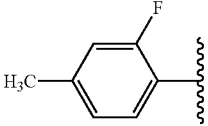 | H | 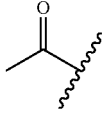 |
| YA1103 | CH3— | 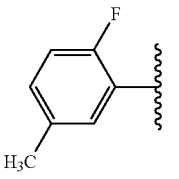 | H | 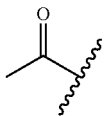 |
| YA1104 | CH3— | 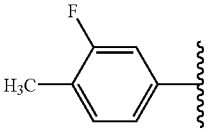 | H | 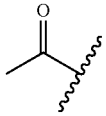 |
| YA1105 | CH3— | 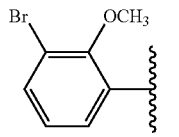 | H | 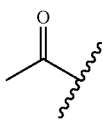 |
| YA1106 | CH3— | 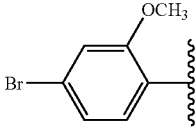 | H | 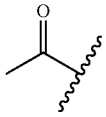 |
| YA1107 | CH3— | 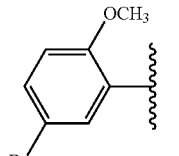 | H | 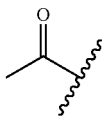 |
| YA1108 | CH3— | 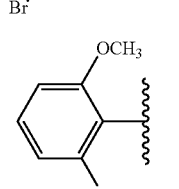 | H | 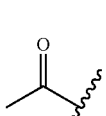 |
| YA1109 | CH3— | 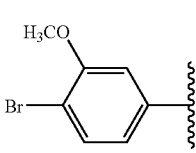 | H | 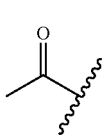 |
| YA1110 | CH3— | 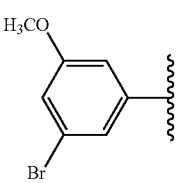 | H | 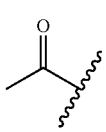 |

-continued
| | | | | |
|---|---|---|---|---|
| YA1111 | CH3— | 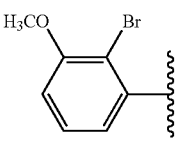 2-Br, 3-OCH3 phenyl | H | 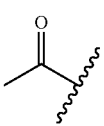 acetyl |
| YA1112 | CH3— | 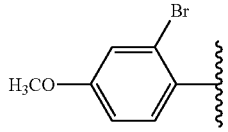 2-Br, 4-OCH3 phenyl | H | 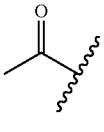 acetyl |
| YA1113 | CH3— | 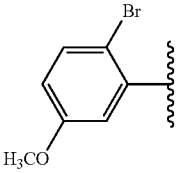 2-Br, 5-OCH3 phenyl | H | 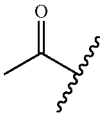 acetyl |
| YA1114 | CH3— | 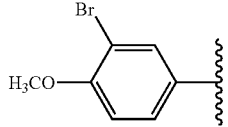 3-Br, 4-OCH3 phenyl | H | 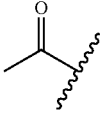 acetyl |
| YA1115 | CH3— | 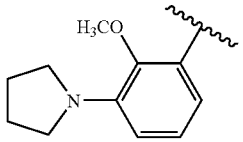 2-OCH3, 3-pyrrolidinyl phenyl | H | 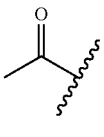 acetyl |
| YA1116 | CH3— | 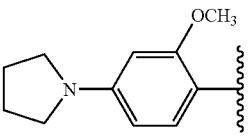 3-OCH3, 4-pyrrolidinyl phenyl | H | 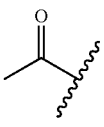 acetyl |
| YA1117 | CH3— | 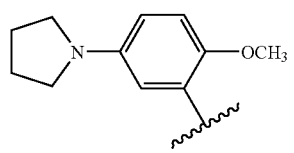 2-OCH3, 5-pyrrolidinyl phenyl | H | 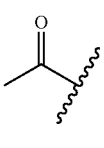 acetyl |
| YA1118 | CH3— | 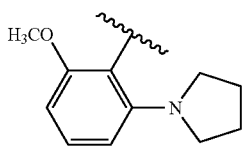 2-OCH3, 3-pyrrolidinyl phenyl | H | 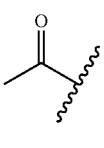 acetyl |
| YA1119 | CH3— | 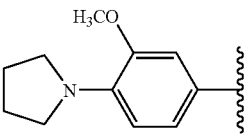 3-OCH3, 4-pyrrolidinyl phenyl | H | 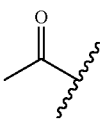 acetyl |
| YA1120 | CH3— | 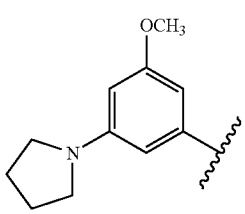 3-OCH3, 5-pyrrolidinyl phenyl | H | 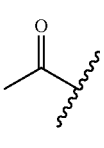 acetyl |

-continued
| | | | | |
|---|---|---|---|---|
| YA1121 | CH3— | 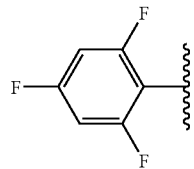 | H | 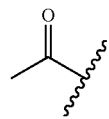 |
| YA1122 | CH3— | 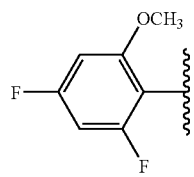 | H | 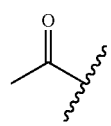 |
| YA1123 | CH3— | 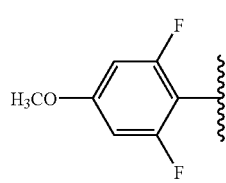 | H | 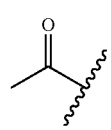 |
| YA1124 | CH3— | 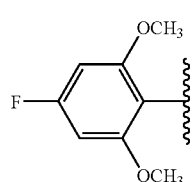 | H | 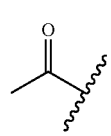 |
| YA1125 | CH3— | 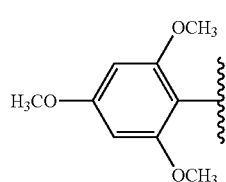 | H | 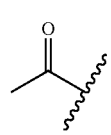 |
| YA1126 | CH3— | 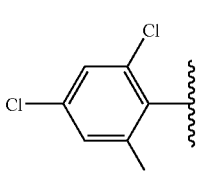 | H | 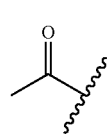 |
| YA1127 | CH3— | 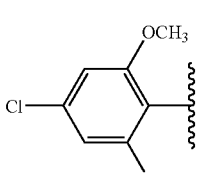 | H | 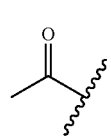 |
| YA1128 | CH3— | 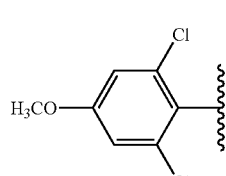 | H | 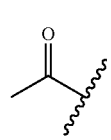 |

-continued
| | | | | |
|---|---|---|---|---|
| YA1129 | CH3— | 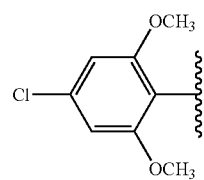 | H | 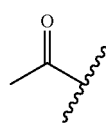 |
| YA1130 | CH3— | 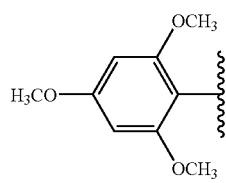 | H | 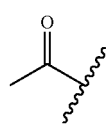 |
| YA1131 | CH3— | 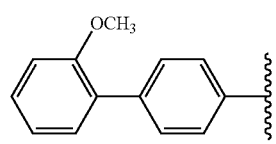 | H | 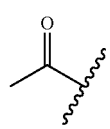 |
| YA1132 | CH3— | 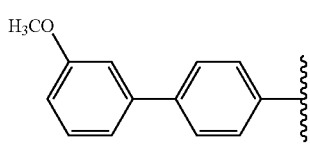 | H | 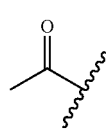 |
| YA1133 | CH3— | 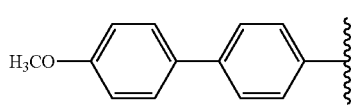 | H | 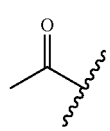 |
| YA1134 | CH3— | 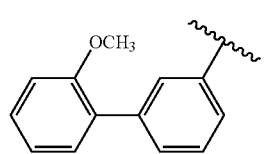 | H | 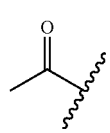 |
| YA1135 | CH3— | 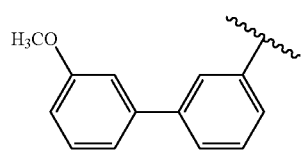 | H | 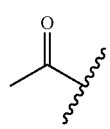 |
| YA1136 | CH3— | 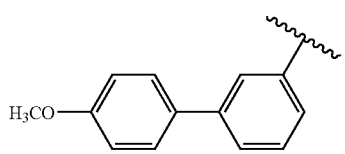 | H | 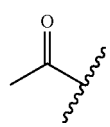 |
| YA1137 | CH3— | 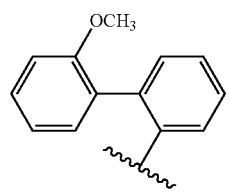 | H | 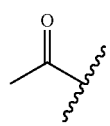 |

-continued
| | | | | |
|---|---|---|---|---|
| YA1138 | CH3— | 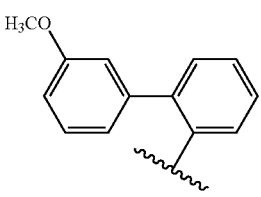 | H | 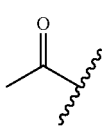 |
| YA1139 | CH3— | 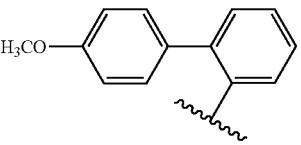 | H | 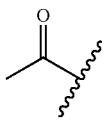 |
| YA1140 | CH3— | 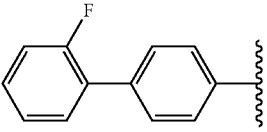 | H | 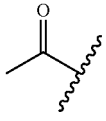 |
| YA1141 | CH3— | 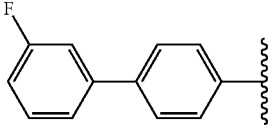 | H | 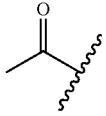 |
| YA1142 | CH3— | 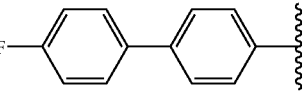 | H | 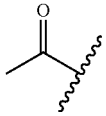 |
| YA1143 | CH3— | 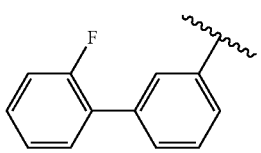 | H | 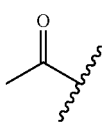 |
| YA1144 | CH3— | 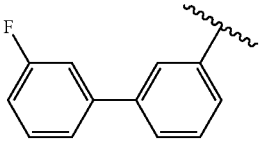 | H | 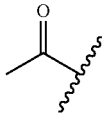 |
| YA1145 | CH3— | 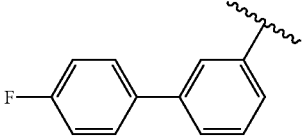 | H | 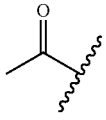 |
| YA1146 | CH3— | 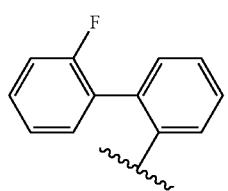 | H | 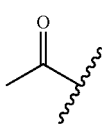 |

-continued
| | | | | |
|---|---|---|---|---|
| YA1147 | CH3— | 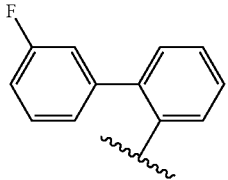 | H | 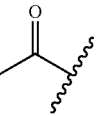 |
| YA1148 | CH3— | 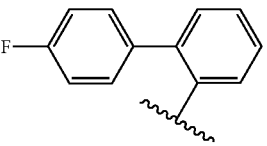 | H | 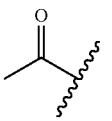 |
| YA1149 | CH3— | 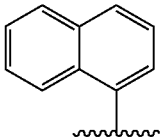 | H | 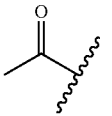 |
| YA1150 | CH3— | 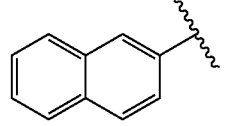 | H | 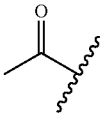 |
| YA1151 | CH3— | 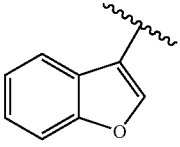 | H | 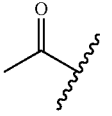 |
| YA1152 | CH3— | 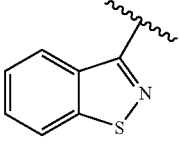 | H | 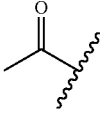 |
| YA1153 | CH3— | 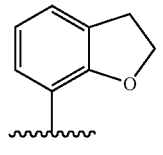 | H | 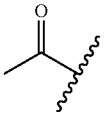 |
| YA1154 | CH3— | CH3— | CH3— | H |
| YA1155 | CH3— | CH3CH2— | CH3— | H |
| YA1156 | CH3— | 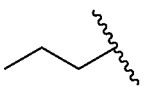 | CH3— | H |
| YA1157 | CH3— | 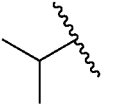 | CH3— | H |
| YA1158 | CH3— | 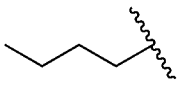 | CH3— | H |
| YA1159 | CH3— | 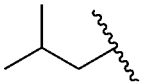 | CH3— | H |

-continued
| | | | | |
|---|---|---|---|---|
| YA1160 | CH3— | 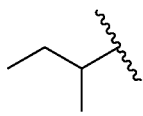 | CH3— | H |
| YA1161 | CH3— | 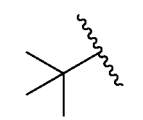 | CH3— | H |
| YA1162 | CH3— | 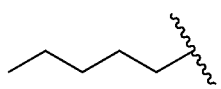 | CH3— | H |
| YA1163 | CH3— | 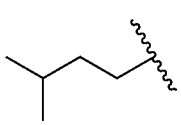 | CH3— | H |
| YA1164 | CH3— | 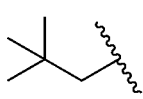 | CH3— | H |
| YA1165 | CH3— | 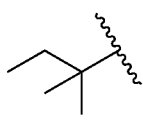 | CH3— | H |
| YA1166 | CH3— | 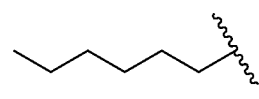 | CH3— | H |
| YA1167 | CH3— | 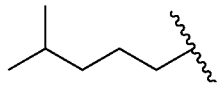 | CH3— | H |
| YA1168 | CH3— | 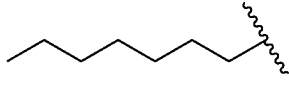 | CH3— | H |
| YA1169 | CH3— | 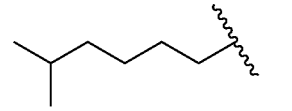 | CH3— | H |
| YA1170 | CH3— | 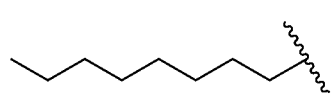 | CH3— | H |
| YA1171 | CH3— | 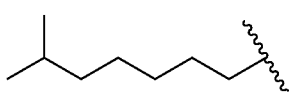 | CH3— | H |
| YA1172 | CH3— | 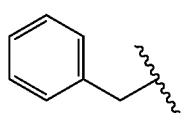 | CH3— | H |
| YA1173 | CH3— | 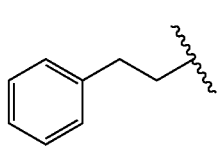 | CH3— | H |

-continued
| | | | | |
|---|---|---|---|---|
| YA1174 | CH3— | 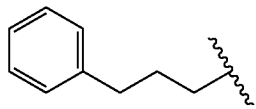 | CH3— | H |
| YA1175 | CH3— | 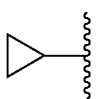 | CH3— | H |
| YA1176 | CH3— | 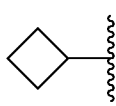 | CH3— | H |
| YA1177 | CH3— | 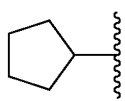 | CH3— | H |
| YA1178 | CH3— | 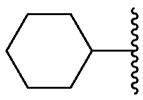 | CH3— | H |
| YA1179 | CH3— | 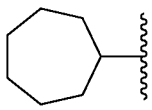 | CH3— | H |
| YA1180 | CH3— | 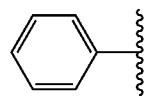 | CH3— | H |
| YA1181 | CH3— | 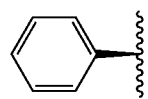 | CH3— | H |
| YA1182 | CH3— | 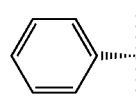 | CH3— | H |
| YA1183 | CH3— |  | CH3— | H |
| YA1184 | CH3— | 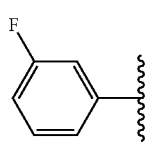 | CH3— | H |
| YA1185 | CH3— | 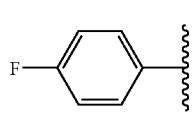 | CH3— | H |
| YA1186 | CH3— | 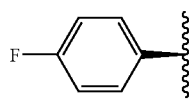 | CH3— | H |

-continued
| | | | | |
|---|---|---|---|---|
| YA1187 | CH3— | 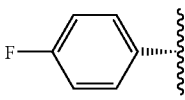 4-F-C6H4 | CH3— | H |
| YA1188 | CH3— | 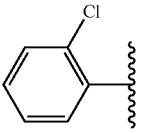 2-Cl-C6H4 | CH3— | H |
| YA1189 | CH3— | 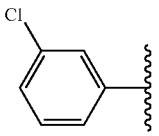 3-Cl-C6H4 | CH3— | H |
| YA1190 | CH3— | 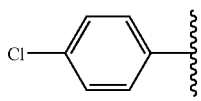 4-Cl-C6H4 | CH3— | H |
| YA1191 | CH3— | 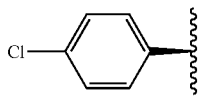 4-Cl-C6H4 | CH3— | H |
| YA1192 | CH3— | 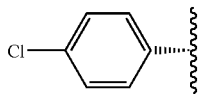 4-Cl-C6H4 | CH3— | H |
| YA1193 | CH3— | 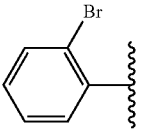 2-Br-C6H4 | CH3— | H |
| YA1194 | CH3— | 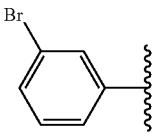 3-Br-C6H4 | CH3— | H |
| YA1195 | CH3— | 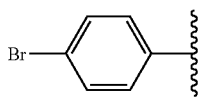 4-Br-C6H4 | CH3— | H |
| YA1196 | CH3— | 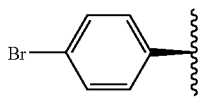 4-Br-C6H4 | CH3— | H |
| YA1197 | CH3— | 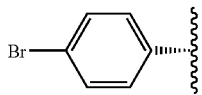 4-Br-C6H4 | CH3— | H |
| YA1198 | CH3— | 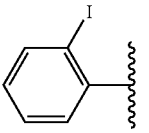 2-I-C6H4 | CH3— | H |

-continued
| | | | | |
|---|---|---|---|---|
| YA1199 | CH3— | 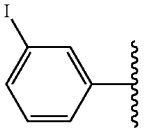 | CH3— | H |
| YA1200 | CH3— | 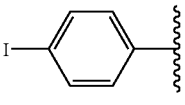 | CH3— | H |
| YA1201 | CH3— | 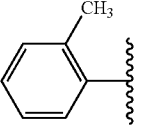 | CH3— | H |
| YA1202 | CH3— | 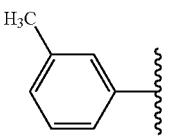 | CH3— | H |
| YA1203 | CH3— | 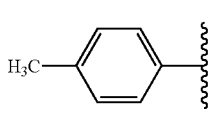 | CH3— | H |
| YA1204 | CH3— | 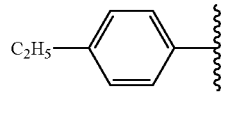 | CH3— | H |
| YA1205 | CH3— | 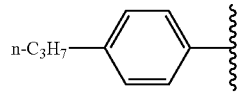 | CH3— | H |
| YA1206 | CH3— | 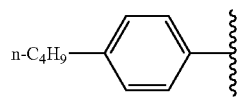 | CH3— | H |
| YA1207 | CH3— | 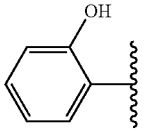 | CH3— | H |
| YA1208 | CH3— | 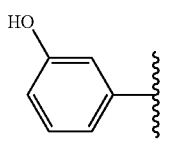 | CH3— | H |
| YA1209 | CH3— | 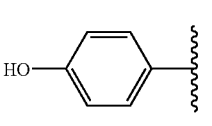 | CH3— | H |
| YA1210 | CH3— | 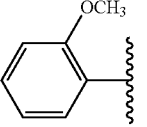 | CH3— | H |

-continued
| | | | | |
|---|---|---|---|---|
| YA1211 | CH3— | 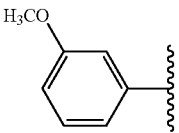 | CH3— | H |
| YA1212 | CH3— | 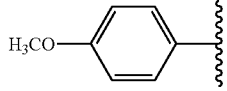 | CH3— | H |
| YA1213 | CH3— | 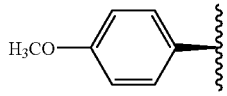 | CH3— | H |
| YA1214 | CH3— | 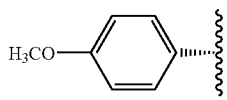 | CH3— | H |
| YA1215 | CH3— | 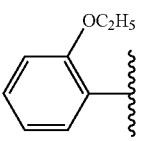 | CH3— | H |
| YA1216 | CH3— | 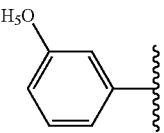 | CH3— | H |
| YA1217 | CH3— | 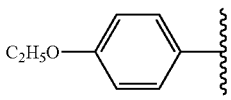 | CH3— | H |
| YA1218 | CH3— | 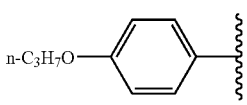 | CH3— | H |
| YA1219 | CH3— | 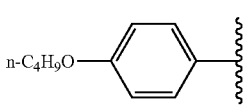 | CH3— | H |
| YA1220 | CH3— | 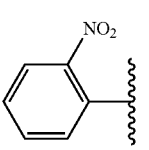 | CH3— | H |
| YA1221 | CH3— | 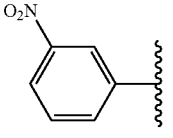 | CH3— | H |
| YA1222 | CH3— | 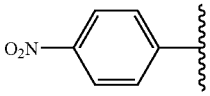 | CH3— | H |

-continued
| | | | | |
|---|---|---|---|---|
| YA1223 | CH3— | 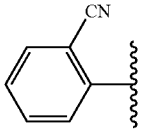 | CH3— | H |
| YA1224 | CH3— | 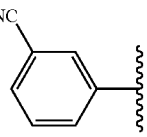 | CH3— | H |
| YA1225 | CH3— | 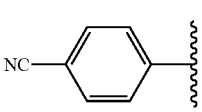 | CH3— | H |
| YA1226 | CH3— | 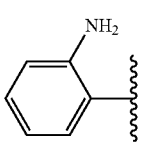 | CH3— | H |
| YA1227 | CH3— | 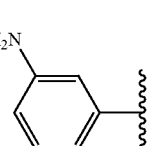 | CH3— | H |
| YA1228 | CH3— | 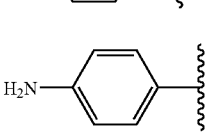 | CH3— | H |
| YA1229 | CH3— | 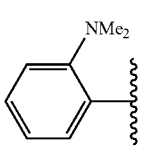 | CH3— | H |
| YA1230 | CH3— | 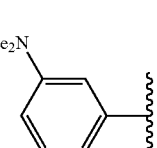 | CH3— | H |
| YA1231 | CH3— | 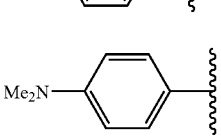 | CH3— | H |
| YA1232 | CH3— | 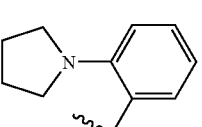 | CH3— | H |
| YA1233 | CH3— | 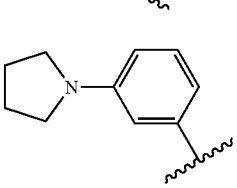 | CH3— | H |

-continued
| | | | | |
|---|---|---|---|---|
| YA1234 | CH3— | 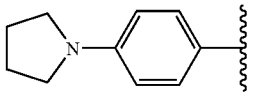 | CH3— | H |
| YA1235 | CH3— | 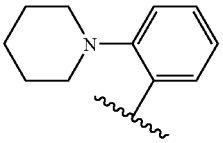 | CH3— | H |
| YA1236 | CH3— | 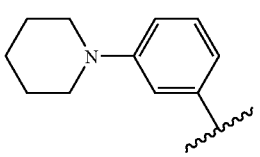 | CH3— | H |
| YA1237 | CH3— | 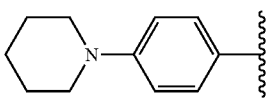 | CH3— | H |
| YA1238 | CH3— | 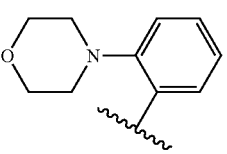 | CH3— | H |
| YA1239 | CH3— | 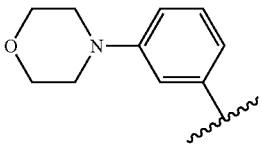 | CH3— | H |
| YA1240 | CH3— | 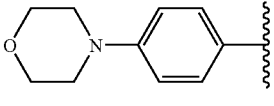 | CH3— | H |
| YA1241 | CH3— | 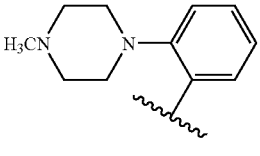 | CH3— | H |
| YA1242 | CH3— | 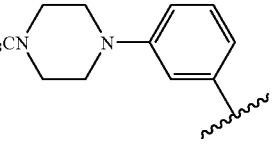 | CH3— | H |
| YA1243 | CH3— | 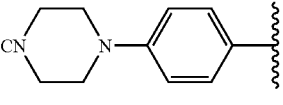 | CH3— | H |
| YA1244 | CH3— | 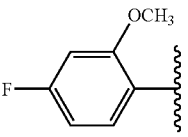 | CH3— | H |

-continued
| | | | | |
|---|---|---|---|---|
| YA1245 | CH3— | 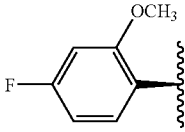 | CH3— | H |
| YA1246 | CH3— | 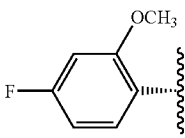 | CH3— | H |
| YA1247 | CH3— | 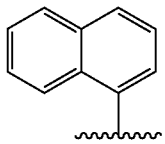 | CH3— | H |
| YA1248 | CH3— | 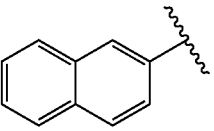 | CH3— | H |
| YA1249 | CH3— | CH3— | H | CH3— |
| YA1250 | CH3— | CH3CH2— | H | CH3— |
| YA1251 | CH3— | 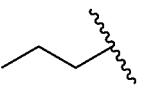 | H | CH3— |
| YA1252 | CH3— | 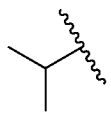 | H | CH3— |
| YA1253 | CH3— | 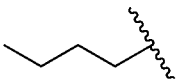 | H | CH3— |
| YA1254 | CH3— | 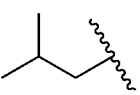 | H | CH3— |
| YA1255 | CH3— | 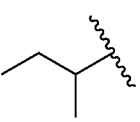 | H | CH3— |
| YA1256 | CH3— | 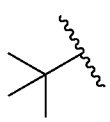 | H | CH3— |
| YA1257 | CH3— | 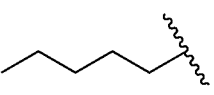 | H | CH3— |
| YA1258 | CH3— | 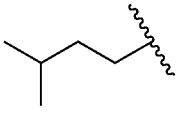 | H | CH3— |

-continued
| | | | | |
|---|---|---|---|---|
| YA1259 | CH3— | 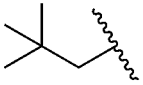 | H | CH3— |
| YA1260 | CH3— |  | H | CH3— |
| YA1261 | CH3— | 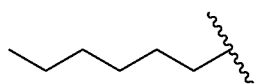 | H | CH3— |
| YA1262 | CH3— | 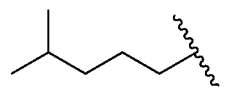 | H | CH3— |
| YA1263 | CH3— | 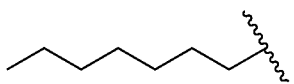 | H | CH3— |
| YA1264 | CH3— | 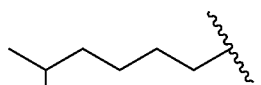 | H | CH3— |
| YA1265 | CH3— |  | H | CH3— |
| YA1266 | CH3— |  | H | CH3— |
| YA1267 | CH3— | 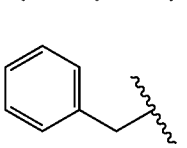 | H | CH3— |
| YA1268 | CH3— | 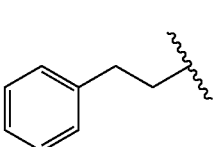 | H | CH3— |
| YA1269 | CH3— | 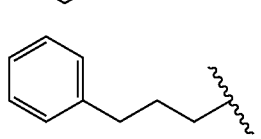 | H | CH3— |
| YA1270 | CH3— |  | H | CH3— |
| YA1271 | CH3— | 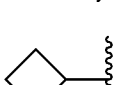 | H | CH3— |
| YA1272 | CH3— | 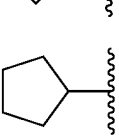 | H | CH3— |

-continued
| | | | | |
|---|---|---|---|---|
| YA1273 | CH3— | 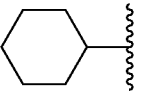 | H | CH3— |
| YA1274 | CH3— | 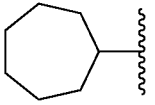 | H | CH3— |
| YA1275 | CH3— | 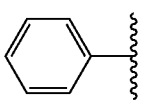 | H | CH3— |
| YA1276 | CH3— | 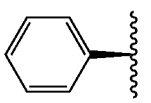 | H | CH3— |
| YA1277 | CH3— | 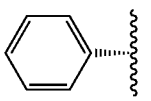 | H | CH3— |
| YA1278 | CH3— | 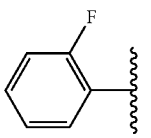 | H | CH3— |
| YA1279 | CH3— | 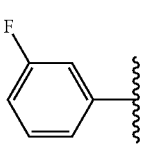 | H | CH3— |
| YA1280 | CH3— | 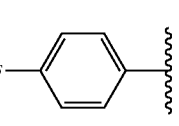 | H | CH3— |
| YA1281 | CH3— | 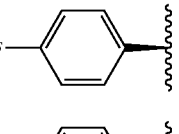 | H | CH3— |
| YA1282 | CH3— | 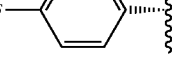 | H | CH3— |
| YA1283 | CH3— | 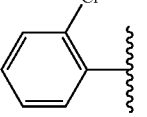 | H | CH3— |
| YA1284 | CH3— | 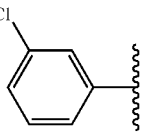 | H | CH3— |
| YA1285 | CH3— | 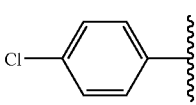 | H | CH3— |

-continued
| | | | | |
|---|---|---|---|---|
| YA1286 | CH3— | 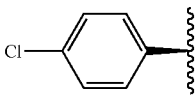 | H | CH3— |
| YA1287 | CH3— | 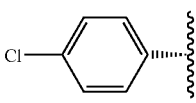 | H | CH3— |
| YA1288 | CH3— | 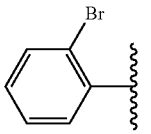 | H | CH3— |
| YA1289 | CH3— | 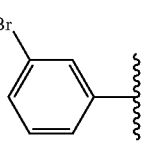 | H | CH3— |
| YA1290 | CH3— | 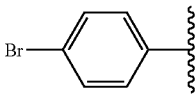 | H | CH3— |
| YA1291 | CH3— | 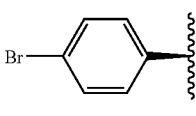 | H | CH3— |
| YA1292 | CH3— | 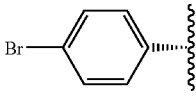 | H | CH3— |
| YA1293 | CH3— | 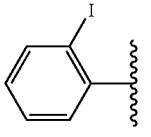 | H | CH3— |
| YA1294 | CH3— | 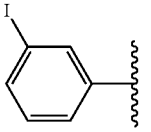 | H | CH3— |
| YA1295 | CH3— | 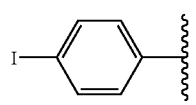 | H | CH3— |
| YA1296 | CH3— | 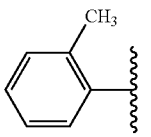 | H | CH3— |
| YA1297 | CH3— | 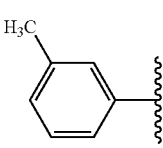 | H | CH3— |

-continued
| | | | | |
|---|---|---|---|---|
| YA1298 | CH3— | 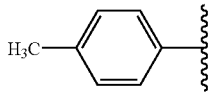 | H | CH3— |
| YA1299 | CH3— | 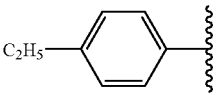 | H | CH3— |
| YA1300 | CH3— | 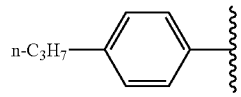 | H | CH3— |
| YA1301 | CH3— | 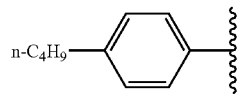 | H | CH3— |
| YA1302 | CH3— | 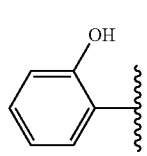 | H | CH3— |
| YA1303 | CH3— | 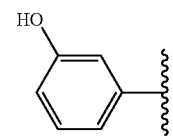 | H | CH3— |
| YA1304 | CH3— | 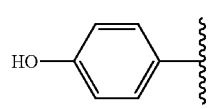 | H | CH3— |
| YA1305 | CH3— | 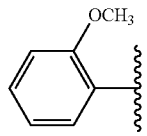 | H | CH3— |
| YA1306 | CH3— | 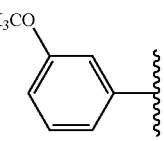 | H | CH3— |
| YA1307 | CH3— | 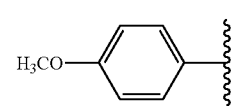 | H | CH3— |
| YA1308 | CH3— | 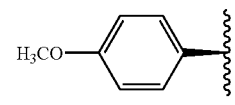 | H | CH3— |
| YA1309 | CH3— | 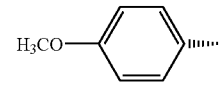 | H | CH3— |
| YA1310 | CH3— | 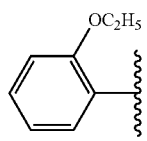 | H | CH3— |

-continued
| | | | | |
|---|---|---|---|---|
| YA1311 | CH3— | 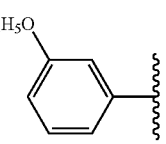 3-C2H5O-C6H4— | H | CH3— |
| YA1312 | CH3— | 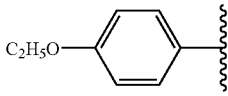 4-C2H5O-C6H4— | H | CH3— |
| YA1313 | CH3— | 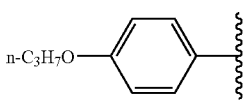 4-n-C3H7O-C6H4— | H | CH3— |
| YA1314 | CH3— | 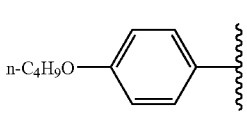 4-n-C4H9O-C6H4— | H | CH3— |
| YA1315 | CH3— | 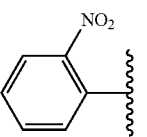 2-NO2-C6H4— | H | CH3— |
| YA1316 | CH3— | 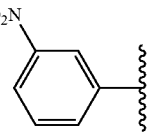 3-NO2-C6H4— | H | CH3— |
| YA1317 | CH3— | 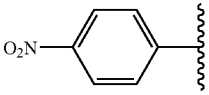 4-NO2-C6H4— | H | CH3— |
| YA1318 | CH3— | 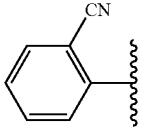 2-CN-C6H4— | H | CH3— |
| YA1319 | CH3— | 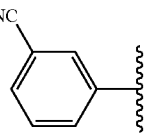 3-CN-C6H4— | H | CH3— |
| YA1320 | CH3— | 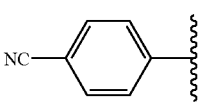 4-CN-C6H4— | H | CH3— |
| YA1321 | CH3— | 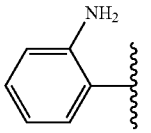 2-NH2-C6H4— | H | CH3— |
| YA1322 | CH3— | 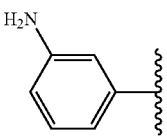 3-NH2-C6H4— | H | CH3— |

-continued
| | | | | |
|---|---|---|---|---|
| YA1323 | CH3— | 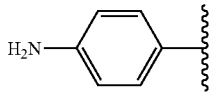 | H | CH3— |
| YA1324 | CH3— | 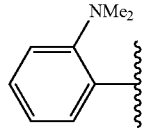 | H | CH3— |
| YA1325 | CH3— | 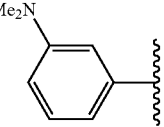 | H | CH3— |
| YA1326 | CH3— | 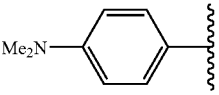 | H | CH3— |
| YA1327 | CH3— | 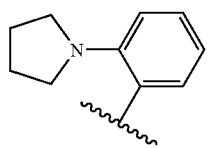 | H | CH3— |
| YA1328 | CH3— | 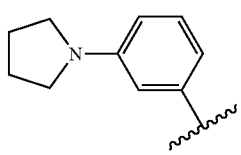 | H | CH3— |
| YA1329 | CH3— | 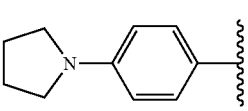 | H | CH3— |
| YA1330 | CH3— | 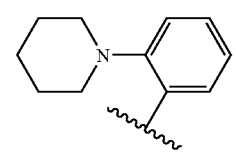 | H | CH3— |
| YA1331 | CH3— | 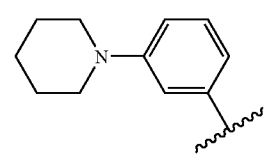 | H | CH3— |
| YA1332 | CH3— | 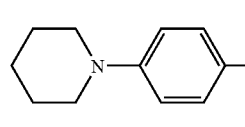 | H | CH3— |
| YA1333 | CH3— | 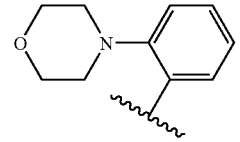 | H | CH3— |

-continued
| | | | | |
|---|---|---|---|---|
| YA1334 | CH3— | 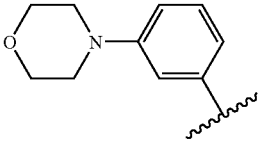 | H | CH3— |
| YA1335 | CH3— | 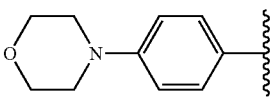 | H | CH3— |
| YA1336 | CH3— | 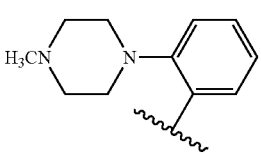 | H | CH3— |
| YA1337 | CH3— | 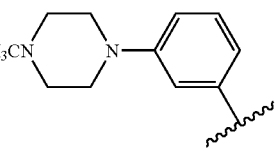 | H | CH3— |
| YA1338 | CH3— | 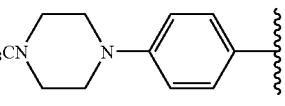 | H | CH3— |
| YA1339 | CH3— | 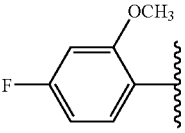 | H | CH3— |
| YA1340 | CH3— | 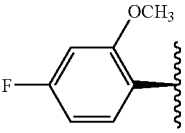 | H | CH3— |
| YA1341 | CH3— | 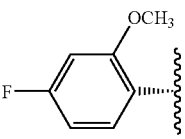 | H | CH3— |
| YA1342 | CH3— | 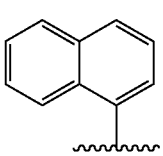 | H | CH3— |
| YA1343 | CH3— | 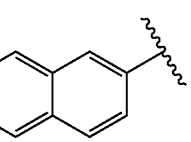 | H | CH3— |
| YA1344 | CH3CH2— | CH3— | H | H |
| YA1345 | CH3CH2— | CH3CH2— | H | H |
| YA1346 | CH3CH2— | 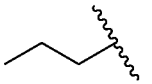 | H | H |

-continued
| | | | | |
|---|---|---|---|---|
| YA1347 | CH3CH2— | 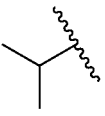 | H | H |
| YA1348 | CH3CH2— | 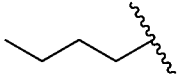 | H | H |
| YA1349 | CH3CH2— | 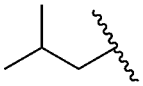 | H | H |
| YA1350 | CH3CH2— | 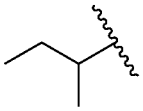 | H | H |
| YA1351 | CH3CH2— |  | H | H |
| YA1352 | CH3CH2— | 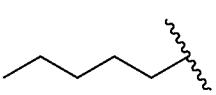 | H | H |
| YA1353 | CH3CH2— | 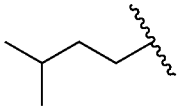 | H | H |
| YA1354 | CH3CH2— | 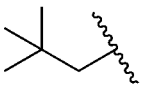 | H | H |
| YA1355 | CH3CH2— | 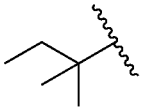 | H | H |
| YA1356 | CH3CH2— | 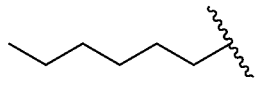 | H | H |
| YA1357 | CH3CH2— | 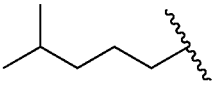 | H | H |
| YA1358 | CH3CH2— | 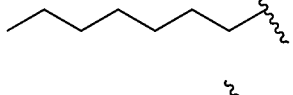 | H | H |
| YA1359 | CH3CH2— | 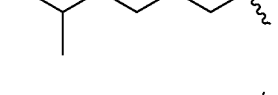 | H | H |
| YA1360 | CH3CH2— | 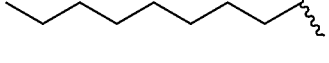 | H | H |

-continued
| | | | | |
|---|---|---|---|---|
| YA1361 | CH3CH2— | 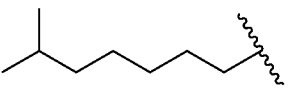 | H | H |
| YA1362 | CH3CH2— | 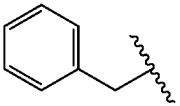 | H | H |
| YA1363 | CH3CH2— | 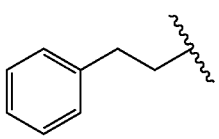 | H | H |
| YA1364 | CH3CH2— | 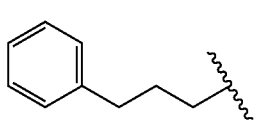 | H | H |
| YA1365 | CH3CH2— |  | H | H |
| YA1366 | CH3CH2— | 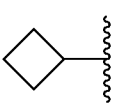 | H | H |
| YA1367 | CH3CH2— | 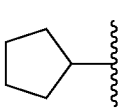 | H | H |
| YA1368 | CH3CH2— | 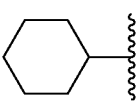 | H | H |
| YA1369 | CH3CH2— | 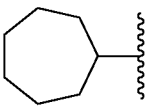 | H | H |
| YA1370 | CH3CH2— | 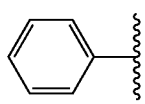 | H | H |
| YA1371 | CH3CH2— | 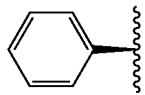 | H | H |
| YA1372 | CH3CH2— | 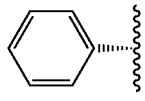 | H | H |
| YA1373 | CH3CH2— | 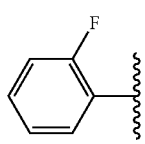 | H | H |

-continued
| | | | | |
|---|---|---|---|---|
| YA1374 | CH3CH2— | 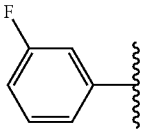 | H | H |
| YA1375 | CH3CH2— | 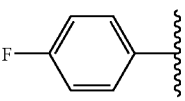 | H | H |
| YA1376 | CH3CH2— | 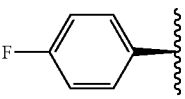 | H | H |
| YA1377 | CH3CH2— | 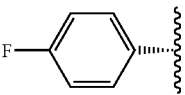 | H | H |
| YA1378 | CH3CH2— | 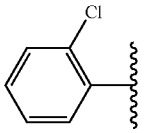 | H | H |
| YA1379 | CH3CH2— | 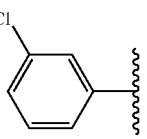 | H | H |
| YA1380 | CH3CH2— | 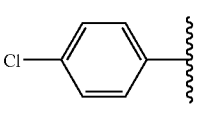 | H | H |
| YA1381 | CH3CH2— | 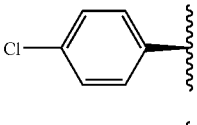 | H | H |
| YA1382 | CH3CH2— | 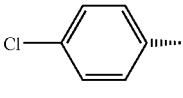 | H | H |
| YA1383 | CH3CH2— | 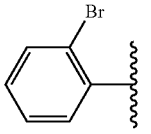 | H | H |
| YA1384 | CH3CH2— | 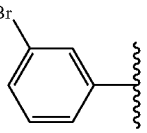 | H | H |
| YA1385 | CH3CH2— | 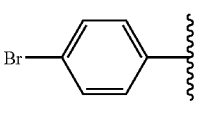 | H | H |
| YA1386 | CH3CH2— | 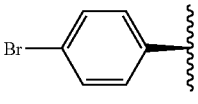 | H | H |

-continued
| | | | | |
|---|---|---|---|---|
| YA1387 | CH3CH2— | 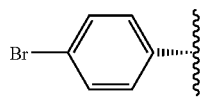 | H | H |
| YA1388 | CH3CH2— | 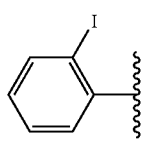 | H | H |
| YA1389 | CH3CH2— | 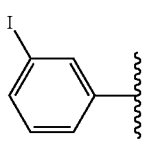 | H | H |
| YA1390 | CH3CH2— | 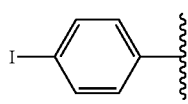 | H | H |
| YA1391 | CH3CH2— | 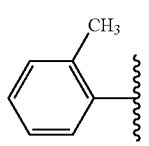 | H | H |
| YA1392 | CH3CH2— | 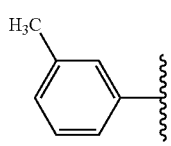 | H | H |
| YA1393 | CH3CH2— | 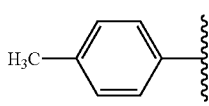 | H | H |
| YA1394 | CH3CH2— | 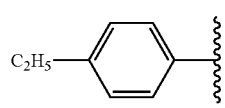 | H | H |
| YA1395 | CH3CH2— | 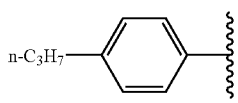 | H | H |
| YA1396 | CH3CH2— | 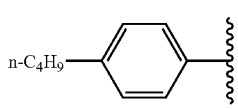 | H | H |
| YA1397 | CH3CH2— | 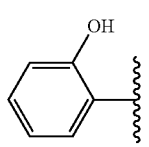 | H | H |
| YA1398 | CH3CH2— | 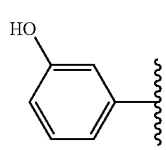 | H | H |

-continued
| | | | | |
|---|---|---|---|---|
| YA1399 | CH3CH2— | 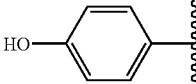 | H | H |
| YA1400 | CH3CH2— | 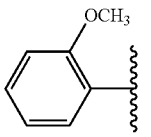 | H | H |
| YA1401 | CH3CH2— | 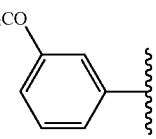 | H | H |
| YA1402 | CH3CH2— | 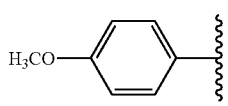 | H | H |
| YA1403 | CH3CH2— | 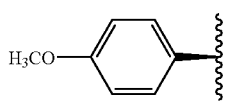 | H | H |
| YA1404 | CH3CH2— | 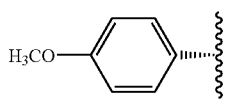 | H | H |
| YA1405 | CH3CH2— | 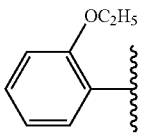 | H | H |
| YA1406 | CH3CH2— | 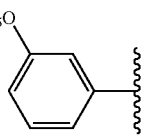 | H | H |
| YA1407 | CH3CH2— | 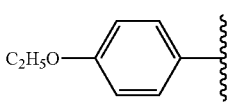 | H | H |
| YA1408 | CH3CH2— | 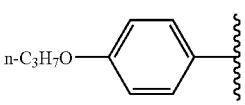 | H | H |
| YA1409 | CH3CH2— | 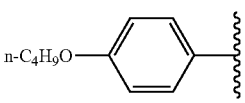 | H | H |
| YA1410 | CH3CH2— | 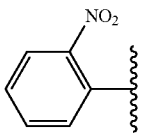 | H | H |

-continued
| | | | | |
|---|---|---|---|---|
| YA1411 | CH3CH2— | 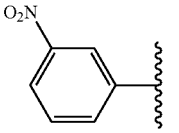 | H | H |
| YA1412 | CH3CH2— | 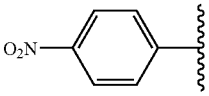 | H | H |
| YA1413 | CH3CH2— | 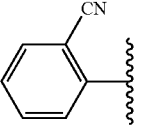 | H | H |
| YA1414 | CH3CH2— | 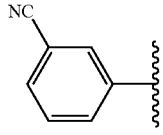 | H | H |
| YA1415 | CH3CH2— | 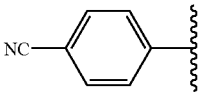 | H | H |
| YA1416 | CH3CH2— | 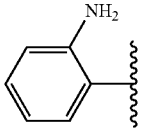 | H | H |
| YA1417 | CH3CH2— | 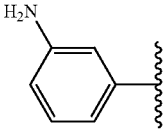 | H | H |
| YA1418 | CH3CH2— | 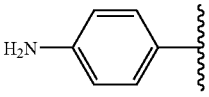 | H | H |
| YA1419 | CH3CH2— | 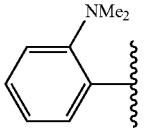 | H | H |
| YA1420 | CH3CH2— | 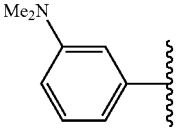 | H | H |
| YA1421 | CH3CH2— | 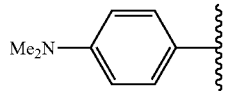 | H | H |

-continued

| | | | | |
|---|---|---|---|---|
| YA1422 | CH3CH2— | 2-pyrrolidin-1-yl-phenyl | H | H |
| YA1423 | CH3CH2— | 3-pyrrolidin-1-yl-phenyl | H | H |
| YA1424 | CH3CH2— | 4-pyrrolidin-1-yl-phenyl | H | H |
| YA1425 | CH3CH2— | 2-piperidin-1-yl-phenyl | H | H |
| YA1426 | CH3CH2— | 3-piperidin-1-yl-phenyl | H | H |
| YA1427 | CH3CH2— | 4-piperidin-1-yl-phenyl | H | H |
| YA1428 | CH3CH2— | 2-morpholin-4-yl-phenyl | H | H |
| YA1429 | CH3CH2— | 3-morpholin-4-yl-phenyl | H | H |
| YA1430 | CH3CH2— | 4-morpholin-4-yl-phenyl | H | H |
| YA1431 | CH3CH2— | 2-(4-methylpiperazin-1-yl)-phenyl | H | H |
| YA1432 | CH3CH2— | 3-(4-methylpiperazin-1-yl)-phenyl | H | H |

-continued
| | | | | |
|---|---|---|---|---|
| YA1433 | CH3CH2— | 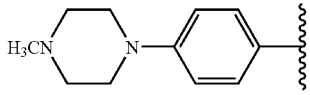 | H | H |
| YA1434 | CH3CH2— | 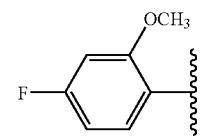 | H | H |
| YA1435 | CH3CH2— | 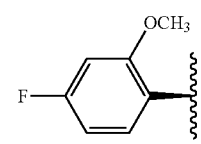 | H | H |
| YA1436 | CH3CH2— | 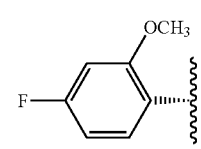 | H | H |
| YA1437 | CH3CH2— | 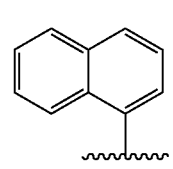 | H | H |
| YA1438 | CH3CH2— | 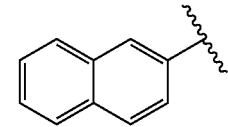 | H | H |
| YA1439 | CH3CH2— | CH3— | H | CH3— |
| YA1440 | CH3CH2— | CH3CH2— | H | CH3— |
| YA1441 | CH3CH2— | 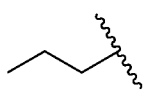 | H | CH3— |
| YA1442 | CH3CH2— | 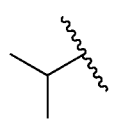 | H | CH3— |
| YA1443 | CH3CH2— | 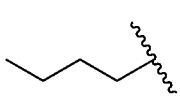 | H | CH3— |
| YA1444 | CH3CH2— | 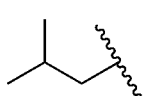 | H | CH3— |
| YA1445 | CH3CH2— | 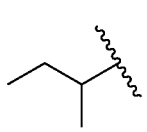 | H | CH3— |
| YA1446 | CH3CH2— | 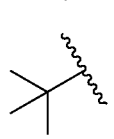 | H | CH3— |

-continued
| | | | | |
|---|---|---|---|---|
| YA1447 | CH3CH2— | 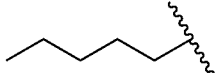 | H | CH3— |
| YA1448 | CH3CH2— | 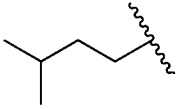 | H | CH3— |
| YA1449 | CH3CH2— | 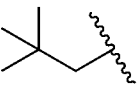 | H | CH3— |
| YA1450 | CH3CH2— | 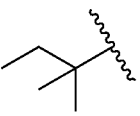 | H | CH3— |
| YA1451 | CH3CH2— | 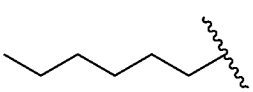 | H | CH3— |
| YA1452 | CH3CH2— | 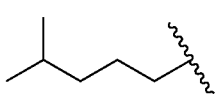 | H | CH3— |
| YA1453 | CH3CH2— | 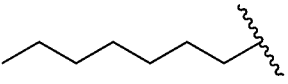 | H | CH3— |
| YA1454 | CH3CH2— | 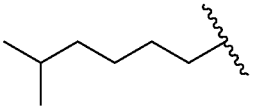 | H | CH3— |
| YA1455 | CH3CH2— | 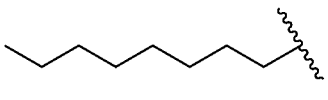 | H | CH3— |
| YA1456 | CH3CH2— | 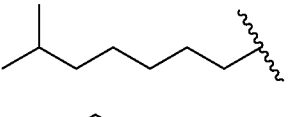 | H | CH3— |
| YA1457 | CH3CH2— | 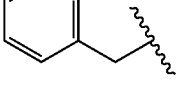 | H | CH3— |
| YA1458 | CH3CH2— | 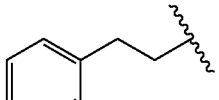 | H | CH3— |
| YA1459 | CH3CH2— | 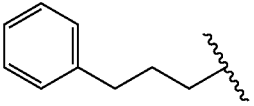 | H | CH3— |
| YA1460 | CH3CH2— |  | H | CH3— |

-continued
| | | | | |
|---|---|---|---|---|
| YA1461 | CH3CH2— | 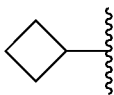 | H | CH3— |
| YA1462 | CH3CH2— | 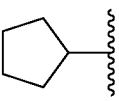 | H | CH3— |
| YA1463 | CH3CH2— | 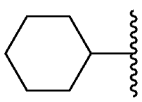 | H | CH3— |
| YA1464 | CH3CH2— | 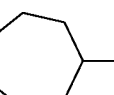 | H | CH3— |
| YA1465 | CH3CH2— | 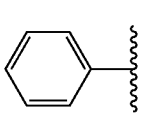 | H | CH3— |
| YA1466 | CH3CH2— | 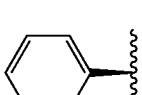 | H | CH3— |
| YA1467 | CH3CH2— | 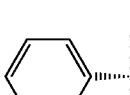 | H | CH3— |
| YA1468 | CH3CH2— | 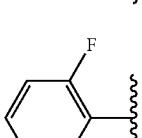 | H | CH3— |
| YA1469 | CH3CH2— | 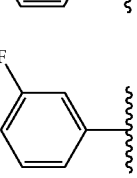 | H | CH3— |
| YA1470 | CH3CH2— | 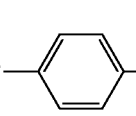 | H | CH3— |
| YA1471 | CH3CH2— | 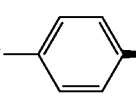 | H | CH3— |
| YA1472 | CH3CH2— | 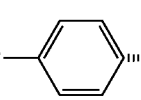 | H | CH3— |
| YA1473 | CH3CH2— | 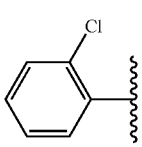 | H | CH3— |

-continued
| | | | | |
|---|---|---|---|---|
| YA1474 | CH3CH2— | 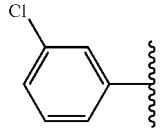 | H | CH3— |
| YA1475 | CH3CH2— | 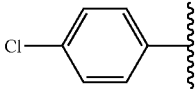 | H | CH3— |
| YA1476 | CH3CH2— | 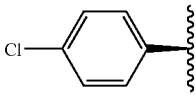 | H | CH3— |
| YA1477 | CH3CH2— | 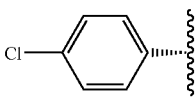 | H | CH3— |
| YA1478 | CH3CH2— | 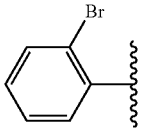 | H | CH3— |
| YA1479 | CH3CH2— | 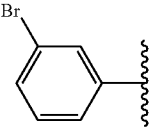 | H | CH3— |
| YA1480 | CH3CH2— | 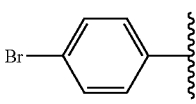 | H | CH3— |
| YA1481 | CH3CH2— | 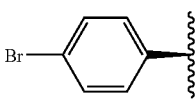 | H | CH3— |
| YA1482 | CH3CH2— | 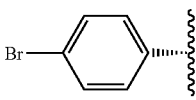 | H | CH3— |
| YA1483 | CH3CH2— | 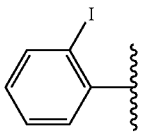 | H | CH3— |
| YA1484 | CH3CH2— | 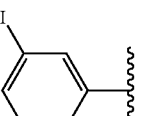 | H | CH3— |
| YA1485 | CH3CH2— | 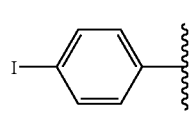 | H | CH3— |

-continued
| | | | | |
|---|---|---|---|---|
| YA1486 | CH3CH2— | 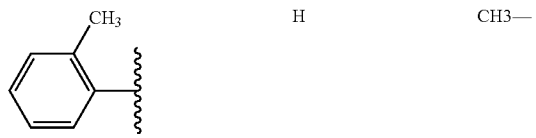 | H | CH3— |
| YA1487 | CH3CH2— | 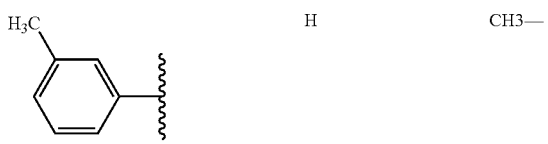 | H | CH3— |
| YA1488 | CH3CH2— | 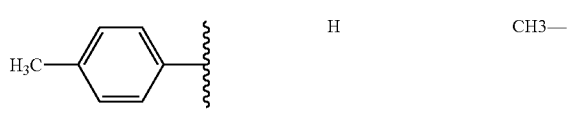 | H | CH3— |
| YA1489 | CH3CH2— | 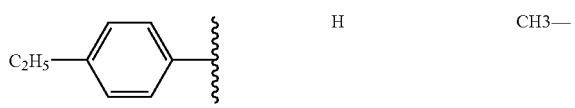 | H | CH3— |
| YA1490 | CH3CH2— |  | H | CH3— |
| YA1491 | CH3CH2— |  | H | CH3— |
| YA1492 | CH3CH2— | 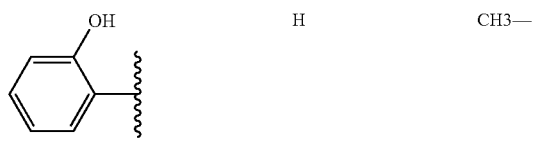 | H | CH3— |
| YA1493 | CH3CH2— |  | H | CH3— |
| YA1494 | CH3CH2— |  | H | CH3— |
| YA1495 | CH3CH2— | 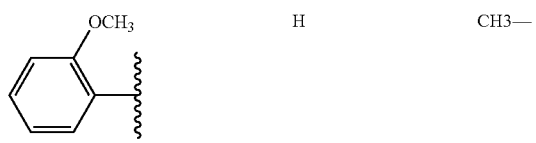 | H | CH3— |
| YA1496 | CH3CH2— | 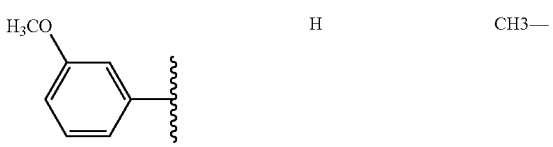 | H | CH3— |
| YA1497 | CH3CH2— | 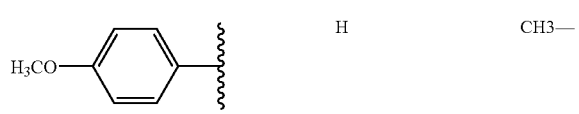 | H | CH3— |

-continued
| | | | | |
|---|---|---|---|---|
| YA1498 | CH3CH2— | 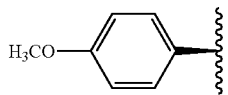 | H | CH3— |
| YA1499 | CH3CH2— | 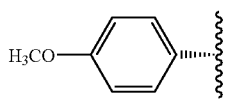 | H | CH3— |
| YA1500 | CH3CH2— | 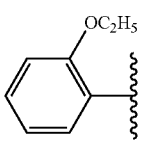 | H | CH3— |
| YA1501 | CH3CH2— | 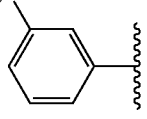 | H | CH3— |
| YA1502 | CH3CH2— | 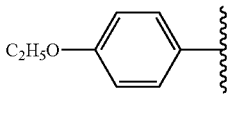 | H | CH3— |
| YA1503 | CH3CH2— | 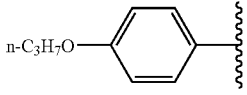 | H | CH3— |
| YA1504 | CH3CH2— | 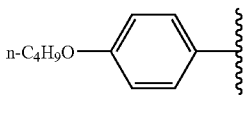 | H | CH3— |
| YA1505 | CH3CH2— | 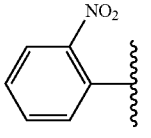 | H | CH3— |
| YA1506 | CH3CH2— | 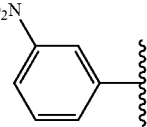 | H | CH3— |
| YA1507 | CH3CH2— | 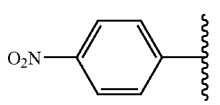 | H | CH3— |
| YA1508 | CH3CH2— | 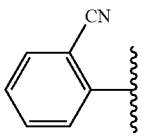 | H | CH3— |
| YA1509 | CH3CH2— | 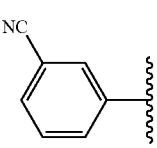 | H | CH3— |

-continued
| | | | | |
|---|---|---|---|---|
| YA1510 | CH3CH2— | 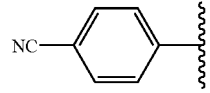 | H | CH3— |
| YA1511 | CH3CH2— | 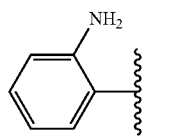 | H | CH3— |
| YA1512 | CH3CH2— | 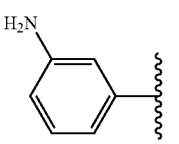 | H | CH3— |
| YA1513 | CH3CH2— | 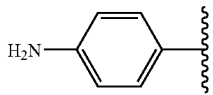 | H | CH3— |
| YA1514 | CH3CH2— | 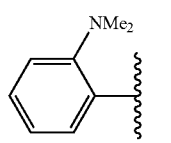 | H | CH3— |
| YA1515 | CH3CH2— | 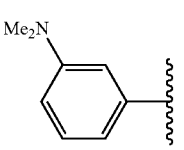 | H | CH3— |
| YA1516 | CH3CH2— | 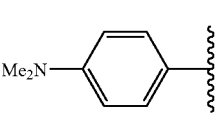 | H | CH3— |
| YA1517 | CH3CH2— | 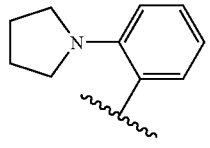 | H | CH3— |
| YA1518 | CH3CH2— | 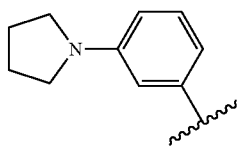 | H | CH3— |
| YA1519 | CH3CH2— | 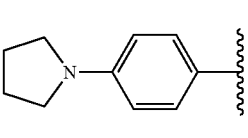 | H | CH3— |
| YA1520 | CH3CH2— | 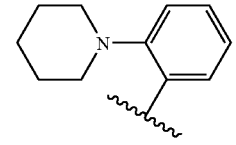 | H | CH3— |

-continued
| | | | | |
|---|---|---|---|---|
| YA1521 | CH3CH2— | 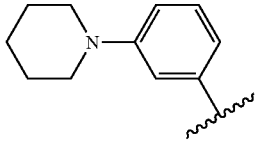 | H | CH3— |
| YA1522 | CH3CH2— | 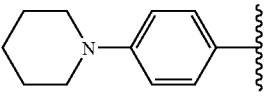 | H | CH3— |
| YA1523 | CH3CH2— | 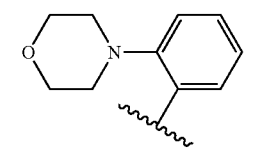 | H | CH3— |
| YA1524 | CH3CH2— | 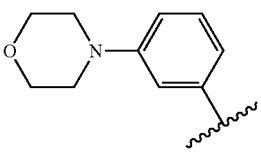 | H | CH3— |
| YA1525 | CH3CH2— | 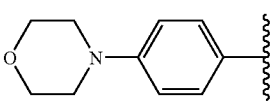 | H | CH3— |
| YA1526 | CH3CH2— | 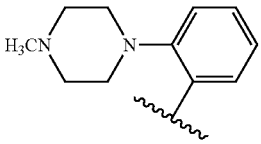 | H | CH3— |
| YA1527 | CH3CH2— | 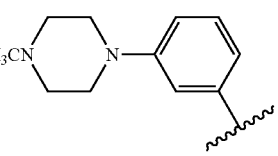 | H | CH3— |
| YA1528 | CH3CH2— | 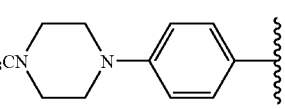 | H | CH3— |
| YA1529 | CH3CH2— | 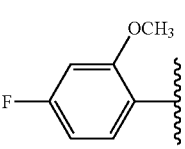 | H | CH3— |
| YA1530 | CH3CH2— | 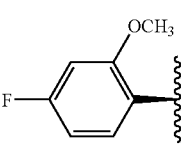 | H | CH3— |
| YA1531 | CH3CH2— | 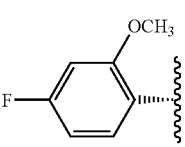 | H | CH3— |

-continued
| | | | | |
|---|---|---|---|---|
| YA1532 | CH3CH2— | 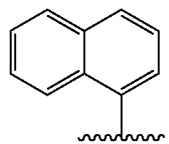 | H | CH3— |
| YA1533 | CH3CH2— | 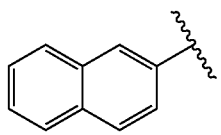 | H | CH3— |
| No. | STRUCTURE |
|---|---|
| YA1534 | 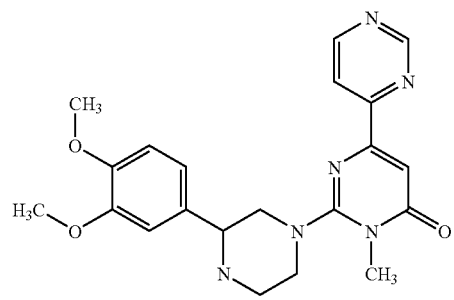 |
| YA1535 | 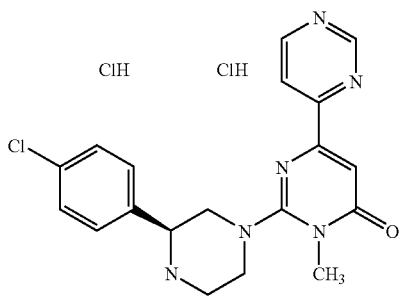 |
| YA1536 | 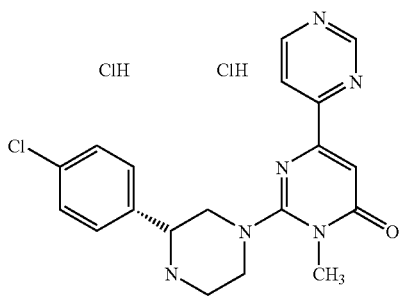 |

-continued
YA1537 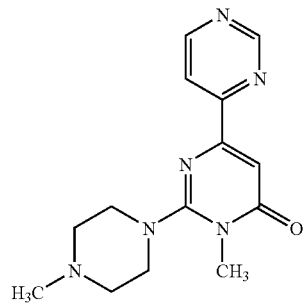
YA1538 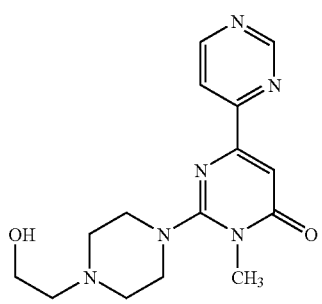
YA1539 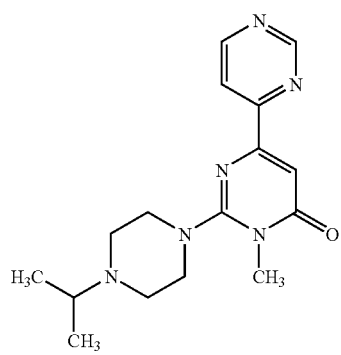
YA1540 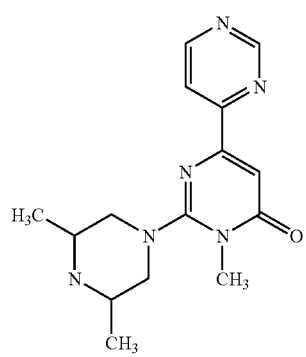
YA1541 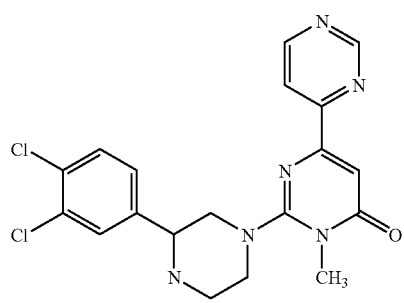

-continued
YA1542 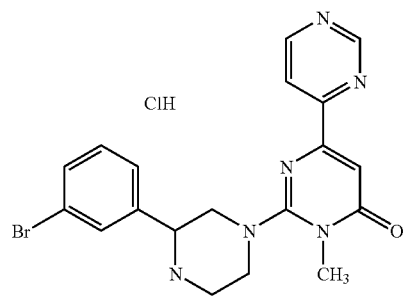
YA1543 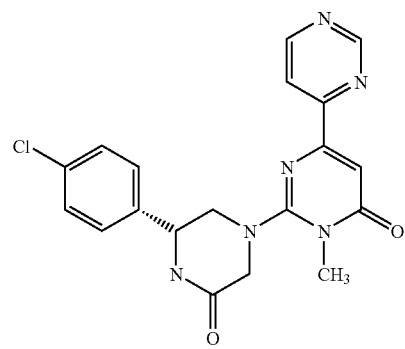
YA1544 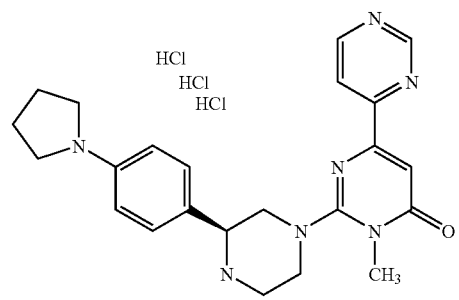
YA1545 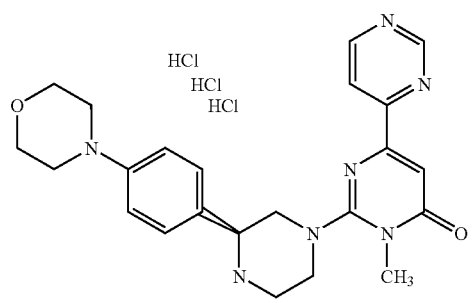
YA1546 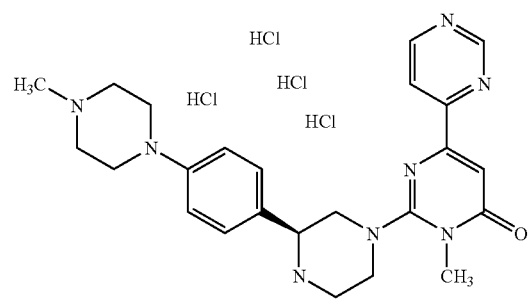

-continued
YA1547
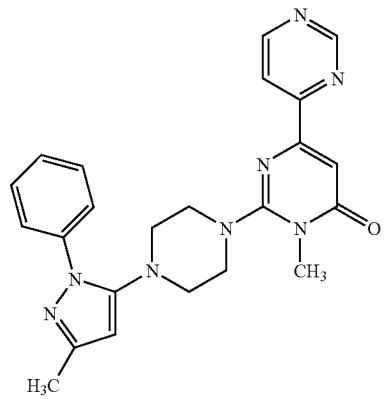
YA1548
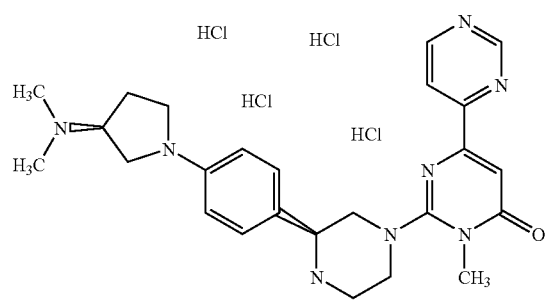
YA1549
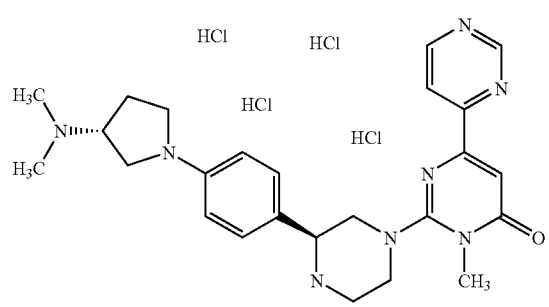
YA1550
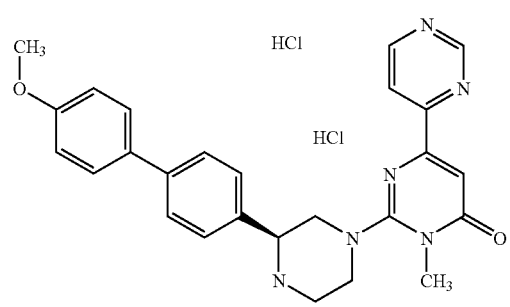
YA1551
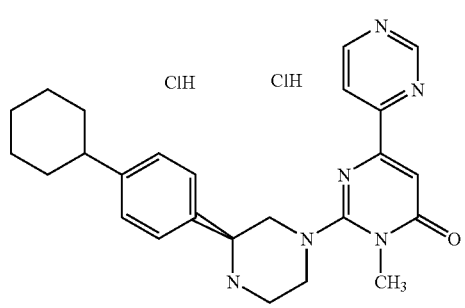

-continued
YA1552 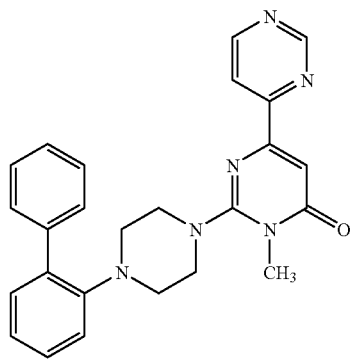
YA1553 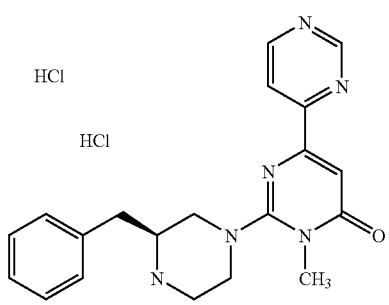
YA1554 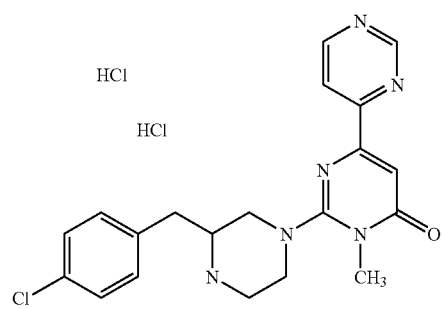
YA1555 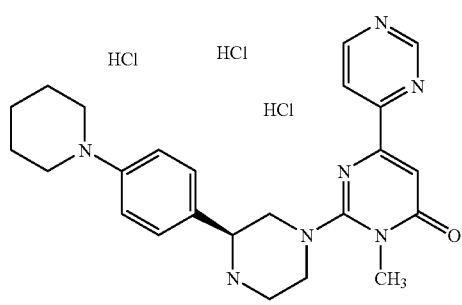
YA1556 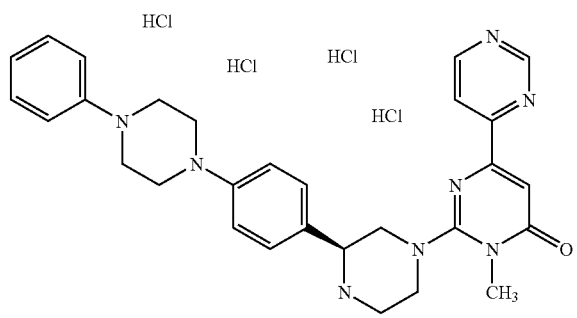

YA1557 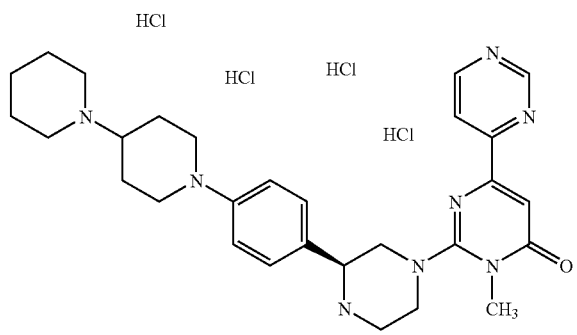
YA1558 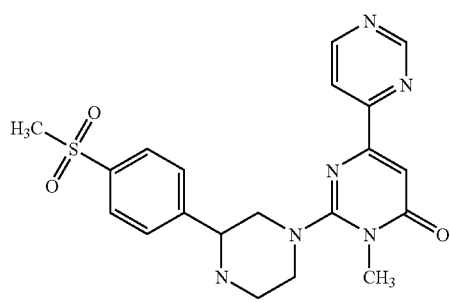
YA1559 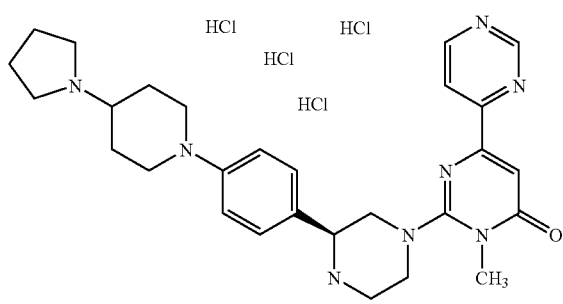
YA1560 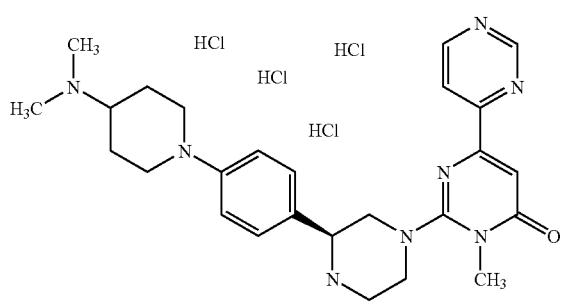
YA1561 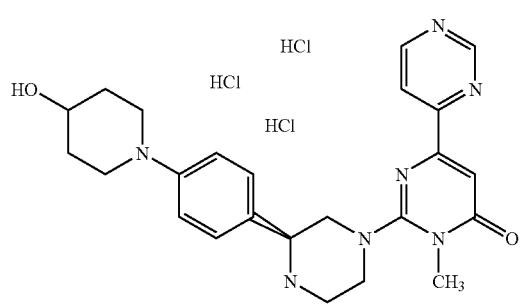

YA1562 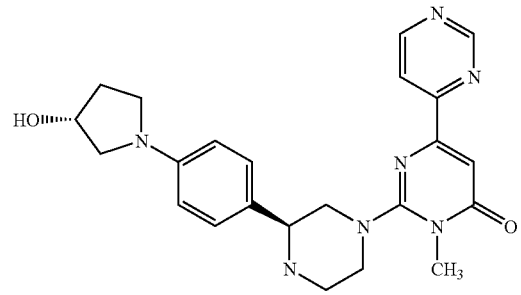
YA1563 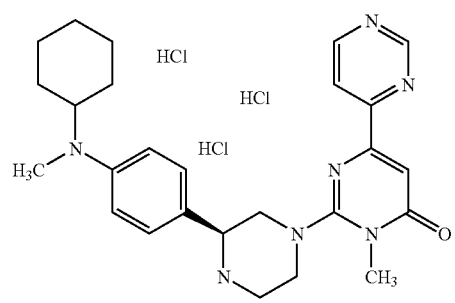
YA1564 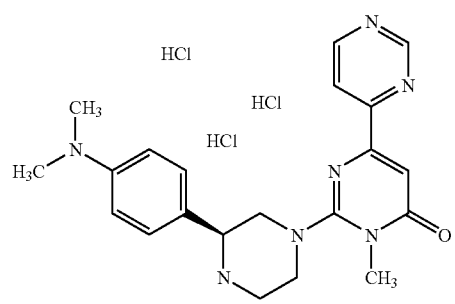
YA1565 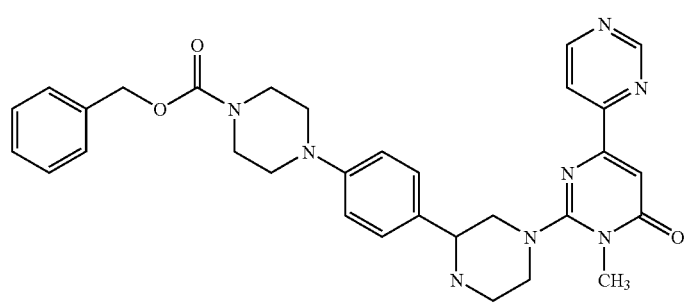
YA1566 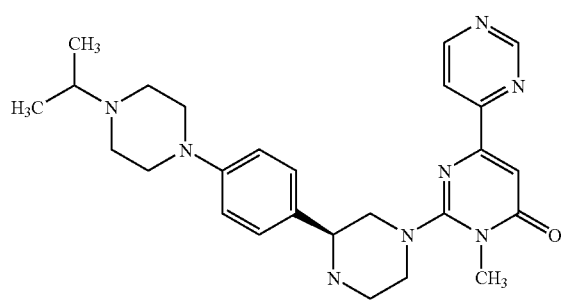

YA1567 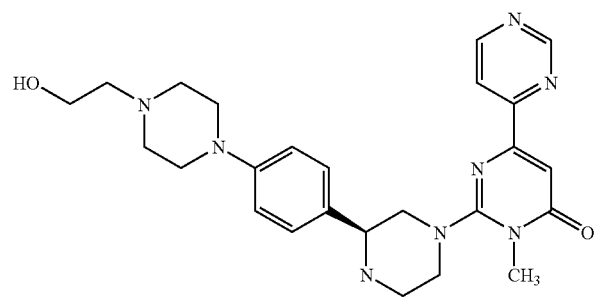
YA1568 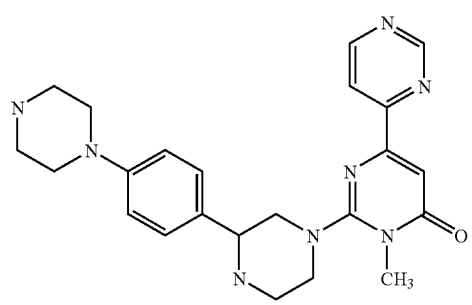
YA1569 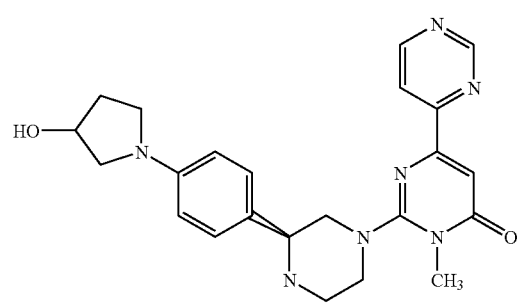
YA1570 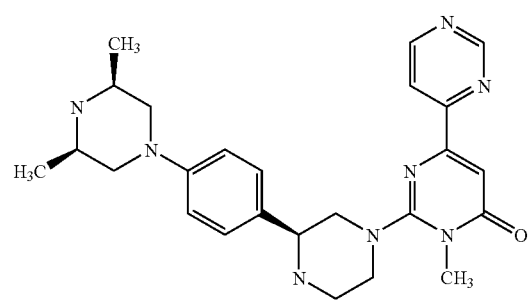
YA1571 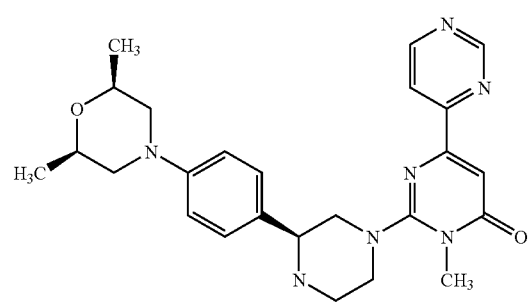

YA1572 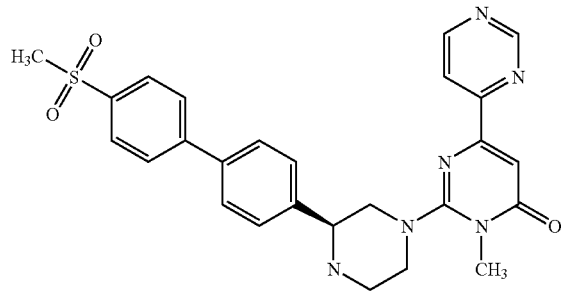
YA1573 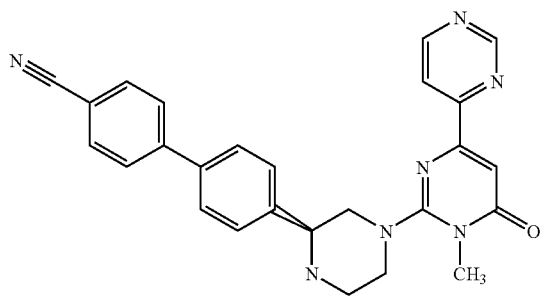
YA1574 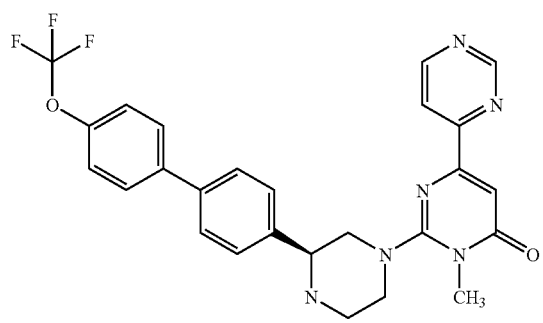
YA1575 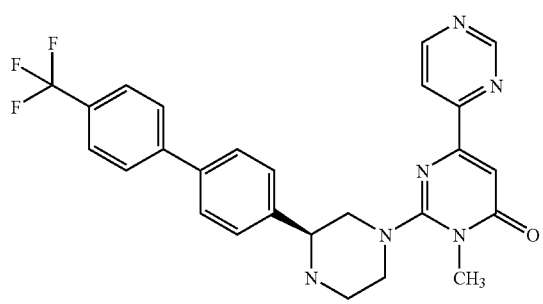
YA1576 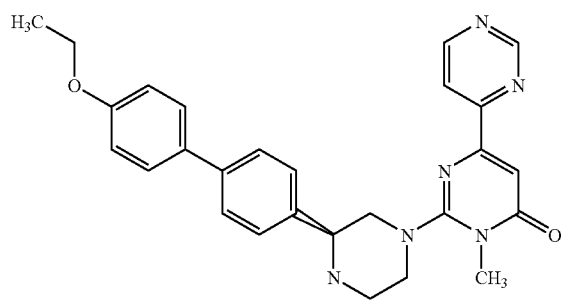

-continued
YA1577 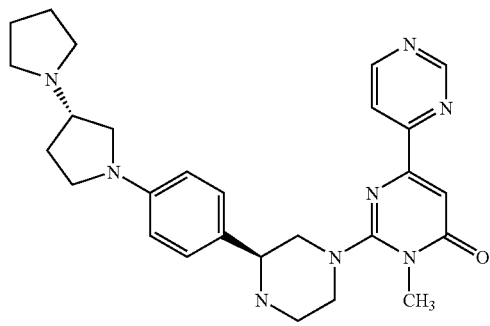
YA1578 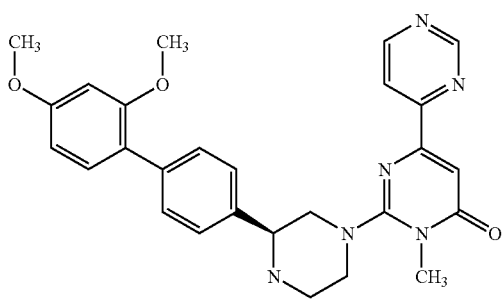
YA1579 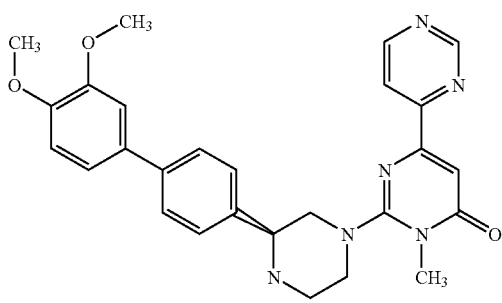
YA1580 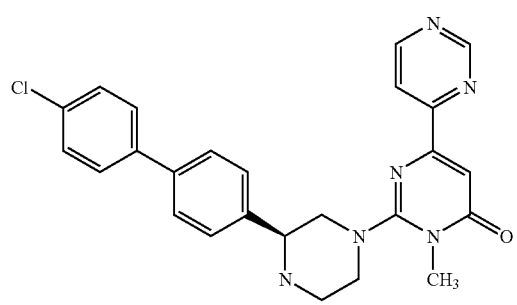
YA1581 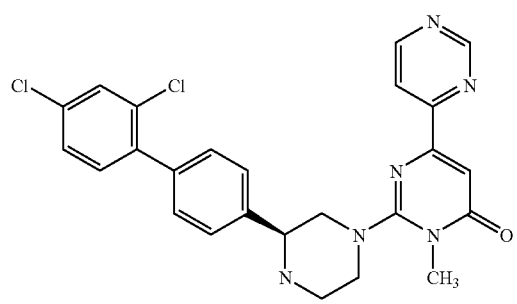

-continued
YA1582 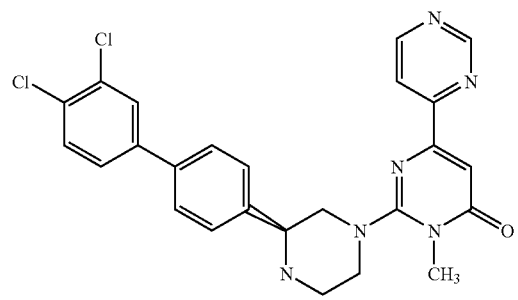
YA1583 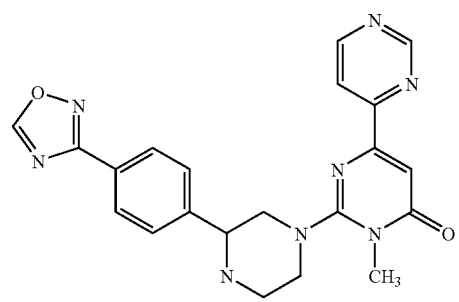
YA1584 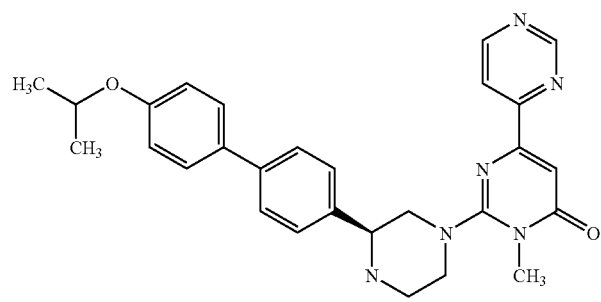
YA1585 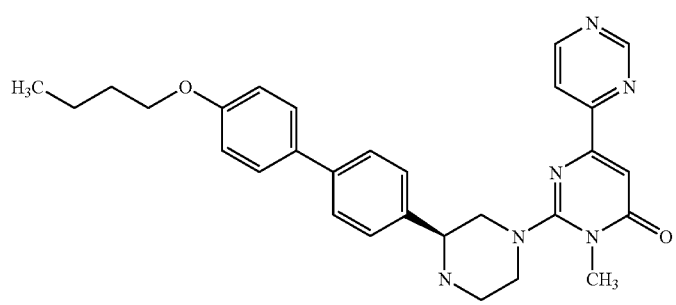
YA1586 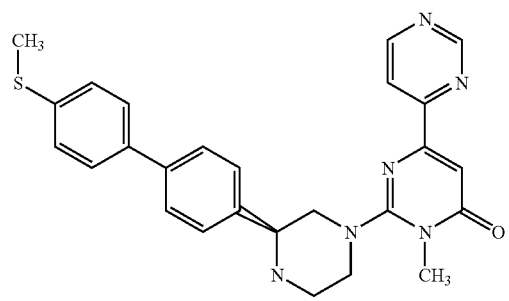

YA1587
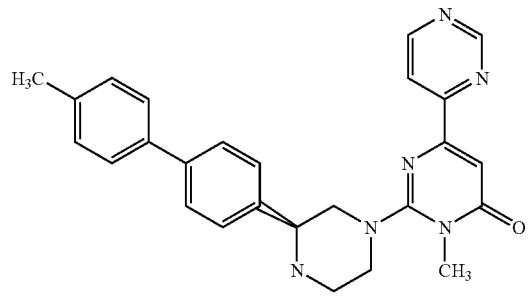
YA1588
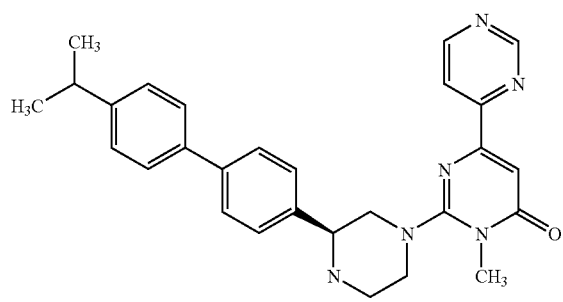
YA1589
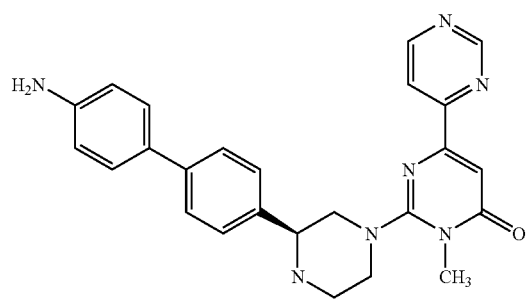
YA1590
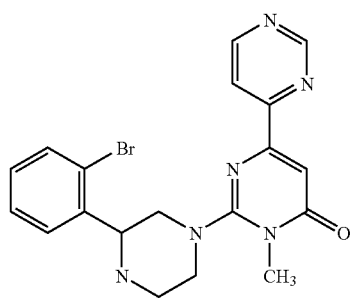

TABLE 4
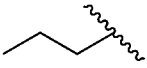
| No. | R1 | R2 | R3 | R4 | R5 |
|---|---|---|---|---|---|
| YB1 | CH3— | CH3— | H | H | H |
| YB2 | CH3— | CH3CH2— | H | H | H |
| YB3 | CH3— | 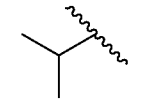 | H | H | H |
| YB4 | CH3— | 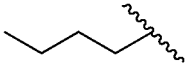 | H | H | H |
| YB5 | CH3— | 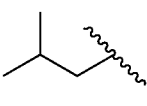 | H | H | H |
| YB6 | CH3— | 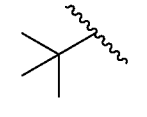 | H | H | H |
| YB7 | CH3— | 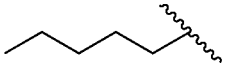 | H | H | H |
| YB8 | CH3— | 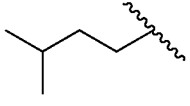 | H | H | H |
| YB9 | CH3— | 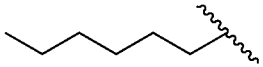 | H | H | H |
| YB10 | CH3— | 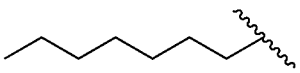 | H | H | H |
| YB11 | CH3— | 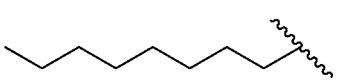 | H | H | H |
| YB12 | CH3— | 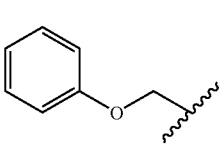 | H | H | H |
| YB13 | CH3— |  | H | H | H |

-continued
| | | | | | |
|---|---|---|---|---|---|
| YB14 | CH3— | 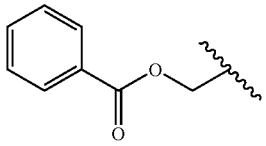 | H | H | H |
| YB15 | CH3— | 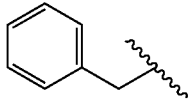 | H | H | H |
| YB16 | CH3— | 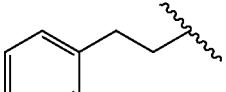 | H | H | H |
| YB17 | CH3— | 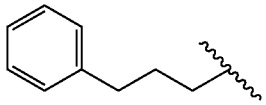 | H | H | H |
| YB18 | CH3— | 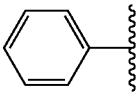 | H | H | H |
| YB19 | CH3— | 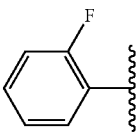 | H | H | H |
| YB20 | CH3— | 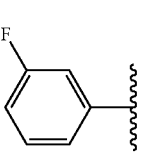 | H | H | H |
| YB21 | CH3— | 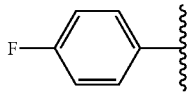 | H | H | H |
| YB22 | CH3— | 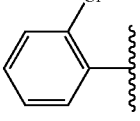 | H | H | H |
| YB23 | CH3— | 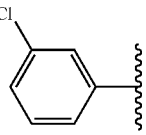 | H | H | H |
| YB24 | CH3— | 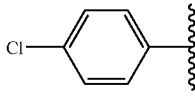 | H | H | H |
| YB25 | CH3— | 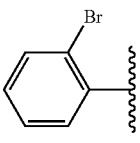 | H | H | H |

-continued
| | | | | | |
|---|---|---|---|---|---|
| YB26 | CH3— | 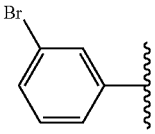 | H | H | H |
| YB27 | CH3— | 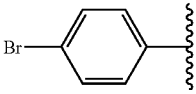 | H | H | H |
| YB28 | CH3— | 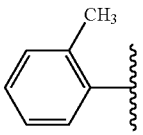 | H | H | H |
| YB29 | CH3— | 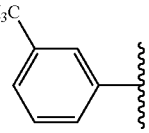 | H | H | H |
| YB30 | CH3— | 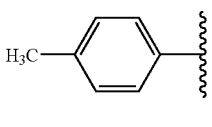 | H | H | H |
| YB31 | CH3— | 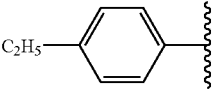 | H | H | H |
| YB32 | CH3— | 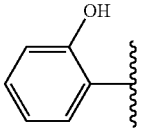 | H | H | H |
| YB33 | CH3— | 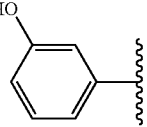 | H | H | H |
| YB34 | CH3— | 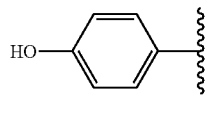 | H | H | H |
| YB35 | CH3— | 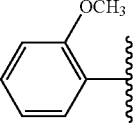 | H | H | H |
| YB36 | CH3— | 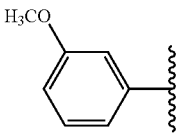 | H | H | H |
| YB37 | CH3— | 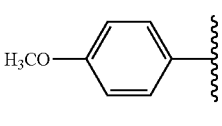 | H | H | H |

-continued
| | | | | | |
|---|---|---|---|---|---|
| YB38 | CH3— | 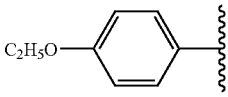 | H | H | H |
| YB39 | CH3— | 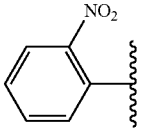 | H | H | H |
| YB40 | CH3— | 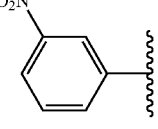 | H | H | H |
| YB41 | CH3— | 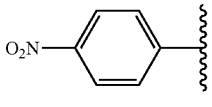 | H | H | H |
| YB42 | CH3— | 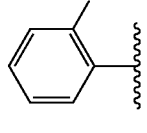 | H | H | H |
| YB43 | CH3— | 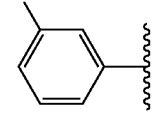 | H | H | H |
| YB44 | CH3— | 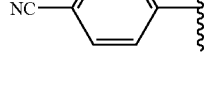 | H | H | H |
| YB45 | CH3— | 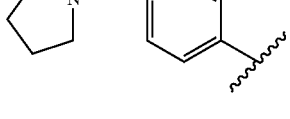 | H | H | H |
| YB46 | CH3— | 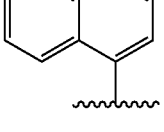 | H | H | H |
| YB47 | CH3— | 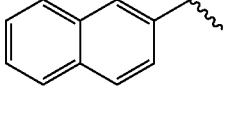 | H | H | H |
| YB48 | CH3— | 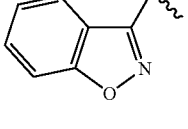 | H | H | H |

-continued

| | | | | | |
|---|---|---|---|---|---|
| YB49 | CH3— | 6-fluoro-1,2-benzisoxazol-3-yl | H | H | H |
| YB50 | CH3— | 1,2-benzisoxazol-3-yl | H | H | H |
| YB51 | CH3— | 1,2-benzisoxazol-3-yl | H | H | H |
| YB52 | CH3— | phenyl | OH | H | H |
| YB53 | CH3— | 2-fluorophenyl | OH | H | H |
| YB54 | CH3— | 3-fluorophenyl | OH | H | H |
| YB55 | CH3— | 4-fluorophenyl | OH | H | H |
| YB56 | CH3— | 2-chlorophenyl | OH | H | H |
| YB57 | CH3— | 3-chlorophenyl | OH | H | H |
| YB58 | CH3— | 4-chlorophenyl | OH | H | H |
| YB59 | CH3— | 2-bromophenyl | OH | H | H |

-continued

| | | | | | |
|---|---|---|---|---|---|
| YB60 | CH3— | 3-bromophenyl | OH | H | H |
| YB61 | CH3— | 4-bromophenyl | OH | H | H |
| YB62 | CH3— | 2-methylphenyl | OH | H | H |
| YB63 | CH3— | 3-methylphenyl | OH | H | H |
| YB64 | CH3— | 4-methylphenyl | OH | H | H |
| YB65 | CH3— | 4-ethylphenyl | OH | H | H |
| YB66 | CH3— | 2-hydroxyphenyl | OH | H | H |
| YB67 | CH3— | 3-hydroxyphenyl | OH | H | H |
| YB68 | CH3— | 4-hydroxyphenyl | OH | H | H |
| YB69 | CH3— | 2-methoxyphenyl | OH | H | H |
| YB70 | CH3— | 3-methoxyphenyl | OH | H | H |
| YB71 | CH3— | 4-methoxyphenyl | OH | H | H |

-continued
| | | | | | |
|---|---|---|---|---|---|
| YB72 | CH3— | 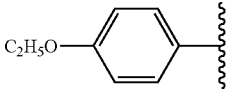 | OH | H | H |
| YB73 | CH3— | 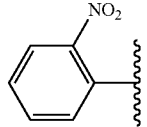 | OH | H | H |
| YB74 | CH3— | 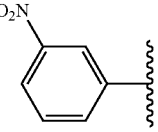 | OH | H | H |
| YB75 | CH3— | 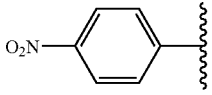 | OH | H | H |
| YB76 | CH3— | 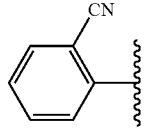 | OH | H | H |
| YB77 | CH3— | 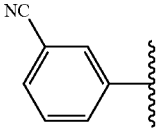 | OH | H | H |
| YB78 | CH3— | 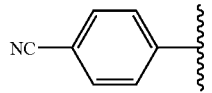 | OH | H | H |
| YB79 | CH3— | 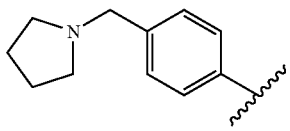 | OH | H | H |
| YB80 | CH3— | 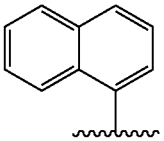 | OH | H | H |
| YB81 | CH3— | 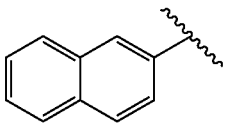 | OH | H | H |
| YB82 | CH3— | 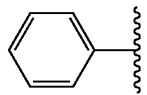 | CN | H | H |
| YB83 | CH3— | 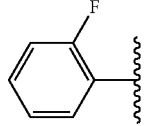 | CN | H | H |

-continued
| | | | | | |
|---|---|---|---|---|---|
| YB84 | CH3— | 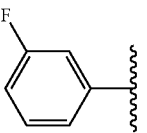 | CN | H | H |
| YB85 | CH3— | 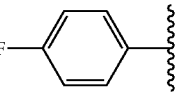 | CN | H | H |
| YB86 | CH3— | 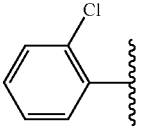 | CN | H | H |
| YB87 | CH3— | 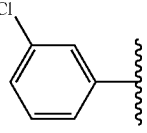 | CN | H | H |
| YB88 | CH3— | 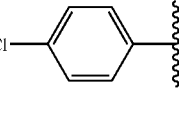 | CN | H | H |
| YB89 | CH3— | 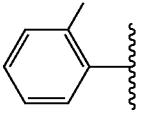 | CN | H | H |
| YB90 | CH3— | 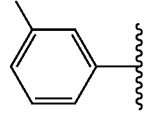 | CN | H | H |
| YB91 | CH3— | 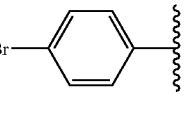 | CN | H | H |
| YB92 | CH3— | 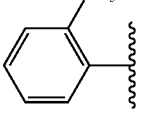 | CN | H | H |
| YB93 | CH3— | 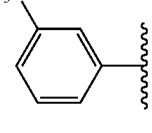 | CN | H | H |
| YB94 | CH3— | 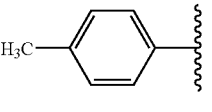 | CN | H | H |
| YB95 | CH3— | 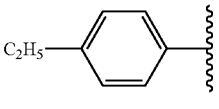 | CN | H | H |

-continued
| | | | | | |
|---|---|---|---|---|---|
| YB96 | CH3— | 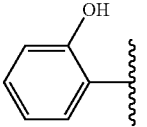 | CN | H | H |
| YB97 | CH3— | 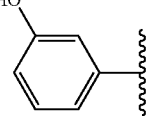 | CN | H | H |
| YB98 | CH3— | 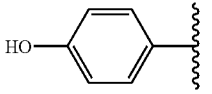 | CN | H | H |
| YB99 | CH3— | 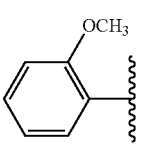 | CN | H | H |
| YB100 | CH3— | 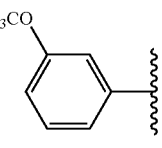 | CN | H | H |
| YB101 | CH3— | 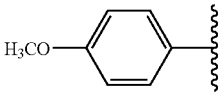 | CN | H | H |
| YB102 | CH3— | 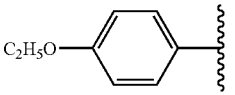 | CN | H | H |
| YB103 | CH3— | 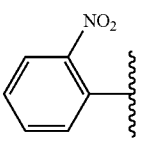 | CN | H | H |
| YB104 | CH3— | 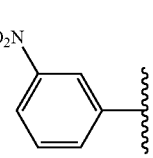 | CN | H | H |
| YB105 | CH3— | 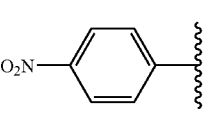 | CN | H | H |
| YB106 | CH3— | 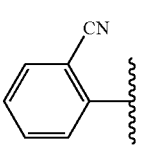 | CN | H | H |
| YB107 | CH3— | 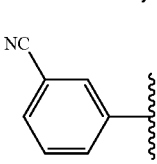 | CN | H | H |

| | | | | | |
|---|---|---|---|---|---|
| YB108 | CH3— | 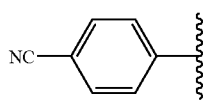 | CN | H | H |
| YB109 | CH3— | 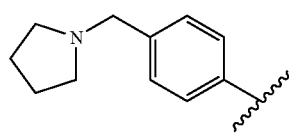 | CN | H | H |
| YB110 | CH3— | 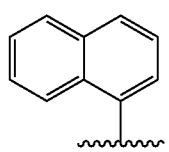 | CN | H | H |
| YB111 | CH3— | 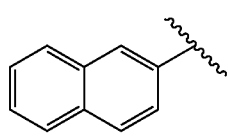 | CN | H | H |
| YB112 | CH3— | H | H | CH3— | H |
| YB113 | CH3— | H | H | CH3CH2— | H |
| YB114 | CH3— | H | H | 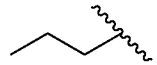 | H |
| YB115 | CH3— | H | H | 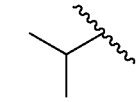 | H |
| YB116 | CH3— | H | H | 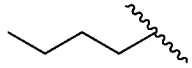 | H |
| YB117 | CH3— | H | H | 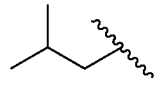 | H |
| YB118 | CH3— | H | H | 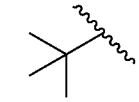 | H |
| YB119 | CH3— | H | H | 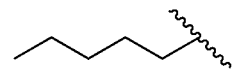 | H |
| YB120 | CH3— | H | H | 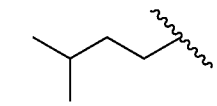 | H |
| YB121 | CH3— | H | H | 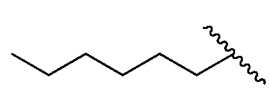 | H |
| YB122 | CH3— | H | H | 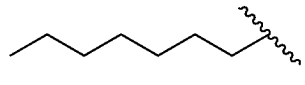 | H |
| YB123 | CH3— | H | H | 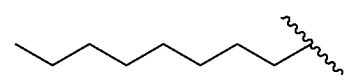 | H |

-continued

| | | | | | |
|---|---|---|---|---|---|
| YB124 | CH3— | H | H | benzyl (CH2-Ph) | H |
| YB125 | CH3— | H | H | phenethyl (CH2CH2-Ph) | H |
| YB126 | CH3— | H | H | phenylpropyl (CH2CH2CH2-Ph) | H |
| YB127 | CH3— | H | H | phenyl | H |
| YB128 | CH3— | H | H | 2-fluorophenyl | H |
| YB129 | CH3— | H | H | 3-fluorophenyl | H |
| YB130 | CH3— | H | H | 4-fluorophenyl | H |
| YB131 | CH3— | H | H | 2-chlorophenyl | H |
| YB132 | CH3— | H | H | 3-chlorophenyl | H |
| YB133 | CH3— | H | H | 4-chlorophenyl | H |
| YB134 | CH3— | H | H | 3,4-dichlorophenyl | H |
| YB135 | CH3— | H | H | 2-bromophenyl | H |

-continued
| | | | | | |
|---|---|---|---|---|---|
| YB136 | CH3— | H | H | 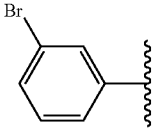 3-Br-C6H4— | H |
| YB137 | CH3— | H | H | 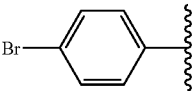 4-Br-C6H4— | H |
| YB138 | CH3— | H | H | 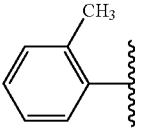 2-CH3-C6H4— | H |
| YB139 | CH3— | H | H | 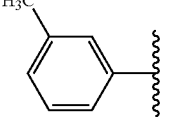 3-CH3-C6H4— | H |
| YB140 | CH3— | H | H | 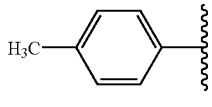 4-CH3-C6H4— | H |
| YB141 | CH3— | H | H | 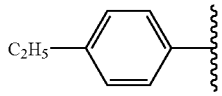 4-C2H5-C6H4— | H |
| YB142 | CH3— | H | H | 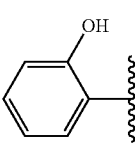 2-OH-C6H4— | H |
| YB143 | CH3— | H | H | 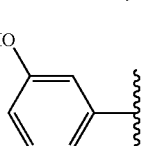 3-OH-C6H4— | H |
| YB144 | CH3— | H | H | 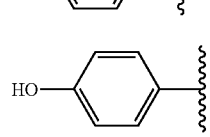 4-OH-C6H4— | H |
| YB145 | CH3— | H | H | 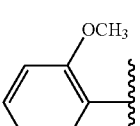 2-OCH3-C6H4— | H |
| YB146 | CH3— | H | H | 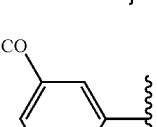 3-OCH3-C6H4— | H |
| YB147 | CH3— | H | H | 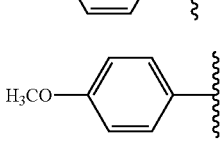 4-OCH3-C6H4— | H |

-continued
| | | | | | |
|---|---|---|---|---|---|
| YB148 | CH3— | H | H | 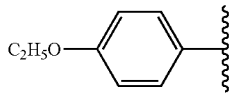 4-C2H5O-C6H4— | H |
| YB149 | CH3— | H | H | 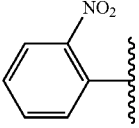 2-NO2-C6H4— | H |
| YB150 | CH3— | H | H | 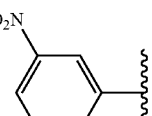 3-NO2-C6H4— | H |
| YB151 | CH3— | H | H | 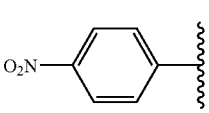 4-NO2-C6H4— | H |
| YB152 | CH3— | H | H | 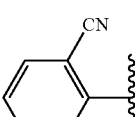 2-CN-C6H4— | H |
| YB153 | CH3— | H | H | 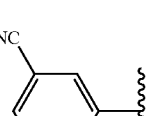 3-CN-C6H4— | H |
| YB154 | CH3— | H | H | 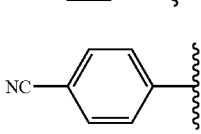 4-CN-C6H4— | H |
| YB155 | CH3— | H | H | 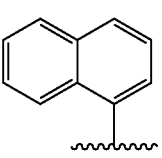 1-naphthyl | H |
| YB156 | CH3— | H | H | 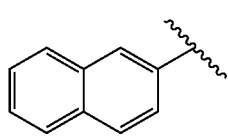 2-naphthyl | H |
| YB157 | CH3— | H | H | 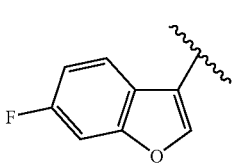 6-fluorobenzofuran-3-yl | H |
| YB158 | CH3— | H | H | 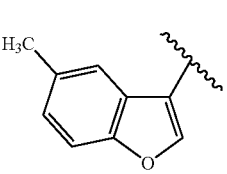 5-methylbenzofuran-3-yl | H |

-continued
| | | | | | |
|---|---|---|---|---|---|
| YB159 | CH3— | H | H | 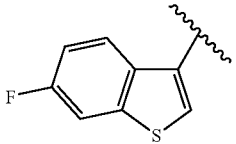 | H |
| YB160 | CH3— | H | H | 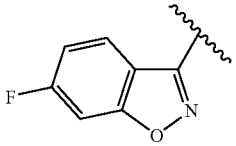 | H |
| YB161 | CH3— | H | H | 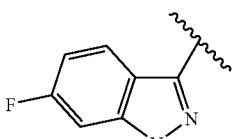 | H |
| YB162 | CH3— | H | H | 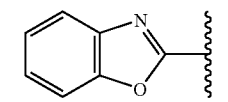 | H |
| YB163 | CH3— | H | H | 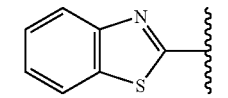 | H |
| YB164 | CH3— | H | H | 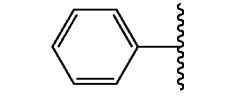 | OH |
| YB165 | CH3— | H | H | 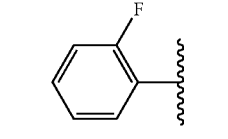 | OH |
| YB166 | CH3— | H | H | 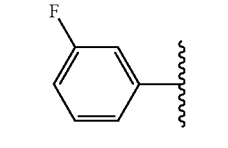 | OH |
| YB167 | CH3— | H | H | 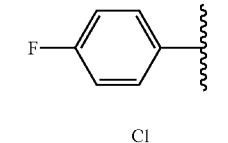 | OH |
| YB168 | CH3— | H | H | 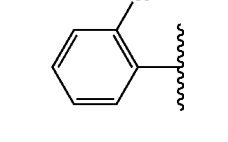 | OH |
| YB169 | CH3— | H | H | 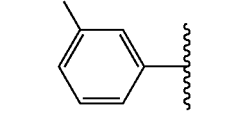 | OH |

-continued
| | | | | | |
|---|---|---|---|---|---|
| YB170 | CH3— | H | H | 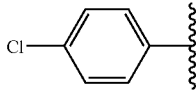 4-Cl-phenyl | OH |
| YB171 | CH3— | H | H | 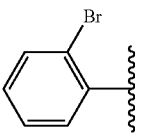 2-Br-phenyl | OH |
| YB172 | CH3— | H | H | 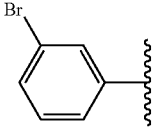 3-Br-phenyl | OH |
| YB173 | CH3— | H | H | 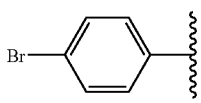 4-Br-phenyl | OH |
| YB174 | CH3— | H | H | 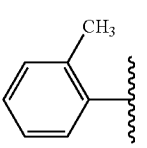 2-CH3-phenyl | OH |
| YB175 | CH3— | H | H | 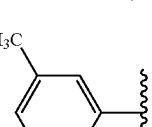 3-CH3-phenyl | OH |
| YB176 | CH3— | H | H | 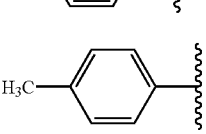 4-CH3-phenyl | OH |
| YB177 | CH3— | H | H | 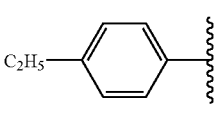 4-C2H5-phenyl | OH |
| YB178 | CH3— | H | H | 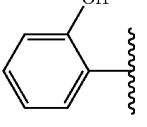 2-OH-phenyl | OH |
| YB179 | CH3— | H | H | 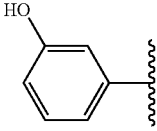 3-OH-phenyl | OH |
| YB180 | CH3— | H | H | 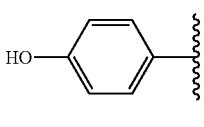 4-OH-phenyl | OH |
| YB181 | CH3— | H | H | 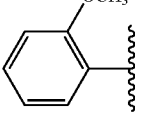 2-OCH3-phenyl | OH |

-continued
| | | | | | |
|---|---|---|---|---|---|
| YB182 | CH3— | H | H | 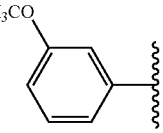 3-methoxyphenyl | OH |
| YB183 | CH3— | H | H | 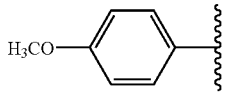 4-methoxyphenyl | OH |
| YB184 | CH3— | H | H | 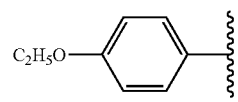 4-ethoxyphenyl | OH |
| YB185 | CH3— | H | H | 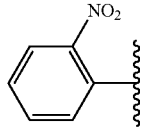 2-nitrophenyl | OH |
| YB186 | CH3— | H | H | 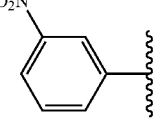 3-nitrophenyl | OH |
| YB187 | CH3— | H | H | 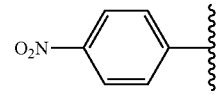 4-nitrophenyl | OH |
| YB188 | CH3— | H | H | 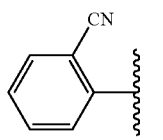 2-cyanophenyl | OH |
| YB189 | CH3— | H | H | 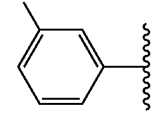 3-cyanophenyl | OH |
| YB190 | CH3— | H | H | 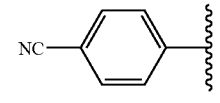 4-cyanophenyl | OH |
| YB191 | CH3— | H | H | 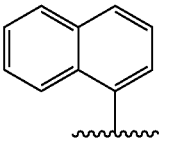 1-naphthyl | OH |
| YB192 | CH3— | H | H | 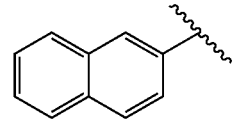 2-naphthyl | OH |
| YB193 | CH3— | H | H | 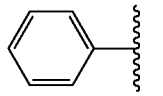 phenyl | CN |

-continued
| | | | | | |
|---|---|---|---|---|---|
| YB194 | CH3— | H | H | 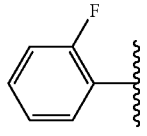 2-F-phenyl | CN |
| YB195 | CH3— | H | H | 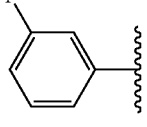 3-F-phenyl | CN |
| YB196 | CH3— | H | H | 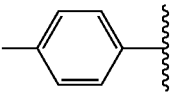 4-F-phenyl | CN |
| YB197 | CH3— | H | H | 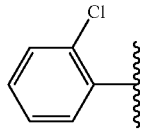 2-Cl-phenyl | CN |
| YB198 | CH3— | H | H | 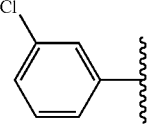 3-Cl-phenyl | CN |
| YB199 | CH3— | H | H | 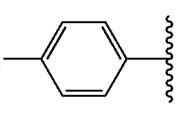 4-Cl-phenyl | CN |
| YB200 | CH3— | H | H | 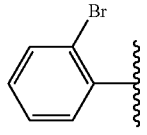 2-Br-phenyl | CN |
| YB201 | CH3— | H | H | 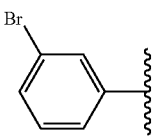 3-Br-phenyl | CN |
| YB202 | CH3— | H | H | 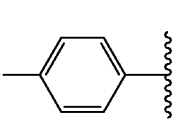 4-Br-phenyl | CN |
| YB203 | CH3— | H | H | 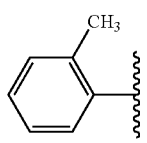 2-CH3-phenyl | CN |
| YB204 | CH3— | H | H | 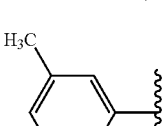 3-CH3-phenyl | CN |
| YB205 | CH3— | H | H | 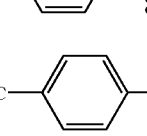 4-CH3-phenyl | CN |

-continued
| | | | | | |
|---|---|---|---|---|---|
| YB206 | CH3— | H | H | 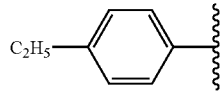 4-ethylphenyl | CN |
| YB207 | CH3— | H | H | 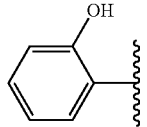 2-hydroxyphenyl | CN |
| YB208 | CH3— | H | H | 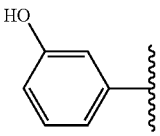 3-hydroxyphenyl | CN |
| YB209 | CH3— | H | H | 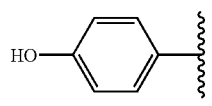 4-hydroxyphenyl | CN |
| YB210 | CH3— | H | H | 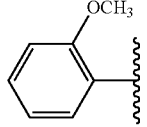 2-methoxyphenyl | CN |
| YB211 | CH3— | H | H | 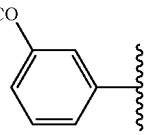 3-methoxyphenyl | CN |
| YB212 | CH3— | H | H | 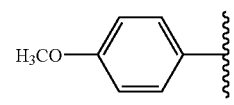 4-methoxyphenyl | CN |
| YB213 | CH3— | H | H | 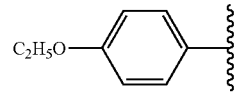 4-ethoxyphenyl | CN |
| YB214 | CH3— | H | H | 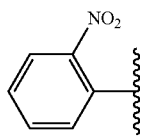 2-nitrophenyl | CN |
| YB215 | CH3— | H | H | 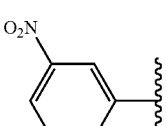 3-nitrophenyl | CN |
| YB216 | CH3— | H | H | 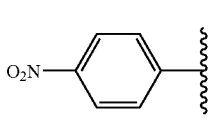 4-nitrophenyl | CN |
| YB217 | CH3— | H | H | 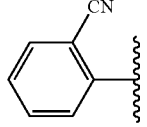 2-cyanophenyl | CN |

-continued
| | | | | | |
|---|---|---|---|---|---|
| YB218 | CH3— | H | H | 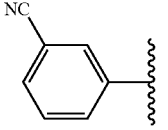 | CN |
| YB219 | CH3— | H | H | 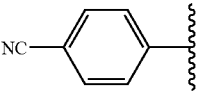 | CN |
| YB220 | CH3— | H | H | 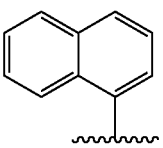 | CN |
| YB221 | CH3— | H | H | 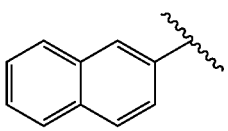 | CN |
| YB222 | CH3— | H | H | 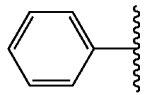 | 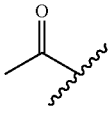 |
| YB223 | CH3— | H | H | 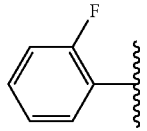 | 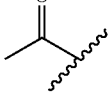 |
| YB224 | CH3— | H | H | 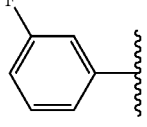 | 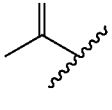 |
| YB225 | CH3— | H | H | 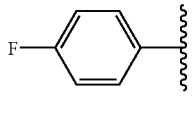 | 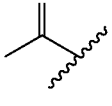 |
| YB226 | CH3— | H | H | 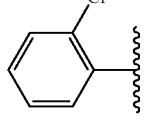 | 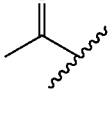 |
| YB227 | CH3— | H | H | 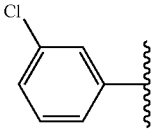 | 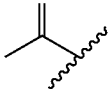 |
| YB228 | CH3— | H | H | 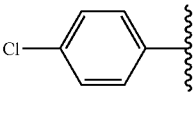 | 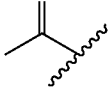 |

-continued

| | | | | | |
|---|---|---|---|---|---|
| YB229 | CH3— | H | H | 2-bromophenyl | acetyl |
| YB230 | CH3— | H | H | 3-bromophenyl | acetyl |
| YB231 | CH3— | H | H | 4-bromophenyl | acetyl |
| YB232 | CH3— | H | H | 2-methylphenyl | acetyl |
| YB233 | CH3— | H | H | 3-methylphenyl | acetyl |
| YB234 | CH3— | H | H | 4-methylphenyl | acetyl |
| YB235 | CH3— | H | H | 4-ethylphenyl | acetyl |
| YB236 | CH3— | H | H | 2-hydroxyphenyl | acetyl |
| YB237 | CH3— | H | H | 3-hydroxyphenyl | acetyl |
| YB238 | CH3— | H | H | 4-hydroxyphenyl | acetyl |
| YB239 | CH3— | H | H | 2-methoxyphenyl | acetyl |

-continued

| | | | | | |
|---|---|---|---|---|---|
| YB240 | CH3— | H | H | 3-methoxyphenyl | acetyl |
| YB241 | CH3— | H | H | 4-methoxyphenyl | acetyl |
| YB242 | CH3— | H | H | 4-ethoxyphenyl | acetyl |
| YB243 | CH3— | H | H | 2-nitrophenyl | acetyl |
| YB244 | CH3— | H | H | 3-nitrophenyl | acetyl |
| YB245 | CH3— | H | H | 4-nitrophenyl | acetyl |
| YB246 | CH3— | H | H | 2-cyanophenyl | acetyl |
| YB247 | CH3— | H | H | 3-cyanophenyl | acetyl |
| YB248 | CH3— | H | H | 4-cyanophenyl | acetyl |
| YB249 | CH3— | H | H | 1-naphthyl | acetyl |
| YB250 | CH3— | H | H | 2-naphthyl | acetyl |

| No. | STRUCTURE |
|---|---|
| YB251 | 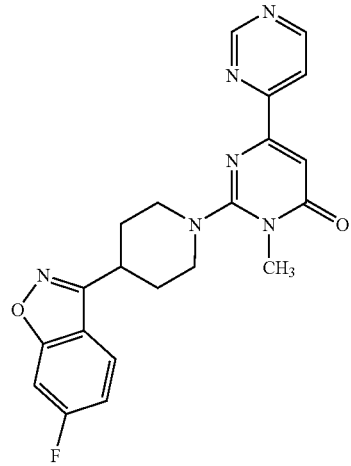 |
| YB252 | 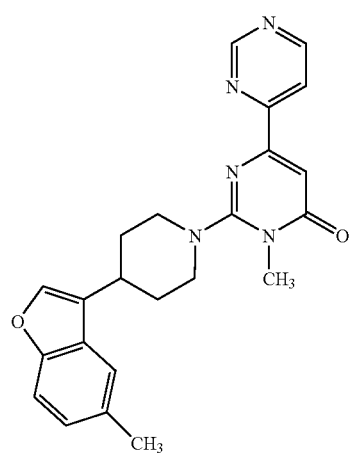 |
| YB253 | 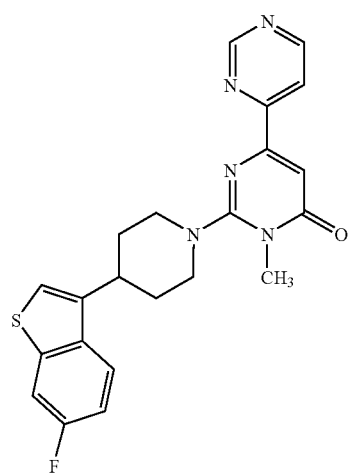 |

YB254 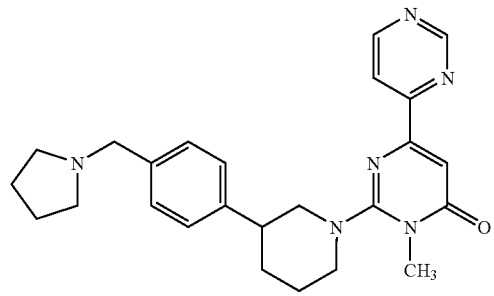
YB255 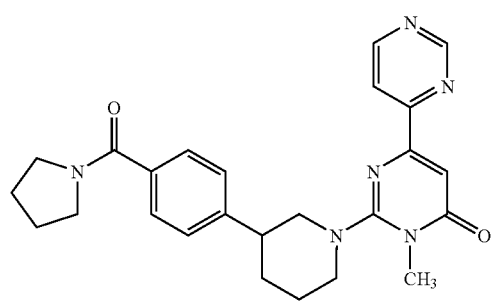
YB256 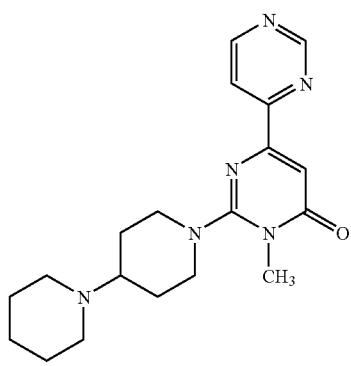
YB257 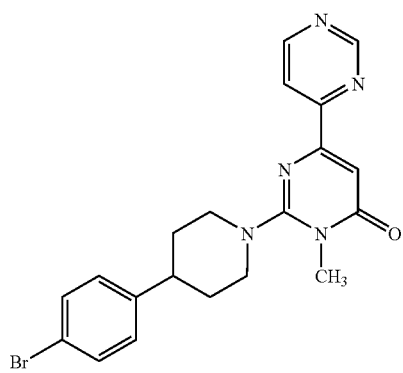

-continued
YB258
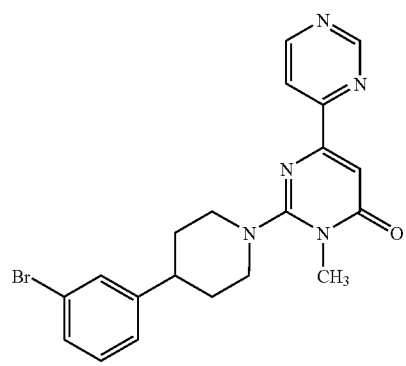
YB259
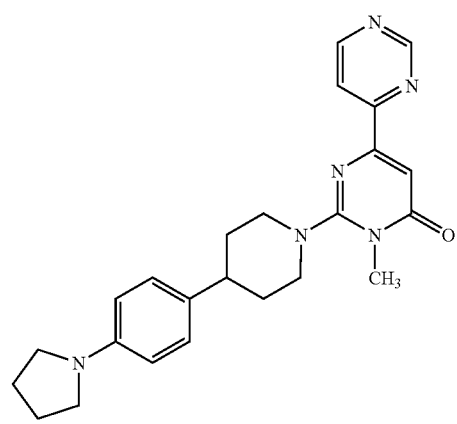
YB260
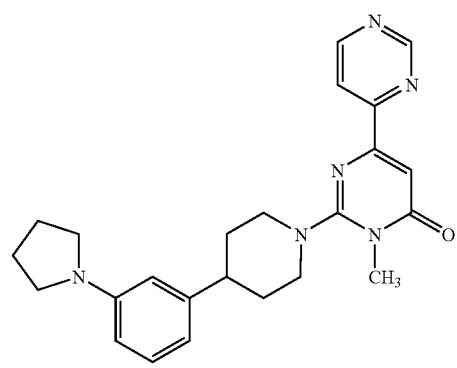
YB261
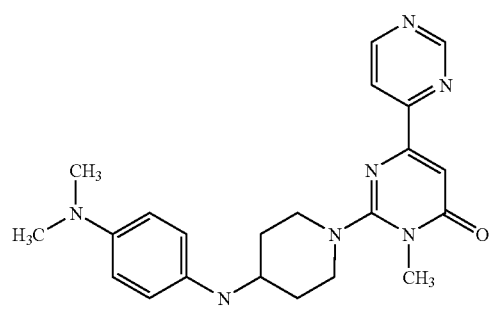

YB262 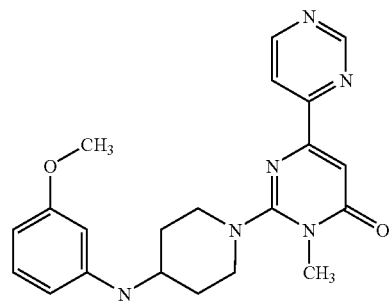
YB263 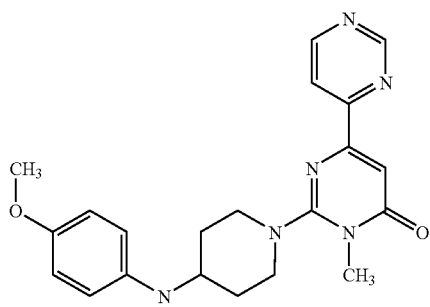
YB264 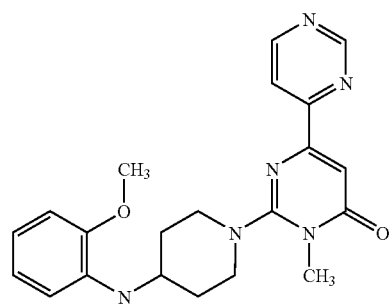
YB265 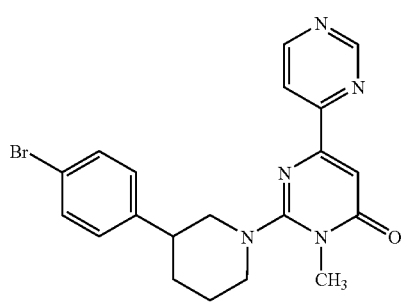
YB266 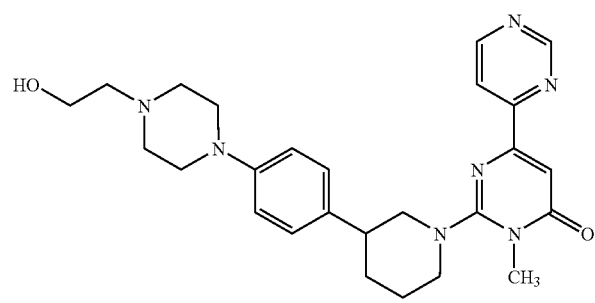

YB267 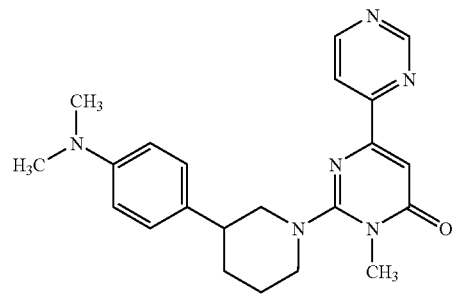
YB268 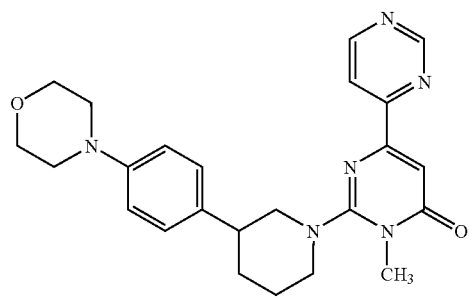
YB269 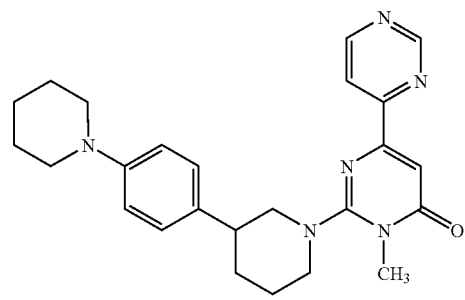
YB270 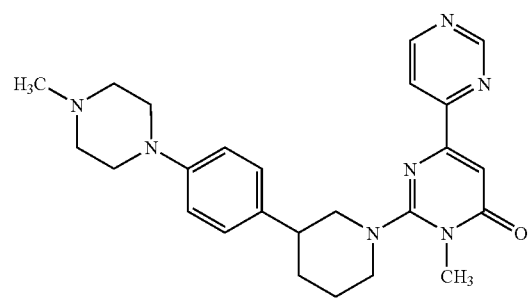
YB271 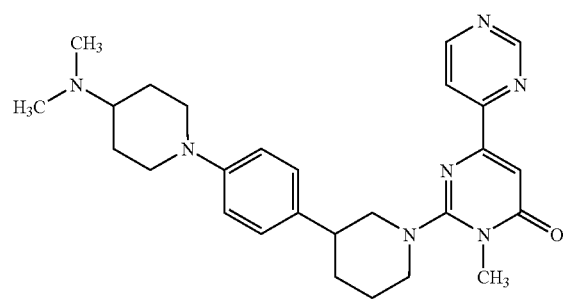

-continued
YB272
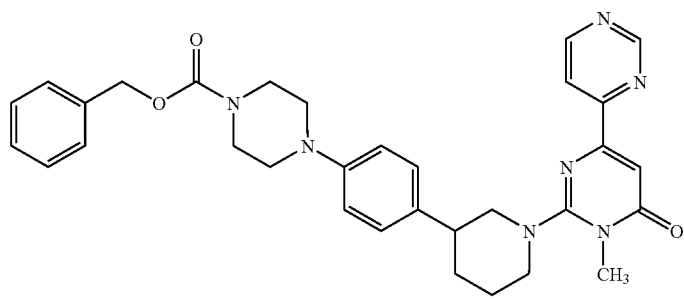
YB273
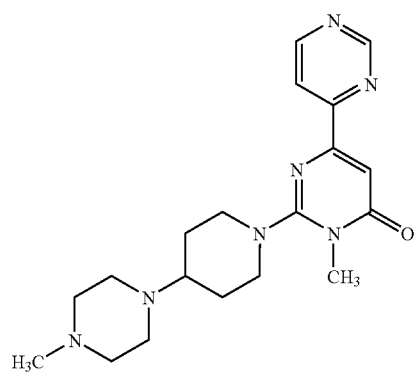
YB274
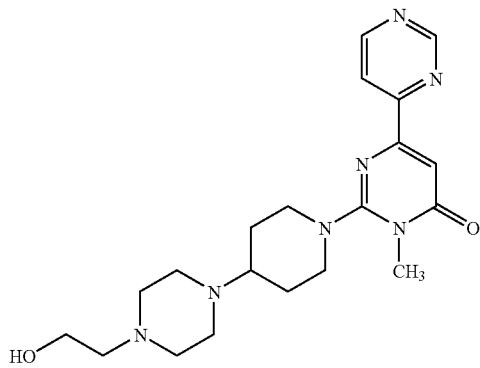
YB275
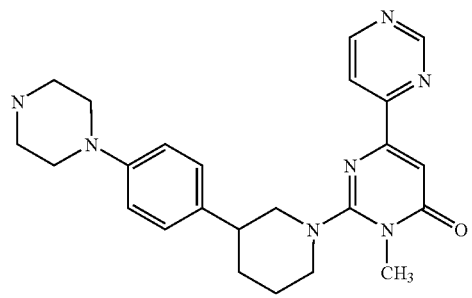

-continued

YB276

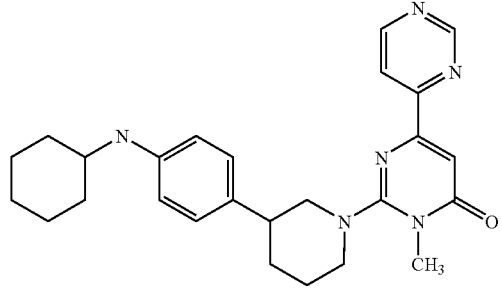

YB277

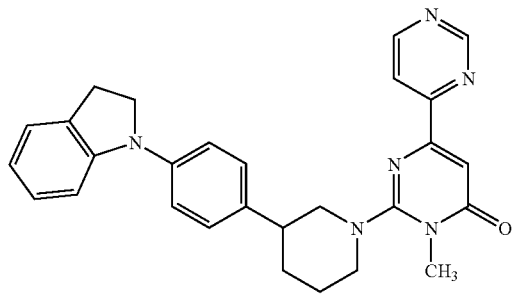

YB278

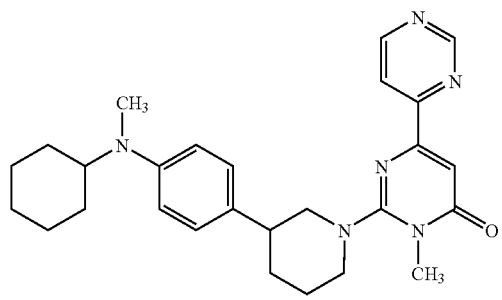

Particularly preferred compounds of the present invention represented by formula (I) include:
2-(3-Phenylpiperazin-1-yl)-3-methyl-6-(4-pyridyl)-3H-pyrimidin-4-one;
2-(3-(4-Fluorophenyl)piperazin-1-yl)-3-methyl-6-(4-pyridyl)-3H-pyrimidin-4-one;
2-(3-(3-Fluorophenyl)piperazin-1-yl)-3-methyl-6-(4-pyridyl)-3H-pyrimidin-4-one;
2-(3-(2-Fluorophenyl)piperazin-1-yl)-3-methyl-6-(4-pyridyl)-3H-pyrimidin-4-one;
2-(3-(4-Chlorophenyl)piperazin-1-yl)-3-methyl-6-(4-pyridyl)-3H-pyrimidin-4-one;
(S)-2-(3-(4-Chlorophenyl)piperazin-1-yl)-3-methyl-6-(4-pyridyl)-3H-pyrimidin-4-one;
(R)-2-(3-(4-Chlorophenyl)piperazin-1-yl)-3-methyl-6-(4-pyridyl)-3H-pyrimidin-4-one;
2-(3-(3-Chlorophenyl)piperazin-1-yl)-3-methyl-6-(4-pyridyl)-3H-pyrimidin-4-one;
2-(3-(2-Chlorophenyl)piperazin-1-yl)-3-methyl-6-(4-pyridyl)-3H-pyrimidin-4-one;
2-(3-(4-Bromophenyl)piperazin-1-yl)-3-methyl-6-(4-pyridyl)-3H-pyrimidin-4-one;
2-(3-(3-Bromophenyl)piperazin-1-yl)-3-methyl-6-(4-pyridyl)-3H-pyrimidin-4-one;
2-(3-(2-Bromophenyl)piperazin-1-yl)-3-methyl-6-(4-pyridyl)-3H-pyrimidin-4-one;
2-(3-(4-Methylphenyl)piperazin-1-yl)-3-methyl-6-(4-pyridyl)-3H-pyrimidin-4-one;
2-(3-(3-Methylphenyl)piperazin-1-yl)-3-methyl-6-(4-pyridyl)-3H-pyrimidin-4-one;
2-(3-(2-Methylphenyl)piperazin-1-yl)-3-methyl-6-(4-pyridyl)-3H-pyrimidin-4-one;
2-(3-(4-Cyanophenyl)piperazin-1-yl)-3-methyl-6-(4-pyridyl)-3H-pyrimidin-4-one;
2-(3-(3-Cyanophenyl)piperazin-1-yl)-3-methyl-6-(4-pyridyl)-3H-pyrimidin-4-one;
2-(3-(2-Cyanophenyl)piperazin-1-yl)-3-methyl-6-(4-pyridyl)-3H-pyrimidin-4-one;
2-(3-(4-Methoxyphenyl)piperazin-1-yl)-3-methyl-6-(4-pyridyl)-3H-pyrimidin-4-one;
2-(3-(3-Methoxyphenyl)piperazin-1-yl)-3-methyl-6-(4-pyridyl)-3H-pyrimidin-4-one;
2-(3-(2-Methoxyphenyl)piperazin-1-yl)-3-methyl-6-(4-pyridyl)-3H-pyrimidin-4-one;
2-(3-(2-Ethoxyphenyl)piperazin-1-yl)-3-methyl-6-(4-pyridyl)-3H-pyrimidin-4-one;
2-(3-(5-Fluoro-2-methoxyphenyl)piperazin-1-yl)-3-methyl-6-(4-pyridyl)-3H-pyrimidin-4-one;
2-(3-(4-Fluoro-3-methoxyphenyl)piperazin-1-yl)-3-methyl-6-(4-pyridyl)-3H-pyrimidin-4-one;
2-(3-(4-Fluoro-2-methoxyphenyl)piperazin-1-yl)-3-methyl-6-(4-pyridyl)-3H-pyrimidin-4-one;

(S)-2-(3-(4-Fluoro-2-methoxyphenyl)piperazin-1-yl)-3-methyl-6-(4-pyridyl)-3H-pyrimidin-4-one;
(R)-2-(3-(4-Fluoro-2-methoxyphenyl)piperazin-1-yl)-3-methyl-6-(4-pyridyl)-3H-pyrimidin-4-one;
2-(3-(4-Chloro-2-methoxyphenyl)piperazin-1-yl)-3-methyl-6-(4-pyridyl)-3H-pyrimidin-4-one;
2-(3-(4-Fluoro-2-methylphenyl)piperazin-1-yl)-3-methyl-6-(4-pyridyl)-3H-pyrimidin-4-one;
2-(3-(2-Fluoro-6-methoxyphenyl)piperazin-1-yl)-3-methyl-6-(4-pyridyl)-3H-pyrimidin-4-one;
2-(3-(5-Bromo-2-methoxyphenyl)piperazin-1-yl)-3-methyl-6-(4-pyridyl)-3H-pyrimidin-4-one;
2-(3-(2-Bromo-4-fluorophenyl)piperazin-1-yl)-3-methyl-6-(4-pyridyl)-3H-pyrimidin-4-one;
2-(3-(2-Chloro-6-fluorophenyl)piperazin-1-yl)-3-methyl-6-(4-pyridyl)-3H-pyrimidin-4-one;
2-(3-(2,4-Difluorophenyl)piperazin-1-yl)-3-methyl-6-(4-pyridyl)-3H-pyrimidin-4-one;
2-(3-(2,6-Difluorophenyl)piperazin-1-yl)-3-methyl-6-(4-pyridyl)-3H-pyrimidin-4-one;
2-(3-(2,6-Dichlorophenyl)piperazin-1-yl)-3-methyl-6-(4-pyridyl)-3H-pyrimidin-4-one;
2-(3-(2,4-Dimethoxyphenyl)piperazin-1-yl)-3-methyl-6-(4-pyridyl)-3H-pyrimidin-4-one;
2-(3-(3,4-Dimethoxyphenyl)piperazin-1-yl)-3-methyl-6-(4-pyridyl)-3H-pyrimidin-4-one;
2-(3-(2,5-Dimethoxyphenyl)piperazin-1-yl)-3-methyl-6-(4-pyridyl)-3H-pyrimidin-4-one;
2-(3-(2,6-Dimethoxyphenyl)piperazin-1-yl)-3-methyl-6-(4-pyridyl)-3H-pyrimidin-4-one;
2-(3-(2,4-Difluoro-6-methoxyphenyl)piperazin-1-yl)-3-methyl-6-(4-pyridyl)-3H-pyrimidin-4-one;
2-(3-(5-Cyano-2-methoxyphenyl)piperazin-1-yl)-3-methyl-6-(4-pyridyl)-3H-pyrimidin-4-one;
2-(3-(4-Cyano-2-methoxyphenyl)piperazin-1-yl)-3-methyl-6-(4-pyridyl)-3H-pyrimidin-4-one;
2-(3-(1-Naphthyl)piperazin-1-yl)-3-methyl-6-(4-pyridyl)-3H-pyrimidin-4-one;
2-(3-(2-Naphthyl)piperazin-1-yl)-3-methyl-6-(4-pyridyl)-3H-pyrimidin-4-one;
2-(3-(2,3-Dihydrobenzofuran-7-yl)piperazin-1-yl)-3-methyl-6-(4-pyridyl)-3H-pyrimidin-4-one;
2-(3-(Benzofuran-2-yl)piperazin-1-yl)-3-methyl-6-(4-pyridyl)-3H-pyrimidin-4-one;
(S)-2-(3-(Benzofuran-2-yl)piperazin-1-yl)-3-methyl-6-(4-pyridyl)-3H-pyrimidin-4-one;
2-(3-(4-(Pyrrolidin-1-yl-methyl)phenyl)piperazin-1-yl)-3-methyl-6-(4-pyridyl)-3H-pyrimidin-4-one;
2-(3-(4-(Pyrrolidin-1-yl)phenyl)piperazin-1-yl)-3-methyl-6-(4-pyridyl)-3H-pyrimidin-4-one;
2-(3-(2-methoxy-4-(pyrrolidin-1-yl)phenyl)piperazin-1-yl)-3-methyl-6-(4-pyridyl)-3H-pyrimidin-4-one;
2-(3-(2-methoxy-5-(pyrrolidin-1-yl)phenyl)piperazin-1-yl)-3-methyl-6-(4-pyridyl)-3H-pyrimidin-4-one;
2-(3-(4-(Phenyl)phenyl)piperazin-1-yl)-3-methyl-6-(4-pyridyl)-3H-pyrimidin-4-one;
2-(3-(4-(4-Fluorophenyl)phenyl)piperazin-1-yl)-3-methyl-6-(4-pyridyl)-3H-pyrimidin-4-one;
2-(3-(4-(4-Methoxyphenyl)phenyl)piperazin-1-yl)-3-methyl-6-(4-pyridyl)-3H-pyrimidin-4-one;
2-(3-(4-(2-Methoxyphenyl)phenyl)piperazin-1-yl)-3-methyl-6-(4-pyridyl)-3H-pyrimidin-4-one;
2-(3-(4-(Morpholin-4-yl)phenyl)piperazin-1-yl)-3-methyl-6-(4-pyridyl)-3H-pyrimidin-4-one;
2-(3-(4-(4-Methylpiperazin-1-yl)phenyl)piperazin-1-yl)-methyl-6-(4-pyridyl)-3H-pyrimidin-4-one;
2-(4-Phenylpiperazin-1-yl)-3-methyl-6-(4-pyridyl)-3H-pyrimidin-4-one;
2-(4-Benzylpiperazin-1-yl)-3-methyl-6-(4-pyridyl)-3H-pyrimidin-4-one;
2-(4-Benzoylpiperazin-1-yl)-3-methyl-6-(4-pyridyl)-3H-pyrimidin-4-one;
2-(4-(1,2-Benzisothiazol-3-yl)piperazin-1-yl)-3-methyl-6-(4-pyridyl)-3H-pyrimidin-4-one;
2-(4-Methyl-3-phenylpiperazin-1-yl)-3-methyl-6-(4-pyridyl)-3H-pyrimidin-4-one;
2-(3-(4-Fluoro-2-methoxyphenyl)-4-methylpiperazin-1-yl)-3-methyl-6-(4-pyridyl)-3H-pyrimidin-4-one;
(S)-2-(3-(4-Fluoro-2-methoxyphenyl)-4-methylpiperazin-1-yl)-3-methyl-6-(4-pyridyl)-3H-pyrimidin-4-one;
(R)-2-(3-(4-Fluoro-2-methoxyphenyl)-4-methylpiperazin-1-yl)-3-methyl-6-(4-pyridyl)-3H-pyrimidin-4-one;
2-(4-Acetyl-3-(4-fluoro-2-methoxyphenyl)piperazin-1-yl)-3-methyl-6-(4-pyridyl)-3H-pyrimidin-4-one;
2-(4-Benzyl-3-(4-fluoro-2-methoxyphenyl)piperazin-1-yl)-3-methyl-6-(4-pyridyl)-3H-pyrimidin-4-one;
2-(4-Benzyl-3-(ethoxycarbonyl)piperazin-1-yl)-3-methyl-6-(4-pyridyl)-3H-pyrimidin-4-one;
2-(4-methyl-3-(1-naphthyl)piperazin-1-yl)-3-methyl-6-(4-pyridyl)-3H-pyrimidin-4-one;
2-(5,5-Dimethyl-3-(2-methoxyphenyl)piperazin-1-yl)-3-methyl-6-(4-pyridyl)-3H-pyrimidin-4-one;
2-(3-Phenylpiperidin-1-yl)-3-methyl-6-(4-pyridyl)-3H-pyrimidin-4-one;
2-(3-(4-Fluorophenyl)piperidin-1-yl)-3-methyl-6-(4-pyridyl)-3H-pyrimidin-4-one;
2-(3-(3-Fluorophenyl)piperidin-1-yl)-3-methyl-6-(4-pyridyl)-3H-pyrimidin-4-one;
2-(3-(2-Fluorophenyl)piperidin-1-yl)-3-methyl-6-(4-pyridyl)-3H-pyrimidin-4-one;
2-(3-(4-Chlorophenyl)piperidin-1-yl)-3-methyl-6-(4-pyridyl)-3H-pyrimidin-4-one;
2-(3-(4-Bromophenyl)piperidin-1-yl)-3-methyl-6-(4-pyridyl)-3H-pyrimidin-4-one;
2-(3-(4-Methoxyphenyl)piperidin-1-yl)-3-methyl-6-(4-pyridyl)-3H-pyrimidin-4-one;
2-(3-(3-Methoxyphenyl)piperidin-1-yl)-3-methyl-6-(4-pyridyl)-3H-pyrimidin-4-one;
2-(3-(2-Methoxyphenyl)piperidin-1-yl)-3-methyl-6-(4-pyridyl)-3H-pyrimidin-4-one;
2-(3-(4-((Pyrrolidin-1-yl)methyl)phenyl)piperidin-1-yl)-3-methyl-6-(4-pyridyl)-3H-pyrimidin-4-one;
(S)-2-(3-(4-(Pyrrolidin-1-yl-methyl)phenyl)piperidin-1-yl)-3-methyl-6-(4-pyridyl)-3H-pyrimidin-4-one;
(R)-2-(3-(4-(Pyrrolidin-1-yl-methyl)phenyl)piperidin-1-yl)-3-methyl-6-(4-pyridyl)-3H-pyrimidin-4-one;
2-(3-Hydroxy-3-phenylpiperidin-1-yl)-3-methyl-6-(4-pyridyl)-3H-pyrimidin-4-one;
2-(3-Phenylpiperazin-1-yl)-3-methyl-6-(4-pyrimidyl)-3H-pyrimidin-4-one;
2-(3-(4-Fluorophenyl)piperazin-1-yl)-3-methyl-6-(4-pyrimidyl)-3H-pyrimidin-4-one;
2-(3-(3-Fluorophenyl)piperazin-1-yl)-3-methyl-6-(4-pyrimidyl)-3H-pyrimidin-4-one;
2-(3-(2-Fluorophenyl)piperazin-1-yl)-3-methyl-6-(4-pyrimidyl)-3H-pyrimidin-4-one;
2-(3-(4-Chlorophenyl)piperazin-1-yl)-3-methyl-6-(4-pyrimidyl)-3H-pyrimidin-4-one;
2-(3-(3-Chlorophenyl)piperazin-1-yl)-3-methyl-6-(4-pyrimidyl)-3H-pyrimidin-4-one;
2-(3-(2-Chlorophenyl)piperazin-1-yl)-3-methyl-6-(4-pyrimidyl)-3H-pyrimidin-4-one;

2-(3-(4-Bromophenyl)piperazin-1-yl)-3-methyl-6-(4-pyrimidyl)-3H-pyrimidin-4-one;
2-(3-(3-Bromophenyl)piperazin-1-yl)-3-methyl-6-(4-pyrimidyl)-3H-pyrimidin-4-one;
2-(3-(2-Bromophenyl)piperazin-1-yl)-3-methyl-6-(4-pyrimidyl)-3H-pyrimidin-4-one;
2-(3-(4-Cyanophenyl)piperazin-1-yl)-3-methyl-6-(4-pyrimidyl)-3H-pyrimidin-4-one;
2-(3-(3-Cyanophenyl)piperazin-1-yl)-3-methyl-6-(4-pyrimidyl)-3H-pyrimidin-4-one;
2-(3-(2-Cyanophenyl)piperazin-1-yl)-3-methyl-6-(4-pyrimidyl)-3H-pyrimidin-4-one;
2-(3-(4-Methoxyphenyl)piperazin-1-yl)-3-methyl-6-(4-pyrimidyl)-3H-pyrimidin-4-one;
2-(3-(3-Methoxyphenyl)piperazin-1-yl)-3-methyl-6-(4-pyrimidyl)-3H-pyrimidin-4-one;
2-(3-(2-Methoxyphenyl)piperazin-1-yl)-3-methyl-6-(4-pyrimidyl)-3H-pyrimidin-4-one;
2-(3-(2-Ethoxyphenyl)piperazin-1-yl)-3-methyl-6-(4-pyrimidyl)-3H-pyrimidin-4-one;
2-(3-(6-Fluoro-2-methoxyphenyl)piperazin-1-yl)-3-methyl-6-(4-pyrimidyl)-3H-pyrimidin-4-one;
2-(3-(5-Fluoro-2-methoxyphenyl)piperazin-1-yl)-3-methyl-6-(4-pyrimidyl)-3H-pyrimidin-4-one;
2-(3-(4-Fluoro-2-methoxyphenyl)piperazin-1-yl)-3-methyl-6-(4-pyrimidyl)-3H-pyrimidin-4-one;
(S)-2-(3-(4-Fluoro-2-methoxyphenyl)piperazin-1-yl)-3-methyl-6-(4-pyrimidyl)-3H-pyrimidin-4-one;
(R)-2-(3-(4-Fluoro-2-methoxyphenyl)piperazin-1-yl)-3-methyl-6-(4-pyrimidyl)-3H-pyrimidin-4-one;
2-(3-(4-Chloro-2-methoxyphenyl)piperazin-1-yl)-3-methyl-6-(4-pyrimidyl)-3H-pyrimidin-4-one;
2-(3-(5-Bromo-2-methoxyphenyl)piperazin-1-yl)-3-methyl-6-(4-pyrimidyl)-3H-pyrimidin-4-one;
2-(3-(2,6-Dichlorophenyl)piperazin-1-yl)-3-methyl-6-(4-pyridyl)-3H-pyrimidin-4-one;
2-(3-(2,4-Dimethoxyphenyl)piperazin-1-yl)-3-methyl-6-(4-pyridyl)-3H-pyrimidin-4-one;
2-(3-(3,4-Dimethoxyphenyl)piperazin-1-yl)-3-methyl-6-(4-pyrimidyl)-3H-pyrimidin-4-one;
2-(3-(2,5-Dimethoxyphenyl)piperazin-1-yl)-3-methyl-6-(4-pyrimidyl)-3H-pyrimidin-4-one;
2-(3-(2,6-Dimethoxyphenyl)piperazin-1-yl)-3-methyl-6-(4-pyrimidyl)-3H-pyrimidin-4-one;
2-(3-(2,4-Difluoro-6-methoxyphenyl)piperazin-1-yl)-3-methyl-6-(4-pyrimidyl)-3H-pyrimidin-4-one;
2-(3-(1-Naphthyl)piperazin-1-yl)-3-methyl-6-(4-pyrimidyl)-3H-pyrimidin-4-one;
2-(3-(2-Naphthyl)piperazin-1-yl)-3-methyl-6-(4-pyrimidyl)-3H-pyrimidin-4-one;
2-(3-(2,3-Dihydrobenzofuran-7-yl)piperazin-1-yl)-3-methyl-6-(4-pyrimidyl)-3H-pyrimidin-4-one;
2-(3-(Benzofuran-2-yl)piperazin-1-yl)-3-methyl-6-(4-pyrimidyl)-3H-pyrimidin-4-one;
2-(3-(4-(Pyrrolidin-1-yl-methyl)phenyl)piperazin-1-yl)-3-methyl-6-(4-pyrimidyl)-3H-pyrimidin-4-one;
2-(3-(4-(Pyrrolidin-1-yl)phenyl)piperazin-1-yl)-3-methyl-6-(4-pyrimidyl)-3H pyrimidin-4-one;
2-(3-(2-methoxy-4-(pyrrolidin-1-yl)phenyl)piperazin-1-yl)-3-methyl-6-(4-pyrimidyl)-3H-pyrimidin-4-one;
2-(3-(2-methoxy-5-(pyrrolidin-1-yl)phenyl)piperazin-1-yl)-3-methyl-6-(4-pyrimidyl)-3H-pyrimidin-4-one;
2-(3-(4-(Phenyl)phenyl)piperazin-1-yl)-3-methyl-6-(4-pyrimidyl)-3H-pyrimidin-4-one;
2-(3-(4-(4-Fluorophenyl)phenyl)piperazin-1-yl)-3-methyl-6-(4-pyrimidyl)-3H-pyrimidin-4-one;
2-(3-(4-(4-Methoxyphenyl)phenyl)piperazin-1-yl)-3-methyl-6-(4-pyrimidyl)-3H-pyrimidin-4-one;
2-(3-(4-(2-Methoxyphenyl)phenyl)piperazin-1-yl)-3-methyl-6-(4-pyrimidyl)-3H-pyrimidin-4-one;
2-(3-(4-(Morpholin-4-yl)phenyl)piperazin-1-yl)-3-methyl-6-(4-pyrimidyl)-3H-pyrimidin-4-one;
2-(3-(4-(4-Methylpiperazin-1-yl)phenyl)piperazin-1-yl)-3-methyl-6-(4-pyrimidyl)-3H-pyrimidin-4-one;
2-(3-(4-Fluoro-2-methoxyphenyl)-4-methylpiperazin-1-yl)-3-methyl-6-(4-pyrimidyl)-3H-pyrimidin-4-one;
(S)-2-(3-(4-Fluoro-2-methoxyphenyl)-4-methylpiperazin-1-yl)-3-methyl-6-(4-pyrimidyl)-3H-pyrimidin-4-one;
(R)-2-(3-(4-Fluoro-2-methoxyphenyl)-4-methylpiperazin-1-yl)-3-methyl-6-(4-pyrimidyl)-3H-pyrimidin-4-one;
2-(4-Acetyl-3-(4-fluoro-2-methoxyphenyl)piperazin-1-yl)-3-methyl-6-(4-pyrimidyl)-3H-pyrimidin-4-one;
2-(4-Benzyl-3-(4-fluoro-2-methoxyphenyl)piperazin-1-yl)-3-methyl-6-(4-pyrimidyl)-3H-pyrimidin-4-one;
2-(4-(4-Fluorophenyl)piperidin-1-yl)-3-methyl-6-(4-pyrimidyl)-3H-pyrimidin-4-one;
2-(4-Cyano-4-phenylpiperidin-1-yl)-3-methyl-6-(4-pyrimidyl)-3H-pyrimidin-4-one;
2-(4-(6-Fluorobenofuran-3-yl)piperidin-1-yl)-3-methyl-6-(4-pyrimidyl)-3H-pyrimidin-4-one;
2-(3-(Benzoisoxazol-3-yl)piperidin-1-yl)-3-methyl-6-(4-pyrimidyl)-3H-pyrimidin-4-one;
(S)-2-(3-(Benzoisoazol-3-yl)piperidin-1-yl)-3-methyl-6-(4-pyrimidyl)-3H-pyrimidin-4-one;
(R)-2-(3-(Benzoisoxazol-3-yl)piperidin-1-yl)-3-methyl-6-(4-pyrimidyl)-3H-pyrimidin-4-one;
2-(3-(6-Fluorobenzoisoxazol-3-yl)piperidin-1-yl)-3-methyl-6-(4-pyrimidyl)-3H-pyrimidin-4-one;
2-(4-(6-Fluorobenzoisoxazol-3-yl)piperidin-1-yl)-3-methyl-6-(4-pyrimidyl)-3H-pyrimidin-4-one;
2-(4-(5-Methylbenzofuran-3-yl)piperidin-1-yl)-3-methyl-6-(4-pyrimidyl)-3H-pyrimidin-4-one; and
2-(4-(6-Fluorobenzothiophene-3-yl)piperidin-1-yl)-3-methyl-6-(4-pyrimidyl)-3H-pyrimidin-4-one.

Salts of the aforementioned preferred compound, and solvates or hydrates of the aforementioned compounds and salts thereof are also preferred.

The 3-substituted-4-pyrimidone compounds represented by the aforementioned formula (I) can be prepared, for example, according to the method explained below.

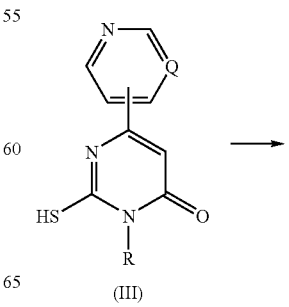

(III)

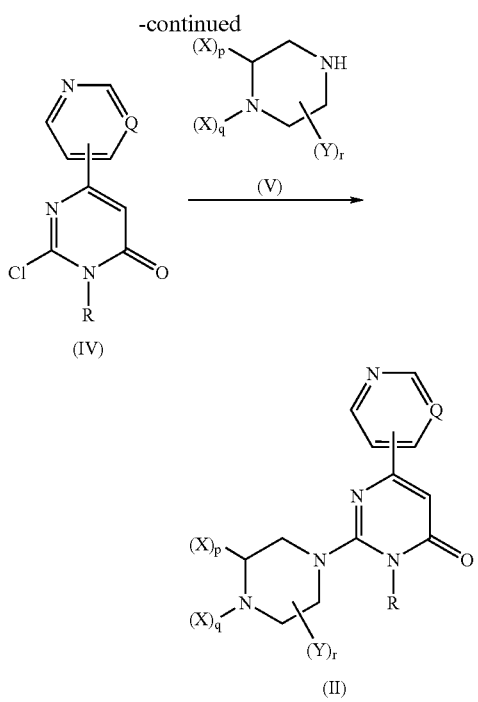

(In the above scheme, definitions of Q, R, X and Y are the same as those already described.)

The 2-thiopyrimidone represented by the above formula (III) is prepared easily by a modification of the method described in EP 354,179. The reaction may be carried out in the presence of a base such as sodium hydroxide, potassium hydroxide, sodium methoxide, sodium ethoxide, potassium tert-butoxide, sodium carbonate, sodium hydrogencarbonate, potassium carbonate, triethylamine, diisopropylethylamine, and 1,8-diazabicyclo[5,4,0]undec-7-en for 1 to 100 hours at a suitable temperature ranging from 0° C. to 200° C. under nitrogen or argon atmosphere or under ordinary air to afford the desired compound (III). Examples of a solvent for the reactions include, for example, alcoholic solvent such as methanol, ethanol, 1-propanol, isopropanol, tert-butanol, ethylene glycol, propylene glycol; etheric solvents such as diethyl ether, tert-butyl methyl ether, tetrahydrofuran, isopropyl ether; hydrocarbonic solvents such as benzene, toluene, xylene; halogenated hydrocarbonic solvents such as dichloromethane, chloroform, dichloroethane; aprotic polar solvents such as formamide, N,N-dimethylformamide, N,N-dimethylacetamide, N-methylpyrrolidone, dimethyl sulfoxide, sulfolane, hexamethylphosphoric triamide, water and the like. Generally, a single solvent or a mixture of two or more solvents may be used so as to be suitable to a base used.

Then the 2-thiopyrimidone derivative (III) is transformed into the 2-chloropyrimidone (IV) by a chlorinating agent. The reaction time and temperature depend on the chlorinating agent used. Examples of a chlorinating agent for the reactions include, for example, thionyl chloride, thionyl chloride and dimethylformamide, phosphorus oxychloride, phosphorus oxychloride and dimethylformamide, oxalyl chloride, phosphorous oxychloride and dimethylformamide, and phosphorus pentachloride.

The amine represented by the above formula (V) may be prepared by a modification of the method described in Japanese Patent Unexamined Publication [Kokai] No. 52-139085/1977 or according to well-known methods of one skilled in the art.

Then the chloride derivative (IV) is allowed to react with the amine (V) or salts thereof in the presence of a base such as sodium hydroxide, potassium hydroxide, sodium methoxide, sodium ethoxide, sodium carbonate, sodium hydrogencarbonate, potassium carbonate, triethylamine, diisopropylethylamine, and 1,8-diazabicyclo[5,4,0]undec-7-en for 0.1 to 100 hours at a suitable temperature ranging from 0° C. to 200° C. under nitrogen or argon atmosphere or under ordinary air to afford the desired compound (II).

Examples of a solvent for the reactions include, for example, alcoholic solvent such as methanol, ethanol, 1-propanol, isopropanol, tert-butanol, ethylene glycol, propylene glycol; etheric solvents such as diethyl ether, tert-butyl methyl ether, tetrahydrofuran, isopropyl ether; hydrocarbonic solvents such as benzene, toluene, xylene; halogenated hydrocarbonic solvents such as dichloromethane, chloroform, dichloroethane; aprotic polar solvents such as formamide, N,N-dimethylformamide, N,N-dimethylacetamide, N-methylpyrrolidone, dimethyl sulfoxide, sulfolane, hexamethylphosphoric triamide, water and the like. Generally, a single solvent or a mixture of two or more solvents may be used so as to be suitable to a base used.

The compounds of the present invention have inhibitory activity against TPK1, and they inhibit TPK1 activity in neurodegenerative diseases like Alzheimer disease, thereby suppress the neurotoxicity of A β and the formation of PHF and inhibit the nerve cell death. Accordingly, the compounds of the present invention are useful as an active ingredient of a medicament which radically enables preventive and/or therapeutic treatment of Alzheimer disease. In addition, the compounds of the present invention are also useful as an active ingredient of a medicament for preventive and/or therapeutic treatment of ischemic cerebrovascular accidents, Down syndrome, cerebral bleeding due to solitary cerebral amyloid angiopathy, progressive supranuclear palsy, subacute sclerosing panencephalitis, postencephalitic parkinsonism, pugilistic encephalosis, Guam parkinsonism-dementia complex, Lewy body disease, Pick's disease, corticobasal degeneration frontotemporal dementia, vascular dementia, acute stroke and traumatic injuries, brain and spinal cord trauma, peripheral neuropathies, retinopathies and glaucoma, non-insulin dependent diabetes (such as diabetes type II), and obesity, manic depressive illness, schizophrenia, alopecia, cancers such as breast cancer, non-small cell lung carcinoma, thyroid cancer, T or B-cell leukemia and several virus-induced tumors.

As the active ingredient of the medicament of the present invention, a substance may be used which is selected from the group consisting of the compound represented by the aforementioned formula (I) and pharmacologically acceptable salts thereof, and solvates thereof and hydrates thereof. The substance, per se, may be administered as the medicament of the present invention, however, it is desirable to administer the medicament in a form of a pharmaceutical composition which comprises the aforementioned substance as an active ingredient and one or more of pharmaceutical additives. As the active ingredient of the medicament of the present invention, two or more of the aforementioned substance may be used in combination. The above pharmaceutical composition may be supplemented with an active ingredient of other medicament for the treatment of, for example, Alzheimer disease, vascular dementia, acute stroke and traumatic injuries, brain and spinal cord trauma, peripheral neuropathies, retinopathies and glaucoma, non-insulin dependent diabetes (such as diabetes type II), and obesity, manic depressive illness, schizophrenia, alopecia, cancers such as breast cancer, non-small cell lung carcinoma, thyroid cancer, T or B-cell leukemia and several virus-induced tumors.

A type of the pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like. Injections or drip infusions may be prepared as powdery preparations such as in the form of lyophilized preparations, and may be used by dissolving just before use in an appropriate aqueous medium such as physiological saline. Sustained-release preparations such as those coated with a polymer may be directly administered intracerebrally.

Types of pharmaceutical additives used for the manufacture of the pharmaceutical composition, content rations of the pharmaceutical additives relative to the active ingredient, and methods for preparing the pharmaceutical composition may be appropriately chosen by those skilled in the art. Inorganic or organic substances, or solid or liquid substances may be used as pharmaceutical additives. Generally, the pharmaceutical additives may be incorporated in a ratio ranging from 1% by weight to 90% by weight based on the weight of an active ingredient.

Examples of excipients used for the preparation of solid pharmaceutical compositions include, for example, lactose, sucrose, starch, talc, cellulose, dextrin, kaolin, calcium carbonate and the like. For the preparation of liquid compositions for oral administration, a conventional inert diluent such as water or a vegetable oil may be used. The liquid composition may contain, in addition to the inert diluent, auxiliaries such as moistening agents, suspension aids, sweeteners, aromatics, colorants, and preservatives. The liquid composition may be filled in capsules made of an absorbable material such as gelatin. Examples of solvents or suspension mediums used for the preparation of compositions for parenteral administration, e.g. injections, suppositories, include water, propylene glycol, polyethylene glycol, benzyl alcohol, ethyl oleate, lecithin and the like. Examples of base materials used for suppositories include, for example, cacao butter, emulsified cacao butter, lauric lipid, witepsol.

Dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 100 mg (the weight of an active ingredient) to an adult.

EXAMPLES

The present invention will be explained more specifically with reference to examples. However, the scope of the present invention is not limited to the following examples. The compound numbers in the examples correspond to those in the table above.

Reference Example 1

Synthesis of 2-mercapto-3-methyl-6-(4-pyridyl)-3H-pyrimidin-4-one

A solution of ethyl 3-oxo-3-(4-pyridyl)propionate (29.0 g, 150 mmol), N-methyl thiourea (40.6 g, 450 mmol) and 1,8-diazabicyclo[5,4,0]-7-undecene (22.4 ml, 150 mmol) was refluxed for 4 hours and the solution of methanesulfonic acid (14.4 g, 150 mmol) in water (50 ml) was added after cooling by ice-water. The precipitate was washed with water, filtered and dried to give the title compound (23.7 g, 72%).
$^1$H-NMR (DMSO-$d_6$) δ: 3.58(s, 3H), 6.40(s, 1H), 7.72(dd, J=1.8, 4.5 Hz, 2H), 8.73(dd, J=1.5, 4.8 Hz, 2H), 12.92(brd, 1H).

Reference Example 2

Synthesis of 2-chloro-3-methyl-6-(4-pyridyl)-3H-pyrimidin-4-one

Phosphorous oxychloride (26.11 g, 170 mmol) was added to dimethyl-formamide (180 ml) and stirred 20 min. 2-Mercapto-3-methyl-6-(4-pyridyl)-pyrimidine-4-one (24.15 g, 110 mmol) was added to the solution and stirred 5 min and then stirred at 70° C. for 2 hours. Ethyl acetate (630 ml) was added to the ice-cooled solution and precipitate was collected by filtration after stirring for 20 minutes. After drying, the precipitate was dissolved in water (400 ml) and pH was adjusted to 10 by using aqueous sodium hydroxide. The precipitate was washed with water, filtered and dried to give the title compound (18.82 g, 77%).
$^1$H-NMR (CDCl$_3$) δ: 3.72(s, 3H), 6.90(s, 1H), 7.78(dd, J=1.7, 4.5 Hz, 2H), 8.75(dd, J=1.6, 4.5 Hz, 2H).

Reference Example 3

Synthesis of 2-mercapto-3-methyl-6-(4-pyrimidyl)-3H-pyrimidin-4-one

A solution of ethyl 3-oxo-3-(4-pyrimidyl)propionate (34.1 g, 176 mmol), N-methyl thiourea (47.5 g, 527 mmol) and 1,8-diazabicyclo[5,4,0]-7-undecene (26.3 ml, 176 mmol) in ethanol (340 ml) was refluxed for 2 hours and the solution of methanesulfonic acid (16.9 g, 176 mmol) in water (70 ml) was added after cooling by ice-water. The precipitate was washed with water, filtered and dried to give the title compound (30.2 g, 78%).
$^1$H-NMR (DMSO-$d_6$) δ: 3.56(s, 3H), 6.88(s, 1H), 8.24(dd, J=1.2, 5.4 Hz, 2H), 9.05 (dd, J=5.4 Hz, 1H), 11.94(s, 1H).

Reference Example 4

Synthesis of 2-chloro-3-methyl-6-(4-pyrimidyl)-3H-pyrimidin-4-one

Phosphorous oxychloride (4.60 g, 30 mmol) was added to dimethyl-formamide (32 ml) and stirred for 20 min at 0° C. 2-Mercapto-3-methyl-6-(4-pyrimidyl)-3H-pyrimidine-4-one (4.40 g, 20 mmol) was added to the solution and stirred 5 min and then stirred at 70° C. for 2 hours. The reaction mixture was poured into ice water, neutralized by solid potassium carbonate, and extracted with ethyl acetate. The organic layer was washed with brine, dried over sodium sulfate, and evaporated under reduced pressure. Purification of the residue by silica gel chromatography (ethyl acetate) gave the title compound (1.20 g, 27%).

$^1$H-NMR (CDCl$_3$) δ: 3.74(s, 3H), 7.56(s, 1H), 8.18(d, J=5.1 Hz, 1H), 8.92(d, J=5.1 Hz, 1H), 9.30(s, 1H).
MS[M+H]$^+$: 223.

Example 1

Synthesis of 2-(2-(4-fluoro-2-methoxyphenyl)piperazin-4-yl)-3-methyl-6-(4-pyridyl)-3H-pyrimidin-4-one dihydrochloride (No. XA468)

A solution of 2-bromo-5-fluoroanisole (11.8 g, 57.6 mmol) in tetrahydrofuran (60 ml) was dropped into the magnesium (1.40 g, 57.6 mmol) in refluxed tetrahydrofuran (32 ml) containing small amount of 1,2-dibromoethane and refluxed for 15 min. After addition of tetrehydrofuran (50 ml), the solution was cooled to −78° C. and diethyl oxalate (7.41 g, 50.7 mmol) in diethyl ether (50 ml) was dropped into the solution. After stirring at same temperature for 30 min, the solution was warmed to −10° C. and 1N aqueous hydrogen chloride (50 ml) and water were added. Organic layer was extracted with diethyl ether, washed with brine and dried over magnesium sulfate. After removal of the solvent under reduced pressure, purification of the residue by silica gel column chromatography (eluent: hexane/ethyl acetate=5/2) gave ethyl 2-(4-fluoro-2-methoxyphenyl)-2-ozoacetate (6.80 g, 59%)

$^1$H-NMR (CDCl$_3$) δ: 1.40(3H, t, J=7.1 Hz), 3.87(3H, s), 4.89(2H, q, J=7.1 Hz), 6.68(1H, d, J=10.5 Hz), 6.77-6.81(1H, m), 7.91-7.95(1H, m).

Ethylenediamine (0.60 g, 10.0 mmol) was added to a solution of ethyl 2-(4-fluoro-2-methoxyphenyl)-2-oxoacetate (2.26 g, 10.0 mmol) in ethanol (30 ml) and refluxed 4 hr. After removal of the solvent under reduced pressure, residue was washed with ethanol-diethyl ether to give 5,6-dihydro-3-(4-fluoro-2-methoxyphenyl)pyrazinone (1.76 g, 79%).

$^1$H-NMR (CDCl$_3$) δ: 3.50-3.56 (2H, m), 3.81 (3H, s), 3.88-3.92 (2H, m), 6.65(1H, d, J=11.0 Hz), 6.70-6.76 (1H, m), 6.89(1H, bs), 7.36-7.40(1H, m).

5,6-Dihydro-3-(4-fluoro-2-methoxyphenyl)pyrazinone was added to the solution of lithium aluminium hydride (0.46 g, 12 mmol) in diethyl ether (25 ml) and refluxed for 6 hr. Water (0.48 ml), 15% sodium hydroxide solution (0.48 ml) and again water (1.21 ml) were added to the ice-cooled solution and the precipitate was filtered and washed with dichloromethane. Combined organic layer was evaporated to give 2-(4-fluoro-2-methoxyphenyl)piperazine (0.83 g, 99%).

$^1$H-NMR (CDCl$_3$) δ: 2.02(2H, s), 2.57-2.63 (1H, m), 2.80-2.89 (1H, m), 2.92-2.99 (2H, m), 3.06-3.12 (2H, m), 3.80(3H, s), 4.06 (1H, d, J=10.0 Hz), 6.56-6.65 (2H, m), 7.40 (1H, t, J=7.8 Hz).

2-Chloro-3-methyl-6-(4-pyridyl)-pyrimidin-4-one (222 mg, 1.0 mmol) was added to an ice-cooled solution of 2-(4-fluoro-2-methoxyphenyl)piperazine (210 mg, 1.0 mmol), triethylamine (0.15 ml, 1.1 mmol) in N,N-dimethylformamide (10 ml) and stirred at that temperature for 1 hr and then at room temperature for 2 hr. Next day, reaction was quenched by ice-water and the filtrate was washed with water and dried to give 2-(2-(4-fluoro-2-methoxyphenyl)piperazin-4-yl)-3-methyl-6-(4-pyridyl)-pyrimidin-4-one (246 mg, 62%).

$^1$H-NMR (CDCl$_3$) δ: 2.89-2.96 (1H, m), 3.19-3.31 (3H, m), 3.59 (3H, s), 3.62-3.74 (2H, m), 3.85 (3H, s), 4.39-4.44 (1H, m), 6.63-6.71 (2H, m), 6.67 (1H, s), 7.51-7.55 (1H, m), 7.81 (2H, dd, J=1.7, 4.6 Hz), 8.71 (2H, dd, J=1.7, 4.6 Hz).

4N Hydrogen chloride in 1,4-dioxane (0.4 ml) was added to the solution of 2-(2-(4-fluoro-2-methoxyphenyl)piperazin-4-yl)-3-methyl-6-(4-pyridyl)-pyrimidin-4-one (217 mg, 0.6 mmol) in dichloromethane (5 ml) and stirred for 15 min. After addition of diethyl ether, filtration and wash with diethyl ether and dryness gave the title compound (260 mg, quant.).

Example 2

Synthesis of 2-(2-(4-methoxyphenyl)-piperazine-4-yl)-3-methyl-6-(4-pyridyl)pyrimidin-4-one dihydrochloride (No. XA393)

Dimethylslufoxide (50 ml) solution of 4-methyoxyphenacylbromide (9.94 g, 43.4 mmol) and water (1.6 ml, 88.8 mmol) were stirred at 50° C. for 2.5 hr. Water was added and the solution was extracted with ethyl acetate 3 times and washed with brine and then dried over sodium sulfate. Removal of the solvent gave 4-methoxyphenylglyoxal (8.30 g, quant.).

$^1$H-NMR (DMSO) δ: 3.84 (3H, s), 6.60-6.69 (1H, m), 7.04 (2H, d, J=8.8 Hz), 8.05 (2H, d, J=9.1 Hz).

Methanol (5 ml) solution of ethylenediamine (3.74 g, 62.29 mmol) was added to the ice-cooled solution of 4-methoxyphenylglyoxal (8.30 g, 45.5 mmol) in methanol (100 ml) and tetrahydrofuran (50 ml) and stirred for 10 min. After cooling to 0° C., sodium tetrahydroborate (6.14 g, 162.2 mmol) and additional methanol (50 ml) was added and stirred overnight. After removal of the solvent, aqueous sodium hydroxide was added and was extracted with dichloromethane three times and washed with brine and dried over sodium sulfate. After removal of the solvent, purification of the residue by silica gel column chromatography (eluent; dichloromethane/ethanol/diethylamine=20/2/1) gave 2-(4-methoxypheny)-piperazine (3.96 g, 45%).

$^1$H-NMR (CDCl$_3$) δ: 2.69(1H, dd, J=10.3, 11.9 Hz), 2.80-3.01(4H, m), 3.07-3.11 (1H, m), 3.68-3.73(1H, m), 3.79(3H, s), 6.84-6.88 (2H, m), 7.27-7.32 (2H, m).

A solution of triethylamine (697 mg, 6.9 mmol), 2-(4-methoxyphenyl)-piperazine (430 mg, tetrahydrofuran (10 ml) was stirred at room temperature for 30 min and at 50° C. for 3 hr. Solvent was removed under reduced pressure, and 1N aqueous sodium hydroxide solution was added to the residue and extracted by dichloromethane three times and washed with brine and dried over sodium sulfate. After removal of the solvent under reduced pressure, the residue was purified by silica gel column chromatography (eluent; dichloromethane/ethanol=10/1) to give 2-(2-(4-methoxyphenyl)-piperazine-4-yl)-3-methyl-6-(4-pyridyl)pyrimidin-4-one (594 mg, 76%)

$^1$H-NMR (CDCl$_3$) δ: 3.02 (1H, dd, J=10.8, 12.7 Hz), 3.18-3.25 (3H, m), 3.55 (3H, s), 3.57-3.67 (2H, m), 3.82 (3H, s), 3.98(1H, dd, J=2.7, 10.8 Hz), 6.67 (1H, s), 6.92 (2H, d, J=8.7 Hz), 7.37 (2H, d, J=8.7 Hz), 7.80 (2H, d, J=6.0 Hz), 8.71 (2H, d, J=6.0 Hz).

4N Hydrogen chloride in ethyl acetate (5 ml) was added to the solution of 2-(2-(4-methoxyphenyl)-piperazine-4-yl)-3-methyl-6-(4-pyridyl)pyrimidin-4-one (594 mg, 1.6 mmol) in dichloromethane (5 ml) and stirred for 1 hr. Wash with ethyl acetate after removal of the solvent and dryness gave the title compound (683 mg, 96%).

Example 3

Synthesis of 2-(2-(4-chlorophenyl)-piperazine-4-yl)-3-methyl-6-(4-pyridyl)pyrimidin-4-one hydrochloride (No. XA371)

Mixture of methyl(4-chlorophenyl)acetate (5.10 g, 27.6 mmol) and N-bromosuccinimide (5.16 g, 29 mmol) in carbon tetrachloride was treated by Hg lamp. After filtration, solvent was removed under reduced pressure and the residue was dissolved in methanol. Ethylenediamine (2.03 ml, 30.4 mmol) and triethylamine (2.06 ml, 14.8 mmol) and di-tert-butyldicarbonate (3.10 ml, 13.5 mmol) were added to the solution of 3-(4-chlorophenyl)piperazin-2-one (2.60 g, 12.3 mmol) in dichloromethane (100 ml) and stirred. The reaction mixture was washed with 1N aqueous hydrogen chloride, water, brine and then dried. After removal of the solvent under reduced pressure, residue was purified by silica gel column chromatography to give 4-(tert-butoxycarbonyl)-3-(4-chlorophenyl)-piperazin-2-one.

$^1$H-NMR (CDCl$_3$) δ: 1.44 (9H, s), 3.21-3.32 (2H, m), 3.48 (1H, m), 4.04 (1H, brs), 5.66 (1H, brs), 7.10 (1H, brs), 7.30-7.38 (4H, m).

Solution of 4-(tert-butoxycarbonyl)-3-(4-chlorophenyl)-piperazin-2-one (500 mg, 1.6 mmol) and acetic acid (929 µl, 16 mmol) were added to a refluxed solution of sodium borohydride (608 mg, 16 mmol) in 1,4-dioxane (5 ml) and reflux was continued. The reaction was quenched by water and extracted with dichloromethane and washed with brine and dried. After removal of the solvent, residue was purified by silica gel column chromatography to give 4-(tert-butoxycarbonyl)-3-(4-chlorophenyl)piperazine (330 mg, 69%).

$^1$H-NMR (CDCl$_3$) δ: 1.46(9H, s), 2.76-2.99(3H, m), 3.13 (1H, dd, J=13.0 Hz, 4.3 Hz), 3.45-3.49(2H, m), 3.92(1H, m), 5.15(1H, s), 7.27-7.33(4H, m).

A solution of 4-(tert-butoxycarbonyl)-3-(4-chlorophenyl) piperazine (330 mg, 1.1 mmol), 2-chloro-3-methyl-6-(4-pyridyl)pyrimidin-4-one (246 mg, 1.1 mmol) and triethylamine (170 µl, 1.22 mmol) in tetrahydrofuran were refluxed. Usual workup and purification by silica gel column chromatography gave 2-(1-(tert-butoxy-carbonyl)-2-(4-chlorophenyl)-piperazine-4-yl)-3-methyl-6-(4-pyridyl)pyrimidin-4-one (500 mg, 93%).

$^1$H-NMR (CDCl$_3$) δ: 1.45(9H, s), 3.09(1H, m), 3.35(3H, s), 3.40-3.63(4H, m), 3.96-4.19(2H, m), 5.43(1H, s), 6.68 (1H, s), 7.23(2H, d, J=8.3 Hz), 7.32(2H, d, J=8.3 Hz), 7.78 (2H, d, J=5.9 Hz), 8.72(2H, d, J=5.9 Hz).

4N Hydrogen chloride in ethyl acetate was added to the solution of 2-(1-(tert-butoxycarbonyl)-2-(4-chlorophenyl)-piperazine-4-yl)-3-methyl-6-(4-pyridyl)pyrimidin-4-one (500 mg, 1.0 mmol) in ethyl acetate and stirred. Filtration and successive dryness gave the title compound (373 mg, 79%).

Example 4

Synthesis of 3-methyl-2-(3-(4-((1-pyrrolidinyl)methyl)phenyl)piperidine-1-yl)-6-(4-pyridyl)pyrimidin-4-one fumarate (No. XB43)

Tetrakis(triphenylphosphine)palladium (0.65 g, 0.56 mmol), 4-formylphenylboric acid (2.81 g, 18.7 mmol), 2M aqueous sodium carbonate (18.7 ml, 37.4 mmol) and ethanol were added to the nitrogen-saturated solution of 3-bromopyridine (2.66 g, 16.8 mmol) in toluene and refluxed under nitrogen for 8 hrs. Water was added to the solution and extracted with ethyl acetate, washed with water and brine and dried. Solvents were removed under reduced pressure and the residue was purified by silica gel column chromatography (eluent; hexane/ethyl acetate=1/1.5) to give 4-(3-pyridyl) benzaldehyde (0.78 g, 25%).

Methyl iodide (0.8 ml, 12.9 mmol) was added to a solution of 4-(3-pyridyl)benzaldehyde (0.78 g, 4.3 mmol) in dichloromethane and stirred 2 days. Additional methyl iodide (0.8 ml, 12.9 mmol) was added and stirred for 3 hr. After removal of the solvent, methanol was added to the residue and ice-cooled. Sodium tetrahydroborate (6.4 g, 17.0 mmol) was added to the solution and stirred for 1.5 hr with warming to room temperature. Organic solvents were removed under reduced pressure after addition of water and extracted with ethyl acetate, washed with water and brine and dried over sodium sulfate. After removal of the solvent under reduced pressure, residue was purified by silica gel chromatography (eluent ethyl acetate to methanol) to give 3-(4-hydroxymethylphenyl)-1-methyl-1,2,5,6-tetrahydropyridine (0.63 g, 72%).

Triethylamine (1.29 ml, 9.2 mmol), acetic anhydride (0.35 ml, 3.7 mmol) were added to a solution of 4-(hydroxymethyl) phenyl-1-methyl-1,2,5,6-tetrahydropyridine (0.63 g, 3.1 mmol) in dichloromethane and stirred overnight. Organic solvents were removed under reduced pressure after addition of water and extracted with ethyl acetate, washed with water and brine and dried over sodium sulfate. Removal of the solvent under reduced pressure gave 3-(4-acetozymethylphenyl)-1-methyl-1,2,5,6-tetrahydropyridine (0.67 g, 89%).

A solution of 3-(4-acetoxymethylphenyl)-1-methyl-1,2,5,6-tetrahydropyridine (0.67 g, 2.7 mmol) and 1-chloroethyl chloroformate (0.36 ml, 3.3 mmol) in dichloroethane was refluxed for 2 hr. Organic solvents were removed under reduced pressure after addition of water and extracted with ethyl acetate, washed with water and brine and dried over sodium sulfate. After removal of the solvent, methanol was added and refluxed for 1.5 hr. Tetrahydrofuran and water were added to the residue after removal of the solvent under reduced pressure and triethylamine (1.9 ml, 13.6 mmol) and di-tert-butyl dicarbonate (0.66 g, 3.0 mmol) were added and stirred. Organic solvents were removed under reduced pressure after addition of water and extracted with ethyl acetate, washed with water and brine and dried over sodium sulfate. Removal of the solvent under reduced pressure and the residue was purified by silica gel chromatography to give 3-(4-acetoxymethylphenyl)-1-(tert-butoxycarbonyl)-1,2,5,6-tetrahydropyridine (0.71 g, 78%).

Palladium on charcoal was added to the solution of 3-(4-acetoxymethylphenyl)-1-(tert-butoxycarbonyl)-1,2,5,6-tetrahydropyridine (0.71 g, 2.1 mmol) in ethyl acetate and stirred under hydrogen atmosphere. After filtration with celite and removal of the solvent under reduced pressure, methanol and 1N aqueous sodium hydroxide were added and stirred. Organic solvents were removed under reduced pressure after addition of water and extracted with ethyl acetate, washed with water and brine and dried over sodium sulfate. Removal of the solvent under reduced pressure and the residue was purified by silica gel chromatography (eluent; hexane/ethyl acetate=3/1) to give 3-(4-hydroxymethylphenyl)-1-(tert-butoxycarbonyl)piperidine (0.39 g, 62%).

Triethylamine (0.47 g, 3.4 mmol) and methanesulfonyl chloride (0.12 ml, 1.6 mmol) were added to an ice-cooled solution of 3-(4-hydroxymethylphenyl)-1-(tert-butoxycarbonyl)piperidine (0.39 g, 1.34 mmol) in dichloromethane and stirred for 7.5 hr. Pyrrolidine (1.0 ml, 12 mmol) was added to the solution and stirred overnight. Organic solvents were removed under reduced pressure after addition of water and extracted with ethyl acetate, washed with water and brine and dried over sodium sulfate. Removal of the solvent under reduced pressure and the residue was purified by silica gel chromatography (eluent; ethyl acetate to ethyl acetate/methanol=1/1, then methanol only) to give 3-(4-(1-pyrrolidinyl)methylphenyl)-1-(tert-butoxycarbonyl)piperidine (0.26 g, 56%).

4N Hydrogen chloride in ethyl acetate was added to 3-(4-(1-pyrrolidinyl)-methylphenyl)-1-(tert-butoxycarbonyl)piperidine (0.26 g, 0.75 mmol) and stirred overnight. After filtration and dryness, triethylamine (0.5 ml, 3.6 mmol), 2-chloro-3-methyl-6-(4-pyridyl)-pyrimidin-4-one (0.14 g, 0.63 mmol) and tetrahydrofuran were added and stirred at 70° C. Organic solvents were removed under reduced pressure after addition of water and extracted with ethyl acetate, washed with water and brine and dried over sodium sulfate. Removal of the solvent under reduced pressure and the residue was dissolved into ethyl acetate. A solution of fumaric acid (0.095 g, 0.82 mmol) in acetone was added and the resulting precipitate was filtered and dried to give the title compound (0.29 g, 76%).

Example 5

Synthesis of (R)-2-(2-(4-chlorophenyl)piperazin-4-yl)-3-methyl-6-(4-pyridyl)-pyrimidin-4-one (No. XA372)

To a solution of (S)-2-methyl-CBS-oxazaborolidine (27.6 mL, 1.0 M solution in toluene, 27.6 mmol) was added borane-tetrahydrofuran complex (166 ml, 1.0 M solution in tetrahydrofuran, 166 mmol) at −40° C. To the resulting solution was added a solution of 4'-chlorophenacyl bromide (32.25 g, 138.1 mmol) in tetrahydrofuran (200 ml) through dropping funnel over 1 h at −40° C. After stirring for 3 hours below 0° C., methanol (ca. 50 ml) was added dropwise. After stirring the resulting solution for additional 30 min at room temperature, solvent was removed under reduced pressure. The residue, dissolved in ethyl acetate, was treated with 1 N hydrochloric acid to form white precipitate, which was filtered off. The layers of the filtrate was separated, and the organic layer was washed with hydrochloric acid and brine successively, dried over anhydrous sodium sulfate, filtered, and concentrated under reduced pressure. The residue was used for the next reaction without further purification.

The residue was dissolved in ether (250 ml), and stirred with potassium hydroxide (15.5 g, 276 mmol) in water (250 ml) vigorously. After consumption of the starting material, the layers were separated. The organic layer was washed with brine, dried over anhydrous sodium sulfate, filtered, and concentrated under reduced pressure. The residue was used for the next reaction without further purification.

The residue was heated with benzylamine (37.7 ml, 345 mmol) at 80° C. for 4.5 h. After cooling at room temperature, the resulting white crystals was washed with ether/hexane and collected to afford (S)-2-benzylamino-1-(4-chlorophenyl)ethanol (23.8 g, 65.8%). The excess benzylamine in the filtrate was distilled off at 120° C. under reduced pressure. From the residue, another (S)-2-benzylamino-1-(4-chlorophenyl)ethanol (2.41 g, 6.7%) was obtained.

$^1$H NMR (CDCl$_3$)™: 2.68(1H, dd, J=12.3, 8.9 Hz), 2.92 (1H, dd, J=12.3, 3.7 Hz), 3.80(1H, d, J=11.9 Hz), 3.86(1H, d, J=11.9 Hz), 4.68(1H, dd, J=8.9, 3.7 Hz), 7.30(9H, m).

To a suspension of (S)-2-benzylamino-1-(4-chlorophenyl) ethanol (15.76 g, 60.21 mmol) and triethylamine (33.6 ml, 241 mmol) in dichloromethane (300 ml) was added a solution of thionyl chloride (4.83 ml, 66.2 mmol) in dichloromethane (20 ml) at −78° C. over 20 min. The resulting suspension was stirred at −78° C. for 20 min and at 0° C. for additional 20 min.

The reaction mixture was partitioned between ether and water, and the organic layer was washed with brine, dried over anhydrous sodium sulfate, filtered, and concentrated under reduced pressure. The residue was purified by silica gel column chromatography (eluent: 10-20% ethyl acetate-hexane) to afford (2RS,5S)-3-benzyl-5-(4-chlorophenyl)-1,2,3-oxathiazolidine 2-oxide (16.2 g 87.4%) as a pale yellow solid.

The resulting product was obtained as a mixture of two diastereomers due to the S-oxide.

major isomer: $^1$H NMR (CDCl$_3$) δ: 3.31(1H, dd, J=10.5, 9.9 Hz), 3.55(1H, dd, J=9.0, 6.3 Hz), 3.88(1H, d, J=13.2 Hz), 4.37(1H, d, J=13.2 Hz), 5.49(1H, dd, J=10.5, 6.3 Hz), 7.22-7.43(9H, m).

minor isomer: $^1$H NMR (CDCl$_3$) δ: 3.21(1H, dd, J=13.5, 4.5 Hz), 3.77(1H, dd, J=13.5, 11.4 Hz), 4.05(1H, d, J=13.5 Hz), 4.38(1H, d, J=13.5 Hz), 5.99(1H, dd, J=11.4, 4.5 Hz), 7.22-7.43(9H, m).

A solution of (2RS,5S)-3-benzyl-5-(4-chlorophenyl)-1,2,3-oxathiazolidine 2-oxide (16.2 g, 52.6 mmol) and sodium azide (17.11 g, 263.2 mmol) in N,N-dimethylformamide (100 ml) was heated at 70° C. for 24 hours. The reaction mixture was partitioned between ether and water, and the organic layer was washed with water and brine successively, dried over anhydrous sodium sulfate, and concentrated under reduced pressure. The residue was purified by silica gel column chromatography (eluent: 10-20% ethyl acetate-hexane) to afford (R)-N-benzyl-2-azido-2-(4-chlorophenyl)ethylamine (12.7 g, 83.8%) as a yellow oil.

$^1$H NMR (CDCl$_3$) δ: 2.81(1H, dd, J=12.5, 5.1 Hz), 2.89 (1H, dd, J=12.5, 8.5 Hz), 3.82(2H, s), 4.64(1H, dd, J=8.5, 5.1 Hz), 7.23-7.36(9H, m).

A solution of (R)-N-benzyl-2-azido-2-(4-chlorophenyl) ethylamine (12.7 g, 44.1 mmol) in tetrahydrofuran (176 mL) was treated with triphenylphosphine (13.9 g, 52.9 mmol) at room temperature. After addition of water (20 ml), the reaction mixture was heated at 60° C. for 1 h. The reaction mixture was condensed, and partitioned between ether and 1 N hydrochloric acid. The aqueous layer was treated with 1 N aqueous sodium hydroxide solution until the solution became basic. The resulting solution was extracted with dichlromethane thoroughly. The combined organic layer was washed with water, dried over anhydrous sodium sulfate, filtered, and concentrated under reduced pressure. The residue was used for the next reaction without further purification.

The residue was heated with diethyl oxalate (18 ml, 132 mmol) at 120° C. for 1.5 h. The resulting white precipitate was washed with ether and collected to afford (R)-1-benzyl-5-(4-chlorophenyl)-2,3-dioxopiperazine (11.4 g, 82.2%).

$^1$H NMR (CDCl$_3$) δ: 3.46(1H, dd, J=12.9, 8.1 Hz), 3.60 (1H, dd, J=12.9, 3.8 Hz), 4.48(1H, d, J=14.7 Hz), 4.79(1H, d, J=14.7 Hz), 4.80(1H, dd, J=8.9, 3.8 Hz), 6.83(1H, s), 7.13 (4H, m), 7.27(5H, m).

To a suspension of (R)-1-benzyl-5-(4-chlorophenyl)-2,3-dioxopiperazine (11.4 g, 36.3 mmol) in tetrahydrofuran (300 ml) was added borane-tetrahydrofuran complex (181 mL, 1.0 M solution in tetrahydrofuran, 181 mmol) at room temperature. After stirring for 24 hours, the reaction mixture was quenched with methanol (50 ml) at 0° C., and concentrated under reduced pressure. The residue was treated with 10% aqueous sodium hydroxide solution (300 ml) and heated at 100° C. for 2 hours. After cooling at room temperature, the mixture was extracted with dichloromethane thoroughly. The combined organic layer was dried over anhydrous sodium sulfated, filtered, and concentrated under reduced pressure. The residue was used for the next reaction without further purification.

To a solution of the residue and triethylamine (7.58 ml, 54.4 mmol) in dichloromethane (150 ml) was added di-tert-butyl dicarbonate (9.49 g, 43.5 mmol) at room temperature. After stirring for 45 min, the resulting mixture was partitioned between dichloromethane and water, dried over anhydrous sodium sulfate, filtered, and concentrated under reduced pressure. The residue was purified by silica gel column chromatography (eluent: 10-20% ethyl acetate-hexane) to afford (R)-1-benzyl-4-(tert-butoxycarbonyl)-3-(4-chlorophenyl)piperazine (11.6 g, 82.8%) as an oil.

$^1$H NMR (CDCl$_3$) δ: 1.43(9H, s), 2.16(1H, dt, J=4.4, 11.7 Hz), 2.40(1H, dd, J=4.4, 11.7 Hz), 2.78(1H, dd, J=4.4, 11.7 Hz), 2.98(1H, dt, J=4.4, 11.7 Hz), 3.20(1H, d, J=12.8 Hz), 3.42(1H, d, J=12.9 Hz), 3.57(1H, d, J=12.9 Hz), 3.89(1H, d, J=12.8 Hz), 5.17(1H, s), 7.24-7.36(9H, m).

To a solution of (R)-1-benzyl-4-(tert-butoxycarbonyl)-3-(4-chlorophenyl)piperazine (11.6 g, 30.1 mmol) in 1,2-dichloroethane (80 ml) was added 1-chloroethyl chloroformate (4.91 ml, 45.1 mmol) at room temperature. Upon disappearance of the starting material, the reaction mixture was concentrated under reduced pressure. The residue was then dissolved in methanol (100 ml) and refluxed for 30 min. The resulting white precipitate was filtered and washed with methanol to afford (R)-2-(4-chlorophenyl)piperazine dihydrochloride, which was liberated with aqueous sodium hydroxide solution, and extracted with dichloromethane to afford (R)-2-(4-chlorophenyl)piperazine (3.04 g, 51.4%) as white solid.

$^1$H NMR (CDCl$_3$) δ: 2.65(1H, dd, J=12.0, 10.5 Hz), 2.82-3.04(4H, m), 3.09(1H, d, J=12.6 Hz), 3.73(1H, dd, J=10.1, 2.7 Hz), 7.29(4H, m)

The filtrate was concentrated under reduced pressure and partitioned between ether and 1 N hydrochloric acid. The aqueous layer was neutralized with 1 N aqueous sodium hydroxide solution, and extracted with dichloromethane thoroughly. The combined organic extracts were dried over anhydrous sodium sulfate, filtered, and concentrated under reduced pressure. The residue was purified after Boc-protection (Boc$_2$O, Et$_3$N, CH$_2$Cl$_2$) to furnish (R)-1,4-di(tert-butoxycarbonyl)-2-(4-chlorophenyl)piperazine (2.70 g, 22.6%) as pale yellow solid.

$^1$H NMR (CDCl$_3$) δ: 1.43(9H, s), 1.46(9H, s), 2.96(2H, m), 3.32(1H, dd, J=13.8, 4.2 Hz), 3.74(1H, m), 3.94(1H, d, J=11.4 Hz), 4.40(1H, d, J=13.2 Hz), 5.23(1H, s), 7.25(2H, m)

To a suspension of (R)-2-(4-chlorophenyl)piperazine dihydrochloride (1.09 g, 4.05 mmol) in tetrahydrofuran (24 ml) was added triethylamine (2.82 ml, 20.3 mmol). After stirring for 15 min at room temperature, 2-chloro-3-methyl-6-(4-pyridyl)-3H-pyrimidin-4-one (748 mg, 3.38 mmol) was added portionwise. Upon disappearance of the chloropyrimidone, the reaction mixture was condensed under reduced pressure. The residue was partitioned between saturated aqueous sodium bicarbonate solution and dichloromethane. The organic layer was dried over anhydrous sodium sulfate, filtered, and concentrated under reduced pressure to give pale yellow solid, which was recrystallized from ethanol to afford (R)-2-(2-(4-chlorophenyl)piperazin-4-yl)-3-methyl-6-(4-pyridyl)-pyrimidin-4-one (998 mg, 77.4%) as white crystals. The enantiomer excess was determined by HPLC (>99% ee). The crystals were converted into its dihydrochloride salt.

$^1$H NMR (DMSO-d$_6$) δ: 3.40(3H, m), 3.46(3H, s), 3.62 (1H, dd, J=12.0, 13.2 Hz), 3.72(1H, m), 3.92(1H, t, J=15.5 Hz), 4.68(1H, t, J=10.1 Hz), 7.18(1H, s), 7.58(2H, d, J=8.6 Hz), 7.83(2H, d, J=8.6 Hz), 8.57(2H, d, J=6.6 Hz), 9.01(2H, d, J=6.6 Hz), 10.20(1H, d, J=7.8 Hz), 10.76(1H, br s) MS: 382(M+H)

$[α]_D^{24}$=+62.2° (c 1.00, H$_2$O)

Example 6

Synthesis of (S)-2-(2-(4-chlorophenyl)piperazin-4-yl)-3-methyl-6-(4-pyridyl)-pyrimidin-4-one (No. XA373)

(S)-isomer was prepared same as above by using (R)-2-methyl-CBS-oxazaborolidine instead of (S)-2-methyl-CBS-oxazaborolidine.

$^1$H NMR (DMSO-d$_6$) δ: 3.40 (3H, m), 3.45 (3H, s), 3.53-3.96 (3H, m), 4.68 (1H, t, J=13.5 Hz), 7.10 (1H, s), 7.60 (2H, d, J=8.3 Hz), 7.76 (2H, d, J=8.3 Hz), 8.38 (1H, br s), 8.91 (1H, d, J=4.8 Hz), 9.88 (1H, br s), 10.31 (1H, br s)

MS: 382(M+H)

$[α]_D^{24}$=−63.3° (c 1.00, H$_2$O)

Example 7

Synthesis of 2-(2-(4-fluoro-2-methoxyphenyl)piperazin-4-yl)-3-methyl-6-(4-pyrimidyl)-pyrimidin-4-one (No. YA0366)

A solution of 2-bromo-5-fluoroanisole (11.8 g, 57.6 mmol) in tetrahydrofuran (60 ml) was dropped into the magnesium (1.40 g, 57.6 mmol) in refluxed tetrahydrofuran (32 ml) containing small amount of 1,2-dibromoethane and refluxed for 15 min. After addition of tetrahydrofuran (50 ml), the solution was cooled to −78° C. and diethyl oxalate (7.41 g; 50.7 mmol) in diethyl ether (50 ml) was dropped into the solution. After stirring at the same temperature for 30 min, the solution was warmed to −10° C. and 1N aqueous hydrogen chloride (50 ml) and water were added. Organic layer was extracted with diethyl ether, washed with brine and dried over magnesium sulfate. After removal of the solvent under reduced pressure, purification of the residue by silica gel column chromatography (eluent: hexane/ethyl acetate=5/2) gave ethyl 2-(4-fluoro-2-methoxyphenyl)-2-oxoacetate (6.80 g, 59%)

$^1$H-NMR (CDCl$_3$) δ: 1.40(3H, t, J=7.1 Hz), 3.87(3H, s), 4.89(2H, q, J=7.1 Hz), 6.68(1H, d, J=10.5 Hz), 6.77-6.81(1H, m), 7.91-7.95(1H, m).

Ethylenediamine (0.60 g, 10.0 mmol) was added to a solution of ethyl 2-(4-fluoro-2-methoxyphenyl)-2-oxoacetate (2.26 g, 10.0 mmol) in ethanol (30 ml) and refluxed 4 hr; After removal of the solvent under reduced pressure, residue was washed with ethanol-diethyl ether to give 5,6-dihydro-3-(4-fluoro-2-methoxyphenyl)pyrazinone (1.76 g, 79%).

$^1$H-NMR (CDCl$_3$) δ: 3.50-3.56 (2H, m), 3.81 (3H, s), 3.88-3.92 (2H, m), 6.65(1H, d, J=11.0 Hz), 6.70-6.76 (1H, m), 6.89(1H, bs), 7.36-7.40(1H, m).

5,6-Dihydro-3-(4-fluoro-2-methoxyphenyl)pyrazinone was added to the solution of lithium aluminium hydride (0.46 g, 12 mmol) in diethyl ether (25 ml) and refluxed for 6 hr. Water (0.48 ml), 15% sodium hydroxide solution (0.48 ml) and again water (1.21 ml) were added to the ice-cooled solution and the precipitate was filtered and washed with dichloromethane. Combined organic layer was evaporated to give 2-(4-fluoro-2-methoxyphenyl)piperazine (0.83 g, 99%).

$^1$H-NMR (CDCl$_3$) δ: 2.02(2H, s), 2.57-2.63 (1H, m), 2.80-2.89 (1H, m), 2.92-2.99 (2H, m), 3.06-3.12 (2H, m), 3.80(3H, s), 4.06 (1H, d, J=10.0 Hz), 6.56-6.65 (2H, m), 7.40 (1H, t, J=7.8 Hz).

2-Chloro-3-methyl-6-(4-pyrimidyl)-pyrimidin-4-one (223 mg, 1:0 mmol) was added to an ice-cooled solution of 2-(4-fluoro-2-methoxyphenyl)piperazine (210 mg, 1.0 mmol), triethylamine (0.15 ml, 1.1 mmol) in N,N-dimethylformamide (10 ml) and stirred at that temperature for 0.5 hr and then at room temperature for 3 hours. Reaction was quenched by ice-water and the filtrate was washed with water and dried to give 2-(2-(4-fluoro-2-methoxyphenyl)piperazin-4-yl)-3-methyl-6-(4-pyrimidyl)-pyrimidin-4-one (262 mg, 66%).

$^1$H-NMR (CDCl$_3$) δ: 2.89-2.98 (1H, m), 3.22-3.31 (3H, m), 3.60 (3H, s), 3.62-3.71 (2H, m), 3.86 (3H, s), 4.39-4.44 (1H, m), 6.43-6.73 (2H, m), 7.33 (1H, s), 7.52-7.56 (1H, m), 8.19 (1H, d, J=5.1 Hz), 8.87 (1H, d, J=5.2 Hz), 9.28 (1H, d, J=1.2 Hz).

4N Hydrogen chloride in 1,4-dioxane (0.2 ml) was added to the solution of 2-(2-(4-fluoro-2-methoxyphenyl)piperazin-4-yl)-3-methyl-6-(4-pyrimidyl)-pyrimidin-4-one (238 mg, 0.6 mmol) in dichloromethane (5 ml) and stirred for 15 min. Wash with methanol and ethyl acetate after removal of the solvent and dryness gave the title compound (223 mg, 86%).

Example 8

Synthesis of 2-(2-(4-chlorophenyl)-piperazine-4-yl)-3-methyl-6-(4-pyrimidyl)pyrimidin-4-one (No. YA0269)

Dimethyl sulfoxide (60 ml) solution of 4-chlorophenacyl-bromide (11.11 g, 65.9 mmol) and water (1.7 ml) were stirred. The solution was extracted with ethyl acetate 3 times and washed with water twice and brine and then dried over sodium sulfate. After removal of the solvent, the residue was washed with hexane-ethyl acetate and dried to give 4-chlorophenylglyoxal (4.43 g, 50%).

$^1$H-NMR (CDCl$_3$) δ: 4.02-4.16(2H, m), 5.90-5.95(1H, m), 7.45-7.53(2H, m), 8.05-8.11(2H, m).

A methanol (10 ml) solution of ethylenediamine (1.90 g, 31.6 mmol) was added to the ice-cooled solution of 4-chlorophenylglyozal (4.43 g, 26.3 mmol) in methanol (100 ml) and tetrahydrofuran (30 ml) and stirred for 10 min. After addition of sodium tetrahydroborate (3.26 g, 86.3 mmol), additional methanol (50 ml) was added and stirred overnight. After removal of the solvent, diluted hydrochloric acid was added and extracted with ether twice. After addition of sodium hydroxide, basic aqueous layer was extracted with dichloromethane three times and washed with brine and dried over sodium sulfate. After removal of the solvent by filtration, purification of the residue by silica gel column chromatography (eluent; dichloromethane/ethanol=10/1 to dichloromethane/ethanol/diethylamine=20/2/1) to give 2-(4-chlorophenyl)-piperazine (0.43 g, 9%)

$^1$H-NMR (CDCl$_3$) δ: 2.67(1H, dd, J=10.5, 12.0 Hz), 2.87-3.03(4H, m), 3.07-3.13(1H, m), 3.77(1H, dd, J=2.7, 10.2 Hz), 7.27-7.36(4H, m).

Triethylamine (528 mg, 5.2 mmol) was added to a solution of 4-(chlorophenyl)piperazine (216 mg, 1.1 mmol) and 2-chloro-3-methyl-6-(4-pyrimidyl)pyrimidin-4-one and stirred at 50° C. for 2 hr. Solvent was removed under reduced pressure, and 1N aqueous sodium hydroxide solution was added to the residue and extracted by dichloromethane. After washing with brine and dryness by sodium sulfate, solvent was removed under reduced pressure, and the residue was purified using ISOLUTE(registered trade mark) SI (International Sorvent Technology, UK) (eluent; dichloromethane/ethanol=10/1) to give the title compound (396 mg, 95%).

Example 9

Synthesis of 2-(2-(4-chlorophenyl)-6,6-dimethyl-piperazin-4-yl)-3-methyl-6-pyridin-4-yl-3H-pyrimidin-4-one dihydrochloride (No. XA1986)

A solution of 4'-chloro-2-bromoacetophenone (25.0 g, 107 mmol), water (1.92 mL, 107 mmol) and 47% hydrobromic acid (0.20 mL) in dimethylsulfoxide (160 mL) was stirred at 80° C. for 5 h. After the reaction mixture was poured into water, the precipitate was filtered, washed with diethylether and dried, affording 4'-chloro-2,2-dihydroxyacetophenone (14.0 g, 70%). $^1$H NMR (300 MHz, CDCl$_3$), δ 5.92(1H, s), 7.45-7.52(2H, m), 8.05-8.20(2H, m).

2,2-dimethly-ethylenediamine (2.10 mL, 20.0 mmol) was added to a solution of 4'-chloro-2,2-dihydroxyacetophenone (3.70 g, 20.0 mmol) in methanol (120 mL) and tetrahydrofuran (30 mL) at room temperature. After 2 h, sodium borohydride (1.50 g, 40.0 mmol) was added to the reaction mixture at 0° C. The reaction mixture was stirred overnight, then quenched with 1N hydrochloric acid and evaporated in vacuo. The acidic solution was extracted with ethyl acetate, then basified to pH 11 using 15% aqueous sodium hydroxide, and extracted with dichloromethane. The extract was dried over sodium sulfate and concentrated in vacuo. Di-t-butyldicarbonate (6.40 mL, 27.9 mmol) was added to the solution of the residue in 1N aqueous sodium hydroxide (40 mL) and tetrahydrofuran (60 mL). The resulting suspension was heated at 40° C. for 8 h, then diluted with ethyl acetate and water. The organic layer was extracted with additional ethyl acetate, dried and concentrated in vacuo. The crude product was purified by flash column chromatography, affording 2-(4-chlorophenyl)-4-t-butoxycarbonyl-6,6-dimethylpiperazine (1.69 g, 28%, 2 steps). $^1$H NMR (300 MHz, CDCl$_3$), δ 1.15(3H, s), 1.21(3H, s), 2.47-2.70(2H, m), 3.72-4.16(3H, m), 7.26-7.37 (4H, m).

4 M Hydrogen chloride in ethyl acetate (5.0 mL, 20.0 mmol) was added to a solution of 2-(4-chlorophenyl)-4-t-butoxycarbonyl-6,6-dimethyl-piperazine (1.69 g, 5.2 mmol). After 12 h, removing the solvent, filtrating and washing the precipitate with ethyl acetate gave 2-(4-chlorophenyl)-6,6-dimethyl-piperazine dihydrochloride (1.43 g, 95%). $^1$H NMR (300 MHz, DMSO-d$_6$), δ 1.40 (3H, s), 1.58(3H, s), 3.24-3.99 (4H, m), 4.73(1H, m), 7.69(2H, d, J=8.4 Hz), 7.79(2H, m), 9.99-10.12(2H, m).

A solution of 2-(4-chlorophenyl)-6,6-dimethyl-piperazine hydrochloride (155 mg, 0.52 mmol), 2-chloro-3-methyl-6-(4-pyridyl)-pyrimidine-4-one (111 mg, 0.50 mmol) and triethylamine (0.42 mL, 2.50 mmol) in tetrahydrofuran (5 mL) was stirred at room temperature for 6 h. The whole was evaporated in vacuo and the residue was extracted with dichloromethane. The organic layer was washed with water, dried and concentrated in vacuo. The residue was dissolved in methanol (5 mL) and treated with 4M hydrogen chloride in ethyl acetate (0.50 mL, 2.0 mmol) for 20 min. After removing the solvent, filtrating and washing the precipitate with ethanol gave 2-(2-(4-chlorophenyl)-6,6-dimethyl-piperazin-4-yl)-3-methyl-6-pyridin-4-yl-3H-pyrimidin-4-one dihydrochloride (235 mg, 97%).

Example 10

Synthesis of 2-(2S-(4-bromophenyl)-piperazin-1-yl)-3-methyl-6-pyridin-4-yl-3H-pyrimidin-4-one (No. XA2051)

Benzyl chloroformate (2.40 mL, 15.0 mmol) was added to a solution of 2S-(4-bromophenyl)-piperazine dihydrochloride in 1N aqueous sodium hydroxide (30 mL) and dichloromethane (60 mL). The resulting suspension was stirred at room temperature for 1.5 h. After partitioned between ethylacetate, the organic layer was extracted with additional ethyl acetate, dried and concentrated in vacuo. The precipitate was washed with ether, affording 2S-(4-bromophenyl)-4-benzyloxycarbonyl-piperazine (2.92 g, 57%). $^1$H NMR (300 MHz, CDCl$_3$), δ 2.87-3.01(2H, m), 3.47(2H, m), 3.93-3.97(1H, m), 4.20(2H, m), 5.16(2H, s), 7.36(5H, m), 7.42-7.61(4H, m).

A solution of 2S-(4-bromophenyl)-4-benzyloxycarbonyl-piperazine (788 mg, 2.10 mmol), 2-chloro-3-methyl-6-(4-pyridyl)-pyrimidine-4-one (444 mg, 2.00 mmol) and diisopropylethylamine (0.70 mL, 4.00 mmol) in dimethylformamide (20 mL) was stirred at 80° C. for 3 h. The reaction mixture was poured into water and the whole was extracted with ethyl acetate. The organic layer was washed with brine, dried and concentrated in vacuo. Chromatographic purification of the residue provided 2-(2S-(4-bromophenyl)-4-benzyloxycarbonyl-piperazin-1-yl)}-3-methyl-6-pyridin-4-yl-3H-pyrimidin-4-one (601 mg, 54%). $^1$H NMR (300 MHz, CDCl$_3$), δ 3.05(1H, m), 3.30-3.48(3H, m), 3.64(3H, s), 4.08-4.22(2H, m), 4.68(1H, m), 5.15(1H, d, J=12.3 Hz), 5.21(1H, d, J=12.6 Hz), 6.63(1H, s), 7.21(2H, d, J=8.4 Hz), 7.28-7.39(7H, m), 7.59(2H, d, J=6.3 Hz), 8.68(2H, d, J=6.3 Hz).

Potassium hydroxide (168 mg, 3.0 mmol) was added to a solution of 2-{2S-(4-bromophenyl)-4-benzyloxycarbonyl-piperazin-1-yl}-3-methyl-6-pyridin-4-yl-3H-pyrimidin-4-one in ethanol (2.0 mL). After stirring for 8 h at room temperature, purifying by preparative HPLC gave 2-(2S-(4-bromophenyl)-piperazin-1-yl)-3-methyl-6-pyridin-4-yl-3H-pyrimidin-4-one (40 mg, 26%).

Example 11

Synthesis of (S)-3-methyl-6-(4-pyridyl)-2-(3-(4-(3-(pyrrolidin-1-yl) pyrrolidin-1-yl)phenyl)piperazin-1-yl)pyrimidin-4-one (No. XA2032)

A suspension of (S)-2-(4-bromophenyl)-1,4-di(t-butoxycarbonyl) piperazine (1.33 g, 3.00 mmol), (R)-3-pyrrolidinol (520 mg, 4.20 mmol), palladium acetate (27 mg, 0.12 mmol), 2-(di-t-butylphosphino)biphenyl (72 mg, 0.24 mmol), and sodium t-butoxide (808 mg, 8.41 mmol) in tert-butanol (20 mL) was heated at 90° C. for 3.5 h. After dilution with ethyl acetate, the resulting mixture was passed through a Celite column. The filtrate was concentrated in vacuo, and the residue was purified by silica gel column chromatography eluting 10-50% ethyl acetate-hexane to afford (S)-1,4-di-(t-butoxycarbonyl)-2-(4-((R)-3-hydroxypyrrolidino) phenyl)piperazine (733 mg, 54.5%) as a yellow foam.

To a solution of (S)-1,4-di(t-butoxycarbonyl)-2-(4-((R)-3-hydroxy pyrrolidino)phenyl)piperazine (733 mg, 1.64 mmol) and triethylamine (0.34 mL, 2.46 mmol) in dichloromethane (20 mL) was added methanesulfonyl chloride (0.152 mL, 1.97 mmol) at 0° C. After stirring for 20 min, the reaction mixture was partitioned between ethyl acetate and water. The organic layer was washed with brine, dried over anhydrous sodium sulfate, and concentrated in vacuo to afford (S)-1,4-di(t-butoxycarbonyl)-2-(4-((R)-3-(methansulfonyloxy)pyrrolidin-1-yl) phenyl)piperazine (877 mg, quant.) as a brown solid.

To a solution of (S)-1,4-di(t-butoxycarbonyl)-2-(4-((R)-3-methansulfonyloxy-pyrrolidino)phenyl)piperazine (877 mg, 1.64 mmol) in toluene (10 mL) was added pyrrolidine (0.64 mL, 8.19 mmol), and the resulting solution was heated at 90° C. for 8 h. After checking consumption of the starting material with TLC, the reaction mixture was partitioned between ethyl acetate and saturated sodium bicarbonate aqueous solution. The organic layer was washed with brine, dried over anhydrous sodium sulfate, and concentrated in vacuo. The residue was purified by silica gel column chromatography eluting 30-100% ethyl acetate-hexane and then 3-10% methanol-ethyl acetate to afford (S)-1,4-di(t-butoxycarbonyl)-2-(4-((S)-3-(pyrrolidin-1-yl)pyrrolidin-1-yl)phenyl)piperazine (479 mg, 58%) as a pale yellow powder.

To a solution of (S)-1,4-di(t-butoxycarbonyl)-2-(4-((S)-3-(pyrrolidin-1-yl) pyrrolidin-1-yl)phenyl)piperazine (479 mg, 0.957 mmol) in dichloromethane (4 mL) was added 4 N hydrogen chloride in ethyl acetate (4 mL) at room temperature. After stirring for 3 h, the resulting precipitate was collected and dried in vacuo to afford (S)-2-(4-((S)-3-(pyrrolidin-1-yl)pyrrolidin-1-yl)phenyl)piperazine tetrahydrochloride (370 mg, 87%) as a white solid.

To a suspension of (S)-2-(4-((S)-3-(pyrrolidin-1-yl)pyrrolidin-1-yl)phenyl) piperazine tetrahydrochloride (98 mg, 0.22 mmol) in tetrahydrofuran (5 mL) was added triethylamine (0.20 mL, 1.40 mmol) and 2-chloro-3-methyl-6-(4-pyridyl)-3H-pyrimidin-4-one (44 mg, 0.20 mmol) at room temperature. After stirring for 24 h, the reaction mixture was concentrated in vacuo. The residue was dissolved in dichloromethane and sodium bicarbonate aqueous solution, and the solution was passed through CHEM ELUT CE1010 (manufactured by VARIAN). The filtrate was concentrated, and the resulting crystals were washed in a mixture of diisopropyl ether and ethanol to afford (S)-2-(3-(4-(3-(pyrrolidin-1-yl) pyrrolidin-1-yl)phenyl)piperazin-1-yl)-3-methyl-6-(4-pyridyl)pyrimidin-4-one (80 mg, 82%) as a pale yellow solid.

Example 12

Synthesis of (S)-3-methyl-6-(4-pyrimidinyl)-2-(3-(4-(3-(pyrrolidin-1-yl) pyrrolidin-1-yl)phenyl)piperazin-1-yl)pyrimidin-4-one (No. YA1577)

To a suspension of (S)-2-(4-((S)-3-(pyrrolidin-1-yl)pyrrolidin-1-yl)phenyl) piperazine tetrahydrochloride (99 mg, 0.22 mmol) in tetrahydrofuran (5 mL) was added triethylamine (0.20 mL, 1.40 mmol) and 2-chloro-3-methyl-6-(4-pyrimidinyl)-3H-pyrimidin-4-one (45 mg, 0.20 mmol) at room temperature. After stirring for 24 h, the reaction mixture was concentrated in vacuo. The residue was dissolved in dichloromethane and sodium bicarbonate aqueous solution, and the solution was passed through CHEM ELUT CE1010 (manufactured by VARIAN). The filtrate was concentrated, and the resulting crystals were washed in a mixture of diisopropyl ether and ethanol to afford (S)-3-methyl-6-(4-pyrimidinyl)-2-(3-(4-(3-(pyrrolidin-1-yl)pyrrolidin-1-yl)phenyl) piperazin-1-yl)-pyrimidin-4-one (65 mg, 66%) as a pale yellow solid.

Example 13

Synthesis of (S)-2-(3-(4-(N-cyclohexyl-N-methylamino)phenyl) piperazin-1-yl)-3-methyl-6-(4-pyridyl)pyrimidin-4-one (No. XA1999)

A suspension of (S)-2-(4-bromophenyl)-1,4-di(t-butoxycarbonyl) piperazine (1.21 g, 2.75 mmol), N-methylcyclohexylamine (0.43 mL, 3.30 mmol), palladium acetate (25 mg, 0.11 mmol), 2-(di-t-butylphosphino)biphenyl (66 mg, 0.22 mmol), and sodium t-butoxide (370 mg, 3.85 mmol) in t-butanol (15 mL) was heated at 80° C. for 8 h. The resulting solution was partitioned between ethyl acetate and water. The organic layer was washed with brine, dried over anhydrous sodium sulfate, and concentrated in vacuo. The residue was purified by silica gel column chromatography eluting 10-15% ethyl acetate-hexane to afford (S)-1,4-di(t-butoxycarbonyl)-2-(4-(N-cyclohexyl-N-methylamino)phenyl)piperazine (917 mg) as white crystals.

To a solution of (S)-1,4-di(t-butoxycarbonyl)-2-(4-(N-cyclohexyl-N-methylamino)phenyl)piperazine in dichloromethane (4 mL) was added 4 N hydrogen chloride in ethyl acetate (4 mL). After stirring for 40 min, the white precipitate was collected, which included impurities. The mixture was purified by a reverse phase chromatography eluting 0.05% TFA in water-acetonitrile to afford (S)-2-(4-(N-cyclohexyl-N-methylamino)phenyl)piperazine (59 mg 8% in 2 steps) as a clear oil.

To a solution of (S)-2-(4-(N-cyclohexyl-N-methylamino) phenyl) piperazine (50 mg, 0.183 mmol) and triethylamine (0.077 mL, 0.55 mmol) was added 2-chloro-3-methyl-6-(4-pyridyl)-3H-pyrimidin-4-one (37 mg, 0.17 mmol) at room temperature. After stirring for 4.5 h, the reaction mixture was concentrated in vacuo. The residue was partitioned between dichloromethane and saturated sodium bicarbonate aqueous solution. The organic layer was dried over anhydrous sodium sulfate and concentrated. The residue was purified by a reverse phase chromatography eluting 0.05% TFA in water-acetonitrile to afford (S)-2-(3-(4-(N-cyclohexyl-N-methylamino)phenyl)piperazin-1-yl)-3-methyl-6-(4-pyridyl)pyrimidin-4-one (67 mg, 88%) as a oil, which was dissolved in ethyl acetate and treated with 4 N hydrogen chloride in ethyl acetate to yield its trihydrochloride.

Example 14

Synthesis of (S)-2-(3-(4-(N,N-dimethylamino)phenyl)piperazin-1-yl)-3-methyl-6-(4-pyridyl)pyrimidin-4-one trihydrochloride (No. XA2017)

A suspension of (S)-2-(4-bromophenyl)-1,4-di(t-butoxycarbonyl) piperazine (1.14 g, 2.59 mmol), N,N-dimethylamine hydrochloride (422 mg, 5.17 mmol), palladium acetate (23 mg, 0.10 mmol), 2-(di-t-butylphosphino)biphenyl (62 mg, 0.21 mmol), and sodium t-butoxide (845 mg, 8.80 mmol) in t-butanol (15 mL) was heated at 90° C. for 3 h. After dilution with ethyl acetate, the resulting solution was passed through a Celite column. The filtrate was concentrated, and the residue was purified by silica gel column chromatography eluting 10-20% ethyl acetate-hexane to afford (S)-1,4-di(t-butoxycarbonyl)-2-(4-(N,N-dimethylamino) phenyl)piperazine (556 mg, 53%) as white crystals.

To a solution of (S)-1,4-di(t-butoxycarbonyl)-2-(4-(N,N-dimethylamino) phenyl)piperazine (556 mg, 1.37 mmol) in dichloromethane (4 mL) was added 4 N hydrogen chloride in ethyl acetate (4 mL). After stirring for 8.5 h, the white precipitate was collected and dried in vacuo to afford (S)-2-(4-(N,N-dimethylamino) phenyl)piperazine trihydrochloride (413 mg, 96%) as white crystals.

To a suspension of (S)-2-(4-(N,N-dimethylamino)phenyl) piperazine trihydrochloride (115 mg, 0.365 mmol) in tetrahydrofuran (5 mL) was added triethylamine (0.28 mL, 2.0 mmol) and then 2-chloro-3-methyl-6-(4-pyridyl)-3H-pyrimidin-4-one (74 mg, 0.33 mmol) at room temperature. After stirring for 10 h, the resulting mixture was concentrated in vacuo. The residue was dissolved in dichloromethane and saturated sodium bicarbonate aqueous solution, and the solution was passed through CHEM ELUT CE1010 (manufactured by VARIAN). The filtrate was concentrated in vacuo to yield crystals, which were washed with diisopropyl ether. After the crystals were dissolved in ethyl acetate, the solution was treated with 4 N hydrogen chloride in ethyl acetate. White precipitate was collected and dried in vacuo to afford (S)-2-(3-(4-(N,N-dimethylamino)phenyl) piperazin-1-yl)-3-methyl-6-(4-pyridyl)pyrimidin-4-one trihydrochloride (135 mg, 81%).

Example 15

Synthesis of (S)-2-(3-(4-methoxybiphen-4-yl)piperazin-1-yl)-3-methyl-6-(4-pyridyl)pyrimidin-4-one (No. XA1991)

A mixture of (S)-2-(4-bromophenyl)-1,4-di(t-butoxycarbonyl)piperazine (1.82 g, 4.11 mmol), 4-methoxyphenylboronic acid (937 mg, 6.17 mmol), sodium carbonate (2.18 g, 20.6 mmol), and tetrakis(triphenylphosphine)palladium(0) (238 mg, 0.206 mmol) was dissolved in dimethoxyethane (20 mL) and water (20 mL), and the resulting solution was refluxed for 3 h. After cooling to room temperature, the mixture was partitioned between ethyl acetate and water. The organic layer was washed with brine, dried over anhydrous sodium sulfate, and concentrated in vacuo. The resulting solid was washed with ethyl acetate to afford (S)-1,4-di(t-butoxycarbonyl)-2-(4'-methoxybiphen-4-yl)piperazine (1.46 g, 75.9%) as a white solid.

To a solution of (S)-1,4-di(t-butoxycarbonyl)-2-(4'-methoxybiphen-4-yl)-piperazine (1.46 g, 3.12 mmol) in dichloromethane (8 mL) was added 4 N hydrogen chloride in ethyl acetate (8 mL) at room temperature. After stirring for 1 h, the precipitate was collected and dried in vacuo to afford (S)-2-(4'-methoxybiphen-4-yl) piperazine dihydrochloride (1.00 g, 94%) as white solid.

To a suspension of (S)-2-(4'-methoxybiphen-4-yl)-piperazine dihydrochloride (237 mg, 0.694 mmol) in tetrahydrofuran (5 mL) was added triethylamine (0.40 mL, 2.9 mmol) and then 2-chloro-3-methyl-6-(4-pyridyl)-3H-pyrimidin-4-one (128 mg, 0.579 mmol) at room temperature. After stirring for 28 h, the resulting mixture was concentrated in vacuo. The residue was partitioned between dichloromethane and saturated sodium bicarbonate aqueous solution, and the organic layer was dried over anhydrous sodium sulfate and then concentrated in vacuo. The resulting solid was washed with hot ethanol to afford (S)-2-(3-(4-methoxybiphen-4-yl)piperazin-1-yl)-3-methyl-6-(4-pyridyl)pyrimidin-4-one (252 mg, 96%), which was treated with 4 N hydrogen chloride in ethyl acetate to yield its dihydrochloride salt (252 mg) as pale yellow crystals.

Example 16

Synthesis of (S)-2-(3-benzylpiperazin-1-yl)-3-methyl-6-(4-pyridyl) pyrimidin-4-one (No. XA2004)

To a solution of L-phenylalanine ethyl ester hydrochloride (3.875 g, 16.87 mmol), Boc-glycine (2.815 g, 16.07 mmol) in dichloromethane (100 mL) was added triethylamine (2.35 mL, 16.87 mmol) and then 1-(3-dimethylaminopropyl)-3-ethylcarbodiimide hydrochloride (3.23 g, 16.87 mmol) at room temperature. After the resulting mixture was stirred for 2.5 h, it was partitioned between ethyl acetate and water. The organic layer was washed with 1 N hydrochloric acid, brine, and then saturated sodium bicarbonate aqueous solution, dried over anhydrous sodium sulfate, and concentrated in vacuo to afford Boc-glyclylphenylalanine ethyl ester (5.96 g).

To a solution of Boc-glycylphenylalanine ethyl ester (5.96 g) in dichloromethane (20 ml) was added trifluoroacetic acid (20 mL) at room temperature. After stirring 1.5 h, the resulting solution was concentrated in vacuo. The residue was dissolved in water, into which sodium bicarbonate was added until the pH was 9. After the solution was stirred for several hours, the resulting white crystals were collected and dried in vacuo to afford (S)-3-benzyl-2,5-dioxopiperazine (2.29 g, 70% in 2 steps) as a white powder.

To a suspension of (S)-3-benzyl-2,5-dioxopiperazine (2.284 g, 11.18 mmol) in tetrahydrofuran (20 mL) was added borane-tetrahydrofuran complex (49 mL, 1.0 M solution in THF, 49 mmol) at room temperature. The resulting mixture was refluxed for several hours before it was quenched with methanol at 0° C. After concentration in vacuo, the residue was treated with 10% sodium hydroxide aqueous solution, which was extracted with dichloromethane thoroughly. The organic layer was washed with water, dried over anhydrous sodium sulfate, and concentrated in vacuo to afford white crystals, which were washed with ether to yield (S)-2-benzylpiperazine (795 mg, 40.3%).

To a solution of (S)-2-benzylpiperazine (48 mg, 0.27 mmol) in tetrahydrofuran (5 mL) was added triethylamine (0.10 mL, 0.74 mmol) and then 2-chloro-3-methyl-6-(4-pyridyl)-3H-pyrimidin-4-one (55 mg, 0.248 mmol) at room temperature. After refluxing for 24 h, the resulting mixture was concentrated in vacuo. The residue was partitioned between dichloromethane and saturated sodium bicarbonate aqueous solution, and the organic layer was dried over anhydrous sodium sulfate and then concentrated in vacuo. The residue was purified by a reverse phase chromatography eluting 0.05% TFA in water-acetonitrile to afford (S)-2-(3-benzylpiperazin-1-yl)-3-methyl-6-(4-pyridyl) pyrimidin-4-one (73 mg 81%), which was treated with 4 N hydrogen chloride in ethyl acetate to yield its dihydrochloride salt as a yellow powder.

Example 17

Synthesis of (S)-3-methyl-2-(3-(4-(1,2,4-oxadiazol-3-yl)phenyl) piperazin-1-yl)-6-(4-pyridyl)pyrimidin-4-one (No. XA2039)

To a solution of 4-cyanoacetophenone (11.32 g, 77.98 mmol) in dichloromethane (200 mL) was added bromine (4.00 mL, 78.0 mmol) dropwise at room temperature. After stirring several minutes, the reaction mixture was washed with water, dried over anhydrous sodium sulfate, and concentrated in vacuo to afford 4-cyanophenacyl bromide (17.73 g) as a white solid.

A solution of 4-cyanophenacyl bromide (11.20 g, 49.99 mmol) in dimethylsulfoxide (83 mL) was treated with water (0.90 mL, 49.99 mmol). After stirring for 24 h at room temperature, the solution was poured into ice-water, and extracted with ether. The organic layer was washed with water and then brine, dried over anhydrous sodium sulfate, and concentrated in vacuo. The residue was purified by a silica gel column chromatography eluting 20-50% ethyl acetate in hexane to afford 4-cyanophenylglyoxal (5.10 g, 64.1%) as a yellow solid.

To a solution of 4-cyanophenylglyoxal (2.21 g, 12.5 mmol) in methanol (30 mL) and tetrahydrofuran (10 mL) was added ethylenediamine (1.00 mL, 14.96 mmol) at room temperature. After the mixture was stirred at room temperature for 1 h, sodium borohydride (943 mg, 24.92 mmol) was added at 0° C. The solution was warmed up to room temperature and stirred for another 2 h before it was quenched with 1 N hydrochloric acid. After concentration in vacuo, the mixture was partitioned between ether and water. The aqueous layer was alkalized with sodium hydroxide, and extracted with dichloromethane. The extract was dried over anhydrous sodium sulfate, and then concentrated in vacuo to afford reddish oil (1.69 g). The oil was dissolved in dichloromethane (30 mL), into which triethylamine (3.82 mL, 27.41 mmol) and di-tert-butyl dicarbonate (5.98 g, 27.41 mmol) at room temperature. The reaction mixture was stirred for several hours before it was partitioned between ethyl acetate and water. The organic layer was dried over anhydrous sodium sulfate, and then concentrated in vacuo. The residue was purified by a silica gel column chromatography eluting 5-20% ethyl acetate in hexane to afford 1,4-di(t-butoxycarbonyl)-2-(4-cyanophenyl)piperazine (2.46 g, 50.9%) as white crystals.

A solution of 1,4-di(t-butoxycarbonyl)-2-(4-cyanophenyl) piperazine (558 mg, 1.44 mmol), hydroxylamine hydrochloride (300 mg, 4.23 mmol), and sodium carbonate (763 mg, 7.20 mmol) in ethanol (3 mL) and water (3 mL) was heated at 80° C. for 2.5 h before it was partitioned between dichloromethane and water. The aqueous layer was extracted with dichloromethane. The combined organic layer was dried over sodium sulfate, and concentrated in vacuo to afford white foam (680 mg), which was dissolved in toluene (5 mL) and treated with triethyl orthoformate (2.4 mL, 14.4 mmol) and p-toluenesulfonic acid (27 mg, 0.14 mmol). The solution was heated at 90° C. for 1 h before it was partitioned between dichloromethane and saturated sodium bicarbonate aqueous solution. The organic layer was dried over anhydrous sodium sulfate, and concentrated in vacuo. The resulting white crystals were washed with ethyl acetate, and dried in vacuo to afford 1,4-di(t-butoxycarbonyl)-2-(4-(1,2,4-oxadiazol-3-yl) phenyl)piperazine (464 mg, 75% in 2 steps).

To a solution of 1,4-di(t-butoxycarbonyl)-2-(4-(1,2,4-oxadiazol-3-yl) phenyl)piperazine (464 mg, 1.08 mmol) in dichloromethane (2 mL) was added 4 N hydrogen chloride in ethyl acetate (3 mL) at room temperature. After stirring for 1.5 h, the precipitate was collected and dried in vacuo to afford 2-(4-(1,2,4-oxadiazol-3-yl)phenyl)piperazine dihydrochloride (321 mg, 98%) as a white powder.

To a suspension of 2-(4-(1,2,4-oxadiazol-3-yl)piperazine dihydrochloride (102 mg, 0.34 mmol) in tetrahydrofuran (6 mL) was added triethylamine (0.23 mL, 1.65 mmol) and then 2-chloro-3-methyl-6-(4-pyridyl)-3H-pyrimidin-4-one (73 mg, 0.33 mmol) at room temperature. After stirring for 24 h, the resulting mixture was concentrated in vacuo. The residue was dissolved in dichloromethane and saturated sodium bicarbonate aqueous solution, and the solution was passed through CHEM ELUT CE1010 (manufactured by VARIAN). The filtrate was concentrated in vacuo to yield crystals, which were washed with diisopropyl ether and ethanol to afford (S)-2-(3-(4-(1,2,4-oxadiazol-3-yl)phenyl) piperazin-1-yl)-3-methyl-6-(4-pyridyl)pyrimidin-4-one (102 mg 74%) as a white powder.

Example 18

Synthesis of 2-[4-(2-Methoxyphenylamino)-piperidin-1-yl]-3-methyl-6-(pyridin-4-yl)-3H-pyrimidin-4-one (No. XB276)

To a solution of anisidine (3.1 g, 25.2 mmol) and 4-oxo-piperidine-1-carboxylic acid tert-butyl ester (5.0 g, 25.1 mmol) in methanol (100 mL) was added sodium triacetoxyborohydride (13.4 g, 63.2 mmol) at room temperature. After stirring for 6 h, the resulting suspension was partitioned between ethyl acetate and 1N sodium hydroxide. The aqueous layer was extracted with ethyl acetate. The combined organic layer was washed with brine, dried over magnesium sulfate, and concentrated in vacuo. The residue was purified by silica gel chromatography eluting 10-20% ethyl acetate in hexane to furnish 4-(2-methoxyphenylamino)-piperidine-1-carboxylic acid tert-butyl ester (2.7 g, 8.8 mmol, 35%) as a pale yellow oil.

To a solution of 4-(2-methoxyphenylamino)-piperidine-1-carboxylic acid tert-butyl ester (2.7 g, 8.8 mmol) in methanol (30 mL) was added 4N hydrochloric acid in ethyl acetate (20 mL) at room temperature. After stirring for 1 h, the resulting suspension was concentrated in vacuo. The residue was partitioned between chloroform and 1N sodium hydroxide. The aqueous layer was extracted with chloroform. The combined organic layer was washed with brine, dried over magnesium sulfate, and concentrated in vacuo. The residue was purified by silica gel chromatography eluting 10-20% methanol in chloroform to furnish 4-(2-methoxyphenylamino)-piperidine (1.8 g, 8.7 mmol, 99%) as white crystals.

To a solution of 4-(2-methoxyphenylamino)-piperidine (0.8 g, 3.87 mmol) and triethylamine (1.3 g, 12.8 mmol) in tetrahydrofuran (20 mL) was added 2-chloro-3-methyl-6-(pyridin-4-yl)-3H-pyrimidin-4-one (0.8 g, 3.61 mmol) portionwise. After stirring for 12 h, the resulting suspension was partitioned between chloroform and 1N sodium hydroxide. The aqueous layer was extracted with chloroform. The combined organic layer was washed with brine, dried over magnesium sulfate, and concentrated in vacuo. The residue was purified by silica gel chromatography eluting 5-10% methanol in chloroform to furnish 2-(4-(2-methoxyphenylamino)-piperidin-1-yl)-3-methyl-6-(pyridin-4-yl)-3H-pyrimidin-4-one (1.2 g, 3.07 mmol, 85%) as white crystals.

Example 19

Synthesis of 3-Methyl-2-(3-(4-(4-methylpiperazin-1-yl)-phenyl)-piperidin-1-yl)-6-(pyridin-4-yl)-3H-pyrimidin-4-one (No. XB278)

A solution of (4-bromo-phenyl)-acetic acid ethyl ester (2.31 g, 9.50 mmol) in dimethylsulfoxide (6 mL) was added to the suspension of sodium hydride (407 mg, 60% in oil, 10.17 mmol) and stirred 3 min. A solution of (3-bromopropyl)-carbamic acid tert-butyl ester (2.03 g, 8.52 mmol) in dimethylsulfoxide (6 mL) was added to the solution and stirred at 50° C. for 30 min. The resulting solution was partitioned between ethyl acetate and saturated aqueous ammonium chloride. The aqueous layer was extracted with ethyl acetate. The combined organic layer was washed with water and brine, dried by passing through Celite column, and concentrated in vacuo. The residue was purified by silica gel chromatography eluting ethyl acetate/hexane (4/1 to 3/1, v/v) to afford 3-(4-Bromo-phenyl)-6-tert-butoxycarbonylamino-hexanoic acid ethyl ester (2.43 g, 74%).

To a solution of 3-(4-Bromo-phenyl)-6-tert-butoxycarbonylamino-hexanoic acid ethyl ester (2.43 g, 6.32 mmol) in ethyl acetate (3 mL) was added 4 N hydrogen chloride in ethyl acetate (6 mL) at room temperature. Removal of the solvent in vacuo after stirring for 30 min afforded 6-Amino-3-(4-bromo-phenyl)-hexanoic acid ethyl ester hydrochloride that was used in the next step without further purification.

A solution of 6-amino-3-(4-bromo-phenyl)-hexanoic acid ethyl ester hydrochloride, potassium carbonate (1039 mg, 7.52 mmol) in ethanol (50 ml) was refluxed for 20 hr. Solvent was removed in vacuo after addition of dilute hydrochloric acid and water was added to the residue. Filtration, wash with water and dryness afforded 3-(4-Bromo-phenyl)-piperidin-2-one (1387 mg, 86%, 2 steps).

To an ice-cooled solution of 3-(4-bromo-phenyl)-piperidin-2-one (37.97 g, 149 mmol) in tetrahydrofuran (250 ml) was added borane-tetrahydrofuran complex (335 ml, 1.0 M solution in THF, 335 mmol). The solution was stirred overnight at room temperature, and then refluxed 1.5 hr after addition of 10% aqueous hydrochloric acid. Solvents was removed in vacuo, and the residue was partitioned between dichloromethane and 1N sodium hydroxide. The aqueous layer was extracted with dichlorometane. The combined organic layer was washed with water and brine, dried over sodium sulfate, and concentrated in vacuo. The residue was dissolved in water (100 mL) and concentrated hydrochloric acid (100 mL) and refluxed for 3 hr. Sodium hydroxide was added to the solution and the resulting solution was extracted with dichlorometane. The organic layer was washed with water and brine, dried over sodium sulfate Concentration in vacuo afforded 3-(4-bromo-phenyl)-piperidine (32 18 g, 90%).

To a suspension of 3-(4-bromophenyl)-piperidine (25.2 g, 105 mmol), and triethylamine (13 g, 128 mmol) in tetrahydrofuran (250 mL) was added di-tert-butyl-dicarbonate (25.2 g, 105 mmol) at room temperature. After stirring for 1 h, the resulting suspension was partitioned between ethyl acetate and 1N sodium hydroxide. The aqueous layer was extracted with ethyl acetate. The combined organic layer was washed with brine, dried over magnesium sulfate, and concentrated in vacuo. The residue was washed by hexane to furnish 3-(4-bromophenyl)-piperidine-1-carboxylic acid tert-butyl ester (35.7 g, 105 mmol, 100%) as white crystals.

To a suspension of 3-(4-bromophenyl)-piperidine-1-carboxylic acid tert-butyl ester (3.0 g, 8.8 mmol), palladium acetate (80 mg, 0.36 mmol), 2-(di-t-butyl phosphino)biphenyl (210 mg, 0.70 mmol), and sodium t-butoxide (1.2 g, 125 mmol) in toluene (30 mL) was added N-methylpiperazine (1.3 g, 13.0 mmol) at room temperature. After heating at 90° C. for 5 h, the resulting suspension was passed through a Celite column. The filtrate was concentrated under reduced pressure, and the residue was purified by silica gel chromatography eluting 5-25% of ethyl acetate in hexane to afford 3-(4-(4-methylpiperazin-1-yl)-phenyl)-piperidine-1-carboxylic acid tert-butyl ester (2.0 g, 5.56 mmol, 63%) as white crystals.

To a solution of 3-(4-(4-methylpiperazin-1-yl)-phenyl)-piperidine-1-carboxylic acid tert-butyl ester (2.0 g, 5.56 mmol) in methanol (20 mL) was added 4N hydrochloric acid in ethyl acetate (20 mL) at room temperature. After stirring for 1 h, the resulting suspension was concentrated in vacuo. The residue was washed with ethyl acetate to furnish 3-(4-(4-methylpiperazin-1-yl)-phenyl)-piperidine trihydrochloride (1.84 g, 4.99 mmol, 90%) as white crystals.

To a solution of 3-(4-(4-methylpiperazin-1-yl)-phenyl)-piperidine trihydrochloride salt (0.4 g, 1.08 mmol) and triethylamine (0.6 g, 5.93 mmol) in tetrahydrofuran (10 mL) was added 2-chloro-3-methyl-6-(pyridin-4-yl)-3H-pyrimidin-4-one (0.22 g, 0.99 mmol) portionwise. After stirring for 12 h, the resulting suspension was partitioned between chloroform and 1N sodium hydroxide. The aqueous layer was extracted with chloroform. The combined organic layer was washed with brine, dried over magnesium sulfate, and concentrated in vacuo. The residue was purified by silica gel chromatography eluting 5-10% methanol in chloroform to furnish 3-methyl-2-(3-(4-(4-methylpiperazin-1-yl)-phenyl)-piperidin-1-yl)-6-(piridin-4-yl)-3H-pyrimidin-4-one (0.31 g, 0.70 mmol; 71%) as white crystals.

Example 20

Synthesis of 2-(3-(4-cyclohexylaminophenyl)-piperidin-1-yl)-3-methyl-6-(pyridin-4-yl)-3H-pyrimidin-4-one (No. XB301)

To a suspension of 3-(4-bromophenyl)-piperidine-1-carboxylic acid tert-butyl ester (8.0 g, 23.5 mmol), palladium acetate (210 mg, 0.94 mmol), 2-(di-t-butyl phosphino)biphenyl (560 mg, 1.88 mmol), and sodium t-butoxide (3.2 g, 33.3 mmol) in toluene (80 mL) was added cyclohexylamine (2.8 g, 28.2 mmol) at room temperature. After heating at 90° C. for 5 h, the resulting suspension was passed through a Celite column. The filtrate was concentrated under reduced pressure, and the residue was purified by silica gel chromatography eluting 5-25% of ethyl acetate in hexane to afford 3-(4-cyclohexylaminophenyl)-piperidine-1-carboxylic acid tert-butyl ester (6.74 g, 18.8 mmol, 80%) as white crystals.

To a solution of 3-(4-cyclohexylaminophenyl)-piperidine-1-carboxylic acid tert-butyl ester (6.74 g, 18.8 mmol) in methanol (50 mL) was added 4N hydrochloric acid in ethyl acetate (40 mL) at room temperature. After stirring for 1 h, the resulting suspension was concentrated in vacuo. The residue was washed with ethyl acetate to furnish 3-(4-cyclohexylaminophenyl)-piperidine dihydrochloride (5.84 g, 17.6 mmol, 94%) as white crystals.

To a solution of 3-(4-cyclohexylaminophenyl)-piperidine dihydrochloride salt (1.0 g, 3.02 mmol) and triethylamine (1.5 g, 14.8 mmol) in tetrahydrofuran (20 mL) was added 2-chloro-3-methyl-6-(pyridin-4-yl)-3H-pyrimidin-4-one (0.64 g, 2.89 mmol) portionwise. After stirring for 12 h, the resulting suspension was partitioned between chloroform and 1N sodium hydroxide. The aqueous layer was extracted with chloroform. The combined organic layer was washed with brine, dried over magnesium sulfate, and concentrated in vacuo. The residue was purified by silica gel chromatography eluting 5-10% methanol in chloroform to furnish 2-(3-(4-cyclohexylaminophenyl)-piperidin-1-yl)-3-methyl-6-(pyridin-4-yl)-3H-pyrimidin-4-one (1.23 g, 2.77 mmol, 96%) as white crystals.

Example 21

Synthesis of 2-(4-(4-Bromo-phenyl)-piperidin-1-yl)-3-methyl-6-pyridin-4-yl-3H-pyrimidin-4-one (No. XB267)

Mixture of 4-bromobenzaldehyde (22.40 g, 121.1 mmol), dimethyl malonate (19.37 g, 146.6 mmol), cat. acetic acid and cat. piperidine in toluene (100 ml) were refluxed for 6 h with azeotropically removal of water. Resulting solution was partitioned between ethyl acetate and water. The aqueous layer was extracted with ethyl acetate. The combined organic layer was washed with water, saturated aqueous sodium bicarbonate and brine, dried over sodium sulfate. Concentration of the organic solvent in vacuo afforded 2-(4-bromo-benzylidene)-malonic acid diethyl ester as an oil that was used in the next step without further purification.

To an ice-cooled solution of dimethyl malonate (19.35 g, 146.5 mmol) and sodium methoxide (30.12 g in 28% methanol solution, 156.1 mmol) in methanol (300 ml) was added 2-(4-bromo-benzylidene)-malonic acid diethyl ester in methanol (50 ml). After stirring for 3 h, the solvent was removed in vacuo and the residue was partitioned between ethyl acetate and dilute hydrochloric acid. The aqueous layer was extracted with ethyl acetate. The combined organic layer was washed with brine, dried over sodium sulfate. Concentration of the organic solvent in vacuo afforded 3-(4-bromo-phenyl)-2,4-bis-ethoxycarbonyl-pentanedioic acid diethyl ester as an oil that was used in the next step without further purification.

A solution of 3-(4-bromo-phenyl)-2,4-bis-ethoxycarbonyl-pentanedioic acid diethyl ester in concentrated hydrochloric acid (100 ml) and acetic acid (100 ml) was refluxed for 8 h. Removal of the solvent in vacuo and recrystallization of the residue from acetonitrile yielded 3-(4-bromo-phenyl)-pentanedioic acid (22.84 g in $1^{st}$ crop, 65%, 3.84 g in $2^{nd}$ crop, 11.05% from 4-bromobenzaldehyde).

A solution 3-(4-bromo-phenyl)-pentanedioic acid (26.68 g, 92.9 mmol) in acetic anhydride (100 ml) was refluxed for 1.5 hr. Removal of the solvent in vacuo, and remaining solvent were azeotropically removed using toluene. Teterahydrofuran (200 ml) and aqueous ammonia (28%, 50 ml) was added to the residue and stirred overnight. After removal of the solvent in vacuo, acetic anhydride (100 ml) was added and refluxed for 4 hr. After removal of the solvent in vacuo and succeeding azeotropic distillation with toluene, residue was partitioned between ethyl ether and water. Filtration of the suspension and dryness afforded the 4-(4-bromo-phenyl)-piperidine-2,6-dione (12.53 g, 50%) as a solid.

To an ice-cooled solution of lithium tetrahydroborate (4.13 g, 189.6 mmol) in tetrahydrofuran (200 ml) was added chlorotrimethylsilane (41.52 g, 382.2 mmol). After stirring 5 min, a solution of 4-(4-bromo-phenyl)-piperidine-2,6-dione (12.53 g, 46.7 mmol) was added and stirred overnight. The resulting solution was concentrated in vacuo after addition of 10% aqueous hydrochloric acid. The residue was dissolved in aqueous sodium hydroxide solution and methanol, and a solution of di-tert-butyl dicarbonate (11.45 g, 52.5 mmol) in methanol (10 ml) was added and stirred for 6 h. After removal of the solvent in vacuo, concentrated hydrochloric acid wad added and stirred overnight. After extraction of the solution by diethyl ether, sodium hydroxide was added to the aqueous layer to turn basic, and extracted with dichloromethane. The organic layer was washed with brine, dried over sodium sulfate. The residue of the diethyl ether and dichloromethane after removal of the solvents under reduced pressure was mixed and dissolved in tetrahydrofuran (200 ml). A solution of di-tert-butyl dicarbonate (7.45 g, 34.1 mmol) in tetrahydrofuran (10 ml) and triethylamine were added and stirred overnight. The resulting solution was concentrated in vacuo. Purification of the residue by silica gel chromatography eluting hexane/ethyl acetate (5/1, v/v) furnished 4-(4-bromo-phenyl)-piperidine-1-carboxylic acid tert-butyl ester (14.4 g, 91%) as a solid.

To a solution of furnished 4-(4-bromophenyl)-piperidine-1-carboxylic acid tert-butyl ester (1114 mg, 3.27 mmol) in ethyl acetate (1 mL) was added 4 N hydrogen chloride in ethyl acetate (2 mL) at room temperature. After stirring for 5 h, solvent was removed in vacuo, and the resulting solid was washed with ethyl acetate and dried in vacuo to afford (4-(4-bromophenyl)-piperidine hydrochloride (884 mg, 98%) as a white solid.

A solution of (4-(4-bromophenyl)-piperidine hydrochloride (279 mg, 1.01 mmol) and triethylamine (554 mg, 5.47 mmol), 2-chloro-3-methyl-6-(pyridin-4-yl)-3H-pyrimidin-4-one (206 mg, 0.929 mmol) in tetrahydrofuran (20 mL) was stirred for 3 hr. The resulting solution was diluted with tetrahydrofuran and filtrated. After removal of the solvents under reduced pressure and the purification of the resulting residue by CHEM ELUT CE1010 (manufactured by VARIAN) eluting dichloromethane/ethanol (15/1, v/v) and wash with ethyl acetate afforded 2-(4-(4-Bromophenyl)-piperidin-1-yl)-3-methyl-6-pyridin-4-yl-3H-pyrimidin-4-one (368 mg, 93%) as a solid.

Example 22

Synthesis of 3-Methyl-6-pyridin-4-yl-2-[4-(4-pyrrolidin-1-yl-phenyl)-piperidin-1-yl]-3H-pyrimidin-4-one (No. XB269)

A suspension of 4-(4-Bromophenyl)-piperidine-1-carboxylic acid tert-butyl ester (1.97 g, 5.79 mmol), palladium acetate (54 mg, 0.24 mmol), 2-(di-t-butylphosphino)biphenyl (154 mg, 0.52 mmol), and sodium t-butoxide (846 mg, 8.80 mmol), pyrrolidine (587 mg, 8.25 mmol) in toluene (80 mL) was heated at 90° C. for 3 h under nitrogen atmosphere. The resulting suspension was passed through a Celite column and partitioned between ethyl acetate and water. The aqueous layer was extracted with ethyl acetate. The combined organic layer was washed with brine, dried over sodium sulfate, and concentrated in vacuo. Purification of the residue by HPLC afforded 4-(4-pyrrolidin-1-yl-phenyl)-piperidine-1-carboxylic acid tert-butyl ester as a solid that was used in the next step without further purification.

To a solution of furnished 4-(4-Pyrrolidin-1-yl-phenyl)-piperidine-1-carboxylic acid tert-butyl ester in ethyl acetate (5 mL) was added 4 N hydrogen chloride in ethyl acetate (10 mL) at room temperature. After stirring for 3 h, solvent was removed in vacuo, and the resulting solid was purified by HPLC. Sodium hydroxide was added to the resulting fractions and the aqueous layer was extracted by dichloromethane. Organic layer was washed with brine, and passed through Cerite. Removal of the solvent under reduced pressure afforded 4-(4-pyrrolidin-1-yl-phenyl)-piperidine (1.01 g, 76%).

A solution of 4-(4-pyrrolidin-1-yl-phenyl)-piperidine (215 mg, 0.933 mmol) and triethylamine (391 mg, 3.86 mmol), 2-chloro-3-methyl-6-(pyridin-4-yl)-3H-pyrimidin-4-one (187 mg, 0.844 mmol) in tetrahydrofuran (10 mL) was refluxed for 5 hr. The resulting solution was diluted with tetrahydrofuran and filtrated. After removal of the solvents under reduced pressure and the purification of the resulting residue by CHEM ELUT CE1010 (manufactured by VARIAN) eluting dichloromethane/ethanol (15/1, v/v) and wash with ethyl acetate afforded 3-methyl-6-pyridin-4-yl-2-(4-(4-pyrrolidin-1-yl-phenyl)-piperidin-1-yl)-3H-pyrimidin-4-one (284 mg, 81%) as a solid.

Example 23

Synthesis of 2-(4-(6-Fluorobenzo[b]thiophen-3-yl) piperidin-1-yl)-1-methyl-1H-[4,4']bipyrimidinyl-6-one (No. YB253)

The key intermediate 4-(6-fluorobenzo[b]thiophen-3-yl) piperidine hydrochloride of 2-[4-(6-fluorobenzo[b]thiophen-3-yl)piperidin-1-yl]-1-methyl-1H-[4,4']bipyrimidinyl-6-one was synthesized from 1-acetylpipridine-4-carboxylic acid which was prepared according to the method reported by Watanabe (*J. Heterocyclic Chem.*, 30, 445 (1993)).

To a solution of 1-benzoylpiperidine-4-carboxylic acid (66 g, 285 mmol) in dichloromethane (160 mL) was added thionyl chloride (26 mL, 388 mmol). After stirring at 60° C. for 1 h, the mixture was added portionwise to a stirred suspension of 2,4-difluorobenzene (45 g, 397 mmol) and anhydrous aluminum chloride (88 g, 666 mmol) in dichloromethane (245 mL), and the reaction mixture was refluxed for 5 h. The reaction mixture was poured into a mixture of ice and concentrated hydrochloric acid and extracted with chloroform. The organic layer was dried over sodium sulfate and the solvent was evaporated under reduced pressure. Recrystallization from hexane gave 1-benzoyl-4-(2,4-difluorobenzoyl) piperidine (46 g, 50%) as colorless crystals.

A solution of 1-benzoyl-4-(2,4-difluorobenzoyl)piperidine (40 g, 120 mmol), methyl thioglycolate (12 mL, 130 mmol) in dimethylformamide (500 mL) was stirred at room temperatute for 12 h. The solvent was evaporated off in vacuo and the residue treated with water and ethyl acetate. The organic layer was dried over sodium sulfate and the solvent was evaporated under reduced pressure. The obtained residue was purified by silica gel column chromatography eluting hexane/ethyl acetate to give 3-(1-benzoylpiperidin-4-yl)-6-fluorobenzo[b]thiophene-2-carboxylic acid (11.8 g, 26%) as an oil.

3-(1-Benzoylpiperidin-4-yl)-6-fluorobenzo[b]thiophene-2-carboxylic acid (10 g, 26 mmol) was suspended in quinoline (100 mL) and cupper powder (0.5 g) was added. After stirring at 200° C. for 1 h, the mixture was cooled to room temperature and partitioned between ethyl acetate and water. The organic layer was dried over magnesium sulfate and evaporated. The obtained residue was purified by silica gel column chromatography eluting hexane/ethyl acetate to give (4-(6-fluorobenzo[b]thiophen-3-yl)piperidin-1-yl)phenylmethanone (5.0 g, 48%) as yellow crystals.

A solution of (4-(6-fluorobenzo[b]thiophen-3-yl)piperidin-1-yl) phenylmethanone (6.5 g, 19 mmol) in acetic acid (100 mL) and concentrated hydrochloric acid (100 mL) was stirred at 90° C. for 10 h. To a solution of reaction mixture was added ethyl acetate. The precipitated crystals were collected by filtration and washed with ethyl acetate to give 4-(6-fluorobenzo[b]thiophen-3-yl)piperidine hydrochloride (4.8 g, 89%) as yellow crystals.

To a solution of 4-(6-fluorobenzo[b]thiophen-3-yl)piperidine hydrochloride (200 mg, 0.74 mmol) and 2-chloro-1-methyl-1H-[4,4']bipyrimidinyl-6-one (160 mg, 0.70 mmol) in tetrahydrofuran (10 mL) was added triethylamine (212 mg, 2.1 mmol). The mixture was stirred at 90° C. for 6 h. The solvent was evaporated off in vacuo and the residue was treated with water and chloroform. The organic layer was dried over sodium sulfate and the solvent was evaporated under reduced pressure. Recrystallization from ethyl acetate gave 2-[4-(6-fluorobenzo[b]thiophen-3-yl)piperidin-1-yl]-1-methyl-1H-[4,4']bipyrimidinyl-6-one (220 mg, 96%) as colorless crystals.

Example 24

Synthesis of 2-(4-(Biphenyl-2-yl)piperazin-1-yl)-1-methyl-1H-[4,4']bipyrimidinyl-6-one (No. YA1552)

To a solution of 1-biphenyl-2-yl-piperazine dihydrochloride (311 mg, 1.0 mmol) and 2-chloro-1-methyl-1H-[4,4']bipyrimidinyl-6-one (202 mg, 0.91 mmol) in tetrahydrofuran (20 mL) was added triethylamine (404 mg, 4.0 mmol). The mixture was stirred at 90° C. for 4 h. The solvent was evaporated off in vacuo and the residue treated with water and chloroform. The organic layer was dried over sodium sulfate and the solvent was evaporated under reduced pressure. Recrystallization from ethyl acetate gave 2-[4-(biphenyl-2-yl)piperazin-1-yl]-1-methyl-1H-[4,4']bipyrimidinyl-6-one (250 mg, 65%) as colorless crystals.

The compounds in the following table were prepared in the same manner as the methods described above. The compound numbers in the following table correspond to those shown in the above-described table of preferred compounds.

TABLE 5

| NO | NMR | Exact-MS |
|---|---|---|
| XA19 | 2.51-2.89(4H, m), 3.31-3.34(4H, m), 3.39(3H, s), 3.56(2H, s), 6.80(1H, s), 7.25-7.31(1H, m), 7.31-7.36(4H, m), 7.98(2H, dd, J=1.5, 4.8Hz), 8.68(2H, dd, J=1.5, 4.5Hz) (DMSO-d6) | 362 |
| XA25 | 3.32-3.34(4H, m), 3.46(3H, s), 3.48-3.51(4H, m), 6.80-6.85(1H, m), 6.84(1H, s), 7.01(2H, d, J=8.0Hz), 7.23-7.28(2H, m), 8.00(2H, dd, J=1.3, 4.6Hz), 8.70(2H, dd, J=1.5, 4.5Hz) (DMSO-d6) | 348 |
| XA156 | 3.47(3H, s), 3.51-3.60(4H, m), 3.62-3.71(4H, m), 6.85(1H, s), 7.41-7.49(1H, m), 7.56-7.61(1H, m), 8.02(2H, dd, J=1.5, 4.5Hz), 8.09(1H, d, J=8.1Hz), 8.16(1H, d, J=8.1Hz), 8.70(2H, dd, J=1.5, 4.8Hz) (DMSO-d6) | 405 |
| XA289 | 1.11-1.28(3H, m), 2.98-3.16(1H, m), 3.28-3.41(1H, m), 3.39(3H, s), 3.54-3.80(3H, m), 3.88-3.99(1H, m), 4.08-4.26(4H, m), 4.32-4.45(1H, m), 7.13(1H, s), 7.37-7.53(5H, m), 8.45(2H, d, J=5.8Hz), 8.96(2H, d, J=6.0Hz) (DMSO-d6) | 434 |
| XA361 | 3.44(3H, s), 3.54-3.95(6H, m), 4.64(1H, brs), 7.11(1H, s), 7.42-7.51(3H, m), 7.74(2H, d, J=6.6Hz), 8.46(2H, d, J=5.7Hz), 8.94(2H, d, J=5.7Hz), 9.98(1H, brs), 10.46(1H, brs) (DMSO-d6). | 348 |
| XA364 | (DMSO-d6): 3.41-3.76(4H, m), 3.48(3H, s), 3.89-4.01(2H, m), 4.96(1H, m), 7.16(1H, s), 7.33-7.58(3H, m), 8.11(1H, dd, J=7.2, 7.2Hz), 8.52(2H, d, J=6.6Hz), 8.97(2H, d, J=6.6Hz), 10.04(1H, m), 10.66(1H, m). | 366 |
| XA365 | 3.43(s, 3H), 3.51-3.96(m, 6H), 4.70(m, 1H), 7.00(s, 1H), 7.25(m, 1H), 7.54(m, 2H), 7.60(m, 1H), 8.20(d, J=5.7Hz, 2H), 8.80(d, J=5.7Hz, 2H) (CDCl3) | 366 |
| XA366 | 2.27-2.85(1H, m), 2.94-3.08(3H, m), 3.43(3H, s), 3.59-3.67(2H, m), 3.94-3.97(1H, m), 6.81(1H, s), 7.19(2H, t, J=8.9Hz), 7.50-7.55(2H, m), 7.96(2H, dd, J=1.6, 4.5Hz), 8.68(2H, dd, J=1.5, 4.6Hz) (DMSO-d6) | 366 |
| XA366 (HCl) | 3.35-3.50(2H, m), 3.46(3H, s), 3.58-3.75(2H, m), 3.86-3.97(2H, m), 4.68(1H, t, J=9.3Hz), 7.15(1H, s), 7.35(2H, t, J=9.0Hz), 7.82-7.87(2H, m), 8.48(2H, d, J=6.6Hz), 8.96(2H, d, J=6.3Hz), 9.55-10.08(1H, m), 10.54-10.70(1H, m) (DMSO-d6) | 366 |
| XA369 | (CDCl3): 2.81(1H, dd, J=10.4, 12.5Hz), 3.18-3.40(3H, m), 3.50-3.80(5H, m), 4.50(1H, dd, J=2.5, 10.1Hz), 6.67(1H, s), 7.20-7.45(3H, m), 7.74(1H, dd, J=1.9, 7.6Hz), 7.81(2H, dd, J=1.4, 4.6Hz), 8.70(2H, dd, J=1.4, 4.6Hz). | 382 |
| XA370 | (CDCl3): 3.01(1H, dd, J=10.4, 12.5Hz), 3.10-3.30(3H, m), 3.50-3.80(5H, m), 4.04(1H, dd, J=2.7, 10.8Hz), 6.67(1H, s), 7.20-7.45(4H, m), 7.50(1H, s), 7.80(2H, dd, J=1.5, 4.8Hz), 8.71(2H, dd, J=1.5, 5.1Hz). | 382 |
| XA371 | 3.44(3H, s), 3.44-3.71(7H, m), 3.90(2H, m), 4.66(1H, brs), 7.11(1H, s), 7.55(2H, d, J=8.4Hz), 7.78(2H, d, J=8.4Hz), 8.50(2H, d, J=5.7Hz), 8.95(2H, d, J=5.7Hz), 10.13(1H, brs), 10.60(1H, brs) (DMSO-d6) | 382 |
| XA376 | (DMSO-d6): 3.45(3H, s), 3.50-4.20(6H, m), 4.66(1H, br s), 7.12(1H, s), 7.72(4H, s), 8.44(2H, d, J=6.6Hz), 8.94(2H, d, J=6.6Hz), 10.00(1H, br s), 10.05(1H, br s) | 426 |
| XA391 | 3.37-3.93(6H, m), 3.48(3H, s), 3.87(3H, s), 4.89-4.95(1H, m), 7.04-7.12(2H, m), 7.17(1H, d, J=8.5Hz), 7.45-7.51(1H, m), 7.75-7.81(1H, m), 8.29-8.38(2H, m), 8.83-8.91(2H, m), 9.66-9.77(1H, m), 9.91-10.10(1H, m) (DMSO) | 378 |
| XA392 | (DMSO-d6): 3.30-3.58(5H, m), 3.58-3.80(2H, m), 3.81(3H, s), 3.85-4.00(2H, m), 4.58-4.75(1H, m), 7.03(1H, dd, J=1.8, 8.1Hz), 7.11(1H, s), 7.26(1H, d, J=7.8Hz), 7.35-7.50(2H, m), 8.41(2H, d, J=5.7Hz), 8.92(2H, d, J=6.0Hz), 9.80-10.00(1H, brd), 10.30-10.60(1H, brd). | 378 |
| XA393 | 3.40-3.43(5H, m), 3.51-3.63(2H, m), 3.78(3H, s), 3.93(2H, m), 4.58(1H, br), 7.02-7.06(3H, m), 7.64(2H, d, J=8.7Hz), 8.34(2H, d, J=6.3Hz), 8.88(2H, d, J=8.7Hz), 9.76(1H, br), 10.16(1H, br) (DMSO-d6) | 378 |
| XA396 | 1.30(3H, t, J=6.9Hz), 3.38-3.54(1H, m), 3.49(3H, s), 3.65-3.79(1H, m), 3.84-3.98(2H, m), 4.02-4.18(2H, m), 4.84(1H, t, J=10.5Hz), 7.04-7.16(2H, m), 7.15(1H, s), 7.39-7.45(1H, m), 7.89(1H, d, J=6.6Hz), 8.49(2H, d, J=6.3Hz), 8.95(2H, d, J=6.6Hz), 9.92(1H, d, J=9.3Hz), 10.51-10.64(1H, m) (DMSO-d6) | 392 |
| XA406 | (DMSO-d6): 3.64(2H, m), 3.94(2H, t, J=11.4Hz), 4.02-4.40(5H, m), 4.78(1H, t, J=10.4Hz), 7.06(1H, s), 7.98(2H, d, J=8.3Hz), 8.01(2H, d, J=8.3Hz), 8.23(1H, dd, J=1.2, 5.1Hz), 9.02(1H, d, J=5.1Hz), 9.31(1H, d, J=1.2Hz), 10.03(1H, d, J=8.7Hz), 10.57(1H, s). | 373 |
| XA433 | (CDCl3): 2.00(4H, m), 3.03(1H, dd, J=10.8, 12.0Hz), 3.21(3H, m), 3.29(4H, m), 3.57(3H, s), 3.62(2H, m), 3.90(1H, dd, J=2.7, 10.8Hz), 6.57(2H, d, J=8.7Hz), 6.66(1H, s), 7.29(2H, d, J=8.7Hz), 7.80(2H, d, J=4.8Hz), 8.70(2H, d, J=4.8Hz). | 417 |
| XA439 | (CDCl3): 3.02(1H, dd, J=10.7, 12.4Hz), 3.18(7H, m), 3.55(3H, s), 3.62(2H, m), 3.87(4H, m), 3.96(1H, dd, J=2.5, 11.1Hz), 6.66(1H, S), 6.93(2H, d, J=8.7Hz), 7.36(2H, d, J=8.7Hz), 7.79(2H, d, J=4.5Hz), 8.70(2H, d, J=4.5Hz). | 434 |
| XA442 | (CDCl3): 2.36(3H, s), 2.59(4H, m), 3.02(1H, t, J=11.6Hz), 3.22(7H, m), 3.55(3H, s), 3.63(2H, m), 3.94(1H, d, J=10.5Hz), 6.66(1H, s), 6.93(2H, d, J=8.7Hz), 7.34(2H, d, J=8.7Hz), 7.80(2H, d, J=4.5Hz), 8.70(2H, d, J=4.5Hz). | 446 |
| XA463 | 3.41-3.54(3H, m), 3.48(3H, s), 3.69-3.73(1H, m), 3.78(3H, s), 3.82(3H, s), 3.86-3.93(2H, m), 4.89(1H, t, J=10.5Hz), 6.97-7.01(1H, m), 7.08(1H, d, J=9.0Hz), 7.15(1H, s), 7.66(1H, d, J=3.0Hz), 8.51(2H, d, J=6.3Hz), 8.96(2H, d, J=6.3Hz), 9.93(1H, d, J=9.0Hz), 10.60-10.73(1H, m) (DMSO-d6) | 408 |
| XA464 | (DMSO-d6): 3.45(3H, s), 3.38-3.81(6H, m), 3.88(6H, s), 5.06(1H, m), 6.82(2H, d, J=8.7Hz), 7.04(1H, s), 7.44(1H, t, J=8.4Hz), | 408 |

TABLE 5-continued

| | | |
|---|---|---|
| | 8.20(1H, m), 8.30(2H, d, J=6.3Hz), 8.87(2H, d, J=6.3Hz), 10.07(1H, m). | |
| XA468 | 3.40-3.50(4H, m), 3.47(3H, s), 3.83-3.94(2H, m), 3.88(3H, s), 4.81-4.91(1H, m), 6.92-6.99(1H, m), 7.07-7.10(1H, m), 7.12(1H, s), 7.79-7.91(1H, m), 8.30-8.40(2H, m), 8.85-8.92(2H, m), 9.70-9.79(1H, m), 10.02-10.23(1H, m) (DMSO) | 396 |
| XA469/ XA470 | (DMSO-d6): 3.38-3.60(6H, m), 3.60-3.80(1H, m) 3.80-4.00(5H, m), 4.80-4.97(1H, m), 6.85-7.00(1H, m), 7.09(1H, dd, J=2.4, 11.4Hz), 7.13(1H, s), 7.95(1H, dd, J=6.9, 8.7Hz), 8.46(2H, d, J=6.6Hz), 8.94(2H, d, J=6.3Hz), 9.80-10.00(1H, brd), 10.35-10.60(1H, brd). | 396 |
| XA472 | 3.36-4.00(6H, m), 3.46(3H, s), 3.94(3H, s), 4.94-5.02(1H, m), 6.96-7.01(1H, m), 7.05(1H, d, J=8.6Hz), 7.14(1H, s), 7.49-7.58(1H, m), 8.44-8.50(2H, m), 8.52-8.64(1H, m), 8.96(2H, d, J=6.6Hz), 10.49-10.60(1H, m) (DMSO) | 396 |
| XA480 | 2.78(1H, dd, J=10.0, 12.1Hz), 3.18-3.27(3H, m), 3.59(3H, s), 3.64-3.74(2H, m), 3.86(3H, s), 4.37(1H, dd, J=2.4, 10.1Hz), 6.67(1H, s), 6.89(1H, d, J=2.1Hz), 6.99(1H, dd, J=1.7, 8.0Hz), 7.50(1H, d, J=8.2Hz), 7.82(2H, dd, J=1.5, 4.8Hz), 8.71(2H, dd, J=1.8, 4.5Hz) (CDCl3) | 412 |
| XA490 (2HCl) | 3.35-3.94(6H, m), 3.49(3H, s), 4.71-4.80(1H, m), 7.02-7.11(1H, m), 7.18-7.28(2H, m), 7.98-8.10(1H, m), 8.31-8.48(2H, m), 8.87-8.97(2H, m), 9.79-9.92(1H, m), 10.18-10.39(1H, m) (DMSO) | 380 |
| XA501 | (CDCl3): 2.77(1H, dd, J=10.2, 12.0Hz), 3.15-3.35(3H, m), 3.50-3.80(5H, m), 3.84(3H, s), 4.39(1H, d, J=7.8Hz), 6.67(1H, s), 6.78(1H, d, J=8.8Hz), 7.39(1H, dd, J=2.4, 8.7Hz), 7.71(1H, d, J=2.3Hz), 7.82(2H, d, J=6.0Hz), 8.71(2H, d, J=6.0Hz). | 456 |
| XA510 | (CDCl3): 1.98-2.05(4H, m), 2.85(1H, dd, J=12, 10.5Hz), 3.17-3.24(7H, m), 3.58(3H, s), 3.65-3.72(2H, m), 3.85(3H, s), 4.28(1H, dd, 10.5, 2.7Hz), 6.10(1H, d, J=2.1Hz), 6.18(1H, dd, J=8.7, 2.1Hz), 6.65(1H, s), 7.33(1H, d, J=8.4Hz), 7.83(2H, dd, J=4.5, 1.8Hz), 8.70(2H, dd, J=4.5, 1.5Hz). | 447 |
| XA511 | (CDCl3): 1.90-2.05(4H, m), 2.93(1H, t, J=12.0Hz), 3.15-3.40(7H, m), 3.59(3H, s), 3.65-3.85(5H, m), 4.11(1H, dd, J=2.1, 10.2Hz), 6.49(1H, dd, J=3.0, 9.0Hz), 6.66(1H, s), 7.83(2H, dd, J=1.8, 4.5Hz), 8.70(2H, dd, J=1.5, 4.5Hz). | 447 |
| XA516 | (DMSO-d6): 3.20-3.70(4H, m), 3.70(1H, m), 3.98(3H, s), 3.99(3H, s), 4.00(1H, m), 4.96(1H, d, J=10.2Hz), 7.01(1H, s), 7.03(2H, m), 8.26(2H, d, J=6.1Hz), 8.53(1H, s), 8.84(2H, d, J=6.1Hz), 10.25(1H, d, J=10.7Hz) | 414 |
| XA525 | (DMSO-d6): 3.30-3.50(2H, m), 3.48(3H, s), 3.55-3.78(2H, m), 3.78(3H, s), 3.96(2H, d, J=13.5Hz), 4.69(1H, t, J=10.4Hz), 7.06(1H, t, J=7.4Hz), 7.12(1H, s), 7.14(1H, d, J=7.4Hz), 7.31(1H, d, J=7.4Hz), 7.39(1H, t, J=7.4Hz), 7.59(2H, d, J=8.3Hz), 7.77(2H, d, J=8.3Hz), 8.43(2H, d, J=6.5Hz), 8.93(2H, d, J=6.5Hz), 9.89(1H, d, J=8.7Hz), 10.34(1H, s). | 454 |
| XA527 | (DMSO-d6): 3.40-4.10(9H, m), 3.81(3H, s), 4.69(1H, m), 7.05(1H, s), 7.05(2H, d, J=9.0Hz), 7.67(2H, d, J=9.0Hz), 7.75(4H, m), 8.27(2H, d, J=5.7Hz), 8.85(2H, d, J=5.7Hz), 9.75(1H, s), 10.04(1H, s). | 454 |
| XA536 | (DMSO-d6): 3.40-3.60(2H, m), 3.47(3H, s), 3.68(2H, m), 3.95(2H, m), 4.71(1H, t, J=9.9Hz), 7.16(1H, s), 7.33(2H, t, J=8.85Hz), 7.78(6H, m), 8.50(2H, d, J=6.3Hz), 8.97(2H, d, J=6.3Hz), 10.02(1H, s), 10.50(1H, s). | 443 |
| XA543 | 3.52(s, 3H), 3.57-4.10(m, 6H), 5.57(m, 1H), 7.02(s, 1H), 7.53-7.70(m, 2H), 8.06(d, J=7.2Hz, 2H), 8.21-8.34(m, 3H), 8.82(d, J=6.3Hz, 2H), 9.88-9.92(m, 1H), 10.58-10.61(m, 1H) (DMSO d6) | 398 |
| XA544 | 3.41-3.59(2H, m), 3.49(3H, s), 3.68-3.76(2H, m), 3.97-4.02(2H, m), 4.78-4.89(1H, m), 7.15(1H, s), 7.58-7.63(2H, m), 7.89-8.07(4H, m), 8.30(1H, m), 8.49(2H, d, J=6.3Hz), 8.95(2H, d, J=6.3Hz), 10.17(1H, d, J=8.4Hz), 10.57-10.70(1H, m) (DMSO-d6) | 398 |
| XA619 | (CDCl3): 2.98(1H, dd, J=12.6, 10.8Hz), 3.17-3.28(5H, m), 3.58(3H, s), 3.62(1H, m), 3.79(1H, m), 4.26(1H, dd, 10.5, 2.7Hz), 4.62(2H, m), 6.66(1H, s), 6.88(1H, t, J=7.5Hz), 7.16(1H, d, J=7.2Hz), 7.27(1H, m), 7.84(2H, d, J=6.0), 8.70(2H, dd, J=4.8, 1.2Hz). | 390 |
| XA626 | 3.33-3.41(4H, m), 3.42(3H, s), 3.47-3.87(4H, m), 6.84(1H, s), 7.44-7.49(5H, m), 7.99(2H, dd, J=1.5, 4.5Hz), 8.69(2H, dd, J=1.4, 4.8Hz) (DMSO-d6) | 376 |
| XA649 | 3.44(3H, s), 3.37-4.04(9H, m), 4.67(1H, d, J=9.6Hz), 7.10(1H, s), 7.45-7.55(3H, m), 7.83(2H, d, J=6.0Hz), 8.47(2H d, J=6.6Hz), 8.95(2H, d, J=6.6Hz), 12.15(1H, brs) (DMSO-d6) | 362 |
| XA756 | (CDCl3): 2.50-2.61(1H, m), 2.80-2.95(1H, m), 3.05-3.20(1H, m), 3.25-3.40(1H, m), 3.50-3.60(1H, m), 3.57(3H, s), 3.65-3.75(1H, m), 3.75-3.80(1H, m), 3.85(3H, s), 6.60-6.80(3H, m), 7.47(1H, dd, J=7.2, 8.4Hz), 7.82(2H, dd, J=1.5, 4.5Hz), 8.71(2H, dd, J=1.5, 4.5Hz). | 410 |
| XA757/ XA758 | (DMSO-d6): 2.54(3H, s), 3.40-3.79(3H, m), 3.46(3H, s), 3.80-4.10(6H, m), 4.83-5.10(1H, m), 6.90-7.05(1H, m), 7.08(1H, s), 7.13(1H, dd, J=2.7, 11.4Hz), 8.00-8.25(1H, brd), 8.37(2H, d, J=6.3Hz), 8.91(2H, d, J=6.6Hz), 11.80-12.20(1H, brd). | 410 |
| XA831 | 2.55(s, 3H), 3.51(s, 3H), 3.67-3.82(m, 4H), 4.04-4.08(m, 2H), 5.64(m, 1H), 7.05(s, 1H), 7.59-7.72(m, 3H), 8.06-8.11(m, 2H), 8.35(d, J=6.6Hz, 2H), 8.41(d, J=7.8Hz, 1H), 8.49(d, J=6.9Hz, 1H), 8.84(d, J=6.6Hz, 2H) (DMSO d6) | 412 |
| XA1016 | (DMSO-d6): 3.15-3.35(1H, m), 3.38-3.60(4H, m), 3.75-4.15(8H, m), 4.18-4.25(1H, m), 4.90-5.20(1H, m), 7.00-7.20(3H, m), 7.30-7.55(6H, m), 8.50-8.70(3H, m), 9.00(2H, d, J=6.3Hz). | 486 |
| XA1276 | (CDCl3): 1.80-2.42(3H, m), 3.08-3.39(4H, m), 3.40-3.62(1H, m), 3.65-4.23(6.8H, m), 4.63-4.90(0.6H, m), 5.40-5.62(0.7H, m), 5.80-6.00(0.1H, m), 6.52-6.78(3H, m), 6.90-7.2(1H, m), 7.68-7.90(2H, m), 8.64-8.80(2H, m) | 438 |
| XA1649 | 1.48(3H, s), 1.57(3H, s), 3.50(3H, s), 3.51-3.66(2H, m), 3.72-3.76(2H, m), 3.90(3H, s), 3.99(1H, d, J=13.4Hz), 5.15-5.23(1H, m), 7.08-7.12(2H, m), 7.18(1H, d, J=8.6Hz), 7.46-7.49(1H, m), 8.04-8.11(1H, m), 8.37-8.45(2H, m), 8.89-8.97(2H, m), 9.49-9.60(1H, m), 9.95-10.11(1H, m) (DMSO) | 406 |
| XA1973 | 3.01(1H, dd, J=10.8, 12.9Hz), 3.10-3.30(3H, m), 3.50-3.75(5H, m), 4.04(1H, dd, J=2.7, 10.8Hz), 6.67(1H, s), 7.20-7.40(4H, m), 7.50(1H, s), 7.80(2H, dd, J=1.5, 4.8Hz), 8.71(2H, dd, J=1.5, 5.1Hz) (CDCl3) | 382 |
| XA1974 | 2.80(1H, dd, J=10.3, 12.2Hz), 3.15-3.30(3H, m), 3.50-3.80(5H, m), 4.44(1H, dd, J=2.6, 10.3Hz), 6.67(1H, s), 7.10-7.20(1H, m), 7.25-7.40(1H, m), 7.58(1H, dd, J=1.0, 8.1Hz), 7.73(1H, dd, J=1.6, 7.8Hz), 7.81(2H, dd, J=1.6, 4.5Hz), 8.70(2H, dd, J=1.6, 4.5Hz) (CDCl3) | 426 |
| XA1975 | 2.95-3.10(1H, m), 3.10-3.35(3H, m), 3.56(3H, s), 3.60-3.70(2H, m), 3.80-4.05(7H, m), | 407 |

TABLE 5-continued

| | | |
|---|---|---|
| | 6.67(1H, s), 6.87(1H, d, J=8.1Hz), 6.90-7.10(2H, m), 7.80(2H, dd, J=1.8, 6.3Hz), 8.71(2H, dd, J=1.5, 4.8Hz) (CDCl3) | |
| XA1976 | 3.40(3H, m), 3.45(3H, s), 3.53-3.96(3H, m), 4.68(1H, t, J=13.5Hz), 7.10(1H, s), 7.60(2H, d, J=8.3Hz), 7.76(2H, d, J=8.3Hz), 8.38(1H, br s), 8.91(1H, d, J=4.8Hz), 9.88(1H, br s), 10.31(1H, br s) (DMSO-d6) | 382 |
| XA1977 | 3.40(3H, m), 3.46(3H, s), 3.62(1H, dd, J=12.0, 13.2Hz), 3.72(1H, m), 3.92(1H, t, J=15.5Hz), 4.68(1H, t, J=10.1Hz), 7.18(1H, s), 7.58(2H, d, J=8.6Hz), 7.83(2H, d, J=8.6Hz), 8.57(2H, d, J=6.6Hz), 9.01(2H, d, J=6.6Hz), 10.20(1H, d, J=7.8Hz), 10.76(1H, br s) (DMSO-d6) | 382 |
| XA1978 | 2.98(1H, t, J=10.9Hz), 3.22(m, 3H), 3.56(3H, s), 3.60(2H, m), 4.03(1H, d, J=8.7Hz), 6.68(1H, s), 7.28(1H, d, J=8.2Hz), 7.46(1H, d, J=8.2Hz), 7.61(1H, s), 7.79(2H, d, J=5.6Hz), 8.71(2H, d, J=5.6Hz) (CDCl3) | |
| XA1979 | 3.31(1H, dd, J=13.8, 8.9Hz), 3.46(3H, s), 3.85(1H, dd, J=13.8, 3.6Hz), 4.10(1H, d, J=17.7Hz), 4.19(1H, d, J=17.7Hz), 4.91(1H, dd, J=8.9, 3.6Hz), 6.11(1H, s), 6.74(1H, s), 7.32(1H, d, J=8.4Hz), 7.42(2H, d, J=8.4Hz), 7.79(2H, dd, J=4.8, 1.5Hz), 8.74(2H, dd, J=4.8, 1.5Hz) (CDCl3) | 396 |
| XA1980 | 1.97(4H, m), 3.26(4H, m), 3.38(2H, m), 3.45(3H, s), 3.60(2H, m), 3.80(1H, d, J=13.8Hz), 3.92(1H, d, J=14.1Hz), 4.48(1H, t, J=10.4Hz), 6.65(2H, d, J=8.7Hz), 7.16(1H, s), 7.54(2H, d, J=8.7Hz), 8.57(2H, d, J=6.6Hz), 9.00(2H, d, J=6.6Hz), 9.83(1H, d, J=9.3Hz), 10.32(1H, br s) (DMSO-d6) | 417 |
| XA1981 | 3.21(4H, m), 3.40(2H, m), 3.46(3H, s), 3.65(2H, m), 3.78(4H, m), 3.91(2H, t, J=13.7Hz), 4.55(1H, t, J=10.1Hz), 7.14(2H, d, J=8.7Hz), 7.20(1H, s), 7.64(2H, d, J=8.7Hz), 8.60(2H, d, J=6.6Hz), 9.02(2H, d, J=6.6Hz), 9.93(1H, d, J=9.0Hz), 10.47(1H, br s) (DMSO-d6) | 433 |
| XA1982 | 2.80(3H, d, J=4.5Hz), 3.15(4H, m), 3.44(4H, m), 3.45(3H, s), 3.60(2H, m), 3.82(1H, d, J=13.5Hz), 3.90(3H, m), 4.54(1H, t, J=10.5, 7.10(2H, d, J=8.7Hz), 7.17(1H, s), 7.64(2H, d, J=8.7Hz), 8.54(2H, d, J=6.3Hz), 8.99(2H, d, J=6.3Hz), 9.94(1H, d, J=8.7Hz), 10.47(1H, br s), 11.26(1H, br s) (DMSO-d6) | 446 |
| XA1983 | 1.27(3H, t, J=6.6Hz), 3.46-4.14(8H, m), 4.70(1H, m), 7.11(1H, s), 7.60(2H, d, J=8.4Hz), 7.76(2H, d, J=8.4Hz), 8.32(2H, d, J=6Hz), 8.89(2H, d, J=6.0Hz), 9.87(1H, m), 10.23(1H, m), (DMSO-d6) | 396 |
| XA1984 | 1.27(6H, dd, J=6.9, 6.9Hz), 3.37-4.36(6H, m), 4.66-4.79(2H, m), 7.03(1H, s), 7.62(2H, d, J=8.7Hz), 7.78(2H, d, J=8.7Hz), 8.33(2H, d, J=6Hz), 8.90(2H, d, J=6.0Hz), 9.93(1H, m), 10.25(1H, m), (DMSO-d6) | 410 |
| XA1985 | 1.40(3H, d, J=6.3Hz), 3.44-4.04(5H, m), 3.48(3H, s), 4.69(1H, m), 7.08(1H, s), 7.60(2H, d, J=8.4Hz), 7.79(2H, d, J=8.4Hz), 8.33(2H, d, J=6.3Hz), 8.90(2H, d, J=6.3Hz), 9.83(1H, m), 10.00(1H, m), (DMSO-d6) | 396 |
| XA1986 | 1.57(6H, s), 3.50(3H, s), 3.51-3.93(4H, m), 4.98(1H, m), 7.11(1H, s), 7.60(2H, d, J=7.4Hz), 7.94(2H, d, J=7.4Hz), 8.41(2H, d, J=6.0Hz), 8.93(2H, d, J=6.0Hz), 9.88(1H, m), 10.05(1H, m), (DMSO-d6) | 410 |
| XA1987 | 1.43(3H, d, J=6.6Hz), 3.38-3.93(5H, m), 3.48(3H, s), 4.72(1H, m), 7.12(1H, s), 7.59(2H, d, J=8.4Hz), 7.84(2H, d, J=8.4Hz), 8.43(2H, d, J=6.6Hz), 8.95(2H, d, J=6.6Hz), 9.65(1H, m), 10.23(1H, m), (DMSO-d6) | 396 |
| XA1988 | 2.34(1H, m), 2.42(1H, m), 2.80(3H, d, J=5.6Hz), 2.81(3H, d, J=5.6Hz), 3.28(1H, q, J=8.8Hz), 3.43(2H, m), 3.45(3H, s), 3.57(5H, m), 3.80(1H, d, J=11.4Hz), 3.96(2H, m), 4.50(1H, t, J=10.4Hz), 6.69(2H, d, J=8.4Hz), 7.14(1H, s), 7.55(2H, d, J=8.4Hz), 8.47(2H, d, J=5.6Hz), 8.96(2H, d, J=5.6Hz), 9.75(1H, d, J=8.0Hz), 10.16(1H, br s), 11.40(1H, br s) (DMSO-d6) | 460 |
| XA1989 | 1.65(2H, br s), 1.91(4H, br s), 3.46(9H, s), 3.70(2H, m), 3.92(2H, t, J=16.6Hz), 4.66(1H, br s), 7.16(1H, s), 7.85(4H, br s), 8.50(2H, d, J=6.4Hz), 8.97(2H, d, J=6.4Hz), 10.01(1H, br s), 10.59(1H, br s) (DMSO-d6) | 431 |
| XA1990 | 2.32(1H, m), 2.42(1H, m), 2.79(3H, d, J=5.2Hz), 2.81(3H, d, J=5.2Hz), 3.27(1H, m), 3.39(2H, m), 3.45(3H, s), 3.59(5H, m), 3.79(1H, d, J=13.3Hz), 3.95(2H, m), 4.50(1H, t, J=11.6Hz), 6.69(2H, d, J=8.4Hz), 7.16(1H, s), 7.56(2H, d, J=8.4Hz), 8.50(2H, d, J=6.4Hz), 8.98(2H, d, J=5.6Hz), 9.78(1H, br s), 10.19(1H, br s), 11.44(1H, br s) (DMSO-d6) | 460 |
| XA1991 | 3.47(3H, s), 3.61(3H, m), 3.81(3H, s), 4.02(3H, m), 4.69(1H, t, J=10.6Hz), 7.05(2H, d, J=8.8Hz), 7.10(1H, s), 7.67(2H, d, J=8.8Hz), 7.77(4H, s), 8.38(2H, br s), 8.91(2H, d, J=5.2Hz), 9.90(1H, br s), 10.28(1H, br s) (DMSO-d6) | 454 |
| XA1992 | 1.26(3H, t, J=6.9Hz), 1.41(3H, d, J=6.3Hz), 3.43-4.06(7H, m), 4.74(1H, m), 7.09(1H, s), 7.58(2H, d, J=8.4Hz), 7.84(2H, d, J=8.4Hz), 8.32(2H, d, J=6.6Hz), 8.90(2H, d, J=6.6Hz), 9.90(1H, m), 10.03(1H, m), (DMSO-d6) | 410 |
| XA1993 | 1.41(3H, t, J=6.3Hz), 1.55(6H, dd, J=6.6, 6.6Hz), 3.49-3.73(5H, m), 4.64(1H, m), 4.78(1H, m), 6.99(1H, s), 7.58(2H, d, J=8.7Hz), 7.81(2H, d, J=8.7Hz), 8.28(2H, d, J=6.3Hz), 8.87(2H, d, J=6.3Hz), 9.91(2H, m) (DMSO-d6) | 424 |
| XA1994 | 1.27(3H, t, J=6.9Hz), 1.55(3H, s), 1.60(3H, s), 3.42-4.14(6H, m), 5.04(1H, m), 7.13(1H, s), 7.60(2H, d, J=8.4Hz), 7.91(2H, d, J=8.4Hz), 8.32(2H, d, J=6.3Hz), 8.89(2H, d, J=6.3Hz), 9.80-9.84(2H, m) (DMSO-d6) | 424 |
| XA1995 | 1.52(3H, d, J=6.6Hz), 1.58(6H, d, J=6.6Hz), 1.59(3H, d, J=6.6Hz), 3.40-3.68(4H, m), 4.75(1H, m), 5.09(1H, m), 7.03(1H, s), 7.60(2H, d, J=8.4Hz), 7.93(2H, d, J=8.4Hz), 8.33(2H, d, J=6.0Hz), 8.89(2H, d, J=6.0Hz), 9.89(2H, m) (DMSO-d6) | 438 |
| XA1996 | 1.29(3H, t, J=6.8Hz), 3.47(2H, br s), 3.66(3H, m), 3.81(3H, s), 3.83(1H, m), 4.04(2H, m), 4.71(1H, d, J=10.6Hz), 7.05(2H, d, J=8.8Hz), 7.12(1H, s), 7.67(2H, d, J=8.8Hz), 7.75(2H, d, J=8.4Hz), 7.79(2H, d, J=8.4Hz), 8.36(2H, d, J=6.4Hz), 8.91(2H, d, J=6.4Hz), 9.92(1H, d, J=8.8Hz), 10.29(1H, br s) (DMSO-d6) | 468 |
| XA1997 | 1.56(3H, d, J=6.4Hz), 1.58(3H, d, J=6.4Hz), 3.47(2H, br s), 3.60(1H, m), 3.77(2H, m), 3.81(3H, s), 4.72(3H, m), 7.05(2H, d, J=8.8Hz), 7.06(1H, s), 7.68(2H, d, J=8.8Hz), 7.76(2H, d, J=8.4Hz), 7.80(2H, d, J=8.4Hz), 8.42(2H, d, J=6.4Hz), 8.94(2H, d, J=6.4Hz), 10.02(1H, d, J=9.6Hz), 10.39(1H, br s) (DMSO-d6) | 482 |
| XA1998 | 1.24(1H, m), 1.39(4H, m), 1.72(1H, m), 1.79(4H, m), 2.55(1H, m), 3.45(3H, s), 4.00-3.45(6H, m), 4.61(1H, t, J=11.2Hz), 7.09(1H, s), 7.35(2H, d, J=8.4Hz), 7.62(2H, d, J=8.4Hz), 8.37(2H, d, J=4.0Hz), 8.90(2H, d, J=4.0Hz), 9.75(1H, d, J=9.6Hz), 10.17(1H, br s), (DMSO-d6) | 430 |
| XA1999 | 1.04(1H, m), 1.17(2H, m), 1.43(2H, m), 1.60(1H, m), 1.79(4H, m), 2.96(3H, br s), 3.45(3H, s), 4.18-3.44(6H, m), 4.62(1H, br s), 7.13(1H, s), 7.75(4H, br s), 8.46(1H, br s), 8.95(1H, br s), 9.87(1H, br s), 10.40(1H, br s) (DMSO-d6) | 459 |
| XA2000 | 1.40(3H, d, J=6.6Hz), 3.44-4.04(5H, m), 3.48(3H, s), 4.72(1H, m), 7.05(1H, s), 7.61(2H, d, J=8.4Hz), 7.78(2H, d, J=8.4Hz), | 396 |

TABLE 5-continued

| | | |
|---|---|---|
| XA2001 | 8.29(2H, d, J=6.0Hz), 8.90(2H, d, J=6.0Hz), 9.78-10.00(2H, m), (DMSO-d6) | |
| | 1.26(3H, t, J=6.9Hz), 1.41(3H, d, J=6.0Hz), 3.43-4.06(7H, m), 4.74(1H, m), 7.08(1H, s), 7.58(2H, d, J=8.4Hz), 7.81(2H, d, J=8.4Hz), 8.29(2H, d, J=6.3Hz), 8.88(2H, d, J=6.3Hz), 9.84-10.00(2H, m), (DMSO-d6) | 410 |
| XA2002 | 1.41(3H, t, J=6.0Hz), 1.56(6H, dd, J=6.6, 6.6Hz), 3.49-3.73(5H, m), 4.62(1H, m), 4.78(1H, m), 7.00(1H, s), 7.59(2H, d, J=8.4Hz), 7.81(2H, d, J=8.4Hz), 8.30(2H, d, J=6.3Hz), 8.88(2H, d, J=6.3Hz), 9.91(2H, m) (DMSO-d6) | 424 |
| XA2003 | 3.03(4H, td, J=4.6Hz), 3.26(4H, t, J=4.5Hz), 3.48(3H, s), 6.65(1H, s), 7.10(2H, m), 7.20-7.45(5H, m), 7.65(2H, d, J=8.5Hz), 7.79(2H, d, J=6.3Hz), 8.71(2H, d, J=1.5, 4.8Hz) (CDCl3) | 425 |
| XA2004 | 2.93(1H, m), 3.20(2H, m), 3.30(3H, s), 3.36(1H, m), 3.42(1H, t, J=12.0Hz), 3.73(4H, m), 7.03(2H, m), 7.33(2H, m), 7.42(3H, m), 8.16(2H, d, J=6.4Hz), 8.86(2H, d, J=6.4Hz), 9.61(1H, d, J=10.0Hz), 9.95(1H, d, J=8.4Hz) (DMSO-d6) | 362 |
| XA2005 | 2.93(1H, dd, J=14.8, 8.4Hz), 3.07(1H, m), 3.19(1H, m), 3.33(3H, s), 3.41(3H, s), 3.69(1H, m), 3.80(2H, d, J=14.0Hz), 6.96(1H, br s), 7.39(2H, d, J=8.0Hz), 7.49(2H, d, J=8.0Hz), 8.00(2H, br s), 8.77(2H, br s), 9.24(1H, s), 9.54(1H, s) (DMSO-d6) | 396 |
| XA2006 | 3.39(2H, m), 3.46(3H, m), 3.56(2H, m), 3.85(1H, d, J=13.2Hz), 3.93(1H, d, J=13.6Hz), 4.55(1H, t, J=10.4Hz), 6.94(1H, br s), 7.13(1H, s), 7.14(4H, m), 7.30(2H, m), 7.59(2H, d, J=8.0Hz), 8.45(2H, s), 8.95(2H, s), 9.73(1H, br s), 10.10(1H, br s) (DMSO-d6) | 508 |
| XA2007 | 1.39(1H, m), 1.80(8H, m), 2.18(2H, d, J=11.2Hz), 2.76(2H, t, J=11.4Hz), 3.90(2H, m), 3.33(1H, m), 3.40(3H, m), 3.45(3H, s), 3.58(2H, m), 3.82(1H, d, J=13.3Hz), 3.93(3H, m), 4.53(1H, t, J=10.4Hz), 7.09(2H, d, J=8.8Hz), 7.11(1H, s), 7.56(2H, d, J=8.8Hz), 8.40(2H, d, J=6.0Hz), 8.92(2H, d, J=6.0Hz), 9.75(1H, d, J=8.8Hz), 10.14(1H, br s), 10.39(1H, br s) (DMSO-d6) | 514 |
| XA2008 | 2.82-2.90(1H, m), 3.01-3.05(4H, m), 3.22(3H, s), 3.44(3H, s), 3.58-3.66(2H, m), 4.08(1H, dd, J=1.2, 10.2Hz), 6.81(1H, s), 7.77(2H, d, J=7.2Hz), 7.92-7.98(4H, m), 8.69(2H, d, J=4.2Hz) (DMSO-d6) | 426 |
| XA2009 | 1.21(3H, d, J=6.6Hz), 3.17-3.45(4H, m), 3.52(3H, s), 4.02(1H, m), 4.69(1H, m), 7.20(1H, s), 7.54(2H, d, J=8.4Hz), 7.70(2H, d, J=8.4Hz), 8.26(2H, d, J=6.3Hz), 8.88(2H, d, J=6.3Hz), 9.90(1H, m), 10.16(1H, m), (DMSO-d6) | 396 |
| XA2010 | 1.21(3H, d, J=6.0Hz), 3.17-3.45(4H, m), 3.53(3H, s), 4.02(1H, m), 4.70(1H, m), 7.24(1H, s), 7.54(2H, d, J=8.7Hz), 7.73(2H, d, J=8.7Hz), 8.33(2H, d, J=5.7Hz), 8.93(2H, d, J=5.7Hz), 10.04(1H, m), 1037(1H, m), (DMSO-d6) | 396 |
| XA2011 | 3.02(1H, t, J=11.9Hz), 3.17(6H, m), 3.55(3H, s), 3.63(2H, m), 3.86(4H, m), 3.96(1H, d, J=10.2Hz), 6.66(1H, m), 6.92(2H, d, J=8.4Hz), 7.35(2H, d, J=8.4Hz), 7.80(2H, d, J=5.1Hz), 8.70(2H, d, J=5.1Hz) (CDCl3) | 433 |
| XA2012 | 2.31(3.6H, s), 3.16(4H, t, J=4.8Hz), 3.44(3H, s), 3.45(4H, m), 3.75(4H, t, J=4.8Hz), 3.86(1H, d, J=14.0Hz), 3.92(1H, d, J=12.4Hz), 4.56(1H, d, J=10.4Hz), 6.95(1H, s), 7.06(2H, d, J=8.8Hz), 7.43(2H, d, J=8.8Hz), 8.06(2H, d, J=6.0Hz), 8.75(2H, d, J=6.0Hz), 9.03(1H, s), 9.33(1H, d, J=10.0Hz) (DMSO-d6) | 433 |
| XA2013 | 1.82(4H, m), 1.97(2H, m), 2.12(2H, m), 2.77(2H, t, J=11.6Hz), 3.01(2H, m), 3.27(1H, m), 3.40(2H, m), 3.45(3H, m), 3.49(2H, m), 3.57(1H, m), 3.63(1H, m), 3.84(1H, d, J=13.6Hz), 3.92(3H, d, J=12.8Hz), 4.53(1H, t, J=11.2Hz), 7.12(2H, d, J=8.4Hz), 7.14(1H, s), 7.58(2H, d, J=8.9Hz), 8.49(2H, d, J=5.2Hz), 8.97(2H, d, J=5.2Hz), 9.82(1H, br s), 10.24(1H, br s), 11.12(1H, br s) (DMSO-d6) | 500 |
| XA2014 | 1.75(2H, m), 2.14(2H, m), 2.72(6H, d, J=4.5Hz), 2.74-2.80(3H, m), 3.30-3.95(8H, m), 3.45(3H, s), 4.54(1H, m), 7.10(2H, d, J=9.0Hz), 7.15(1H, s), 7.60(2H, d, J=9.0Hz), 8.51(2H, d, J=6.6Hz), 8.98(2H, d, J=6.6Hz), 9.86(1H, m), 10.32(1H, m), 10.93(1H, m), (DMSO-d6) | 474 |
| XA2015 | 1.68(2H, m), 2.09(2H, m), 3.16-3.90(10H, m), 3.45(3H, s), 4.60(1H, m), 7.13(1H, s), 7.45-7.71(4H, m), 8.45(2H, d, J=6.0Hz), 8.94(2H, d, J=6.0Hz), 9.83(1H, m), 10.22(1H, m) (DMSO-d6) | 447 |
| XA2016 | 1.91-2.03(2H, m), 3.09(1H, m), 3.28-3.57(7H, m), 3.40(3H, s), 4.41(2H, m), 6.58(2H, d, J=8.7Hz), 7.13(1H, s), 7.46(2H, d, J=8.7Hz), 8.44(2H, d, J=6.3Hz), 8.94(2H, d, J=6.3Hz), 9.61(1H, m), 9.89(1H, m) (DMSO-d6) | 433 |
| XA2017 | 2.97(6H, m), 3.45(3H, s), 4.20-3.30(6H, m), 4.53(1H, t, J=9.8Hz), 6.69(2H, br s), 7.14(1H, s), 7.57(2H, br s), 8.48(2H, br s), 8.96(2H, br s), 9.72(1H, br s), 10.09(1H, br s) (DMSO-d6) | 391 |
| XA2018 | 3.18-3.22(1H, m), 3.44-3.80(15H, m), 4.51-4.55(1H, m), 5.11(2H, s), 7.04-7.07(3H, m), 7.32-7.39(5H, m), 7.52-7.55(2H, m), 8.33-8.35(2H, m), 8.82-8.87(2H, m), 9.65-9.75(2H, br) (DMSO-d6) | 566 |
| XA2019 | 1.32(6H, d, J=6.8Hz), 3.04-3.88(18H, m), 4.52-4.55(1H, m), 7.09-7.12(3H, m), 7.62(2H, d, J=7.2Hz), 8.45(2H, d, J=4.2Hz), 8.94(2H, d, J=4.2Hz), 9.83-10.34(3H, br), 11.00-11.04(1H, br) (DMSO-d6) | 474 |
| XA2020 | 1.32(6H, d, J=6.8Hz), 3.04-3.88(18H, m), 4.52-4.55(1H, m), 7.09-7.12(3H, m), 7.62(2H, d, J=7.2Hz), 8.45(2H, d, J=4.2Hz), 8.94(2H, d, J=4.2Hz), 9.83-10.34(3H, br), 11.00-11.04(1H, br) (DMSO-d6) | 476 |
| XA2021 | 2.09(3H, s), 3.19-4.00(20H, m), 4.43-4.54(3H, m), 7.06-7.19(3H, m), 7.62(2H, d, J=7.2Hz), 8.44(2H, d, J=4.2Hz), 8.94(2H, d, J=4.2Hz), 9.82-9.85(1H, br), 10.26-10.30(1H, br), 11.30-11.40(1H, br) (DMSO-d6) | 518 |
| XA2022 | 3.17-3.21(4H, m), 3.38-4.16(14H, m), 4.51-4.54(1H, m), 7.08-7.18(3H, m), 7.60(2H, d, J=7.2Hz), 8.43(2H, d, J=4.2Hz), 8.93(2H, d, J=4.2Hz), 9.26-9.34(2H, br), 9.81-84(1H, br), 10.25-10.30(1H, br) (DMSO-d6) | 432 |
| XA2023 | 1.82(3H, m), 3.29(3H, m), 3.40-3.96(9H, m), 3.48(3H, s), 4.55(1H, m), 7.10(1H, s), 7.13(2H, d, J=8.4Hz), 7.56(2H, d, J=8.4Hz), 8.39(2H, d, J=6.0Hz), 8.91(2H, d, J=6.0Hz), 9.67(1H, m), 9.97(1H, m) (DMSO-d6) | 445 |
| XA2024 | 1.89-2.03(2H, m), 2.95-3.07(5H, m), 3.29-3.83(5H, m), 3.40(3H, s), 4.40(1H, m), 4.94(1H, m), 6.49(2H, d, J=8.4Hz), 7.13(1H, s), 7.25(2H, d, J=8.4Hz), 7.95(2H, d, J=6.0Hz), 8.69(2H, d, J=6.0Hz) (DMSO-d6) | 433 |
| XA2025 | 1.16(6H, d, J=6.3Hz), 2.28-2.36(2H, m), 2.97-3.21(6H, m), 3.54(3H, s), 3.55-3.62(4H, m), 3.95(1H, m), 6.66(1H, s), 6.93(2H, d, J=8.7Hz), 7.32(2H, d, J=8.7Hz), 7.80(2H, d, J=6.3Hz), 8.70(2H, d, J=6.3Hz) (CDCl3) | 460 |
| XA2026 | 1.26(6H, d, J=6.3Hz), 2.42(2H, dd, J=11.1, 11.1Hz), 3.02(1H, dd, J=12.3, 10.8Hz), 3.17-3.22(3H, m), 3.45-3.63(4H, m), 3.55(3H, s), 3.81(1H, m), 3.95(1H, dd, J=13.2, 2.1Hz), 6.66(1H, s), 6.92(2H, d, J=8.4Hz), 7.34(2H, d, J=8.4Hz), 7.80(2H, d, J=6.0Hz), 8.70(2H, d, J=6.0Hz) (CDCl3) | 461 |

TABLE 5-continued

| | | |
|---|---|---|
| XA2027 | 2.91-3.09(5H, m), 3.26(3H, s), 3.46(3H, s), 3.69-3.73(2H, m), 4.07-4.11(1H, m), 6.81(1H, s), 7.64(2H, d, J=7.2Hz), 7.77(2H, d, J=7.2Hz), 7.94-8.02(6H, m), 8.68(1H, d, J=4.2Hz) (DMSO-d6) | 502 |
| XA2028 | 3.28-3.32(4H, m), 3.46(3H, s), 3.86-3.91(2H, m), 4.59-4.61(1H, m), 6.90(1H, s), 7.77-8.06(10H, m), 8.70(2H, d, J=4.2Hz), 9.36-9.44(1H, br) (DMSO-d6) | 449 |
| XA2029 | 3.08(1H, dd, J=12.4, 10.4Hz), 3.25(3H, m), 3.58(3H, s), 3.68(2H, m), 4.09(1H, dd, J=10.4, 2.4Hz), 6.68(1H, s), 7.29(2H, d, J=8.4Hz), 7.54(2H, d, J=8.4Hz), 7.56(2H, d, J=8.4Hz), 7.59(2H, d, J=8.4Hz), 7.81(2H, dd, J=4.4, 1.6Hz), 8.71(2H, dd, J=4.4, 1.6Hz) (CDCl3) | 508 |
| XA2030 | 3.08(1H, dd, J=12.4, 10.4Hz), 3.27(3H, m), 3.58(3H, s), 3.70(2H, m), 4.11(1H, dd, J=10.4, 2.4Hz), 6.68(1H, s), 7.57(2H, d, J=8.0Hz), 7.63(2H, d, J=8.0Hz), 7.70(4H, s), 7.81(2H, dd, J=4.8, 1.2Hz), 8.71(2H, dd, J=4.8, 1.2Hz) (CDCl3) | 492 |
| XA2031 | 1.45(3H, t, J=12.4Hz), 3.08(1H, dd, J=12.4, 10.8Hz), 3.24(3H, m), 3.57(3H, s), 3.67(2H, m), 4.07(1H, m), 4.09(2H, q, J=7.0Hz), 6.67(1H, s), 6.97(2H, d, J=8.4Hz), 7.51(2H, d, J=8.4Hz), 7.51(2H, d, J=8.4Hz), 7.54(2H, d, J=8.4Hz), 7.57(2H, d, J=8.4Hz), 7.81(2H, dd, J=4.8, 1.2Hz), 8.71(2H, dd, J=4.8, 1.2Hz) (CDCl3) | 468 |
| XA2032 | 1.94(4H, m), 2.02(1H, m), 2.21(1H, m), 2.62(4H, m), 2.91(1H, m), 3.03(1H, dd, J=12.4, 10.4Hz), 3.20(4H, m), 3.33(1H, m), 3.48(2H, m), 3.54(3H, s), 3.62(2H, m), 3.91(1H, dd, J=10.4, 2.4Hz), 6.55(2H, d, J=8.4Hz), 6.66(1H, s), 7.29(2H, d, J=8.4Hz), 7.81(2H, dd, J=4.4, 0.8Hz), 8.70(2H, dd, J=4.4, 0.8Hz) (CDCl3) | 468 |
| XA2033 | 2.29(3H, s), 3.06(4H, t, J=4.8Hz), 3.38(4H, t, J=4.8Hz), 3.51(3H, s), 5.70(1H, s), 6.67(1H, s), 7.24-7.29(5H, m), 7.83(1H, dd, J=1.6, 4.3Hz), 8.72(1H, dd, J=1.3, 4.5Hz) (CDCl3) | 427 |
| XA2034 | 3.09(1H, dd, J=12.0, 10.8Hz), 3.23(3H, m), 3.57(3H, s), 3.66(2H, m), 3.82(3H, s), 3.86(3H, s), 4.06(1H, dd, J=10.8, 2.4Hz), 6.58(2H, m), 6.67(1H, s), 7.24(2H, m), 7.47(2H, d, J=8.0Hz), 7.53(2H, d, J=8.0Hz), 7.82(2H, dd, J=4.8, 1.2Hz), 8.71(2H, dd, J=4.8, 1.2Hz) (CDCl3) | 484 |
| XA2035 | 3.08(3H, dd, J=12.4, 10.8Hz), 3.25(3H, m), 3.57(3H, s), 3.67(2H, m), 3.93(3H, s), 3.96(3H, s), 4.08(1H, dd, J=10.0, 2.0Hz), 6.68(1H, s), 6.95(1H, d, J=8.4Hz), 7.11(1H, d, J=2.4Hz), 7.16(1H, dd, J=8.4, 2.4Hz), 7.51(2H, d, J=8.0Hz), 7.58(2H, d, J=8.0Hz), 7.81(2H, dd, J=4.8, 1.2Hz), 8.71(2H, dd, J=4.8, 1.2Hz) (CDCl3) | 484 |
| XA2036 | 3.08(1H, dd, J=12.4, 10.8Hz), 3.26(3H, m), 3.57(3H, s), 3.67(2H, m), 4.09(1H, dd, J=10.0, 2.0Hz), 6.68(1H, s), 7.42(2H, d, J=8.4Hz), 7.53(4H, d, J=8.4Hz), 7.58(2H, d, J=8.4Hz), 7.80(2H, dd, J=4.8, 1.6Hz), 8.71(2H, dd, J=4.8, 1.6Hz) (CDCl3) | 458 |
| XA2037 | 3.09(1H, dd, J=12.4, 10.8Hz), 3.25(3H, m), 3.58(3H, s), 3.69(2H, m), 4.11(1H, dd, J=10.4, 2.4Hz), 6.68(1H, s), 7.28(2H, m), 7.44(2H, d, J=8.0Hz), 7.51(3H, m), 8.81(2H, dd, J=4.0, 1.2Hz), 8.72(2H, dd, J=4.0, 1.2Hz) (CDCl3) | 492 |
| XA2038 | 3.07(1H, dd, J=12.3, 11.0Hz), 3.26(3H, m), 3.57(3H, s), 3.67(2H, m), 4.10(1H, dd, J=10.2, 2.1Hz), 6.68(1H, s), 7.42(1H, dd, J=8.1, 2.2Hz), 7.55(5H, m), 7.68(1H, d, J=2.2Hz), 7.80(2H, dd, J=4.8, 1.3Hz), 8.70(2H, dd, J=4.8, 1.3Hz) (CDCl3) | 492 |
| XA2039 | 3.06(1H, dd, J=12.0, 10.8Hz), 3.24(3H, m), 3.58(3H, s), 3.67(2H, m), 4.13(1H, dd, J=10.4, 2.4Hz), 6.68(1H, s), 7.61(2H, d, J=8.4Hz), 7.80(2H, d, J=4.4Hz), 8.15(2H, d, J=8.4Hz), 8.71(2H, d, J=4.4Hz), 8.77(1H, s) (CDCl3) | 416 |
| XA2040 | 3.04-3.26(4H, m), 3.57(3H, s), 3.66-3.71(2H, m), 4.07(1H, m), 5.12(2H, s), 6.68(1H, s), 7.06(2H, d, J=8.7Hz), 7.40-7.59(11H, m), 7.81(2H, d, J=6.0Hz), 8.71(2H, d, J=6.0Hz) (CDCl3) | 530 |
| XA2041 | 0.38(2H, m), 0.67(2H, m), 1.32(1H, m), 3.09(1H, dd, J=12.6, 11.1Hz), 3.22-3.28(3H, m), 3.58(3H, s), 3.67-3.71(2H, m), 3.86(2H, d, J=6.9Hz), 4.08(1H, m), 6.68(1H, s), 7.06(2H, d, J=9.0Hz), 7.49-7.60(6H, m), 7.82(2H, d, J=6.0Hz), 8.72(2H, d, J=6.0Hz) (CDCl3) | 494 |
| XA2042 | 1.37(6H, d, J=6.0Hz), 3.08(1H, dd, J=12.3, 11.1Hz), 3.20-3.28(3H, m), 3.57(3H, s), 3.65-3.70(2H, m), 4.06(1H, m), 4.59(1H, m), 6.67(1H, s), 7.06(2H, d, J=9.0Hz), 7.48-7.59(6H, m), 7.81(2H, d, J=6.0Hz), 8.71(2H, d, J=6.0Hz) (CDCl3) | 482 |
| XA2043 | 0.99(3H, t, J=7.5Hz), 1.40-1.85(4H, m), 3.05-3.30(4H, m), 3.57(3H, s), 3.65-3.70(2H, m), 4.00-4.10(3H, m), 6.67(1H, s), 6.97(2H, d, J=8.7Hz), 7.50-7.56(6H, m), 7.81(2H, d, J=6.0Hz), 8.71(2H, d, J=6.0Hz) (CDCl3) | 496 |
| XA2044 | 1.66(1H, br.s), 2.52(3H, s), 3.05(1H, dd, J=10.5, 12.6Hz), 3.20-3.26(3H, m), 3.57(3H, s), 3.62-3.72(2H, m), 4.07(1H, dd, J=2.1, 10.5Hz), 6.67(1H, s), 7.33(2H, d, J=8.4Hz), 7.50-7.61(6H, m), 7.81(2H, d, J=1.6, 4.3Hz), 8.70(2H, dd, J=1.3, 4.5Hz) (CDCl3) | 469 |
| XA2045 | 1.72(1H, br.s), 2.40(3H, s), 2.98-3.26(5H, m), 3.57(3H, s), 3.57-3.67(1H, m), 4.07(1H, dd, J=2.1, 10.5Hz), 6.67(1H, s), 7.24(2H, d, J=8.1Hz), 7.49-7.52(4H, m), 7.60(2H, d, J=8.1Hz), 7.81(2H, dd, J=1.6, 4.3Hz), 8.70(2H, dd, J=1.3, 4.5Hz) (CDCl3) | 437 |
| XA2046 | 1.36(9H, s), 1.72(1H, br.s), 3.06(1H, dd, J=10.5, 12.4Hz), 3.20-3.28(3H, m), 3.57(3H, s), 3.57-3.67(2H, m), 4.07(1H, dd, J=2.1, 10.5Hz), 6.67(1H, s), 7.24(2H, d, J=8.1Hz), 7.43-7.56(6H, m), 7.81(2H, dd, J=1.6, 4.3Hz), 8.71(2H, dd, J=1.3, 4.5Hz) (CDCl3) | 479 |
| XA2047 | 1.29(6H, d, J=6.9Hz), 1.73(1H, br.s), 2.96(1H, m), 3.06(1H, dd, J=10.5, 12.4Hz), 3.21-3.29(3H, m), 3.57(3H, s), 3.62-3.71(2H, m), 4.07(1H, dd, J=2.1, 10.5Hz), 6.67(1H, s), 7.31(2H, d, J=8.1Hz), 7.45-7.54(4H, m), 7.63(2H, d, J=8.1Hz), 7.81(2H, dd, J=1.6, 4.3Hz), 8.71(2H, dd, J=1.3, 4.5Hz), (CDCl3) | 465 |
| XA2048 | 1.68(2H, br.s), 2.98(1H, dd, J=10.5, 12.6Hz), 3.20-3.27(2H, m), 3.56(3H, s), 3.64-3.74(1H, m), 4.04(1H, dd, J=3.3, 11.1Hz), 4.80(3H, s), 6.66(1H, s), 6.72(1H, d, J=8.5Hz), 7.49-7.52(4H, m), 7.63(2H, d, J=8.1Hz), 7.81(2H, dd, J=1.6, 4.3Hz), 8.70(2H, dd, J=1.3, 4.5Hz) (DMSO-d6) | 438 |
| XA2049 | 2.67(3H, s), 3.06(1H, dd, J=12.4, 10.8Hz), 3.25(3H, m), 3.57(3H, s), 3.62(2H, m), 4.12(1H, dd, J=10.0, 2.0Hz), 6.68(1H, s), 7.59(2H, d, J=8.0Hz), 7.80(1H, dd, J=4.8, 1.2Hz), 8.09(1H, d, J=8.0Hz), 8.71(1H, dd, J=4.8, 1.2Hz) (CDCl3) | 430 |
| XA2050 | 3.05(1H, m), 3.30-3.48(3H, m), 3.64(3H, s), 4.08-4.22(2H, m), 4.68(1H, m), 5.15(1H, d, J=12.3Hz), 5.21(1H, d, J=12.6Hz), 6.63(1H, s), 7.21(2H, d, J=8.4Hz), 7.28-7.39(7H, m), 7.59(2H, d, J=6.3Hz), 8.68(2H, d, J=6.3Hz) (CDCl3) | 560 |
| XA2051 | 2.88-3.34(6H, m), 3.67(3H, s), 4.56(1H, dd, J=9.9, 3.3Hz), 6.62(1H, s), 7.19(2H, d, J=10.8Hz), 7.36(2H, d, J=10.8Hz), 7.58(2H, dd, J=4.5, 1.5Hz), 8.67(2H, dd, J=4.5, 1.5Hz) (CDCl3) | 426 |
| XA2052 | 3.04(1H, m), 3.29-3.48(3H, m), 3.64(3H, s), 4.10-4.15(2H, m), 4.68(1H, m), 5.15(1H, d, J=12.3Hz), 5.21(1H, d, J=12.6Hz), 6.63(1H, s), 7.21(2H, d, J=8.1Hz), | 560 |

TABLE 5-continued

| | | |
|---|---|---|
| | 7.32-7.39(7H, m), 7.59(2H, d, J=6.0Hz), 8.68(2H, d, J=6.0Hz) (CDCl3) | |
| XA2053 | 3.01(1H, m), 3.29-3.41(3H, m), 3.66(3H, s), 4.05-4.13(2H, m), 4.67(1H, s), 6.64(1H, s), 7.23(2H, d, J=8.4Hz), 7.41(2H, d, J=8.4Hz), 7.60(2H, dd, J=4.5, 1.5Hz), 8.69(2H, dd, J=4.5, 1.5Hz) (CDCl3) | 527 |
| XA2054 | 2.28(3H, s), 3.07(4H, m), 3.59(4H, m), 3.73(3H, s), 5.78(1H, s), 6.70(1H, s), 6.98(1H, m), 7.40(1H, m), 7.60-7.66(2H, m), 7.81(2H, dd, J=1.6, 4.3Hz), 8.72(2H, dd, J=1.3, 4.5Hz) (DMSO-d6) | 445 |
| XA2055 | 2.31(3H, s), 3.19(4H, m), 3.46(4H, m), 3.54(3H, s), 5.79(1H, s), 6.69(1H, s), 7.18-7.23(1H, m), 7.79(2H, d, J=5.4Hz), 7.79-7.87(2H, m), 8.54(1H, d, J=5.2Hz), 8.72(2H, d, J=4.5Hz) (CDCl3) | 428 |
| XB13 | 1.16-1.28(1H, m), 1.50-1.64(1H, m), 1.70-1.82(2H, m), 1.90-2.01(1H, m), 2.58(1H, d, J=7.3Hz), 2.64-2.72(1H, m), 2.89-2.97(1H, m), 3.28(3H, s), 3.57-3.67(2H, m), 6.93(1H, s), 7.20-7.35(5H, m), 8.26(2H, d, J=5.7Hz), 8.87(2H, d, J=5.9Hz) (DMSO-d6) | 361 |
| XB16 | 1.75-2.16(4H, m), 2.96-3.08(3H, m, s), 3.55(3H, s), 3.69-3.79(2H, m), 6.66(1H, s), 7.26-7.40(5H, m), 7.81(2H, d, J=6.0Hz), 8.70(2H, d, J=6.0Hz) (CDCl3) | 347 |
| XB17 | 1.76-1.99(5H, m), 2.97-3.10(2H, m), 3.75(1H, d, J=12.4Hz), 6.81(1H, s), 7.18-7.24(2H, m), 7.28-7.35(1H, m), 7.47(1H, t, J=7.1Hz), 7.98(2H, d, J=5.8Hz), 8.68(2H, d, J=5.8Hz) (DMSO-d6) | 365 |
| XB19 | 1.86-2.14(4H, m), 2.94-3.03(3H, m), 3.55(3H, s), 3.68-3.75(2H, m), 6.66(1H, s), 7.05(2H, m), 7.23(2H, m), 7.80(2H, d, J=6.3Hz), 8.70(2H, d, J=6.3Hz) (CDCl3) | 365 |
| XB33 | 1.75-2.08(4H, m), 2.80(1H, m), 3.03(1H, m), 3.42(3H, s), 3.77(2H, m), 3.85(3H, s), 6.65(1H, s), 6.89-7.00(2H, m), 7.22-7.28(2H, m), 7.82(2H, d, J=6.0Hz), 8.70(2H, d, J=6.0Hz) (CDCl3) | 377 |
| XB35 | 1.73-1.83(4H, m), 2.90-3.02(3H, m), 3.42(3H, s), 3.67-3.81(2H, m), 3.74(3H, s), 6.80(1H, s), 6.91(1H, d, J=8.7Hz), 7.27(2H, d, J=8.5Hz), 7.97(2H, d, J=5.9Hz), 8.69(2H, d, J=5.7Hz) (DMSO-d6) | 377 |
| XB43 | 1.69-1.90(7H, m), 1.94-2.00(1H, m), 2.59-2.68(4H, m), 2.92-3.02(3H, m), 3.43(3H, s), 3.69-3.80(4H, m), 6.59(3H, s), 6.79(1H, s), 7.29-7.36(4H, m), 7.96(2H, d, J=5.9Hz), 8.68(2H, d, J=5.1Hz) (DMSO-d6) | 430 |
| XB46 | (CDCl3): 1.95-2.09(3H, m), 2.39(1H, m), 3.15(1H, m), 3.45(1H, dd, J=12.9, 10.8Hz), 3.57(3H, s), 3.61-3.72(2H, m), 4.08(1H, m), 6.67(1H, s), 7.32(1H, m), 7.58-7.60(2H, m), 7.74(1H, d, J=7.8Hz), 7.80(2H, dd, J=4.5, 1.5Hz), 8.69(2H, dd, J=4.5, 1.5Hz). | 388 |
| XB47 | (CDCl3): 1.90-2.06(3H, m), 2.36(1H, m), 3.14(1H, m), 3.42(1H, m), 3.57(3H, s), 3.61-3.71(2H, m), 4.06(1H, m), 6.68(1H, s), 7.09(1H, m), 7.28(1H, m), 7.68(1H, dd, J=8.8, 5.1Hz), 7.79(2H, d, J=4.7Hz), 8.69(2H, d, J=5.9Hz). | 406 |
| XB48 | 1.90-2.10(3H, m), 2.32-2.44(1H, m), 3.11-3.20(1H, m), 3.45(1H, dd, J=10.5, 12.6Hz), 3.57(3H, s), 3.61-3.72(2H, m), 4.08(1H, d, J=11.1Hz), 6.67(1H, s), 7.30-7.35(1H, m), 7.56-7.62(2H, m), 7.74(1H, d, J=13.8Hz), 7.80(2H, dd, J=1.8, 4.5Hz), 8.70(2H, dd, J=1.8, 4.8Hz) (CDCl3) | 388 |
| XB49 | 1.91-2.09(3H, m), 2.37-2.42(1H, m), 3.12-3.19(1H, m), 3.45(1H, dd, J=10.8, 12.9Hz), 3.57(3H, s), 3.60-3.72(2H, m), 4.08(1H, d, J=11.1Hz), 6.67(1H, s), 7.30-7.35(1H, m), 7.54-7.62(2H, m), 7.75(1H, d, J=8.1Hz), 7.80(2H, dd, J=1.5, 4.5Hz), 8.70(2H, dd, J=1.8, 4.5Hz) (CDCl3) | 388 |
| XB50 | 1.59-1.67(1H, m), 1.72-1.81(1H, m), 2.08(1H, dt, J=3.4, 12.7Hz), 2.23-2.40(1H, m), 3.06-3.14(1H, m), 3.41-3.54(2H, m), 3.42(3H, s), 3.93(1H, d, J=14.0Hz), 7.02(1H, s), 7.24-7.29(1H, m), 7.34-7.39(2H, m), 7.56-7.59(2H, m), 8.55(1H, d, J=6.6Hz), 8.98(2H, d, J=6.5Hz) (DMSO-d6) | 363 |
| XB80 | 2.21-2.36(4H, m), 3.19-3.31(2H, m), 3.46(3H, s), 3.88(2H, d, J=13.2Hz), 6.86(1H, s), 7.38-7.42(1H, m), 7.46-7.51(2H, m), 7.58-7.64(2H, m), 8.01(2H, d, J=5.1Hz), 8.70(2H, d, J=5.1Hz) (DMSO-d6) | 372 |
| XB122 | 1.44(2H, m), 1.75-1.83(3H, m), 2.63(2H, d, J=6.9Hz), 2.90(2H, m), 3.51(3H, s), 3.64(2H, m), 6.65(1H, s), 7.17-7.34(5H, m), 7.80(2H, d, J=6.3Hz), 8.70(2H, d, J=6.3Hz) (CDCl3) | 361 |
| XB123 | 1.44-2.16(5H, m), 2.86-2.97(2H, m), 3.49(3H, s), 3.62(1H, m), 3.72(1H, m), 4.48(1H, d, J=7.2Hz), 6.64(1H, s), 7.07(2H, m), 7.32(2H, m), 7.79(2H, d, J=6.3Hz), 8.69(2H, d, J=6.3Hz) (CDCl3) | 395 |
| XB124 | 1.38-1.60(3H, m), 1.78(1H, m), 2.16(1H, m), 2.79-2.94(2H, m), 3.20(1H, m), 3.49(3H, s), 3.59(1H, m), 3.69(1H, m), 3.88(1H, d, J=7.5Hz, 1H), 6.64(1H, s), 7.08(2H, m), 7.25(2H, m), 7.79(2H, d, J=6.0Hz), 8.70(2H, d, J=6.0Hz) (CDCl3) | 409 |
| XB127 | 1.87-2.06(4H, m), 2.79(1H, m), 3.10(2H, m), 3.57(3H, s), 3.78(2H, m), 6.68(1H, s), 7.23-7.29(3H, m), 7.34(2H, m), 7.84(2H, d, J=6.0Hz), 8.72(2H, d, J=6.0Hz) (CDCl3) | 347 |
| XB130 | 1.81-2.03(4H, m), 2.78(1H, m), 3.09(2H, m), 3.57(3H, s), 3.79(2H, m), 6.69(1H, s), 7.03(2H, m), 7.23(2H, m), 7.84(2H, d, J=5.4Hz), 8.72(2H, br s) (CDCl3) | 365 |
| XB134 | 1.78-1.95(4H, m), 2.80-2.91(1H, m), 2.96-3.09(2H, m), 3.45(3H, s), 3.81(2H, d, J=13.1Hz), 6.80(1H, s), 7.33(1H, dd, J=2.0, 8.3Hz), 7.56-7.60(2H, m), 7.99(2H, dd, J=1.6, 4.5Hz), 8.69(2H, dd, J=1.5, 4.5Hz) (DMSO-d6) | 415 |
| XB145 | 1.82-2.02(4H, m), 3.09-3.27(3H, m), 3.57(3H, s), 3.79(2H, m), 3.86(3H, s), 6.67(1H, s), 6.89-6.99(2H, m), 7.21-7.26(2H, m), 7.84(2H, d, J=6.0Hz), 8.72(2H, d, J=6.0Hz) (CDCl3) | 377 |
| XB157 | 1.85-2.07(2H, m), 2.17-2.30(2H, m), 2.91-3.10(1H, m), 3.10-3.24(2H, m), 3.57(3H, s), 3.71-3.88(2H, m), 6.69(1H, s), 6.99-7.06(1H, m), 7.21(1H, dd, J=2.1, 8.7Hz), 7.45(1H, s), 7.49-7.65(1H, m), 7.83(2H, dd, J=1.8, 4.5Hz), 8.72(2H, dd, J=1.2, 4.8Hz) (CDCl3) | 405 |
| XB158 | 2.22-2.32(4H, m), 3.22(2H, m), 3.37(1H, m), 3.58(3H, s), 3.82(2H, m), 6.71(1H, s), 7.10(1H, m), 7.29(1H, m), 7.67(1H, m), 7.83(2H, d, J=6.3Hz), 8.72(2H, d, J=6.3Hz) (CDCl3) | 406 |
| XB159 | 2.19-2.26(4H, m), 3.21(2H, m), 3.35(1H, m), 3.59(3H, m), 3.82(2H, m), 6.70(1H, s), 6.95(1H, dt, J=9.0, 2.1Hz), 7.13(1H, dd, J=9.0, 2.1Hz), 7.71(1H, m), 7.85(2H, d, J=6.3Hz), 8.72(2H, d, J=6.3Hz) (CDCl3) | 405 |
| XB160 | 2.13-2.34(2H, m), 2.34-2.43(2H, m), 3.10-3.38(3H, m), 3.57(3H, s), 3.68-3.83(2H, m), 6.69(1H, s), 7.29-7.40(2H, m), 7.46-7.59(1H, m), 7.64-7.78(1H, m), 7.80-7.78(2H, m), 8.72(2H, d, J=6.0Hz) (CDCl3) | 388 |
| XB161 | 2.19(2H, m), 2.38(2H, m), 3.18(2H, m), 3.39(1H, m), 3.58(3H, m), 3.80(2H, m), 6.70(1H, s), 7.39(1H, m), 7.50(1H, m), 7.83(2H, d, J=6.0Hz), 7.89(1H, d, J=7.2Hz), 8.01(1H, d, J=7.8Hz), 8.73(2H, d, J=6.0Hz) (CDCl3) | 404 |
| XB162 | 1.96(2H, m), 2.88(2H, m), 3.15(2H, m), 3.60(3H, s), 3.85(2H, m), 4.63(1H, m), 6.73(1H, s), 7.13-7.23(3H, m), 7.46(1H, d, | 420 |

TABLE 5-continued

| | | |
|---|---|---|
| | J=7.5Hz), 7.84(2H, d, J=6.3Hz), 8.73(2H, d, J=6.3Hz) (CDCl3) | |
| XB164 | 1.64(2H, m), 2.23(2H, m), 3.13(2H, m), 3.50(1H, m), 3.53(3H, s), 3.68(2H, m), 6.58(2H, m), 6.68(1H, s), 6.91(2H, m), 7.81(2H, d, J=6.0Hz), 8.72(2H, d, J=6.0Hz) (CDCl3) | 380 |
| XB165 | 1.91-1.99(4H, m), 2.84(3H, s), 3.07(2H, m), 3.55(3H, s), 3.77(2H, m), 3.84(1H, m), 6.69(1H, s), 6.75-6.87(3H, m), 7.27(2H, m), 7.82(2H, d, J=6.3Hz), 8.72(2H, d, J=6.3Hz) (CDCl3) | 376 |
| XB168 | 1.52(2H, m), 1.79(3H, s), 1.96(2H, m), 3.09(2H, m), 3.42(3H, s), 3.64(2H, m), 4.86(1H, m), 6.63(1H, s), 7.09-7.19(4H, m), 7.74(2H, d, J=6.0Hz), 8.70(2H, d, J=6.0Hz) (CDCl3) | 422 |
| XB169 | 1.86(1H, br s), 1.95(2H, m), 2.30(2H, m), 3.47-3.63(7H, m), 6.68(1H, s), 7.30-7.44(3H, m), 7.54(d, J=7.5Hz), 7.84(2H, d, J=6.0Hz), 8.71(2H, d, J=6.0Hz) (CDCl3) | 363 |
| XB201 | 2.20-2.31(4H, m), 3.20-3.29(2H, m), 3.46(3H, s), 3.87(2H, d, J=13.8Hz), 6.86(1H, s), 7.29-7.35(2H, m), 7.64-7.69(2H, m), 8.01(2H, dd, J=1.5, 4.5Hz), 8.70(2H, dd, J=1.5, 4.5Hz) (DMSO-d6) | 390 |
| XB227 | 2.16-2.25(2H, m), 2.48-2.58(2H, m), 3.14-3.21(2H, m), 3.40(3H, s), 3.41-3.50(2H, m), 6.79(1H, s), 7.28-7.33(1H, m), 7.39-7.46(4H, m), 7.97(2H, dd, J=1.5, 4.5Hz), 8.68(2H, dd, J=1.5, 4.5Hz) (DMSO-d6) | 389 |
| XB256 | 1.77-1.85(8H, m), 2.10(1H, m), 2.51(4H, m), 2.97-3.02(3H, m), 3.58(3H, s), 3.55(3H, s), 3.62(2H, s), 3.74(1H, m), 6.66(1H, s), 7.16(2H, d, J=7.8Hz), 7.32(1H, d, J=7.8Hz), 7.80(2H, dd, J=1.5, 4.8Hz), 8.70(2H, dd, J=1.5, 4.8Hz) (CDCl3) | 430 |
| XB257 | 1.77-1.85(8H, m), 2.10(1H, m), 2.51(4H, m), 2.97-3.02(3H, m), 3.58(3H, s), 3.55(3H, s), 3.62(2H, s), 3.74(1H, m), 6.66(1H, s), 7.16(2H, d, J=7.8Hz), 7.32(1H, d, J=7.8Hz), 7.80(2H, dd, J=1.5, 4.8Hz), 8.70(2H, dd, J=1.5, 4.8Hz) (CDCl3) | 430 |
| XB258 | 1.86(4H, m), 1.99(4H, m), 3.03(5H, m), 3.35(4H, m), 3.43(3H, s), 3.73(2H, m), 4.30(2H, s), 6.81(1H, s), 7.43(2H, d, J=8.1Hz), 7.69(2H, d, J=8.1Hz), 7.97(2H, d, J=6.0Hz), 8.69(2H, d, J=6.0Hz), 11.01(1H, br s) (DMSO-d6) | 429 |
| XB259 | 1.75(1H, m), 1.89(3H, m), 1.97(3H, m), 2.13(1H, d, J=13.6Hz), 3.02(3H, m), 3.46(2H, t, J=7.0Hz), 3.55(3H, s), 3.66(2H, t, J=7.0Hz), 3.75(2H, m), 6.66(1H, s), 7.30(2H, d, J=8.0Hz), 7.52(2H, d, J=8.0Hz), 7.80(2H, dd, J=6.0, 1.2Hz), 8.71(2H, dd, J=6.0, 1.2Hz) | 443 |
| XB260 | 1.77-1.86(8H, m), 2.94-3.06(5H, m), 3.43(3H, s), 3.73-3.78(2H, m), 4.28-4.31(2H, m), 6.81(1H, s), 7.44(2H, d, J=7.3Hz), 7.57(2H, d, J=7.3Hz), 7.96(2H, d, J=4.2Hz), 8.63(2H, d, J=4.2Hz), 10.75-10.80(1H, br) (DMSO-d6) | 430 |
| XB261 | 1.45-1.59(6H, m), 1.73-1.94(4H, m), 2.10-2.15(4H, m), 2.98-3.05(3H, m), 3.49(2H, m), 3.55(3H, s), 3.74-3.77(2H, m), 6.65(1H, s), 7.22(2H, d, J=8.4Hz), 7.33(2H, d, J=8.4Hz), 7.80(2H, d, J=6.0Hz), 8.70(2H, d, J=6.0Hz) (CDCl3) | 444 |
| XB262 | 1.19-1.31(6H, m), 1.80-1.94(7H, m), 2.10(1H, m), 2.32(3H, m), 2.45(1H, m), 2.97-3.02(3H, m), 3.54(3H, s), 3.55(2H, m), 3.69-3.74(2H, m), 6.66(1H, s), 7.22(2H, d, J=8.4Hz), 7.33(2H, d, J=8.4Hz), 7.81(2H, d, J=6.0Hz), 8.71(2H, d, J=6.0Hz) (CDCl3) | 472 |
| XB263 | 1.77-1.86(4H, m), 2.44(1H, m), 2.80(6H, s), 2.98-3.16(4H, m), 3.42(3H, s), 3.62-3.79(6H, m), 4.42(3H, m), 6.93(1H, s), 7.45(2H, d, J=8.4Hz), 7.58(2H, d, J=8.4Hz), 8.21(2H, d, J=6.0Hz), 8.82(2H, d, J=6.0Hz) (DMSO-d6) | 473 |
| XB264 | 0.99(3H, t, J=7.2Hz), 1.20-1.24(6H, m), 1.80-1.93(7H, m), 2.10(1H, m), 2.50-2.55(2H, m), 2.97-3.00(3H, m), 3.55(3H, s), 3.60(2H, s), 3.69-3.74(2H, m), 6.65(1H, s), 7.18(2H, d, J=8.4Hz), 7.34(2H, d, J=8.4Hz), 7.80(2H, d, J=6.0Hz), 8.70(2H, d, J=6.0Hz) (CDCl3) | 486 |
| XB265 | 1.02(6H, d, J=6.6Hz), 1.23-1.28(5H, m), 1.72-2.15(9H, m), 2.51(1H, m), 2 97-3.08(4H, m), 3.55(3H, s), 3.70(2H, s), 3.74-3.78(2H, m), 6.65(1H, s), 7.18(2H, d, J=7.8Hz), 7.34(2H, d, J=7.8Hz), 7.81(2H, d, J=6.0Hz), 8.70(2H, d, J=6.0Hz) (CDCl3) | 500 |
| XB266 | 1.77-1.87(4H, m), 2.44(1H, m), 2.80(6H, s), 2.99-3.09(4H, m), 3.42(3H, s), 3.62-3.79(6H, m), 4.42(3H, m), 6.95(1H, s), 7.45(2H, d, J=8.1Hz), 7.58(2H, d, J=8.1Hz), 8.29(2H, d, J=6.0Hz), 8.86(2H, d, J=6.0Hz) (DMSO-d6) | 473 |
| XB267 | 1.85-1.88(4H, m), 2.81(1H, m), 2.99-3.07(2H, m), 3.44(3H, s), 3.79-3.84(2H, m), 6.82(1H, s), 7.29(2H, d, J=8.4Hz), 7.51(2H, d, J=8.4Hz), 8.01(2H, d, J=6.0Hz), 8.70(2H, d, J=6.0Hz) (DMSO-d6) | 425 |
| XB268 | 1.83-1.99(4H, m), 2.83(1H, m), 2.98-3.06(2H, m), 3.45(3H, s), 3.79-3.84(2H, m), 6.82(1H, s), 7.29-7.43(3H, m), 7.53(1H, s), 8.01(2H, d, J=6.0Hz), 8.70(2H, d, J=6.0Hz) (DMSO-d6) | 425 |
| XB269 | 1.74-1.96(8H, m), 2.51(1H, m), 2.65-3.01(2H, m), 3.04-3.18(4H, m), 3.44(3H, s), 3.77-3.81(2H, m), 6.49(2H, d, J=8.4Hz), 6.80(1H, s), 7.09(2H, d, J=8.4Hz), 8.00(2H, dd, J=4.5, 1.8Hz), 8.69(2H, dd, J=4.5, 1.8Hz) (DMSO-d6) | 416 |
| XB270 | 1.83-1.99(8H, m), 2.72(1H, m), 2.97-3.07(2H, m), 3.19-3.23(4H, m), 3.45(3H, s), 3.78-3.83(2H, m), 6.38(1H, d, J=7.8Hz) 6.44(1H, s), 6.53(1H, d, J=7.5Hz), 6.81(1H, s), 7.09(1H, dd, J=7.8, 7.8Hz), 8.00(2H, d, J=5.4Hz), 8.70(2H, d, J=5.7Hz) (DMSO-d6) | 416 |
| XB271 | 1.81-1.92(2H, m), 2.07-2.15(2H, m), 3.02-3.21(3H, m), 3.51(3H, s), 3.79-3.83(2H, m), 6.80-6.86(2H, m), 7.10-7.17(2H, m), 7.58-7.63(1H, m), 8.00(2H, d, J=4.2Hz), 8.69(2H, d, J=4.2Hz), 10.90(1H, brs) (DMSO-d6) | 404 |
| XB272 | 1.53-1.63(2H, m), 2.02-2.07(2H, m), 3.11-3.19(2H, m), 3.41(3H, s), 3.60-3.72(3H, m), 6.12(1H, d, J=8.2Hz), 6.79-6.80(1H, m), 6.88-6.91(2H, m), 7.25-7.31(1H, m), 8.00(2H, d, J=4.2Hz), 8.70(2H, d, J=4.2Hz) (DMSO-d6) | 430 |
| XB273 | 1.47-1.57(2H, m), 2.00-2.07(2H, m), 2.71(6H, s), 3.04-3.12(2H, m), 3.37-3.42(4H, m), 3.67-3.71(2H, m), 4.87(1H, d, J=8.2Hz), 6.56-6.65(4H, m), 6.79(1H, s), 7.99(2H, d, J=4.2Hz), 8.69(2H, d, J=4.2Hz) (DMSO-d6) | 405 |
| XB274 | 1.51-1.61(2H, m), 2.01-2.07(2H, m), 3.08-3.16(2H, m), 3.43(3H, s), 3.50-3.53(1H, m), 3.67(3H, s), 3.70-3.73(2H, m), 5.56(1H, d, J=8.2Hz), 6.09-6.24(3H, m), 6.78(1H, s), 6.96(1H, dd, J=7.2Hz, 7.3Hz), 7.99(2H, d, J=4.2Hz), 8.69(2H, d, J=4.2Hz) (DMSO-d6) | 392 |
| XB275 | 1.48-1.59(2H, m), 2.00-2.07(2H, m), 3.06-3.13(2H, m), 3.40(3H, s), 3.44-3.46(1H, m), 3.64(3H, s), 3.66-3.71(2H, m), 5.07(1H, d, J=8.2Hz), 6.59(2H, d, J=7.2Hz), 6.70(2H, d, J=7.2Hz), 6.79(1H, s), 7.98(2H, d, J=4.2Hz), 8.68(2H, d, J=4.2Hz) (DMSO-d6) | 392 |
| XB276 | 1.57-1.68(2H, m), 2.03-2.07(2H, m), 3.05-3.09(2H, m), 3.41(3H, s), 3.51-3.77(6H, m), 4.57(1H, d, J=8.2Hz), 6.53-6.58(1H, m), 6.66-6.69(1H, m), 6.74-6.82(3H, m), 7.99(2H, d, J=4.2Hz), 8.68(2H, d, J=4.2Hz) (DMSO-d6) | 392 |
| XB277 | 1.78-1.92(4H, m), 2.94-3.07(5H, m), 3.41-3.86(10H, m), 6.88-6.92(1H, m), 7.04(1H, s), 7.21-7.24(2H, m), 7.39-7.44(1H, | 406 |

TABLE 5-continued

| | | |
|---|---|---|
| | m), 8.48(2H, d, J=4.2Hz), 8.95(2H, d, J=4.2Hz) (DMSO-d6) | |
| XB278 | 1.68-2.08(4H, m), 2.90-2.96(2H, m), 3.15(3H, s), 3.38(3H, s), 3.81-4.04(7H, m), 7.03(1H, s), 7.13(2H, d, J=7.2Hz), 7.81(2H, d, J=7.2Hz), 8.45(2H, d, J=4.2Hz), 8.94(2H, d, J=4.2Hz) (DMSO-d6) | 406 |
| XB279 | 1.76-1.85(4H, m), 2.65(4H, s), 2.85-2.94(2H, m), 3.41-3.42(1H, m), 3.44(3H, s), 3.74-3.79(2H, m), 4.02(3H, s), 6.78(1H, s), 6.83-6.99(4H, m), 7.97(2H, d, J=4.2Hz), 8.68(2H, d, J=4.2Hz) (DMSO-d6) | 406 |
| XB280 | 1.86-1.98(4H, m), 2.98(6H, s), 3.01-3.10(2H, m), 3.40-3.92(11H, m), 7.00-7.13(2H, m), 7.42-7.50(2H, m), 8.51(2H, d, J=4.2Hz), 8.97(2H, d, J=4.2Hz) (DMSO-d6) | 419 |
| XB281 | 1.69-1.88(3H, m), 1.92-2.00(1H, m), 2.92-3.06(3H, m), 3.42(3H, s), 3.63-3.88(2H, m), 6.79(1H, s), 7.33(2H, d, J=8.4Hz), 7.54(2H, d, J=8.4Hz), 7.96(2H, d, J=5.7Hz), 8.68(2H, d, J=6.0Hz) (DMSO-d6) | 425 |
| XB282 | 2.51-2.60(4H, m), 3.47(3H, s), 3.65-3.68(4H, m), 6.54(1H, s), 8.00(2H, d, J=4.2Hz), 8.70(1H, d, J=4.2Hz) (DMSO-d6) | 285 |
| XB283 | 1.71-1.82(4H, m), 2.40-2.49(2H, m), 2.50-2.53(4H, m), 2.86-2.94(3H, m), 3.06-3.09(4H, m), 3.41(3H, s), 3.50-3.68(4H, m), 4.43-4.46(1H, m), 6.78(1H, s), 6.89(2H, d, J=7.2Hz), 7.17(2H, d, J=7.2Hz), 7.95(2H, d, J=4.2Hz), 8.67(2H, d, J=4.2Hz) (DMSO-d6) | 475 |
| XB284 | 1.71-1.93(4H, m), 2.86(6H, s), 2.88-2.97(3H, m), 3.41(3H, s), 3.65-3.75(2H, m), 6.73(2H, d, J=7.2Hz), 6.78(1H, s), 7.15(2H, d, J=7.2Hz), 7.96(2H, d, J=4.2Hz), 8.68(2H, d, J=4.2Hz) (DMSO-d6) | 390 |
| XB285 | 1.72-1.83(4H, m), 2.89-2.96(3H, m), 3.05-3.09(4H, m), 3.42(3H, s), 3.71-3.75(4H, m), 6.78(1H, s), 6.91(2H, d, J=7.2Hz), 7.20(2H, d, J=7.2Hz), 7.96(2H, d, J=4.2Hz), 8.68(2H, d, J=4.2Hz) (DMSO-d6) | 432 |
| XB286 | 1.52-1.91(10H, m), 2.86-2.94(3H, m), 3.07-3.10(4H, m), 3.41(3H, s), 3.66-3.75(2H, m), 6.78(1H, s), 6.89(2H, d, J=7.2Hz), 7.16(2H, d, J=7.2Hz), 7.95(2H, d, J=4.2Hz), 8.68(2H, d, J=4.2Hz) (DMSO-d6) | 430 |
| XB287 | 1.64-1.88(4H, m), 2.21(3H, s), 2.42-2.45(4H, m), 2.89-2.94(3H, m), 3.07-3.11(4H, m), 3.41(3H, s), 3.69-3.75(2H, m), 6.78(1H, s), 6.90(2H, d, J=7.2Hz), 7.18(2H, d, J=7.2Hz), 7.96(2H, d, J=4.2Hz), 8.68(2H, d, J=4.2Hz) (DMSO-d6) | 445 |
| XB288 | 1.43-1.47(2H, m), 1.71-1.90(6H, m), 2.19(6H, s), 2.58-2.66(2H, m), 2.87-2.95(2H, m), 2.87-2.98(3H, m), 3.30-3.32(1H, m), 3.41(3H, s), 3.64-3.75(4H, m), 6.78(1H, s), 6.90(2H, d, J=7.2Hz), 7.16(2H, d, J=7.2Hz), 7.96(2H, d, J=4.2Hz), 8.68(2H, d, J=4.2Hz) (DMSO-d6) | 473 |
| XB289 | 1.72-1.94(4H, m), 2.92-2.99(3H, m), 3.08-3.11(4H, m), 3.41(3H, s), 3.52-3.56(4H, m), 3.66-3.75(2H, m), 5.11(2H, s), 6.78(1H, s), 6.93(2H, d, J=7.2Hz), 7.20(2H, d, J=7.2Hz), 7.28-7.39(5H, m), 7.95(2H, d, J=4.2Hz), 8.69(2H, d, J=4.2Hz) (DMSO-d6) | 565 |
| XB290 | 1.53-1.63(2H, m), 1.85-1.89(2H, m), 2.14(3H, s), 2.31-2.46(8H, m), 2.86-2.94(2H, m), 3.34-3.35(1H, m), 3.39(3H, s), 3.70-3.74(2H, m), 6.79(1H, s), 7.98(2H, d, J=4.2Hz), 8.69(2H, d, J=4.2Hz) (DMSO-d6) | 369 |
| XB291 | 1.52-1.63(2H, m), 1.85-1.90(2H, m), 2.34-2.42(11H, m), 2.86-2.94(2H, m), 3.39(3H, s), 3.45-3.50(2H, m), 3.70-3.74(2H, m), 4.38-4.40(1H, m), 6.80(1H, s), 7.98(2H, d, J=4.2Hz), 8.69(2H, d, J=4.2Hz) (DMSO-d6) | 399 |
| XB292 | 1.71-1.83(4H, m), 2.81-3.00(11H, m), 3.28-3.30(1H, m), 3.41(3H, s), 3.66-3.75(2H, m), 6.78(1H, s), 6.89(2H, d, J=7.2Hz), 7.17(2H, d, J=7.2Hz), 7.96(2H, d, J=4.2Hz), 8.68(2H, d, J=4.2Hz) (DMSO-d6) | 431 |
| XB293 | 1.43-1.53(2H, m), 1.93-1.98(3H, m), 2.63-2.66(1H, m), 2.92-3.00(2H, m), 3.39(3H, s), 3.62-3.79(7H, m), 6.78(1H, s), 6.88-6.97(2H, m), 7.18-7.22(1H, m), 7.35(1H, d, J=7.3Hz), 7.98(2H, d, J=4.2Hz), 8.68(2H, d, J=4.2Hz) (DMSO-d6) | 406 |
| XB294 | 1.42-1.53(2H, m), 1.96-2.08(3H, m), 2.61-2.67(1H, m), 2.91-2.99(2H, m), 3.39(3H, s), 3.62-3.80(7H, m), 6.77(1H, s), 6.86(2H, d, J=7.2Hz), 7.25(2H, d, J=7.2Hz), 7.97(2H, d, J=4.2Hz), 8.68(2H, d, J=4.2Hz) (DMSO-d6) | 406 |
| XB295 | 1.81-1.91(2H, m), 2.61-2.20(2H, m), 2.96-3.17(6H, m), 3.41-3.47(5H, m), 3.74-3.86(4H, m), 6.90-7.03(3H, m), 7.21-7.29(2H, m), 8.44(2H, d, J=4.2Hz), 8.93(2H, d, J=4.2Hz), 9.30-9.38(2H, br) (DMSO-d6) | 420 |
| XB296 | 1.80-1.91(2H, m), 2.07-2.21(2H, m), 2.96-3.11(6H, m), 3.34-3.41(5H, m), 3.69-3.86(4H, m), 6.91(2H, d, J=7.2Hz), 7.05(1H, s), 7.20(2H, d, J=7.2Hz), 8.49(2H, d, J=4.2Hz), 8.96(2H, d, J=4.2Hz), 9.44-9.50(2H, br) (DMSO-d6) | 420 |
| XB297 | 1.41-1.51(2H, m), 1.91-1.96(3H, m), 2.61-2.65(1H, m), 2.86(6H, s), 2.91-2.98(2H, m), 3.38(3H, s), 3.61-3.67(4H, m), 6.70(2H, d, J=7.2Hz), 6.77(1H, s), 7.20(2H, d, J=7.2Hz), 7.97(2H, d, J=4.2Hz), 8.68(2H, d, J=4.2Hz) (DMSO-d6) | 419 |
| XB298 | 2.04(2H, d, J=13.1Hz), 2.34(3H, s), 2.53(2H, m), 2.91(2H, m), 3.55(3H, s), 3.70(2H, d, J=13.1Hz), 4.27(1H, m), 6.08(1H, m), 6.86(1H, s), 7.36-7.48(5H, m), 7.80(2H, dd, J=1.6, 4.3Hz), 8.69(2H, dd, J=1.3, 4.5Hz) (CDCl3) | 426 |
| XB299 | 2.06(2H, d, J=13.1Hz), 2.22(2H, m), 2.99(2H, m), 3.13(1H, m), 3.54(3H, s), 3.70(2H, d, J=13.1Hz), 6.68(1H, s), 7.25(1H, s), 7.44-7.48(2H, m), 7.64-7.67(3H, m), 7.78(2H, dd, J=1.6, 4.3Hz), 8.69(2H, dd, J=1.3, 4.5Hz) (CDCl3) | 413 |
| XB300 | 1.75-1.85(4H, m), 2.97-3.10(5H, m), 3.43(3H, s), 3.71-3.76(2H, m), 3.88-3.93(2H, m), 6.70(1H, dd, J=7.2, 7.3Hz), 6.79(1H, s), 7.02-7.06(2H, m), 7.15-7.23(3H, m), 7.31-7.35(2H, m), 7.97(2H, d, J=4.2Hz), 8.69(2H, d, J=4.2Hz) (DMSO-d6) | 464 |
| XB301 | 1.09-1.34(5H, m), 1.57-1.88(9H, m), 2.78-2.93(3H, m), 3.08-3.18(1H, m), 3.41(3H, s), 3.62-3.74(2H, m), 5.27(1H, d, J=8.2Hz), 6.52(2H, d, J=7.2Hz), 6.79(1H, s), 7.01(2H, d, J=7.2Hz), 7.96(2H, d, J=4.2Hz), 8.68(2H, d, J=4.2Hz) (DMSO-d6) | 444 |
| XB302 | 1.10-1.16(1H, m), 1.32-1.46(4H, m), 1.64-1.82(9H, m), 2.68(3H, s), 2.82-2.93(3H, m), 3.41(3H, s), 3.54-3.74(3H, m), 6.72(2H, d, J=7.2Hz), 6.78(1H, s), 7.12(2H, d, J=7.2Hz), 7.95(2H, d, J=4.2Hz), 8.68(2H, d, J=4.2Hz) (DMSO-d6) | 458 |

| No. | NMR | MS [M+1] |
|---|---|---|
| YA0262 | (DMSO-d6): 3.47(3H, s), 3.48-3.66(4H, m), 3.89-4.02(2H, m), 4.98(1H, m), 7.06(1H, s), 7.35-7.59(3H, m), 7.99(1H, dd, J=7.2, 6.9Hz), 8.25(1H, dd, J=5.4, 1.2Hz), 9.01(1H, d, J=5.1Hz), 9.31(1H, s), 9.84(1H, s), 10.19(1H, m). | 367 |
| YA0263 | (CDCl3): 3.01(1H, dd, J=10.5, 12.4Hz), 3.10-3.35(3H, m), 3.57(3H, s), 3.55-3.65(2H, m), 4.05(1H, dd, J=2.4, 10.4Hz), 7.00-7.10(1H, m), 7.30(1H, s), 7.22(2H, m), 7.30-7.42(2H, m), 8.15(1H, dd, J=1.3, 5.2Hz), 8.86(1H, d, J=5.2Hz), 9.27(1H, d, J=1.0Hz). | 367 |

TABLE 5-continued

| | | |
|---|---|---|
| YA0264 | 2.83(1H, dd, J=11.0, 11.9Hz), 2.93(1H, s), 2.99-3.10(3H, m), 3.45(3H, s), 3.61-3.69(2H, m), 3.95(1H, dd, J=2.1, 10.3Hz), 6.97(1H, s), 7.19(2H, t, J=8.8Hz), 7.48-7.56(2H, m), 8.17(1H, dd, J=1.0, 5.0Hz), 8.99(1H, d, J=5.1Hz), 9.29(1H, d, J=1.0Hz) (DMSO-d6) | 367 |
| YA0264 (HCl) | 3.39-3.47(2H, m), 3.45(3H, s), 3.55-3.66(2H, m), 3.86-3.96(2H, m), 4.64-4.71(1H, m), 7.05(1H, s), 7.36(2H, t, J=8.7Hz), 7.77-7.81(2H, m), 8.23(1H, dd, J=1.2, 5.1Hz), 9.02(1H, d, J=5.1Hz), 9.32(1H, d, J=1.2Hz), 9.79(1H, d, J=10.2Hz), 10.13-10.28(1H, m) (DMSO-d6) | 367 |
| YA0267 | (CDCl3): 2.81(1H, dd, J=10.5, 12.6Hz), 3.15-3.40(3H, m), 3.50-3.65(4H, m), 3.65-3.80(1H, m), 4.51(1H, dd, J=2.7, 10.5Hz), 7.20-7.45(4H, m), 7.74(1H, dd, J=1.5, 7.5Hz), 8.15-8.20(1H, m), 8.85(1H, d, J=5.1Hz), 9.27(1H, s). | 383 |
| YA0268 | (CDCl3): 3.00(1H, dd, J=10.5, 12.6Hz), 3.10-3.35(3H, m), 3.50-3.70(5H, m), 4.03(1H, dd, J=2.4, 10.5Hz), 7.32(4H, m), 7.50(1H, s), 8.15(1H, dd, J=1.2, 5.1Hz), 8.87(1H, d, J=5.1Hz), 9.27(1H, d, J=1.5Hz). | 383 |
| YA0269 | 3.40-3.50(2H, m), 3.45(3H, s), 3.53-3.65(2H, m), 3.87-3.97(2H, m), 4.68(1H, t, J=10.2Hz), 7.05(1H, s), 7.59(2H, d, J=11.1Hz), 7.75(2H, d, J=11.1Hz), 8.22(1H, dd, J=1.5, 5.4Hz), 9.02(1H, d, J=5.1Hz), 9.31(1H, s), 9.83(1H, d, J=9.6Hz), 10.11-10.25(1H, m) (DMSO-d6) | 383 |
| YA0274 | (DMSO-d6): 3.45(3H, s), 3.40-3.70(4H, m), 3.92(2H, t, J=14.1Hz), 4.67(1H, br t), 7.06(1H, s), 7.68(2H, d, J=10.0Hz), 7.72(2H, d, J=10.0Hz), 8.22(1H, dd, J=4.8Hz), 9.03(1H, d, J=4.8Hz), 9.31(1H, s), 9.88(1H, br s), 10.22(1H, br s). | 427 |
| YA0289 | 3.38-3.57(4H, m), 3.35(3H, s), 3.89(3H, s), 3.91-3.97(2H, m), 4.84-4.94(1H, m), 7.06(1H, s), 7.08-7.15(1H, m), 7.18(1H, d, J=8.4Hz), 7.41-7.49(1H, m), 7.68(1H, d, J=7.6Hz), 8.25(1H, d, J=4.9Hz), 9.04(1H, d, J=5.1Hz), 9.32(1H, s) (DMSO) | 379 |
| YA0290 | (DMSO-d6): 3.40-3.75(7H, m), 3.92(2H, t, J=13.2Hz), 4.64(1H, t, J=9.1Hz), 7.00-7.10(2H, m), 7.23(1H, d, J=7.6Hz), 7.35(1H, s), 7.42(1H, t, J=7.8Hz), 8.23(1H, dd, J=5.6Hz), 9.03(1H, d, J=5.2Hz), 9.32(1H, s), 9.65-9.80(1H, brd), 9.90-10.15(1H, brd). | 379 |
| YA0291 | (DMSO-d6): 3.42(3H, s), 3.36-3.58(4H, m), 3.79(3H, s), 3.83-3.95(2H, m), 4.61(1H, m), 7.05(1H, s), 7.07(2H, d, J=8.1Hz), 7.60(2H, d, J=8.7Hz), 8.22(1H, dd, J=5.1, 1.2Hz), 9.02(1H, d, J=5.4Hz), 9.31(1H, s), 9.58-9.74(2H, m). | 379 |
| YA0294 | 1.31(3H, t, J=6.8Hz), 3.44-3.59(2H, m), 3.48(3H, s), 3.87-3.97(2H, m), 4.09-4.20(2H, m), 4.80-4.91(1H, m), 7.06(1H, s), 7.09-7.17(2H, m), 7.44(1H, t, J=7.4Hz), 7.64(1H, d, J=7.5Hz), 8.23(1H, d, J=5.3Hz), 9.03(1H, d, J=5.2Hz), 9.32(1H, s), 9.49-9.60(2H, m) (DMSO-d6) | 393 |
| YA0304 | (DMSO-d6): 3.45(3H, s), 3.64(3H, m), 3.93(3H, m), 4.78(1H, t, J=9.6Hz), 7.13(1H, s), 7.97(2H, d, J=8.7Hz), 8.01(2H, d, J=8.7Hz), 8.43(1H, d, J=6.2Hz), 8.93(1H, d, J=6.2Hz), 10.12(1H, s), 10.70(1H, s). | 374 |
| YA0331 | (CDCl3): 2.00(4H, m), 3.05(1H, t, J=11.7Hz), 3.18-3.30(3H, m), 3.29(4H, m), 3.56(3H, m), 3.62(2H, m), 3.91(1H, d, J=8.4Hz), 6.57(2H, d, J=8.7Hz), 7.31(3H, m), 8.17(1H, dd, J=1.2, 5.1Hz), 8.85(1H, d, J=5.1Hz), 9.27(1H, d, J=1.2Hz). | 418 |
| YA0337 | (CDCl3): 3.02(1H, dd, J=10.8, 12.6Hz), 3.18(8H, m), 3.56(3H, m), 3.61(1H, t, J=9.0Hz), 3.87(4H, m), 3.95(1H, dd, J=2.7, 10.8Hz), 6.93(2H, d, J=8.9Hz), 7.31(1H, s), 7.36(2H, d, J=8.9Hz), 8.16(1H, dd, J=1.5, 5.4Hz), 8.85(1H, d, J=5.4Hz), 9.27(1H, d, J=1.5Hz). | 434 |
| YA0340 | (CDCl3): 2.36(3H, s), 2.59(4H, m), 3.02(1H, t, J=11.4Hz), 3.16-3.29(7H, m), 3.26(3H, s), 3.61(2H, m), 3.94(1H, d, J=8.0Hz), 6.94(2H, d, J=8.7Hz), 7.31(1H, s), | 447 |
| | 7.34(2H, d, J=8.7Hz), 8.16(1H, d, J=5.1Hz), 8.85(1H, d, J=5.1Hz), 9.27(1H, s). | |
| YA0361 | 3.39-3.50(2H, m), 3.47(3H, s), 3.61-3.73(1H, m), 3.78(3H, s), 3.83(3H, s), 3.87-3.92(3H, m), 4.92(1H, t, J=10.5Hz), 6.99-7.11(3H, m), 7.57(1H, d, J=2.7Hz), 8.25(1H, dd, J=1.2, 5.1Hz), 9.03(1H, d, J=4.8Hz), 9.31(1H, d, J=0.9Hz), 9.78(1H, d, J=9.0Hz), 10.21-10.38(1H, m) (DMSO-d6) | 409 |
| YA0362 | (DMSO-d6): 3.47(3H, s), 3.37-4.04(6H, m), 3.94(6H, s), 5.09(1H, m), 6.82(2H, d, J=8.4Hz), 7.05(1H, s), 7.45(1H, t, J=8.4Hz), 8.22(1H, m), 8.24(1H, dd, J=5.4, 1.5Hz), 9.05(1H, d, J=5.1Hz), 9.32(1H, s), 10.06(1H, m). | 409 |
| YA0366 | 3.38-3.60(4H, m), 3.47(3H, s), 3.88-3.95(2H, m), 3.90(3H, s), 4.86-4.92(1H, m), 6.96-7.01(1H, m), 7.06(1H, s), 7.12(1H, d, J=8.8Hz), 7.71-7.79(1H, m), 8.23-8.24(1H, m), 9.03(1H, d, J=5.1Hz), 9.32(1H, d, J=1.2Hz), 9.55-9.72(2H, m) (DMSO) | 397 |
| YA0367/ YA0368 | (DMSO-d6): 3.30-3.75(7H, m), 3.80-4.00(5H, m), 4.80-5.00(1H, m), 6.93-7.00(1H, m), 7.05(1H, s), 7.11(1H, dd, J=2.4, 11.4Hz), 7.84(1H, m), 8.23(1H, d, J=5.1Hz), 9.03(1H, d, J=5.1Hz), 9.31(1H, s), 9.60-9.80(1H, brd), 9.90-10.15(1H, brd). | 397 |
| YA0370 | 3.31-3.56(3H, m), 3.45(3H, s), 3.69-3.78(1H, m), 3.90-3.99(2H, m), 3.94(3H, s), 4.95-5.03(1H, m), 6.96-7.02(1H, m), 7.03-7.09(2H, m), 7.49-7.56(1H, m), 8.24(1H, d, J=4.4Hz), 8.51-8.69(1H, m), 9.03(1H, d, J=5.1Hz), 9.32(1H, s), 10.55-10.67(1H, m) (DMSO) | 397 |
| YA0378 | 2.77(1H, dd, J=10.5, 12.0Hz), 3.18-3.30(3H, m), 3.61(3H, s), 3.64-3.71(2H, m), 3.86(3H, s), 4.37(1H, dd, J=2.1, 10.1Hz), 6.89(1H, d, J=1.7Hz), 6.99(1H, dd, J=1.6, 8.2Hz), 7.32(1H, s), 7.50(1H, d, J=8.2Hz), 8.19(1H, d, J=5.2Hz), 8.86(1H, d, J=5.2Hz), 9.27(1H, d, J=1.2Hz) (CDCl3) | 413 |
| YA0399 | (CDCl3): 2.76(1H, dd, J=10.2, 12.3Hz), 3.10-3.40(3H, m), 3.55-3.80(5H, m), 3.85(3H, s), 4.39(1H, dd, J=2.4, 10.2Hz), 6.78(1H, d, J=8.7Hz), 7.32(1H, s), 7.39(1H, dd, J=2.7, 8.7Hz), 7.72(1H, d, J=2.4Hz), 8.20(1H, d, J=1.2, 5.1Hz), 8.87(1H, d, J=5.1Hz), 9.27(1H, d, J=1.2Hz). | 457 |
| YA0408 | (CDCl3): 1.98-2.03(4H, m), 2.84(1H, m), 3.17-3.32(7H, m), 3.60(3H, m), 3.59-3.71(2H, m), 3.85(3H, s), 4.28(1H, d, J=8.4Hz), 6.10(1H, d, J=1.8Hz), 6.18(1H, d, J=8.3Hz), 7.29(1H, s), 7.33(1H, d, J=8.4Hz), 8.21(1H, d, J=5.2Hz), 8.85(1H, d, J=5.2Hz), 9.27(1H, s). | 448 |
| YA0409 | (CDCl3): 1.95-2.10(4H, m), 2.95-3.10(1H, m), 3.19-3.45(7H, m), 3.59(3H, m), 3.50-3.80(2H, m), 3.80(3H, s), 4.48(1H, dd, J=2.2, 10.2Hz), 6.49(1H, dd, J=3.0, 8.9Hz), 6.63-6.87(2H, m), 7.32(1H, s), 8.20(1H, dd, J=1.4, 5.2Hz), 8.86(2H, d, J=5.2Hz), 9.27(1H, d, J=1.1Hz). | 448 |
| YA0414 | (CDCl3): 3.14(2H, m), 3.22(1H, t, J=11.6Hz), 3.41(1H, t, J=11.6Hz), 3.82(2H, m), 3.83(3H, s), 3.88(3H, s), 4.58(1H, dd, J=3.1, 11.0Hz), 6.51(2H, m), 7.32(1H, s), 8.19(1H, dd, J=1.5, 5.3Hz), 8.86(1H, d, J=5.3Hz), 9.27(1H, d, J=1.5Hz). | 415 |
| YA0423 | (DMSO-d6): 3.35-3.70(4H, m), 3.48(3H, s), 3.78(3H, s), 3.97(2H, m), 4.70(1H, m), 7.06(1H, t, J=7.7Hz), 7.07(1H, s), 7.15(1H, d, J=7.7Hz), 7.31(1H, d, J=7.7Hz), 7.39(1H, t, J=7.7Hz), 7.61(2H, d, J=8.1Hz), 7.70(2H, d, J=8.1Hz), 8.25(1H, d, J=4.5Hz), 9.07(1H, d, J=4.5Hz), 9.33(1H, s), 9.66(1H, br s). | 455 |
| YA0425 | (DMSO-d6): 3.61(3H, m), 3.76(3H, s), 3.81(3H, s), 4.01(3H, m), 4.69(1H, t, J=9.9Hz), 7.05(2H, d, J=9.0Hz), 7.07(1H, s), 7.67(2H, d, J=9.0Hz), 7.76(4H, s), 8.24(1H, dd, J=1.2, 5.1Hz), 9.03(1H, d, J=5.1Hz), 9.32(1H, d, J=1.2Hz), 9.79(1H, d, J=10.2Hz), 10.07(1H, s). | 455 |
| YA0434 | (DMSO-d6): 3.30-3.70(4H, m), 3.42(3H, s), 3.96(2H, d, J=13.8Hz), 4.71(1H, t, J=11.3Hz), 7.06(1H, s), 7.33(2H, t, J=8.0Hz), 7.77(6H, m), | 443 |

TABLE 5-continued

| | | |
|---|---|---|
| | 8.24(1H, d, J=5.4Hz), 9.03(1H, d, J=5.4Hz), 9.32(1H, s), 9.80(1H, d, J=8.7Hz), 10.03(1H, s). | |
| YA0442 | 3.43-3.59(2H, m), 3.48(3H, s), 3.63-3.75(2H, m), 3.97-4.01(2H, m), 4.80-4.86(1H, m), 7.06(1H, s), 7.60-7.64(2H, m), 7.86-7.88(1H, m), 7.95-8.00(2H, m), 8.05-8.07(1H, m), 8.24-8.27(2H, m), 9.02(1H, d, J=5.4Hz), 9.32(1H, s), 10.01(1H, d, J=10.2Hz), 10.30-10.41(1H, m) (DMSO-d6) | 399 |
| YA0517 | (CDCl3): 2.97(1H, dd, J=12.3, 10.5Hz), 3.18-3.28(5H, m), 3.58(3H, s), 3.59(1H, m), 3.77(1H, m), 4.27(1H, dd, 10.2, 2.7Hz), 4.62(2H, m), 6.89(1H, t, J=7.5Hz), 7.16(1H, m), 7.27(1H, m), 7.28(1H, s), 8.26(1H, dd, J=5.4, 1.5Hz), 8.86(1H, d, J=5.4Hz), 9.26(1H, s). | 391 |
| YA0864 | (DMSO-d6): 3.15-3.35(1H, m), 3.38-3.50(4H, m), 3.70-4.30(9H, m), 5.00-5.20(1H, m), 7.00-7.10(2H, m), 7.10-7.20(1H, m), 7.30-7.50(6H, m), 8.15-8.20(1H, m), 8.30-8.40(1H, brd), 9.05(1H, d, J=5.1Hz), 9.31(1H, d, J=0.9Hz). | 487 |
| YA1074 | (CDCl3): 1.80-2.40(3H, m), 3.12-3.34(4H, m), 3.39-4.20(7.6H, m), 4.50-5.07(0.6H, m), 5.30-5.60(0.7H, m), 5.72-6.05(0.1H, m), 6.52-6.80(2H, m), 6.82-7.22(1H, m), 7.28(1H, s), 8.18(1H, d, J=4.8Hz), 8.89(1H, d, J=5.1Hz), 9.28(1H, d, J=1.2Hz) | 439 |
| YA1339 | (CDCl3): 2.50-2.62(1H, m), 2.80-2.95(1H, m), 3.02-3.20(1H, m), 3.25-3.40(1H, m), 3.50-3.74(5H, m), 3.75-3.80(1H, m), 3.85(3H, s), 6.60-6.80(2H, m), 7.30(1H, s), 7.48(1H, t, J=8.4Hz), 8.19(1H, dd, J=1.2, 5.1Hz), 8.86(1H, d, J=5.1Hz), 9.27(1H, d, J=1.5Hz). | 411 |
| YA1340/ YA1341 | (DMSO-d6): 2.55(3H, d, J=3.9Hz), 3.40-3.80(3H, m), 3.45(3H, s), 3.80-4.15(6H, m), 4.85-5.15(1H, m), 6.90-7.05(1H, m), 7.05(1H, s), 7.13(1H, dd, J=2.4, 11.4Hz), 8.21(1H, dd, J=1.2, 5.1Hz), 9.04(1H, d, J=5.1Hz), 9.31(1H, d, J=1.2Hz), 11.50-12.20(1H, brd). | 411 |
| YA1534 | 2.90-3.10(1H, m), 3.15-3.35(3H, m), 3.50-3.70(5H, m), 3.80-4.05(7H, m), 6.87(1H, d, J=8.1Hz), 6.90-7.10(2H, m), 7.31(1H, s), 8.16(1H, d, J=4.6Hz), 8.85(1H, d, J=5.0Hz), 9.27(1H, s) (CDCl3) | 408 |
| YA1535 | 3.45(3H, s), 3.46(2H, m), 3.64(m, 2H), 3.91(2H, t, J=16.1Hz), 4.68(1H, t, J=10.5Hz), 7.05(1H, s), 7.59(2H, d, J=8.4Hz), 7.79(2H, d, J=8.4Hz), 8.23(1H, dd, J=5.1, 1.2Hz), 9.02(1H, d, J=5.1Hz), 9.31(1H, d, J=1.2Hz), 10.00(1H, d, J=8.7Hz), 10.49(1H, br s) (DMSO-6) | 383 |
| YA1536 | 3.45(3H, s), 3.46(2H, m), 3.64(m, 2H), 3.91(2H, t, J=16.1Hz), 4.68(1H, t, J=10.5Hz), 7.05(1H, s), 7.59(2H, d, J=8.4Hz), 7.79(2H, d, J=8.4Hz), 8.23(1H, dd, J=5.1, 1.2Hz), 9.02(1H, d, J=5.1Hz), 9.31(1H, d, J=1.2Hz), 10.00(1H, d, J=8.7Hz), 10.49(1H, br s) (DMSO-6) | 383 |
| YA1537 | 2.39(3H, s), 2.60(4H, t, J=4.6Hz), 3.37(4H, t, J=4.8Hz), 3.53(3H, s), 7.27(1H, s), 8.18(1H, dd, J=1.2, 5.4Hz), 8.87(1H, d, J=5.1Hz), 9.28(1H, s) (CDCl3) | 286 |
| YA1538 | 2.64-2.74(1H, br.s), 2.66(2H, t, J=5.3Hz), 2.73(4H, t, J=4.4Hz), 3.39(4H, t, J=4.0Hz), 3.54(3H, s), 3.69-3.70(2H, m), 7.26(1H, s), 8.18(1H, d, J=5.0Hz), 8.88(1H, t, J=5.0Hz), 9.28(1H, s) (CDCl3) | 316 |
| YA1539 | 1.10(6H, t, J=6.6Hz), 2.71(4H, t, J=4.9Hz), 2.77(1H, m), 3.36(4H, t, J=4.9Hz), 3.54(3H, s), 7.27(1H, s), 8.18(1H, dd, J=1.1, 5.2Hz), 8.87(2H, d, J=5.1Hz), 9.27(1H, s) (CDCl3) | 314 |
| YA1540 | 1.15(6H, d, J=6.2Hz), 1.50(1H, br.s), 2.61(2H, dd, J=1.6, 12.4Hz), 3.06-3.16(2H, m), 3.49(2H, d, J=13.0Hz), 3.52(3H, s), 7.27(1H, s), 8.16(1H, dd, J=1.3, 5.0Hz), 8.88(1H, d, J=5.0Hz), 9.27(1H, d, J=1.3Hz) | 300 |
| YA1541 | 2.98(1H, t, J=11.5Hz), 3.20(3H, m), 3.57(3H, s), 3.58(2H, m), 4.02(1H, dd, J=10.5, 2.2Hz), 7.27(1H, s), 7.29(1H, d, J=8.3Hz), 7.46(1H, d, J=8.3Hz), 7.61(1H, s), 8.13(1H, d, J=5.2Hz), 8.86(1H, d, J=5.2Hz), 9.27(1H, s) (CDCl3) | 417 |
| YA1542 | 3.44(3H, s), 3.62-3.73(2H, m), 3.86-3.93(2H, m), 4.66(1H, m), 7.05(1H, s), 7.45(1H, dd, J=8.4, 8.4Hz), 7.67(1H, d, J=8.4Hz), 7.81(1H, d, J=8.4Hz), 8.04(1H, s), 8.25(1H, dd, J=5.4, 1.5Hz), 9.02(1H, d, J=5.4Hz), 8.18(1H, dd, J=5.4, 1.2Hz), 8.99(1H, d, J=5.1Hz), 9.32(1H, d, J=1.5Hz), 10.13(1H, m), 10.67(1H, m) (DMSO) | 427 |
| YA1543 | 3.33(1H, dd, J=13.5, 8.9Hz), 3.47(3H, s), 3.79(1H, dd, J=13.5, 3.9Hz), 4.73(1H, d, J=17.1Hz), 4.22(1H, d, J=17.1Hz), 4.82(1H, dd, J=8.9, 3.9Hz), 6.08(1H, s), 7.31(2H, d, J=8.4Hz), 7.42(2H, d, J=8.4Hz), 8.14(1H, d, J=5.1, 1.5Hz), 8.90(1H, d, J=5.1Hz), 9.29(1H, d, J=1.5Hz) (CDCl3) | 397 |
| YA1544 | 1.97(4H, m), 3.26(4H, m), 3.39(2H, m), 3.44(3H, s), 3.60(2H, m), 3.79(1H, d, J=13.5Hz), 3.91(1H, d, J=13.8Hz), 4.48(1H, t, J=10.1Hz), 6.66(2H, d, J=8.4Hz), 7.04(1H, s), 7.51(2H, d, J=8.4Hz), 8.21(1H, d, J=5.1Hz), 9.02(1H, d, J=5.1Hz), 9.31(1H, s), 9.70(1H, d, J=10.8Hz), 10.07(1H, br s) (DMSO-d6) | 418 |
| YA1545 | 3.21(4H, m), 3.42(2H, m), 3.44(3H, s), 3.62(2H, m), 3.79(4H, m), 3.90(2H, t, J=14.6Hz), 4.54(1H, t, J=10.5Hz), 7.05(1H, s), 7.13(2H, d, J=8.7Hz), 7.62(2H, d, J=8.7Hz), 8.22(1H, d, J=4.8Hz), 9.02(1H, d, J=4.8Hz), 9.31(1H, s), 9.80(1H, d, J=9.3Hz), 10.23(1H, br s) (DMSO-d6) | 434 |
| YA1546 | 2.80(3H, d, J=4.5Hz), 3.26(4H, m), 3.44(3H, s), 3.45(4H, m), 3.60(2H, m), 3.80(1H, d, J=3.5Hz), 3.90(3H, m), 4.54(1H, t, J=10.5Hz), 7.04(1H, s), 7.10(2H, d, J=8.7Hz), 7.62(2H, d, J=8.7Hz), 8.20(1H, dd, J=5.1, 1.2Hz), 9.02(1H, d, J=5.1Hz), 9.32(1H, d, J=1.2Hz), 9.86(1H, d, J=10.2Hz), 10.33(1H, br s), 11.15(1H, br s) (DMSO-d6) | 447 |
| YA1547 | 2.28(3H, s), 3.07(4H, t, J=4.7Hz), 3.37(4H, t, J=4.8Hz), 3.75(3H, s), 5.76(1H, s), 7.26-7.33(2H, m), 7.45(2H, dd, J=7.8, 7.8Hz), 7.79(2H, d, J=7.8Hz), 8.14(1H, d, J=5.4Hz), 8.87(1H, dd, J=7.8, 7.8Hz), 9.28(1H, d, J=1.2Hz) (CDCl3) | 428 |
| YA1548 | 2.37(1H, m), 2.43(1H, m), 2.80(3H, d, J=5.2Hz), 2.81(3H, d, J=5.2Hz), 3.28(1H, q, J=8.8Hz), 3.40(2H, m), 3.44(3H, s), 3.57(5H, m), 3.79(1H, d, J=11.4Hz), 3.97(2H, m), 4.50(1H, t, J=10.0Hz), 6.69(2H, d, J=8.4Hz), 7.05(1H, s), 7.54(2H, d, J=8.4Hz), 8.20(1H, dd, J=4.8, 1.2Hz), 9.03(1H, d, J=4.8Hz), 9.32(1H, d, J=1.2Hz), 9.71(1H, br s), 10.06(1H, br s), 11.35(1H, br s) (DMSO-d6) | 461 |
| YA1549 | 2.33(1H, m), 2.41(1H, m), 2.79(3H, d, J=4.8Hz), 2.81(3H, d, J=4.8Hz), 3.28(1H, d, J=8.4Hz), 3.39(2H, m), 3.44(3H, s), 3.57(5H, m), 3.79(1H, d, J=13.3Hz), 3.97(2H, m), 4.50(1H, t, J=11.6Hz), 6.69(2H, d, J=8.4Hz), 7.04(1H, s), 7.55(2H, d, J=8.4Hz), 8.21(2H, d, J=5.2Hz), 9.02(2H, d, J=5.2Hz), 9.32(1H, s), 9.75(1H, br s), 10.14(1H, br s), 11.45(1H, br s) (DMSO-d6) | 461 |
| YA1550 | 3.47(3H, s), 3.60(2H, m), 3.76(2H, m), 3.81(3H, s), 3.94(2H, m), 4.68(1H, m), 7.05(1H, d, J=8.6Hz), 7.06(1H, s), 7.67(2H, d, J=8.6Hz), 7.76(4H, m), 8.25(1H, d, J=5.0Hz), 9.03(1H, d, J=5.0Hz), 9.32(1H, s) (DMSO-d6) | 455 |
| YA1551 | 1.18(1H, m), 1.40(4H, m), 1.70(1H, m), 1.80(4H, m), 2.55(1H, m), 3.43(2H, m), 3.45(3H, s), 3.60(2H, m), 3.91(2H, m), 4.60(1H, t, J=10.8Hz), 7.05(1H, s), 7.35(2H, d, J=8.0Hz), 7.64(2H, d, J=8.0Hz), 9.03(1H, d, J=4.8Hz), 9.31(1H, s), 9.80(1H, d, J=8.8Hz), 10.24(1H, m) (DMSO-d6) | 431 |
| YA1552 | 3.02(4H, m), 3.23(4H, m), 3.49(3H, s), 7.08-7.67(10H, m), 8.15(1H, d, J=5.1Hz), 8.87(1H, d, J=5.1Hz), 9.27(1H, s) (CDCl3) | 424 |
| YA1553 | 2.90(1H, dd, J=13.2, 9.6Hz), 3.16(2H, m), 3.24(1H, d, 14.4Hz), 3.31(3H, s), 3.34(1H, d, J=13.6Hz), 3.47(1H, t, J=13.2Hz), 3.80(3H, m), 6.97(1H, s), 7.38(2H, m), 7.45(3H, m), 7.64(1H, dd, J=5.2, 1.2Hz), 8.94(1H, d, J=5.2Hz), | 363 |

TABLE 5-continued

| | | |
|---|---|---|
| | 9.28(1H, d, J=1.2Hz), 9.54(1H, br s), 9.78(1H, br s) (DMSO-d6) | |
| YA1554 | 2.95(1H, m), 3.29-3.05(3H, m), 3.34(3H, s), 3.35(1H, m), 3.44(1H, t, J=12.4Hz), 3.79(3H, m), 6.99(1H, s), 7.40(2H, d, J=8.4Hz), 7.51(2H, d, J=8.4Hz), 7.76(1H, dd, J=4.8, 1.2Hz), 8.96(1H, d, J=4.8Hz), 9.29(1H, d, J=1.2Hz), 9.38(1H, br s), 9.71(1H, br s) (DMSO-d6) | 397 |
| YA1555 | 1.65(2H, br s), 1.90(4H, br s), 3.44(6H, m), 3.45(3H, s), 3.61(2H, m), 3.88(1H, d, J=13.6Hz), 3.94(1H, d, J=13.6Hz), 4.66(1H, t, J=8.8Hz), 7.05(1H, s), 7.82(4H, br s), 8.23(1H, dd, J=5.2, 1.2Hz), 9.02(1H, d, J=5.2Hz), 9.31(1H, d, J=1.2Hz), 9.89(1H, br s), 10.37(1H, br s) (DMSO-d6) | 432 |
| YA1556 | 3.42(2H, m), 3.45(3H, s), 3.56(2H, m), 3.85(1H, d, J=13.2Hz), 3.93(1H, d, J=14.0Hz), 4.55(1H, t, J=10.8Hz), 6.94(1H, br s), 7.05(1H, s), 7.15(4H, br s), 7.31(2H, br s), 7.57(2H, br s), 8.22(1H, d, J=4.8Hz), 9.03(1H, d, J=4.8Hz), 9.32(1H, s), 9.66(1H, br s), 9.90(1H, br s) (DMSO-d6) | 509 |
| YA1557 | 1.40(1H, m), 1.78(8H, m), 2.18(2H, d, J=11.2Hz), 2.78(2H, m), 2.91(2H, m), 3.30(1H, m), 3.40(3H, m), 3.44(3H, s), 3.58(2H, m), 3.82(1H, d, J=13.3Hz), 3.93(3H, m), 4.53(1H, m), 7.05(1H, s), 7.11(2H, d, J=8.8Hz), 7.57(2H, d, J=8Hz), 8.21(1H, d, J=5.2Hz), 9.02(1H, d, J=5.2Hz), 9.32(1H, s), 9.73(1H, d, J=8.4Hz), 10.09(1H, br s), 10.39(1H, br s) (DMSO-d6) | 515 |
| YA1558 | 2.84-2.91(1H, m), 3.01-3.05(4H, m), 3.22(3H, s), 3.46(3H, s), 3.68-3.72(2H, m), 4.07-4.11(1H, m), 6.95(1H, s), 7.78(2H, d, J=7.2Hz), 7.93(2H, d, J=7.2Hz), 8.31(1H, d, J=4.2Hz), 8.99(1H, d, J=4.2Hz), 9.28(1H, s) (DMSO-d6) | 427 |
| YA1559 | 1.84(4H, m), 1.97(2H, m), 2.13(2H, m), 2.79(2H, t, J=11.6Hz), 3.04(2H, m), 3.24(1H, m), 3.40(2H, m), 3.44(3H, m), 3.59(2H, m), 3.80(1H, d, J=14.0Hz), 3.91(3H, m), 4.53(1H, t, J=11.2Hz), 7.05(1H, s), 7.13(2H, d, J=8.4Hz), 7.58(2H, d, J=8.4Hz), 8.22(1H, d, J=5.2Hz), 9.02(1H, d, J=5.2Hz), 9.31(1H, s), 9.75(1H, d, J=8.4Hz), 10.10(1H, br s), 11.04(1H, br s) (DMSO-d6) | 501 |
| YA1560 | 1.71(2H, m), 2.12(2H, m), 2.74(6H, d, J=4.8Hz), 2.74-2.80(3H, m), 3.30-3.96(8H, m), 3.40(3H, s), 4.54(1H, m), 7.05(1H, s), 7.10(2H, d, J=9.0Hz), 7.54(2H, d, J=9.0Hz), 8.21(1H, dd, J=5.1, 1.2Hz), 9.03(1H, d, J=5.4Hz), 9.32(1H, s), 9.68(1H, m), 9.92(1H, m), 10.54(1H, m), (DMSO-d6) | 475 |
| YA1561 | 1.51(2H, m), 1.84(2H, m), 3.00-3.20(3H, m), 3.38(3H, s), 3.38-3.91(8H, m), 4.55(1H, m), 7.05(1H, s), 7.18(2H, d, J=9.0Hz), 7.51(2H, d, J=9.0Hz), 8.21(1H, d, J=6.0Hz), 9.02(1H, d, J=5.1Hz), 9.31(1H, s), 9.54-9.62(3H, m), (DMSO-d6) | 448 |
| YA1562 | 1.89-2.05(2H, m), 2.65-3.20(5H, m), 3.25-3.82(5H, m), 3.41(3H, s), 4.39(1H, m), 4.91(1H, m), 6.49(2H, d, J=8.4Hz), 6.96(1H, s), 7.25(2H, d, J=8.4Hz), 8.18(1H, dd, J=4.2, 0.9Hz), 8.99(1H, d, J=5.1Hz), 9.28(1H, s), (DMSO-d6) | 434 |
| YA1563 | 1.06(1H, m), 1.30(2H, m), 1.43(2H, m), 1.60(2H, m), 1.79(3H, m), 2.97(1H, m), 3.45(3H, s), 3.60(2H, m), 3.80(3H, s), 3.90(2H, m), 4.63(1H, m), 7.05(1H, s), 7.70(4H, br s), 8.23(1H, d, J=5.2Hz), 9.03(1H, d, J=5.2Hz), 9.32(1H, s), 9.75(1H, br s) (DMSO-d6) | 460 |
| YA1564 | 2.99(6H, m), 3.44(1H, m), 3.45(3H, s), 3.57(3H, m), 3.82(1H, d, J=13.2Hz), 4.92(1H, d, J=14.4Hz), 4.55(1H, t, J=10.0Hz), 7.05(1H, s), 7.06(2H, br s), 7.61(2H, br s), 8.22(1H, d, J=5.2Hz), 9.03(1H, d, J=5.2Hz), 9.32(1H, s), 9.73(1H, br s), 10.11(1H, br s) (DMSO-d6) | 392 |
| YA1565 | 3.20-3.22(4H, m), 3.44-3.89(15H, m), 4.51-4.55(1H, m), 5.11(2H, s), 7.04-7.07(3H, m), 7.35-7.39(5H, m), 7.53(2H, d, J=7.2Hz), 8.20(1H, d, J=4.2Hz), 9.01(1H, d, J=4.2Hz), 9.31(1H, s), 9.78-9.92(2H, br) (DMSO-d6) | 567 |
| YA1566 | 1.33(6H, d, J=6.8Hz), 3.02-3.55(13H, m), 3.89-3.93(5H, m), 4.52-4.55(1H, m), 6.99-7.13(3H, m), 7.60(2H, d, J=7.2Hz), 8.21(1H, d, J=4.2Hz), 9.02(1H, d, J=4.2Hz), 9.32(1H, s), 9.67-10.15(3H, br), 10.84-10.88(1H, br) (DMSO-d6) | 475 |
| YA1567 | 3.17-3.26(8H, m), 3.44-3.55(6H, m), 3.80-3.94(9H, m), 4.50-4.57(1H, m), 7.05-7.12(3H, m), 7.60(2H, d, J=7.2Hz), 8.21(1H, d, J=4.2Hz), 9.02(1H, d, J=4.2Hz), 9.32(1H, s), 9.77-9.80(1H, br), 10.16-10.20(1H, br), 10.49-10.52(1H, br) (DMSO-d6) | 477 |
| YA1568 | 3.18-3.24(3H, m), 3.40-3.59(13H, m), 4.02-4.06(2H, m), 4.51-4.55(1H, m), 7.03-7.11(3H, m), 7.52(2H, d, J=7.2Hz), 8.21(1H, d, J=4.2Hz), 9.02(1H, d, J=4.2Hz), 9.18-9.22(1H, br), 9.38(1H, s), 9.72-9.78(1H, br), 10.04-10.10(1H, br) (DMSO-d6) | 433 |
| YA1569 | 1.90-2.02(2H, m), 2.80-3.06(5H, m), 3.25-3.82(5H, m), 3.65(3H, s), 4.39(1H, m), 4.94(1H, m), 6.49(2H, d, J=8.4Hz), 6.96(1H, s), 7.25(2H, d, J=8.4Hz), 8.16(1H, dd, J=5.4, 0.9Hz), 8.99(1H, d, J=5.1Hz), 9.29(1H, s) (DMSO-d6) | 434 |
| YA1570 | 1.15(6H, d, J=6.3Hz), 2.31(2H, dd, J=11.1Hz), 2.98-3.23(6H, m), 3.48-3.62(4H, m), 3.56(3H, s), 3.94(1H, dd, J=10.2, 2.1Hz), 6.94(2H, d, J=8.7Hz), 7.31(1H, s), 7.34(2H, d, J=8.7Hz), 8.16(1H, dd, J=5.1, 1.2Hz), 8.86(1H, d, J=5.1Hz), 9.26(1H, s) (CDCl3) | 461 |
| YA1571 | 1.27(6H, d, J=6.0Hz), 2.43(2H, dd, J=11.1, 11.1Hz), 3.02(1H, dd, J=12.0, 10.5Hz), 3.17-3.23(3H, m), 3.45-3.61(4H, m), 3.56(3H, s), 3.81(1H, m), 3.95(1H, m), 6.92(2H, d, J=8.7Hz), 7.32(1H, s), 7.35(2H, d, J=8.7Hz), 8.17(1H, m), 8.86(1H, d, J=5.1Hz), 9.26(1H, d, J=1.2Hz) (CDCl3) | 462 |
| YA1572 | 3.27-3.32(8H, m), 3.47(3H, s), 3.82-3.86(2H, m), 4.36-4.39(1H, m), 7.02(1H, s), 7.72(2H, d, J=7.2Hz), 7.84(2H, d, J=7.2Hz), 7.96-8.04(4H, m), 8.22(1H, d, J=4.2Hz), 9.01(1H, d, J=4.2Hz), 9.30(1H, s) (DMSO-d6) | 503 |
| YA1573 | 2.93-3.10(5H, m), 3.46(3H, s), 3.69-3.71(1H, m), 4.01-4.04(1H, m), 6.99(1H, s), 7.63(2H, d, J=7.2Hz), 7.77(2H, d, J=7.2Hz), 7.88-7.95(4H, m), 8.18(1H, d, J=4.2Hz), 8.99(1H, d, J=4.2Hz), 9.29(1H, s) (DMSO-d6) | 450 |
| YA1574 | 3.08(1H, dd, J=12.5, 10.4Hz), 3.24(3H, m), 3.59(3H, s), 3.66(2H, m), 4.09(1H, dd, J=10.4, 2.4Hz), 7.29(2H, d, J=8.3Hz), 7.33(1H, s), 7.54(2H, d, J=8.3Hz), 7.56(2H, d, J=8.3Hz), 7.59(2H, d, J=8.3Hz), 8.17(1H, d, J=4.9Hz), 8.86(1H, d, J=4.9Hz), 9.27(1H, s) (CDCl3) | 509 |
| YA1575 | 3.08(1H, dd, J=12.4, 10.0Hz), 3.25(3H, m), 3.59(3H, s), 3.67(2H, m), 4.11(1H, dd, J=10.0, 2.0Hz), 7.33(1H, s), 7.57(2H, d, J=8.0Hz), 7.63(2H, d, J=8.0Hz), 7.71(4H, s), 8.16(1H, dd, J=5.2, 1.2Hz), 8.16(1H, dd, J=5.2, 1.2Hz), 8.86(1H, d, J=5.2Hz), 9.27(1H, d, J=1.2Hz) (CDCl3) | 493 |
| YA1576 | 1.45(3H, t, J=7.0Hz), 3.08(1H, dd, J=12.5, 10.6Hz), 3.22(3H, m), 3.58(3H, s), 3.62(2H, m), 4.05(1H, m), 4.08(2H, q, J=7.0Hz), 6.98(2H, d, J=8.0Hz), 7.32(1H, s), 7.49(2H, d, J=8.0Hz), 7.52(2H, d, J=8.0Hz), 7.58(2H, d, J=8.0Hz), 8.17(1H, d, J=5.3Hz), 8.86(1H, d, J=5.3Hz), 9.27(1H, s), (CDCl3) | 469 |
| YA1577 | 1.83(4H, m), 1.99(1H, m), 2.21(1H, m), 2.61(4H, m), 2.87(1H, m), 3.03(1H, dd, J=12.0, 10.0Hz), 3.20(4H, m), 3.33(1H, m), 3.42(1H, m), 3.49(1H, m), 3.56(3H, s), 3.61(2H, m), 3.90(1H, dd, J=10.0, 2.0Hz), 6.55(2H, d, J=8.8Hz), 7.29(2H, d, J=8.8Hz), 7.30(1H, s), 8.16(1H, d, J=5.2Hz), 8.85(1H, d, J=5.2Hz), 9.26(1H, s) (CDCl3) | 487 |
| YA1578 | 3.09(1H, dd, J=12.4, 10.8Hz), 3.20(3H, m), 3.58(3H, s), 3.64(2H, m), 3.82(3H, s), 3.86(3H, s), 4.05(1H, dd, J=10.4, 2.8Hz), 6.58(2H, m), 7.24(2H, m), 7.32(1H, s), 7.47(2H, d, J=8.4Hz), | 485 |

TABLE 5-continued

| | | |
|---|---|---|
| | 7.53(2H, d, J=8.4Hz), 8.17(1H, dd, J=5.2, 1.2Hz), 8.86(1H, d, J=5.2Hz), 9.27(1H, d, J=1.2Hz) (CDCl3) | |
| YA1579 | 3.08(1H, dd, J=12.5, 10.6Hz), 3.23(3H, m), 3.59(3H, s), 3.66(2H, m), 3.93(3H, s), 3.96(3H, s), 4.07(1H, dd, J=10.3, 2.2Hz), 6.95(1H, d, J=8.3Hz), 7.11(1H, d, J=2.0Hz), 7.16(1H, dd, J=8.3, 2.0Hz), 7.33(1H, s), 7.52(1H, d, J=8.1Hz), 7.59(1H, d, J=8.1Hz), 8.17(1H, dd, J=5.3, 1.2Hz), 8.85(1H, d, J=5.3Hz), 9.27(1H, d, J=1.2Hz) (CDCl3) | 485 |
| YA1580 | 3.07(1H, dd, J=12.4, 10.4Hz), 3.23(3H, m), 3.59(3H, s), 3.65(2H, m), 4.08(1H, dd, J=10.4, 2.0Hz), 7.32(1H, s), 7.41(2H, d, J=8.4Hz), 7.52(2H, d, J=8.4Hz), 7.53(2H, d, J=8.4Hz), 7.58(2H, d, J=8.4Hz), 8.16(1H, d, J=4.8Hz), 8.86(1H, d, J=4.8Hz), 9.27(1H, s) (CDCl3) | 459 |
| YA1581 | 3.09(1H, dd, J=12.2, 11.0Hz), 3.24(3H, m), 3.59(3H, s), 3.66(2H, m), 4.10(1H, dd, J=10.4, 2.4Hz), 7.29(2H, m), 7.33(1H, s), 7.44(2H, d, J=8.0Hz), 7.52(3H, d), 8.18(1H, dd, J=5.3, 1.0Hz), 8.87(1H, d, J=5.3Hz), 9.27(1H, d, J=1.0Hz) (CDCl3) | 493 |
| YA1582 | 3.06(1H, dd, J=12.4, 10.4Hz), 3.25(3H, m), 3.58(3H, s), 3.65(2H, m), 4.09(1H, dd, J=10.0, 2.0Hz), 7.33(1H, s), 7.42(1H, dd, J=8.0, 2.0Hz), 7.56(5H, m), 7.68(1H, d, J=2.0Hz), 8.16(1H, dd, J=5.2, 1.2Hz), 8.85(1H, d, J=5.2Hz), 9.27(1H, d, J=1.2Hz) (CDCl3) | 493 |
| YA1583 | 3.06(1H, dd, J=12.3, 10.8Hz), 3.23(3H, m), 3.59(3H, s), 3.65(2H, m), 4.13(1H, dd, J=10.2, 2.2Hz), 7.33(1H, s), 8.14(1H, d, J=5.3Hz), 8.15(2H, d, J=8.4Hz), 8.78(1H, d), 8.86(1H, d, J=5.3Hz), 9.27(1H, s) (CDCl3) | 417 |
| YA1584 | 1.37(6H, d, J=6.0Hz), 3.07(1H, dd, J=12.6, 10.8Hz), 3.20-3.26(3H, m), 3.58(3H, s), 3.65-3.68(2H, m), 4.07(1H, m), 4.59(1H, m), 6.98(2H, d, J=8.7Hz), 7.48(1H, s), 7.50-7.61(6H, m), 8.17(1H, d, J=4.8Hz), 8.86(1H, d, J=5.1Hz), 9.26(1H, d, J=1.2Hz) (CDCl3) | 483 |
| YA1585 | 0.99(3H, t, J=7.5Hz), 1.47-1.82(4H, m), 3.07(1H, dd, J=12.3, 10.5Hz), 3.22-3.27(3H, m), 3.58(3H, s), 3.62-3.65(2H, m), 4.03(2H, t, J=6.3Hz), 4.04(1H, m), 6.98(2H, d, J=8.7Hz), 7.48(1H, s), 7.50-7.59(6H, m), 8.17(1H, dd, J=5.1, 1.2Hz), 8.86(1H, d, J=5.1Hz), 9.26(1H, d, J=1.2Hz) (CDCl3) | 497 |
| YA1586 | 1.28(1H, br.s), 2.51(3H, s), 3.07(1H, dd, J=10.8, 12.6Hz), 3.21-3.28(3H, m), 3.58(3H, s), 3.64(2H, m), 4.08(1H, dd, J=2.5, 19.5Hz), 7.34(2H, d, J=7.8Hz), 7.45-7.67(7H, m), 8.17(1H, d, J=5.4Hz), 8.86(1H, d, J=5.1Hz), 9.27(1H, d, J=1.2Hz) (CDCl3) | 470 |
| YA1587 | 1.86(1H, br.s), 2.40(3H, s), 3.07(1H, dd, J=10.8, 12.6Hz), 3.20-3.27(2H, m), 3.58(3H, s), 3.62-3.68(3H, m), 4.06(1H, dd, J=2.5, 19.5Hz), 7.24-7.27(2H, m), 7.49-7.52(5H, m), 7.60(2H, d, J=8.2Hz), 8.17(1H, d, J=5.4Hz), 8.85(1H, d, J=5.2Hz), 9.27(1H, s) (CDCl3) | 438 |
| YA1588 | 1.29(6H, s), 1.85(1H, br.s), 2.94-2.96(1H, m), 3.08(1H, dd, J=10.8, 12.6Hz), 3.21-3.27(3H, m), 3.59(3H, s), 3.65(2H, m), 4.07(1H, dd, J=2.5, 19.5Hz), 7.28-7.62(9H, m), 8.17(1H, dd, J=1.2, 5.7Hz), 8.86(1H, d, J=5.1Hz), 9.27(1H, d, J=1.2Hz) (CDCl3) | 466 |
| YA1589 | 1.72(1H, br.s), 3.10(1H, m), 3.21-3.24(3H, m), 3.58(3H, s), 3.58-3.73(4H, m), 4.09(1H, dd, J=2.5, 19.5Hz), 6.75(2H, dd, J=2.1, 6.6Hz), 7.23-7.57(7H, m), 8.16(1H, d, J=5.4Hz), 8.86(1H, d, J=5.1Hz), 9.27(1H, d, J=1.2Hz) (CDCl3) | 439 |
| YA1590 | 2.79(1H, dd, J=10.5, 12.6Hz), 3.20-3.40(3H, m), 3.50-3.80(5H, m), 4.45(1H, dd, J=3.0, 10.2Hz), 7.10-7.20(1H, m), 7.30-7.40(2H, m), 7.58(1H, dd, J=0.9, 7.8Hz), 7.73(1H, dd, J=1.5, 7.8Hz), 8.19(1H, dd, J=0.9, 4.8Hz), 8.85(1H, d, J=5.1Hz), 9.26(1H, d, J=0.9Hz) (CDCl3) | 427 |
| YB013 | 1.31-1.46(1H, m), 1.60-1.96(3H, m), 2.17-2.30(1H, m), 2.89-3.02(2H, m), 3.41(3H, s), 3.61(1H, d, J=12.4Hz), 3.80(1H, d, J=13.5Hz), 3.90-4.01(2H, m), 6.89-7.01(3H, m), 6.96(1H, s), 7.27-7.32(2H, m), 8.18(1H, d, J=4.4Hz), 8.96(1H, d, J=5.0Hz), 9.28(1H, s) (DMSO-d6) | 378 |
| YB014 | 1.33-1.49(1H, m), 1.60-1.93(3H, m), 2.20-2.32(1H, m), 2.89-3.04(2H, m), 3.41(3H, s), 3.63(1H, d, J=13.3Hz), 3.82(1H, d, J=11.1Hz), 4.22-4.37(2H, m), 6.95(1H, s), 7.51-7.56(2H, m), 7.65-7.70(1H, m), 8.00-8.03(1H, m), 8.17(1H, dd, J=1.1, 5.1Hz), 8.87(1H, d, J=5.1Hz), 9.28(1H, d, J=1.0Hz) (DMSO-d6) | 406 |
| YB048 | (CDCl3): 1.93-2.07(3H, m), 2.38(1H, m), 3.09(1H, m), 3.46(1H, m), 3.57(3H, s), 3.61-3.70(2H, m), 4.05(1H, m), 7.26-7.34(2H, m), 7.59-7.61(2H, m), 7.76(1H, m), 8.16(1H, m), 8.83(1H, m), 9.27(1H, s). | 389 |
| YB049 | (CDCl3): 1.92-2.08(3H, m), 2.36(1H, m), 3.11(1H, m), 3.44(1H, dd, J=12.9, 10.8Hz), 3.58(3H, s), 3.61-3.70(2H, m), 4.06(1H, m), 7.11(1H, m), 7.28-7.33(2H, m), 7.70(1H, dd, J=8.7, 4.8Hz), 8.15(1H, m), 8.86(1H, d, J=5.4Hz), 9.28(1H, s). | 407 |
| YB050 | 1.93-2.11(3H, m), 2.33-2.45(1H, m), 3.08-3.16(1H, m), 3.46(1H, dd, J=11.4, 12.9Hz), 3.59(3H, s), 3.62-3.71(2H, m), 4.06(1H, d, J=12.6Hz), 7.32-7.37(1H, m), 7.32(1H, s), 7.57-7.64(2H, m), 7.75(1H, d, J=8.1Hz), 8.16(1H, dd, J=1.2, 5.4Hz), 8.84(1H, d, J=4.8Hz), 9.28(1H, d, J=0.9Hz) (CDCl3) | 389 |
| YB051 | 1.91-2.11(3H, m), 2.35-2.43(1H, m), 3.08-3.16(1H, m), 3.42-3.50(1H, m), 3.59(3H, s), 3.62-3.71(2H, m), 4.05(1H, d, J=11.1Hz), 7.32(1H, s), 7.33-7.37(1H, m), 7.57-7.65(2H, m), 7.75(1H, d, J=7.8Hz), 8.16(1H, d, J=5.7Hz), 8.84(1H, d, J=5.4Hz), 9.28(1H, d, J=1.2Hz) (CDCl3) | 389 |
| YB130 | 1.78-1.96(4H, m), 2.73-2.90(1H, m), 3.02-3.09(2H, m), 3.46(3H, s), 3.84(2H, d, J=12.6Hz), 6.98(1H, s), 7.11-7.17(2H, m), 7.33-7.38(2H, m), 8.25(1H, d, J=5.1Hz), 9.01(1H, d, J=4.8Hz), 9.30(1H, s) (DMSO-d6) | 366 |
| YB157 | 1.90-2.05(2H, m), 2.18-2.35(2H, m), 2.92-3.09(1H, m), 3.10-3.23(2H, m), 3.58(3H, s), 3.72-3.83(2H, m), 6.95-7.07(1H, m), 7.22(1H, dd, J=2.2, 9.0Hz), 7.34(1H, s), 7.46(1H, m), 7.48-7.55(1H, m), 8.20(1H, d, J=5.3Hz), 8.88(1H, d, J=5.2Hz), 9.29(1H, s) (CDCl3) | 406 |
| YB158 | 1.91-2.04(2H, m), 2.23(2H, d, J=8.9Hz), 2.44(3H, s), 2.97-3.11(1H, m), 3.16(2H, dd, J=11.1, 12.4Hz), 3.58(3H, s), 3.77(2H, d, J=13.0Hz), 7.12(1H, d, J=8.5Hz), 7.36-7.41(4H, m), 8.20(1H, d, J=5.3Hz), 8.87(1H, d, J=4.8Hz), 9.28(1H, s) (CDCl3) | 402 |
| YB159 | 1.93-2.05(2H, m), 2.23(2H, d, J=12.6Hz), 3.19(3H, m), 3.58(3H, s), 3.81(2H, d, J=13.2Hz), 7.12-7.16(1H, m), 7.26(1H, s), 7.34(1H, s), 7.56(1H, dd, J=2.4, 8.7Hz), 7.77-7.76(1H, m), 8.20(1H, dd, J=1.2, 5.1Hz), 8.87(1H, d, J=5.1Hz), 9.29(1H, s) (CDCl3) | 422 |
| YB160 | 2.01-2.22(5H, m), 3.20(2H, dd, J=1.4, 11.7Hz), 3.47(3H, s), 3.84(2H, d, J=13.2Hz), 6.99(1H, s), 7.32(1H, m), 7.72(1H, dd, J=2.1, 9.0Hz), 8.09(1H, dd, J=2.7, 9.1Hz), 8.27(1H, m), 9.01(1H, d, J=5.1Hz), 9.31(1H, d, J=1.5Hz) (DMSO-d6) | 407 |
| YB162 | 2.13-2.43(4H, m), 3.10-3.38(3H, m), 3.57(3H, s), 3.65-3.83(2H, m), 7.30-7.40(3H, m), 7.45-7.59(1H, m), 7.62-7.80(1H, m), 8.10-8.22(1H, m), 8.88(1H, d, J=5.1Hz), 9.28(1H, s) (CDCl3) | 389 |
| YB193 | 2.22-2.39(4H, m), 3.21-3.35(2H, m), 3.48(3H, s), 3.90(2H, d, J=13.5Hz), 7.03(1H, s), 7.38-7.43(1H, m), 7.46-7.51(2H, m), 7.59-7.66(2H, m), 8.28(1H, d, J=5.0Hz), 9.01(1H, d, J=5.0Hz), 9.30(1H, s) (DMSO-d6) | 373 |
| YB251 | 2.01-2.22(5H, m), 3.20(2H, dd, J=11.4, 11.7Hz), 3.47(3H, s), 3.82(2H, d, J=13.2Hz), 7.32(1H, m), 6.70(1H, s), 7.72(1H, dd, J=2.1, 9.0Hz), 8.09(1H, | 406 |

TABLE 5-continued

| | | |
|---|---|---|
| | dd, J=2.7, 9.1Hz), 8.27(1H, m), 9.01(1H, d, J=5.1Hz), 9.31(1H, d, J=1.5Hz) (DMSO-d6) | |
| YB252 | 1.64(2H, m), 2.23(2H, d, J=8.9Hz), 2.44(3H, s), 2.97-3.11(1H, m), 3.16(2H, dd, J=11.1, 11.4Hz), 3.58(3H, s), 3.77(2H, d, J=13.0Hz) 7.12(1H, d, J=8.5Hz), 7.36-7.41(4H, m), 8.20(1H, d, J=5.3Hz), 8.87(1H, d, J=4.8Hz), 9.28(1H, s) (CDCl3) | 401 |
| YB253 | 1.93-2.05(2H, m), 2.23(2H, d, J=12.6Hz), 3.19(3H, m), 3.58(3H, s), 3.81(2H, d, J=13.2Hz), 7.12-7.16(1H, m), 7.26(1H, s) 7.34(1H, s), 7.56(1H, dd, J=2.4, 8.7Hz), 7.11-7.76(1H, m), 8.20(1H, dd, J=1.2, 5.1Hz), 8.87(1H, d, J=5.1Hz), 9.29(1H, s) (CDCl3) | 421 |
| YB254 | 1.72-1.94(8H, m), 2.52(4H, m), 2.97-3.05(3H, m), 3.56(3H, s), 3.61(2H, s), 3.67-3.73(2H, m), 7.21-7.34(4H, m), 8.17(1H, d, J=5.4Hz), 8.86(1H, d, J=5.1Hz), 9.27(1H, s) (CDCl3) | 431 |
| YB255 | 1.78(1H, m), 1.89(3H, m), 1.96(3H, m), 2.13(1H, d, J=13.6Hz), 3.46(2H, m), 3.56(3H, s), 3.66(2H, t, J=6.8Hz), 3.73(2H, m), 7.30(2H, d, J=8.0Hz), 7.31(1H, s), 7.52(2H, d, J=5.2Hz), 8.15(1H, d, J=5.2Hz), 8.86(1H, d, J=5.2Hz), 9.27(1H, s) | 444 |
| YB256 | 1.46-1.73(9H, m), 2.01(2H, d, J=12.1Hz), 2.56(4H, t, J=5.0Hz), 2.94(2H, td, J=1.3, 12.7Hz), 3.52(3H, s), 3.70(2H, d, J=13.8Hz), 7.27(1H, s), 8.18(1H, dd, J=1.3, 5.3Hz), 8.86(1H, d, J=5.3Hz), 9.27(1H, d, J=1.3Hz) (CDCl3) | 354 |
| YB257 | 1.81-1.88(4H, m), 2.80(1H, m), 2.99-3.08(2H, m), 3.46(3H, s), 3.82-3.86(2H, m), 6.98(1H, s), 7.26-7.43(3H, m), 7.53(1H, s), 8.26(1H, d, J=4.8Hz), 9.01(1H, d, J=4.8Hz), 9.30(1H, s) (DMSO-d6) | 425 |
| YB258 | 1.80-1.90(4H, m), 2.83(1H, m), 2.99-3.08(2H, m), 3.46(3H, s), 3.81-3.86(2H, m), 6.98(1H, s), 7.26-7.43(3H, m), 7.53(1H, s), 8.26(1H, d, J=4.8Hz), 9.01(1H, d, J=4.8Hz), 9.30(1H, s) (DMSO-d6) | 425 |
| YB259 | 1.76-1.96(8H, m), 2.67(1H, m), 2.99-3.07(2H, m), 3.16-3.21(4H, m), 3.45(3H, s), 3.79-3.84(2H, m), 6.49(2H, d, J=8.4Hz) 6.97(1H, s), 7.09(2H, d, J=8.4Hz), 8.24(1H, d, J=5.1Hz), 9.01(1H, d, J=5.1Hz), 9.30(1H, s) (DMSO-d6) | 417 |
| YB260 | 1.87-1.99(8H, m), 2.72(1H, m), 2.99-3.09(2H, m), 3.19-3.23(4H, m), 3.46(3H, s), 3.80-3.85(2H, m), 6.38(1H, d, J=7.8Hz) 6.44(1H, d), 6.53(1H, d, J=7.8Hz), 6.98(1H, s), 7.09(1H, dd, J=7.8, 7.8Hz), 8.25(1H, d, J=5.1Hz), 9.01(1H, d, J=5.1Hz), 9.30(1H, s) (DMSO-d6) | 417 |
| YB261 | 1.48-1.58(2H, m), 2.00-2.07(2H, m), 2.71(6H, s), 3.07-3.14(2H, m), 3.34-3.36(1H, m), 3.48(3H, s), 3.69-3.73(2H, m), 4.87(1H, d, J=8.2Hz), 6.56-6.66(4H, m), 6.96(1H, s), 8.24(1H, d, J=4.2Hz), 9.00(1H, d, J=4.2Hz), 9.30(1H, s) (DMSO-d6) | 406 |
| YB262 | 1.51-1.62(2H, m), 2.02-2.08(2H, m), 3.10-3.18(2H, m), 3.42(3H, s), 3.46-3.50(1H, m), 3.67(3H, s), 3.69-3.73(2H, m), 5.56(1H, d, J=8.2Hz), 6.10-6.24(3H, m), 6.94-6.99(2H, m), 8.24(1H, d, J=4.2Hz), 9.00(1H, d, J=4.2Hz), 9.29(1H, s) (DMSO-d6) | 393 |
| YB263 | 1.48-1.58(2H, m), 2.01-2.08(2H, m), 3.08-3.17(2H, m), 3.40(3H, s), 3.41-3.43(1H, m), 3.63(3H, s), 3.69-3.73(2H, m), 5.09(1H, d, J=8.2Hz), 6.59(2H, d, J=7.2Hz), 6.72(2H, d, J=4.2Hz), 6.96(1H, s), 8.24(1H, d, J=4.2Hz), 9.01(1H, d, J=4.2Hz), 9.29(1H, s) (DMSO-d6) | 393 |
| YB264 | 1.58-1.69(2H, m), 2.04-2.08(2H, m), 3.08-3.15(2H, m), 3.42(3H, s), 3.55-3.83(6H, m), 4.57(1H, d, J=8.2Hz), 6.53-6.90(4H, m), 7.03(1H, s), 8.25(1H, d, J=4.2Hz), 9.00(1H, d, J=4.2Hz), 9.30(1H, s) (DMSO-d6) | 393 |
| YB265 | 1.66-1.87(3H, m), 1.91-1.99(1H, m), 2.93-3.08(3H, m), 3.43(3H, s), 3.72-3.78(2H, m), 6.97(1H, s), 7.34(2H, d, J=5.7Hz), 7.54(2H, d, J=5.4Hz), 8.18(1H, dd, J=5.4, 1.2Hz), 8.99(1H, d, J=5.1Hz), 9.29(1H, d, J=0.9Hz) (DMSO) | 426 |
| YB266 | 1.71-1.91(4H, m), 2.41-2.45(2H, m), 2.53-2.56(4H, m), 2.93-3.00(3H, m), 3.08-3.10(4H, m), 3.43(3H, s), 3.50-3.54(2H, m), 3.67-3.71(2H, m), 4.42-4.46(1H, m), 6.90(2H, d, J=7.2Hz), 6.96(1H, s), 7.19(2H, d, J=7.2Hz), 8.17(1H, dd, J=1.2, 4.2Hz), 8.99(1H, d, J=4.2Hz), 9.29(1H, d, J=1.2Hz) (DMSO-d6) | 476 |
| YB267 | 1.70-1.94(4H, m), 2.86(6H, m), 2.89-2.90(3H, m), 3.43(3H, s), 3.66-3.77(2H, m), 6.71(2H, d, J=7.2Hz), 6.96(1H, s), 7.15(2H, d, J=7.2Hz), 8.17(1H, d, J=4.2Hz), 8.99(1H, d, J=4.2Hz), 9.28(1H, s) (DMSO-d6) | 391 |
| YB268 | 1.72-1.84(4H, m), 2.89-3.08(7H, m), 3.43(3H, s), 3.67-3.77(6H, m), 6.90-6.96(3H, m), 7.21(2H, d, J=7.2Hz), 8.17(1H, d, J=4.2Hz), 8.99(1H, d, J=4.2Hz), 9.29(1H, s) (DMSO-d6) | 433 |
| YB269 | 1.51-1.83(10H, m), 2.87-3.00(3H, m), 3.07-3.10(4H, m), 3.43(3H, s), 3/68-3.77(2H, m), 6.89(2H, d, J=7.2Hz), 6.96(1H, s), 7.17(2H, d, J=7.2Hz), 8.18(1H, d, J=4.2Hz), 8.99(1H, d, J=4.2Hz), 9.29(1H, s) (DMSO-d6) | 431 |
| YB270 | 1.72-1.90(4H, m), 2.21(3H, s), 2.42-2.45(4H, m), 2.87-2.97(3H, m), 3.08-3.10(4H, m), 3.43(3H, s), 3.67-3.77(2H, m), 6.90(2H, d, J=7.2Hz), 6.96(1H, s), 7.19(2H, d, J=7.2Hz), 8.17(1H, d, J=4.2Hz), 8.98(1H, d, J=4.2Hz), 9.29(1H, s) (DMSO-d6) | 446 |
| YB271 | 1.63-1.95(6H, m), 2.04-2.08(2H, m), 2.61-2.65(2H, m), 2.69(6H, s), 2.86-3.00(3H, m), 3.13-3.16(1H, m), 3.43(3H, s), 3.67-3.81(4H, m) 6.92-6.96(3H, m), 7.20(2H, d, J=7.2Hz), 8.17(1H, d, J=4.2Hz), 9.00(1H, d, J=4.2Hz), 9.29(1H, s) (DMSO-d6) | 474 |
| YB272 | 1.72-1.83(4H, m), 2.89-3.09(7H, m), 3.42(3H, s), 3.54-3.57(4H, m), 3.67-3.77(2H, m), 5.11(2H, s), 6.91-6.96(3H, m), 7.21(2H, d, J=7.2Hz), 7.26-7.44(5H, m), 8.17(1H, d, J=4.2Hz), 8.99(1H, d, J=4.2Hz), 9.29(1H, s) (DMSO-d6) | 566 |
| YB273 | 1.57-1.63(2H, m), 1.82-1.89(2H, m), 2.51-2.98(13H, m), 3.41(3H, s), 3.76-3.80(3H, m), 6.70(1H, s), 8.22(1H, d, J=4.2Hz), 9.01(1H, d, J=4.2Hz), 9.30(1H, s) (DMSO-d6) | 370 |
| YB274 | 1.52-1.63(2H, m), 1.84-1.90(2H, m), 2.36-2.42(11H, m), 2.86-2.94(2H, m), 3.40(3H, s), 3.49-3.53(2H, m), 3.73-3.77(2H, m), 4.40-4.43(1H, m), 6.96(1H, s), 8.22(1H, d, J=4.2Hz), 9.01(1H, d, J=4.2Hz), 9.30(1H, s) (DMSO-d6) | 400 |
| YB275 | 1.72-1.92(4H, m), 2.80-3.02(11H, m), 3.28-3.30(1H, m), 3.43(3H, s), 6.88(2H, d, J=7.2Hz), 6.96(1H, s), 7.18(2H, d, J=7.2Hz), 8.18(1H, d, J=4.2Hz), 8.99(1H, d, J=4.2Hz), 9.29(1H, s) (DMSO-d6) | 432 |
| YB276 | 1.06-1.38(5H, m), 1.61-1.92(9H, m), 2.77-2.91(3H, m), 3.03-3.12(1H, m), 3.42(3H, s), 3.64-3.75(2H, m), 5.27(1H, d, J=8.2Hz), 6.52(2H, d, J=7.2Hz), 6.96(1H, s), 7.02(2H, d, J=7.2Hz), 8.17(1H, d, J=4.2Hz), 8.99(1H, d, J=4.2Hz), 9.28(1H, s) (DMSO-d6) | 445 |
| YB277 | 1.76-1.97(4H, m), 2.97-3.10(5H, m), 3.47(3H, s), 3.73-3.76(2H, m), 3.88-3.93(2H, m), 6.71(1H, dd, J=7.2, 7.3Hz), 6.96-7.34(8H, m), 8.19(1H, d, J=4.2Hz), 9.00(1H, d, J=4.2Hz), 9.29(1H, s) (DMSO-d6) | 465 |
| YB278 | 1.10-1.15(1H, m), 1.32-1.47(4H, m), 1.64-1.82(9H, m), 2.69(3H, s), 2.82-2.97(3H, m), 3.42(3H, s), 3.54-3.75(3H, m), 6.73(2H, d, J=7.2Hz), 6.95(1H, s), 7.13(2H, d, J=7.2Hz), 8.16(1H, d, J=4.2Hz), 8.98(1H, d, J=4.2Hz), 9.28(1H, s) (DMSO-d6) | 459 |

Test Example

Inhibitory Activity of the Medicament of the Present Invention against P-GS1 Phosphorylation by Bovine Cerebral TPK1

A mixture containing 100 mM MES-sodium hydroxide (pH 6.5), 1 mM magnesium acetate, 0.5 mM EGTA, 5 mM β-mercaptoethanol, 0.02% Tween 20, 10% glycerol, 12 μg/ml P-GS1, 41.7 μM [γ-$^{32}$P] ATP (68 kBq/ml), bovine cerebral TPK1 and a compound shown in Table (a final mixture contained 1.7% DMSO deriving from a solution of a test compound prepared in the presence of 10% DMSO) was used as a reaction system. The phosphorylation was started by adding ATP, and the reaction was conducted at 25° C. for 2 hours, and then stopped by adding 21% perchloric acid on ice cooling. The reaction mixture was centrifuged at 12,000 rpm for 5 minutes and adsorbed on P81 paper (Whatmann), and then the paper was washed four times with 75 mM phosphoric acid, three times with water and once with acetone. The paper was dried, and the residual radioactivity was measured using a liquid scintillation counter. The results are shown in the table below. The test compound markedly inhibited the P-GS1 phosphorylation by TPK1. The results strongly suggest that the medicaments of the present invention inhibit the TPK1 activity, thereby suppress the A β neurotoxicity and the PHF formation, and that the medicaments of the present invention are effective for preventive and/or therapeutic treatment of Alzheimer disease and the above-mentioned diseases.

TABLE 6

| Compound No. | IC$_{50}$ |
|---|---|
| XA361 | 0.018 μM |
| XB80 | 0.23 μM |
| YA0864 | 0.216 μM |
| YB257 | 0.014 μM |

Formulation Example (1) Tablets

The ingredients below were mixed by an ordinary method and compressed by using a conventional apparatus.

| | |
|---|---|
| Compound of Example 1 | 30 mg |
| Crystalline cellulose | 60 mg |
| Corn starch | 100 mg |
| Lactose | 200 mg |
| Magnesium stearate | 4 mg |

(2) Soft Capsules

The ingredients below were mixed by an ordinary method and filled in soft capsules.

| | |
|---|---|
| Compound of Example 1 | 30 mg |
| Olive oil | 300 mg |
| Lecithin | 20 mg |

INDUSTRIAL APPLICABILITY

The compounds of the present invention have TPK1 inhibitory activity and are useful as an active ingredient of a medicament for preventive and/or therapeutic treatment of diseases caused by abnormal advance of TPK1 such as neurodegenerative diseases (e.g. Alzheimer disease) and the above-mentioned diseases.

The invention claimed is:

1. A pyrimidone derivative represented by formula (I) or a salt thereof:

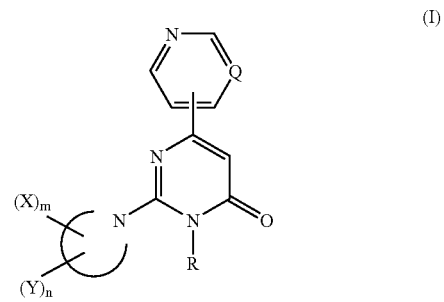

wherein Q represents CH or nitrogen atom;
R represents a C$_1$-C$_{12}$ alkyl group;
the ring of:

represents piperazine ring or piperidine ring;
each X independently represents $X^1$—$X^2$— wherein $X^1$ represents
an optionally partially hydrogenated C$_6$-C$_{10}$ aryl ring which may be substituted;
an optionally substituted heterocyclic ring having 1 to 4 hetero atoms selected from oxygen atom, sulfur atom, and nitrogen atom, and having 5 to 10 ring-constituting atoms in total;
a group represented by —N(Ra)(Rb)
wherein Ra and Rb are the same or different and each is hydrogen,
a C$_1$-C$_4$ alkyl group,
an aralkyl group which may be substituted,
an aryl group which may be substituted, or
$X^2$ represents
a bond,
a C$_1$-C$_4$ alkylene group, or
N-Rd
wherein Rd represents
a hydrogen atom,
a C$_1$-C$_4$ alkyl group, or
C$_1$-C$_8$ alkylcarbonyl group;
m represents an integer of 1 to 3;
each Y independently represents
a hydroxy group, or
a C$_1$-C$_8$ alkyl group;
n represents an integer of 0 to 8;

when the ring represented by X has one or more substituents, the ring may have one or more substituents selected from:
a $C_1$-$C_5$ alkyl group;
$C_3$-$C_6$ cycloalkyl group;
a $C_3$-$C_6$ cycloalkyl-$C_1$-$C_4$ alkyl group;
a $C_1$-$C_4$ hydroxyalkyl group;
a halogen atom;
a $C_1$-$C_5$ halogenated alkyl group;
cyano group;
nitro group;
formyl group;
a benzene ring which may be substituted;
a naphthalene ring which may be substituted;
an optionally substituted heterocyclic ring having 1 to 4 hetero atoms selected from oxygen atom, sulfur atom and nitrogen atom, and having 5 to 10 ring-constituting atoms in total;
an amino group;
dimethylamino group;
an N—$C_3$-$C_6$ cycloalkyl-N—$C_1$-$C_4$ alkylaminoalkyl group wherein said $C_1$-$C_4$ alkyl may be substituted by hydroxy group or $C_1$-$C_4$ alkoxy group;
a $C_1$-$C_5$ monoalkylaminomethyl group;
a $C_2$-$C_{10}$ dialkylaminomethyl group;
pyrrolidinylmethyl group;
piperidinylmethyl group;
morpholinomethyl group;
piperazinylmethyl group;
pyrrolylmethyl group;
imidazolylmethyl group;
pyrazolylmethyl group;
triazolylmethyl group;
and a group of the formula -E-Rf wherein
E represents O, S, SO, $SO_2$, CO or $N(R^4)$ and
Rf represents
a $C_1$-$C_5$ alkyl group,
a $C_4$-$C_7$ cycloalkyl group,
a $C_4$-$C_7$ cycloalkylalkl group,
a $C_1$-$C_5$ hydroxyalkyl group,
a benzene ring which may be substituted,
a naphthalene ring which may be substituted,
an optionally substituted heterocyclic ring having 1 to 4 hetero atoms selected from oxygen atom, sulfur atom and nitrogen atom, and having 5 to 10 ring-constituting atoms in total,
an N—$C_3$-$C_6$ cycloalkyl-N—$C_1$-$C_4$ alkylaminoalkyl group,
a $C_1$-$C_5$ monoalkylaminoalkyl group,
$C_2$-$C_{10}$ dialkylaminoalkyl group,
pyrrolidinylmethyl group,
piperidinylmethyl group,
morpholinomethyl group,
piperazinylmethyl group,
pyrrolylmethyl group,
imidazolylmethyl group,
pyrazolylmethyl group or
triazolylmethyl group,
$C_1$-$C_8$ alkylcarbonyl group,
$C_3$-$C_8$ cycloalkylcarbonyl group which may be substituted,
aralkycarbonyl group which may be substituted,
$C_6$-$C_{10}$ arylcarbonyl group which may be substituted,
$C_1$-$C_8$ alkysulfonyl group,
$C_3$-$C_8$ cycloalkylsulfonyl group which may be substituted,
aralkysulfonyl group which may be substituted,
$C_6$-$C_{10}$ arylsulfonyl group which may be substituted,
$C_1$-$C_8$ alkyloxycarbonyl group,
$C_3$-$C_8$ cycloalkyloxycarbonyl group which may be substituted,
aralkyoxycarbonyl group which may be substituted,
$C_6$-$C_{10}$ aryloxycarbonyl group which may be substituted,
aminocarbonyl,
N—$C_1$-$C_8$ alkylaminocarbonyl group,
N, N'—$C_1$-$C_8$ dialkylaminocarbonyl group,
N—$C_1$-$C_8$ alkyl-N'—$C_3$-$C_8$ cycloalkylaminocarbonyl group,
N—$C_1$-$C_8$ alkyl-N'-aralkylaminocarbonyl group,
N—$C_1$-$C_8$ alkyl-N'—$C_6$-$C_{10}$ arylaminocarbonyl group,
$C_3$-$C_8$ cycloalkylaminocarbonyl group,
N,N'—$C_3$-$C_8$ dicycloalkylaminoycarbonyl group,
N—$C_3$-$C_8$ cycloalkyl-N'-aralkylaminocarbonyl group,
N—$C_3$-$C_8$ cycloalkyl-N'—$C_6$-$C_{10}$ arylaminocarbonyl group, aralkylaminocarbonyl group,
N,N'-diaralkylaminocarbonyl group,
N-aralkyl-N'—$C_6$-$C_{10}$ arylaminocarbonyl group,
$C_6$-$C_{10}$ arylaminocarbonyl group,
N,N'—$C_6$-$C_{10}$ diarylaminocarbonyl group, and
$R^4$ represents
a hydrogen atom,
a $C_1$-$C_4$ alkyl group,
an aralkyl group,
$C_3$-$C_8$ cycloalkyl group or
an aryl group which may be substituted; and
when the ring represented by X has one or more substituents, the substituent may further have one or more substituents selected from:
a $C_1$-$C_5$ alkyl group;
$C_3$-$C_6$ cycloalkyl group;
a $C_3$-$C_6$ cycloalkyloxy group;
$C_1$-$C_4$ hydroxyalkyl group;
a $C_1$-$C_5$ alkoxy group;
a $C_4$-$C_7$ cycloalkylalkoxy group;
a $C_1$-$C_5$ alkylthio group;
a $C_1$-$C_5$ alkylsulfonyl group;
a halogen atom;
a $C_1$-$C_5$ halogenated alkyl group;
a $C_1$-$C_5$ halogenated alkoxy group;
hydroxyl group;
cyano group;
nitro group;
formyl group;
a $C_2$-$C_6$ alkylcarbonyl group;
amino group;
a $C_1$-$C_5$ monoalkylamino group;
a $C_2$-$C_{10}$ dialkylamino group;
a cyclic amino group;
a $C_2$-$C_{10}$ monoalkylaminomethyl group;
a $C_3$-$C_{11}$ dialkylaminomethyl group;
a phenyl group;
an aralkyloxy group;
an aralkyloxycarbonyl group;
an $C_2$-$C_4$ alkanoyloxy-$C_1$-$C_4$ alkyl group;
an alkanoylamino group;
N—$C_1$-$C_4$ alkyl-N-alkanoylamino;
N—$C_1$-$C_4$ alkyl-N-heterocyclic ring amino group; and
a diheterocyclic ring amino group.

2. The pyrimidone derivative or the salt thereof according to claim 1 having the following fonnula(II)

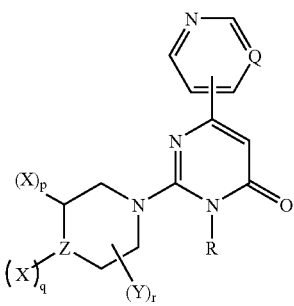

(II)

wherein Q, R, X and Y are the same as those defined in claim 1;
p is 0 or 1; q is 0 or 1; r is an integer of 0 to 6; p+q is 1 or 2; and Z represents N or $CZ^1$ wherein $Z^1$ represents hydrogen atom or Y.

3. The pyrimidone derivative or the salt thereof according to claim 2, wherein R is a $C_1$-$C_3$ alkyl group.

4. The pyrimidone derivative or the salt thereof according to claim 3, wherein R is methyl group or ethyl group; Y is in 3-, 4- or 5-position of the piperazine ring or the piperidine ring; p+q is 1; and r is an integer of 0 to 3.

5. The pyrimidone derivative or the salt thereof according to claim 4, wherein X is a $C_1$-$C_8$ alkyl group which may be substituted or a $C_6$-$C_{10}$ aryl ring which may be substituted; Y is a $C_1$-$C_6$ alkyl group; p is 1; q is 0; r is an integer of 0 to 3; and Z is N or CH.

6. The pyrimidone derivative or the salt thereof according to claim 5, wherein X is a benzene ring which may be substituted, a benzyl group which may be substituted; Y is a methyl group; Z is N and r is 0 or 1.

7. The pyrimidone derivative or the salt thereof according to claim 4, wherein X is a benzene ring which may be substituted, or a benzyl group which may be substituted; Y is a methyl group which may be substituted; Z is N and p is 0.

8. The pyrimidone derivative or the salt thereof according to claim 4, wherein X is a $C_1$-$C_8$ alkyl group substituted by a benzene ring which may be substituted or a benzene ring which may be substituted; Y is a hydroxy group; Z is CH or C-Y and r is 0 or 1.

9. The pyrimidone derivative or the salt thereof according to claim 8, wherein X is a benzyl group which may be substituted or a benzene ring which may be substituted; Y is a hydroxy group; Z is CH or C-Y and r is 0 or 1.

10. A pyrimidone derivative which is selected from the group consisting of:
2-(3-Phenylpiperazin-1-yl)-3-methyl-6-(4-pyridyl)-3H-pyrimidin-4-one;
2-(3-(4-Fluorophenyl)piperazin-1-yl)-3-methyl-6-(4-pyridyl)-3H-pyrimidin-4-one;
2-(3-(3-Fluorophenyl)piperazin-1-yl)-3-methyl-6-(4-pyridyl)-3H-pyrimidin-4-one;
2-(3-(2-Fluorophenyl)piperazin-1-yl)-3-methyl-6-(4-pyridyl)-3H-pyrimidin-4-one;
2-(3-(4-Chlorophenyl)piperazin-1-yl)-3-methyl-6-(4-pyridyl)-3H-pyrimidin-4-one; (S)-2-(3-(4-Chlorophenyl)piperazin-1-yl)-3-methyl-6-(4-pyridyl)-3H-pyrimidin-4-one;
(R)-2-(3-(4-Chlorophenyl)piperazin-1-yl)-3-methyl-6-(4-pyridyl)-3H-pyrimidin-4-one;
2-(3-(3-Chlorophenyl)piperazin-1-yl)-3-methyl-6-(4-pyridyl)-3H-pyrimidin-4-one;
2-(3-(2-Chlorophenyl)piperazin-1-yl)-3-methyl-6-(4-pyridyl)-3H-pyrimidin-4-one;
2-(3-(4-Bromophenyl)piperazin-1-yl)-3-methyl-6-(4-pyridyl)-3H-pyrimidin-4-one;
2-(3-(3-Bromophenyl)piperazin-1-yl)-3-methyl-6-(4-pyridyl)-3H-pyrimidin-4-one;
2-(3-(2-Bromophenyl)piperazin-1-yl)-3-methyl-6-(4-pyridyl)-3H-pyrimidin-4-one;
2-(3-(4-Methylphenyl)piperazin-1-yl)-3-methyl-6-(4-pyridyl)-3H-pyrimidin-4-one;
2-(3-(3-Methylphenyl)piperazin-1-yl)-3-methyl-6-(4-pyridyl)-3H-pyrimidin-4-one;
2-(3-(2-Methylphenyl)piperazin-1-yl)-3-methyl-6-(4-pyridyl)-3H-pyrimidin-4-one;
2-(3-(4-Cyanophenyl)piperazin-1-yl)-3-methyl-6-(4-pyridyl)-3H-pyrimidin-4-one;
2-(3-(3-Cyanophenyl)piperazin-1-yl)-3-methyl-6-(4-pyridyl)-3H-pyrimidin-4-one;
2-(3-(2-Cyanophenyl)piperazin-1-yl)-3-methyl-6-(4-pyridyl)-3H-pyrimidin-4-one;
2-(3-(4-Methoxyphenyl)piperazin-1-yl)-3-methyl-6-(4-pyridyl)-3H-pyrimidin-4-one;
2-(3-(3-Methoxyphenyl)piperazin-1-yl)-3-methyl-6-(4-pyridyl)-3H-pyrimidin-4-one;
2-(3-(2-Methoxyphenyl)piperazin-1-yl)-3-methyl-6-(4-pyridyl)-3H-pyrimidin-4-one;
2-(3-(2-Ethoxyphenyl)piperazin-1-yl)-13-methyl-6-(4-pyridyl)-3H-pyrimidin-4-one;
2-(3-(5-Fluoro-2-methoxyphenyl)piperazin-1-yl)-3-methyl-6-(4-pyridyl)-3H-pyrimidin-4-one;
2-(3-(4-Fluoro-3-methoxyphenyl)piperazin-1-yl)-3-methyl-6-(4-pyridyl)-3H-pyrimidin-4-one;
2-(3-(4-Fluoro-2-methoxyphenyl)piperazin-1-yl)-3-methyl-6-(4-pyridyl)-3H-pyrimidin-4-one;
(S)-2-(3-(4-Fluoro-2-methoxyphenyl)piperazin-1-yl)-13-methyl-6-(4-pyridyl)-3H-pyrimidin-4-one;
(R)-2-(3-(4-Fluoro-2-methoxyphenyl)piperazin-1-yl)-3-methyl-6-(4-pyridyl)-3H-pyrimidin-4-one;
2-(3-(4-Chloro-2-methoxyphenyl)piperazin-1-yl)-3-methyl-6-(4-pyridyl)-3H-pyrimidin-4-one;
2-(3-(4-Fluoro-2-methylphenyl)piperazin-1-yl)-3-methyl-6-(4-pyridyl)-3H-pyrimidin-4-one;
2-(3-(2-Fluoro-6-methoxyphenyl)piperazin-1-yl)-3-methyl-6-(4-pyridyl)-3H-pyrimidin-4-one;
2-(3-(5-Bromo-2-methoxyphenyl)piperazin-1-yl)-3-methyl-6-(4-pyridyl)-3H-pyrimidin-4-one;
2-(3-(2-Bromo-4-fluorophenyl)piperazin-1-yl)-3-methyl-6-(4-pyridyl)-3H-pyrimidin-4-one;
2-(3-(2-Chloro-6-fluorophenyl)piperazin-1-yl)-3-methyl-6-(4-pyridyl)-3H-pyrimidin-4-one;
2-(3-(2,4-Difluorophenyl)piperazin-1-yl)-3-methyl-6-(4-pyridyl)-3H-pyrimidin-4-one;
2-(3-(2,6-Difluorophenyl)piperazin-1-yl)-3-methyl-6-(4-pyridyl)-3H-pyrimidin-4-one;
2-(3-(2,6-Dichlorophenyl)piperazin-1-yl)-3-methyl-6-(4-pyridyl)-3H-pyrimidin-4-one;
2-(3-(2,4-Dimethoxyphenyl)piperazin-1-yl)-3-methyl-6-(4-pyridyl)-3H-pyrimidin-4-one;
2-(3-(3,4-Dimethoxyphenyl)piperazin-1-yl)-3-methyl-6-(4-pyridyl)-3H-pyrimidin-4-one;
2-(3-(2,5-Dimethoxyphenyl)piperazin-1-yl)-3-methyl-6-(4-pyridyl)-3H-pyrimidin-4-one;
2-(3-(2,6-Dimethoxyphenyl)piperazin-1-yl)-3-methyl-6-(4-pyridyl)-3H-pyrimidin-4-one;
2-(3-(2,4-Difluoro-6-methoxyphenyl)piperazin-1-yl)-3-methyl-6-(4-pyridyl)-3H-pyrimidin-4-one;(1034)

2-(3-(5-Cyano-2-methoxyphenyl)piperazin-1-yl)-3-methyl-6-(4-pyridyl)-3H-pyrimidin-4-one;
2-(3-(4-Cyano-2-methoxyphenyl)piperazin-1-yl)-3-methyl-6-(4-pyridyl)-3H-pyrimidin-4-one;
2-(3-(1-Naphthyl)piperazin-1-yl)-3-methyl-6-(4-pyridyl)-3H-pyrimidin-4-one;
2-(3-(2-Naphthyl)piperazin-1-yl)-3-methyl-6-(4-pyridyl)-3H-pyrimidin-4-one;
2-(3-(2,3-Dihydrobenzofuran-7-yl)piperazin-1-yl)-3-methyl-6-(4-pyridyl)-3H-pyrimidin-4-one;
2-(3-(Benzofuran-2-yl)piperazin-1-yl)-3-methyl-6-(4-pyridyl)-3H-pyrimidin-4-one;
(S)-2-(3-(Benzofuran-2-yl)piperazin-1-yl)-3-methyl-6-(4-pyridyl)-3H-pyrimidin-4-one;
2-(3-(4-(Pyrrolidin-1-yl-methyl)phenyl)piperazin-1-yl)-3-methyl-6-(4-pyridyl)-3H-pyrimidin-4-one;
2-(3-(4-(Pyrrolidin-1-yl)phenyl)piperazin-1-yl)-3-methyl-6-(4-pyridyl)-3H-pyrimidin-4-one;
2-(3-(2-methoxy-4-(pyrrolidin-1-yl)phenyl)piperazin-1-yl)-3-methyl-6-(4-pyridyl)-3H-pyrimidin-4-one;
2-(3-(2-methoxy-5-(pyrrolidin-1-yl)phenyl)piperazin-1-yl)-3-methyl-6-(4-pyridyl)-3H-pyrimidin-4-one;
2-(3-(4-(Phenyl)phenyl)piperazin-1-yl)-3-methyl-6-(4-pyridyl)-3H-pyrimidin-4-one;
2-(3-(4-(4-Fluorophenyl)phenyl)piperazin-1-yl)-3-methyl-6-(4-pyridyl)-3H-pyrimidin-4-one;
2-(3-(4-(4-Methoxyphenyl)phenyl)piperazin-1-yl)-3-methyl-6-(4-pyridyl)-3H-pyrimidin-4-one;
2-(3-(4-(2-Methoxyphenyl)phenyl)piperazin-1-yl)-3-methyl-6-(4-pyridyl)-3H-pyrimidin-4-one;
2-(3-(4-(Morpholin-4-yl)phenyl)piperazin-1-yl)-3-methyl-6-(4-pyridyl)-3H-pyrimidin-4-one;
2-(3-(4-(4-Methylpiperazin-1-yl)phenyl)piperazin-1-yl)-3-methyl-6-(4-pyridyl)-3H-pyrimidin-4-one;
2-(4-Phenylpiperazin-1-yl)-3-methyl-6-(4-pyridyl)-3H-pyrimidin-4-one;
2-(4-Benzylpiperazin-1-yl)-3-methyl-6-(4-pyridyl)-3H-pyrimidin-4-one;
2-(4-Benzoylpiperazin-1-yl)-3-methyl-6-(4-pyridyl)-3H-pyrimidin-4-one;
2-(4-(1,2-Benzisothiazol-3-yl)piperazin-1-yl)-3-methyl-6-(4-pyridyl)-3H-pyrimidin-4-one;
2-(4-Methyl-3-phenylpiperazin-1-yl)-3-methyl-6-(4-pyridyl)-3H-pyrimidin-4-one;
2-(3-(4-Fluoro-2-methoxyphenyl)-4-methylpiperazin-1-yl)-3-methyl-6-(4-pyridyl)-3H-pyrimidin-4-one;
(S)-2-(3-(4-Fluoro-2-methoxyphenyl)-4-methylpiperazin-1-yl)-3-methyl-6-(4-pyridyl)-3H-pyrimidin-4-one;
(R)-2-(3-(4-Fluoro-2-methoxyphenyl)-4-methylpiperazin-1-yl)-3-methyl-6-(4-pyridyl)-3H-pyrimidin-4-one;
2-(4-Acetyl-3-(4-fluoro-2-methoxyphenyl)piperazin-1-yl)-3-methyl-6-(4-pyridyl)-3H-pyrimidin-4-one;
2-(4-Benzyl-3-(4-fluoro-2-methoxyphenyl)piperazin-1-yl)-3-methyl-6-(4-pyridyl)-3H-pyrimidin-4-one;
2-(4-Benzyl-3-(ethoxycarbonyl)piperazin-1-yl)-3-methyl-6-(4-pyridyl)-3H-pyrimidin-4-one;
2-(4-methyl-3-(1-naphthyl)piperazin-1-yl)-3-methyl-6-(4-pyridyl)-3H-pyrimidin-4-one;
2-(5,5-Dimethyl-3-(2-methoxyphenyl)piperazin-1-yl)-3-methyl-6-(4-pyridyl)-3H-pyrimidin-4-one;
2-(3-Phenylpiperidin-1-yl)-13-methyl-6-(4-pyridyl)-3H-pyrimidin-4-one;
2-(3-(4-Fluorophenyl)piperidin-1-yl)-3-methyl-6-(4-pyridyl)-3H-pyrimidin-4-one;
2-(3-(3-Fluorophenyl)piperidin-1-yl)-3-methyl-6-(4-pyridyl)-3H-pyrimidin-4-one;
2-(3-(2-Fluorophenyl)piperidin-1-yl)-3-methyl-6-(4-pyridyl)-3H-pyrimidin-4-one;
2-(3-(4-Chlorophenyl)piperidin-1-yl)-3-methyl-6-(4-pyridyl)-3H-pyrimidin-4-one;
2-(3-(4-Bromophenyl)piperidin-1-yl)-3-methyl-6-(4-pyridyl)-3H-pyrimidin-4-one;
2-(3-(4-Methoxyphenyl)piperidin-1-yl)-3-methyl-6-(4-pyridyl)-3H-pyrimidin-4-one;
2-(3-(3-Methoxyphenyl)piperidin-1-yl)-3-methyl-6-(4-pyridyl)-3H-pyrimidin-4-one;
2-(3-(2-Methoxyphenyl)piperidin-1-yl)-3-methyl-6-(4-pyridyl)-3H-pyrimidin-4-one;
2-(3-(4-((Pyrrolidin-1-yl)methyl)phenyl)piperidin-1-yl)-3-methyl-6-(4-pyridyl)-3H-pyrimidin-4-one;
(S)-2-(3-(4-(Pyrrolidin-1-yl-methyl)phenyl)piperidin-1-yl)-3-methyl-6-(4-pyridyl)-3H-pyrimidin-4-one;
(R)-2-(3-(4-(Pyrrolidin-1-yl-methyl)phenyl)piperidin-1-yl)-3-methyl-6-(4-pyridyl)-3H-pyrimidin-4-one;
2-(3-Hydroxy-3-phenylpiperidin-1-yl)-3-methyl-6-(4-pyridyl)-3H-pyrimidin-4-one;
2-(3-Phenylpiperazin-1-yl)-3-methyl-6-(4-pyrimidyl)-3H-pyrimidin-4-one;
2-(3-(4-Fluorophenyl)piperazin-1-yl)-3-methyl-6-(4-pyrimidyl)-3H-pyrimidin-4-one;
2-(3-(3-Fluorophenyl)piperazin-1-yl)-3-methyl-6-(4-pyrimidyl)-3H-pyrimidin-4-one;
2-(3-(2-Fluorophenyl)piperazin-1-yl)-3-methyl-6-(4-pyrimidyl)-3H-pyrimidin-4-one;
2-(3-(4-Chlorophenyl)piperazin-1-yl)-3-methyl-6-(4-pyrimidyl)-3H-pyrimidin-4-one;
2-(3-(3-Chlorophenyl)piperazin-1-yl)-3-methyl-6-(4-pyrimidyl)-3H-pyrimidin-4-one;
2-(3-(2-Chlorophenyl)piperazin-1-yl)-3-methyl-6-(4-pyrimidyl)-3H-pyrimidin-4-one;
2-(3-(4-Bromophenyl)piperazin-1-yl)-3-methyl-6-(4-pyrimidyl)-3H-pyrimidin-4-one;
2-(3-(3-Bromophenyl)piperazin-1-yl)-3-methyl-6-(4-pyrimidyl)-3H-pyrimidin-4-one;
2-(3-(2-Bromophenyl)piperazin-1-yl)-3-methyl-6-(4-pyrimidyl)-3H-pyrimidin-4-one;
2-(3-(4-Cyanophenyl)piperazin-1-yl)-3-methyl-6-(4-pyrimidyl)-3H-pyrimidin-4-one;
2-(3-(3-Cyanophenyl)piperazin-1-yl)-3-methyl-6-(4-pyrimidyl)-3H-pyrimidin-4-one;
2-(3-(2-Cyanophenyl)piperazin-1-yl)-3-methyl-6-(4-pyrimidyl)-3H-pyrimidin-4-one;
2-(3-(4-Methoxyphenyl)piperazin-1-yl)-3-methyl-6-(4-pyrimidyl)-3H-pyrimidin-4-one;
2-(3-(3-Methoxyphenyl)piperazin-1-yl)-3-methyl-6-(4-pyrimidyl)-3H-pyrimidin-4-one;
2-(3-(2-Methoxyphenyl)piperazin-1-yl)-3-methyl-6-(4-pyrimidyl)-3H-pyrimidin-4-one;
2-(3-(2-Ethoxyphenyl)piperazin-1-yl)-3-methyl-6-(4-pyrimidyl)-3H-pyrimidin-4-one;
2-(3-(6-Fluoro-2-methoxyphenyl)piperazin-1-yl)-3-methyl-6-(4-pyrimidyl)-3H-pyrimidin-4-one;
2-(3-(5-Fluoro-2-methoxyphenyl)piperazin-1-yl)-3-methyl-6-(4-pyrimidyl)-3H-pyrimidin-4-one;
2-(3-(4-Fluoro-2-methoxyphenyl)piperazin-1-yl)-3-methyl-6-(4-pyrimidyl)-3H-pyrimidin-4-one;
(S)-2-(3-(4-Fluoro-2-methoxyphenyl)piperazin-1-yl)-3-methyl-6-(4-pyrimidyl)-3H-pyrimidin-4-one;
(R)-2-(3-(4-Fluoro-2-methoxyphenyl)piperazin-1-yl)-3-methyl-6-(4-pyrimidyl)-3H-pyrimidin-4-one;

2-(3-(4-Chloro-2-methoxyphenyl)piperazin-1-yl)-3-methyl-6-(4-pyrimidyl)-3H-pyrimidin-4-one;
2-(3-(5-Bromo-2-methoxyphenyl)piperazin-1-yl)-3-methyl-6-(4-pyrimidyl)-3H-pyrimidin-4-one;
2-(3-(2,6-Dichlorophenyl)piperazin-1-yl)-3-methyl-6-(4-pyridyl)-3H-pyrimidin-4-one;
2-(3-(2,4-Dimethoxyphenyl)piperazin-1-yl)-3-methyl-6-(4-pyridyl)-3H-pyrimidin-4-one;
2-(3-(3,4-Dimethoxyphenyl)piperazin-1-yl)-3-methyl-6-(4-pyrimidyl)-3H-pyrimidin-4-one;
2-(3-(2,5-Dimethoxyphenyl)piperazin-1-yl)-3-methyl-6-(4-pyrimidyl)-3H-pyrimidin-4-one;
2-(3-(2,6-Dimethoxyphenyl)piperazin-1-yl)-3-methyl-6-(4-pyrimidyl)-3H-pyrimidin-4-one;
2-(3-(2,4-Difluoro-6-methoxyphenyl)piperazin-1-yl)-3-methyl-6-(4-pyrimidyl)-3H-pyrimidin-4-one;
2-(3-(1-Naphthyl)piperazin-1-yl)-3-methyl-6-(4-pyrimidyl)-3H-pyrimidin-4-one;
2-(3-(2-Naphthyl)piperazin-1-yl)-3-methyl-6-(4-pyrimidyl)-3H-pyrimidin-4-one;
2-(3-(2,3-Dihydrobenzofuran-7-yl)piperazin-1-yl)-3-methyl-6-(4-pyrimidyl)-3H-pyrimidin-4-one;
2-(3-(Benzofuran-2-yl)piperazin-1-yl)-3-methyl-6-(4-pyrimidyl)-3H-pyrimidin-4-one;
2-(3-(4-(Pyrrolidin-1-yl-methyl)phenyl)piperazin-1-yl)-3-methyl-6-(4-pyrimidyl)-3H-pyrimidin-4-one;
2-(3-(4-(Pyrrolidin-1-yl)phenyl)piperazin-1-yl)-3-methyl-6-(4-pyrimidyl)-3H-pyrimidin-4-one;
2-(3-(2-methoxy-4-(pyrrolidin-1-yl)phenyl)piperazin-1-yl)-3-methyl-6-(4-pyrimidyl)-3H-pyrimidin-4-one;
2-(3-(2-methoxy-5-(pyrrolidin-1-yl)phenyl)piperazin-1-yl)-3-methyl-6-(4-pyrimidyl)-3H-pyrimidin-4-one;
2-(3-(4-(Phenyl)phenyl)piperazin-1-yl)-3-methyl-6-(4-pyrimidyl)-3H-pyrimidin-4-one;
2-(3-(4-(4-Fluorophenyl)phenyl)piperazin-1-yl)-3-methyl-6-(4-pyrimidyl)-3H-pyrimidin-4-one;
2-(3-(4-(4-Methoxyphenyl)phenyl)piperazin-1-yl)-3-methyl-6-(4-pyrimidyl)-3H-pyrimidin-4-one;
2-(3-(4-(2-Methoxyphenyl)phenyl)piperazin-1-yl)-3-methyl-6-(4-pyrimidyl)-3H-pyrimidin-4-one;
2-(3-(4-(Morpholin-4-yl)phenyl)piperazin-1-yl)-3-methyl-6-(4-pyrimidyl)-3H-pyrimidin-4-one;
2-(3-(4-(4-Methylpiperazin-1-yl)phenyl)piperazin-1-yl)-3-methyl-6-(4-pyrimidyl)-3H-pyrimidin-4-one;
2-(3-(4-Fluoro-2-methoxyphenyl)-4-methylpiperazin-1-yl)-3-methyl-6-(4-pyrimidyl)-3H-pyrimidin-4-one;
(S)-2-(3-(4-Fluoro-2-methoxyphenyl)-4-methylpiperazin-1-yl)-3-methyl-6-(4-pyrimidyl)-3H-pyrimidin-4-one;
(R)-2-(3-(4-Fluoro-2-methoxyphenyl)-4-methylpiperazin-1-yl)-3-methyl-6-(4-pyrimidyl)-3H-pyrimidin-4-one;
2-(4-Acetyl-3-(4-fluoro-2-methoxyphenyl)piperazin-1-yl)-3-methyl-6-(4-pyrimidyl)-3H-pyrimidin-4-one;
2-(4-Benzyl-3-(4-fluoro-2-methoxyphenyl)piperazin-1-yl)-3-methyl-6-(4-pyrimidyl)-3H-pyrimidin-4-one;
2-(4-(4-Fluorophenyl)piperidin-1-yl)-3-methyl-6-(4-pyrimidyl)-3H-pyrimidin-4-one;
2-(4-Cyano-4-phenylpiperidin-1-yl)-3-methyl-6-(4-pyrimidyl)-3H-pyrimidin-4-one;
2-(4-(6-Fluorobenofiuran-3-yl)piperidin-1-yl)-3-methyl-6-(4-pyrimidyl)-3H-pyrimidin-4-one;
2-(3-(Benzoisoxazol-3-yl)piperidin-1-yl)-3-methyl-6-(4-pyrimidyl)-3H-pyrimidin-4-one;
(S)-2-(3-(Benzoisoxazol-3-yl)piperidin-1-yl)-3-methyl-6-(4-pyrimidyl)-3H-pyrimidin-4-one;
(R)-2-(3-(Benzoisoxazol-3-yl)piperidin-1-yl)-3-methyl-6-(4-pyrimidyl)-3H-pyrimidin-4-one;
2-(3-(6-Fluorobenzoisoxazol-3-yl)piperidin-1-yl)-3-methyl-6-(4-pyrimidyl)-3H-pyrimidin-4-one;
2-(4-(6-Fluorobenzoisoxazol-3-yl)piperidin-1-yl)-3-methyl-6-(4-pyrimidyl)-3H-pyrimidin-4-one;
2-(4-(5-Methylbenzofuran-3-yl)piperidin-1-yl)-3-methyl-6-(4-pyrimidyl)-3H-pyrimidin-4-one; and
2-(4-(6-Fluorobenzothiophene-3-yl)piperidin-1-yl)-3-methyl-6-(4-pyrimidyl)-3H-pyrimidin-4-one
or a salt thereof.

11. A medicament composition comprising as an active ingredient at least one pyrimidone derivative represented by formula (I) or a salt thereof according to claim 1.

12. A method for therapeutic treatment of a disease selected from Alzheimer disease and non-insulin dependent diabetes comprising administering to a patient a therapeutically effective amount of the composition according to claim 11.

* * * * *